US011779330B2

(12) United States Patent
Huang

(10) Patent No.: US 11,779,330 B2
(45) Date of Patent: Oct. 10, 2023

(54) SURGICAL INSTRUMENT COMPRISING A JAW ALIGNMENT SYSTEM

(71) Applicant: Cilag GmbH International, Zug (CH)

(72) Inventor: Zhifan F. Huang, Mason, OH (US)

(73) Assignee: Cilag GMBH International, Zug (CH)

( * ) Notice: Subject to any disclaimer, the term of this patent is extended or adjusted under 35 U.S.C. 154(b) by 233 days.

(21) Appl. No.: 17/084,215

(22) Filed: Oct. 29, 2020

(65) Prior Publication Data

US 2022/0133312 A1 May 5, 2022

(51) Int. Cl.
*A61B 17/072* (2006.01)
*A61B 17/00* (2006.01)
*A61B 90/00* (2016.01)

(52) U.S. Cl.
CPC .... *A61B 17/072* (2013.01); *A61B 2017/0019* (2013.01); *A61B 2017/00039* (2013.01); *A61B 2017/00115* (2013.01); *A61B 2017/00398* (2013.01); *A61B 2017/07228* (2013.01); *A61B 2017/07257* (2013.01); *A61B 2017/07271* (2013.01); *A61B 2017/07285* (2013.01); *A61B 2090/035* (2016.02); *A61B 2090/036* (2016.02); *A61B 2090/0807* (2016.02)

(58) Field of Classification Search
CPC ........ A61B 17/072; A61B 2017/07285; A61B 2017/07257; A61B 2017/07271
USPC ....................................................... 227/176.1
See application file for complete search history.

(56) References Cited

U.S. PATENT DOCUMENTS

| | | | |
|---|---|---|---|
| 66,052 | A | 6/1867 | Smith |
| 662,587 | A | 11/1900 | Blake |
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |

(Continued)

FOREIGN PATENT DOCUMENTS

| | | | |
|---|---|---|---|
| AU | 2012200594 | A1 | 2/2012 |
| AU | 2012203035 | A1 | 6/2012 |

(Continued)

OTHER PUBLICATIONS

ASTM procedure D2240-00, “Standard Test Method for Rubber Property-Durometer Hardness,” (Published Aug. 2000).

(Continued)

*Primary Examiner* — Valentin Neacsu

(57) ABSTRACT

A surgical instrument comprising an end effector including a first jaw and a second jaw rotatable relative to the first jaw is disclosed. One or both of the first jaw and the second jaw comprise alignment features.

16 Claims, 147 Drawing Sheets

(56) References Cited

U.S. PATENT DOCUMENTS 2,028,635 A 1/1936 Wappler
2,037,727 A 4/1936 La Chapelle
2,120,951 A 6/1938 Hodgman
2,132,295 A 10/1938 Hawkins
2,161,632 A 6/1939 Nattenheimer
D120,434 S 5/1940 Gold
2,211,117 A 8/1940 Hess
2,214,870 A 9/1940 West
2,224,108 A 12/1940 Ridgway
2,224,882 A 12/1940 Peck
2,256,295 A 9/1941 Schmid
2,318,379 A 5/1943 Davis et al.
2,329,440 A 9/1943 La Place
2,377,581 A 6/1945 Shaffrey
2,406,389 A 8/1946 Lee
2,420,552 A 5/1947 Morrill
2,441,096 A 5/1948 Happe
2,448,741 A 9/1948 Scott et al.
2,450,527 A 10/1948 Smith
2,491,872 A 12/1949 Neuman
2,507,872 A 5/1950 Unsinger
2,526,902 A 10/1950 Rublee
2,527,256 A 10/1950 Jackson
2,578,686 A 12/1951 Fish
2,638,901 A 5/1953 Sugarbaker
2,674,149 A 4/1954 Benson
2,701,489 A 2/1955 Osborn
2,711,461 A 6/1955 Happe
2,724,289 A 11/1955 Wight
2,742,955 A 4/1956 Dominguez
2,804,848 A 9/1957 O'Farrell et al.
2,808,482 A 10/1957 Zanichkowsky et al.
2,825,178 A 3/1958 Hawkins
2,853,074 A 9/1958 Olson
2,856,192 A 10/1958 Schuster
2,887,004 A 5/1959 Stewart
2,957,353 A 10/1960 Lewis
2,959,974 A 11/1960 Emrick
3,026,744 A 3/1962 Rouse
3,032,769 A 5/1962 Palmer
3,035,256 A 5/1962 Egbert
3,060,972 A 10/1962 Sheldon
3,075,062 A 1/1963 Laccarino
3,078,465 A 2/1963 Bobrov
3,079,606 A 3/1963 Bobrov et al.
3,080,564 A 3/1963 Strekopitov et al.
3,166,072 A 1/1965 Sullivan, Jr.
3,180,236 A 4/1965 Beckett
3,196,869 A 7/1965 Scholl
3,204,731 A 9/1965 Bent et al.
3,252,643 A 5/1966 Strekopytov et al.
3,266,494 A 8/1966 Brownrigg et al.
3,269,630 A 8/1966 Fleischer
3,269,631 A 8/1966 Takaro
3,275,211 A 9/1966 Hirsch et al.
3,315,863 A 4/1967 O'Dea
3,317,103 A 5/1967 Cullen et al.
3,317,105 A 5/1967 Astafjev et al.
3,357,296 A 12/1967 Lefever
3,359,978 A 12/1967 Smith, Jr.
3,377,893 A 4/1968 Shorb
3,480,193 A 11/1969 Ralston
3,490,675 A 1/1970 Green et al.
3,494,533 A 2/1970 Green et al.
3,499,591 A 3/1970 Green
3,503,396 A 3/1970 Pierie et al.
3,509,629 A 5/1970 Kidokoro
3,551,987 A 1/1971 Wilkinson
3,568,675 A 3/1971 Harvey
3,572,159 A 3/1971 Tschanz
3,583,393 A 6/1971 Takahashi
3,589,589 A 6/1971 Akopov
3,598,943 A 8/1971 Barrett
3,604,561 A 9/1971 Mallina et al.
3,608,549 A 9/1971 Merrill
3,616,278 A 10/1971 Jansen
3,618,842 A 11/1971 Bryan
3,635,394 A 1/1972 Natelson
3,638,652 A 2/1972 Kelley
3,640,317 A 2/1972 Panfili
3,643,851 A 2/1972 Green et al.
3,650,453 A 3/1972 Smith, Jr.
3,661,339 A 5/1972 Shimizu
3,661,666 A 5/1972 Foster et al.
3,662,939 A 5/1972 Bryan
3,685,250 A 8/1972 Henry et al.
3,688,966 A 9/1972 Perkins et al.
3,692,224 A 9/1972 Astafiev et al.
3,695,646 A 10/1972 Mommsen
3,709,221 A 1/1973 Riely
3,717,294 A 2/1973 Green
3,724,237 A 4/1973 Wood
3,726,755 A 4/1973 Shannon
3,727,904 A 4/1973 Gabbey
3,734,207 A 5/1973 Fishbein
3,740,994 A 6/1973 De Carlo, Jr.
3,744,495 A 7/1973 Johnson
3,746,002 A 7/1973 Haller
3,747,603 A 7/1973 Adler
3,747,692 A 7/1973 Davidson
3,751,902 A 8/1973 Kingsbury et al.
3,752,161 A 8/1973 Bent
3,797,494 A 3/1974 Zaffaroni
3,799,151 A 3/1974 Fukaumi et al.
3,808,452 A 4/1974 Hutchinson
3,815,476 A 6/1974 Green et al.
3,819,100 A 6/1974 Noiles et al.
3,821,919 A 7/1974 Knohl
3,822,818 A 7/1974 Strekopytov et al.
3,825,007 A 7/1974 Rand
3,826,978 A 7/1974 Kelly
3,836,171 A 9/1974 Hayashi et al.
3,837,555 A 9/1974 Green
3,841,474 A 10/1974 Maier
3,851,196 A 11/1974 Hinds
3,863,639 A 2/1975 Kleaveland
3,863,940 A 2/1975 Cummings
3,883,624 A 5/1975 McKenzie et al.
3,885,491 A 5/1975 Curtis
3,887,393 A 6/1975 La Rue, Jr.
3,892,228 A 7/1975 Mitsui
3,894,174 A 7/1975 Cartun
3,899,829 A 8/1975 Storm et al.
3,902,247 A 9/1975 Fleer et al.
3,940,844 A 3/1976 Colby et al.
3,944,163 A 3/1976 Hayashi et al.
3,950,686 A 4/1976 Randall
3,952,747 A 4/1976 Kimmell, Jr.
3,955,581 A 5/1976 Spasiano et al.
3,959,879 A 6/1976 Sellers
RE28,932 E 8/1976 Noiles et al.
3,972,734 A 8/1976 King
3,973,179 A 8/1976 Weber et al.
3,981,051 A 9/1976 Brumlik
3,993,072 A 11/1976 Zaffaroni
3,999,110 A 12/1976 Ramstrom et al.
4,025,216 A 5/1977 Hives
4,027,746 A 6/1977 Kine
4,034,143 A 7/1977 Sweet
4,038,987 A 8/1977 Komiya
4,047,654 A 9/1977 Alvarado
4,054,108 A 10/1977 Gill
4,060,089 A 11/1977 Noiles
4,066,133 A 1/1978 Voss
4,085,337 A 4/1978 Moeller
4,100,820 A 7/1978 Evett
4,106,446 A 8/1978 Yamada et al.
4,106,620 A 8/1978 Brimmer et al.
4,108,211 A 8/1978 Tanaka
4,111,206 A 9/1978 Vishnevsky et al.
4,127,227 A 11/1978 Green
4,129,059 A 12/1978 Van Eck
4,132,146 A 1/1979 Uhlig
4,135,517 A 1/1979 Reale

(56) References Cited

U.S. PATENT DOCUMENTS 4,149,461 A 4/1979 Simeth
4,154,122 A 5/1979 Severin
4,160,857 A 7/1979 Nardella et al.
4,169,476 A 10/1979 Hiltebrandt
4,169,990 A 10/1979 Lerdman
4,180,285 A 12/1979 Reneau
4,185,701 A 1/1980 Boys
4,190,042 A 2/1980 Sinnreich
4,198,734 A 4/1980 Brumlik
4,198,982 A 4/1980 Fortner et al.
4,203,444 A 5/1980 Bonnell et al.
4,207,898 A 6/1980 Becht
4,213,562 A 7/1980 Garrett et al.
4,226,242 A 10/1980 Jarvik
4,239,431 A 12/1980 Davini
4,241,861 A 12/1980 Fleischer
4,244,372 A 1/1981 Kapitanov et al.
4,250,436 A 2/1981 Weissman
4,250,817 A 2/1981 Michel
4,261,244 A 4/1981 Becht et al.
4,272,002 A 6/1981 Moshofsky
4,272,662 A 6/1981 Simpson
4,274,304 A 6/1981 Curtiss
4,274,398 A 6/1981 Scott, Jr.
4,275,813 A 6/1981 Noiles
4,278,091 A 7/1981 Borzone
4,282,573 A 8/1981 Imai et al.
4,289,131 A 9/1981 Mueller
4,289,133 A 9/1981 Rothfuss
4,290,542 A 9/1981 Fedotov et al.
D261,356 S 10/1981 Robinson
4,293,604 A 10/1981 Campbell
4,296,654 A 10/1981 Mercer
4,296,881 A 10/1981 Lee
4,304,236 A 12/1981 Conta et al.
4,305,539 A 12/1981 Korolkov et al.
4,312,363 A 1/1982 Rothfuss et al.
4,312,685 A 1/1982 Riedl
4,317,451 A 3/1982 Cerwin et al.
4,319,576 A 3/1982 Rothfuss
4,321,002 A 3/1982 Froehlich
4,321,746 A 3/1982 Grinage
4,328,839 A 5/1982 Lyons et al.
4,331,277 A 5/1982 Green
4,340,331 A 7/1982 Savino
4,347,450 A 8/1982 Colligan
4,348,603 A 9/1982 Huber
4,349,028 A 9/1982 Green
4,350,151 A 9/1982 Scott
4,353,371 A 10/1982 Cosman
4,357,940 A 11/1982 Muller
4,361,057 A 11/1982 Kochera
4,366,544 A 12/1982 Shima et al.
4,369,013 A 1/1983 Abildgaard et al.
4,373,147 A 2/1983 Carlson, Jr.
4,376,380 A 3/1983 Burgess
4,379,457 A 4/1983 Gravener et al.
4,380,312 A 4/1983 Landrus
4,382,326 A 5/1983 Rabuse
4,383,634 A 5/1983 Green
4,389,963 A 6/1983 Pearson
4,393,728 A 7/1983 Larson et al.
4,394,613 A 7/1983 Cole
4,396,139 A 8/1983 Hall et al.
4,397,311 A 8/1983 Kanshin et al.
4,402,445 A 9/1983 Green
4,406,621 A 9/1983 Bailey
4,408,692 A 10/1983 Sigel et al.
4,409,057 A 10/1983 Molenda et al.
4,415,112 A 11/1983 Green
4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,523,707 A 6/1985 Blake, III et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.

(56) References Cited

U.S. PATENT DOCUMENTS

| | | | |
|---|---|---|---|
| 4,605,004 | A | 8/1986 | Di Giovanni et al. |
| 4,606,343 | A | 8/1986 | Conta et al. |
| 4,607,636 | A | 8/1986 | Kula et al. |
| 4,607,638 | A | 8/1986 | Crainich |
| 4,608,980 | A | 9/1986 | Aihara |
| 4,608,981 | A | 9/1986 | Rothfuss et al. |
| 4,610,250 | A | 9/1986 | Green |
| 4,610,383 | A | 9/1986 | Rothfuss et al. |
| 4,612,933 | A | 9/1986 | Brinkerhoff et al. |
| D286,180 | S | 10/1986 | Korthoff |
| D286,442 | S | 10/1986 | Korthoff et al. |
| 4,617,893 | A | 10/1986 | Donner et al. |
| 4,617,914 | A | 10/1986 | Ueda |
| 4,617,935 | A | 10/1986 | Cartmell et al. |
| 4,619,262 | A | 10/1986 | Taylor |
| 4,619,391 | A | 10/1986 | Sharkany et al. |
| 4,624,401 | A | 11/1986 | Gassner et al. |
| D287,278 | S | 12/1986 | Spreckelmeier |
| 4,628,459 | A | 12/1986 | Shinohara et al. |
| 4,628,636 | A | 12/1986 | Folger |
| 4,629,107 | A | 12/1986 | Fedotov et al. |
| 4,632,290 | A | 12/1986 | Green et al. |
| 4,633,861 | A | 1/1987 | Chow et al. |
| 4,633,874 | A | 1/1987 | Chow et al. |
| 4,634,419 | A | 1/1987 | Kreizman et al. |
| 4,635,638 | A | 1/1987 | Weintraub et al. |
| 4,641,076 | A | 2/1987 | Linden |
| 4,642,618 | A | 2/1987 | Johnson et al. |
| 4,642,738 | A | 2/1987 | Meller |
| 4,643,173 | A | 2/1987 | Bell et al. |
| 4,643,731 | A | 2/1987 | Eckenhoff |
| 4,646,722 | A | 3/1987 | Silverstein et al. |
| 4,646,745 | A | 3/1987 | Noiles |
| 4,651,734 | A | 3/1987 | Doss et al. |
| 4,652,820 | A | 3/1987 | Maresca |
| 4,654,028 | A | 3/1987 | Suma |
| 4,655,222 | A | 4/1987 | Florez et al. |
| 4,662,555 | A | 5/1987 | Thornton |
| 4,663,874 | A | 5/1987 | Sano et al. |
| 4,664,305 | A | 5/1987 | Blake, III et al. |
| 4,665,916 | A | 5/1987 | Green |
| 4,667,674 | A | 5/1987 | Korthoff et al. |
| 4,669,647 | A | 6/1987 | Storace |
| 4,671,278 | A | 6/1987 | Chin |
| 4,671,280 | A | 6/1987 | Dorband et al. |
| 4,671,445 | A | 6/1987 | Barker et al. |
| 4,672,964 | A | 6/1987 | Dee et al. |
| 4,675,944 | A | 6/1987 | Wells |
| 4,676,245 | A | 6/1987 | Fukuda |
| 4,679,460 | A | 7/1987 | Yoshigai |
| 4,679,719 | A | 7/1987 | Kramer |
| 4,684,051 | A | 8/1987 | Akopov et al. |
| 4,688,555 | A | 8/1987 | Wardle |
| 4,691,703 | A | 9/1987 | Auth et al. |
| 4,693,248 | A | 9/1987 | Failla |
| 4,698,579 | A | 10/1987 | Richter et al. |
| 4,700,703 | A | 10/1987 | Resnick et al. |
| 4,705,038 | A | 11/1987 | Sjostrom et al. |
| 4,708,141 | A | 11/1987 | Inoue et al. |
| 4,709,120 | A | 11/1987 | Pearson |
| 4,715,520 | A | 12/1987 | Roehr, Jr. et al. |
| 4,719,917 | A | 1/1988 | Barrows et al. |
| 4,721,099 | A | 1/1988 | Chikama |
| 4,722,340 | A | 2/1988 | Takayama et al. |
| 4,724,840 | A | 2/1988 | McVay et al. |
| 4,726,247 | A | 2/1988 | Hormann |
| 4,727,308 | A | 2/1988 | Huljak et al. |
| 4,728,020 | A | 3/1988 | Green et al. |
| 4,728,876 | A | 3/1988 | Mongeon et al. |
| 4,729,260 | A | 3/1988 | Dudden |
| 4,730,726 | A | 3/1988 | Holzwarth |
| 4,741,336 | A | 5/1988 | Failla et al. |
| 4,743,214 | A | 5/1988 | Tai-Cheng |
| 4,744,363 | A | 5/1988 | Hasson |
| 4,747,820 | A | 5/1988 | Hornlein et al. |
| 4,750,902 | A | 6/1988 | Wuchinich et al. |
| 4,752,024 | A | 6/1988 | Green et al. |
| 4,754,909 | A | 7/1988 | Barker et al. |
| 4,755,070 | A | 7/1988 | Cerutti |
| 4,761,326 | A | 8/1988 | Barnes et al. |
| 4,763,669 | A | 8/1988 | Jaeger |
| 4,767,044 | A | 8/1988 | Green |
| D297,764 | S | 9/1988 | Hunt et al. |
| 4,773,420 | A | 9/1988 | Green |
| 4,777,780 | A | 10/1988 | Holzwarth |
| 4,781,186 | A | 11/1988 | Simpson et al. |
| 4,784,137 | A | 11/1988 | Kulik et al. |
| 4,787,387 | A | 11/1988 | Burbank, III et al. |
| 4,788,485 | A | 11/1988 | Kawagishi et al. |
| D298,967 | S | 12/1988 | Hunt |
| 4,788,978 | A | 12/1988 | Strekopytov et al. |
| 4,790,225 | A | 12/1988 | Moody et al. |
| 4,790,314 | A | 12/1988 | Weaver |
| 4,805,617 | A | 2/1989 | Bedi et al. |
| 4,805,823 | A | 2/1989 | Rothfuss |
| 4,807,628 | A | 2/1989 | Peters et al. |
| 4,809,695 | A | 3/1989 | Gwathmey et al. |
| 4,815,460 | A | 3/1989 | Porat et al. |
| 4,817,643 | A | 4/1989 | Olson |
| 4,817,847 | A | 4/1989 | Redtenbacher et al. |
| 4,819,495 | A | 4/1989 | Hormann |
| 4,819,853 | A | 4/1989 | Green |
| 4,821,939 | A | 4/1989 | Green |
| 4,827,552 | A | 5/1989 | Bojar et al. |
| 4,827,911 | A | 5/1989 | Broadwin et al. |
| 4,828,542 | A | 5/1989 | Hermann |
| 4,828,944 | A | 5/1989 | Yabe et al. |
| 4,830,855 | A | 5/1989 | Stewart |
| 4,832,158 | A | 5/1989 | Farrar et al. |
| 4,833,937 | A | 5/1989 | Nagano |
| 4,834,096 | A | 5/1989 | Oh et al. |
| 4,834,720 | A | 5/1989 | Blinkhorn |
| 4,838,859 | A | 6/1989 | Strassmann |
| 4,844,068 | A | 7/1989 | Arata et al. |
| 4,848,637 | A | 7/1989 | Pruitt |
| 4,856,078 | A | 8/1989 | Konopka |
| 4,860,644 | A | 8/1989 | Kohl et al. |
| 4,862,891 | A | 9/1989 | Smith |
| 4,863,423 | A | 9/1989 | Wallace |
| 4,865,030 | A | 9/1989 | Polyak |
| 4,868,530 | A | 9/1989 | Ahs |
| 4,868,958 | A | 9/1989 | Suzuki et al. |
| 4,869,414 | A | 9/1989 | Green et al. |
| 4,869,415 | A | 9/1989 | Fox |
| 4,873,977 | A | 10/1989 | Avant et al. |
| 4,875,486 | A | 10/1989 | Rapoport et al. |
| 4,880,015 | A | 11/1989 | Nierman |
| 4,890,613 | A | 1/1990 | Golden et al. |
| 4,892,244 | A | 1/1990 | Fox et al. |
| 4,893,622 | A | 1/1990 | Green et al. |
| 4,894,051 | A | 1/1990 | Shiber |
| 4,896,584 | A | 1/1990 | Stoll et al. |
| 4,896,678 | A | 1/1990 | Ogawa |
| 4,900,303 | A | 2/1990 | Lemelson |
| 4,903,697 | A | 2/1990 | Resnick et al. |
| 4,909,789 | A | 3/1990 | Taguchi et al. |
| 4,915,100 | A | 4/1990 | Green |
| 4,919,679 | A | 4/1990 | Averill et al. |
| 4,921,479 | A | 5/1990 | Grayzel |
| 4,925,082 | A | 5/1990 | Kim |
| 4,928,699 | A | 5/1990 | Sasai |
| 4,930,503 | A | 6/1990 | Pruitt |
| 4,930,674 | A | 6/1990 | Barak |
| 4,931,047 | A | 6/1990 | Broadwin et al. |
| 4,931,737 | A | 6/1990 | Hishiki |
| 4,932,960 | A | 6/1990 | Green et al. |
| 4,933,800 | A | 6/1990 | Yang |
| 4,933,843 | A | 6/1990 | Scheller et al. |
| D309,350 | S | 7/1990 | Sutherland et al. |
| 4,938,408 | A | 7/1990 | Bedi et al. |
| 4,941,623 | A | 7/1990 | Pruitt |
| 4,943,182 | A | 7/1990 | Hoblingre |
| 4,944,443 | A | 7/1990 | Oddsen et al. |
| 4,946,067 | A | 8/1990 | Kelsall |

(56) References Cited

U.S. PATENT DOCUMENTS 4,948,327 A 8/1990 Crupi, Jr.
4,949,707 A 8/1990 Levahn et al.
4,949,927 A 8/1990 Madocks et al.
4,950,268 A 8/1990 Rink
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,222 A 4/1991 Her
5,009,661 A 4/1991 Michelson
5,012,411 A 4/1991 Policastro et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,019,077 A 5/1991 De Bastiani et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,100,422 A 3/1992 Berguer et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,129,570 A 7/1992 Schulze et al.
5,137,198 A 8/1992 Nobis et al.
5,139,513 A 8/1992 Segato
5,141,144 A 8/1992 Foslien et al.
5,142,932 A 9/1992 Moya et al.
5,151,102 A 9/1992 Kamiyama et al.
5,155,941 A 10/1992 Takahashi et al.
5,156,151 A 10/1992 Imran
5,156,315 A 10/1992 Green et al.
5,156,609 A 10/1992 Nakao et al.
5,156,614 A 10/1992 Green et al.
5,158,222 A 10/1992 Green et al.
5,158,567 A 10/1992 Green
D330,699 S 11/1992 Gill
5,163,598 A 11/1992 Peters et al.
5,163,842 A 11/1992 Nonomura
5,164,652 A 11/1992 Johnson et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.
5,176,677 A 1/1993 Wuchinich
5,176,688 A 1/1993 Narayan et al.
5,181,514 A 1/1993 Solomon et al.
5,187,422 A 2/1993 Izenbaard et al.
5,188,102 A 2/1993 Idemoto et al.
5,188,111 A 2/1993 Yates et al.
5,188,126 A 2/1993 Fabian et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
D338,729 S 8/1993 Sprecklemeier et al.
5,234,447 A 8/1993 Kaster et al.

(56) References Cited

U.S. PATENT DOCUMENTS 5,236,269 A 8/1993 Handy
5,236,424 A 8/1993 Imran
5,236,440 A 8/1993 Hlavacek
5,236,629 A 8/1993 Mahabadi et al.
5,239,981 A 8/1993 Anapliotis
5,240,163 A 8/1993 Stein et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,251,801 A 10/1993 Ruckdeschel et al.
5,253,793 A 10/1993 Green et al.
5,258,007 A 11/1993 Spetzler et al.
5,258,008 A 11/1993 Wilk
5,258,009 A 11/1993 Conners
5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.
5,263,937 A 11/1993 Shipp
5,263,973 A 11/1993 Cook
5,264,218 A 11/1993 Rogozinski
5,268,622 A 12/1993 Philipp
5,269,794 A 12/1993 Rexroth
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,281,400 A 1/1994 Berry, Jr.
5,282,806 A 2/1994 Haber et al.
5,282,826 A 2/1994 Quadri
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,310 A 3/1994 Makower et al.
5,291,133 A 3/1994 Gokhale et al.
5,292,053 A 3/1994 Bilotti et al.
5,293,024 A 3/1994 Sugahara et al.
5,297,714 A 3/1994 Kramer
5,300,087 A 4/1994 Knoepfler
5,302,148 A 4/1994 Heinz
5,303,606 A 4/1994 Kokinda
5,304,204 A 4/1994 Bregen
D347,474 S 5/1994 Olson
5,307,976 A 5/1994 Olson et al.
5,308,353 A 5/1994 Beurrier
5,308,358 A 5/1994 Bond et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,935 A 5/1994 Kortenbach et al.
5,313,967 A 5/1994 Lieber et al.
5,314,424 A 5/1994 Nicholas
5,314,445 A 5/1994 Heidmueller nee Degwitz et al.
5,314,466 A 5/1994 Stern et al.
5,318,221 A 6/1994 Green et al.
5,318,589 A 6/1994 Lichtman
5,320,627 A 6/1994 Sorensen et al.
D348,930 S 7/1994 Olson
5,326,013 A 7/1994 Green et al.
5,329,923 A 7/1994 Lundquist
5,330,486 A 7/1994 Wilk
5,330,487 A 7/1994 Thornton et al.
5,330,502 A 7/1994 Hassler et al.
5,331,971 A 7/1994 Bales et al.
5,332,142 A 7/1994 Robinson et al.
5,333,422 A 8/1994 Warren et al.
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,338,317 A 8/1994 Hasson et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,454 A 9/1994 Clarke et al.
5,346,504 A 9/1994 Ortiz et al.
5,348,259 A 9/1994 Blanco et al.
5,350,104 A 9/1994 Main et al.
5,350,355 A 9/1994 Sklar
5,350,388 A 9/1994 Epstein
5,350,391 A 9/1994 Iacovelli
5,350,400 A 9/1994 Esposito et al.
5,352,229 A 10/1994 Goble et al.
5,352,235 A 10/1994 Koros et al.
5,352,238 A 10/1994 Green et al.
5,353,798 A 10/1994 Sieben
5,354,215 A 10/1994 Viracola
5,354,250 A 10/1994 Christensen
5,354,303 A 10/1994 Spaeth et al.
5,355,897 A 10/1994 Pietrafitta et al.
5,356,006 A 10/1994 Alpern et al.
5,356,064 A 10/1994 Green et al.
5,358,506 A 10/1994 Green et al.
5,358,510 A 10/1994 Luscombe et al.
5,359,231 A 10/1994 Flowers et al.
D352,780 S 11/1994 Glaeser et al.
5,359,993 A 11/1994 Slater et al.
5,360,305 A 11/1994 Kerrigan
5,360,428 A 11/1994 Hutchinson, Jr.
5,361,902 A 11/1994 Abidin et al.
5,364,001 A 11/1994 Bryan
5,364,002 A 11/1994 Green et al.
5,364,003 A 11/1994 Williamson, IV
5,366,133 A 11/1994 Geiste
5,366,134 A 11/1994 Green et al.
5,366,479 A 11/1994 McGarry et al.
5,368,015 A 11/1994 Wilk
5,368,592 A 11/1994 Stern et al.
5,368,599 A 11/1994 Hirsch et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,738 A 1/1995 Herbermann

(56) References Cited

U.S. PATENT DOCUMENTS 5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,389,072 A 2/1995 Imran
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,645 A 7/1995 Smith et al.
5,431,654 A 7/1995 Nic
5,431,666 A 7/1995 Sauer et al.
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,824 A 10/1995 Fontayne et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,308 A 12/1995 Cartmell et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,377 A 1/1996 Smith et al.
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 Defonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.

(56) References Cited

U.S. PATENT DOCUMENTS

| | | | |
|---|---|---|---|
| 5,503,638 | A | 4/1996 | Cooper et al. |
| 5,505,363 | A | 4/1996 | Green et al. |
| 5,507,425 | A | 4/1996 | Ziglioli |
| 5,507,426 | A | 4/1996 | Young et al. |
| 5,507,773 | A | 4/1996 | Huitema et al. |
| 5,509,596 | A | 4/1996 | Green et al. |
| 5,509,916 | A | 4/1996 | Taylor |
| 5,509,918 | A | 4/1996 | Romano |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,694 | A | 10/1996 | Sauer et al. |
| 5,562,701 | A | 10/1996 | Huitema et al. |
| 5,562,702 | A | 10/1996 | Huitema et al. |
| 5,563,481 | A | 10/1996 | Krause |
| 5,564,615 | A | 10/1996 | Bishop et al. |
| 5,569,161 | A | 10/1996 | Ebling et al. |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,285 | A | 11/1996 | Chow et al. |
| 5,571,488 | A | 11/1996 | Beerstecher et al. |
| 5,573,169 | A | 11/1996 | Green et al. |
| 5,573,543 | A | 11/1996 | Akopov et al. |
| 5,574,431 | A | 11/1996 | McKeown et al. |
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,279 | A | 2/1997 | Slotman et al. |
| 5,599,344 | A | 2/1997 | Paterson |
| 5,599,350 | A | 2/1997 | Schulze et al. |
| 5,599,852 | A | 2/1997 | Scopelianos et al. |
| 5,601,224 | A | 2/1997 | Bishop et al. |
| 5,601,573 | A | 2/1997 | Fogelberg et al. |
| 5,601,604 | A | 2/1997 | Vincent |
| 5,602,449 | A | 2/1997 | Krause et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,303 | A | 3/1997 | Nakamura |
| 5,607,433 | A | 3/1997 | Polla et al. |
| 5,607,436 | A | 3/1997 | Pratt et al. |
| 5,607,450 | A | 3/1997 | Zvenyatsky et al. |
| 5,607,474 | A | 3/1997 | Athanasiou et al. |
| 5,609,285 | A | 3/1997 | Grant et al. |
| 5,609,601 | A | 3/1997 | Kolesa et al. |
| 5,611,709 | A | 3/1997 | McAnulty |
| 5,611,813 | A | 3/1997 | Lichtman |
| 5,613,499 | A | 3/1997 | Palmer et al. |
| 5,613,937 | A | 3/1997 | Garrison et al. |
| 5,613,966 | A | 3/1997 | Makower et al. |
| 5,614,887 | A | 3/1997 | Buchbinder |
| 5,615,820 | A | 4/1997 | Viola |
| 5,618,294 | A | 4/1997 | Aust et al. |
| 5,618,303 | A | 4/1997 | Marlow et al. |
| 5,618,307 | A | 4/1997 | Donlon et al. |
| 5,619,992 | A | 4/1997 | Guthrie et al. |
| 5,620,289 | A | 4/1997 | Curry |
| 5,620,326 | A | 4/1997 | Younker |
| 5,620,452 | A | 4/1997 | Yoon |
| 5,624,398 | A | 4/1997 | Smith et al. |
| 5,624,452 | A | 4/1997 | Yates |
| 5,626,587 | A | 5/1997 | Bishop et al. |
| 5,626,595 | A | 5/1997 | Sklar et al. |
| 5,626,979 | A | 5/1997 | Mitsui et al. |
| 5,628,446 | A | 5/1997 | Geiste et al. |
| 5,628,743 | A | 5/1997 | Cimino |
| 5,628,745 | A | 5/1997 | Bek |
| 5,630,539 | A | 5/1997 | Plyley et al. |
| 5,630,540 | A | 5/1997 | Blewett |
| 5,630,541 | A | 5/1997 | Williamson, IV et al. |
| 5,630,782 | A | 5/1997 | Adair |
| 5,631,973 | A | 5/1997 | Green |
| 5,632,432 | A | 5/1997 | Schulze et al. |
| 5,632,433 | A | 5/1997 | Grant et al. |

(56) References Cited

U.S. PATENT DOCUMENTS 5,633,374 A 5/1997 Humphrey et al.
5,634,584 A 6/1997 Okorocha et al.
5,636,779 A 6/1997 Palmer
5,636,780 A 6/1997 Green et al.
5,637,110 A 6/1997 Pennybacker et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,656,917 A 8/1997 Theobald
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,683,432 A 11/1997 Goedeke et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,265 A 12/1997 Romano
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,704,792 A 1/1998 Sobhani
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,712 A 3/1998 Adair
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,736,271 A 4/1998 Cisar et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,746,770 A 5/1998 Zeitels et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,752,973 A 5/1998 Kieturakis
5,755,717 A 5/1998 Yates et al.
5,755,726 A 5/1998 Pratt et al.
5,758,814 A 6/1998 Gallagher et al.
5,762,255 A 6/1998 Chrisman et al.
5,762,256 A 6/1998 Mastri et al.
5,762,458 A 6/1998 Wang et al.
5,765,565 A 6/1998 Adair
5,766,186 A 6/1998 Faraz et al.

(56) References Cited

U.S. PATENT DOCUMENTS 5,766,188 A 6/1998 Igaki
5,766,205 A 6/1998 Zvenyatsky et al.
5,769,303 A 6/1998 Knodel et al.
5,769,640 A 6/1998 Jacobus et al.
5,769,748 A 6/1998 Eyerly et al.
5,769,791 A 6/1998 Benaron et al.
5,769,892 A 6/1998 Kingwell
5,772,099 A 6/1998 Gravener
5,772,379 A 6/1998 Evensen
5,772,578 A 6/1998 Heimberger et al.
5,772,659 A 6/1998 Becker et al.
5,773,991 A 6/1998 Chen
5,776,130 A 7/1998 Buysse et al.
5,778,939 A 7/1998 Hok-Yin
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,782,748 A 7/1998 Palmer et al.
5,782,749 A 7/1998 Riza
5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,162 A 8/1998 Jolly et al.
5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,798,752 A 8/1998 Buxton et al.
5,799,857 A 9/1998 Robertson et al.
5,800,379 A 9/1998 Edwards
5,800,423 A 9/1998 Jensen
5,804,726 A 9/1998 Geib et al.
5,804,936 A 9/1998 Brodsky et al.
5,806,676 A 9/1998 Wasgien
5,807,241 A 9/1998 Heimberger
5,807,376 A 9/1998 Viola et al.
5,807,378 A 9/1998 Jensen et al.
5,807,393 A 9/1998 Williamson, IV et al.
5,809,441 A 9/1998 McKee
5,810,240 A 9/1998 Robertson
5,810,721 A 9/1998 Mueller et al.
5,810,811 A 9/1998 Yates et al.
5,810,846 A 9/1998 Virnich et al.
5,810,855 A 9/1998 Rayburn et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,827,323 A 10/1998 Klieman et al.
5,829,662 A 11/1998 Allen et al.
5,830,598 A 11/1998 Patterson
5,833,690 A 11/1998 Yates et al.
5,833,695 A 11/1998 Yoon
5,833,696 A 11/1998 Whitfield et al.
5,836,503 A 11/1998 Ehrenfels et al.
5,836,960 A 11/1998 Kolesa et al.
5,839,369 A 11/1998 Chatterjee et al.
5,839,639 A 11/1998 Sauer et al.
5,841,284 A 11/1998 Takahashi
5,843,021 A 12/1998 Edwards et al.
5,843,096 A 12/1998 Igaki et al.
5,843,097 A 12/1998 Mayenberger et al.
5,843,122 A 12/1998 Riza
5,843,132 A 12/1998 Ilvento
5,843,169 A 12/1998 Taheri
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi
5,855,311 A 1/1999 Hamblin et al.
5,855,583 A 1/1999 Wang et al.
5,860,581 A 1/1999 Robertson et al.
5,860,975 A 1/1999 Goble et al.
5,865,361 A 2/1999 Milliman et al.
5,865,638 A 2/1999 Trafton
5,868,361 A 2/1999 Rinderer
5,868,664 A 2/1999 Speier et al.
5,868,760 A 2/1999 McGuckin, Jr.
5,868,790 A 2/1999 Vincent et al.
5,871,135 A 2/1999 Williamson, IV et al.
5,873,885 A 2/1999 Weidenbenner
5,876,401 A 3/1999 Schulze et al.
5,878,193 A 3/1999 Wang et al.
5,878,607 A 3/1999 Nunes et al.
5,878,937 A 3/1999 Green et al.
5,878,938 A 3/1999 Bittner et al.
5,881,777 A 3/1999 Bassi et al.
5,881,943 A 3/1999 Heck et al.
5,891,094 A 4/1999 Masterson et al.
5,891,160 A 4/1999 Williamson, IV et al.
5,891,558 A 4/1999 Bell et al.
5,893,506 A 4/1999 Powell
5,893,835 A 4/1999 Witt et al.
5,893,855 A 4/1999 Jacobs
5,893,863 A 4/1999 Yoon
5,893,878 A 4/1999 Pierce
5,894,979 A 4/1999 Powell
5,897,552 A 4/1999 Edwards et al.
5,897,562 A 4/1999 Bolanos et al.
5,899,824 A 5/1999 Kurtz et al.
5,899,914 A 5/1999 Zirps et al.
5,901,895 A 5/1999 Heaton et al.
5,902,312 A 5/1999 Frater et al.
5,903,117 A 5/1999 Gregory
5,904,647 A 5/1999 Ouchi
5,904,693 A 5/1999 Dicesare et al.
5,904,702 A 5/1999 Ek et al.
5,906,577 A 5/1999 Beane et al.
5,906,625 A 5/1999 Bito et al.
5,907,211 A 5/1999 Hall et al.
5,907,664 A 5/1999 Wang et al.
5,908,149 A 6/1999 Welch et al.
5,908,402 A 6/1999 Blythe
5,908,427 A 6/1999 McKean et al.
5,909,062 A 6/1999 Krietzman
5,911,353 A 6/1999 Bolanos et al.
5,915,616 A 6/1999 Viola et al.
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,922,001 A 7/1999 Yoon
5,922,003 A 7/1999 Anctil et al.

(56) References Cited

U.S. PATENT DOCUMENTS

| | | | |
|---|---|---|---|
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,980,569 | A | 11/1999 | Scirica |
| 5,984,949 | A | 11/1999 | Levin |
| 5,988,479 | A | 11/1999 | Palmer |
| 5,990,379 | A | 11/1999 | Gregory |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |
| 6,013,076 | A | 1/2000 | Goble et al. |
| 6,013,991 | A | 1/2000 | Philipp |
| 6,015,406 | A | 1/2000 | Goble et al. |
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,019,780 | A | 2/2000 | Lombardo et al. |
| 6,022,352 | A | 2/2000 | Vandewalle |
| 6,023,275 | A | 2/2000 | Horvitz et al. |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |
| 6,027,501 | A | 2/2000 | Goble et al. |
| 6,030,384 | A | 2/2000 | Nezhat |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,126 | A | 3/2000 | Hsieh |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |
| 6,045,560 | A | 4/2000 | McKean et al. |
| 6,047,861 | A | 4/2000 | Vidal et al. |
| 6,049,145 | A | 4/2000 | Austin et al. |
| 6,050,172 | A | 4/2000 | Corves et al. |
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |
| 6,053,390 | A | 4/2000 | Green et al. |
| 6,053,899 | A | 4/2000 | Slanda et al. |
| 6,053,922 | A | 4/2000 | Krause et al. |
| 6,054,142 | A | 4/2000 | Li et al. |
| 6,055,062 | A | 4/2000 | Dina et al. |
| RE36,720 | E | 5/2000 | Green et al. |
| 6,056,735 | A | 5/2000 | Okada et al. |
| 6,056,746 | A | 5/2000 | Goble et al. |
| 6,059,806 | A | 5/2000 | Hoegerle |
| 6,062,360 | A | 5/2000 | Shields |
| 6,063,020 | A | 5/2000 | Jones et al. |
| 6,063,025 | A | 5/2000 | Bridges et al. |
| 6,063,050 | A | 5/2000 | Manna et al. |
| 6,063,095 | A | 5/2000 | Wang et al. |
| 6,063,097 | A | 5/2000 | Oi et al. |
| 6,063,098 | A | 5/2000 | Houser et al. |
| 6,065,679 | A | 5/2000 | Levie et al. |
| 6,065,919 | A | 5/2000 | Peck |
| 6,066,132 | A | 5/2000 | Chen et al. |
| 6,066,151 | A | 5/2000 | Miyawaki et al. |
| 6,068,627 | A | 5/2000 | Orszulak et al. |
| 6,071,233 | A | 6/2000 | Ishikawa et al. |
| 6,072,299 | A | 6/2000 | Kurle et al. |
| 6,074,386 | A | 6/2000 | Goble et al. |
| 6,074,401 | A | 6/2000 | Gardiner et al. |
| 6,075,441 | A | 6/2000 | Maloney |
| 6,077,280 | A | 6/2000 | Fossum |
| 6,077,286 | A | 6/2000 | Cuschieri et al. |
| 6,077,290 | A | 6/2000 | Marini |
| 6,079,606 | A | 6/2000 | Milliman et al. |
| 6,080,181 | A | 6/2000 | Jensen et al. |
| 6,082,577 | A | 7/2000 | Coates et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,600 | A | 7/2000 | Kortenbach |
| 6,090,106 | A | 7/2000 | Goble et al. |
| 6,090,123 | A | 7/2000 | Culp et al. |
| 6,093,186 | A | 7/2000 | Goble |
| 6,094,021 | A | 7/2000 | Noro et al. |
| D429,252 | S | 8/2000 | Haitani et al. |
| 6,099,537 | A | 8/2000 | Sugai et al. |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,701 | A | 9/2000 | Nezhat |
| H1904 | H | 10/2000 | Yates et al. |
| RE36,923 | E | 10/2000 | Hiroi et al. |

(56) References Cited

U.S. PATENT DOCUMENTS

| | | | |
|---|---|---|---|
| 6,126,058 | A | 10/2000 | Adams et al. |
| 6,126,359 | A | 10/2000 | Dittrich et al. |
| 6,126,670 | A | 10/2000 | Walker et al. |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,546 | A | 10/2000 | Koenig et al. |
| 6,142,149 | A | 11/2000 | Steen |
| 6,142,933 | A | 11/2000 | Longo et al. |
| 6,147,135 | A | 11/2000 | Yuan et al. |
| 6,149,660 | A | 11/2000 | Laufer et al. |
| 6,151,323 | A | 11/2000 | O'Connell et al. |
| 6,152,935 | A | 11/2000 | Kammerer et al. |
| 6,155,473 | A | 12/2000 | Tompkins et al. |
| 6,156,056 | A | 12/2000 | Kearns et al. |
| 6,157,169 | A | 12/2000 | Lee |
| 6,159,146 | A | 12/2000 | El Gazayerli |
| 6,159,200 | A | 12/2000 | Verdura et al. |
| 6,159,224 | A | 12/2000 | Yoon |
| 6,162,208 | A | 12/2000 | Hipps |
| 6,162,220 | A | 12/2000 | Nezhat |
| 6,162,537 | A | 12/2000 | Martin et al. |
| 6,165,175 | A | 12/2000 | Wampler et al. |
| 6,165,184 | A | 12/2000 | Verdura et al. |
| 6,165,188 | A | 12/2000 | Saadat et al. |
| 6,167,185 | A | 12/2000 | Smiley et al. |
| 6,168,605 | B1 | 1/2001 | Measamer et al. |
| 6,171,305 | B1 | 1/2001 | Sherman |
| 6,171,316 | B1 | 1/2001 | Kovac et al. |
| 6,171,330 | B1 | 1/2001 | Benchetrit |
| 6,173,074 | B1 | 1/2001 | Russo |
| 6,174,308 | B1 | 1/2001 | Goble et al. |
| 6,174,309 | B1 | 1/2001 | Wrublewski et al. |
| 6,174,318 | B1 | 1/2001 | Bates et al. |
| 6,175,290 | B1 | 1/2001 | Forsythe et al. |
| 6,179,195 | B1 | 1/2001 | Adams et al. |
| 6,179,776 | B1 | 1/2001 | Adams et al. |
| 6,181,105 | B1 | 1/2001 | Cutolo et al. |
| 6,182,673 | B1 | 2/2001 | Kindermann et al. |
| 6,185,356 | B1 | 2/2001 | Parker et al. |
| 6,186,142 | B1 | 2/2001 | Schmidt et al. |
| 6,186,957 | B1 | 2/2001 | Milam |
| 6,187,003 | B1 | 2/2001 | Buysse et al. |
| 6,190,386 | B1 | 2/2001 | Rydell |
| 6,193,129 | B1 | 2/2001 | Bittner et al. |
| 6,197,042 | B1 | 3/2001 | Ginn et al. |
| 6,200,311 | B1 | 3/2001 | Danek et al. |
| 6,200,330 | B1 | 3/2001 | Benderev et al. |
| 6,202,914 | B1 | 3/2001 | Geiste et al. |
| 6,206,894 | B1 | 3/2001 | Thompson et al. |
| 6,206,897 | B1 | 3/2001 | Jamiolkowski et al. |
| 6,206,903 | B1 | 3/2001 | Ramans |
| 6,206,904 | B1 | 3/2001 | Ouchi |
| 6,209,414 | B1 | 4/2001 | Uneme |
| 6,210,403 | B1 | 4/2001 | Klicek |
| 6,211,626 | B1 | 4/2001 | Lys et al. |
| 6,213,999 | B1 | 4/2001 | Platt, Jr. et al. |
| 6,214,028 | B1 | 4/2001 | Yoon et al. |
| 6,220,368 | B1 | 4/2001 | Ark et al. |
| 6,221,007 | B1 | 4/2001 | Green |
| 6,221,023 | B1 | 4/2001 | Matsuba et al. |
| 6,223,100 | B1 | 4/2001 | Green |
| 6,223,835 | B1 | 5/2001 | Habedank et al. |
| 6,224,617 | B1 | 5/2001 | Saadat et al. |
| 6,228,080 | B1 | 5/2001 | Gines |
| 6,228,081 | B1 | 5/2001 | Goble |
| 6,228,083 | B1 | 5/2001 | Lands et al. |
| 6,228,084 | B1 | 5/2001 | Kirwan, Jr. |
| 6,228,089 | B1 | 5/2001 | Wahrburg |
| 6,228,098 | B1 | 5/2001 | Kayan et al. |
| 6,231,565 | B1 | 5/2001 | Tovey et al. |
| 6,234,178 | B1 | 5/2001 | Goble et al. |
| 6,235,036 | B1 | 5/2001 | Gardner et al. |
| 6,237,604 | B1 | 5/2001 | Burnside et al. |
| 6,238,384 | B1 | 5/2001 | Peer |
| 6,241,139 | B1 | 6/2001 | Milliman et al. |
| 6,241,140 | B1 | 6/2001 | Adams et al. |
| 6,241,723 | B1 | 6/2001 | Heim et al. |
| 6,245,084 | B1 | 6/2001 | Mark et al. |
| 6,248,116 | B1 | 6/2001 | Chevillon et al. |
| 6,248,117 | B1 | 6/2001 | Blatter |
| 6,249,076 | B1 | 6/2001 | Madden et al. |
| 6,249,105 | B1 | 6/2001 | Andrews et al. |
| 6,250,532 | B1 | 6/2001 | Green et al. |
| 6,251,485 | B1 | 6/2001 | Harris et al. |
| D445,745 | S | 7/2001 | Norman |
| 6,254,534 | B1 | 7/2001 | Butler et al. |
| 6,254,619 | B1 | 7/2001 | Garabet et al. |
| 6,254,642 | B1 | 7/2001 | Taylor |
| 6,258,107 | B1 | 7/2001 | Balazs et al. |
| 6,261,246 | B1 | 7/2001 | Pantages et al. |
| 6,261,286 | B1 | 7/2001 | Goble et al. |
| 6,261,679 | B1 | 7/2001 | Chen et al. |
| 6,264,086 | B1 | 7/2001 | McGuckin, Jr. |
| 6,264,087 | B1 | 7/2001 | Whitman |
| 6,264,617 | B1 | 7/2001 | Bales et al. |
| 6,269,997 | B1 | 8/2001 | Balazs et al. |
| 6,270,508 | B1 | 8/2001 | Klieman et al. |
| 6,270,916 | B1 | 8/2001 | Sink et al. |
| 6,273,252 | B1 | 8/2001 | Mitchell |
| 6,273,876 | B1 | 8/2001 | Klima et al. |
| 6,273,897 | B1 | 8/2001 | Dalessandro et al. |
| 6,277,114 | B1 | 8/2001 | Bullivant et al. |
| 6,280,407 | B1 | 8/2001 | Manna et al. |
| 6,283,981 | B1 | 9/2001 | Beaupre |
| 6,293,927 | B1 | 9/2001 | McGuckin, Jr. |
| 6,293,942 | B1 | 9/2001 | Goble et al. |
| 6,296,640 | B1 | 10/2001 | Wampler et al. |
| 6,302,311 | B1 | 10/2001 | Adams et al. |
| 6,302,743 | B1 | 10/2001 | Chiu et al. |
| 6,305,891 | B1 | 10/2001 | Burlingame |
| 6,306,134 | B1 | 10/2001 | Goble et al. |
| 6,306,149 | B1 | 10/2001 | Meade |
| 6,306,424 | B1 | 10/2001 | Vyakarnam et al. |
| 6,309,397 | B1 | 10/2001 | Julian et al. |
| 6,309,400 | B2 | 10/2001 | Beaupre |
| 6,309,403 | B1 | 10/2001 | Minor et al. |
| 6,312,435 | B1 | 11/2001 | Wallace et al. |
| 6,315,184 | B1 | 11/2001 | Whitman |
| 6,317,616 | B1 | 11/2001 | Glossop |
| 6,319,510 | B1 | 11/2001 | Yates |
| 6,320,123 | B1 | 11/2001 | Reimers |
| 6,322,494 | B1 | 11/2001 | Bullivant et al. |
| 6,324,339 | B1 | 11/2001 | Hudson et al. |
| 6,325,799 | B1 | 12/2001 | Goble |
| 6,325,805 | B1 | 12/2001 | Ogilvie et al. |
| 6,325,810 | B1 | 12/2001 | Hamilton et al. |
| 6,328,498 | B1 | 12/2001 | Mersch |
| 6,330,965 | B1 | 12/2001 | Milliman et al. |
| 6,331,181 | B1 | 12/2001 | Tierney et al. |
| 6,331,761 | B1 | 12/2001 | Kumar et al. |
| 6,333,029 | B1 | 12/2001 | Vyakarnam et al. |
| 6,334,860 | B1 | 1/2002 | Dorn |
| 6,334,861 | B1 | 1/2002 | Chandler et al. |
| 6,336,926 | B1 | 1/2002 | Goble |
| 6,338,737 | B1 | 1/2002 | Toledano |
| 6,338,738 | B1 | 1/2002 | Bellotti et al. |
| 6,343,731 | B1 | 2/2002 | Adams et al. |
| 6,346,077 | B1 | 2/2002 | Taylor et al. |
| 6,348,061 | B1 | 2/2002 | Whitman |
| 6,349,868 | B1 | 2/2002 | Mattingly et al. |
| D454,951 | S | 3/2002 | Bon |
| 6,352,503 | B1 | 3/2002 | Matsui et al. |
| 6,352,532 | B1 | 3/2002 | Kramer et al. |
| 6,355,699 | B1 | 3/2002 | Vyakarnam et al. |
| 6,356,072 | B1 | 3/2002 | Chass |
| 6,358,224 | B1 | 3/2002 | Tims et al. |
| 6,358,263 | B2 | 3/2002 | Mark et al. |
| 6,358,459 | B1 | 3/2002 | Ziegler et al. |
| 6,361,542 | B1 | 3/2002 | Dimitriu et al. |
| 6,364,828 | B1 | 4/2002 | Yeung et al. |
| 6,364,877 | B1 | 4/2002 | Goble et al. |
| 6,364,888 | B1 | 4/2002 | Niemeyer et al. |

(56) References Cited

U.S. PATENT DOCUMENTS

| | | | |
|---|---|---|---|
| 6,366,441 | B1 | 4/2002 | Ozawa et al. |
| 6,370,981 | B2 | 4/2002 | Watarai |
| 6,371,114 | B1 | 4/2002 | Schmidt et al. |
| 6,373,152 | B1 | 4/2002 | Wang et al. |
| 6,377,011 | B1 | 4/2002 | Ben-Ur |
| 6,383,201 | B1 | 5/2002 | Dong |
| 6,387,092 | B1 | 5/2002 | Burnside et al. |
| 6,387,113 | B1 | 5/2002 | Hawkins et al. |
| 6,387,114 | B2 | 5/2002 | Adams |
| 6,391,038 | B2 | 5/2002 | Vargas et al. |
| 6,392,854 | B1 | 5/2002 | O'Gorman |
| 6,394,998 | B1 | 5/2002 | Wallace et al. |
| 6,398,779 | B1 | 6/2002 | Buysse et al. |
| 6,398,781 | B1 | 6/2002 | Goble et al. |
| 6,398,797 | B2 | 6/2002 | Bombard et al. |
| 6,402,766 | B2 | 6/2002 | Bowman et al. |
| 6,402,780 | B2 | 6/2002 | Williamson, IV et al. |
| 6,406,440 | B1 | 6/2002 | Stefanchik |
| 6,406,472 | B1 | 6/2002 | Jensen |
| 6,409,724 | B1 | 6/2002 | Penny et al. |
| H2037 | H | 7/2002 | Yates et al. |
| 6,412,639 | B1 | 7/2002 | Hickey |
| 6,413,274 | B1 | 7/2002 | Pedros |
| 6,415,542 | B1 | 7/2002 | Bates et al. |
| 6,416,486 | B1 | 7/2002 | Wampler |
| 6,416,509 | B1 | 7/2002 | Goble et al. |
| 6,419,695 | B1 | 7/2002 | Gabbay |
| 6,423,079 | B1 | 7/2002 | Blake, III |
| 6,424,885 | B1 | 7/2002 | Niemeyer et al. |
| RE37,814 | E | 8/2002 | Allgeyer |
| 6,428,070 | B1 | 8/2002 | Takanashi et al. |
| 6,428,487 | B1 | 8/2002 | Burdorff et al. |
| 6,429,611 | B1 | 8/2002 | Li |
| 6,430,298 | B1 | 8/2002 | Kettl et al. |
| 6,432,065 | B1 | 8/2002 | Burdorff et al. |
| 6,436,097 | B1 | 8/2002 | Nardella |
| 6,436,107 | B1 | 8/2002 | Wang et al. |
| 6,436,110 | B2 | 8/2002 | Bowman et al. |
| 6,436,115 | B1 | 8/2002 | Beaupre |
| 6,436,122 | B1 | 8/2002 | Frank et al. |
| 6,439,439 | B1 | 8/2002 | Rickard et al. |
| 6,439,446 | B1 | 8/2002 | Perry et al. |
| 6,440,146 | B2 | 8/2002 | Nicholas et al. |
| 6,441,577 | B2 | 8/2002 | Blumenkranz et al. |
| D462,758 | S | 9/2002 | Epstein et al. |
| 6,443,973 | B1 | 9/2002 | Whitman |
| 6,445,530 | B1 | 9/2002 | Baker |
| 6,447,518 | B1 | 9/2002 | Krause et al. |
| 6,447,523 | B1 | 9/2002 | Middleman et al. |
| 6,447,799 | B1 | 9/2002 | Ullman |
| 6,447,864 | B2 | 9/2002 | Johnson et al. |
| 6,450,391 | B1 | 9/2002 | Kayan et al. |
| 6,450,989 | B2 | 9/2002 | Dubrul et al. |
| 6,454,656 | B2 | 9/2002 | Brissette et al. |
| 6,454,781 | B1 | 9/2002 | Witt et al. |
| 6,457,338 | B1 | 10/2002 | Frenken |
| 6,457,625 | B1 | 10/2002 | Tormala et al. |
| 6,458,077 | B1 | 10/2002 | Boebel et al. |
| 6,458,142 | B1 | 10/2002 | Faller et al. |
| 6,458,147 | B1 | 10/2002 | Cruise et al. |
| 6,460,627 | B1 | 10/2002 | Below et al. |
| 6,463,824 | B1 | 10/2002 | Prell et al. |
| 6,468,275 | B1 | 10/2002 | Wampler et al. |
| 6,468,286 | B2 | 10/2002 | Mastri et al. |
| 6,471,106 | B1 | 10/2002 | Reining |
| 6,471,659 | B2 | 10/2002 | Eggers et al. |
| 6,478,210 | B2 | 11/2002 | Adams et al. |
| 6,482,063 | B1 | 11/2002 | Frigard |
| 6,482,200 | B2 | 11/2002 | Shippert |
| 6,482,217 | B1 | 11/2002 | Pintor et al. |
| 6,485,490 | B2 | 11/2002 | Wampler et al. |
| 6,485,503 | B2 | 11/2002 | Jacobs et al. |
| 6,485,667 | B1 | 11/2002 | Tan |
| 6,486,286 | B1 | 11/2002 | McGall et al. |
| 6,488,196 | B1 | 12/2002 | Fenton, Jr. |
| 6,488,197 | B1 | 12/2002 | Whitman |
| 6,488,659 | B1 | 12/2002 | Rosenman |
| 6,491,201 | B1 | 12/2002 | Whitman |
| 6,491,690 | B1 | 12/2002 | Goble et al. |
| 6,491,701 | B2 | 12/2002 | Tierney et al. |
| 6,491,702 | B2 | 12/2002 | Heilbrun et al. |
| 6,492,785 | B1 | 12/2002 | Kasten et al. |
| 6,494,882 | B1 | 12/2002 | Lebouitz et al. |
| 6,494,885 | B1 | 12/2002 | Dhindsa |
| 6,494,888 | B1 | 12/2002 | Laufer et al. |
| 6,494,896 | B1 | 12/2002 | D'Alessio et al. |
| 6,498,480 | B1 | 12/2002 | Manara |
| 6,500,176 | B1 | 12/2002 | Truckai et al. |
| 6,500,189 | B1 | 12/2002 | Lang et al. |
| 6,500,194 | B2 | 12/2002 | Benderev et al. |
| D468,749 | S | 1/2003 | Friedman |
| 6,503,139 | B2 | 1/2003 | Coral |
| 6,503,257 | B2 | 1/2003 | Grant et al. |
| 6,503,259 | B2 | 1/2003 | Huxel et al. |
| 6,505,768 | B2 | 1/2003 | Whitman |
| 6,506,197 | B1 | 1/2003 | Rollero et al. |
| 6,506,399 | B2 | 1/2003 | Donovan |
| 6,510,854 | B2 | 1/2003 | Goble |
| 6,511,468 | B1 | 1/2003 | Cragg et al. |
| 6,512,360 | B1 | 1/2003 | Goto et al. |
| 6,514,252 | B2 | 2/2003 | Nezhat et al. |
| 6,516,073 | B1 | 2/2003 | Schulz et al. |
| 6,517,528 | B1 | 2/2003 | Pantages et al. |
| 6,517,535 | B2 | 2/2003 | Edwards |
| 6,517,565 | B1 | 2/2003 | Whitman et al. |
| 6,517,566 | B1 | 2/2003 | Hovland et al. |
| 6,520,971 | B1 | 2/2003 | Perry et al. |
| 6,520,972 | B2 | 2/2003 | Peters |
| 6,522,101 | B2 | 2/2003 | Malackowski |
| 6,524,180 | B1 | 2/2003 | Simms et al. |
| 6,525,499 | B2 | 2/2003 | Naganuma |
| D471,206 | S | 3/2003 | Buzzard et al. |
| 6,527,782 | B2 | 3/2003 | Hogg et al. |
| 6,527,785 | B2 | 3/2003 | Sancoff et al. |
| 6,530,942 | B2 | 3/2003 | Fogarty et al. |
| 6,532,958 | B1 | 3/2003 | Buan et al. |
| 6,533,157 | B1 | 3/2003 | Whitman |
| 6,533,723 | B1 | 3/2003 | Lockery et al. |
| 6,533,784 | B2 | 3/2003 | Truckai et al. |
| 6,535,764 | B2 | 3/2003 | Imran et al. |
| 6,539,297 | B2 | 3/2003 | Weiberle et al. |
| D473,239 | S | 4/2003 | Cockerill |
| 6,539,816 | B2 | 4/2003 | Kogiso et al. |
| 6,540,737 | B2 | 4/2003 | Bacher et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,844 | B2 | 4/2003 | Lee et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | Deguillebon et al. |
| 6,569,173 | B1 | 5/2003 | Blatter et al. |
| 6,572,629 | B2 | 6/2003 | Kalloo et al. |
| 6,575,969 | B1 | 6/2003 | Rittman, III et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |

(56) References Cited

U.S. PATENT DOCUMENTS 6,588,931 B2 7/2003 Betzner et al.
6,589,118 B1 7/2003 Soma et al.
6,589,164 B1 7/2003 Flaherty
6,592,538 B1 7/2003 Hotchkiss et al.
6,592,572 B1 7/2003 Suzuta
6,592,597 B2 7/2003 Grant et al.
6,594,552 B1 7/2003 Nowlin et al.
6,595,914 B2 7/2003 Kato
6,596,296 B1 7/2003 Nelson et al.
6,596,304 B1 7/2003 Bayon et al.
6,596,432 B2 7/2003 Kawakami et al.
6,599,295 B1 7/2003 Tornier et al.
6,599,323 B2 7/2003 Melican et al.
D478,665 S 8/2003 Isaacs et al.
D478,986 S 8/2003 Johnston et al.
6,601,749 B2 8/2003 Sullivan et al.
6,602,252 B2 8/2003 Mollenauer
6,602,262 B2 8/2003 Griego et al.
6,603,050 B2 8/2003 Heaton
6,605,078 B2 8/2003 Adams
6,605,669 B2 8/2003 Awokola et al.
6,605,911 B1 8/2003 Klesing
6,607,475 B2 8/2003 Doyle et al.
6,611,793 B1 8/2003 Burnside et al.
6,613,069 B2 9/2003 Boyd et al.
6,616,686 B2 9/2003 Coleman et al.
6,619,529 B2 9/2003 Green et al.
6,620,111 B2 9/2003 Stephens et al.
6,620,161 B2 9/2003 Schulze et al.
6,620,166 B1 9/2003 Wenstrom, Jr. et al.
6,625,517 B1 9/2003 Bogdanov et al.
6,626,834 B2 9/2003 Dunne et al.
6,626,901 B1 9/2003 Treat et al.
6,626,938 B1 9/2003 Butaric et al.
H2086 H 10/2003 Amsler
6,629,630 B2 10/2003 Adams
6,629,974 B2 10/2003 Penny et al.
6,629,988 B2 10/2003 Weadock
6,635,838 B1 10/2003 Kornelson
6,636,412 B2 10/2003 Smith
6,638,108 B2 10/2003 Tachi
6,638,285 B2 10/2003 Gabbay
6,638,297 B1 10/2003 Huitema
RE38,335 E 11/2003 Aust et al.
6,641,528 B2 11/2003 Torii
6,644,532 B2 11/2003 Green et al.
6,645,201 B1 11/2003 Utley et al.
6,646,307 B1 11/2003 Yu et al.
6,648,816 B2 11/2003 Irion et al.
6,648,901 B2 11/2003 Fleischman et al.
6,652,595 B1 11/2003 Nicolo
D484,243 S 12/2003 Ryan et al.
D484,595 S 12/2003 Ryan et al.
D484,596 S 12/2003 Ryan et al.
6,656,177 B2 12/2003 Truckai et al.
6,656,193 B2 12/2003 Grant et al.
6,659,940 B2 12/2003 Adler
6,660,008 B1 12/2003 Foerster et al.
6,663,623 B1 12/2003 Oyama et al.
6,663,641 B1 12/2003 Kovac et al.
6,666,854 B1 12/2003 Lange
6,666,860 B1 12/2003 Takahashi
6,666,875 B1 12/2003 Sakurai et al.
6,667,825 B2 12/2003 Lu et al.
6,669,073 B2 12/2003 Milliman et al.
6,670,806 B2 12/2003 Wendt et al.
6,671,185 B2 12/2003 Duval
D484,977 S 1/2004 Ryan et al.
6,676,660 B2 1/2004 Wampler et al.
6,677,687 B2 1/2004 Ho et al.
6,679,269 B2 1/2004 Swanson
6,679,410 B2 1/2004 Wursch et al.
6,681,978 B2 1/2004 Geiste et al.
6,681,979 B2 1/2004 Whitman
6,682,527 B2 1/2004 Strul
6,682,528 B2 1/2004 Frazier et al.
6,682,544 B2 1/2004 Mastri et al.
6,685,698 B2 2/2004 Morley et al.
6,685,727 B2 2/2004 Fisher et al.
6,689,153 B1 2/2004 Skiba
6,692,507 B2 2/2004 Pugsley et al.
6,692,692 B2 2/2004 Stetzel
6,695,198 B2 2/2004 Adams et al.
6,695,199 B2 2/2004 Whitman
6,695,774 B2 2/2004 Hale et al.
6,695,849 B2 2/2004 Michelson
6,696,814 B2 2/2004 Henderson et al.
6,697,048 B2 2/2004 Rosenberg et al.
6,698,643 B2 3/2004 Whitman
6,699,177 B1 3/2004 Wang et al.
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,773,458 B1 8/2004 Brauker et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.

(56) References Cited

U.S. PATENT DOCUMENTS 6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Baxter, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,927,315 B1 8/2005 Heinecke et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.

(56) References Cited

U.S. PATENT DOCUMENTS 6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,005,828 B2 2/2006 Karikomi
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,412 B1 7/2006 Reynolds et al.
7,075,770 B1 7/2006 Smith
7,077,856 B2 7/2006 Whitman
7,080,769 B2 7/2006 Vresh et al.
7,081,114 B2 7/2006 Rashidi
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,363 B2 9/2006 Nishizawa et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,201 B2 9/2006 Truckai et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.

(56) References Cited

U.S. PATENT DOCUMENTS

| | | | |
|---|---|---|---|
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,134,364 | B2 | 11/2006 | Kageler et al. |
| 7,134,587 | B2 | 11/2006 | Schwemberger et al. |
| 7,135,027 | B2 | 11/2006 | Delmotte |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,153,314 | B2 | 12/2006 | Laufer et al. |
| 7,155,316 | B2 | 12/2006 | Sutherland et al. |
| 7,156,846 | B2 | 1/2007 | Dycus et al. |
| 7,156,863 | B2 | 1/2007 | Sonnenschein et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,160,311 | B2 | 1/2007 | Blatter et al. |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,169,146 | B2 | 1/2007 | Truckai et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,190,147 | B2 | 3/2007 | Gileff et al. |
| 7,193,199 | B2 | 3/2007 | Jang |
| 7,195,627 | B2 | 3/2007 | Amoah et al. |
| 7,196,911 | B2 | 3/2007 | Takano et al. |
| D541,418 | S | 4/2007 | Schechter et al. |
| 7,197,965 | B1 | 4/2007 | Anderson |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,205,959 | B2 | 4/2007 | Henriksson |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,225,959 | B2 | 6/2007 | Patton et al. |
| 7,225,963 | B2 | 6/2007 | Scirica |
| 7,225,964 | B2 | 6/2007 | Mastri et al. |
| 7,226,450 | B2 | 6/2007 | Athanasiou et al. |
| 7,226,467 | B2 | 6/2007 | Lucatero et al. |
| 7,228,505 | B2 | 6/2007 | Shimazu et al. |
| 7,229,408 | B2 | 6/2007 | Douglas et al. |
| 7,234,624 | B2 | 6/2007 | Gresham et al. |
| 7,235,072 | B2 | 6/2007 | Sartor et al. |
| 7,235,089 | B1 | 6/2007 | McGuckin, Jr. |
| 7,235,302 | B2 | 6/2007 | Jing et al. |
| 7,237,708 | B1 | 7/2007 | Guy et al. |
| 7,238,195 | B2 | 7/2007 | Viola |
| 7,238,901 | B2 | 7/2007 | Kim et al. |
| 7,239,657 | B1 | 7/2007 | Gunnarsson |
| 7,241,288 | B2 | 7/2007 | Braun |
| 7,241,289 | B2 | 7/2007 | Braun |
| 7,246,734 | B2 | 7/2007 | Shelton, IV |
| 7,247,161 | B2 | 7/2007 | Johnston et al. |
| 7,249,267 | B2 | 7/2007 | Chapuis |
| 7,252,641 | B2 | 8/2007 | Thompson et al. |
| 7,252,660 | B2 | 8/2007 | Kunz |
| 7,255,012 | B2 | 8/2007 | Hedtke |
| 7,255,696 | B2 | 8/2007 | Goble et al. |
| 7,256,695 | B2 | 8/2007 | Hamel et al. |
| 7,258,262 | B2 | 8/2007 | Mastri et al. |
| 7,258,546 | B2 | 8/2007 | Beier et al. |
| 7,260,431 | B2 | 8/2007 | Libbus et al. |
| 7,265,374 | B2 | 9/2007 | Lee et al. |
| 7,267,677 | B2 | 9/2007 | Johnson et al. |
| 7,267,679 | B2 | 9/2007 | McGuckin, Jr. et al. |
| 7,272,002 | B2 | 9/2007 | Drapeau |
| 7,273,483 | B2 | 9/2007 | Wiener et al. |
| 7,273,488 | B2 | 9/2007 | Nakamura et al. |
| D552,623 | S | 10/2007 | Vong et al. |
| 7,275,674 | B2 | 10/2007 | Racenet et al. |
| 7,276,044 | B2 | 10/2007 | Ferry et al. |
| 7,276,068 | B2 | 10/2007 | Johnson et al. |
| 7,278,562 | B2 | 10/2007 | Mastri et al. |
| 7,278,563 | B1 | 10/2007 | Green |
| 7,278,949 | B2 | 10/2007 | Bader |
| 7,278,994 | B2 | 10/2007 | Goble |
| 7,282,048 | B2 | 10/2007 | Goble et al. |
| 7,283,096 | B2 | 10/2007 | Geisheimer et al. |
| 7,286,850 | B2 | 10/2007 | Frielink et al. |
| 7,287,682 | B1 | 10/2007 | Ezzat et al. |
| 7,289,139 | B2 | 10/2007 | Amling et al. |
| 7,293,685 | B2 | 11/2007 | Ehrenfels et al. |
| 7,295,893 | B2 | 11/2007 | Sunaoshi |
| 7,295,907 | B2 | 11/2007 | Lu et al. |
| 7,296,722 | B2 | 11/2007 | Ivanko |
| 7,296,724 | B2 | 11/2007 | Green et al. |
| 7,297,149 | B2 | 11/2007 | Vitali et al. |
| 7,300,373 | B2 | 11/2007 | Jinno et al. |
| 7,300,431 | B2 | 11/2007 | Dubrovsky |
| 7,300,450 | B2 | 11/2007 | Vleugels et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,303,502 | B2 | 12/2007 | Thompson |
| 7,303,556 | B2 | 12/2007 | Metzger |

(56) References Cited

U.S. PATENT DOCUMENTS 7,306,597 B2 12/2007 Manzo
7,308,998 B2 12/2007 Mastri et al.
7,311,238 B2 12/2007 Liu
7,311,709 B2 12/2007 Truckai et al.
7,313,430 B2 12/2007 Urquhart et al.
7,314,473 B2 1/2008 Jinno et al.
7,317,955 B2 1/2008 McGreevy
7,320,704 B2 1/2008 Lashinski et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,398 B2 4/2008 Kanazawa
7,354,440 B2 4/2008 Truckai et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,430,849 B1 10/2008 Coutts et al.
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
D580,942 S 11/2008 Oshiro et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.

(56) References Cited

U.S. PATENT DOCUMENTS 7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,497,137 B2 3/2009 Tellenbach et al.
7,500,979 B2 3/2009 Hueil et al.
7,501,198 B2 3/2009 Barley et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,790 B1 5/2009 Knodel et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 De La Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.
7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.
7,572,298 B2 8/2009 Roller et al.
7,575,144 B2 8/2009 Ortiz et al.
7,578,825 B2 8/2009 Huebner
D600,712 S 9/2009 Lamanna et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Iio et al.
7,604,150 B2 10/2009 Boudreaux
7,604,151 B2 10/2009 Hess et al.
7,604,668 B2 10/2009 Farnsworth et al.
7,605,826 B2 10/2009 Sauer
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola
7,618,427 B2 11/2009 Ortiz et al.
D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,625,662 B2 12/2009 Vaisnys et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,016 B2 1/2010 Nycz et al.
7,644,484 B2 1/2010 Vereschagin
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.

(56) References Cited

U.S. PATENT DOCUMENTS 7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh, II et al.
7,670,334 B2 3/2010 Hueil et al.
7,670,337 B2 3/2010 Young
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,758 B2 5/2010 Lee et al.
7,708,768 B2 5/2010 Danek et al.
7,709,136 B2 5/2010 Touchton et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,735,704 B2 6/2010 Bilotti
7,736,254 B2 6/2010 Schena
7,736,306 B2 6/2010 Brustad et al.
7,736,356 B2 6/2010 Cooper et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,614 B1 8/2010 McGonagle et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,782,382 B2 8/2010 Fujimura
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.

(56) References Cited

U.S. PATENT DOCUMENTS 7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,076 B2 10/2010 Borovsky et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,845,912 B2 12/2010 Sung et al.
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,877,869 B2 2/2011 Mehdizadeh et al.
7,879,063 B2 2/2011 Khosravi
7,879,070 B2 2/2011 Ortiz et al.
7,879,367 B2 2/2011 Heublein et al.
7,883,461 B2 2/2011 Albrecht et al.
7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,887,755 B2 2/2011 Mingerink et al.
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
7,934,630 B2 5/2011 Shelton, IV et al.
7,934,631 B2 5/2011 Balbierz et al.
7,934,896 B2 5/2011 Schnier
7,935,130 B2 5/2011 Williams

(56) References Cited

U.S. PATENT DOCUMENTS 7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,300 B2 5/2011 Rethy et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,948,381 B2 5/2011 Lindsay et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,166 B2 5/2011 Orban, III et al.
7,952,464 B2 5/2011 Nikitin et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,508 B2 7/2011 Hoag
7,976,563 B2 7/2011 Summerer
7,979,137 B2 7/2011 Tracey et al.
7,980,443 B2 7/2011 Scheib et al.
7,981,025 B2 7/2011 Pool et al.
7,981,102 B2 7/2011 Patel et al.
7,981,132 B2 7/2011 Dubrul et al.
7,987,405 B2 7/2011 Turner et al.
7,988,015 B2 8/2011 Mason, II et al.
7,988,026 B2 8/2011 Knodel et al.
7,988,027 B2 8/2011 Olson et al.
7,988,028 B2 8/2011 Farascioni et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,997,054 B2 8/2011 Bertsch et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,010,180 B2 8/2011 Quaid et al.
8,011,550 B2 9/2011 Aranyi et al.
8,011,551 B2 9/2011 Marczyk et al.
8,011,553 B2 9/2011 Mastri et al.
8,011,555 B2 9/2011 Tarinelli et al.
8,012,170 B2 9/2011 Whitman et al.
8,016,176 B2 9/2011 Kasvikis et al.
8,016,177 B2 9/2011 Bettuchi et al.
8,016,178 B2 9/2011 Olson et al.
8,016,849 B2 9/2011 Wenchell
8,016,855 B2 9/2011 Whitman et al.
8,016,858 B2 9/2011 Whitman
8,016,881 B2 9/2011 Furst
8,020,741 B2 9/2011 Cole et al.
8,020,742 B2 9/2011 Marczyk
8,020,743 B2 9/2011 Shelton, IV
8,021,375 B2 9/2011 Aldrich et al.
8,025,199 B2 9/2011 Whitman et al.
8,025,896 B2 9/2011 Malaviya et al.
8,028,835 B2 10/2011 Yasuda et al.
8,028,882 B2 10/2011 Viola
8,028,883 B2 10/2011 Stopek
8,028,884 B2 10/2011 Sniffin et al.
8,028,885 B2 10/2011 Smith et al.
8,029,510 B2 10/2011 Hoegerle
8,031,069 B2 10/2011 Cohn et al.
8,033,438 B2 10/2011 Scirica
8,033,439 B2 10/2011 Racenet et al.
8,033,440 B2 10/2011 Wenchell et al.
8,033,442 B2 10/2011 Racenet et al.
8,034,077 B2 10/2011 Smith et al.
8,034,337 B2 10/2011 Simard
8,034,363 B2 10/2011 Li et al.
8,035,487 B2 10/2011 Malackowski
8,037,591 B2 10/2011 Spivey et al.
8,038,044 B2 10/2011 Viola
8,038,045 B2 10/2011 Bettuchi et al.
8,038,046 B2 10/2011 Smith et al.
8,038,686 B2 10/2011 Huitema et al.
8,043,207 B2 10/2011 Adams
8,043,328 B2 10/2011 Hahnen et al.
8,044,536 B2 10/2011 Nguyen et al.
8,044,604 B2 10/2011 Hagino et al.
8,047,236 B2 11/2011 Perry
8,048,503 B2 11/2011 Farnsworth et al.
8,052,636 B2 11/2011 Moll et al.
8,052,697 B2 11/2011 Phillips
8,056,787 B2 11/2011 Boudreaux et al.
8,056,788 B2 11/2011 Mastri et al.
8,056,789 B1 11/2011 White et al.
8,057,508 B2 11/2011 Shelton, IV
8,058,771 B2 11/2011 Giordano et al.
8,060,250 B2 11/2011 Reiland et al.
8,061,014 B2 11/2011 Smith et al.
8,061,576 B2 11/2011 Cappola
8,062,236 B2 11/2011 Soltz
8,062,306 B2 11/2011 Nobis et al.
8,062,330 B2 11/2011 Prommersberger et al.
8,063,619 B2 11/2011 Zhu et al.
8,066,158 B2 11/2011 Vogel et al.
8,066,166 B2 11/2011 Demmy et al.
8,066,167 B2 11/2011 Measamer et al.
8,066,168 B2 11/2011 Vidal et al.
8,066,720 B2 11/2011 Knodel et al.
D650,074 S 12/2011 Hunt et al.
D650,789 S 12/2011 Arnold
8,070,033 B2 12/2011 Milliman et al.
8,070,034 B1 12/2011 Knodel
8,070,035 B2 12/2011 Holsten et al.
8,070,743 B2 12/2011 Kagan et al.

(56) References Cited

U.S. PATENT DOCUMENTS

| | | | |
|---|---|---|---|
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |
| 8,102,138 | B2 | 1/2012 | Sekine et al. |
| 8,102,278 | B2 | 1/2012 | Deck et al. |
| 8,105,320 | B2 | 1/2012 | Manzo |
| 8,105,350 | B2 | 1/2012 | Lee et al. |
| 8,107,925 | B2 | 1/2012 | Natsuno et al. |
| 8,108,033 | B2 | 1/2012 | Drew et al. |
| 8,108,072 | B2 | 1/2012 | Zhao et al. |
| 8,109,426 | B2 | 2/2012 | Milliman et al. |
| 8,110,208 | B1 | 2/2012 | Hen |
| 8,113,405 | B2 | 2/2012 | Milliman |
| 8,113,407 | B2 | 2/2012 | Holsten et al. |
| 8,113,408 | B2 | 2/2012 | Wenchell et al. |
| 8,113,410 | B2 | 2/2012 | Hall et al. |
| 8,114,017 | B2 | 2/2012 | Bacher |
| 8,114,100 | B2 | 2/2012 | Smith et al. |
| 8,114,345 | B2 | 2/2012 | Dlugos, Jr. et al. |
| 8,118,206 | B2 | 2/2012 | Zand et al. |
| 8,118,207 | B2 | 2/2012 | Racenet et al. |
| 8,120,301 | B2 | 2/2012 | Goldberg et al. |
| 8,122,128 | B2 | 2/2012 | Burke, II et al. |
| 8,123,103 | B2 | 2/2012 | Milliman |
| 8,123,523 | B2 | 2/2012 | Carron et al. |
| 8,123,766 | B2 | 2/2012 | Bauman et al. |
| 8,123,767 | B2 | 2/2012 | Bauman et al. |
| 8,125,168 | B2 | 2/2012 | Johnson et al. |
| 8,127,975 | B2 | 3/2012 | Olson et al. |
| 8,127,976 | B2 | 3/2012 | Scirica et al. |
| 8,128,624 | B2 | 3/2012 | Couture et al. |
| 8,128,643 | B2 | 3/2012 | Aranyi et al. |
| 8,128,645 | B2 | 3/2012 | Sonnenschein et al. |
| 8,128,662 | B2 | 3/2012 | Altarac et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,133,500 | B2 | 3/2012 | Ringeisen et al. |
| 8,134,306 | B2 | 3/2012 | Drader et al. |
| 8,136,711 | B2 | 3/2012 | Beardsley et al. |
| 8,136,712 | B2 | 3/2012 | Zingman |
| 8,136,713 | B2 | 3/2012 | Hathaway et al. |
| 8,137,339 | B2 | 3/2012 | Jinno et al. |
| 8,140,417 | B2 | 3/2012 | Shibata |
| 8,141,762 | B2 | 3/2012 | Bedi et al. |
| 8,141,763 | B2 | 3/2012 | Milliman |
| 8,142,200 | B2 | 3/2012 | Crunkilton et al. |
| 8,142,425 | B2 | 3/2012 | Eggers |
| 8,142,461 | B2 | 3/2012 | Houser et al. |
| 8,142,515 | B2 | 3/2012 | Therin et al. |
| 8,143,520 | B2 | 3/2012 | Cutler |
| 8,146,790 | B2 | 4/2012 | Milliman |
| 8,147,421 | B2 | 4/2012 | Farquhar et al. |
| 8,147,456 | B2 | 4/2012 | Fisher et al. |
| 8,147,485 | B2 | 4/2012 | Wham et al. |
| 8,152,041 | B2 | 4/2012 | Kostrzewski |
| 8,152,756 | B2 | 4/2012 | Webster et al. |
| 8,154,239 | B2 | 4/2012 | Katsuki et al. |
| 8,157,145 | B2 | 4/2012 | Shelton, IV et al. |
| 8,157,148 | B2 | 4/2012 | Scirica |
| 8,157,151 | B2 | 4/2012 | Ingmanson et al. |
| 8,157,152 | B2 | 4/2012 | Holsten et al. |
| 8,157,153 | B2 | 4/2012 | Shelton, IV et al. |
| 8,157,793 | B2 | 4/2012 | Omori et al. |
| 8,157,834 | B2 | 4/2012 | Conlon |
| 8,161,977 | B2 | 4/2012 | Shelton, IV et al. |
| 8,162,138 | B2 | 4/2012 | Bettenhausen et al. |
| 8,162,197 | B2 | 4/2012 | Mastri et al. |
| 8,162,668 | B2 | 4/2012 | Toly |
| 8,162,933 | B2 | 4/2012 | Francischelli et al. |
| 8,162,965 | B2 | 4/2012 | Reschke et al. |
| 8,167,185 | B2 | 5/2012 | Shelton, IV et al. |
| 8,167,622 | B2 | 5/2012 | Zhou |
| 8,167,895 | B2 | 5/2012 | D'Agostino et al. |
| 8,167,898 | B1 | 5/2012 | Schaller et al. |
| 8,170,241 | B2 | 5/2012 | Roe et al. |
| 8,172,004 | B2 | 5/2012 | Ho |
| 8,172,120 | B2 | 5/2012 | Boyden et al. |
| 8,172,122 | B2 | 5/2012 | Kasvikis et al. |
| 8,172,124 | B2 | 5/2012 | Shelton, IV et al. |
| 8,177,776 | B2 | 5/2012 | Humayun et al. |
| 8,177,797 | B2 | 5/2012 | Shimoji et al. |
| 8,179,705 | B2 | 5/2012 | Chapuis |
| 8,180,458 | B2 | 5/2012 | Kane et al. |
| 8,181,839 | B2 | 5/2012 | Beetel |
| 8,181,840 | B2 | 5/2012 | Milliman |
| 8,182,422 | B2 | 5/2012 | Bayer et al. |
| 8,182,444 | B2 | 5/2012 | Uber, III et al. |
| 8,183,807 | B2 | 5/2012 | Tsai et al. |
| 8,186,555 | B2 | 5/2012 | Shelton, IV et al. |
| 8,186,556 | B2 | 5/2012 | Viola |
| 8,186,558 | B2 | 5/2012 | Sapienza |
| 8,186,560 | B2 | 5/2012 | Hess et al. |
| 8,190,238 | B2 | 5/2012 | Moll et al. |
| 8,191,752 | B2 | 6/2012 | Scirica |
| 8,192,350 | B2 | 6/2012 | Ortiz et al. |
| 8,192,460 | B2 | 6/2012 | Orban, III et al. |
| 8,192,651 | B2 | 6/2012 | Young et al. |
| 8,193,129 | B2 | 6/2012 | Tagawa et al. |
| 8,196,795 | B2 | 6/2012 | Moore et al. |
| 8,196,796 | B2 | 6/2012 | Shelton, IV et al. |
| 8,197,501 | B2 | 6/2012 | Shadeck et al. |
| 8,197,502 | B2 | 6/2012 | Smith et al. |
| 8,197,837 | B2 | 6/2012 | Jamiolkowski et al. |
| 8,201,720 | B2 | 6/2012 | Hessler |
| 8,201,721 | B2 | 6/2012 | Zemlok et al. |
| 8,202,549 | B2 | 6/2012 | Stucky et al. |
| 8,205,779 | B2 | 6/2012 | Ma et al. |
| 8,205,780 | B2 | 6/2012 | Sorrentino et al. |
| 8,205,781 | B2 | 6/2012 | Baxter, III et al. |
| 8,207,863 | B2 | 6/2012 | Neubauer et al. |
| 8,210,411 | B2 | 7/2012 | Yates et al. |
| 8,210,414 | B2 | 7/2012 | Bettuchi et al. |
| 8,210,415 | B2 | 7/2012 | Ward |
| 8,210,416 | B2 | 7/2012 | Milliman et al. |
| 8,210,721 | B2 | 7/2012 | Chen et al. |
| 8,211,125 | B2 | 7/2012 | Spivey |
| 8,214,019 | B2 | 7/2012 | Govari et al. |
| 8,215,531 | B2 | 7/2012 | Shelton, IV et al. |
| 8,215,532 | B2 | 7/2012 | Marczyk |
| 8,215,533 | B2 | 7/2012 | Viola et al. |
| 8,220,468 | B2 | 7/2012 | Cooper et al. |
| 8,220,688 | B2 | 7/2012 | Laurent et al. |
| 8,220,690 | B2 | 7/2012 | Hess et al. |
| 8,221,402 | B2 | 7/2012 | Francischelli et al. |
| 8,221,424 | B2 | 7/2012 | Cha |
| 8,221,433 | B2 | 7/2012 | Lozier et al. |
| 8,225,799 | B2 | 7/2012 | Bettuchi |
| 8,225,979 | B2 | 7/2012 | Farascioni et al. |

(56) References Cited

U.S. PATENT DOCUMENTS 8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,230,235 B2 7/2012 Goodman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,948 B2 1/2013 Bahney
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.

(56) References Cited

U.S. PATENT DOCUMENTS 8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,377,059 B2 2/2013 Deville et al.
8,381,828 B2 2/2013 Whitman et al.
8,381,834 B2 2/2013 Barhitte et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,409,234 B2 4/2013 Stahler et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel
8,439,830 B2 5/2013 McKinley et al.
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,486,047 B2 7/2013 Stopek
8,487,199 B2 7/2013 Palmer et al.
8,487,487 B2 7/2013 Dietz et al.
8,490,851 B2 7/2013 Blier et al.
8,490,852 B2 7/2013 Viola

(56) References Cited

U.S. PATENT DOCUMENTS 8,490,853 B2 7/2013 Criscuolo et al.
8,491,581 B2 7/2013 Deville et al.
8,491,603 B2 7/2013 Yeung et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,531,153 B2 9/2013 Baarman et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,598 B2 11/2013 Razzaque et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,591,400 B2 11/2013 Sugiyama
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.

(56) References Cited

U.S. PATENT DOCUMENTS 8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.

(56) References Cited

U.S. PATENT DOCUMENTS 8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,855,822 B2 10/2014 Bartol et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Robetakamp et al.
8,869,913 B2 10/2014 Matthias et al.
8,870,049 B2 10/2014 Amid et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein
8,911,460 B2 12/2014 Neurohr et al.
8,911,471 B2 12/2014 Spivey et al.
8,912,746 B2 12/2014 Reid et al.
8,915,842 B2 12/2014 Weisenburgh, II et al.
8,920,368 B2 12/2014 Sandhu et al.
8,920,433 B2 12/2014 Barrier et al.
8,920,435 B2 12/2014 Smith et al.
8,920,438 B2 12/2014 Aranyi et al.
8,920,443 B2 12/2014 Hiles et al.
8,920,444 B2 12/2014 Hiles et al.
8,922,163 B2 12/2014 MacDonald
8,925,782 B2 1/2015 Shelton, IV
8,925,783 B2 1/2015 Zemlok et al.
8,925,788 B2 1/2015 Hess et al.
8,926,506 B2 1/2015 Widenhouse et al.
8,926,598 B2 1/2015 Mollere et al.
8,931,576 B2 1/2015 Iwata
8,931,679 B2 1/2015 Kostrzewski
8,931,680 B2 1/2015 Milliman
8,931,682 B2 1/2015 Timm et al.
8,931,692 B2 1/2015 Sancak
8,936,614 B2 1/2015 Allen, IV
8,937,408 B2 1/2015 Ganem et al.
8,939,343 B2 1/2015 Milliman et al.
8,939,344 B2 1/2015 Olson et al.
8,939,898 B2 1/2015 Omoto
8,944,069 B2 2/2015 Miller et al.
8,945,095 B2 2/2015 Blumenkranz et al.
8,945,098 B2 2/2015 Seibold et al.
8,945,163 B2 2/2015 Voegele et al.
8,955,732 B2 2/2015 Zemlok et al.
8,956,342 B1 2/2015 Russo et al.
8,956,390 B2 2/2015 Shah et al.
8,958,860 B2 2/2015 Banerjee et al.
8,960,519 B2 2/2015 Whitman et al.
8,960,520 B2 2/2015 McCuen
8,960,521 B2 2/2015 Kostrzewski
8,961,191 B2 2/2015 Hanshew
8,961,504 B2 2/2015 Hoarau et al.
8,961,542 B2 2/2015 Whitfield et al.
8,963,714 B2 2/2015 Medhal et al.
D725,674 S 3/2015 Jung et al.
8,967,443 B2 3/2015 McCuen
8,967,444 B2 3/2015 Beetel
8,967,446 B2 3/2015 Beardsley et al.
8,967,448 B2 3/2015 Carter et al.
8,968,276 B2 3/2015 Zemlok et al.
8,968,308 B2 3/2015 Horner et al.
8,968,312 B2 3/2015 Marczyk et al.
8,968,337 B2 3/2015 Whitfield et al.
8,968,340 B2 3/2015 Chowaniec et al.
8,968,355 B2 3/2015 Malkowski et al.
8,968,358 B2 3/2015 Reschke
8,970,507 B2 3/2015 Holbein et al.
8,973,803 B2 3/2015 Hall et al.
8,973,804 B2 3/2015 Hess et al.
8,973,805 B2 3/2015 Scirica et al.
8,974,440 B2 3/2015 Farritor et al.
8,974,542 B2 3/2015 Fujimoto et al.
8,974,932 B2 3/2015 McGahan et al.
8,978,954 B2 3/2015 Shelton, IV et al.
8,978,955 B2 3/2015 Aronhalt et al.
8,978,956 B2 3/2015 Schall et al.
8,979,843 B2 3/2015 Timm et al.
8,979,890 B2 3/2015 Boudreaux
8,982,195 B2 3/2015 Claus et al.

(56) References Cited

U.S. PATENT DOCUMENTS 8,984,711 B2 3/2015 Ota et al.
8,985,240 B2 3/2015 Winnard
8,985,429 B2 3/2015 Balek et al.
8,986,302 B2 3/2015 Aldridge et al.
8,989,903 B2 3/2015 Weir et al.
8,991,676 B2 3/2015 Hess et al.
8,991,677 B2 3/2015 Moore et al.
8,991,678 B2 3/2015 Wellman et al.
8,992,042 B2 3/2015 Eichenholz
8,992,422 B2 3/2015 Spivey et al.
8,992,565 B2 3/2015 Brisson et al.
8,996,165 B2 3/2015 Wang et al.
8,998,058 B2 4/2015 Moore et al.
8,998,059 B2 4/2015 Smith et al.
8,998,060 B2 4/2015 Bruewer et al.
8,998,061 B2 4/2015 Williams et al.
8,998,939 B2 4/2015 Price et al.
9,000,720 B2 4/2015 Stulen et al.
9,002,518 B2 4/2015 Manzo et al.
9,004,339 B1 4/2015 Park
9,004,799 B1 4/2015 Tibbits
9,005,230 B2 4/2015 Yates et al.
9,005,238 B2 4/2015 Desantis et al.
9,005,243 B2 4/2015 Stopek et al.
9,010,606 B2 4/2015 Aranyi et al.
9,010,608 B2 4/2015 Casasanta, Jr. et al.
9,010,611 B2 4/2015 Ross et al.
9,011,437 B2 4/2015 Woodruff et al.
9,011,439 B2 4/2015 Shalaby et al.
9,011,471 B2 4/2015 Timm et al.
9,014,856 B2 4/2015 Manzo et al.
9,016,539 B2 4/2015 Kostrzewski et al.
9,016,540 B2 4/2015 Whitman et al.
9,016,541 B2 4/2015 Viola et al.
9,016,542 B2 4/2015 Shelton, IV et al.
9,016,545 B2 4/2015 Aranyi et al.
9,017,331 B2 4/2015 Fox
9,017,355 B2 4/2015 Smith et al.
9,017,369 B2 4/2015 Renger et al.
9,017,371 B2 4/2015 Whitman et al.
9,017,849 B2 4/2015 Stulen et al.
9,017,851 B2 4/2015 Felder et al.
D729,274 S 5/2015 Clement et al.
9,021,684 B2 5/2015 Lenker et al.
9,023,014 B2 5/2015 Chowaniec et al.
9,023,069 B2 5/2015 Kasvikis et al.
9,023,071 B2 5/2015 Miller et al.
9,026,347 B2 5/2015 Gadh et al.
9,027,817 B2 5/2015 Milliman et al.
9,028,468 B2 5/2015 Scarfogliero et al.
9,028,494 B2 5/2015 Shelton, IV et al.
9,028,495 B2 5/2015 Mueller et al.
9,028,510 B2 5/2015 Miyamoto et al.
9,028,511 B2 5/2015 Weller et al.
9,028,519 B2 5/2015 Yates et al.
9,028,529 B2 5/2015 Fox et al.
9,030,166 B2 5/2015 Kano
9,030,169 B2 5/2015 Christensen et al.
9,033,203 B2 5/2015 Woodard, Jr. et al.
9,033,204 B2 5/2015 Shelton, IV et al.
9,034,505 B2 5/2015 Detry et al.
9,038,881 B1 5/2015 Schaller et al.
9,039,690 B2 5/2015 Kersten et al.
9,039,694 B2 5/2015 Ross et al.
9,039,720 B2 5/2015 Madan
9,039,736 B2 5/2015 Scirica et al.
9,040,062 B2 5/2015 Maeda et al.
9,043,027 B2 5/2015 Durant et al.
9,044,227 B2 6/2015 Shelton, IV et al.
9,044,228 B2 6/2015 Woodard, Jr. et al.
9,044,229 B2 6/2015 Scheib et al.
9,044,230 B2 6/2015 Morgan et al.
9,044,238 B2 6/2015 Orszulak
9,044,241 B2 6/2015 Barner et al.
9,044,261 B2 6/2015 Houser
9,044,281 B2 6/2015 Pool et al.
9,050,083 B2 6/2015 Yates et al.
9,050,084 B2 6/2015 Schmid et al.
9,050,089 B2 6/2015 Orszulak
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,866 B2 8/2015 Felder et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.

(56) References Cited

U.S. PATENT DOCUMENTS 9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,154,189 B2 10/2015 Von Novak et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,167,960 B2 10/2015 Yamaguchi et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,686 B2 1/2016 Blair
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,226,799 B2 1/2016 Lightcap et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,268 B2 2/2016 Behnke, II et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,283,334 B2 3/2016 Mantell et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean

(56) References Cited

U.S. PATENT DOCUMENTS

| | | | |
|---|---|---|---|
| 9,295,784 | B2 | 3/2016 | Eggert et al. |
| D753,167 | S | 4/2016 | Yu et al. |
| 9,301,691 | B2 | 4/2016 | Hufnagel et al. |
| 9,301,752 | B2 | 4/2016 | Mandakolathur Vasudevan et al. |
| 9,301,753 | B2 | 4/2016 | Aldridge et al. |
| 9,301,755 | B2 | 4/2016 | Shelton, IV et al. |
| 9,301,759 | B2 | 4/2016 | Spivey et al. |
| 9,301,811 | B2 | 4/2016 | Goldberg et al. |
| 9,307,965 | B2 | 4/2016 | Ming et al. |
| 9,307,986 | B2 | 4/2016 | Hall et al. |
| 9,307,987 | B2 | 4/2016 | Swensgard et al. |
| 9,307,988 | B2 | 4/2016 | Shelton, IV |
| 9,307,989 | B2 | 4/2016 | Shelton, IV et al. |
| 9,307,994 | B2 | 4/2016 | Gresham et al. |
| 9,308,009 | B2 | 4/2016 | Madan et al. |
| 9,308,011 | B2 | 4/2016 | Chao et al. |
| 9,308,646 | B2 | 4/2016 | Lim et al. |
| 9,313,915 | B2 | 4/2016 | Niu et al. |
| 9,314,246 | B2 | 4/2016 | Shelton, IV et al. |
| 9,314,247 | B2 | 4/2016 | Shelton, IV et al. |
| 9,314,261 | B2 | 4/2016 | Bales, Jr. et al. |
| 9,314,291 | B2 | 4/2016 | Schall et al. |
| 9,314,339 | B2 | 4/2016 | Mansmann |
| 9,314,908 | B2 | 4/2016 | Tanimoto et al. |
| 9,320,518 | B2 | 4/2016 | Henderson et al. |
| 9,320,520 | B2 | 4/2016 | Shelton, IV et al. |
| 9,320,521 | B2 | 4/2016 | Shelton, IV et al. |
| 9,320,523 | B2 | 4/2016 | Shelton, IV et al. |
| 9,325,516 | B2 | 4/2016 | Pera et al. |
| D755,196 | S | 5/2016 | Meyers et al. |
| D756,373 | S | 5/2016 | Raskin et al. |
| D756,377 | S | 5/2016 | Connolly et al. |
| D757,028 | S | 5/2016 | Goldenberg et al. |
| 9,326,767 | B2 | 5/2016 | Koch et al. |
| 9,326,768 | B2 | 5/2016 | Shelton, IV |
| 9,326,769 | B2 | 5/2016 | Shelton, IV et al. |
| 9,326,770 | B2 | 5/2016 | Shelton, IV et al. |
| 9,326,771 | B2 | 5/2016 | Baxter, III et al. |
| 9,326,788 | B2 | 5/2016 | Batross et al. |
| 9,326,812 | B2 | 5/2016 | Waaler et al. |
| 9,326,824 | B2 | 5/2016 | Inoue et al. |
| 9,327,061 | B2 | 5/2016 | Govil et al. |
| 9,331,721 | B2 | 5/2016 | Martinez Nuevo et al. |
| 9,332,890 | B2 | 5/2016 | Ozawa |
| 9,332,974 | B2 | 5/2016 | Henderson et al. |
| 9,332,984 | B2 | 5/2016 | Weaner et al. |
| 9,332,987 | B2 | 5/2016 | Leimbach et al. |
| 9,333,040 | B2 | 5/2016 | Shellenberger et al. |
| 9,333,082 | B2 | 5/2016 | Wei et al. |
| 9,337,668 | B2 | 5/2016 | Yip |
| 9,339,226 | B2 | 5/2016 | van der Walt et al. |
| 9,339,342 | B2 | 5/2016 | Prisco et al. |
| 9,345,477 | B2 | 5/2016 | Anim et al. |
| 9,345,479 | B2 | 5/2016 | (Tarinelli) Racenet et al. |
| 9,345,480 | B2 | 5/2016 | Hessler et al. |
| 9,345,481 | B2 | 5/2016 | Hall et al. |
| 9,345,503 | B2 | 5/2016 | Ishida et al. |
| 9,351,726 | B2 | 5/2016 | Leimbach et al. |
| 9,351,727 | B2 | 5/2016 | Leimbach et al. |
| 9,351,728 | B2 | 5/2016 | Sniffin et al. |
| 9,351,730 | B2 | 5/2016 | Schmid et al. |
| 9,351,731 | B2 | 5/2016 | Carter et al. |
| 9,351,732 | B2 | 5/2016 | Hodgkinson |
| 9,352,071 | B2 | 5/2016 | Landgrebe et al. |
| D758,433 | S | 6/2016 | Lee et al. |
| D759,063 | S | 6/2016 | Chen |
| 9,358,003 | B2 | 6/2016 | Hail et al. |
| 9,358,004 | B2 | 6/2016 | Sniffin et al. |
| 9,358,005 | B2 | 6/2016 | Shelton, IV et al. |
| 9,358,015 | B2 | 6/2016 | Sorrentino et al. |
| 9,358,031 | B2 | 6/2016 | Manzo |
| 9,358,065 | B2 | 6/2016 | Ladtkow et al. |
| 9,364,217 | B2 | 6/2016 | Kostrzewski et al. |
| 9,364,219 | B2 | 6/2016 | Olson et al. |
| 9,364,220 | B2 | 6/2016 | Williams |
| 9,364,223 | B2 | 6/2016 | Scirica |
| 9,364,226 | B2 | 6/2016 | Zemlok et al. |
| 9,364,228 | B2 | 6/2016 | Straehnz et al. |
| 9,364,229 | B2 | 6/2016 | D'Agostino et al. |
| 9,364,230 | B2 | 6/2016 | Shelton, IV et al. |
| 9,364,231 | B2 | 6/2016 | Wenchell |
| 9,364,233 | B2 | 6/2016 | Alexander, III et al. |
| 9,364,279 | B2 | 6/2016 | Houser et al. |
| 9,368,991 | B2 | 6/2016 | Qahouq |
| 9,370,341 | B2 | 6/2016 | Ceniccola et al. |
| 9,370,358 | B2 | 6/2016 | Shelton, IV et al. |
| 9,370,361 | B2 | 6/2016 | Viola et al. |
| 9,370,362 | B2 | 6/2016 | Petty et al. |
| 9,370,364 | B2 | 6/2016 | Smith et al. |
| 9,370,400 | B2 | 6/2016 | Parihar |
| 9,375,206 | B2 | 6/2016 | Vidal et al. |
| 9,375,218 | B2 | 6/2016 | Wheeler et al. |
| 9,375,230 | B2 | 6/2016 | Ross et al. |
| 9,375,232 | B2 | 6/2016 | Hunt et al. |
| 9,375,255 | B2 | 6/2016 | Houser et al. |
| D761,309 | S | 7/2016 | Lee et al. |
| 9,381,058 | B2 | 7/2016 | Houser et al. |
| 9,383,881 | B2 | 7/2016 | Day et al. |
| 9,385,640 | B2 | 7/2016 | Sun et al. |
| 9,386,983 | B2 | 7/2016 | Swensgard et al. |
| 9,386,984 | B2 | 7/2016 | Aronhalt et al. |
| 9,386,985 | B2 | 7/2016 | Koch, Jr. et al. |
| 9,386,988 | B2 | 7/2016 | Baxter, III et al. |
| 9,387,003 | B2 | 7/2016 | Kaercher et al. |
| 9,392,885 | B2 | 7/2016 | Vogler et al. |
| 9,393,015 | B2 | 7/2016 | Laurent et al. |
| 9,393,017 | B2 | 7/2016 | Flanagan et al. |
| 9,393,018 | B2 | 7/2016 | Wang et al. |
| 9,393,354 | B2 | 7/2016 | Freedman et al. |
| 9,396,369 | B1 | 7/2016 | Whitehurst et al. |
| 9,396,669 | B2 | 7/2016 | Karkanias et al. |
| 9,398,905 | B2 | 7/2016 | Martin |
| 9,398,911 | B2 | 7/2016 | Auld |
| D763,277 | S | 8/2016 | Ahmed et al. |
| D764,498 | S | 8/2016 | Capela et al. |
| 9,402,604 | B2 | 8/2016 | Williams et al. |
| 9,402,625 | B2 | 8/2016 | Coleman et al. |
| 9,402,626 | B2 | 8/2016 | Ortiz et al. |
| 9,402,627 | B2 | 8/2016 | Stevenson et al. |
| 9,402,629 | B2 | 8/2016 | Ehrenfels et al. |
| 9,402,679 | B2 | 8/2016 | Ginnebaugh et al. |
| 9,402,682 | B2 | 8/2016 | Worrell et al. |
| 9,402,688 | B2 | 8/2016 | Min et al. |
| 9,408,604 | B2 | 8/2016 | Shelton, IV et al. |
| 9,408,605 | B1 | 8/2016 | Knodel et al. |
| 9,408,606 | B2 | 8/2016 | Shelton, IV |
| 9,408,622 | B2 | 8/2016 | Stulen et al. |
| 9,411,370 | B2 | 8/2016 | Benni et al. |
| 9,413,128 | B2 | 8/2016 | Tien et al. |
| 9,414,838 | B2 | 8/2016 | Shelton, IV et al. |
| 9,414,849 | B2 | 8/2016 | Nagashimada |
| 9,414,880 | B2 | 8/2016 | Monson et al. |
| 9,420,967 | B2 | 8/2016 | Zand et al. |
| 9,421,003 | B2 | 8/2016 | Williams et al. |
| 9,421,014 | B2 | 8/2016 | Ingmanson et al. |
| 9,421,030 | B2 | 8/2016 | Cole et al. |
| 9,421,060 | B2 | 8/2016 | Monson et al. |
| 9,421,062 | B2 | 8/2016 | Houser et al. |
| 9,421,682 | B2 | 8/2016 | McClaskey et al. |
| 9,427,223 | B2 | 8/2016 | Park et al. |
| 9,427,231 | B2 | 8/2016 | Racenet et al. |
| 9,429,204 | B2 | 8/2016 | Stefan et al. |
| D767,624 | S | 9/2016 | Lee et al. |
| 9,433,411 | B2 | 9/2016 | Racenet et al. |
| 9,433,414 | B2 | 9/2016 | Chen et al. |
| 9,433,419 | B2 | 9/2016 | Gonzalez et al. |
| 9,433,420 | B2 | 9/2016 | Hodgkinson |
| 9,439,649 | B2 | 9/2016 | Shelton, IV et al. |
| 9,439,650 | B2 | 9/2016 | McGuckin, Jr. et al. |
| 9,439,651 | B2 | 9/2016 | Smith et al. |
| 9,439,668 | B2 | 9/2016 | Timm et al. |
| 9,445,808 | B2 | 9/2016 | Woodard, Jr. et al. |
| 9,445,813 | B2 | 9/2016 | Shelton, IV et al. |
| 9,445,816 | B2 | 9/2016 | Swayze et al. |

(56) References Cited

U.S. PATENT DOCUMENTS

| | | | |
|---|---|---|---|
| 9,445,817 | B2 | 9/2016 | Bettuchi |
| 9,446,226 | B2 | 9/2016 | Zilberman |
| 9,451,938 | B2 | 9/2016 | Overes et al. |
| 9,451,958 | B2 | 9/2016 | Shelton, IV et al. |
| 9,452,020 | B2 | 9/2016 | Griffiths et al. |
| D768,152 | S | 10/2016 | Gutierrez et al. |
| D768,156 | S | 10/2016 | Frincke |
| D768,167 | S | 10/2016 | Jones et al. |
| D769,315 | S | 10/2016 | Scotti |
| D769,930 | S | 10/2016 | Agrawal |
| 9,461,340 | B2 | 10/2016 | Li et al. |
| 9,463,012 | B2 | 10/2016 | Bonutti et al. |
| 9,463,040 | B2 | 10/2016 | Jeong et al. |
| 9,463,260 | B2 | 10/2016 | Stopek |
| 9,468,438 | B2 | 10/2016 | Baber et al. |
| 9,468,447 | B2 | 10/2016 | Aman et al. |
| 9,470,297 | B2 | 10/2016 | Aranyi et al. |
| 9,471,969 | B2 | 10/2016 | Zeng et al. |
| 9,474,506 | B2 | 10/2016 | Magnin et al. |
| 9,474,513 | B2 | 10/2016 | Ishida et al. |
| 9,474,523 | B2 | 10/2016 | Meade et al. |
| 9,474,540 | B2 | 10/2016 | Stokes et al. |
| 9,475,180 | B2 | 10/2016 | Eshleman et al. |
| 9,477,649 | B1 | 10/2016 | Davidson et al. |
| D770,476 | S | 11/2016 | Jitkoff et al. |
| D770,515 | S | 11/2016 | Cho et al. |
| D771,116 | S | 11/2016 | Dellinger et al. |
| D772,905 | S | 11/2016 | Ingenlath |
| 9,480,476 | B2 | 11/2016 | Aldridge et al. |
| 9,480,492 | B2 | 11/2016 | Aranyi et al. |
| 9,483,095 | B2 | 11/2016 | Tran et al. |
| 9,486,186 | B2 | 11/2016 | Fiebig et al. |
| 9,486,213 | B2 | 11/2016 | Altman et al. |
| 9,486,214 | B2 | 11/2016 | Shelton, IV |
| 9,486,215 | B2 | 11/2016 | Olson et al. |
| 9,486,302 | B2 | 11/2016 | Boey et al. |
| 9,488,197 | B2 | 11/2016 | Wi |
| 9,492,146 | B2 | 11/2016 | Kostrzewski et al. |
| 9,492,167 | B2 | 11/2016 | Shelton, IV et al. |
| 9,492,170 | B2 | 11/2016 | Bear et al. |
| 9,492,172 | B2 | 11/2016 | Weisshaupt et al. |
| 9,492,189 | B2 | 11/2016 | Williams et al. |
| 9,492,192 | B2 | 11/2016 | To et al. |
| 9,492,237 | B2 | 11/2016 | Kang et al. |
| 9,498,213 | B2 | 11/2016 | Marczyk et al. |
| 9,498,219 | B2 | 11/2016 | Moore et al. |
| 9,498,231 | B2 | 11/2016 | Haider et al. |
| 9,504,455 | B2 | 11/2016 | Whitman et al. |
| 9,504,483 | B2 | 11/2016 | Houser et al. |
| 9,504,520 | B2 | 11/2016 | Worrell et al. |
| 9,504,521 | B2 | 11/2016 | Deutmeyer et al. |
| 9,504,528 | B2 | 11/2016 | Ivinson et al. |
| 9,507,399 | B2 | 11/2016 | Chien |
| D774,547 | S | 12/2016 | Capela et al. |
| D775,336 | S | 12/2016 | Shelton, IV et al. |
| 9,510,827 | B2 | 12/2016 | Kostrzewski |
| 9,510,828 | B2 | 12/2016 | Yates et al. |
| 9,510,830 | B2 | 12/2016 | Shelton, IV et al. |
| 9,510,846 | B2 | 12/2016 | Sholev et al. |
| 9,510,895 | B2 | 12/2016 | Houser et al. |
| 9,510,925 | B2 | 12/2016 | Hotter et al. |
| 9,515,366 | B2 | 12/2016 | Herbsommer et al. |
| 9,517,063 | B2 | 12/2016 | Swayze et al. |
| 9,517,065 | B2 | 12/2016 | Simms et al. |
| 9,517,068 | B2 | 12/2016 | Shelton, IV et al. |
| 9,517,326 | B2 | 12/2016 | Hinman et al. |
| 9,521,996 | B2 | 12/2016 | Armstrong |
| 9,522,003 | B2 | 12/2016 | Weir et al. |
| 9,522,005 | B2 | 12/2016 | Williams et al. |
| 9,522,014 | B2 | 12/2016 | Nishizawa et al. |
| 9,522,029 | B2 | 12/2016 | Yates et al. |
| 9,526,481 | B2 | 12/2016 | Storz et al. |
| 9,526,499 | B2 | 12/2016 | Kostrzewski et al. |
| 9,526,563 | B2 | 12/2016 | Twomey |
| 9,526,564 | B2 | 12/2016 | Rusin |
| 9,526,921 | B2 | 12/2016 | Kimball et al. |
| D776,683 | S | 1/2017 | Gobinski et al. |
| D777,773 | S | 1/2017 | Shi |
| 9,532,783 | B2 | 1/2017 | Swayze et al. |
| 9,539,060 | B2 | 1/2017 | Lightcap et al. |
| 9,539,726 | B2 | 1/2017 | Simaan et al. |
| 9,545,253 | B2 | 1/2017 | Worrell et al. |
| 9,545,258 | B2 | 1/2017 | Smith et al. |
| 9,549,732 | B2 | 1/2017 | Yates et al. |
| 9,549,733 | B2 | 1/2017 | Knodel |
| 9,549,735 | B2 | 1/2017 | Shelton, IV et al. |
| 9,549,750 | B2 | 1/2017 | Shelton, IV et al. |
| 9,554,794 | B2 | 1/2017 | Baber et al. |
| 9,554,796 | B2 | 1/2017 | Kostrzewski |
| 9,554,803 | B2 | 1/2017 | Smith et al. |
| 9,554,812 | B2 | 1/2017 | Inkpen et al. |
| 9,554,854 | B2 | 1/2017 | Yates et al. |
| 9,559,624 | B2 | 1/2017 | Philipp |
| 9,561,013 | B2 | 2/2017 | Tsuchiya |
| 9,561,029 | B2 | 2/2017 | Scheib et al. |
| 9,561,030 | B2 | 2/2017 | Zhang et al. |
| 9,561,031 | B2 | 2/2017 | Heinrich et al. |
| 9,561,032 | B2 | 2/2017 | Shelton, IV et al. |
| 9,561,038 | B2 | 2/2017 | Shelton, IV et al. |
| 9,561,045 | B2 | 2/2017 | Hinman et al. |
| 9,561,072 | B2 | 2/2017 | Ko |
| 9,561,082 | B2 | 2/2017 | Yen et al. |
| 9,566,061 | B2 | 2/2017 | Aronhalt et al. |
| 9,566,062 | B2 | 2/2017 | Boudreaux |
| 9,566,064 | B2 | 2/2017 | Williams et al. |
| 9,566,065 | B2 | 2/2017 | Knodel |
| 9,566,067 | B2 | 2/2017 | Milliman et al. |
| 9,572,552 | B1 | 2/2017 | Bodor et al. |
| 9,572,574 | B2 | 2/2017 | Shelton, IV et al. |
| 9,572,576 | B2 | 2/2017 | Hodgkinson et al. |
| 9,572,577 | B2 | 2/2017 | Lloyd et al. |
| 9,572,592 | B2 | 2/2017 | Price et al. |
| 9,574,644 | B2 | 2/2017 | Parihar |
| 9,579,088 | B2 | 2/2017 | Farritor et al. |
| 9,579,143 | B2 | 2/2017 | Ullrich et al. |
| 9,579,158 | B2 | 2/2017 | Brianza et al. |
| D780,803 | S | 3/2017 | Gill et al. |
| D781,879 | S | 3/2017 | Butcher et al. |
| D782,530 | S | 3/2017 | Paek et al. |
| 9,585,550 | B2 | 3/2017 | Abel et al. |
| 9,585,657 | B2 | 3/2017 | Shelton, IV et al. |
| 9,585,658 | B2 | 3/2017 | Shelton, IV |
| 9,585,659 | B2 | 3/2017 | Viola et al. |
| 9,585,660 | B2 | 3/2017 | Laurent et al. |
| 9,585,662 | B2 | 3/2017 | Shelton, IV et al. |
| 9,585,663 | B2 | 3/2017 | Shelton, IV et al. |
| 9,585,672 | B2 | 3/2017 | Bastia |
| 9,590,433 | B2 | 3/2017 | Li |
| 9,592,050 | B2 | 3/2017 | Schmid et al. |
| 9,592,052 | B2 | 3/2017 | Shelton, IV |
| 9,592,053 | B2 | 3/2017 | Shelton, IV et al. |
| 9,592,054 | B2 | 3/2017 | Schmid et al. |
| 9,597,073 | B2 | 3/2017 | Sorrentino et al. |
| 9,597,075 | B2 | 3/2017 | Shelton, IV et al. |
| 9,597,078 | B2 | 3/2017 | Scirica et al. |
| 9,597,080 | B2 | 3/2017 | Milliman et al. |
| 9,597,104 | B2 | 3/2017 | Nicholas et al. |
| 9,597,143 | B2 | 3/2017 | Madan et al. |
| 9,603,595 | B2 | 3/2017 | Shelton, IV et al. |
| 9,603,598 | B2 | 3/2017 | Shelton, IV et al. |
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |

(56) References Cited

U.S. PATENT DOCUMENTS 9,629,628 B2 4/2017 Aranyi
9,629,629 B2 4/2017 Leimbach et al.
9,629,631 B2 4/2017 Nicholas et al.
9,629,632 B2 4/2017 Linder et al.
9,629,652 B2 4/2017 Mumaw et al.
9,629,814 B2 4/2017 Widenhouse et al.
D785,794 S 5/2017 Magno, Jr.
D786,280 S 5/2017 Ma
D786,896 S 5/2017 Kim et al.
D787,547 S 5/2017 Basargin et al.
D788,123 S 5/2017 Shan et al.
D788,140 S 5/2017 Hemsley et al.
9,636,091 B2 5/2017 Beardsley et al.
9,636,111 B2 5/2017 Wenchell
9,636,112 B2 5/2017 Penna et al.
9,636,113 B2 5/2017 Wenchell
9,636,850 B2 5/2017 Stopek (Nee Prommersberger) et al.
9,641,122 B2 5/2017 Romanowich et al.
9,642,620 B2 5/2017 Baxter, III et al.
9,642,642 B2 5/2017 Lim
9,649,096 B2 5/2017 Sholev
9,649,110 B2 5/2017 Parihar et al.
9,649,111 B2 5/2017 Shelton, IV et al.
9,649,190 B2 5/2017 Mathies
9,651,032 B2 5/2017 Weaver et al.
9,655,613 B2 5/2017 Schaller
9,655,614 B2 5/2017 Swensgard et al.
9,655,615 B2 5/2017 Knodel et al.
9,655,616 B2 5/2017 Aranyi
9,655,624 B2 5/2017 Shelton, IV et al.
9,661,991 B2 5/2017 Glossop
9,662,108 B2 5/2017 Williams
9,662,110 B2 5/2017 Huang et al.
9,662,111 B2 5/2017 Holsten et al.
9,662,116 B2 5/2017 Smith et al.
9,662,130 B2 * 5/2017 Bartels ............... A61B 17/2816
9,662,131 B2 5/2017 Omori et al.
D788,792 S 6/2017 Alessandri et al.
D789,384 S 6/2017 Lin et al.
D790,570 S 6/2017 Butcher et al.
9,668,728 B2 6/2017 Williams et al.
9,668,729 B2 6/2017 Williams et al.
9,668,732 B2 6/2017 Patel et al.
9,668,733 B2 6/2017 Williams
9,668,734 B2 6/2017 Kostrzewski et al.
9,668,735 B2 6/2017 Beetel
9,675,344 B2 6/2017 Combrowski et al.
9,675,348 B2 6/2017 Smith et al.
9,675,351 B2 6/2017 Hodgkinson et al.
9,675,354 B2 6/2017 Weir et al.
9,675,355 B2 6/2017 Shelton, IV et al.
9,675,368 B2 6/2017 Guo et al.
9,675,372 B2 6/2017 Laurent et al.
9,675,375 B2 6/2017 Houser et al.
9,675,405 B2 6/2017 Trees et al.
9,675,819 B2 6/2017 Dunbar et al.
9,681,870 B2 6/2017 Baxter et al.
9,681,873 B2 6/2017 Smith et al.
9,681,884 B2 6/2017 Clem et al.
9,687,230 B2 6/2017 Leimbach et al.
9,687,231 B2 6/2017 Baxter, III et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,315 B2 7/2017 Chen et al.
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,700,334 B2 7/2017 Hinman et al.
9,700,381 B2 7/2017 Amat Girbau
9,702,823 B2 7/2017 Maher et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,466 B2 7/2017 Kostrzewski
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,730,757 B2 8/2017 Brudniok
9,731,410 B2 8/2017 Hirabayashi et al.
9,733,663 B2 8/2017 Leimbach et al.
9,737,297 B2 8/2017 Racenet et al.
9,737,298 B2 8/2017 Isbell, Jr.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,323 B2 8/2017 Thapliyal et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,751,176 B2 9/2017 McRoberts et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.

(56) References Cited

U.S. PATENT DOCUMENTS

| | | | |
|---|---|---|---|
| 9,775,608 | B2 | 10/2017 | Aronhalt et al. |
| 9,775,609 | B2 | 10/2017 | Shelton, IV et al. |
| 9,775,610 | B2 | 10/2017 | Nicholas et al. |
| 9,775,611 | B2 | 10/2017 | Kostrzewski |
| 9,775,613 | B2 | 10/2017 | Shelton, IV et al. |
| 9,775,614 | B2 | 10/2017 | Shelton, IV et al. |
| 9,775,618 | B2 | 10/2017 | Bettuchi et al. |
| 9,775,635 | B2 | 10/2017 | Takei |
| 9,775,678 | B2 | 10/2017 | Lohmeier |
| 9,782,169 | B2 | 10/2017 | Kimsey et al. |
| 9,782,170 | B2 | 10/2017 | Zemlok et al. |
| 9,782,180 | B2 | 10/2017 | Smith et al. |
| 9,782,187 | B2 | 10/2017 | Zergiebel et al. |
| 9,782,193 | B2 | 10/2017 | Thistle |
| 9,782,214 | B2 | 10/2017 | Houser et al. |
| 9,788,834 | B2 | 10/2017 | Schmid et al. |
| 9,788,835 | B2 | 10/2017 | Morgan et al. |
| 9,788,836 | B2 | 10/2017 | Overmyer et al. |
| 9,788,847 | B2 | 10/2017 | Jinno |
| 9,788,851 | B2 | 10/2017 | Dannaher et al. |
| 9,788,902 | B2 | 10/2017 | Inoue et al. |
| 9,795,379 | B2 | 10/2017 | Leimbach et al. |
| 9,795,380 | B2 | 10/2017 | Shelton, IV et al. |
| 9,795,381 | B2 | 10/2017 | Shelton, IV |
| 9,795,382 | B2 | 10/2017 | Shelton, IV |
| 9,795,383 | B2 | 10/2017 | Aldridge et al. |
| 9,795,384 | B2 | 10/2017 | Weaner et al. |
| 9,797,486 | B2 | 10/2017 | Zergiebel et al. |
| 9,801,626 | B2 | 10/2017 | Parihar et al. |
| 9,801,627 | B2 | 10/2017 | Harris et al. |
| 9,801,628 | B2 | 10/2017 | Harris et al. |
| 9,801,634 | B2 | 10/2017 | Shelton, IV et al. |
| 9,801,679 | B2 | 10/2017 | Trees et al. |
| 9,802,033 | B2 | 10/2017 | Hibner et al. |
| 9,804,618 | B2 | 10/2017 | Leimbach et al. |
| D803,234 | S | 11/2017 | Day et al. |
| D803,235 | S | 11/2017 | Markson et al. |
| D803,850 | S | 11/2017 | Chang et al. |
| 9,808,244 | B2 | 11/2017 | Leimbach et al. |
| 9,808,246 | B2 | 11/2017 | Shelton, IV et al. |
| 9,808,247 | B2 | 11/2017 | Shelton, IV et al. |
| 9,808,248 | B2 | 11/2017 | Hoffman |
| 9,808,249 | B2 | 11/2017 | Shelton, IV |
| 9,814,460 | B2 | 11/2017 | Kimsey et al. |
| 9,814,462 | B2 | 11/2017 | Woodard, Jr. et al. |
| 9,814,463 | B2 | 11/2017 | Williams et al. |
| 9,814,530 | B2 | 11/2017 | Weir et al. |
| 9,814,561 | B2 | 11/2017 | Forsell |
| 9,815,118 | B1 | 11/2017 | Schmitt et al. |
| 9,820,445 | B2 | 11/2017 | Simpson et al. |
| 9,820,737 | B2 | 11/2017 | Beardsley et al. |
| 9,820,738 | B2 | 11/2017 | Lytle, IV et al. |
| 9,820,741 | B2 | 11/2017 | Kostrzewski |
| 9,820,768 | B2 | 11/2017 | Gee et al. |
| 9,825,455 | B2 | 11/2017 | Sandhu et al. |
| 9,826,976 | B2 | 11/2017 | Parihar et al. |
| 9,826,977 | B2 | 11/2017 | Leimbach et al. |
| 9,826,978 | B2 | 11/2017 | Shelton, IV et al. |
| 9,829,698 | B2 | 11/2017 | Haraguchi et al. |
| D806,108 | S | 12/2017 | Day |
| 9,833,235 | B2 | 12/2017 | Penna et al. |
| 9,833,236 | B2 | 12/2017 | Shelton, IV et al. |
| 9,833,238 | B2 | 12/2017 | Baxter, III et al. |
| 9,833,239 | B2 | 12/2017 | Yates et al. |
| 9,833,241 | B2 | 12/2017 | Huitema et al. |
| 9,833,242 | B2 | 12/2017 | Baxter, III et al. |
| 9,839,420 | B2 | 12/2017 | Shelton, IV et al. |
| 9,839,421 | B2 | 12/2017 | Zerkle et al. |
| 9,839,422 | B2 | 12/2017 | Schellin et al. |
| 9,839,423 | B2 | 12/2017 | Vendely et al. |
| 9,839,427 | B2 | 12/2017 | Swayze et al. |
| 9,839,428 | B2 | 12/2017 | Baxter, III et al. |
| 9,839,429 | B2 | 12/2017 | Weisenburgh, II et al. |
| 9,839,480 | B2 | 12/2017 | Pribanic et al. |
| 9,839,481 | B2 | 12/2017 | Blumenkranz et al. |
| 9,844,368 | B2 | 12/2017 | Boudreaux et al. |
| 9,844,369 | B2 | 12/2017 | Huitema et al. |
| 9,844,372 | B2 | 12/2017 | Shelton, IV et al. |
| 9,844,373 | B2 | 12/2017 | Swayze et al. |
| 9,844,374 | B2 | 12/2017 | Lytle, IV et al. |
| 9,844,375 | B2 | 12/2017 | Overmyer et al. |
| 9,844,376 | B2 | 12/2017 | Baxter, III et al. |
| 9,844,379 | B2 | 12/2017 | Shelton, IV et al. |
| 9,848,871 | B2 | 12/2017 | Harris et al. |
| 9,848,873 | B2 | 12/2017 | Shelton, IV |
| 9,848,875 | B2 | 12/2017 | Aronhalt et al. |
| 9,848,877 | B2 | 12/2017 | Shelton, IV et al. |
| 9,850,994 | B2 | 12/2017 | Schena |
| D808,989 | S | 1/2018 | Ayvazian et al. |
| 9,855,039 | B2 | 1/2018 | Racenet et al. |
| 9,855,040 | B2 | 1/2018 | Kostrzewski |
| 9,855,662 | B2 | 1/2018 | Ruiz Morales et al. |
| 9,861,261 | B2 | 1/2018 | Shahinian |
| 9,861,359 | B2 | 1/2018 | Shelton, IV et al. |
| 9,861,361 | B2 | 1/2018 | Aronhalt et al. |
| 9,861,362 | B2 | 1/2018 | Whitman et al. |
| 9,861,366 | B2 | 1/2018 | Aranyi |
| 9,861,382 | B2 | 1/2018 | Smith et al. |
| 9,861,446 | B2 | 1/2018 | Lang |
| 9,867,612 | B2 | 1/2018 | Parihar et al. |
| 9,867,613 | B2 | 1/2018 | Marczyk et al. |
| 9,867,615 | B2 | 1/2018 | Fanelli et al. |
| 9,867,617 | B2 | 1/2018 | Ma |
| 9,867,618 | B2 | 1/2018 | Hall et al. |
| 9,867,620 | B2 | 1/2018 | Fischvogt et al. |
| 9,868,198 | B2 | 1/2018 | Nicholas et al. |
| 9,872,682 | B2 | 1/2018 | Hess et al. |
| 9,872,683 | B2 | 1/2018 | Hopkins et al. |
| 9,872,684 | B2 | 1/2018 | Hall et al. |
| 9,872,722 | B2 | 1/2018 | Lech |
| 9,877,721 | B2 | 1/2018 | Schellin et al. |
| 9,877,722 | B2 | 1/2018 | Schellin et al. |
| 9,877,723 | B2 | 1/2018 | Hall et al. |
| 9,877,776 | B2 | 1/2018 | Boudreaux |
| D810,099 | S | 2/2018 | Riedel |
| 9,883,843 | B2 | 2/2018 | Garlow |
| 9,883,860 | B2 | 2/2018 | Leimbach |
| 9,883,861 | B2 | 2/2018 | Shelton, IV et al. |
| 9,884,456 | B2 | 2/2018 | Schellin et al. |
| 9,888,914 | B2 | 2/2018 | Martin et al. |
| 9,888,919 | B2 | 2/2018 | Leimbach et al. |
| 9,888,921 | B2 | 2/2018 | Williams et al. |
| 9,888,924 | B2 | 2/2018 | Ebersole et al. |
| 9,889,230 | B2 | 2/2018 | Bennett et al. |
| 9,895,147 | B2 | 2/2018 | Shelton, IV |
| 9,895,148 | B2 | 2/2018 | Shelton, IV et al. |
| 9,895,813 | B2 | 2/2018 | Blumenkranz et al. |
| 9,901,339 | B2 | 2/2018 | Farascioni |
| 9,901,341 | B2 | 2/2018 | Kostrzewski |
| 9,901,342 | B2 | 2/2018 | Shelton, IV et al. |
| 9,901,344 | B2 | 2/2018 | Moore et al. |
| 9,901,345 | B2 | 2/2018 | Moore et al. |
| 9,901,346 | B2 | 2/2018 | Moore et al. |
| 9,901,358 | B2 | 2/2018 | Faller et al. |
| 9,901,406 | B2 | 2/2018 | State et al. |
| 9,901,412 | B2 | 2/2018 | Lathrop et al. |
| D813,899 | S | 3/2018 | Erant et al. |
| 9,907,456 | B2 | 3/2018 | Miyoshi |
| 9,907,552 | B2 | 3/2018 | Measamer et al. |
| 9,907,553 | B2 | 3/2018 | Cole et al. |
| 9,907,600 | B2 | 3/2018 | Stulen et al. |
| 9,907,620 | B2 | 3/2018 | Shelton, IV et al. |
| 9,913,641 | B2 | 3/2018 | Takemoto et al. |
| 9,913,642 | B2 | 3/2018 | Leimbach et al. |
| 9,913,644 | B2 | 3/2018 | McCuen |
| 9,913,646 | B2 | 3/2018 | Shelton, IV |
| 9,913,647 | B2 | 3/2018 | Weisenburgh, II et al. |
| 9,913,648 | B2 | 3/2018 | Shelton, IV et al. |
| 9,913,694 | B2 | 3/2018 | Brisson |
| 9,913,733 | B2 | 3/2018 | Piron et al. |
| 9,918,704 | B2 | 3/2018 | Shelton, IV et al. |
| 9,918,714 | B2 | 3/2018 | Gibbons, Jr. |
| 9,918,715 | B2 | 3/2018 | Menn |
| 9,918,716 | B2 | 3/2018 | Baxter, III et al. |

(56) References Cited

U.S. PATENT DOCUMENTS 9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,117 B2 4/2018 Hathaway et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,740 B2 5/2018 Krause et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,006 B2 6/2018 Morgan et al.
9,987,008 B2 6/2018 Scirica et al.
9,987,095 B2 6/2018 Chowaniec et al.
9,987,097 B2 6/2018 Van Der Weide et al.
9,987,099 B2 6/2018 Chen et al.
9,993,248 B2 6/2018 Shelton, IV et al.
9,993,258 B2 6/2018 Shelton, IV et al.
9,993,284 B2 6/2018 Boudreaux
9,999,408 B2 6/2018 Boudreaux et al.
9,999,423 B2 6/2018 Schuckmann et al.
9,999,426 B2 6/2018 Moore et al.
9,999,431 B2 6/2018 Shelton, IV et al.
9,999,472 B2 6/2018 Weir et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
10,004,552 B1 6/2018 Kleyman et al.
D822,206 S 7/2018 Shelton, IV et al.
10,010,322 B2 7/2018 Shelton, IV et al.
10,010,324 B2 7/2018 Huitema et al.
10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,120 B2 7/2018 Martin et al.
10,022,123 B2 7/2018 Williams et al.
10,022,125 B2 7/2018 (Prommersberger) Stopek et al.
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,642 B2 9/2018 Marczyk et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 (Soda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.

(56) References Cited

U.S. PATENT DOCUMENTS

| | | | |
|---|---|---|---|
| 10,098,640 | B2 | 10/2018 | Bertolero et al. |
| 10,098,642 | B2 | 10/2018 | Baxter, III et al. |
| 10,099,303 | B2 | 10/2018 | Yoshida et al. |
| 10,101,861 | B2 | 10/2018 | Kiyoto |
| 10,105,126 | B2 | 10/2018 | Sauer |
| 10,105,128 | B2 | 10/2018 | Cooper et al. |
| 10,105,136 | B2 | 10/2018 | Yates et al. |
| 10,105,139 | B2 | 10/2018 | Yates et al. |
| 10,105,140 | B2 | 10/2018 | Malinouskas et al. |
| 10,105,142 | B2 | 10/2018 | Baxter, III et al. |
| 10,105,149 | B2 | 10/2018 | Haider et al. |
| 10,106,932 | B2 | 10/2018 | Anderson et al. |
| 10,111,657 | B2 | 10/2018 | McCuen |
| 10,111,658 | B2 | 10/2018 | Chowaniec et al. |
| 10,111,660 | B2 | 10/2018 | Hemmann |
| 10,111,665 | B2 | 10/2018 | Aranyi et al. |
| 10,111,679 | B2 | 10/2018 | Baber et al. |
| 10,111,698 | B2 | 10/2018 | Scheib et al. |
| 10,111,702 | B2 | 10/2018 | Kostrzewski |
| D833,608 | S | 11/2018 | Miller et al. |
| 10,117,649 | B2 | 11/2018 | Baxter et al. |
| 10,117,650 | B2 | 11/2018 | Nicholas et al. |
| 10,117,652 | B2 | 11/2018 | Schmid et al. |
| 10,117,653 | B2 | 11/2018 | Leimbach et al. |
| 10,117,654 | B2 | 11/2018 | Ingmanson et al. |
| 10,123,798 | B2 | 11/2018 | Baxter et al. |
| 10,123,845 | B2 | 11/2018 | Yeung |
| 10,124,493 | B2 | 11/2018 | Rothfuss et al. |
| 10,130,352 | B2 | 11/2018 | Widenhouse et al. |
| 10,130,359 | B2 | 11/2018 | Hess et al. |
| 10,130,360 | B2 | 11/2018 | Olson et al. |
| 10,130,361 | B2 | 11/2018 | Yates et al. |
| 10,130,363 | B2 | 11/2018 | Huitema et al. |
| 10,130,366 | B2 | 11/2018 | Shelton, IV et al. |
| 10,130,367 | B2 | 11/2018 | Cappola et al. |
| 10,130,382 | B2 | 11/2018 | Gladstone |
| 10,130,738 | B2 | 11/2018 | Shelton, IV et al. |
| 10,130,830 | B2 | 11/2018 | Miret Carceller et al. |
| 10,133,248 | B2 | 11/2018 | Fitzsimmons et al. |
| 10,135,242 | B2 | 11/2018 | Baber et al. |
| 10,136,879 | B2 | 11/2018 | Ross et al. |
| 10,136,887 | B2 | 11/2018 | Shelton, IV et al. |
| 10,136,889 | B2 | 11/2018 | Shelton, IV et al. |
| 10,136,890 | B2 | 11/2018 | Shelton, IV et al. |
| 10,136,891 | B2 | 11/2018 | Shelton, IV et al. |
| 10,136,949 | B2 | 11/2018 | Felder et al. |
| D835,659 | S | 12/2018 | Anzures et al. |
| D836,124 | S | 12/2018 | Fan |
| 10,143,474 | B2 | 12/2018 | Bucciaglia et al. |
| 10,146,423 | B1 | 12/2018 | Reed et al. |
| 10,149,679 | B2 | 12/2018 | Shelton, IV et al. |
| 10,149,680 | B2 | 12/2018 | Parihar et al. |
| 10,149,682 | B2 | 12/2018 | Shelton, IV et al. |
| 10,149,683 | B2 | 12/2018 | Smith et al. |
| 10,149,712 | B2 | 12/2018 | Manwaring et al. |
| 10,152,789 | B2 | 12/2018 | Carnes et al. |
| 10,154,841 | B2 | 12/2018 | Weaner et al. |
| 10,159,481 | B2 | 12/2018 | Whitman et al. |
| 10,159,482 | B2 | 12/2018 | Swayze et al. |
| 10,159,483 | B2 | 12/2018 | Beckman et al. |
| 10,159,506 | B2 | 12/2018 | Boudreaux et al. |
| 10,161,816 | B2 | 12/2018 | Jackson et al. |
| 10,163,065 | B1 | 12/2018 | Koski et al. |
| 10,163,589 | B2 | 12/2018 | Zergiebel et al. |
| 10,164,466 | B2 | 12/2018 | Calderoni |
| D837,244 | S | 1/2019 | Kuo et al. |
| D837,245 | S | 1/2019 | Kuo et al. |
| 10,166,023 | B2 | 1/2019 | Vendely et al. |
| 10,166,025 | B2 | 1/2019 | Leimbach et al. |
| 10,166,026 | B2 | 1/2019 | Shelton, IV et al. |
| 10,172,611 | B2 | 1/2019 | Shelton, IV et al. |
| 10,172,615 | B2 | 1/2019 | Marczyk et al. |
| 10,172,616 | B2 | 1/2019 | Murray et al. |
| 10,172,617 | B2 | 1/2019 | Shelton, IV et al. |
| 10,172,618 | B2 | 1/2019 | Shelton, IV et al. |
| 10,172,619 | B2 | 1/2019 | Harris et al. |
| 10,172,620 | B2 | 1/2019 | Harris et al. |
| 10,172,636 | B2 | 1/2019 | Stulen et al. |
| 10,172,669 | B2 | 1/2019 | Felder et al. |
| 10,175,127 | B2 | 1/2019 | Collins et al. |
| 10,178,992 | B2 | 1/2019 | Wise et al. |
| 10,180,463 | B2 | 1/2019 | Beckman et al. |
| 10,182,813 | B2 | 1/2019 | Leimbach et al. |
| 10,182,815 | B2 | 1/2019 | Williams et al. |
| 10,182,816 | B2 | 1/2019 | Shelton, IV et al. |
| 10,182,818 | B2 | 1/2019 | Hensel et al. |
| 10,182,819 | B2 | 1/2019 | Shelton, IV |
| 10,182,868 | B2 | 1/2019 | Meier et al. |
| 10,188,385 | B2 | 1/2019 | Kerr et al. |
| 10,188,389 | B2 | 1/2019 | Vendely et al. |
| 10,188,393 | B2 | 1/2019 | Smith et al. |
| 10,188,394 | B2 | 1/2019 | Shelton, IV et al. |
| 10,190,888 | B2 | 1/2019 | Hryb et al. |
| D839,900 | S | 2/2019 | Gan |
| D841,667 | S | 2/2019 | Coren |
| 10,194,801 | B2 | 2/2019 | Elhawary et al. |
| 10,194,904 | B2 | 2/2019 | Viola et al. |
| 10,194,907 | B2 | 2/2019 | Marczyk et al. |
| 10,194,908 | B2 | 2/2019 | Duque et al. |
| 10,194,910 | B2 | 2/2019 | Shelton, IV et al. |
| 10,194,911 | B2 | 2/2019 | Miller et al. |
| 10,194,912 | B2 | 2/2019 | Scheib et al. |
| 10,194,913 | B2 | 2/2019 | Nalagatla et al. |
| 10,194,976 | B2 | 2/2019 | Boudreaux |
| 10,194,992 | B2 | 2/2019 | Robinson |
| 10,201,348 | B2 | 2/2019 | Scheib et al. |
| 10,201,349 | B2 | 2/2019 | Leimbach et al. |
| 10,201,363 | B2 | 2/2019 | Shelton, IV |
| 10,201,364 | B2 | 2/2019 | Leimbach et al. |
| 10,201,365 | B2 | 2/2019 | Boudreaux et al. |
| 10,201,381 | B2 | 2/2019 | Zergiebel et al. |
| 10,206,605 | B2 | 2/2019 | Shelton, IV et al. |
| 10,206,676 | B2 | 2/2019 | Shelton, IV |
| 10,206,677 | B2 | 2/2019 | Harris et al. |
| 10,206,678 | B2 | 2/2019 | Shelton, IV et al. |
| 10,206,748 | B2 | 2/2019 | Burbank |
| 10,210,244 | B1 | 2/2019 | Branavan et al. |
| 10,211,586 | B2 | 2/2019 | Adams et al. |
| 10,213,198 | B2 | 2/2019 | Aronhalt et al. |
| 10,213,201 | B2 | 2/2019 | Shelton, IV et al. |
| 10,213,202 | B2 | 2/2019 | Flanagan et al. |
| 10,213,203 | B2 | 2/2019 | Swayze et al. |
| 10,213,204 | B2 | 2/2019 | Aranyi et al. |
| 10,213,262 | B2 | 2/2019 | Shelton, IV et al. |
| D842,328 | S | 3/2019 | Jian et al. |
| 10,219,811 | B2 | 3/2019 | Haider et al. |
| 10,219,832 | B2 | 3/2019 | Bagwell et al. |
| 10,220,522 | B2 | 3/2019 | Rockrohr |
| 10,226,239 | B2 | 3/2019 | Nicholas et al. |
| 10,226,249 | B2 | 3/2019 | Jaworek et al. |
| 10,226,250 | B2 | 3/2019 | Beckman et al. |
| 10,226,251 | B2 | 3/2019 | Scheib et al. |
| 10,226,274 | B2 | 3/2019 | Worrell et al. |
| 10,231,634 | B2 | 3/2019 | Zand et al. |
| 10,231,653 | B2 | 3/2019 | Bohm et al. |
| 10,231,734 | B2 | 3/2019 | Thompson et al. |
| 10,231,794 | B2 | 3/2019 | Shelton, IV et al. |
| 10,238,385 | B2 | 3/2019 | Yates et al. |
| 10,238,386 | B2 | 3/2019 | Overmyer et al. |
| 10,238,387 | B2 | 3/2019 | Yates et al. |
| 10,238,389 | B2 | 3/2019 | Yates et al. |
| 10,238,390 | B2 | 3/2019 | Harris et al. |
| 10,238,391 | B2 | 3/2019 | Leimbach et al. |
| D844,666 | S | 4/2019 | Espeleta et al. |
| D844,667 | S | 4/2019 | Espeleta et al. |
| D845,342 | S | 4/2019 | Espeleta et al. |
| D847,199 | S | 4/2019 | Whitmore |
| 10,244,991 | B2 | 4/2019 | Shademan et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,032 | B2 | 4/2019 | Shelton, IV |
| 10,245,033 | B2 | 4/2019 | Overmyer et al. |

(56) References Cited

U.S. PATENT DOCUMENTS 10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,645 B2 4/2019 Kostrzewski
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,363 B2 4/2019 Worrell et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,697 B2 5/2019 Shelton, IV et al.
10,278,702 B2 5/2019 Shelton, IV et al.
10,278,703 B2 5/2019 Nativ et al.
10,278,707 B2 5/2019 Thompson et al.
10,278,722 B2 5/2019 Shelton, IV et al.
10,278,780 B2 5/2019 Shelton, IV
10,285,694 B2 5/2019 Viola et al.
10,285,695 B2 5/2019 Jaworek et al.
10,285,699 B2 5/2019 Vendely et al.
10,285,700 B2 5/2019 Scheib
10,285,705 B2 5/2019 Shelton, IV et al.
10,285,724 B2 5/2019 Faller et al.
10,285,750 B2 5/2019 Coulson et al.
10,292,701 B2 5/2019 Scheib et al.
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,792 B2 5/2019 Huitema et al.
10,299,817 B2 5/2019 Shelton, IV et al.
10,299,818 B2 5/2019 Riva
10,299,878 B2 5/2019 Shelton, IV et al.
10,303,851 B2 5/2019 Nguyen et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,578 B2 6/2019 Leimbach et al.
10,314,579 B2 6/2019 Chowaniec et al.
10,314,580 B2 6/2019 Scheib et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,589 B2 6/2019 Shelton, IV et al.
10,314,590 B2 6/2019 Shelton, IV et al.
10,315,566 B2 6/2019 Choi et al.
10,321,907 B2 6/2019 Shelton, IV et al.
10,321,909 B2 6/2019 Shelton, IV et al.
10,321,927 B2 6/2019 Hinman
10,327,743 B2 6/2019 St. Goar et al.
10,327,764 B2 6/2019 Harris et al.
10,327,765 B2 6/2019 Timm et al.
10,327,767 B2 6/2019 Shelton, IV et al.
10,327,769 B2 6/2019 Overmyer et al.
10,327,776 B2 6/2019 Harris et al.
10,327,777 B2 6/2019 Harris et al.
D854,032 S 7/2019 Jones et al.
D854,151 S 7/2019 Shelton, IV et al.
10,335,144 B2 7/2019 Shelton, IV et al.
10,335,145 B2 7/2019 Harris et al.
10,335,147 B2 7/2019 Rector et al.
10,335,148 B2 7/2019 Shelton, IV et al.
10,335,149 B2 7/2019 Baxter, III et al.
10,335,150 B2 7/2019 Shelton, IV
10,335,151 B2 7/2019 Shelton, IV et al.
10,337,148 B2 7/2019 Rouse et al.
10,342,533 B2 7/2019 Shelton, IV et al.
10,342,535 B2 7/2019 Scheib et al.
10,342,541 B2 7/2019 Shelton, IV et al.
10,342,543 B2 7/2019 Shelton, IV et al.
10,342,623 B2 7/2019 Huelman et al.
10,349,937 B2 7/2019 Williams
10,349,939 B2 7/2019 Shelton, IV et al.
10,349,941 B2 7/2019 Marczyk et al.
10,349,963 B2 7/2019 Fiksen et al.
10,350,016 B2 7/2019 Burbank et al.
10,357,246 B2 7/2019 Shelton, IV et al.
10,357,247 B2 7/2019 Shelton, IV et al.
10,357,248 B2 7/2019 Dalessandro et al.
10,357,252 B2 7/2019 Harris et al.
10,363,031 B2 7/2019 Alexander et al.
10,363,033 B2 7/2019 Timm et al.
10,363,036 B2 7/2019 Yates et al.
10,363,037 B2 7/2019 Aronhalt et al.
D855,634 S 8/2019 Kim
D856,359 S 8/2019 Huang et al.
10,368,838 B2 8/2019 Williams et al.
10,368,861 B2 8/2019 Baxter et al.
10,368,863 B2 8/2019 Timm et al.
10,368,864 B2 8/2019 Harris et al.
10,368,865 B2 8/2019 Harris et al.
10,368,866 B2 8/2019 Wang et al.
10,368,867 B2 8/2019 Harris et al.
10,368,892 B2 8/2019 Stulen et al.
10,374,544 B2 8/2019 Yokoyama et al.
10,376,263 B2 8/2019 Morgan et al.
10,383,626 B2 8/2019 Soltz
10,383,628 B2 8/2019 Kang et al.
10,383,629 B2 8/2019 Ross et al.
10,383,630 B2 8/2019 Shelton, IV et al.
10,383,631 B2 8/2019 Collings et al.
10,383,633 B2 8/2019 Shelton, IV et al.
10,383,634 B2 8/2019 Shelton, IV et al.
10,390,823 B2 8/2019 Shelton, IV et al.
10,390,825 B2 8/2019 Shelton, IV et al.
10,390,828 B2 8/2019 Vendely et al.
10,390,829 B2 8/2019 Eckert et al.
10,390,830 B2 8/2019 Schulz
10,390,841 B2 8/2019 Shelton, IV et al.
10,390,897 B2 8/2019 Kostrzewski
D859,466 S 9/2019 Okada et al.
D860,219 S 9/2019 Rasmussen et al.
D861,035 S 9/2019 Park et al.
10,398,433 B2 9/2019 Boudreaux et al.
10,398,434 B2 9/2019 Shelton, IV et al.
10,398,436 B2 9/2019 Shelton, IV et al.
10,398,460 B2 9/2019 Overmyer

(56) References Cited

U.S. PATENT DOCUMENTS 10,404,136 B2 9/2019 Oktavec et al.
10,405,854 B2 9/2019 Schmid et al.
10,405,857 B2 9/2019 Shelton, IV et al.
10,405,859 B2 9/2019 Harris et al.
10,405,863 B2 9/2019 Wise et al.
10,405,914 B2 9/2019 Manwaring et al.
10,405,932 B2 9/2019 Overmyer
10,405,937 B2 9/2019 Black et al.
10,413,155 B2 9/2019 Inoue
10,413,291 B2 9/2019 Worthington et al.
10,413,293 B2 9/2019 Shelton, IV et al.
10,413,294 B2 9/2019 Shelton, IV et al.
10,413,297 B2 9/2019 Harris et al.
10,413,370 B2 9/2019 Yates et al.
10,413,373 B2 9/2019 Yates et al.
10,420,548 B2 9/2019 Whitman et al.
10,420,549 B2 9/2019 Yates et al.
10,420,550 B2 9/2019 Shelton, IV
10,420,551 B2 9/2019 Calderoni
10,420,552 B2 9/2019 Shelton, IV et al.
10,420,553 B2 9/2019 Shelton, IV et al.
10,420,554 B2 9/2019 Collings et al.
10,420,555 B2 9/2019 Shelton, IV et al.
10,420,558 B2 9/2019 Nalagatla et al.
10,420,559 B2 9/2019 Marczyk et al.
10,420,560 B2 9/2019 Shelton, IV et al.
10,420,561 B2 9/2019 Shelton, IV et al.
10,420,577 B2 9/2019 Chowaniec et al.
D861,707 S 10/2019 Yang
D862,518 S 10/2019 Niven et al.
D863,343 S 10/2019 Mazlish et al.
D864,388 S 10/2019 Barber
D865,174 S 10/2019 Auld et al.
D865,175 S 10/2019 Widenhouse et al.
10,426,463 B2 10/2019 Shelton, IV et al.
10,426,466 B2 10/2019 Contini et al.
10,426,467 B2 10/2019 Miller et al.
10,426,468 B2 10/2019 Contini et al.
10,426,469 B2 10/2019 Shelton, IV et al.
10,426,471 B2 10/2019 Shelton, IV et al.
10,426,476 B2 10/2019 Harris et al.
10,426,477 B2 10/2019 Harris et al.
10,426,478 B2 10/2019 Shelton, IV et al.
10,426,481 B2 10/2019 Aronhalt et al.
10,426,555 B2 10/2019 Crowley et al.
10,433,837 B2 10/2019 Worthington et al.
10,433,839 B2 10/2019 Scheib et al.
10,433,840 B2 10/2019 Shelton, IV et al.
10,433,842 B2 10/2019 Amariglio et al.
10,433,844 B2 10/2019 Shelton, IV et al.
10,433,845 B2 10/2019 Baxter, III et al.
10,433,846 B2 10/2019 Vendely et al.
10,433,849 B2 10/2019 Shelton, IV et al.
10,433,918 B2 10/2019 Shelton, IV et al.
10,441,279 B2 10/2019 Shelton, IV et al.
10,441,280 B2 10/2019 Timm et al.
10,441,281 B2 10/2019 Shelton, IV et al.
10,441,285 B2 10/2019 Shelton, IV et al.
10,441,286 B2 10/2019 Shelton, IV et al.
10,441,345 B2 10/2019 Aldridge et al.
10,441,369 B2 10/2019 Shelton, IV et al.
10,448,948 B2 10/2019 Shelton, IV et al.
10,448,950 B2 10/2019 Shelton, IV et al.
10,448,952 B2 10/2019 Shelton, IV et al.
10,456,122 B2 10/2019 Koltz et al.
10,456,132 B2 10/2019 Gettinger et al.
10,456,133 B2 10/2019 Yates et al.
10,456,137 B2 10/2019 Vendely et al.
10,456,140 B2 10/2019 Shelton, IV et al.
D865,796 S 11/2019 Xu et al.
10,463,367 B2 11/2019 Kostrzewski et al.
10,463,369 B2 11/2019 Shelton, IV et al.
10,463,370 B2 11/2019 Yates et al.
10,463,371 B2 11/2019 Kostrzewski
10,463,372 B2 11/2019 Shelton, IV et al.
10,463,373 B2 11/2019 Mozdzierz et al.
10,463,382 B2 11/2019 Ingmanson et al.
10,463,383 B2 11/2019 Shelton, IV et al.
10,463,384 B2 11/2019 Shelton, IV et al.
10,470,762 B2 11/2019 Leimbach et al.
10,470,763 B2 11/2019 Yates et al.
10,470,764 B2 11/2019 Baxter, III et al.
10,470,767 B2 11/2019 Gleiman et al.
10,470,768 B2 11/2019 Harris et al.
10,470,769 B2 11/2019 Shelton, IV et al.
10,471,282 B2 11/2019 Kirk et al.
10,471,576 B2 11/2019 Totsu
10,471,607 B2 11/2019 Butt et al.
10,478,181 B2 11/2019 Shelton, IV et al.
10,478,182 B2 11/2019 Taylor
10,478,185 B2 11/2019 Nicholas
10,478,187 B2 11/2019 Shelton, IV et al.
10,478,188 B2 11/2019 Harris et al.
10,478,189 B2 11/2019 Bear et al.
10,478,190 B2 11/2019 Miller et al.
10,478,207 B2 11/2019 Lathrop
10,482,292 B2 11/2019 Clouser et al.
10,485,536 B2 11/2019 Ming et al.
10,485,537 B2 11/2019 Yates et al.
10,485,539 B2 11/2019 Shelton, IV et al.
10,485,541 B2 11/2019 Shelton, IV et al.
10,485,542 B2 11/2019 Shelton, IV et al.
10,485,543 B2 11/2019 Shelton, IV et al.
10,485,546 B2 11/2019 Shelton, IV et al.
10,485,547 B2 11/2019 Shelton, IV et al.
D869,655 S 12/2019 Shelton, IV et al.
D870,742 S 12/2019 Cornell
10,492,783 B2 12/2019 Shelton, IV et al.
10,492,785 B2 12/2019 Overmyer et al.
10,492,787 B2 12/2019 Smith et al.
10,492,814 B2 12/2019 Snow et al.
10,492,847 B2 12/2019 Godara et al.
10,492,851 B2 12/2019 Hughett, Sr. et al.
10,498,269 B2 12/2019 Zemlok et al.
10,499,890 B2 12/2019 Shelton, IV et al.
10,499,914 B2 12/2019 Huang et al.
10,499,917 B2 12/2019 Scheib et al.
10,499,918 B2 12/2019 Schellin et al.
10,500,000 B2 12/2019 Swayze et al.
10,500,004 B2 12/2019 Hanuschik et al.
10,500,309 B2 12/2019 Shah et al.
10,507,034 B2 12/2019 Timm
10,508,720 B2 12/2019 Nicholas
10,512,461 B2 12/2019 Gupta et al.
10,512,462 B2 12/2019 Felder et al.
10,512,464 B2 12/2019 Park et al.
10,517,590 B2 12/2019 Giordano et al.
10,517,592 B2 12/2019 Shelton, IV et al.
10,517,594 B2 12/2019 Shelton, IV et al.
10,517,595 B2 12/2019 Hunter et al.
10,517,596 B2 12/2019 Hunter et al.
10,517,599 B2 12/2019 Baxter, III et al.
10,517,682 B2 12/2019 Giordano et al.
10,524,784 B2 1/2020 Kostrzewski
10,524,787 B2 1/2020 Shelton, IV et al.
10,524,788 B2 1/2020 Vendely et al.
10,524,789 B2 1/2020 Swayze et al.
10,524,790 B2 1/2020 Shelton, IV et al.
10,524,795 B2 1/2020 Nalagatla et al.
10,524,870 B2 1/2020 Saraliev et al.
10,531,874 B2 1/2020 Morgan et al.
10,531,887 B2 1/2020 Shelton, IV et al.
10,537,324 B2 1/2020 Shelton, IV et al.
10,537,325 B2 1/2020 Bakos et al.
10,537,351 B2 1/2020 Shelton, IV et al.
10,542,908 B2 1/2020 Mei et al.
10,542,974 B2 1/2020 Yates et al.
10,542,976 B2 1/2020 Calderoni et al.
10,542,978 B2 1/2020 Chowaniec et al.
10,542,979 B2 1/2020 Shelton, IV et al.
10,542,982 B2 1/2020 Beckman et al.
10,542,985 B2 1/2020 Zhan et al.
10,542,988 B2 1/2020 Schellin et al.
10,542,991 B2 1/2020 Shelton, IV et al.

(56) References Cited

U.S. PATENT DOCUMENTS 10,548,504 B2 2/2020 Shelton, IV et al.
10,548,593 B2 2/2020 Shelton, IV et al.
10,548,600 B2 2/2020 Shelton, IV et al.
10,548,673 B2 2/2020 Harris et al.
10,561,412 B2 2/2020 Bookbinder et al.
10,561,418 B2 2/2020 Richard et al.
10,561,419 B2 2/2020 Beardsley
10,561,420 B2 2/2020 Harris et al.
10,561,422 B2 2/2020 Schellin et al.
10,561,432 B2 2/2020 Estrella et al.
10,561,474 B2 2/2020 Adams et al.
10,562,160 B2 2/2020 Iwata et al.
10,568,493 B2 2/2020 Blase et al.
10,568,621 B2 2/2020 Shelton, IV et al.
10,568,624 B2 2/2020 Shelton, IV et al.
10,568,625 B2 2/2020 Harris et al.
10,568,626 B2 2/2020 Shelton, IV et al.
10,568,629 B2 2/2020 Shelton, IV et al.
10,568,632 B2 2/2020 Miller et al.
10,568,652 B2 2/2020 Hess et al.
10,569,071 B2 2/2020 Harris et al.
D879,808 S 3/2020 Harris et al.
D879,809 S 3/2020 Harris et al.
10,575,868 B2 3/2020 Hall et al.
10,580,320 B2 3/2020 Kamiguchi et al.
10,582,928 B2 3/2020 Hunter et al.
10,588,231 B2 3/2020 Sgroi, Jr. et al.
10,588,623 B2 3/2020 Schmid et al.
10,588,625 B2 3/2020 Weaner et al.
10,588,626 B2 3/2020 Overmyer et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,589,410 B2 3/2020 Aho
10,595,835 B2 3/2020 Kerr et al.
10,595,862 B2 3/2020 Shelton, IV et al.
10,595,882 B2 3/2020 Parfett et al.
10,595,887 B2 3/2020 Shelton, IV et al.
10,595,929 B2 3/2020 Boudreaux et al.
10,603,036 B2 3/2020 Hunter et al.
10,603,039 B2 3/2020 Vendely et al.
10,603,041 B2 3/2020 Miller et al.
10,603,117 B2 3/2020 Schings et al.
10,603,128 B2 3/2020 Zergiebel et al.
D882,783 S 4/2020 Shelton, IV et al.
10,610,224 B2 4/2020 Shelton, IV et al.
10,610,225 B2 4/2020 Reed et al.
10,610,236 B2 4/2020 Baril
10,610,313 B2 4/2020 Bailey et al.
10,610,346 B2 4/2020 Schwartz
10,614,184 B2 4/2020 Solki
10,617,411 B2 4/2020 Williams
10,617,412 B2 4/2020 Shelton, IV et al.
10,617,413 B2 4/2020 Shelton, IV et al.
10,617,414 B2 4/2020 Shelton, IV et al.
10,617,416 B2 4/2020 Leimbach et al.
10,617,417 B2 4/2020 Baxter, III et al.
10,617,418 B2 4/2020 Barton et al.
10,617,420 B2 4/2020 Shelton, IV et al.
10,617,438 B2 4/2020 O'Keefe et al.
10,624,616 B2 4/2020 Mukherjee et al.
10,624,630 B2 4/2020 Deville et al.
10,624,633 B2 4/2020 Shelton, IV et al.
10,624,634 B2 4/2020 Shelton, IV et al.
10,624,635 B2 4/2020 Harris et al.
10,624,709 B2 4/2020 Remm
10,624,861 B2 4/2020 Widenhouse et al.
10,625,062 B2 4/2020 Matlock et al.
10,631,857 B2 4/2020 Kostrzewski
10,631,858 B2 4/2020 Burbank
10,631,859 B2 4/2020 Shelton, IV et al.
10,631,860 B2 4/2020 Bakos et al.
10,636,104 B2 4/2020 Mazar et al.
10,639,018 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,089 B2 5/2020 Manwaring et al.
10,639,115 B2 5/2020 Shelton, IV et al.
10,642,633 B1 5/2020 Chopra et al.
10,645,905 B2 5/2020 Gandola et al.
10,646,220 B2 5/2020 Shelton, IV et al.
10,646,292 B2 5/2020 Solomon et al.
10,653,413 B2 5/2020 Worthington et al.
10,653,417 B2 5/2020 Shelton, IV et al.
10,653,435 B2 5/2020 Shelton, IV et al.
10,660,640 B2 5/2020 Yates et al.
10,667,408 B2 5/2020 Sgroi, Jr. et al.
D888,953 S 6/2020 Baxter, III et al.
10,667,808 B2 6/2020 Baxter, III et al.
10,667,809 B2 6/2020 Bakos et al.
10,667,810 B2 6/2020 Shelton, IV et al.
10,667,811 B2 6/2020 Harris et al.
10,667,818 B2 6/2020 McLain et al.
10,674,895 B2 6/2020 Yeung et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,675,028 B2 6/2020 Shelton, IV et al.
10,675,035 B2 6/2020 Zingman
10,675,080 B2 6/2020 Woloszko et al.
10,675,102 B2 6/2020 Forgione et al.
10,677,035 B2 6/2020 Balan et al.
10,682,134 B2 6/2020 Shelton, IV et al.
10,682,136 B2 6/2020 Harris et al.
10,682,137 B2 6/2020 Stokes et al.
10,682,138 B2 6/2020 Shelton, IV et al.
10,682,141 B2 6/2020 Moore et al.
10,682,142 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,819 B2 6/2020 Stokes et al.
10,687,904 B2 6/2020 Harris et al.
10,695,053 B2 6/2020 Hess et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.
10,695,074 B2 6/2020 Carusillo
10,695,081 B2 6/2020 Shelton, IV et al.
10,695,119 B2 6/2020 Smith
10,695,123 B2 6/2020 Allen, IV
10,695,187 B2 6/2020 Moskowitz et al.
D890,784 S 7/2020 Shelton, IV et al.
10,702,266 B2 7/2020 Parihar et al.
10,702,267 B2 7/2020 Hess et al.
10,702,270 B2 7/2020 Shelton, IV et al.
10,702,271 B2 7/2020 Aranyi et al.
10,705,660 B2 7/2020 Xiao
10,709,446 B2 7/2020 Harris et al.
10,709,468 B2 7/2020 Shelton, IV et al.
10,709,469 B2 7/2020 Shelton, IV et al.
10,709,496 B2 7/2020 Moua et al.
10,716,563 B2 7/2020 Shelton, IV et al.
10,716,565 B2 7/2020 Shelton, IV et al.
10,716,568 B2 7/2020 Hall et al.
10,716,614 B2 7/2020 Yates et al.
10,717,179 B2 7/2020 Koenig et al.
10,722,232 B2 7/2020 Yates et al.
10,722,233 B2 7/2020 Wellman
10,722,292 B2 7/2020 Arya et al.
10,722,293 B2 7/2020 Arya et al.
10,722,317 B2 7/2020 Ward et al.
D893,717 S 8/2020 Messerly et al.
10,729,432 B2 8/2020 Shelton, IV et al.

(56) References Cited

U.S. PATENT DOCUMENTS

| | | | |
|---|---|---|---|
| 10,729,434 | B2 | 8/2020 | Harris et al. |
| 10,729,435 | B2 | 8/2020 | Richard |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,630 | B2 | 8/2020 | Huang et al. |
| 10,736,633 | B2 | 8/2020 | Vendely et al. |
| 10,736,634 | B2 | 8/2020 | Shelton, IV et al. |
| 10,736,636 | B2 | 8/2020 | Baxter, III et al. |
| 10,736,644 | B2 | 8/2020 | Windolf et al. |
| 10,736,702 | B2 | 8/2020 | Harris et al. |
| 10,737,398 | B2 | 8/2020 | Remirez et al. |
| 10,743,849 | B2 | 8/2020 | Shelton, IV et al. |
| 10,743,850 | B2 | 8/2020 | Hibner et al. |
| 10,743,851 | B2 | 8/2020 | Swayze et al. |
| 10,743,868 | B2 | 8/2020 | Shelton, IV et al. |
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,930 | B2 | 8/2020 | Nagtegaal |
| 10,751,048 | B2 | 8/2020 | Whitman et al. |
| 10,751,053 | B2 | 8/2020 | Harris et al. |
| 10,751,076 | B2 | 8/2020 | Laurent et al. |
| 10,751,138 | B2 | 8/2020 | Giordano et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |
| 10,792,038 | B2 | 10/2020 | Becerra et al. |
| 10,796,471 | B2 | 10/2020 | Leimbach et al. |
| 10,799,240 | B2 | 10/2020 | Shelton, IV et al. |
| 10,799,306 | B2 | 10/2020 | Robinson et al. |
| 10,806,448 | B2 | 10/2020 | Shelton, IV et al. |
| 10,806,449 | B2 | 10/2020 | Shelton, IV et al. |
| 10,806,450 | B2 | 10/2020 | Yates et al. |
| 10,806,451 | B2 | 10/2020 | Harris et al. |
| 10,806,453 | B2 | 10/2020 | Chen et al. |
| 10,806,479 | B2 | 10/2020 | Shelton, IV et al. |
| 10,813,638 | B2 | 10/2020 | Shelton, IV et al. |
| 10,813,639 | B2 | 10/2020 | Shelton, IV et al. |
| 10,813,640 | B2 | 10/2020 | Adams et al. |
| 10,813,641 | B2 | 10/2020 | Setser et al. |
| 10,813,683 | B2 | 10/2020 | Baxter, III et al. |
| 10,813,705 | B2 | 10/2020 | Hares et al. |
| 10,813,710 | B2 | 10/2020 | Grubbs |
| 10,820,939 | B2 | 11/2020 | Sartor |
| 10,828,028 | B2 | 11/2020 | Harris et al. |
| 10,828,030 | B2 | 11/2020 | Weir et al. |
| 10,828,032 | B2 | 11/2020 | Leimbach et al. |
| 10,828,033 | B2 | 11/2020 | Shelton, IV et al. |
| 10,828,089 | B2 | 11/2020 | Clark et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,835,249 | B2 | 11/2020 | Schellin et al. |
| 10,835,251 | B2 | 11/2020 | Shelton, IV et al. |
| 10,835,330 | B2 | 11/2020 | Shelton, IV et al. |
| 10,842,357 | B2 | 11/2020 | Moskowitz et al. |
| 10,842,473 | B2 | 11/2020 | Scheib et al. |
| 10,842,488 | B2 | 11/2020 | Swayze et al. |
| 10,842,489 | B2 | 11/2020 | Shelton, IV |
| 10,842,490 | B2 | 11/2020 | Dinardo et al. |
| 10,842,491 | B2 | 11/2020 | Shelton, IV et al. |
| 10,842,492 | B2 | 11/2020 | Shelton, IV et al. |
| D904,612 | S | 12/2020 | Wynn et al. |
| D904,613 | S | 12/2020 | Wynn et al. |
| D906,355 | S | 12/2020 | Messerly et al. |
| 10,849,621 | B2 | 12/2020 | Whitfield et al. |
| 10,849,623 | B2 | 12/2020 | Dunki-Jacobs et al. |
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,663 | B2 | 12/2020 | Shelton, IV et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,879,275 | B2 | 12/2020 | Li et al. |
| D907,647 | S | 1/2021 | Siebel et al. |
| D907,648 | S | 1/2021 | Siebel et al. |
| D908,216 | S | 1/2021 | Messerly et al. |
| 10,881,395 | B2 | 1/2021 | Merchant et al. |
| 10,881,396 | B2 | 1/2021 | Shelton, IV et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,888,318 | B2 | 1/2021 | Parihar et al. |
| 10,888,321 | B2 | 1/2021 | Shelton, IV et al. |
| 10,888,322 | B2 | 1/2021 | Morgan et al. |
| 10,888,323 | B2 | 1/2021 | Chen et al. |
| 10,888,325 | B2 | 1/2021 | Harris et al. |
| 10,888,328 | B2 | 1/2021 | Shelton, IV et al. |
| 10,888,329 | B2 | 1/2021 | Moore et al. |
| 10,888,330 | B2 | 1/2021 | Moore et al. |
| 10,888,369 | B2 | 1/2021 | Messerly et al. |
| 10,892,899 | B2 | 1/2021 | Shelton, IV et al. |
| 10,893,853 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,867 | B2 | 1/2021 | Leimbach et al. |
| 10,898,183 | B2 | 1/2021 | Shelton, IV et al. |
| 10,898,184 | B2 | 1/2021 | Yates et al. |
| 10,898,185 | B2 | 1/2021 | Overmyer et al. |
| 10,898,186 | B2 | 1/2021 | Bakos et al. |
| 10,898,190 | B2 | 1/2021 | Yates et al. |
| 10,898,193 | B2 | 1/2021 | Shelton, IV et al. |
| 10,898,194 | B2 | 1/2021 | Moore et al. |

(56) References Cited

U.S. PATENT DOCUMENTS 10,898,195 B2 1/2021 Moore et al.
10,903,685 B2 1/2021 Yates et al.
D910,847 S 2/2021 Shelton, IV et al.
10,905,415 B2 2/2021 DiNardo et al.
10,905,418 B2 2/2021 Shelton, IV et al.
10,905,420 B2 2/2021 Jasemian et al.
10,905,422 B2 2/2021 Bakos et al.
10,905,423 B2 2/2021 Baber et al.
10,905,426 B2 2/2021 Moore et al.
10,905,427 B2 2/2021 Moore et al.
10,911,515 B2 2/2021 Biasi et al.
10,912,559 B2 2/2021 Harris et al.
10,912,562 B2 2/2021 Dunki-Jacobs et al.
10,912,575 B2 2/2021 Shelton, IV et al.
10,918,364 B2 2/2021 Applegate et al.
10,918,380 B2 2/2021 Morgan et al.
10,918,385 B2 2/2021 Overmyer et al.
10,918,386 B2 2/2021 Shelton, IV et al.
10,919,156 B2 2/2021 Roberts et al.
10,925,600 B2 2/2021 McCuen
10,925,605 B2 2/2021 Moore et al.
D914,878 S 3/2021 Shelton, IV et al.
10,932,772 B2 3/2021 Shelton, IV et al.
10,932,774 B2 3/2021 Shelton, IV
10,932,775 B2 3/2021 Shelton, IV et al.
10,932,778 B2 3/2021 Smith et al.
10,932,779 B2 3/2021 Vendely et al.
10,932,784 B2 3/2021 Mozdzierz et al.
10,932,804 B2 3/2021 Scheib et al.
10,932,806 B2 3/2021 Shelton, IV et al.
10,932,872 B2 3/2021 Shelton, IV et al.
10,944,728 B2 3/2021 Wiener et al.
10,945,727 B2 3/2021 Shelton, IV et al.
10,945,728 B2 3/2021 Morgan et al.
10,945,729 B2 3/2021 Shelton, IV et al.
10,945,731 B2 3/2021 Baxter, III et al.
10,952,708 B2 3/2021 Scheib et al.
10,952,726 B2 3/2021 Chowaniec
10,952,727 B2 3/2021 Giordano et al.
10,952,728 B2 3/2021 Shelton, IV et al.
10,952,759 B2 3/2021 Messerly et al.
10,952,767 B2 3/2021 Kostrzewski et al.
10,959,722 B2 3/2021 Morgan et al.
10,959,725 B2 3/2021 Kerr et al.
10,959,726 B2 3/2021 Williams et al.
10,959,727 B2 3/2021 Hunter et al.
10,959,731 B2 3/2021 Casasanta, Jr. et al.
10,959,744 B2 3/2021 Shelton, IV et al.
10,959,797 B2 3/2021 Licht et al.
D917,500 S 4/2021 Siebel et al.
10,966,627 B2 4/2021 Shelton, IV et al.
10,966,717 B2 4/2021 Shah et al.
10,966,718 B2 4/2021 Shelton, IV et al.
10,966,791 B2 4/2021 Harris et al.
10,973,515 B2 4/2021 Harris et al.
10,973,516 B2 4/2021 Shelton, IV et al.
10,973,517 B2 4/2021 Wixey
10,973,519 B2 4/2021 Weir et al.
10,973,520 B2 4/2021 Shelton, IV et al.
10,980,534 B2 4/2021 Yates et al.
10,980,535 B2 4/2021 Yates et al.
10,980,536 B2 4/2021 Weaner et al.
10,980,537 B2 4/2021 Shelton, IV et al.
10,980,538 B2 4/2021 Nalagatla et al.
10,980,539 B2 4/2021 Harris et al.
10,980,560 B2 4/2021 Shelton, IV et al.
10,983,646 B2 4/2021 Yoon et al.
10,987,102 B2 4/2021 Gonzalez et al.
10,987,178 B2 4/2021 Shelton, IV et al.
10,993,713 B2 5/2021 Shelton, IV et al.
10,993,715 B2 5/2021 Shelton, IV et al.
10,993,716 B2 5/2021 Shelton, IV et al.
10,993,717 B2 5/2021 Shelton, IV et al.
11,000,274 B2 5/2021 Shelton, IV et al.
11,000,275 B2 5/2021 Shelton, IV et al.
11,000,277 B2 5/2021 Giordano et al.
11,000,278 B2 5/2021 Shelton, IV et al.
11,000,279 B2 5/2021 Shelton, IV et al.
11,005,291 B2 5/2021 Calderoni
11,006,951 B2 5/2021 Giordano et al.
11,006,955 B2 5/2021 Shelton, IV et al.
11,007,004 B2 5/2021 Shelton, IV et al.
11,007,022 B2 5/2021 Shelton, IV et al.
11,013,511 B2 5/2021 Huang et al.
11,013,552 B2 5/2021 Widenhouse et al.
11,013,563 B2 5/2021 Shelton, IV et al.
11,020,016 B2 6/2021 Wallace et al.
11,020,112 B2 6/2021 Shelton, IV et al.
11,020,113 B2 6/2021 Shelton, IV et al.
11,020,114 B2 6/2021 Shelton, IV et al.
11,020,115 B2 6/2021 Scheib et al.
11,026,678 B2 6/2021 Overmyer et al.
11,026,680 B2 6/2021 Shelton, IV et al.
11,026,684 B2 6/2021 Shelton, IV et al.
11,026,687 B2 6/2021 Shelton, IV et al.
11,026,712 B2 6/2021 Shelton, IV et al.
11,026,713 B2 6/2021 Stokes et al.
11,026,751 B2 6/2021 Shelton, IV et al.
11,033,267 B2 6/2021 Shelton, IV et al.
11,039,834 B2 6/2021 Harris et al.
11,039,836 B2 6/2021 Shelton, IV et al.
11,039,837 B2 6/2021 Shelton, IV et al.
11,039,849 B2 6/2021 Bucciaglia et al.
11,045,189 B2 6/2021 Yates et al.
11,045,191 B2 6/2021 Shelton, IV et al.
11,045,192 B2 6/2021 Harris et al.
11,045,196 B2 6/2021 Olson et al.
11,045,197 B2 6/2021 Shelton, IV et al.
11,045,199 B2 6/2021 Mozdzierz et al.
11,045,270 B2 6/2021 Shelton, IV et al.
11,051,807 B2 7/2021 Shelton, IV et al.
11,051,810 B2 7/2021 Harris et al.
11,051,811 B2 7/2021 Shelton, IV et al.
11,051,813 B2 7/2021 Shelton, IV et al.
11,051,836 B2 7/2021 Shelton, IV et al.
11,051,840 B2 7/2021 Shelton, IV et al.
11,051,873 B2 7/2021 Wiener et al.
11,058,418 B2 7/2021 Shelton, IV et al.
11,058,420 B2 7/2021 Shelton, IV et al.
11,058,422 B2 7/2021 Harris et al.
11,058,423 B2 7/2021 Shelton, IV et al.
11,058,424 B2 7/2021 Shelton, IV et al.
11,058,425 B2 7/2021 Widenhouse et al.
11,058,426 B2 7/2021 Nalagatla et al.
11,058,498 B2 7/2021 Shelton, IV et al.
11,064,997 B2 7/2021 Shelton, IV et al.
11,064,998 B2 7/2021 Shelton, IV
11,065,048 B2 7/2021 Messerly et al.
11,069,012 B2 7/2021 Shelton, IV et al.
11,071,542 B2 7/2021 Chen et al.
11,071,543 B2 7/2021 Shelton, IV et al.
11,071,545 B2 7/2021 Baber et al.
11,071,554 B2 7/2021 Parfett et al.
11,071,560 B2 7/2021 Deck et al.
11,076,853 B2 8/2021 Parfett et al.
11,076,854 B2 8/2021 Baber et al.
11,076,921 B2 8/2021 Shelton, IV et al.
11,076,929 B2 8/2021 Shelton, IV et al.
11,083,452 B2 8/2021 Schmid et al.
11,083,453 B2 8/2021 Shelton, IV et al.
11,083,454 B2 8/2021 Harris et al.
11,083,455 B2 8/2021 Shelton, IV et al.
11,083,456 B2 8/2021 Shelton, IV et al.
11,083,457 B2 8/2021 Shelton, IV et al.
11,083,458 B2 8/2021 Harris et al.
11,090,045 B2 8/2021 Shelton, IV
11,090,046 B2 8/2021 Shelton, IV et al.
11,090,047 B2 8/2021 Shelton, IV et al.
11,090,048 B2 8/2021 Fanelli et al.
11,090,049 B2 8/2021 Bakos et al.
11,090,075 B2 8/2021 Hunter et al.
11,096,688 B2 8/2021 Shelton, IV et al.
11,096,689 B2 8/2021 Overmyer et al.
11,100,631 B2 8/2021 Yates et al.

(56) References Cited

U.S. PATENT DOCUMENTS 11,103,241 B2 8/2021 Yates et al.
11,103,248 B2 8/2021 Shelton, IV et al.
11,103,268 B2 8/2021 Shelton, IV et al.
11,103,269 B2 8/2021 Shelton, IV et al.
11,109,858 B2 9/2021 Shelton, IV et al.
11,109,859 B2 9/2021 Overmyer et al.
11,109,860 B2 9/2021 Shelton, IV et al.
11,109,866 B2 9/2021 Shelton, IV et al.
11,109,878 B2 9/2021 Shelton, IV et al.
11,109,925 B2 9/2021 Cooper et al.
11,116,485 B2 9/2021 Scheib et al.
11,116,502 B2 9/2021 Shelton, IV et al.
11,116,594 B2 9/2021 Beardsley
11,123,069 B2 9/2021 Baxter, III et al.
11,123,070 B2 9/2021 Shelton, IV et al.
11,129,611 B2 9/2021 Shelton, IV et al.
11,129,613 B2 9/2021 Harris et al.
11,129,615 B2 9/2021 Scheib et al.
11,129,616 B2 9/2021 Shelton, IV et al.
11,129,634 B2 9/2021 Scheib et al.
11,129,636 B2 9/2021 Shelton, IV et al.
11,129,666 B2 9/2021 Messerly et al.
11,129,680 B2 9/2021 Shelton, IV et al.
11,132,462 B2 9/2021 Shelton, IV et al.
11,133,106 B2 9/2021 Shelton, IV et al.
11,134,938 B2 10/2021 Timm et al.
11,134,940 B2 10/2021 Shelton, IV et al.
11,134,942 B2 10/2021 Harris et al.
11,134,943 B2 10/2021 Giordano et al.
11,134,944 B2 10/2021 Wise et al.
11,134,947 B2 10/2021 Shelton, IV et al.
11,135,352 B2 10/2021 Shelton, IV et al.
11,141,153 B2 10/2021 Shelton, IV et al.
11,141,154 B2 10/2021 Shelton, IV et al.
11,141,155 B2 10/2021 Shelton, IV
11,141,156 B2 10/2021 Shelton, IV
11,141,159 B2 10/2021 Scheib et al.
11,141,160 B2 10/2021 Shelton, IV et al.
11,147,547 B2 10/2021 Shelton, IV et al.
11,147,549 B2 10/2021 Timm et al.
11,147,551 B2 10/2021 Shelton, IV
11,147,553 B2 10/2021 Shelton, IV
11,147,554 B2 10/2021 Aronhalt et al.
11,154,296 B2 10/2021 Aronhalt et al.
11,154,297 B2 10/2021 Swayze et al.
11,154,298 B2 10/2021 Timm et al.
11,154,299 B2 10/2021 Shelton, IV et al.
11,154,300 B2 10/2021 Nalagatla et al.
11,154,301 B2 10/2021 Beckman et al.
11,160,551 B2 11/2021 Shelton, IV et al.
11,160,553 B2 11/2021 Simms et al.
11,160,601 B2 11/2021 Worrell et al.
11,166,716 B2 11/2021 Shelton, IV et al.
11,166,717 B2 11/2021 Shelton, IV et al.
11,166,720 B2 11/2021 Giordano et al.
11,166,772 B2 11/2021 Shelton, IV et al.
11,166,773 B2 11/2021 Ragosta et al.
11,172,580 B2 11/2021 Gaertner, II
11,172,927 B2 11/2021 Shelton, IV
11,172,929 B2 11/2021 Shelton, IV
11,179,150 B2 11/2021 Yates et al.
11,179,151 B2 11/2021 Shelton, IV et al.
11,179,152 B2 11/2021 Morgan et al.
11,179,153 B2 11/2021 Shelton, IV
11,179,155 B2 11/2021 Shelton, IV et al.
11,179,208 B2 11/2021 Yates et al.
11,185,325 B2 11/2021 Shelton, IV et al.
11,185,330 B2 11/2021 Huitema et al.
11,191,539 B2 12/2021 Overmyer et al.
11,191,540 B2 12/2021 Aronhalt et al.
11,191,543 B2 12/2021 Overmyer et al.
11,191,545 B2 12/2021 Vendely et al.
11,197,668 B2 12/2021 Shelton, IV et al.
11,197,670 B2 12/2021 Shelton, IV et al.
11,197,671 B2 12/2021 Shelton, IV et al.
11,197,672 B2 12/2021 Dunki-Jacobs et al.
11,202,570 B2 12/2021 Shelton, IV et al.
11,202,631 B2 12/2021 Shelton, IV et al.
11,202,633 B2 12/2021 Harris et al.
11,207,064 B2 12/2021 Shelton, IV et al.
11,207,065 B2 12/2021 Harris et al.
11,207,067 B2 12/2021 Shelton, IV et al.
11,207,089 B2 12/2021 Kostrzewski et al.
11,207,090 B2 12/2021 Shelton, IV et al.
11,207,146 B2 12/2021 Shelton, IV et al.
11,213,293 B2 1/2022 Worthington et al.
11,213,294 B2 1/2022 Shelton, IV et al.
11,213,302 B2 1/2022 Parfett et al.
11,213,359 B2 1/2022 Shelton, IV et al.
11,219,453 B2 1/2022 Shelton, IV et al.
11,219,455 B2 1/2022 Shelton, IV et al.
11,224,423 B2 1/2022 Shelton, IV et al.
11,224,426 B2 1/2022 Shelton, IV et al.
11,224,427 B2 1/2022 Shelton, IV et al.
11,224,428 B2 1/2022 Scott et al.
11,224,454 B2 1/2022 Shelton, IV et al.
11,224,497 B2 1/2022 Shelton, IV et al.
11,229,436 B2 1/2022 Shelton, IV et al.
11,229,437 B2 1/2022 Shelton, IV et al.
11,234,698 B2 2/2022 Shelton, IV et al.
11,234,700 B2 2/2022 Ragosta et al.
11,241,229 B2 2/2022 Shelton, IV et al.
11,241,230 B2 2/2022 Shelton, IV et al.
11,241,235 B2 2/2022 Shelton, IV et al.
11,246,590 B2 2/2022 Swayze et al.
11,246,592 B2 2/2022 Shelton, IV et al.
11,246,616 B2 2/2022 Shelton, IV et al.
11,246,618 B2 2/2022 Hall et al.
11,246,678 B2 2/2022 Shelton, IV et al.
11,253,254 B2 2/2022 Kimball et al.
11,253,256 B2 2/2022 Harris et al.
11,259,799 B2 3/2022 Overmyer et al.
11,259,803 B2 3/2022 Shelton, IV et al.
11,259,805 B2 3/2022 Shelton, IV et al.
11,259,806 B2 3/2022 Shelton, IV et al.
11,259,807 B2 3/2022 Shelton, IV et al.
11,266,405 B2 3/2022 Shelton, IV et al.
11,266,406 B2 3/2022 Leimbach et al.
11,266,409 B2 3/2022 Huitema et al.
11,266,410 B2 3/2022 Shelton, IV et al.
11,266,468 B2 3/2022 Shelton, IV et al.
11,272,927 B2 3/2022 Swayze et al.
11,272,928 B2 3/2022 Shelton, IV
11,272,931 B2 3/2022 Boudreaux et al.
11,272,938 B2 3/2022 Shelton, IV et al.
11,278,279 B2 3/2022 Morgan et al.
11,278,280 B2 3/2022 Shelton, IV et al.
11,278,284 B2 3/2022 Shelton, IV et al.
11,284,890 B2 3/2022 Nalagatla et al.
11,284,891 B2 3/2022 Shelton, IV et al.
11,284,898 B2 3/2022 Baxter, III et al.
11,284,953 B2 3/2022 Shelton, IV et al.
11,291,440 B2 4/2022 Harris et al.
11,291,441 B2 4/2022 Giordano et al.
11,291,443 B2 4/2022 Viola et al.
11,291,444 B2 4/2022 Boudreaux et al.
11,291,445 B2 4/2022 Shelton, IV et al.
11,291,447 B2 4/2022 Shelton, IV et al.
11,291,449 B2 4/2022 Swensgard et al.
11,291,451 B2 4/2022 Shelton, IV
11,291,465 B2 4/2022 Parihar et al.
11,291,510 B2 4/2022 Shelton, IV et al.
11,298,125 B2 4/2022 Ming et al.
11,298,127 B2 4/2022 Shelton, IV
11,298,128 B2 4/2022 Messerly et al.
11,298,129 B2 4/2022 Bakos et al.
11,298,130 B2 4/2022 Bakos et al.
11,298,132 B2 4/2022 Shelton, IV et al.
11,298,134 B2 4/2022 Huitema et al.
11,304,695 B2 4/2022 Shelton, IV et al.
11,304,696 B2 4/2022 Shelton, IV et al.
11,304,697 B2 4/2022 Fanelli et al.
11,304,699 B2 4/2022 Shelton, IV et al.
11,304,704 B2 4/2022 Thomas et al.

(56) References Cited

U.S. PATENT DOCUMENTS

| | | | | |
|---|---|---|---|---|
| 11,311,290 | B2 | 4/2022 | Shelton, IV et al. | |
| 11,311,292 | B2 | 4/2022 | Shelton, IV et al. | |
| 11,311,294 | B2 | 4/2022 | Swayze et al. | |
| 11,311,295 | B2 | 4/2022 | Wingardner et al. | |
| 11,311,342 | B2 | 4/2022 | Parihar et al. | |
| D950,728 | S | 5/2022 | Bakos et al. | |
| D952,144 | S | 5/2022 | Boudreaux | |
| 11,317,910 | B2 | 5/2022 | Miller et al. | |
| 11,317,912 | B2 | 5/2022 | Jenkins et al. | |
| 11,317,913 | B2 * | 5/2022 | Shelton, IV | A61B 90/03 |
| 11,317,915 | B2 | 5/2022 | Boudreaux et al. | |
| 11,317,917 | B2 | 5/2022 | Shelton, IV et al. | |
| 11,317,919 | B2 | 5/2022 | Shelton, IV et al. | |
| 11,317,978 | B2 | 5/2022 | Cameron et al. | |
| 11,324,501 | B2 | 5/2022 | Shelton, IV et al. | |
| 11,324,503 | B2 | 5/2022 | Shelton, IV et al. | |
| 11,324,506 | B2 | 5/2022 | Beckman et al. | |
| 11,324,557 | B2 | 5/2022 | Shelton, IV et al. | |
| 11,331,100 | B2 | 5/2022 | Boudreaux et al. | |
| 11,331,101 | B2 | 5/2022 | Harris et al. | |
| 11,337,691 | B2 | 5/2022 | Widenhouse et al. | |
| 11,337,693 | B2 | 5/2022 | Hess et al. | |
| 11,337,698 | B2 | 5/2022 | Baxter, III et al. | |
| 11,344,299 | B2 | 5/2022 | Yates et al. | |
| 11,344,303 | B2 | 5/2022 | Shelton, IV et al. | |
| 11,350,843 | B2 | 6/2022 | Shelton, IV et al. | |
| 11,350,916 | B2 | 6/2022 | Shelton, IV et al. | |
| 11,350,928 | B2 | 6/2022 | Shelton, IV et al. | |
| 11,350,929 | B2 | 6/2022 | Giordano et al. | |
| 11,350,932 | B2 | 6/2022 | Shelton, IV et al. | |
| 11,350,934 | B2 | 6/2022 | Bakos et al. | |
| 11,350,935 | B2 | 6/2022 | Shelton, IV et al. | |
| 11,350,938 | B2 | 6/2022 | Shelton, IV et al. | |
| 11,357,503 | B2 | 6/2022 | Bakos et al. | |
| 11,361,176 | B2 | 6/2022 | Shelton, IV et al. | |
| 11,364,027 | B2 | 6/2022 | Harris et al. | |
| 11,364,046 | B2 | 6/2022 | Shelton, IV et al. | |
| 11,369,368 | B2 | 6/2022 | Shelton, IV et al. | |
| 11,369,376 | B2 | 6/2022 | Simms et al. | |
| 11,369,377 | B2 | 6/2022 | Boudreaux et al. | |
| 11,373,755 | B2 | 6/2022 | Shelton, IV et al. | |
| 11,376,001 | B2 | 7/2022 | Shelton, IV et al. | |
| 11,376,082 | B2 | 7/2022 | Shelton, IV et al. | |
| 11,376,098 | B2 | 7/2022 | Shelton, IV et al. | |
| 11,382,625 | B2 | 7/2022 | Huitema et al. | |
| 11,382,626 | B2 | 7/2022 | Shelton, IV et al. | |
| 11,382,627 | B2 | 7/2022 | Huitema et al. | |
| 11,382,628 | B2 | 7/2022 | Baxter, III et al. | |
| 11,382,638 | B2 | 7/2022 | Harris et al. | |
| 11,382,697 | B2 | 7/2022 | Shelton, IV et al. | |
| 11,389,160 | B2 | 7/2022 | Shelton, IV et al. | |
| 11,389,161 | B2 | 7/2022 | Shelton, IV et al. | |
| 11,389,162 | B2 | 7/2022 | Baber et al. | |
| 11,389,164 | B2 | 7/2022 | Yates et al. | |
| 11,395,651 | B2 | 7/2022 | Shelton, IV et al. | |
| 11,395,652 | B2 | 7/2022 | Parihar et al. | |
| 11,399,828 | B2 | 8/2022 | Swayze et al. | |
| 11,399,829 | B2 | 8/2022 | Leimbach et al. | |
| 11,399,831 | B2 | 8/2022 | Overmyer et al. | |
| 11,399,837 | B2 | 8/2022 | Shelton, IV et al. | |
| 11,406,377 | B2 | 8/2022 | Schmid et al. | |
| 11,406,378 | B2 | 8/2022 | Baxter, III et al. | |
| 11,406,380 | B2 | 8/2022 | Yates et al. | |
| 11,406,381 | B2 | 8/2022 | Parihar et al. | |
| 11,406,382 | B2 | 8/2022 | Shelton, IV et al. | |
| 11,406,386 | B2 | 8/2022 | Baber et al. | |
| 11,406,390 | B2 | 8/2022 | Shelton, IV et al. | |
| 11,406,442 | B2 | 8/2022 | Davison et al. | |
| 11,410,259 | B2 | 8/2022 | Harris et al. | |
| 11,413,041 | B2 | 8/2022 | Viola et al. | |
| 11,413,042 | B2 | 8/2022 | Shelton, IV et al. | |
| 11,413,102 | B2 | 8/2022 | Shelton, IV et al. | |
| 11,419,606 | B2 | 8/2022 | Overmyer et al. | |
| 11,419,630 | B2 | 8/2022 | Yates et al. | |
| 11,424,027 | B2 | 8/2022 | Shelton, IV | |
| 11,426,160 | B2 | 8/2022 | Shelton, IV et al. | |
| 11,426,167 | B2 | 8/2022 | Shelton, IV et al. | |
| 11,426,251 | B2 | 8/2022 | Kimball et al. | |
| D964,564 | S | 9/2022 | Boudreaux | |
| 11,432,816 | B2 | 9/2022 | Leimbach et al. | |
| 11,432,885 | B2 | 9/2022 | Shelton, IV et al. | |
| 11,439,391 | B2 | 9/2022 | Bruns et al. | |
| 11,439,470 | B2 | 9/2022 | Spivey et al. | |
| 11,446,029 | B2 | 9/2022 | Shelton, IV et al. | |
| 11,446,034 | B2 | 9/2022 | Shelton, IV et al. | |
| 11,452,526 | B2 | 9/2022 | Ross et al. | |
| 11,452,528 | B2 | 9/2022 | Leimbach et al. | |
| D966,512 | S | 10/2022 | Shelton, IV et al. | |
| D967,421 | S | 10/2022 | Shelton, IV et al. | |
| D971,232 | S | 11/2022 | Siebel et al. | |
| 11,523,859 | B2 | 12/2022 | Shelton, IV et al. | |
| D974,560 | S | 1/2023 | Shelton, IV et al. | |
| D975,278 | S | 1/2023 | Shelton, IV et al. | |
| D975,850 | S | 1/2023 | Shelton, IV et al. | |
| D975,851 | S | 1/2023 | Shelton, IV et al. | |
| D976,401 | S | 1/2023 | Shelton, IV et al. | |
| 11,564,682 | B2 | 1/2023 | Timm et al. | |
| D980,425 | S | 3/2023 | Baxter, III | |
| 2001/0000531 | A1 | 4/2001 | Casscells et al. | |
| 2001/0025183 | A1 | 9/2001 | Shahidi | |
| 2001/0025184 | A1 | 9/2001 | Messerly | |
| 2001/0030219 | A1 | 10/2001 | Green et al. | |
| 2001/0034530 | A1 | 10/2001 | Malackowski et al. | |
| 2001/0045442 | A1 | 11/2001 | Whitman | |
| 2002/0014510 | A1 | 2/2002 | Richter et al. | |
| 2002/0022810 | A1 | 2/2002 | Urich | |
| 2002/0022836 | A1 | 2/2002 | Goble et al. | |
| 2002/0022861 | A1 | 2/2002 | Jacobs et al. | |
| 2002/0023126 | A1 | 2/2002 | Flavin | |
| 2002/0029032 | A1 | 3/2002 | Arkin | |
| 2002/0029036 | A1 | 3/2002 | Goble et al. | |
| 2002/0042620 | A1 | 4/2002 | Julian et al. | |
| 2002/0045905 | A1 | 4/2002 | Gerbi et al. | |
| 2002/0054158 | A1 | 5/2002 | Asami | |
| 2002/0065535 | A1 | 5/2002 | Kneifel et al. | |
| 2002/0066764 | A1 | 6/2002 | Perry et al. | |
| 2002/0082612 | A1 | 6/2002 | Moll et al. | |
| 2002/0087048 | A1 | 7/2002 | Brock et al. | |
| 2002/0087148 | A1 | 7/2002 | Brock et al. | |
| 2002/0091374 | A1 | 7/2002 | Cooper | |
| 2002/0095175 | A1 | 7/2002 | Brock et al. | |
| 2002/0103494 | A1 | 8/2002 | Pacey | |
| 2002/0111621 | A1 | 8/2002 | Wallace et al. | |
| 2002/0111624 | A1 | 8/2002 | Witt et al. | |
| 2002/0116063 | A1 | 8/2002 | Giannetti et al. | |
| 2002/0117533 | A1 | 8/2002 | Milliman et al. | |
| 2002/0117534 | A1 | 8/2002 | Green et al. | |
| 2002/0127265 | A1 | 9/2002 | Bowman et al. | |
| 2002/0128633 | A1 | 9/2002 | Brock et al. | |
| 2002/0133236 | A1 | 9/2002 | Rousseau | |
| 2002/0134811 | A1 | 9/2002 | Napier et al. | |
| 2002/0135474 | A1 | 9/2002 | Sylliassen | |
| 2002/0138086 | A1 | 9/2002 | Sixto et al. | |
| 2002/0143340 | A1 | 10/2002 | Kaneko | |
| 2002/0151770 | A1 | 10/2002 | Noll et al. | |
| 2002/0158593 | A1 | 10/2002 | Henderson et al. | |
| 2002/0161277 | A1 | 10/2002 | Boone et al. | |
| 2002/0177848 | A1 | 11/2002 | Truckai et al. | |
| 2002/0185514 | A1 | 12/2002 | Adams et al. | |
| 2002/0188170 | A1 | 12/2002 | Santamore et al. | |
| 2002/0188287 | A1 | 12/2002 | Zvuloni et al. | |
| 2003/0009193 | A1 | 1/2003 | Corsaro | |
| 2003/0011245 | A1 | 1/2003 | Fiebig | |
| 2003/0012805 | A1 | 1/2003 | Chen et al. | |
| 2003/0018323 | A1 | 1/2003 | Wallace et al. | |
| 2003/0028236 | A1 | 2/2003 | Gillick et al. | |
| 2003/0040670 | A1 | 2/2003 | Govari | |
| 2003/0045835 | A1 | 3/2003 | Anderson et al. | |
| 2003/0047230 | A1 | 3/2003 | Kim | |
| 2003/0047582 | A1 | 3/2003 | Sonnenschein et al. | |
| 2003/0050628 | A1 | 3/2003 | Whitman et al. | |
| 2003/0050654 | A1 | 3/2003 | Whitman et al. | |
| 2003/0066858 | A1 | 4/2003 | Holgersson | |
| 2003/0078647 | A1 | 4/2003 | Vallana et al. | |

(56) References Cited

U.S. PATENT DOCUMENTS

| | | | |
|---|---|---|---|
| 2003/0083648 | A1 | 5/2003 | Wang et al. |
| 2003/0084983 | A1 | 5/2003 | Rangachari et al. |
| 2003/0093103 | A1 | 5/2003 | Malackowski et al. |
| 2003/0093160 | A1 | 5/2003 | Maksimovic et al. |
| 2003/0094356 | A1 | 5/2003 | Waldron |
| 2003/0096158 | A1 | 5/2003 | Takano et al. |
| 2003/0105475 | A1 | 6/2003 | Sancoff et al. |
| 2003/0114851 | A1 | 6/2003 | Truckai et al. |
| 2003/0121586 | A1 | 7/2003 | Mitra et al. |
| 2003/0135204 | A1 | 7/2003 | Lee et al. |
| 2003/0135388 | A1 | 7/2003 | Martucci et al. |
| 2003/0139741 | A1 | 7/2003 | Goble et al. |
| 2003/0144660 | A1 | 7/2003 | Mollenauer |
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0158463 | A1 | 8/2003 | Julian et al. |
| 2003/0163029 | A1 | 8/2003 | Sonnenschein et al. |
| 2003/0163085 | A1 | 8/2003 | Tanner et al. |
| 2003/0164172 | A1 | 9/2003 | Chumas et al. |
| 2003/0181800 | A1 | 9/2003 | Bonutti |
| 2003/0181900 | A1 | 9/2003 | Long |
| 2003/0190584 | A1 | 10/2003 | Heasley |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216619 | A1 | 11/2003 | Scirica et al. |
| 2003/0216732 | A1 | 11/2003 | Truckai et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034287 | A1 | 2/2004 | Hickle |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092992 | A1 | 5/2004 | Adams et al. |
| 2004/0093020 | A1 | 5/2004 | Sinton |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0231870 | A1 | 11/2004 | McCormick et al. |
| 2004/0232201 | A1 | 11/2004 | Wenchell et al. |
| 2004/0236352 | A1 | 11/2004 | Wang et al. |
| 2004/0239582 | A1 | 12/2004 | Seymour |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0254680 | A1 | 12/2004 | Sunaoshi |
| 2004/0260315 | A1 | 12/2004 | Dell et al. |
| 2004/0267310 | A1 | 12/2004 | Racenet et al. |
| 2005/0010158 | A1 | 1/2005 | Brugger et al. |
| 2005/0010213 | A1 | 1/2005 | Stad et al. |
| 2005/0021078 | A1 | 1/2005 | Vleugels et al. |
| 2005/0023325 | A1 | 2/2005 | Gresham et al. |
| 2005/0032511 | A1 | 2/2005 | Malone et al. |
| 2005/0033352 | A1 | 2/2005 | Zepf et al. |
| 2005/0044489 | A1 | 2/2005 | Yamagami et al. |
| 2005/0051163 | A1 | 3/2005 | Deem et al. |
| 2005/0054946 | A1 | 3/2005 | Krzyzanowski |
| 2005/0057225 | A1 | 3/2005 | Marquet |
| 2005/0058890 | A1 | 3/2005 | Brazell et al. |
| 2005/0059997 | A1 | 3/2005 | Bauman et al. |
| 2005/0067548 | A1 | 3/2005 | Inoue |
| 2005/0070929 | A1 | 3/2005 | Dalessandro et al. |
| 2005/0075561 | A1 | 4/2005 | Golden |
| 2005/0079088 | A1 | 4/2005 | Wirth et al. |
| 2005/0080342 | A1 | 4/2005 | Gilreath et al. |
| 2005/0085693 | A1 | 4/2005 | Belson et al. |
| 2005/0085838 | A1 | 4/2005 | Thompson et al. |
| 2005/0090709 | A1 | 4/2005 | Okada et al. |
| 2005/0090817 | A1 | 4/2005 | Phan |
| 2005/0096683 | A1 | 5/2005 | Ellins et al. |
| 2005/0116673 | A1 | 6/2005 | Carl et al. |
| 2005/0119524 | A1 | 6/2005 | Sekine et al. |
| 2005/0120836 | A1 | 6/2005 | Anderson |
| 2005/0124855 | A1 | 6/2005 | Jaffe et al. |
| 2005/0125028 | A1 | 6/2005 | Looper et al. |
| 2005/0125897 | A1 | 6/2005 | Wyslucha et al. |
| 2005/0129735 | A1 | 6/2005 | Cook et al. |
| 2005/0130682 | A1 | 6/2005 | Takara et al. |
| 2005/0131173 | A1 | 6/2005 | McDaniel et al. |
| 2005/0131211 | A1 | 6/2005 | Bayley et al. |
| 2005/0131390 | A1 | 6/2005 | Heinrich et al. |
| 2005/0131436 | A1 | 6/2005 | Johnston et al. |
| 2005/0131457 | A1 | 6/2005 | Douglas et al. |
| 2005/0137454 | A1 | 6/2005 | Saadat et al. |
| 2005/0137455 | A1 | 6/2005 | Ewers et al. |
| 2005/0139636 | A1 | 6/2005 | Schwemberger et al. |
| 2005/0143759 | A1 | 6/2005 | Kelly |
| 2005/0143769 | A1 | 6/2005 | White et al. |
| 2005/0145671 | A1 | 7/2005 | Viola |
| 2005/0145672 | A1 | 7/2005 | Schwemberger et al. |
| 2005/0150928 | A1 | 7/2005 | Kameyama et al. |
| 2005/0154258 | A1 | 7/2005 | Tartaglia et al. |
| 2005/0154406 | A1 | 7/2005 | Bombard et al. |
| 2005/0159778 | A1 | 7/2005 | Heinrich et al. |
| 2005/0165419 | A1 | 7/2005 | Sauer et al. |
| 2005/0169974 | A1 | 8/2005 | Tenerz et al. |
| 2005/0171522 | A1 | 8/2005 | Christopherson |
| 2005/0177176 | A1 | 8/2005 | Gerbi et al. |
| 2005/0177181 | A1 | 8/2005 | Kagan et al. |
| 2005/0177249 | A1 | 8/2005 | Kladakis et al. |
| 2005/0182298 | A1 | 8/2005 | Ikeda et al. |
| 2005/0182443 | A1 | 8/2005 | Jonn et al. |
| 2005/0184121 | A1 | 8/2005 | Heinrich |
| 2005/0186240 | A1 | 8/2005 | Ringeisen et al. |
| 2005/0187545 | A1 | 8/2005 | Hooven et al. |
| 2005/0191936 | A1 | 9/2005 | Marine et al. |
| 2005/0197859 | A1 | 9/2005 | Wilson et al. |

(56) References Cited

U.S. PATENT DOCUMENTS

2005/0203550 A1 9/2005 Laufer et al.
2005/0209614 A1 9/2005 Fenter et al.
2005/0216055 A1 9/2005 Scirica et al.
2005/0222587 A1 10/2005 Jinno et al.
2005/0222611 A1 10/2005 Weitkamp
2005/0222616 A1 10/2005 Rethy et al.
2005/0222665 A1 10/2005 Aranyi
2005/0228224 A1 10/2005 Okada et al.
2005/0228446 A1 10/2005 Mooradian et al.
2005/0230453 A1 10/2005 Viola
2005/0240178 A1 10/2005 Morley et al.
2005/0242950 A1 11/2005 Lindsay et al.
2005/0245965 A1 11/2005 Orban, III et al.
2005/0246881 A1 11/2005 Kelly et al.
2005/0251063 A1 11/2005 Basude
2005/0256452 A1 11/2005 Demarchi et al.
2005/0256546 A1 11/2005 Vaisnys et al.
2005/0258963 A1 11/2005 Rodriguez et al.
2005/0261676 A1 11/2005 Hall et al.
2005/0263563 A1 12/2005 Racenet et al.
2005/0267455 A1 12/2005 Eggers et al.
2005/0267464 A1 12/2005 Truckai et al.
2005/0267529 A1 12/2005 Crockett et al.
2005/0274034 A1 12/2005 Hayashida et al.
2005/0283188 A1 12/2005 Loshakove et al.
2005/0283226 A1 12/2005 Haverkost
2006/0008787 A1 1/2006 Hayman et al.
2006/0011698 A1 1/2006 Okada et al.
2006/0015009 A1 1/2006 Jaffe et al.
2006/0020167 A1 1/2006 Sitzmann
2006/0020258 A1 1/2006 Strauss et al.
2006/0020272 A1 1/2006 Gildenberg
2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0116634 A1 6/2006 Shachar
2006/0142656 A1 6/2006 Malackowski et al.
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0226196 A1 10/2006 Hueil et al.
2006/0226957 A1 10/2006 Miller et al.
2006/0235368 A1 10/2006 Oz
2006/0241666 A1 10/2006 Briggs et al.
2006/0241691 A1 10/2006 Wilk
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289600 A1 12/2006 Wales et al.
2006/0289602 A1 12/2006 Wales et al.
2006/0291981 A1 12/2006 Viola et al.
2007/0005045 A1 1/2007 Mintz et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0018958 A1 1/2007 Tavakoli et al.
2007/0026039 A1 2/2007 Drumheller et al.
2007/0026040 A1 2/2007 Crawley et al.
2007/0027459 A1 2/2007 Horvath et al.
2007/0027468 A1 2/2007 Wales et al.
2007/0027551 A1 2/2007 Farnsworth et al.
2007/0043338 A1 2/2007 Moll et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0055305 A1 3/2007 Schnyder et al.
2007/0069851 A1 3/2007 Sung et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084896 A1 * 4/2007 Doll ................. A61B 17/07207
227/19
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0152829 A1 7/2007 Lindsay et al.
2007/0155010 A1 7/2007 Farnsworth et al.
2007/0162056 A1 7/2007 Gerbi et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.
2007/0179476 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0191915 A1 8/2007 Strother et al.
2007/0194079 A1 8/2007 Hueil et al.
2007/0194081 A1 8/2007 Hueil et al.
2007/0194082 A1 8/2007 Morgan et al.

(56) References Cited

U.S. PATENT DOCUMENTS

2007/0197954 A1 8/2007 Keenan
2007/0198039 A1 8/2007 Jones et al.
2007/0203510 A1 8/2007 Bettuchi
2007/0207010 A1 9/2007 Caspi
2007/0208359 A1 9/2007 Hoffman
2007/0208375 A1 9/2007 Nishizawa et al.
2007/0213750 A1 9/2007 Weadock
2007/0221701 A1 9/2007 Ortiz et al.
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0260132 A1 11/2007 Sterling
2007/0260242 A1 11/2007 Dycus et al.
2007/0262592 A1 11/2007 Hwang et al.
2007/0270660 A1 11/2007 Caylor et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0046000 A1 2/2008 Lee et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0069736 A1 3/2008 Mingerink et al.
2008/0071328 A1 3/2008 Haubrich et al.
2008/0077158 A1 3/2008 Haider et al.
2008/0078802 A1 4/2008 Hess et al.
2008/0081948 A1 4/2008 Weisenburgh et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0083811 A1 4/2008 Marczyk
2008/0085296 A1 4/2008 Powell et al.
2008/0086078 A1 4/2008 Powell et al.
2008/0091072 A1 4/2008 Omori et al.
2008/0094228 A1 4/2008 Welch et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0126984 A1 5/2008 Fleishman et al.
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0208058 A1 8/2008 Sabata et al.
2008/0216704 A1 9/2008 Eisenbeis et al.
2008/0217376 A1 9/2008 Clauson et al.
2008/0234709 A1 9/2008 Houser
2008/0234866 A1 9/2008 Kishi et al.
2008/0242939 A1 10/2008 Johnston
2008/0243088 A1 10/2008 Evans
2008/0243143 A1 10/2008 Kuhns et al.
2008/0249536 A1 10/2008 Stahler et al.
2008/0249608 A1 10/2008 Dave
2008/0255413 A1 10/2008 Zemlok et al.
2008/0255420 A1 10/2008 Lee et al.
2008/0255421 A1 10/2008 Hegeman et al.
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296346 A1 12/2008 Shelton, IV et al.
2008/0296347 A1 12/2008 Shelton, IV et al.
2008/0297287 A1 12/2008 Shachar et al.
2008/0298784 A1 12/2008 Kastner
2008/0308504 A1 12/2008 Hallan et al.
2008/0308602 A1 12/2008 Timm et al.
2008/0308603 A1 12/2008 Shelton et al.
2008/0308607 A1 12/2008 Timm et al.
2008/0308807 A1 12/2008 Yamazaki et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0007014 A1 1/2009 Coomer et al.
2009/0012534 A1 1/2009 Madhani et al.
2009/0015195 A1 1/2009 Loth-Krausser
2009/0020958 A1 1/2009 Soul
2009/0030437 A1 1/2009 Houser et al.
2009/0043253 A1 2/2009 Podaima
2009/0048583 A1 2/2009 Williams et al.
2009/0048589 A1 2/2009 Takashino et al.
2009/0053288 A1 2/2009 Eskridge, Jr. et al.
2009/0057369 A1 3/2009 Smith et al.
2009/0069806 A1 3/2009 De La Mora Levy et al.
2009/0076506 A1 3/2009 Baker
2009/0078736 A1 3/2009 Van Lue
2009/0081313 A1 3/2009 Aghion et al.
2009/0088659 A1 4/2009 Graham et al.
2009/0090763 A1 4/2009 Zemlok et al.
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0114701 A1 5/2009 Zemlok et al.
2009/0118762 A1 5/2009 Crainch et al.
2009/0119011 A1 5/2009 Kondo et al.
2009/0120994 A1 5/2009 Murray et al.
2009/0131819 A1 5/2009 Ritchie et al.
2009/0132400 A1 5/2009 Conway
2009/0135280 A1 5/2009 Johnston et al.
2009/0138003 A1 5/2009 Deville et al.
2009/0143797 A1 6/2009 Smith et al.
2009/0143855 A1 6/2009 Weber et al.
2009/0149871 A9 6/2009 Kagan et al.
2009/0167548 A1 7/2009 Sugahara
2009/0171147 A1 7/2009 Lee et al.

(56) References Cited

U.S. PATENT DOCUMENTS

| | | | |
|---|---|---|---|
| 2009/0177218 | A1 | 7/2009 | Young et al. |
| 2009/0177226 | A1 | 7/2009 | Reinprecht et al. |
| 2009/0181290 | A1 | 7/2009 | Baldwin et al. |
| 2009/0188964 | A1 | 7/2009 | Orlov |
| 2009/0192534 | A1 | 7/2009 | Ortiz et al. |
| 2009/0198272 | A1 | 8/2009 | Kerver et al. |
| 2009/0204108 | A1 | 8/2009 | Steffen |
| 2009/0204109 | A1 | 8/2009 | Grove et al. |
| 2009/0204126 | A1 | 8/2009 | Le |
| 2009/0204925 | A1 | 8/2009 | Bhat et al. |
| 2009/0206125 | A1 | 8/2009 | Huitema et al. |
| 2009/0206126 | A1 | 8/2009 | Huitema et al. |
| 2009/0206131 | A1 | 8/2009 | Weisenburgh, II et al. |
| 2009/0206133 | A1 | 8/2009 | Morgan et al. |
| 2009/0206137 | A1 | 8/2009 | Hall et al. |
| 2009/0206139 | A1 | 8/2009 | Hall et al. |
| 2009/0206141 | A1 | 8/2009 | Huitema et al. |
| 2009/0206142 | A1 | 8/2009 | Huitema et al. |
| 2009/0206143 | A1 | 8/2009 | Huitema et al. |
| 2009/0221993 | A1 | 9/2009 | Sohi et al. |
| 2009/0227834 | A1 | 9/2009 | Nakamoto et al. |
| 2009/0234273 | A1 | 9/2009 | Lntoccia et al. |
| 2009/0236401 | A1 | 9/2009 | Cole et al. |
| 2009/0242610 | A1 | 10/2009 | Shelton, IV et al. |
| 2009/0246873 | A1 | 10/2009 | Yamamoto et al. |
| 2009/0247368 | A1 | 10/2009 | Chiang |
| 2009/0247901 | A1 | 10/2009 | Zimmer |
| 2009/0248100 | A1 | 10/2009 | Vaisnys et al. |
| 2009/0253959 | A1 | 10/2009 | Yoshie et al. |
| 2009/0255974 | A1 | 10/2009 | Viola |
| 2009/0261141 | A1 | 10/2009 | Stratton et al. |
| 2009/0262078 | A1 | 10/2009 | Pizzi |
| 2009/0264940 | A1 | 10/2009 | Beale et al. |
| 2009/0270895 | A1 | 10/2009 | Churchill et al. |
| 2009/0273353 | A1 | 11/2009 | Kroh et al. |
| 2009/0277288 | A1 | 11/2009 | Doepker et al. |
| 2009/0278406 | A1 | 11/2009 | Hoffman |
| 2009/0290016 | A1 | 11/2009 | Suda |
| 2009/0292283 | A1 | 11/2009 | Odom |
| 2009/0306639 | A1 | 12/2009 | Nevo et al. |
| 2009/0308907 | A1 | 12/2009 | Nalagatla et al. |
| 2009/0318557 | A1 | 12/2009 | Stockel |
| 2009/0318936 | A1 | 12/2009 | Harris et al. |
| 2009/0325859 | A1 | 12/2009 | Ameer et al. |
| 2010/0002013 | A1 | 1/2010 | Kagaya |
| 2010/0005035 | A1 | 1/2010 | Carpenter et al. |
| 2010/0012703 | A1 | 1/2010 | Calabrese et al. |
| 2010/0015104 | A1 | 1/2010 | Fraser et al. |
| 2010/0016853 | A1 | 1/2010 | Burbank |
| 2010/0016888 | A1 | 1/2010 | Calabrese et al. |
| 2010/0017715 | A1 | 1/2010 | Balassanian |
| 2010/0023024 | A1 | 1/2010 | Zeiner et al. |
| 2010/0030233 | A1 | 2/2010 | Whitman et al. |
| 2010/0030239 | A1 | 2/2010 | Viola et al. |
| 2010/0032179 | A1 | 2/2010 | Hanspers et al. |
| 2010/0036370 | A1 | 2/2010 | Mirel et al. |
| 2010/0036441 | A1 | 2/2010 | Procter |
| 2010/0051668 | A1 | 3/2010 | Milliman et al. |
| 2010/0057118 | A1 | 3/2010 | Dietz et al. |
| 2010/0065604 | A1 | 3/2010 | Weng |
| 2010/0069833 | A1 | 3/2010 | Wenderow et al. |
| 2010/0069942 | A1 | 3/2010 | Shelton, IV |
| 2010/0076483 | A1 | 3/2010 | Imuta |
| 2010/0076489 | A1 | 3/2010 | Stopek et al. |
| 2010/0081883 | A1 | 4/2010 | Murray et al. |
| 2010/0094312 | A1 | 4/2010 | Ruiz Morales et al. |
| 2010/0094340 | A1 | 4/2010 | Stopek et al. |
| 2010/0094400 | A1 | 4/2010 | Bolduc et al. |
| 2010/0100123 | A1 | 4/2010 | Bennett |
| 2010/0100124 | A1 | 4/2010 | Calabrese et al. |
| 2010/0106167 | A1 | 4/2010 | Boulnois et al. |
| 2010/0116519 | A1 | 5/2010 | Gareis |
| 2010/0122339 | A1 | 5/2010 | Boccacci |
| 2010/0125786 | A1 | 5/2010 | Ozawa et al. |
| 2010/0133317 | A1 | 6/2010 | Shelton, IV et al. |
| 2010/0137990 | A1 | 6/2010 | Apatsidis et al. |
| 2010/0138659 | A1 | 6/2010 | Carmichael et al. |
| 2010/0145146 | A1 | 6/2010 | Melder |
| 2010/0147921 | A1 | 6/2010 | Olson |
| 2010/0147922 | A1 | 6/2010 | Olson |
| 2010/0159435 | A1 | 6/2010 | Mueller et al. |
| 2010/0168741 | A1 | 7/2010 | Sanai et al. |
| 2010/0179022 | A1 | 7/2010 | Shirokoshi |
| 2010/0180711 | A1 | 7/2010 | Kilibarda et al. |
| 2010/0187285 | A1 | 7/2010 | Harris et al. |
| 2010/0191255 | A1 | 7/2010 | Crainich et al. |
| 2010/0191262 | A1 | 7/2010 | Harris et al. |
| 2010/0191292 | A1 | 7/2010 | DeMeo et al. |
| 2010/0193566 | A1 | 8/2010 | Scheib et al. |
| 2010/0194541 | A1 | 8/2010 | Stevenson et al. |
| 2010/0198159 | A1 | 8/2010 | Voss et al. |
| 2010/0204717 | A1 | 8/2010 | Knodel |
| 2010/0204721 | A1 | 8/2010 | Young et al. |
| 2010/0217281 | A1 | 8/2010 | Matsuoka et al. |
| 2010/0218019 | A1 | 8/2010 | Eckhard |
| 2010/0222901 | A1 | 9/2010 | Swayze et al. |
| 2010/0228250 | A1 | 9/2010 | Brogna |
| 2010/0234687 | A1 | 9/2010 | Azarbarzin et al. |
| 2010/0241115 | A1 | 9/2010 | Benamou et al. |
| 2010/0241137 | A1 | 9/2010 | Doyle et al. |
| 2010/0245102 | A1 | 9/2010 | Yokoi |
| 2010/0249497 | A1 | 9/2010 | Peine et al. |
| 2010/0249947 | A1 | 9/2010 | Lesh et al. |
| 2010/0256675 | A1 | 10/2010 | Romans |
| 2010/0258327 | A1 | 10/2010 | Esenwein et al. |
| 2010/0267525 | A1 | 10/2010 | Tanner |
| 2010/0267662 | A1 | 10/2010 | Fielder et al. |
| 2010/0274160 | A1 | 10/2010 | Yachi et al. |
| 2010/0291184 | A1 | 11/2010 | Clark et al. |
| 2010/0292540 | A1 | 11/2010 | Hess et al. |
| 2010/0298636 | A1 | 11/2010 | Castro et al. |
| 2010/0301097 | A1 | 12/2010 | Scirica et al. |
| 2010/0310623 | A1 | 12/2010 | Laurencin et al. |
| 2010/0312261 | A1 | 12/2010 | Suzuki et al. |
| 2010/0318085 | A1 | 12/2010 | Austin et al. |
| 2010/0325568 | A1 | 12/2010 | Pedersen et al. |
| 2010/0327041 | A1 | 12/2010 | Milliman et al. |
| 2010/0331856 | A1 | 12/2010 | Carlson et al. |
| 2011/0006101 | A1 | 1/2011 | Hall et al. |
| 2011/0009694 | A1 | 1/2011 | Schultz et al. |
| 2011/0011916 | A1 | 1/2011 | Levine |
| 2011/0016960 | A1 | 1/2011 | Debrailly |
| 2011/0021871 | A1 | 1/2011 | Berkelaar |
| 2011/0022032 | A1 | 1/2011 | Zemlok et al. |
| 2011/0024477 | A1 | 2/2011 | Hall |
| 2011/0024478 | A1 | 2/2011 | Shelton, IV |
| 2011/0025311 | A1 | 2/2011 | Chauvin et al. |
| 2011/0028991 | A1 | 2/2011 | Ikeda et al. |
| 2011/0029003 | A1 | 2/2011 | Lavigne et al. |
| 2011/0029270 | A1 | 2/2011 | Mueglitz |
| 2011/0036891 | A1 | 2/2011 | Zemlok et al. |
| 2011/0046667 | A1 | 2/2011 | Culligan et al. |
| 2011/0052660 | A1 | 3/2011 | Yang et al. |
| 2011/0056717 | A1 | 3/2011 | Herisse |
| 2011/0060363 | A1 | 3/2011 | Hess et al. |
| 2011/0066156 | A1 | 3/2011 | McGahan et al. |
| 2011/0082538 | A1 | 4/2011 | Dahlgren et al. |
| 2011/0087276 | A1 | 4/2011 | Bedi et al. |
| 2011/0088921 | A1 | 4/2011 | Forgues et al. |
| 2011/0091515 | A1 | 4/2011 | Zilberman et al. |
| 2011/0095064 | A1 | 4/2011 | Taylor et al. |
| 2011/0095067 | A1 | 4/2011 | Ohdaira |
| 2011/0101069 | A1 | 5/2011 | Bombard et al. |
| 2011/0101794 | A1 | 5/2011 | Schroeder et al. |
| 2011/0112517 | A1 | 5/2011 | Peine et al. |
| 2011/0112530 | A1 | 5/2011 | Keller |
| 2011/0114697 | A1 | 5/2011 | Baxter, III et al. |
| 2011/0118708 | A1 | 5/2011 | Burbank et al. |
| 2011/0118754 | A1 | 5/2011 | Dachs, II et al. |
| 2011/0125149 | A1 | 5/2011 | Ei-Galley et al. |
| 2011/0125176 | A1 | 5/2011 | Yates et al. |
| 2011/0127945 | A1 | 6/2011 | Yoneda |
| 2011/0129706 | A1 | 6/2011 | Takahashi et al. |
| 2011/0144764 | A1 | 6/2011 | Bagga et al. |

(56) References Cited

U.S. PATENT DOCUMENTS

2011/0147433 A1 6/2011 Shelton, IV et al.
2011/0155780 A1* 6/2011 Boudreaux ...... A61B 17/07207 227/175.1
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0192882 A1 8/2011 Hess et al.
2011/0198381 A1 8/2011 McCardle et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0224543 A1 9/2011 Johnson et al.
2011/0225105 A1 9/2011 Scholer et al.
2011/0230713 A1 9/2011 Kleemann et al.
2011/0235168 A1 9/2011 Sander
2011/0238044 A1 9/2011 Main et al.
2011/0241597 A1 10/2011 Zhu et al.
2011/0251606 A1 10/2011 Kerr
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278035 A1 11/2011 Chen
2011/0278343 A1 11/2011 Knodel et al.
2011/0279268 A1 11/2011 Konishi et al.
2011/0285507 A1 11/2011 Nelson
2011/0290856 A1 12/2011 Shelton, IV et al.
2011/0290858 A1 12/2011 Whitman et al.
2011/0292258 A1 12/2011 Adler et al.
2011/0293690 A1 12/2011 Griffin et al.
2011/0295295 A1 12/2011 Shelton, IV et al.
2011/0295299 A1 12/2011 Braithwaite et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0008880 A1 1/2012 Toth
2012/0010615 A1 1/2012 Cummings et al.
2012/0016239 A1 1/2012 Barthe et al.
2012/0016413 A1 1/2012 Timm et al.
2012/0016467 A1 1/2012 Chen et al.
2012/0029272 A1 2/2012 Shelton, IV et al.
2012/0029550 A1 2/2012 Forsell
2012/0033360 A1 2/2012 Hsu
2012/0059286 A1 3/2012 Hastings et al.
2012/0064483 A1 3/2012 Lint et al.
2012/0074200 A1 3/2012 Schmid et al.
2012/0078243 A1 3/2012 Worrell et al.
2012/0078244 A1 3/2012 Worrell et al.
2012/0080336 A1 4/2012 Shelton, IV et al.
2012/0080344 A1 4/2012 Shelton, IV
2012/0080478 A1 4/2012 Morgan et al.
2012/0080491 A1 4/2012 Shelton, IV et al.
2012/0080498 A1 4/2012 Shelton, IV et al.
2012/0083836 A1 4/2012 Shelton, IV et al.
2012/0086276 A1 4/2012 Sawyers
2012/0095458 A1 4/2012 Cybulski et al.
2012/0101488 A1 4/2012 Aldridge et al.
2012/0109186 A1 5/2012 Parrott et al.
2012/0116261 A1 5/2012 Mumaw et al.
2012/0116262 A1 5/2012 Houser et al.
2012/0116263 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0132663 A1 5/2012 Kasvikis et al.
2012/0143175 A1 6/2012 Hermann et al.
2012/0171539 A1 7/2012 Rejman et al.
2012/0175398 A1 7/2012 Sandborn et al.
2012/0190964 A1 7/2012 Hyde et al.
2012/0197239 A1 8/2012 Smith et al.
2012/0197272 A1 8/2012 Oray et al.
2012/0203213 A1 8/2012 Kimball et al.
2012/0211542 A1 8/2012 Racenet
2012/0220990 A1 8/2012 McKenzie et al.
2012/0233298 A1 9/2012 Verbandt et al.
2012/0234895 A1 9/2012 O'Connor et al.
2012/0234897 A1 9/2012 Shelton, IV et al.
2012/0239068 A1 9/2012 Morris et al.
2012/0241494 A1 9/2012 Marczyk
2012/0241503 A1 9/2012 Baxter, III et al.
2012/0248169 A1 10/2012 Widenhouse et al.
2012/0251861 A1 10/2012 Liang et al.
2012/0253328 A1 10/2012 Cunningham et al.
2012/0256494 A1 10/2012 Kesler et al.
2012/0271327 A1 10/2012 West et al.
2012/0283707 A1 11/2012 Giordano et al.
2012/0286019 A1 11/2012 Hueil et al.
2012/0289811 A1 11/2012 Viola et al.
2012/0289979 A1 11/2012 Eskaros et al.
2012/0292367 A1 11/2012 Morgan et al.
2012/0296316 A1 11/2012 Imuta
2012/0296342 A1 11/2012 Haglund Wendelschafer
2012/0298722 A1 11/2012 Hess et al.
2012/0301498 A1 11/2012 Altreuter et al.
2012/0310254 A1 12/2012 Manzo et al.
2012/0312861 A1 12/2012 Gurumurthy et al.
2012/0316424 A1 12/2012 Stopek
2012/0330285 A1 12/2012 Hartoumbekis et al.
2012/0330329 A1 12/2012 Harris et al.
2013/0006227 A1 1/2013 Takash I No
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0057162 A1 3/2013 Pollischansky
2013/0068816 A1 3/2013 Mandakolathur Vasudevan et al.
2013/0069088 A1 3/2013 Speck et al.
2013/0075447 A1 3/2013 Weisenburgh, II et al.
2013/0087597 A1 4/2013 Shelton, IV et al.
2013/0090534 A1 4/2013 Burns et al.
2013/0096568 A1 4/2013 Justis
2013/0098970 A1 4/2013 Racenet et al.
2013/0106352 A1 5/2013 Nagamine
2013/0112729 A1 5/2013 Beardsley et al.
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153639 A1 6/2013 Hodgkinson et al.
2013/0153641 A1 6/2013 Shelton, IV et al.
2013/0158390 A1 6/2013 Tan et al.
2013/0162198 A1 6/2013 Yokota et al.
2013/0165908 A1 6/2013 Purdy et al.
2013/0169217 A1 7/2013 Watanabe et al.
2013/0172713 A1 7/2013 Kirschenman
2013/0172878 A1 7/2013 Smith
2013/0175315 A1 7/2013 Milliman
2013/0175317 A1 7/2013 Yates et al.
2013/0183769 A1 7/2013 Tajima
2013/0211244 A1 8/2013 Nathaniel
2013/0214025 A1 8/2013 Zemlok et al.
2013/0215449 A1 8/2013 Yamasaki
2013/0231681 A1 9/2013 Robinson et al.
2013/0233906 A1 9/2013 Hess et al.
2013/0238021 A1 9/2013 Gross et al.
2013/0248578 A1 9/2013 Arteaga Gonzalez
2013/0253480 A1 9/2013 Kimball et al.

(56) References Cited

U.S. PATENT DOCUMENTS

2013/0256373 A1 10/2013 Schmid et al.
2013/0256380 A1 10/2013 Schmid et al.
2013/0267950 A1 10/2013 Rosa et al.
2013/0267978 A1 10/2013 Trissel
2013/0270322 A1 10/2013 Scheib et al.
2013/0277410 A1 10/2013 Fernandez et al.
2013/0284792 A1 10/2013 Ma
2013/0289565 A1 10/2013 Hassler, Jr.
2013/0293353 A1 11/2013 McPherson et al.
2013/0303845 A1 11/2013 Skula et al.
2013/0304084 A1 11/2013 Beira et al.
2013/0306704 A1 11/2013 Balbierz et al.
2013/0327552 A1 12/2013 Lovelass et al.
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0002322 A1 1/2014 Kanome et al.
2014/0005550 A1 1/2014 Lu et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0008289 A1 1/2014 Williams et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0088614 A1 3/2014 Blumenkranz
2014/0088639 A1* 3/2014 Bartels ............... A61B 17/2816
606/207
2014/0094681 A1 4/2014 Valentine et al.
2014/0100558 A1 4/2014 Schmitz et al.
2014/0107697 A1 4/2014 Patani et al.
2014/0110453 A1 4/2014 Wingardner et al.
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0148803 A1 5/2014 Taylor
2014/0151433 A1 6/2014 Shelton, IV et al.
2014/0155916 A1 6/2014 Hodgkinson et al.
2014/0158747 A1 6/2014 Measamer et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0207124 A1 7/2014 Aldridge et al.
2014/0209658 A1 7/2014 Skalla et al.
2014/0224857 A1 8/2014 Schmid
2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch et al.
2014/0249573 A1 9/2014 Arav
2014/0262408 A1 9/2014 Woodard
2014/0263541 A1 9/2014 Leimbach et al.
2014/0263552 A1 9/2014 Hall et al.
2014/0263558 A1 9/2014 Hausen et al.
2014/0276720 A1 9/2014 Parihar et al.
2014/0276730 A1 9/2014 Boudreaux et al.
2014/0276776 A1 9/2014 Parihar et al.
2014/0284371 A1 9/2014 Morgan et al.
2014/0287703 A1 9/2014 Herbsommer et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0371764 A1 12/2014 Oyola et al.
2014/0373003 A1 12/2014 Grez et al.
2014/0374130 A1 12/2014 Nakamura et al.
2014/0378950 A1 12/2014 Chiu
2015/0001272 A1 1/2015 Sniffin et al.
2015/0002089 A1 1/2015 Rejman et al.
2015/0022012 A1 1/2015 Kim et al.
2015/0025549 A1 1/2015 Kilroy et al.
2015/0025571 A1 1/2015 Suzuki et al.
2015/0034697 A1 2/2015 Mastri et al.
2015/0039010 A1 2/2015 Beardsley et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060516 A1 3/2015 Collings et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0067582 A1 3/2015 Donnelly et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0080883 A1 3/2015 Haverkost et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0209045 A1 7/2015 Hodgkinson et al.
2015/0216605 A1 8/2015 Baldwin
2015/0222212 A1 8/2015 Iwata
2015/0223868 A1 8/2015 Brandt et al.
2015/0230697 A1 8/2015 Phee et al.
2015/0230794 A1 8/2015 Wellman et al.
2015/0230861 A1 8/2015 Woloszko et al.
2015/0231409 A1 8/2015 Racenet et al.
2015/0238118 A1 8/2015 Legassey et al.

(56) References Cited

U.S. PATENT DOCUMENTS

| | | | |
|---|---|---|---|
| 2015/0272557 | A1 | 10/2015 | Overmyer et al. |
| 2015/0272571 | A1 | 10/2015 | Leimbach et al. |
| 2015/0272580 | A1 | 10/2015 | Leimbach et al. |
| 2015/0272582 | A1 | 10/2015 | Leimbach et al. |
| 2015/0272606 | A1 | 10/2015 | Nobis |
| 2015/0297200 | A1 | 10/2015 | Fitzsimmons et al. |
| 2015/0297222 | A1 | 10/2015 | Huitema et al. |
| 2015/0297223 | A1 | 10/2015 | Huitema et al. |
| 2015/0297225 | A1 | 10/2015 | Huitema et al. |
| 2015/0297228 | A1 | 10/2015 | Huitema et al. |
| 2015/0297824 | A1 | 10/2015 | Cabiri et al. |
| 2015/0303417 | A1 | 10/2015 | Koeder et al. |
| 2015/0305743 | A1 | 10/2015 | Casasanta et al. |
| 2015/0313594 | A1 | 11/2015 | Shelton, IV et al. |
| 2015/0324317 | A1 | 11/2015 | Collins et al. |
| 2015/0352699 | A1 | 12/2015 | Sakai et al. |
| 2015/0366585 | A1 | 12/2015 | Lemay et al. |
| 2015/0367497 | A1 | 12/2015 | Ito et al. |
| 2015/0372265 | A1 | 12/2015 | Morisaku et al. |
| 2015/0374372 | A1 | 12/2015 | Zergiebel et al. |
| 2015/0374378 | A1 | 12/2015 | Giordano et al. |
| 2016/0000437 | A1 | 1/2016 | Giordano et al. |
| 2016/0000452 | A1 | 1/2016 | Yates et al. |
| 2016/0000453 | A1 | 1/2016 | Yates et al. |
| 2016/0029998 | A1 | 2/2016 | Brister et al. |
| 2016/0030042 | A1 | 2/2016 | Heinrich et al. |
| 2016/0030043 | A1 | 2/2016 | Fanelli et al. |
| 2016/0030076 | A1 | 2/2016 | Faller et al. |
| 2016/0051316 | A1 | 2/2016 | Boudreaux |
| 2016/0066913 | A1 | 3/2016 | Swayze et al. |
| 2016/0069449 | A1 | 3/2016 | Kanai et al. |
| 2016/0074035 | A1 | 3/2016 | Whitman et al. |
| 2016/0074040 | A1 | 3/2016 | Widenhouse et al. |
| 2016/0081678 | A1 | 3/2016 | Kappel et al. |
| 2016/0082161 | A1 | 3/2016 | Zilberman et al. |
| 2016/0089175 | A1 | 3/2016 | Hibner et al. |
| 2016/0099601 | A1 | 4/2016 | Leabman et al. |
| 2016/0100838 | A1 | 4/2016 | Beaupré et al. |
| 2016/0118201 | A1 | 4/2016 | Nicholas et al. |
| 2016/0132026 | A1 | 5/2016 | Wingardner et al. |
| 2016/0135835 | A1 | 5/2016 | Onuma |
| 2016/0135895 | A1 | 5/2016 | Faasse et al. |
| 2016/0139666 | A1 | 5/2016 | Rubin et al. |
| 2016/0174969 | A1 | 6/2016 | Kerr et al. |
| 2016/0174983 | A1 | 6/2016 | Shelton, IV et al. |
| 2016/0175021 | A1 | 6/2016 | Hassler, Jr. |
| 2016/0183939 | A1 | 6/2016 | Shelton, IV et al. |
| 2016/0183943 | A1 | 6/2016 | Shelton, IV |
| 2016/0183944 | A1 | 6/2016 | Swensgard et al. |
| 2016/0192927 | A1 | 7/2016 | Kostrzewski |
| 2016/0192960 | A1 | 7/2016 | Bueno et al. |
| 2016/0199063 | A1 | 7/2016 | Mandakolathur Vasudevan et al. |
| 2016/0199956 | A1 | 7/2016 | Shelton, IV et al. |
| 2016/0220150 | A1 | 8/2016 | Sharonov |
| 2016/0235494 | A1 | 8/2016 | Shelton, IV et al. |
| 2016/0242783 | A1 | 8/2016 | Shelton, IV et al. |
| 2016/0242855 | A1 | 8/2016 | Fichtinger et al. |
| 2016/0249910 | A1 | 9/2016 | Shelton, IV et al. |
| 2016/0249922 | A1 | 9/2016 | Morgan et al. |
| 2016/0249929 | A1 | 9/2016 | Cappola et al. |
| 2016/0256159 | A1 | 9/2016 | Pinjala et al. |
| 2016/0256184 | A1 | 9/2016 | Shelton, IV et al. |
| 2016/0256221 | A1 | 9/2016 | Smith |
| 2016/0256229 | A1 | 9/2016 | Morgan et al. |
| 2016/0262745 | A1 | 9/2016 | Morgan et al. |
| 2016/0262921 | A1 | 9/2016 | Balbierz et al. |
| 2016/0270781 | A1 | 9/2016 | Scirica |
| 2016/0287265 | A1 | 10/2016 | MacDonald et al. |
| 2016/0287279 | A1 | 10/2016 | Bovay et al. |
| 2016/0302820 | A1 | 10/2016 | Hibner et al. |
| 2016/0310143 | A1 | 10/2016 | Bettuchi |
| 2016/0314716 | A1 | 10/2016 | Grubbs |
| 2016/0314717 | A1 | 10/2016 | Grubbs |
| 2016/0345972 | A1 | 12/2016 | Beardsley et al. |
| 2016/0367122 | A1 | 12/2016 | Ichimura et al. |
| 2016/0374669 | A1 | 12/2016 | Overmyer et al. |
| 2016/0374716 | A1 | 12/2016 | Kessler |
| 2017/0000549 | A1 | 1/2017 | Gilbert et al. |
| 2017/0007234 | A1 | 1/2017 | Chin et al. |
| 2017/0007244 | A1 | 1/2017 | Shelton, IV et al. |
| 2017/0007245 | A1 | 1/2017 | Shelton, IV et al. |
| 2017/0007347 | A1 | 1/2017 | Jaworek et al. |
| 2017/0020616 | A1 | 1/2017 | Vale et al. |
| 2017/0035419 | A1 | 2/2017 | Decker et al. |
| 2017/0055819 | A1 | 3/2017 | Hansen et al. |
| 2017/0055980 | A1 | 3/2017 | Vendely et al. |
| 2017/0056008 | A1 | 3/2017 | Shelton, IV et al. |
| 2017/0056016 | A1 | 3/2017 | Barton et al. |
| 2017/0056018 | A1 | 3/2017 | Zeiner et al. |
| 2017/0066054 | A1 | 3/2017 | Birky |
| 2017/0079642 | A1 | 3/2017 | Overmyer et al. |
| 2017/0086829 | A1 | 3/2017 | Vendely et al. |
| 2017/0086830 | A1 | 3/2017 | Yates et al. |
| 2017/0086842 | A1 | 3/2017 | Shelton, IV et al. |
| 2017/0086930 | A1 | 3/2017 | Thompson et al. |
| 2017/0086932 | A1 | 3/2017 | Auld et al. |
| 2017/0095922 | A1 | 4/2017 | Licht et al. |
| 2017/0105727 | A1 | 4/2017 | Scheib et al. |
| 2017/0105733 | A1 | 4/2017 | Scheib et al. |
| 2017/0105786 | A1 | 4/2017 | Scheib et al. |
| 2017/0106302 | A1 | 4/2017 | Cummings et al. |
| 2017/0135711 | A1 | 5/2017 | Overmyer et al. |
| 2017/0135717 | A1 | 5/2017 | Boudreaux et al. |
| 2017/0135747 | A1 | 5/2017 | Broderick et al. |
| 2017/0143336 | A1 | 5/2017 | Shah et al. |
| 2017/0168187 | A1 | 6/2017 | Calderoni et al. |
| 2017/0172382 | A1 | 6/2017 | Nir et al. |
| 2017/0172549 | A1 | 6/2017 | Smaby et al. |
| 2017/0172662 | A1 | 6/2017 | Panescu et al. |
| 2017/0181803 | A1 | 6/2017 | Mayer-Ullmann et al. |
| 2017/0182195 | A1 | 6/2017 | Wagner |
| 2017/0182211 | A1 | 6/2017 | Raxworthy et al. |
| 2017/0196558 | A1 | 7/2017 | Morgan et al. |
| 2017/0196649 | A1 | 7/2017 | Yates et al. |
| 2017/0202605 | A1 | 7/2017 | Shelton, IV et al. |
| 2017/0202607 | A1 | 7/2017 | Shelton, IV et al. |
| 2017/0202770 | A1 | 7/2017 | Friedrich et al. |
| 2017/0224332 | A1 | 8/2017 | Hunter et al. |
| 2017/0231628 | A1 | 8/2017 | Shelton, IV et al. |
| 2017/0231629 | A1 | 8/2017 | Stopek et al. |
| 2017/0238962 | A1 | 8/2017 | Hansen et al. |
| 2017/0238991 | A1 | 8/2017 | Worrell et al. |
| 2017/0242455 | A1 | 8/2017 | Dickens |
| 2017/0245880 | A1 | 8/2017 | Honda et al. |
| 2017/0245949 | A1 | 8/2017 | Randle |
| 2017/0249431 | A1 | 8/2017 | Shelton, IV et al. |
| 2017/0252060 | A1 | 9/2017 | Ellingson et al. |
| 2017/0255799 | A1 | 9/2017 | Zhao et al. |
| 2017/0258471 | A1 | 9/2017 | DiNardo et al. |
| 2017/0262110 | A1 | 9/2017 | Polishchuk et al. |
| 2017/0265774 | A1 | 9/2017 | Johnson et al. |
| 2017/0281186 | A1 | 10/2017 | Shelton, IV et al. |
| 2017/0296173 | A1 | 10/2017 | Shelton, IV et al. |
| 2017/0296185 | A1 | 10/2017 | Swensgard et al. |
| 2017/0296213 | A1 | 10/2017 | Swensgard et al. |
| 2017/0303984 | A1 | 10/2017 | Malackowski |
| 2017/0312042 | A1 | 11/2017 | Giordano et al. |
| 2017/0319047 | A1 | 11/2017 | Poulsen et al. |
| 2017/0319201 | A1 | 11/2017 | Morgan et al. |
| 2017/0333034 | A1 | 11/2017 | Morgan et al. |
| 2017/0333035 | A1 | 11/2017 | Morgan et al. |
| 2017/0348010 | A1 | 12/2017 | Chiang |
| 2017/0348043 | A1 | 12/2017 | Wang et al. |
| 2017/0354413 | A1 | 12/2017 | Chen et al. |
| 2017/0358052 | A1 | 12/2017 | Yuan |
| 2017/0360441 | A1 | 12/2017 | Sgroi |
| 2018/0008265 | A1 | 1/2018 | Hatanaka et al. |
| 2018/0042610 | A1 | 2/2018 | Sgroi, Jr. |
| 2018/0042689 | A1 | 2/2018 | Mozdzierz et al. |
| 2018/0049738 | A1 | 2/2018 | Meloul et al. |
| 2018/0049794 | A1 | 2/2018 | Swayze et al. |
| 2018/0051780 | A1 | 2/2018 | Shelton, IV et al. |
| 2018/0055501 | A1 | 3/2018 | Zemlok et al. |
| 2018/0067004 | A1 | 3/2018 | Sgroi, Jr. |

(56) References Cited

U.S. PATENT DOCUMENTS

2018/0085117 A1 3/2018 Shelton, IV et al.
2018/0085120 A1 3/2018 Viola
2018/0092710 A1 4/2018 Bosisio et al.
2018/0114591 A1 4/2018 Pribanic et al.
2018/0116658 A1 5/2018 Aronhalt, IV et al.
2018/0116662 A1 5/2018 Shelton, IV et al.
2018/0125481 A1 5/2018 Yates et al.
2018/0125487 A1 5/2018 Beardsley
2018/0125488 A1 5/2018 Morgan et al.
2018/0125594 A1 5/2018 Beardsley
2018/0132845 A1 5/2018 Schmid et al.
2018/0132849 A1 5/2018 Miller et al.
2018/0132850 A1 5/2018 Leimbach et al.
2018/0132926 A1 5/2018 Asher et al.
2018/0132952 A1 5/2018 Spivey et al.
2018/0133521 A1 5/2018 Frushour et al.
2018/0140299 A1 5/2018 Weaner et al.
2018/0146960 A1 5/2018 Shelton, IV et al.
2018/0153542 A1 6/2018 Shelton, IV et al.
2018/0153634 A1 6/2018 Zemlok et al.
2018/0161034 A1 6/2018 Scheib et al.
2018/0168572 A1 6/2018 Burbank
2018/0168574 A1 6/2018 Robinson et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168610 A1 6/2018 Shelton, IV et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168642 A1* 6/2018 Shelton, IV ........... A61B 34/30
2018/0168647 A1 6/2018 Shelton, IV et al.
2018/0168648 A1 6/2018 Shelton, IV et al.
2018/0168650 A1 6/2018 Shelton, IV et al.
2018/0168754 A1 6/2018 Overmyer
2018/0168756 A1 6/2018 Liao et al.
2018/0206904 A1 7/2018 Felder et al.
2018/0228490 A1 8/2018 Richard et al.
2018/0231111 A1 8/2018 Mika et al.
2018/0231475 A1 8/2018 Brown et al.
2018/0235609 A1 8/2018 Harris et al.
2018/0235617 A1 8/2018 Shelton, IV et al.
2018/0235618 A1 8/2018 Kostrzewski
2018/0235626 A1 8/2018 Shelton, IV et al.
2018/0236181 A1 8/2018 Marlin et al.
2018/0242970 A1 8/2018 Mozdzierz
2018/0247711 A1 8/2018 Terry
2018/0250002 A1 9/2018 Eschbach
2018/0271520 A1 9/2018 Shelton, IV et al.
2018/0271553 A1 9/2018 Worrell
2018/0271604 A1 9/2018 Grout et al.
2018/0273597 A1 9/2018 Stimson
2018/0279994 A1 10/2018 Schaer et al.
2018/0280073 A1 10/2018 Sanai et al.
2018/0289371 A1 10/2018 Wang et al.
2018/0296216 A1 10/2018 Shelton, IV et al.
2018/0296290 A1 10/2018 Namiki et al.
2018/0317905 A1 11/2018 Olson et al.
2018/0317915 A1 11/2018 Mcdonald, II
2018/0325514 A1 11/2018 Harris et al.
2018/0333169 A1 11/2018 Leimbach et al.
2018/0360446 A1 12/2018 Shelton, IV et al.
2018/0360456 A1 12/2018 Shelton, IV et al.
2018/0360473 A1 12/2018 Shelton, IV et al.
2018/0368066 A1 12/2018 Howell et al.
2018/0368833 A1 12/2018 Shelton, IV et al.
2018/0368844 A1 12/2018 Bakos et al.
2018/0372806 A1 12/2018 Laughery et al.
2018/0375165 A1 12/2018 Shelton, IV et al.
2019/0000459 A1 1/2019 Shelton, IV et al.
2019/0000461 A1 1/2019 Shelton, IV et al.
2019/0000462 A1 1/2019 Shelton, IV et al.
2019/0000470 A1 1/2019 Yates et al.
2019/0000475 A1 1/2019 Shelton, IV et al.
2019/0000476 A1 1/2019 Shelton, IV et al.
2019/0000477 A1 1/2019 Shelton, IV et al.
2019/0000481 A1 1/2019 Harris et al.
2019/0000535 A1 1/2019 Messerly et al.
2019/0000536 A1 1/2019 Yates et al.
2019/0006047 A1 1/2019 Gorek et al.
2019/0008515 A1 1/2019 Beardsley et al.
2019/0015102 A1 1/2019 Baber et al.
2019/0015165 A1 1/2019 Giordano et al.
2019/0017311 A1 1/2019 McGettrick et al.
2019/0021733 A1 1/2019 Burbank
2019/0029682 A1 1/2019 Huitema et al.
2019/0029701 A1 1/2019 Shelton, IV et al.
2019/0033955 A1 1/2019 Leimbach et al.
2019/0038281 A1 2/2019 Shelton, IV et al.
2019/0038282 A1 2/2019 Shelton, IV et al.
2019/0038283 A1 2/2019 Shelton, IV et al.
2019/0038285 A1 2/2019 Mozdzierz
2019/0059986 A1 2/2019 Shelton, IV et al.
2019/0076143 A1 3/2019 Smith
2019/0090871 A1 3/2019 Shelton, IV et al.
2019/0091183 A1 3/2019 Tomat et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105039 A1 4/2019 Morgan et al.
2019/0105043 A1 4/2019 Jaworek et al.
2019/0105044 A1 4/2019 Shelton, IV et al.
2019/0110779 A1 4/2019 Gardner et al.
2019/0110791 A1 4/2019 Shelton, IV et al.
2019/0117224 A1 4/2019 Setser et al.
2019/0125320 A1 5/2019 Shelton, IV et al.
2019/0125335 A1 5/2019 Shelton, IV et al.
2019/0125336 A1 5/2019 Deck et al.
2019/0125338 A1 5/2019 Shelton, IV et al.
2019/0125342 A1 5/2019 Beardsley et al.
2019/0125344 A1 5/2019 Dinardo et al.
2019/0125361 A1 5/2019 Shelton, IV et al.
2019/0125377 A1 5/2019 Shelton, IV
2019/0125378 A1 5/2019 Shelton, IV et al.
2019/0125388 A1 5/2019 Shelton, IV et al.
2019/0125430 A1 5/2019 Shelton, IV et al.
2019/0125431 A1 5/2019 Shelton, IV et al.
2019/0125432 A1 5/2019 Shelton, IV et al.
2019/0125454 A1 5/2019 Stokes et al.
2019/0125455 A1 5/2019 Shelton, IV et al.
2019/0125458 A1 5/2019 Shelton, IV et al.
2019/0125459 A1 5/2019 Shelton, IV et al.
2019/0125476 A1 5/2019 Shelton, IV et al.
2019/0133422 A1 5/2019 Nakamura
2019/0133577 A1 5/2019 Weadock et al.
2019/0138770 A1 5/2019 Compaijen et al.
2019/0142421 A1 5/2019 Shelton, IV
2019/0142423 A1 5/2019 Satti, III et al.
2019/0150925 A1 5/2019 Marczyk et al.
2019/0151029 A1 5/2019 Robinson
2019/0175847 A1 6/2019 Pocreva, III et al.
2019/0183502 A1 6/2019 Shelton, IV et al.
2019/0192141 A1 6/2019 Shelton, IV et al.
2019/0192146 A1 6/2019 Widenhouse et al.
2019/0192147 A1 6/2019 Shelton, IV et al.
2019/0192148 A1 6/2019 Shelton, IV et al.
2019/0192151 A1 6/2019 Shelton, IV et al.
2019/0192153 A1 6/2019 Shelton, IV et al.
2019/0192155 A1 6/2019 Shelton, IV et al.
2019/0192157 A1 6/2019 Scott et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200986 A1 7/2019 Shelton, IV et al.
2019/0200987 A1 7/2019 Shelton, IV et al.

(56) References Cited

U.S. PATENT DOCUMENTS

2019/0200988 A1 7/2019 Shelton, IV
2019/0200989 A1 7/2019 Burbank et al.
2019/0200997 A1 7/2019 Shelton, IV et al.
2019/0200998 A1 7/2019 Shelton, IV et al.
2019/0201020 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201029 A1 7/2019 Shelton, IV et al.
2019/0201030 A1 7/2019 Shelton, IV et al.
2019/0201034 A1 7/2019 Shelton, IV et al.
2019/0201045 A1 7/2019 Yates et al.
2019/0201046 A1 7/2019 Shelton, IV et al.
2019/0201047 A1 7/2019 Yates et al.
2019/0201079 A1 7/2019 Shelton, IV et al.
2019/0201104 A1 7/2019 Shelton, IV et al.
2019/0201112 A1 7/2019 Wiener et al.
2019/0201113 A1 7/2019 Shelton, IV et al.
2019/0201115 A1 7/2019 Shelton, IV et al.
2019/0201118 A1 7/2019 Shelton, IV et al.
2019/0201136 A1 7/2019 Shelton, IV et al.
2019/0201137 A1 7/2019 Shelton, IV et al.
2019/0201139 A1 7/2019 Shelton, IV et al.
2019/0201140 A1 7/2019 Yates et al.
2019/0201142 A1 7/2019 Shelton, IV et al.
2019/0201158 A1 7/2019 Shelton, IV et al.
2019/0201594 A1 7/2019 Shelton, IV et al.
2019/0205001 A1 7/2019 Messerly et al.
2019/0205567 A1 7/2019 Shelton, IV et al.
2019/0206551 A1 7/2019 Yates et al.
2019/0206555 A1 7/2019 Morgan et al.
2019/0206561 A1 7/2019 Shelton, IV et al.
2019/0206562 A1 7/2019 Shelton, IV et al.
2019/0206564 A1 7/2019 Shelton, IV et al.
2019/0206569 A1 7/2019 Shelton, IV et al.
2019/0209172 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0216558 A1 7/2019 Giordano et al.
2019/0239873 A1 8/2019 Laurent et al.
2019/0247048 A1 8/2019 Gasparovich et al.
2019/0261982 A1 8/2019 Holsten
2019/0261983 A1 8/2019 Granger et al.
2019/0261984 A1 8/2019 Nelson et al.
2019/0261987 A1 8/2019 Viola et al.
2019/0262153 A1 8/2019 Tassoni et al.
2019/0269400 A1 9/2019 Mandakolathur Vasudevan et al.
2019/0269402 A1 9/2019 Murray et al.
2019/0269428 A1 9/2019 Allen et al.
2019/0274685 A1 9/2019 Olson et al.
2019/0274716 A1 9/2019 Nott et al.
2019/0282233 A1 9/2019 Burbank et al.
2019/0290264 A1 9/2019 Morgan et al.
2019/0290266 A1 9/2019 Scheib et al.
2019/0290267 A1 9/2019 Baxter, III et al.
2019/0290297 A1 9/2019 Haider et al.
2019/0298350 A1 10/2019 Shelton, IV et al.
2019/0298352 A1 10/2019 Shelton, IV et al.
2019/0298353 A1 10/2019 Shelton, IV et al.
2019/0298360 A1 10/2019 Shelton, IV et al.
2019/0298361 A1 10/2019 Shelton, IV et al.
2019/0298362 A1 10/2019 Shelton, IV et al.
2019/0298381 A1 10/2019 Kreidler et al.
2019/0307452 A1 10/2019 Shelton, IV et al.
2019/0307453 A1 10/2019 Shelton, IV et al.
2019/0307454 A1 10/2019 Shelton, IV et al.
2019/0307456 A1 10/2019 Shelton, IV et al.
2019/0314015 A1 10/2019 Shelton, IV et al.
2019/0321040 A1 10/2019 Shelton, IV
2019/0321062 A1 10/2019 Williams
2019/0328387 A1 10/2019 Overmyer et al.
2019/0328390 A1 10/2019 Harris et al.
2019/0343515 A1 11/2019 Morgan et al.
2019/0350581 A1 11/2019 Baxter, III et al.
2019/0357909 A1 11/2019 Huitema et al.
2019/0388091 A1 12/2019 Eschbach et al.
2020/0000531 A1 1/2020 Giordano et al.
2020/0008802 A1 1/2020 Aronhalt et al.
2020/0008809 A1 1/2020 Shelton, IV et al.
2020/0008827 A1 1/2020 Dearden et al.
2020/0015817 A1 1/2020 Harris et al.
2020/0015819 A1 1/2020 Shelton, IV et al.
2020/0015915 A1 1/2020 Swayze et al.
2020/0030020 A1* 1/2020 Wang ................. A61B 18/1445
2020/0037939 A1 2/2020 Castagna et al.
2020/0038016 A1 2/2020 Shelton, IV et al.
2020/0038018 A1 2/2020 Shelton, IV et al.
2020/0038020 A1 2/2020 Yates et al.
2020/0046355 A1 2/2020 Harris et al.
2020/0046356 A1 2/2020 Baxter, III et al.
2020/0054320 A1 2/2020 Harris et al.
2020/0054321 A1 2/2020 Harris et al.
2020/0054329 A1 2/2020 Shelton, IV et al.
2020/0054332 A1 2/2020 Shelton, IV et al.
2020/0054333 A1 2/2020 Shelton, IV et al.
2020/0054334 A1 2/2020 Shelton, IV et al.
2020/0054355 A1 2/2020 Laurent et al.
2020/0060523 A1 2/2020 Matsuda et al.
2020/0060680 A1 2/2020 Shelton, IV et al.
2020/0060713 A1 2/2020 Leimbach et al.
2020/0061385 A1 2/2020 Schwarz et al.
2020/0085431 A1 3/2020 Swayze et al.
2020/0085435 A1 3/2020 Shelton, IV et al.
2020/0085518 A1 3/2020 Giordano et al.
2020/0093484 A1 3/2020 Shelton, IV et al.
2020/0093506 A1 3/2020 Leimbach et al.
2020/0093550 A1 3/2020 Spivey et al.
2020/0100783 A1 4/2020 Yates et al.
2020/0107829 A1 4/2020 Shelton, IV et al.
2020/0114505 A1 4/2020 Kikuchi
2020/0138436 A1 5/2020 Yates et al.
2020/0138507 A1 5/2020 Davison et al.
2020/0138534 A1 5/2020 Garcia Kilroy et al.
2020/0146741 A1 5/2020 Long et al.
2020/0187943 A1 6/2020 Shelton, IV et al.
2020/0197027 A1 6/2020 Hershberger et al.
2020/0205810 A1 7/2020 Posey et al.
2020/0205811 A1 7/2020 Posey et al.
2020/0205823 A1 7/2020 Vendely et al.
2020/0214706 A1 7/2020 Vendely et al.
2020/0214731 A1 7/2020 Shelton, IV et al.
2020/0222047 A1 7/2020 Shelton, IV et al.
2020/0229814 A1 7/2020 Amariglio et al.
2020/0237371 A1 7/2020 Huitema et al.
2020/0253605 A1 8/2020 Swayze et al.
2020/0261078 A1 8/2020 Bakos et al.
2020/0261086 A1 8/2020 Zeiner et al.
2020/0261087 A1 8/2020 Timm et al.
2020/0261106 A1 8/2020 Hess et al.
2020/0268377 A1 8/2020 Schmid et al.
2020/0275927 A1 9/2020 Shelton, IV et al.
2020/0275928 A1 9/2020 Shelton, IV et al.
2020/0275930 A1 9/2020 Harris et al.
2020/0280219 A1 9/2020 Laughery et al.
2020/0281585 A1 9/2020 Timm et al.
2020/0281590 A1 9/2020 Shelton, IV et al.
2020/0289112 A1 9/2020 Whitfield et al.
2020/0297341 A1 9/2020 Yates et al.
2020/0297346 A1 9/2020 Shelton, IV et al.
2020/0305862 A1 10/2020 Yates et al.
2020/0305863 A1 10/2020 Yates et al.
2020/0305864 A1 10/2020 Yates et al.
2020/0305870 A1 10/2020 Shelton, IV
2020/0305871 A1 10/2020 Shelton, IV et al.
2020/0305872 A1 10/2020 Weidner et al.
2020/0305874 A1 10/2020 Huitema et al.
2020/0315612 A1 10/2020 Shelton, IV et al.
2020/0315623 A1 10/2020 Eisinger et al.
2020/0315983 A1 10/2020 Widenhouse et al.
2020/0323526 A1 10/2020 Huang et al.
2020/0330092 A1 10/2020 Shelton, IV et al.

(56) References Cited

U.S. PATENT DOCUMENTS

2020/0330093 A1 10/2020 Shelton, IV et al.
2020/0330096 A1 10/2020 Shelton, IV et al.
2020/0330181 A1 10/2020 Junger et al.
2020/0337693 A1 10/2020 Shelton, IV et al.
2020/0337791 A1 10/2020 Shelton, IV et al.
2020/0345346 A1 11/2020 Shelton, IV et al.
2020/0345349 A1 11/2020 Kimball et al.
2020/0345352 A1 11/2020 Shelton, IV et al.
2020/0345353 A1 11/2020 Leimbach et al.
2020/0345355 A1 11/2020 Baxter, III et al.
2020/0345356 A1 11/2020 Leimbach et al.
2020/0345357 A1 11/2020 Leimbach et al.
2020/0345358 A1 11/2020 Jenkins
2020/0345359 A1* 11/2020 Baxter, III ....... A61B 17/07207
2020/0345363 A1 11/2020 Shelton, IV et al.
2020/0345435 A1 11/2020 Traina
2020/0352562 A1 11/2020 Timm et al.
2020/0367885 A1 11/2020 Yates et al.
2020/0367886 A1 11/2020 Shelton, IV et al.
2020/0375585 A1 12/2020 Swayze et al.
2020/0375592 A1 12/2020 Hall et al.
2020/0375593 A1 12/2020 Hunter et al.
2020/0375597 A1 12/2020 Shelton, IV et al.
2020/0390444 A1 12/2020 Harris et al.
2020/0397430 A1 12/2020 Patel et al.
2020/0397433 A1 12/2020 Lytle, IV et al.
2020/0405290 A1 12/2020 Shelton, IV et al.
2020/0405292 A1 12/2020 Shelton, IV et al.
2020/0405293 A1 12/2020 Shelton, IV et al.
2020/0405294 A1 12/2020 Shelton, IV
2020/0405295 A1 12/2020 Shelton, IV et al.
2020/0405296 A1 12/2020 Shelton, IV et al.
2020/0405302 A1 12/2020 Shelton, IV et al.
2020/0405304 A1 12/2020 Mozdzierz et al.
2020/0405306 A1 12/2020 Shelton, IV et al.
2020/0405307 A1 12/2020 Shelton, IV et al.
2020/0405308 A1 12/2020 Shelton, IV
2020/0405316 A1 12/2020 Shelton, IV et al.
2020/0405341 A1 12/2020 Hess et al.
2020/0405403 A1 12/2020 Shelton, IV et al.
2020/0405404 A1 12/2020 Shelton, IV et al.
2020/0405409 A1 12/2020 Shelton, IV et al.
2020/0405410 A1 12/2020 Shelton, IV
2020/0405437 A1 12/2020 Shelton, IV et al.
2020/0405439 A1 12/2020 Shelton, IV et al.
2020/0410177 A1 12/2020 Shelton, IV
2021/0000466 A1 1/2021 Leimbach et al.
2021/0000467 A1 1/2021 Shelton, IV et al.
2021/0000470 A1 1/2021 Leimbach et al.
2021/0007742 A1 1/2021 Rector et al.
2021/0015480 A1 1/2021 Shelton, IV et al.
2021/0030416 A1 2/2021 Shelton, IV et al.
2021/0045742 A1 2/2021 Shelton, IV et al.
2021/0052271 A1 2/2021 Harris et al.
2021/0059661 A1 3/2021 Schmid et al.
2021/0059662 A1 3/2021 Shelton, IV
2021/0059664 A1 3/2021 Hensel et al.
2021/0059669 A1 3/2021 Yates et al.
2021/0059670 A1 3/2021 Overmyer et al.
2021/0059671 A1 3/2021 Shelton, IV et al.
2021/0059672 A1 3/2021 Giordano et al.
2021/0059673 A1 3/2021 Shelton, IV et al.
2021/0068817 A1 3/2021 Shelton, IV et al.
2021/0068818 A1 3/2021 Overmyer et al.
2021/0068820 A1 3/2021 Parihar et al.
2021/0068829 A1 3/2021 Miller et al.
2021/0068832 A1 3/2021 Yates et al.
2021/0068835 A1 3/2021 Shelton, IV et al.
2021/0077099 A1 3/2021 Shelton, IV et al.
2021/0077100 A1 3/2021 Shelton, IV et al.
2021/0077109 A1 3/2021 Harris et al.
2021/0085313 A1 3/2021 Morgan et al.
2021/0085314 A1 3/2021 Schmid et al.
2021/0085315 A1 3/2021 Aronhalt et al.
2021/0085316 A1 3/2021 Harris et al.
2021/0085317 A1 3/2021 Miller et al.
2021/0085318 A1 3/2021 Swayze et al.
2021/0085320 A1 3/2021 Leimbach et al.
2021/0085321 A1 3/2021 Shelton, IV et al.
2021/0085325 A1 3/2021 Shelton, IV et al.
2021/0085326 A1 3/2021 Vendely et al.
2021/0093321 A1 4/2021 Auld et al.
2021/0093323 A1 4/2021 Scirica et al.
2021/0100541 A1 4/2021 Shelton, IV et al.
2021/0100550 A1 4/2021 Shelton, IV et al.
2021/0100982 A1 4/2021 Laby et al.
2021/0106333 A1 4/2021 Shelton, IV et al.
2021/0107031 A1 4/2021 Bales, Jr. et al.
2021/0121175 A1 4/2021 Yates et al.
2021/0128146 A1 5/2021 Shelton, IV et al.
2021/0128153 A1 5/2021 Sgroi
2021/0137522 A1 5/2021 Shelton, IV et al.
2021/0153866 A1 5/2021 Knapp et al.
2021/0177401 A1 6/2021 Abramek et al.
2021/0177411 A1 6/2021 Williams
2021/0186492 A1 6/2021 Shelton, IV et al.
2021/0186493 A1 6/2021 Shelton, IV et al.
2021/0186494 A1 6/2021 Shelton, IV et al.
2021/0186495 A1 6/2021 Shelton, IV et al.
2021/0186497 A1 6/2021 Shelton, IV et al.
2021/0186498 A1 6/2021 Boudreaux et al.
2021/0186499 A1 6/2021 Shelton, IV et al.
2021/0186500 A1 6/2021 Shelton, IV et al.
2021/0186501 A1 6/2021 Shelton, IV et al.
2021/0186502 A1 6/2021 Shelton, IV et al.
2021/0186504 A1 6/2021 Shelton, IV et al.
2021/0186507 A1 6/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212691 A1 7/2021 Smith et al.
2021/0212776 A1 7/2021 Schmitt et al.
2021/0219976 A1 7/2021 DiNardo et al.
2021/0228209 A1 7/2021 Shelton, IV et al.
2021/0236117 A1 8/2021 Morgan et al.
2021/0236124 A1 8/2021 Shelton, IV et al.
2021/0244406 A1 8/2021 Kerr et al.
2021/0244407 A1 8/2021 Shelton, IV et al.
2021/0244410 A1 8/2021 Swayze et al.
2021/0244411 A1 8/2021 Smith et al.
2021/0244412 A1 8/2021 Vendely et al.
2021/0259681 A1 8/2021 Shelton, IV et al.
2021/0259687 A1 8/2021 Gonzalez et al.
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275175 A1 9/2021 Vadali et al.
2021/0275176 A1 9/2021 Beckman et al.
2021/0282767 A1 9/2021 Shelton, IV et al.
2021/0282769 A1 9/2021 Baxter, III et al.
2021/0282774 A1 9/2021 Shelton, IV et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307744 A1 10/2021 Walcott et al.
2021/0307748 A1 10/2021 Harris et al.
2021/0307754 A1 10/2021 Shelton, IV et al.
2021/0313975 A1 10/2021 Shan et al.
2021/0315566 A1 10/2021 Yates et al.
2021/0315570 A1 10/2021 Shelton, IV
2021/0315571 A1 10/2021 Swayze et al.
2021/0315573 A1 10/2021 Shelton, IV et al.

(56) References Cited

U.S. PATENT DOCUMENTS

2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0353284 A1 11/2021 Yang et al.
2021/0369271 A1 12/2021 Schings et al.
2021/0369273 A1 12/2021 Yates et al.
2021/0378669 A1 12/2021 Shelton, IV et al.
2021/0393260 A1 12/2021 Shelton, IV et al.
2021/0393261 A1 12/2021 Harris et al.
2021/0393262 A1 12/2021 Shelton, IV et al.
2021/0393268 A1 12/2021 Shelton, IV et al.
2021/0393366 A1 12/2021 Shelton, IV et al.
2022/0000478 A1 1/2022 Shelton, IV et al.
2022/0000479 A1 1/2022 Shelton, IV et al.
2022/0015760 A1 1/2022 Beardsley et al.
2022/0031313 A1 2/2022 Bakos et al.
2022/0031314 A1 2/2022 Bakos et al.
2022/0031315 A1 2/2022 Bakos et al.
2022/0031319 A1 2/2022 Witte et al.
2022/0031320 A1 2/2022 Hall et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0049593 A1 2/2022 Groover et al.
2022/0054125 A1 2/2022 Ji et al.
2022/0054130 A1 2/2022 Overmyer et al.
2022/0061642 A1 3/2022 Park et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079586 A1 3/2022 Shelton, IV et al.
2022/0079588 A1 3/2022 Harris et al.
2022/0079589 A1 3/2022 Harris et al.
2022/0079590 A1 3/2022 Harris et al.
2022/0079595 A1 3/2022 Huitema et al.
2022/0079596 A1 3/2022 Huitema et al.
2022/0087676 A1 3/2022 Shelton, IV et al.
2022/0104816 A1 4/2022 Fernandes et al.
2022/0104820 A1 4/2022 Shelton, IV et al.
2022/0117602 A1 4/2022 Wise et al.
2022/0133299 A1 5/2022 Baxter, III
2022/0133300 A1 5/2022 Leimbach et al.
2022/0133301 A1 5/2022 Leimbach
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133311 A1 5/2022 Huang
2022/0133312 A1* 5/2022 Huang ................ A61B 17/072 227/176.1
2022/0133427 A1 5/2022 Baxter, III
2022/0133428 A1 5/2022 Leimbach et al.
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160358 A1 5/2022 Wixey
2022/0167968 A1 6/2022 Worthington et al.
2022/0167970 A1 6/2022 Aronhalt et al.
2022/0167971 A1 6/2022 Shelton, IV et al.
2022/0167972 A1 6/2022 Shelton, IV et al.
2022/0167973 A1 6/2022 Shelton, IV et al.
2022/0167974 A1 6/2022 Shelton, IV et al.
2022/0167975 A1 6/2022 Shelton, IV et al.
2022/0167977 A1 6/2022 Shelton, IV et al.
2022/0167979 A1 6/2022 Yates et al.
2022/0167980 A1 6/2022 Shelton, IV et al.
2022/0167981 A1 6/2022 Shelton, IV et al.
2022/0167982 A1 6/2022 Shelton, IV et al.
2022/0167983 A1 6/2022 Shelton, IV et al.
2022/0167984 A1 6/2022 Shelton, IV et al.
2022/0167995 A1 6/2022 Parfett et al.
2022/0168038 A1 6/2022 Shelton, IV et al.
2022/0175370 A1 6/2022 Shelton, IV et al.
2022/0175371 A1 6/2022 Hess et al.
2022/0175372 A1 6/2022 Shelton, IV et al.
2022/0175375 A1 6/2022 Harris et al.
2022/0175378 A1 6/2022 Leimbach et al.
2022/0175381 A1 6/2022 Scheib et al.
2022/0183685 A1 6/2022 Shelton, IV et al.
2022/0192667 A1 6/2022 Shelton, IV et al.
2022/0211367 A1 7/2022 Schmid et al.
2022/0218332 A1 7/2022 Shelton, IV et al.
2022/0218333 A1 7/2022 Parihar et al.
2022/0218334 A1 7/2022 Parihar et al.
2022/0218336 A1 7/2022 Timm et al.
2022/0218337 A1 7/2022 Timm et al.
2022/0218338 A1 7/2022 Shelton, IV et al.
2022/0218340 A1 7/2022 Harris et al.
2022/0218342 A1 7/2022 Harris et al.
2022/0218344 A1 7/2022 Leimbach et al.
2022/0218345 A1 7/2022 Shelton, IV et al.
2022/0218346 A1 7/2022 Shelton, IV et al.
2022/0218347 A1 7/2022 Shelton, IV et al.
2022/0218348 A1 7/2022 Swensgard et al.
2022/0218349 A1 7/2022 Shelton, IV et al.
2022/0218350 A1 7/2022 Shelton, IV et al.
2022/0218351 A1 7/2022 Shelton, IV et al.
2022/0218376 A1 7/2022 Shelton, IV et al.
2022/0218378 A1 7/2022 Shelton, IV et al.
2022/0218381 A1 7/2022 Leimbach et al.
2022/0218382 A1 7/2022 Leimbach et al.
2022/0225980 A1 7/2022 Shelton, IV et al.
2022/0225981 A1 7/2022 Shelton, IV et al.
2022/0225982 A1 7/2022 Yates et al.
2022/0225986 A1 7/2022 Shelton, IV et al.
2022/0225992 A1 7/2022 Smith et al.
2022/0225993 A1 7/2022 Huitema et al.
2022/0225994 A1 7/2022 Setser et al.
2022/0226012 A1 7/2022 Shelton, IV et al.
2022/0226013 A1 7/2022 Hall et al.
2022/0233184 A1 7/2022 Parihar et al.
2022/0233185 A1 7/2022 Parihar et al.
2022/0233186 A1 7/2022 Timm et al.
2022/0233187 A1 7/2022 Timm et al.
2022/0233188 A1 7/2022 Timm et al.
2022/0233194 A1 7/2022 Baxter, III et al.
2022/0233195 A1 7/2022 Shelton, IV et al.
2022/0233257 A1 7/2022 Shelton, IV et al.
2022/0240928 A1 8/2022 Timm et al.
2022/0240929 A1 8/2022 Timm et al.
2022/0240930 A1 8/2022 Yates et al.
2022/0240936 A1 8/2022 Huitema et al.
2022/0240937 A1 8/2022 Shelton, IV et al.
2022/0249095 A1 8/2022 Shelton, IV et al.
2022/0265272 A1 8/2022 Li et al.
2022/0273291 A1 9/2022 Shelton, IV et al.
2022/0273292 A1 9/2022 Shelton, IV et al.
2022/0273293 A1 9/2022 Shelton, IV et al.
2022/0273294 A1 9/2022 Creamer et al.
2022/0273299 A1 9/2022 Shelton, IV et al.
2022/0273300 A1 9/2022 Shelton, IV et al.
2022/0273301 A1 9/2022 Creamer et al.
2022/0273302 A1 9/2022 Shelton, IV et al.
2022/0273303 A1 9/2022 Creamer et al.
2022/0273304 A1 9/2022 Shelton, IV et al.
2022/0273305 A1 9/2022 Shelton, IV et al.

(56) References Cited

U.S. PATENT DOCUMENTS

| | | | |
|---|---|---|---|
| 2022/0273306 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0278438 | A1 | 9/2022 | Shelton, IV et al. |
| 2022/0287711 | A1 | 9/2022 | Ming et al. |
| 2022/0296230 | A1 | 9/2022 | Adams et al. |
| 2022/0296231 | A1 | 9/2022 | Adams et al. |
| 2022/0296232 | A1 | 9/2022 | Adams et al. |
| 2022/0296233 | A1 | 9/2022 | Morgan et al. |
| 2022/0296234 | A1 | 9/2022 | Shelton, IV et al. |
| 2022/0296235 | A1 | 9/2022 | Morgan et al. |
| 2022/0296236 | A1 | 9/2022 | Bakos et al. |
| 2022/0296237 | A1 | 9/2022 | Bakos et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter, III et al. |
| 2022/0304714 | A1 | 9/2022 | Shelton, IV et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton, IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378420 | A1 | 12/2022 | Leimbach et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378427 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387030 | A1 | 12/2022 | Shelton, IV et al. |
| 2022/0387031 | A1 | 12/2022 | Yates et al. |
| 2022/0387032 | A1 | 12/2022 | Huitema et al. |
| 2022/0387033 | A1 | 12/2022 | Huitema et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |

(56) References Cited

FOREIGN PATENT DOCUMENTS

| | | | |
|---|---|---|---|
| CN | 204520822 | U | 8/2015 |
| CN | 204636451 | U | 9/2015 |
| CN | 103860225 | B | 3/2016 |
| CN | 103750872 | B | 5/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |

(56) References Cited

FOREIGN PATENT DOCUMENTS

| | | | |
|---|---|---|---|
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H07124166 | A | 5/1996 |
| JP | H08164141 | A | 6/1996 |
| JP | H081 82684 | A | 7/1996 |
| JP | H08507708 | A | 8/1996 |
| JP | H08229050 | A | 9/1996 |
| JP | H08289895 | A | 11/1996 |
| JP | H09-323068 | A | 12/1997 |
| JP | H0950795 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016518914 | A | 6/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | C | 5/1993 |
| RU | 2008830 | C1 | 3/1994 |
| RU | 2052979 | C1 | 1/1996 |

(56) References Cited

FOREIGN PATENT DOCUMENTS

| | | | |
|---|---|---|---|
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2017138905 | A1 * | 8/2017 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic Tk Relays Ultra Low Profile 2 A Polarized Relay, Copyright Matsushita Electric Works, Ltd. (Known of at least as early as Aug. 17, 2010), 5 pages.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

(56) References Cited

OTHER PUBLICATIONS

Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, Crc Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDriveT™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-Ds, Rev. 5, 21 pp., http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced Rfid Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileld=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).

(56) References Cited

OTHER PUBLICATIONS

Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec, <http://cdn.mobiusconsulting.com/papers/rfidsystems.pdf>.
Schroeter, John, "*Demystifying UHF Gen 2 RFID, HF RFID,*" *Online Article*, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, Article ID 879294, *Hindawi Publishing Corporation*.
Pushing Pixels (Gif), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed Is Faster", published on Oct 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: a review of the recent literatured," Int. J. Hyg. Environ. Health 211 (2008) 1-29.
Sandvik, "Welding Handbook," https://www.metingss/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.Mar. 2012 (Revision of IEEE Std 802.Mar. 2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE PULSE, Nov./Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.

* cited by examiner

SURGICAL INSTRUMENT COMPRISING A JAW ALIGNMENT SYSTEM

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 103 is a partial detail view of the closure system of the handle of FIG. 90 illustrated in a fully-closed configuration;

FIG. 104 is a partial elevational view of a surgical instrument comprising a handle and a shaft in accordance with at least one embodiment;

FIG. 105 is a partial elevational view of the surgical instrument of FIG. 104 illustrated in a partially-closed configuration;

FIG. 106 is a partial elevational view of the surgical instrument of FIG. 104 illustrated in a fully-closed configuration;

FIG. 107 is a partial elevational view of a surgical instrument comprising a handle and a shaft in accordance with at least one embodiment;

FIG. 108 is a partial elevational view of the surgical instrument of FIG. 107 depicting an actuatable closure lock;

FIG. 109 is a partial perspective view of the handle of the surgical instrument of FIG. 90 illustrated with some components removed;

FIG. 110 is a partial perspective view of the closure system of the surgical instrument of FIG. 90;

FIG. 111 is a partial perspective view of a closure system in accordance with at least embodiment;

FIG. 112A depicts a spring of the closure system of FIG. 110;

FIG. 112B depicts a spring of a closure system in accordance with at least one embodiment;

FIG. 112C depicts a spring system of the closure system of FIG. 111;

Figure 90:
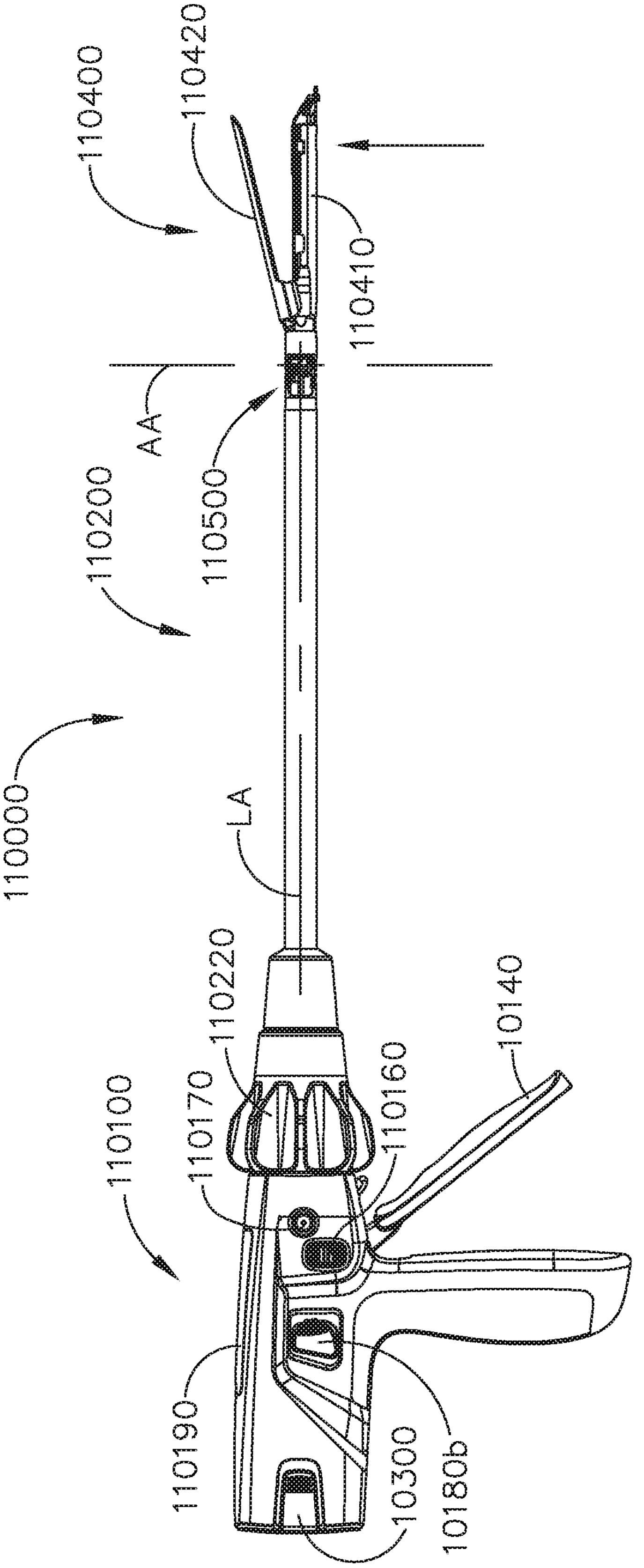
FIG. 90 is an elevational view of a surgical instrument including a handle and a shaft in accordance with at least one embodiment.
Figures 112A, 112B, 112C:
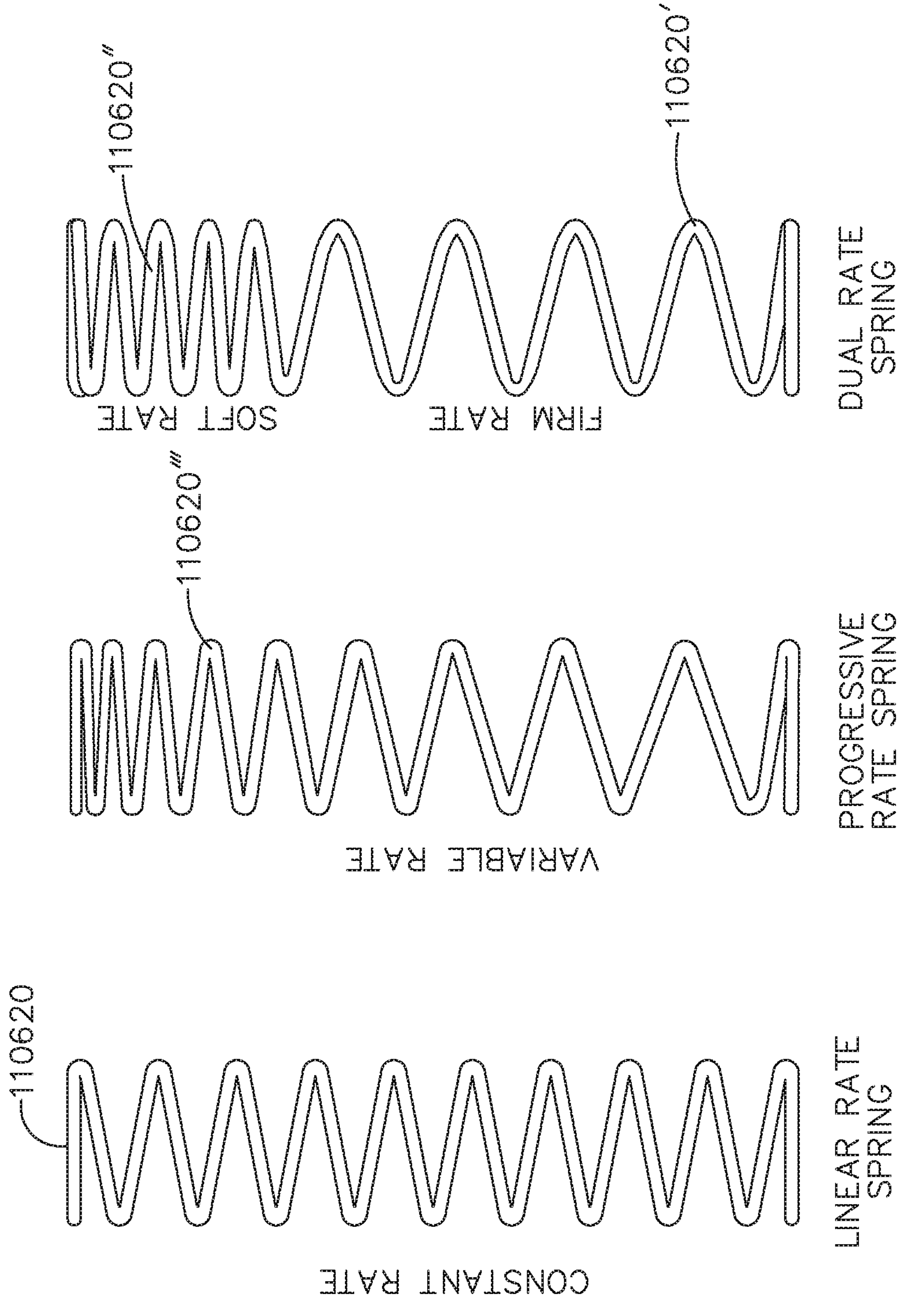
Figure 113:
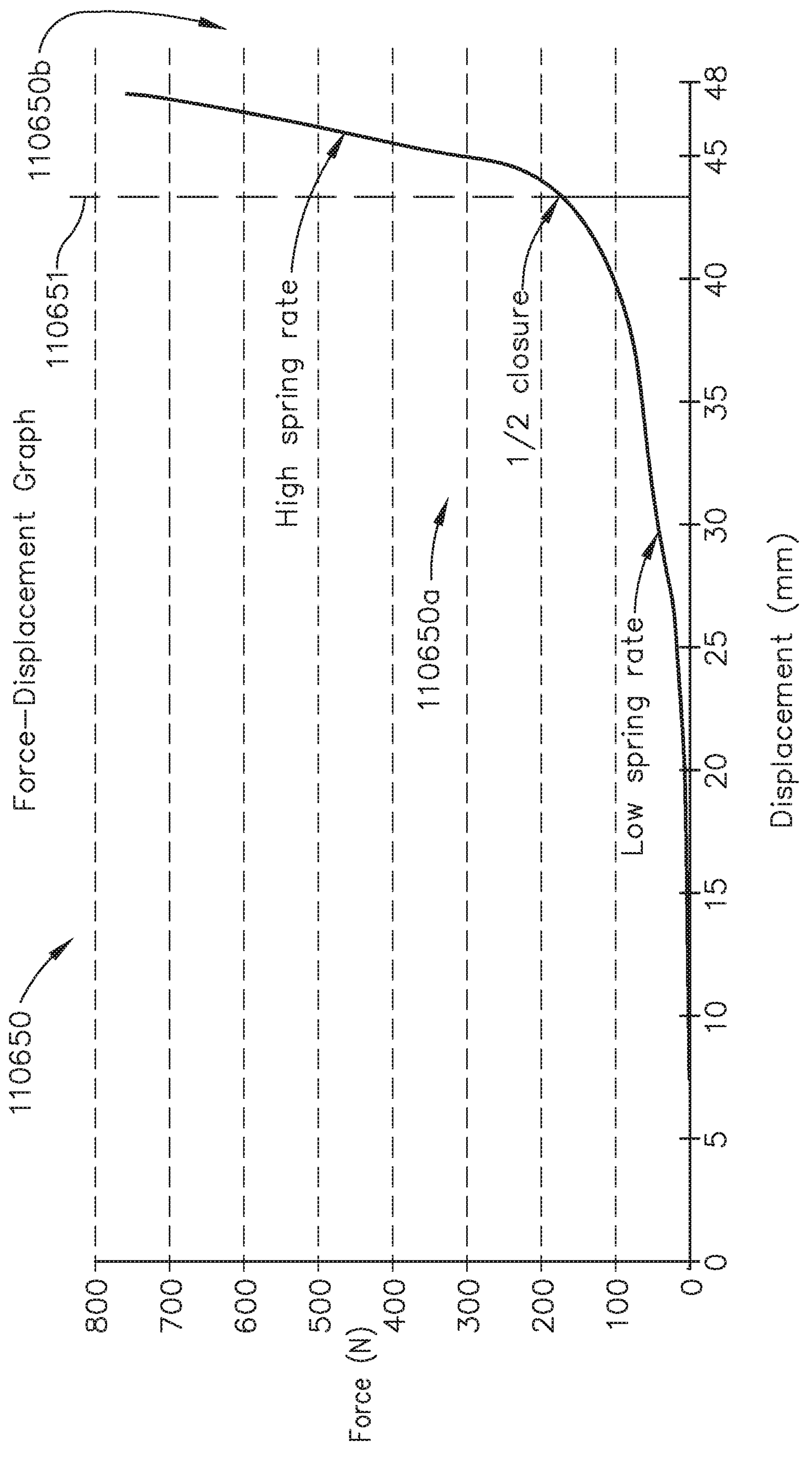
Figure 114:
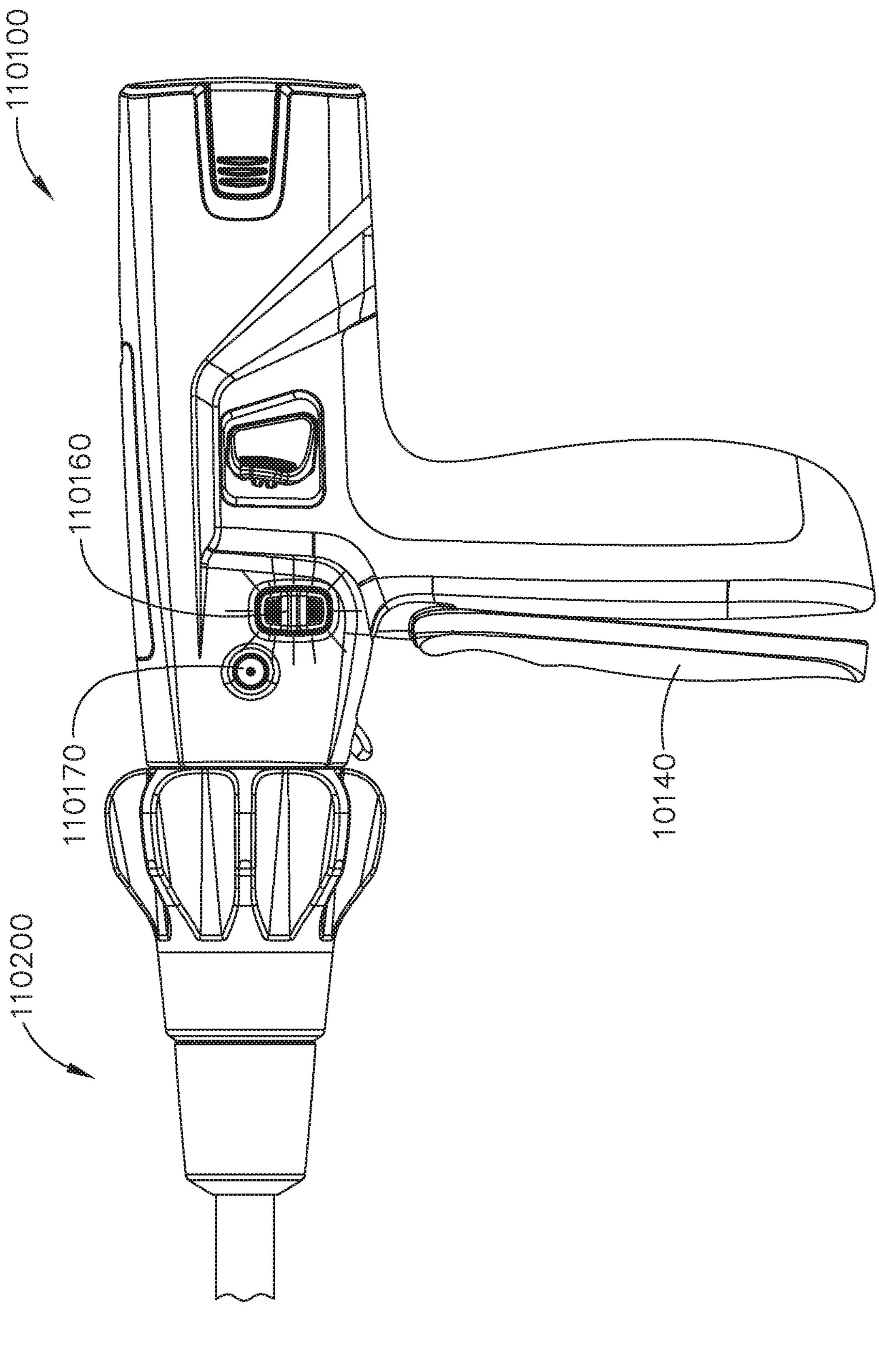
Figure 115:
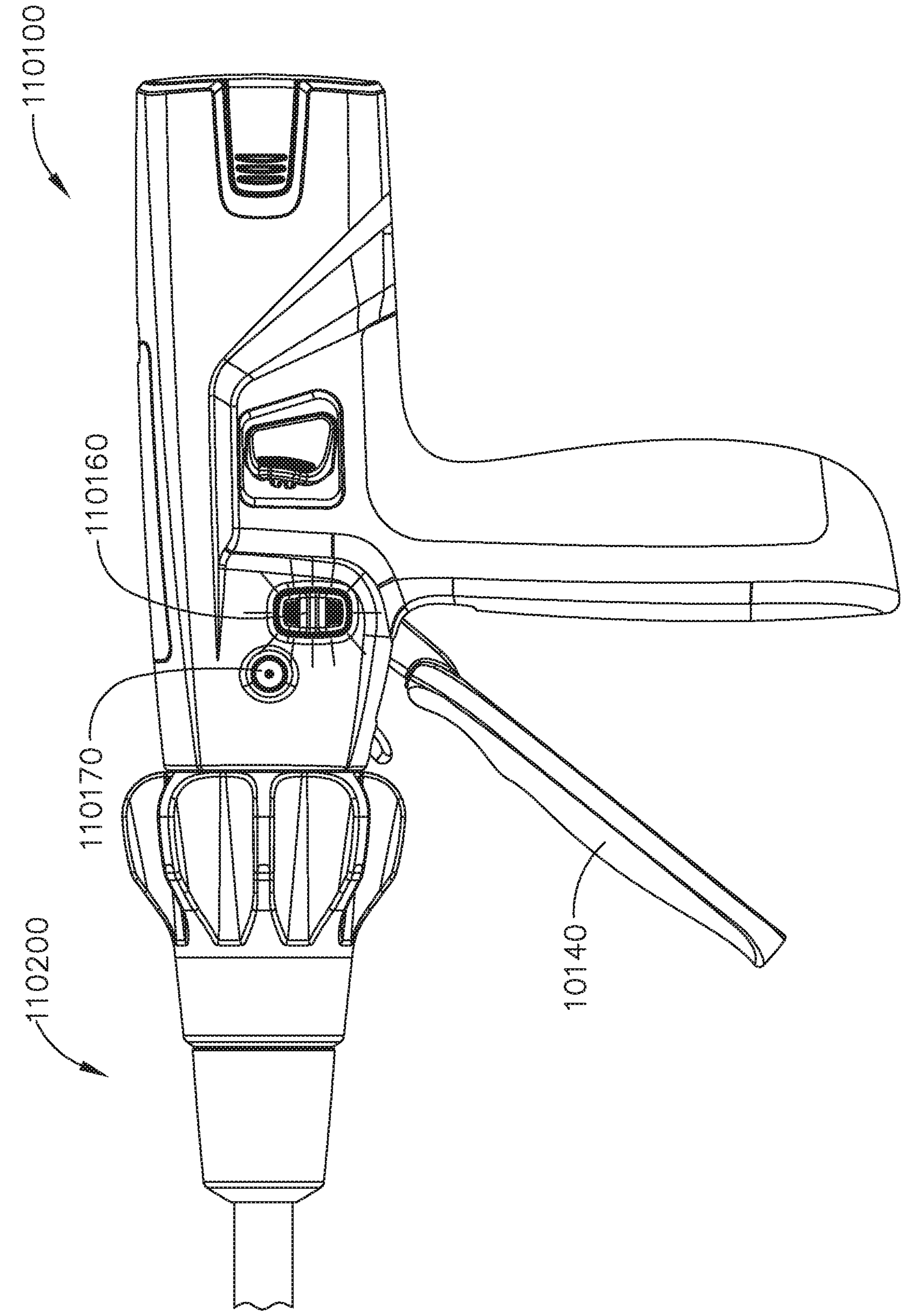
Figure 116:
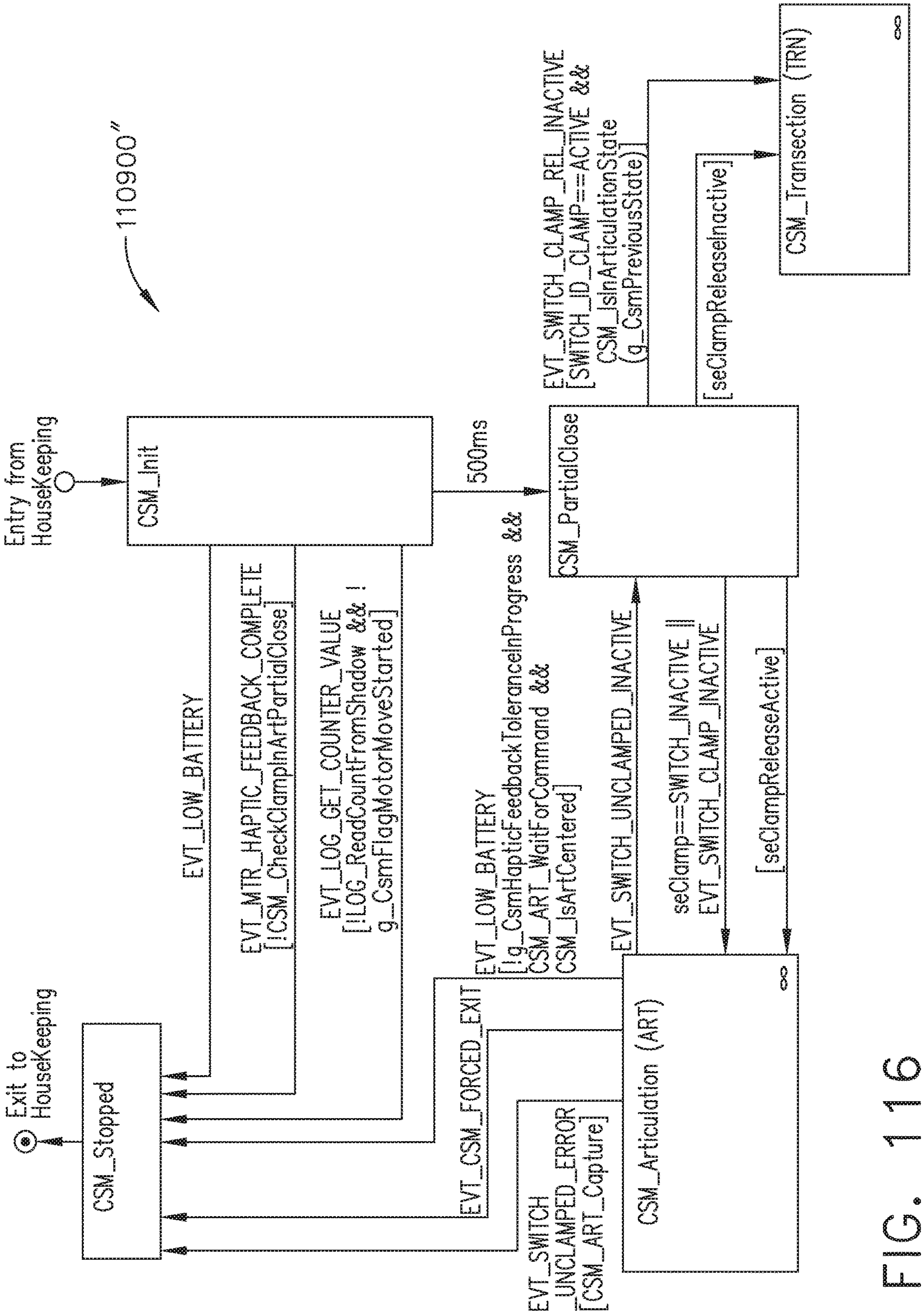
Figure 117:
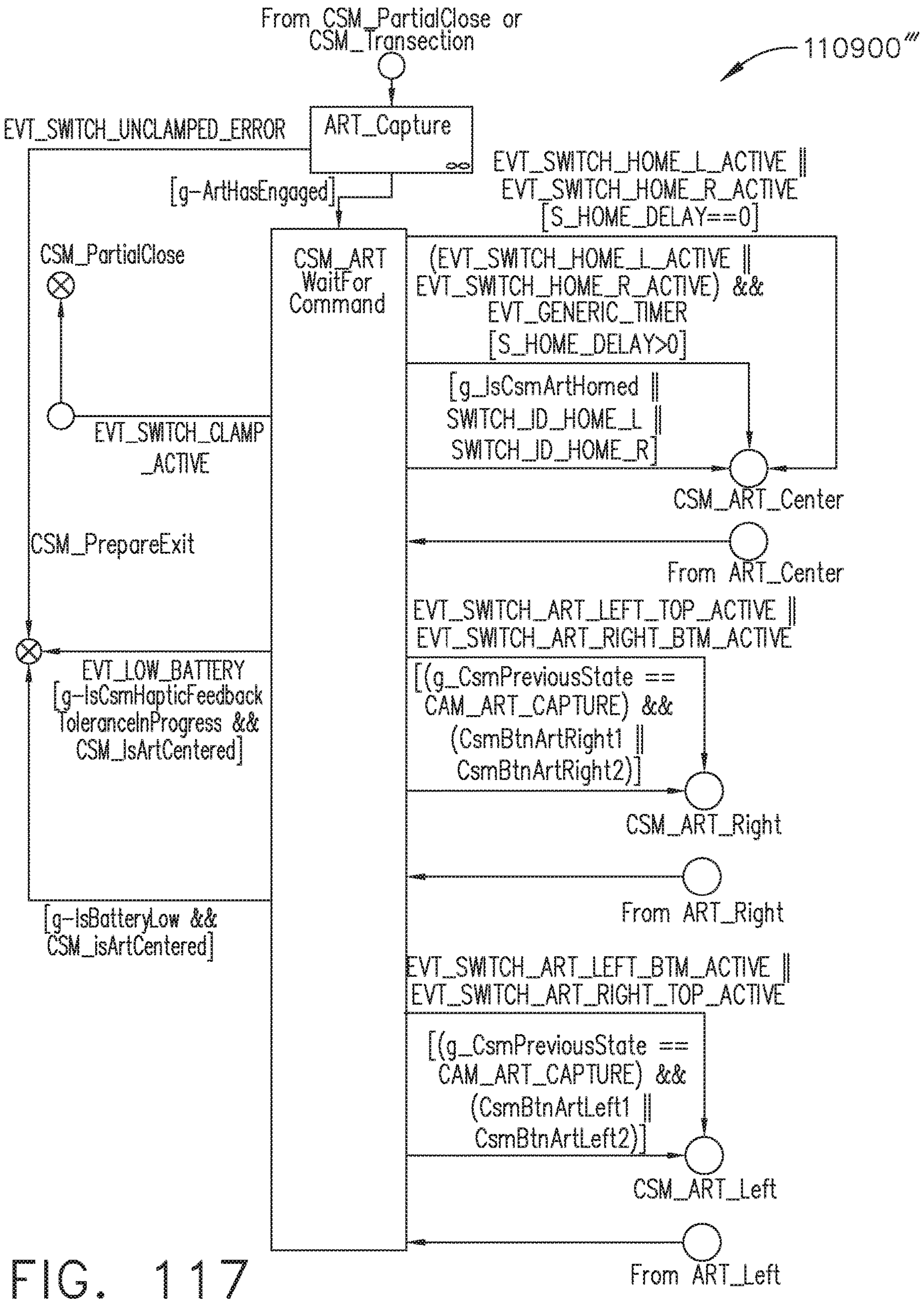
Figure 118:
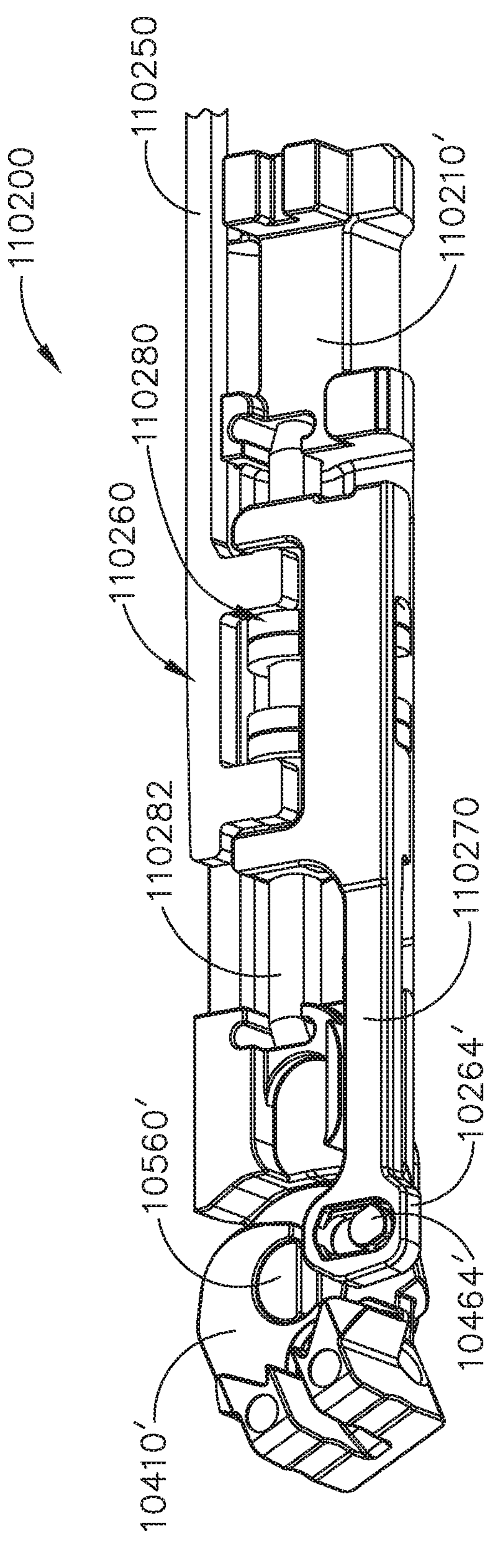
Figure 119:
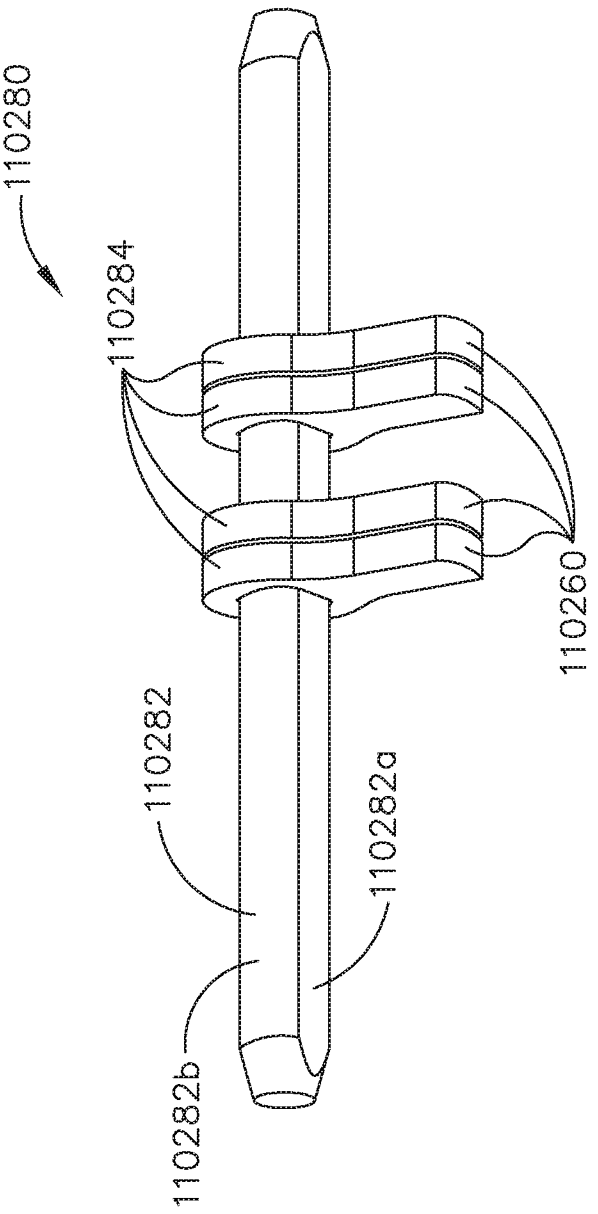
Figure 120:
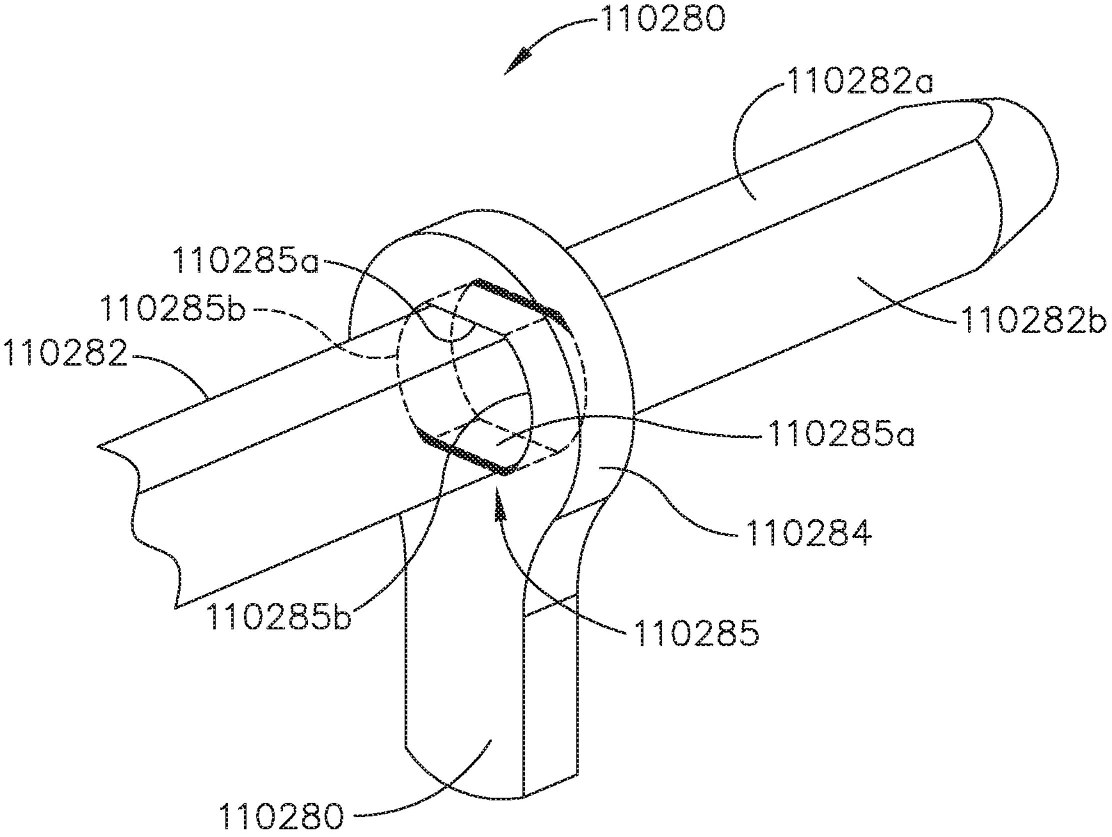
Figure 121:
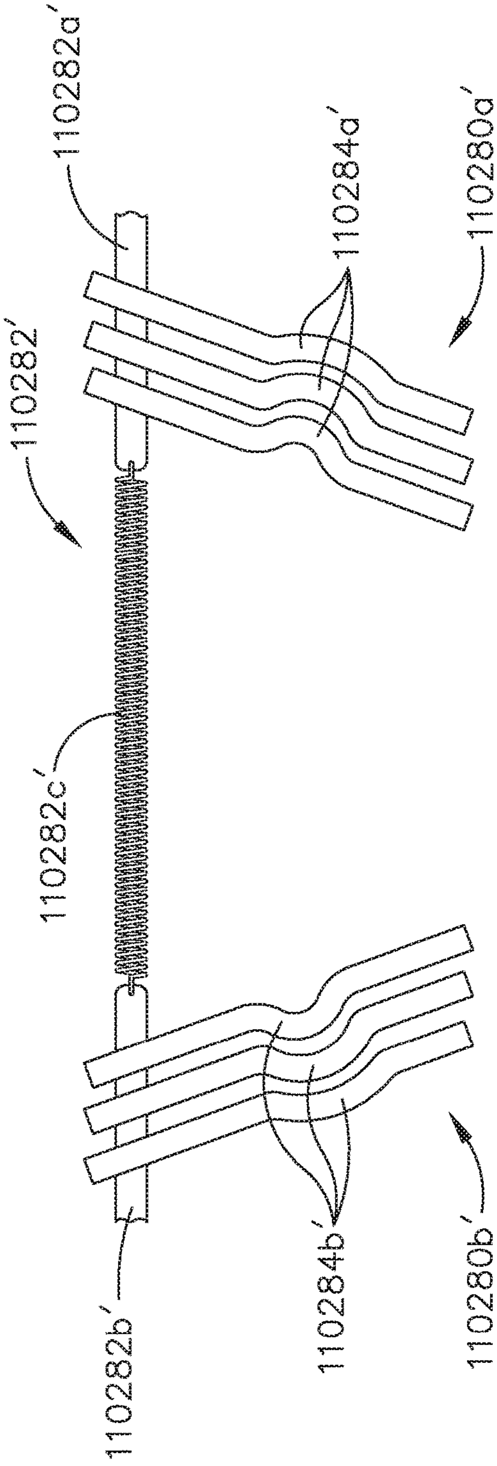
Figure 122:
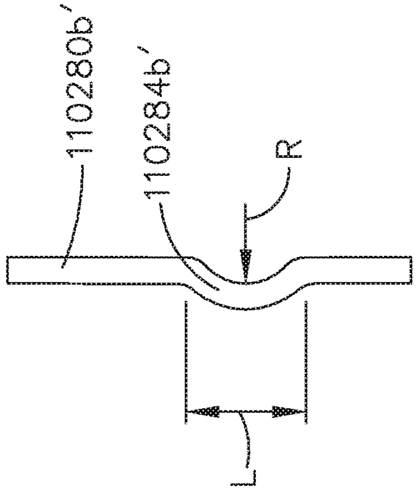
Figure 123:
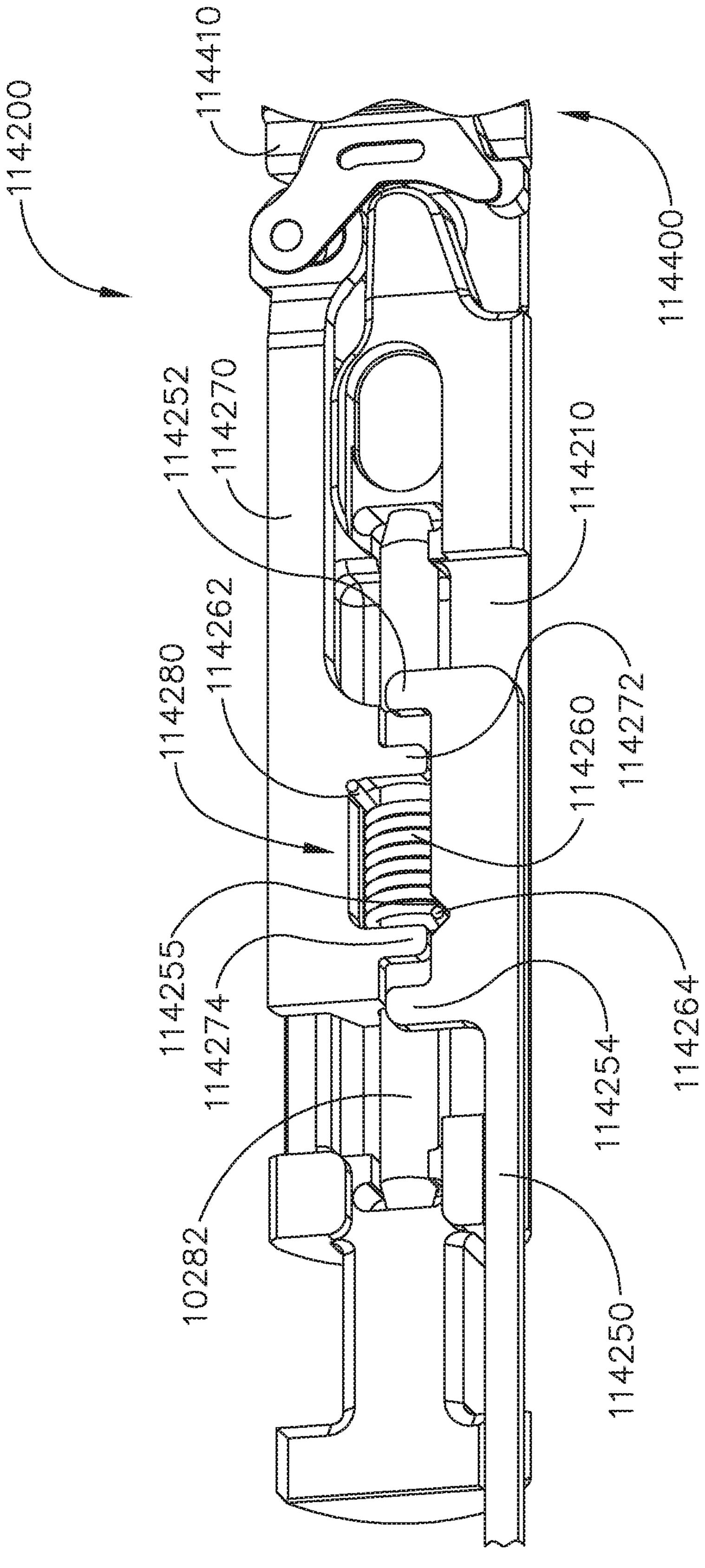
Figure 124:
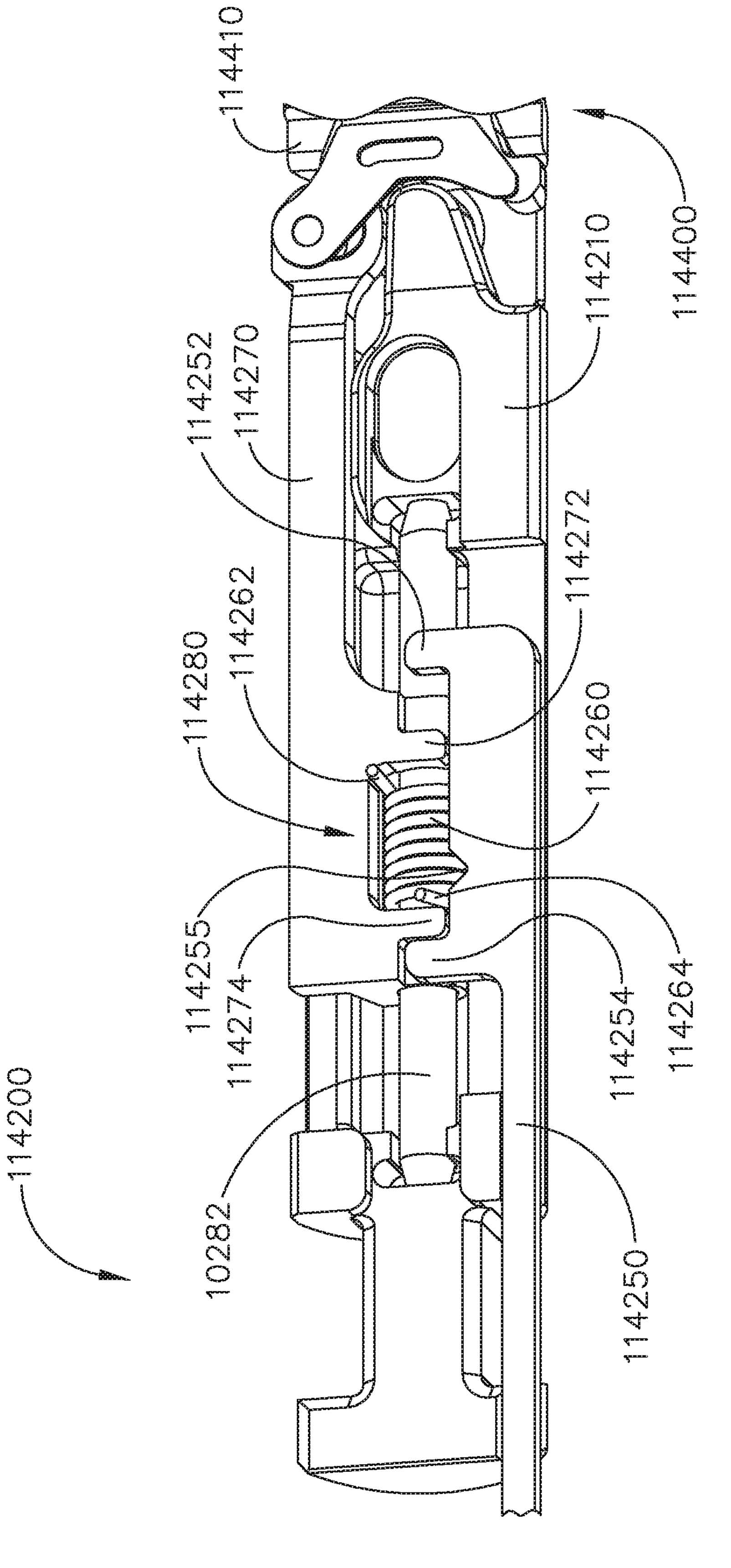
Figure 125:
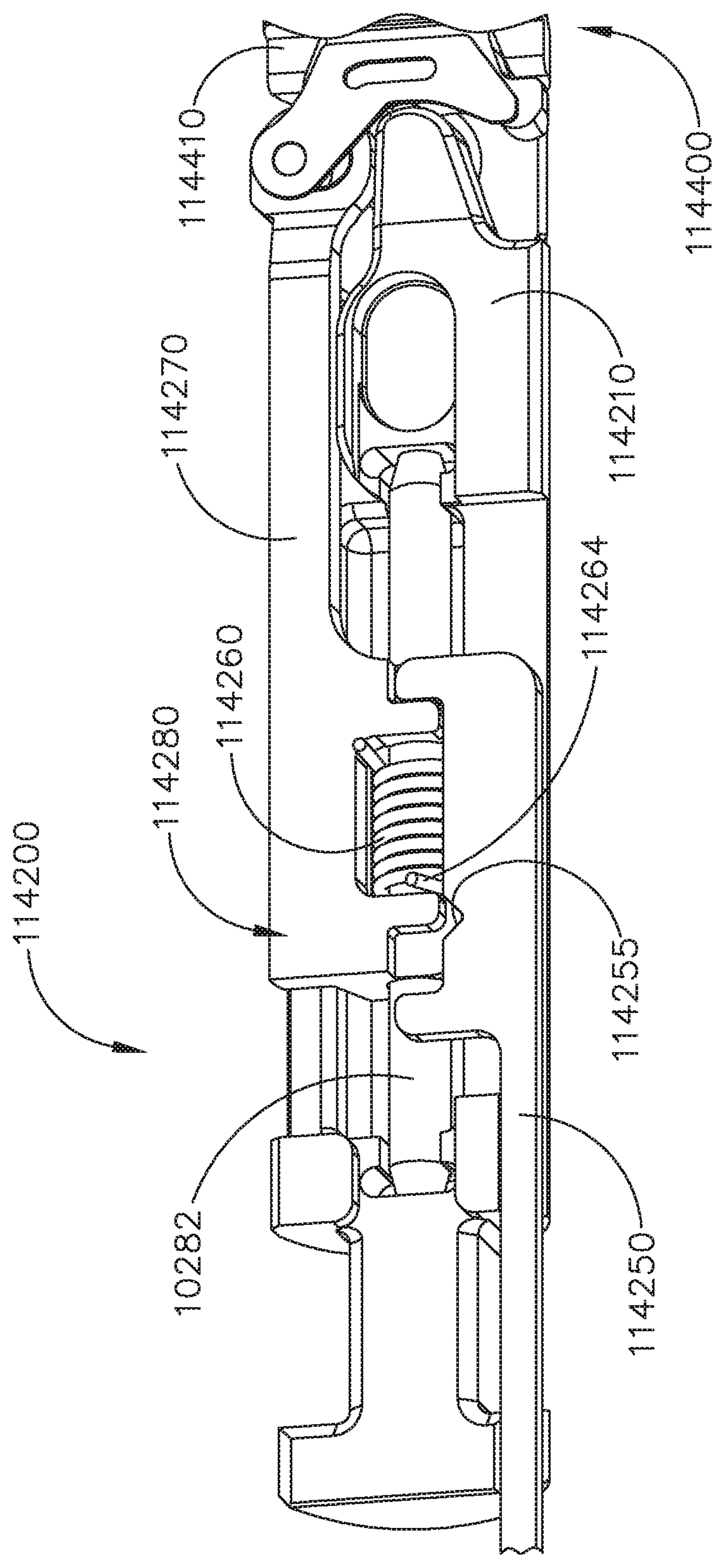
Figure 126:
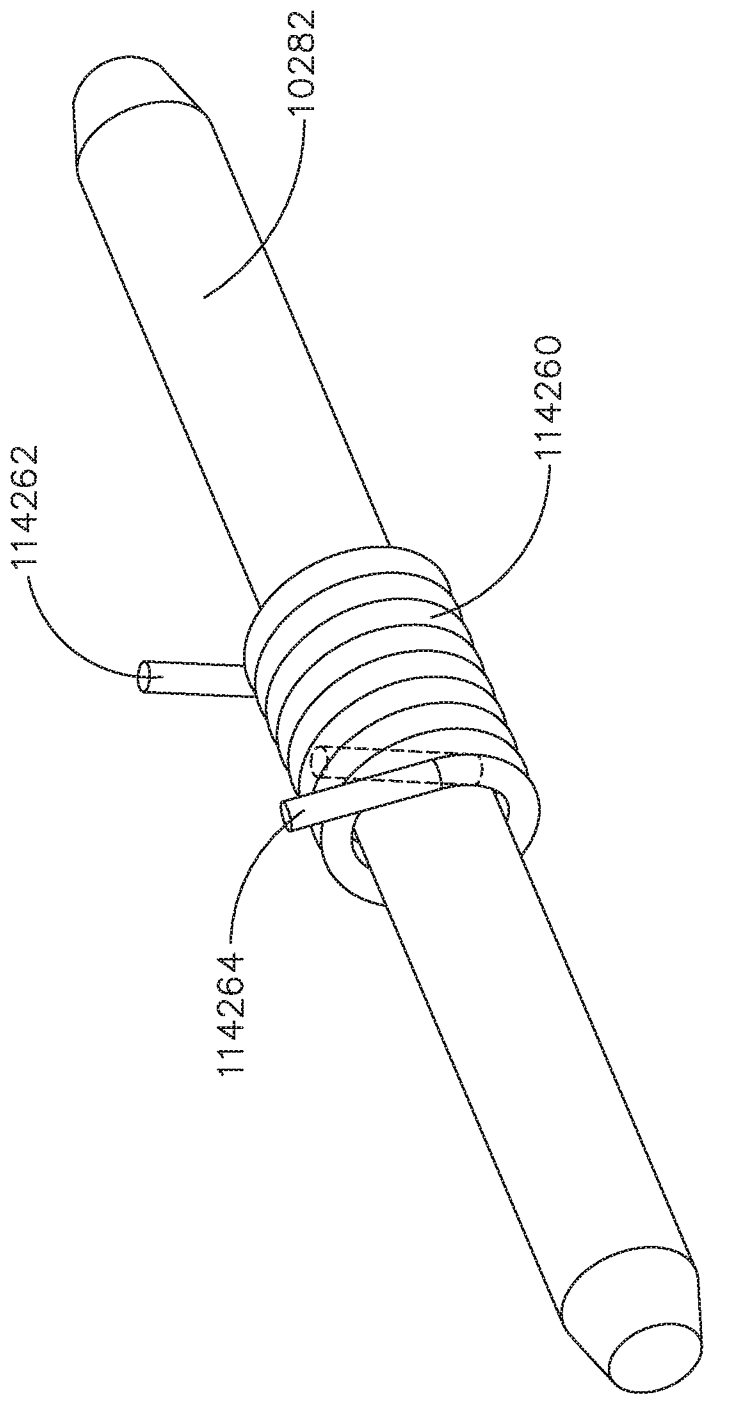
Figure 127:
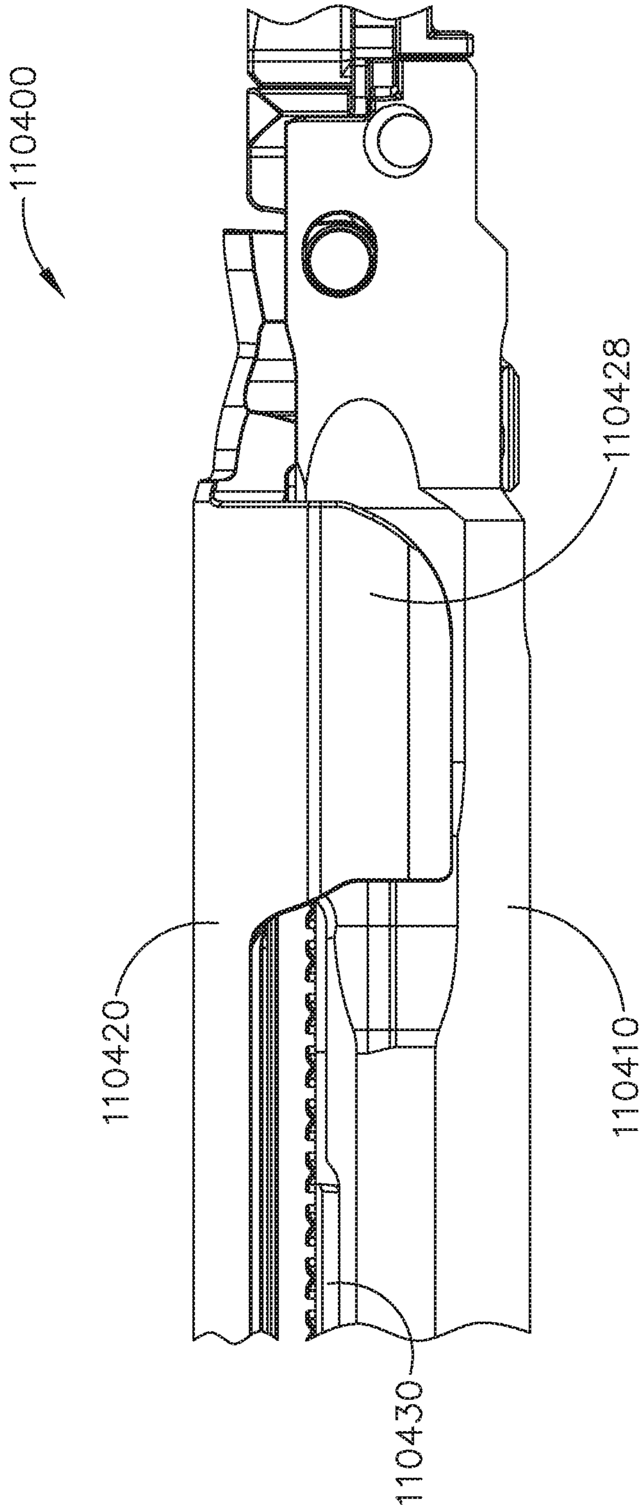
Figure 128:
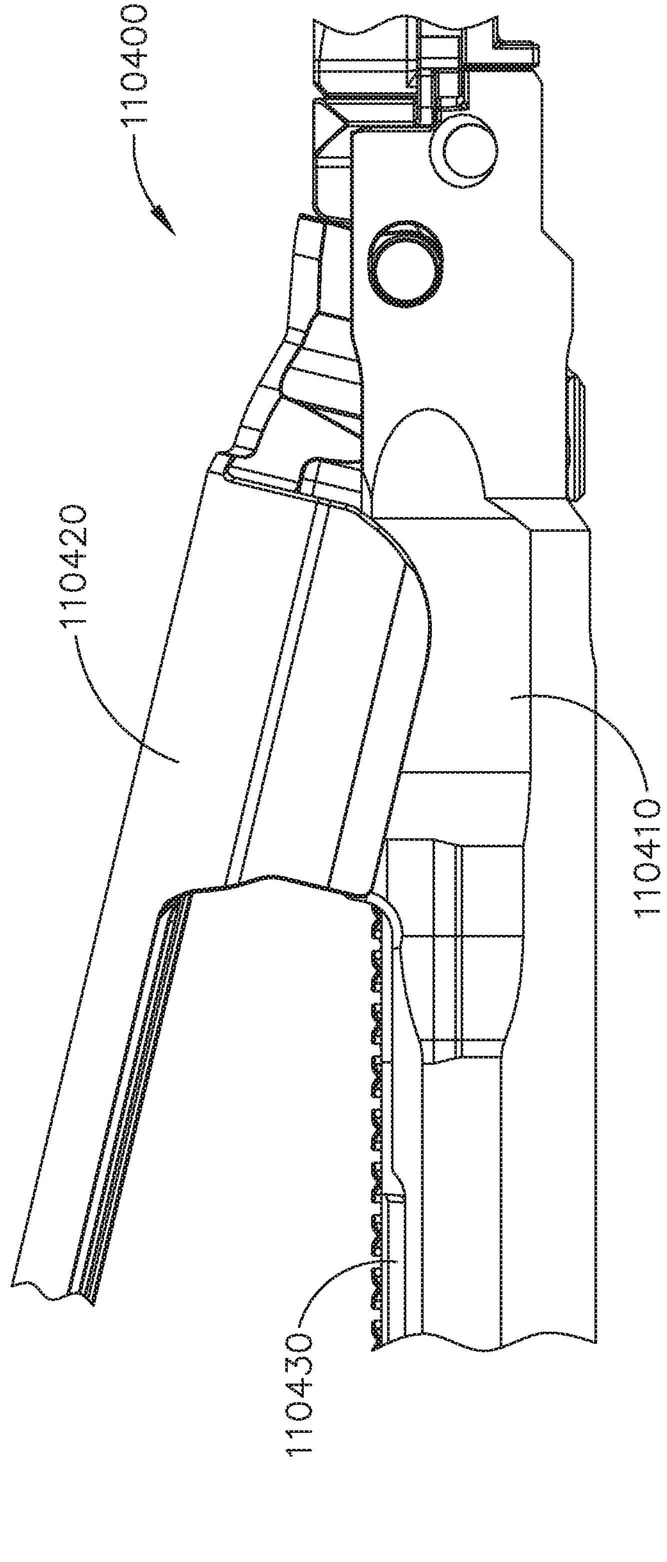
Figure 129:
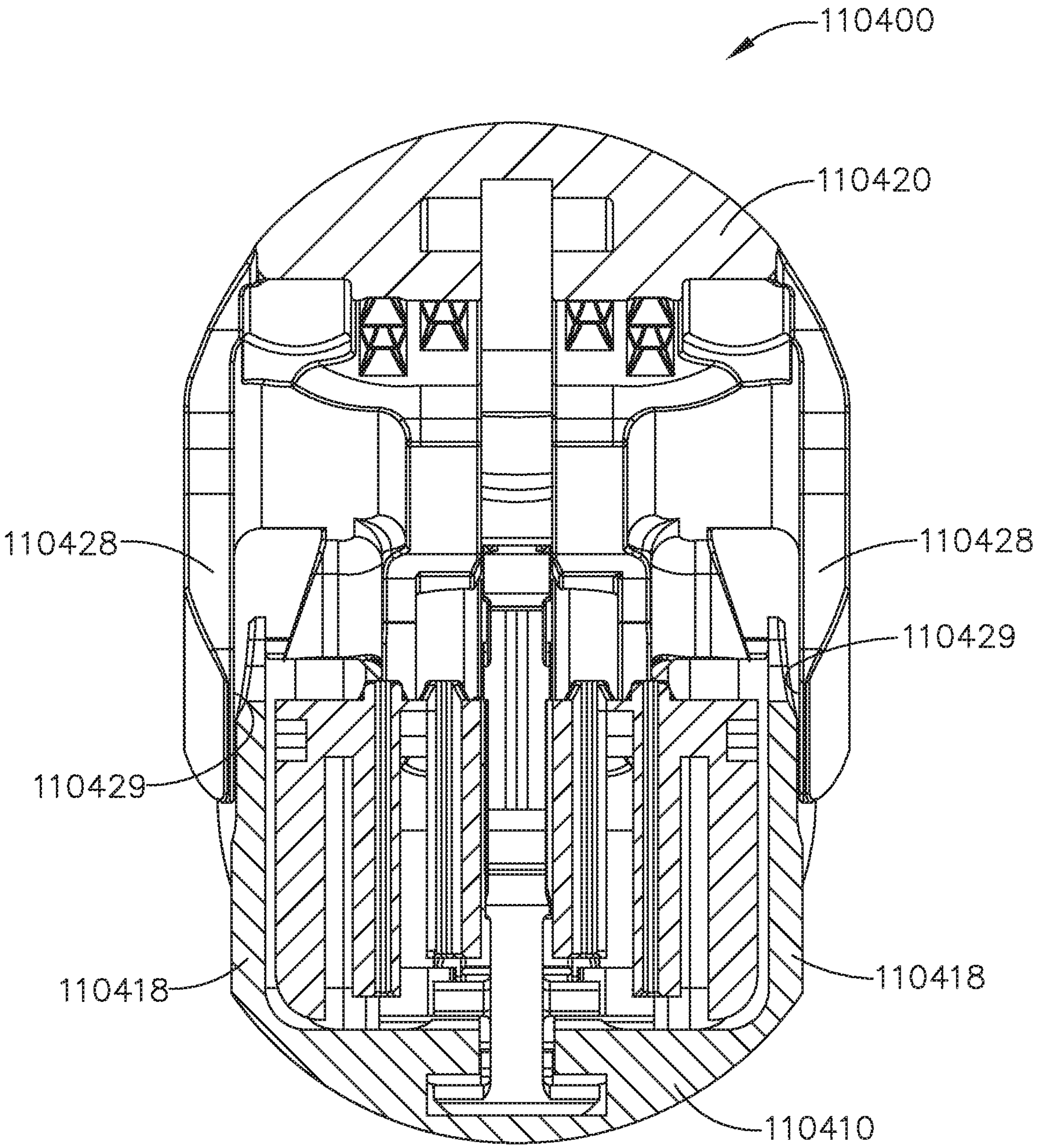
Figure 130:
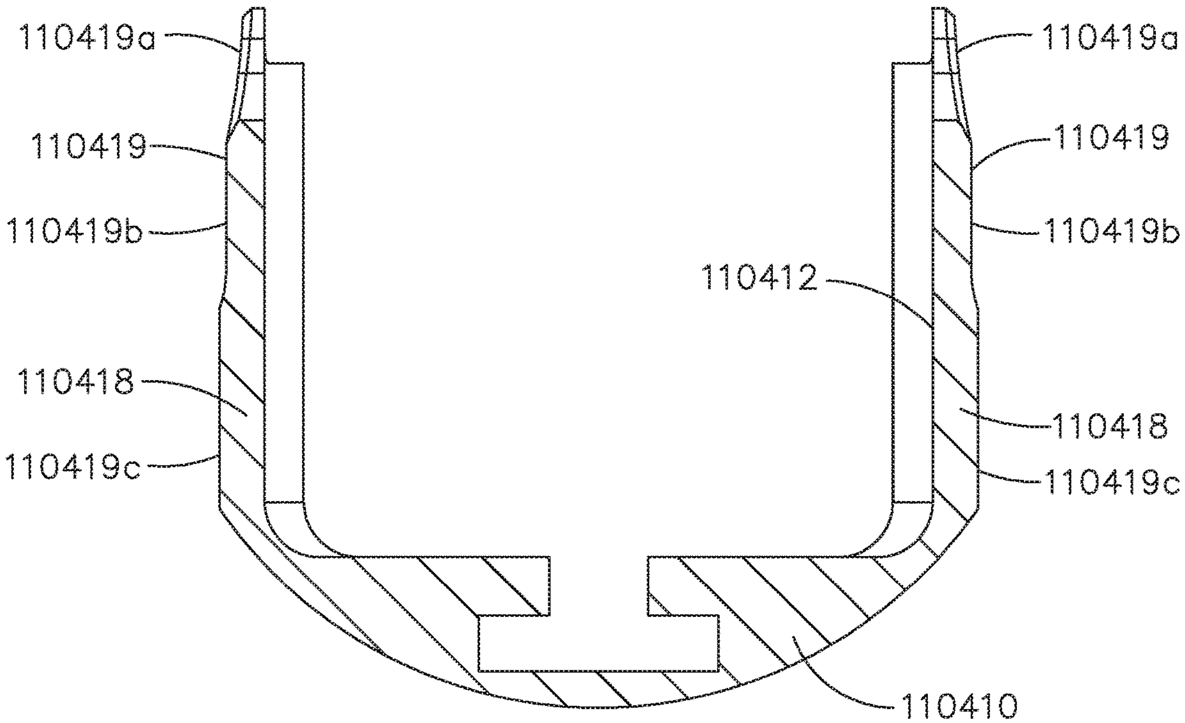
Figure 131:
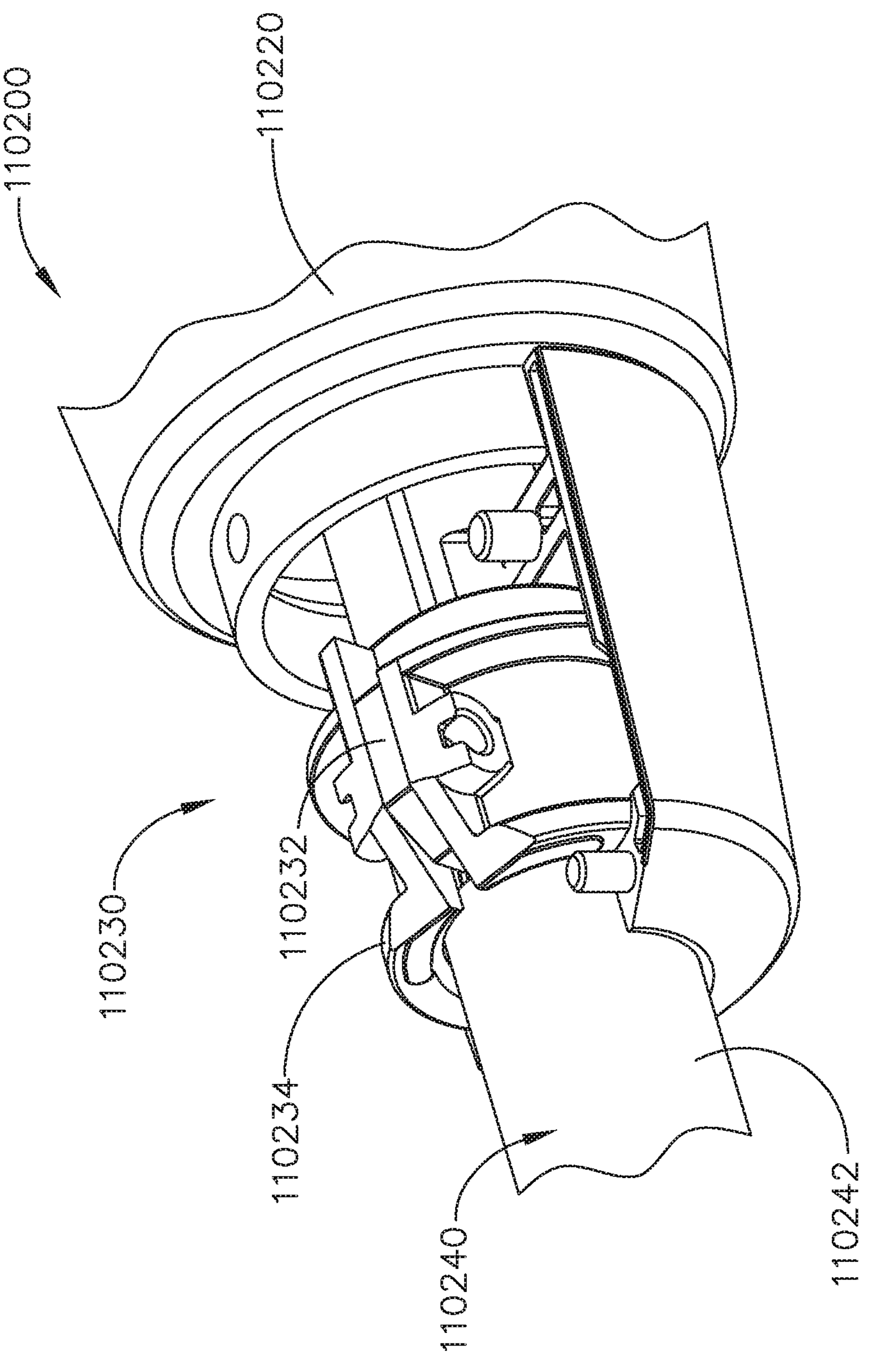
Figure 132:
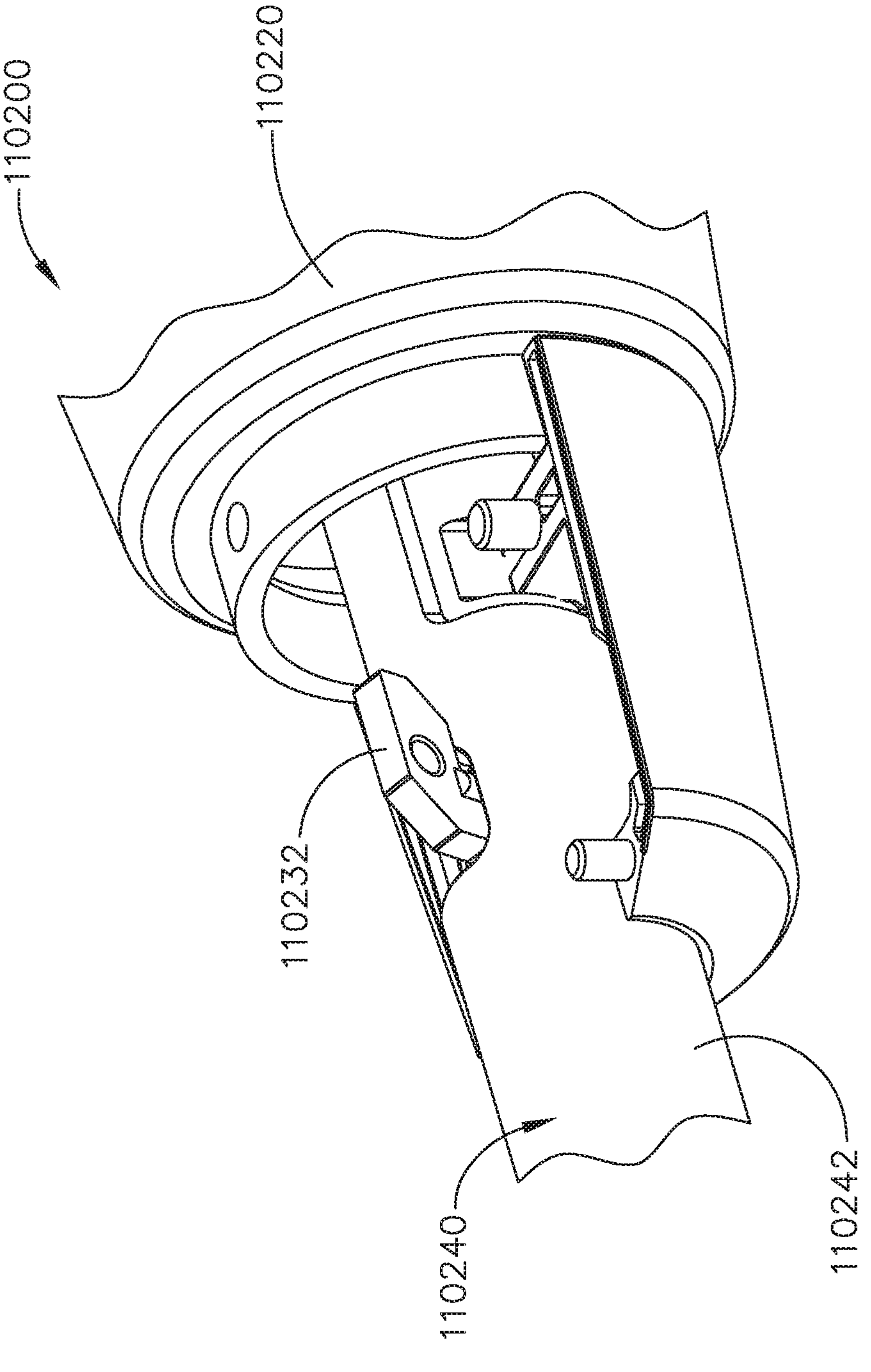
Figure 133:
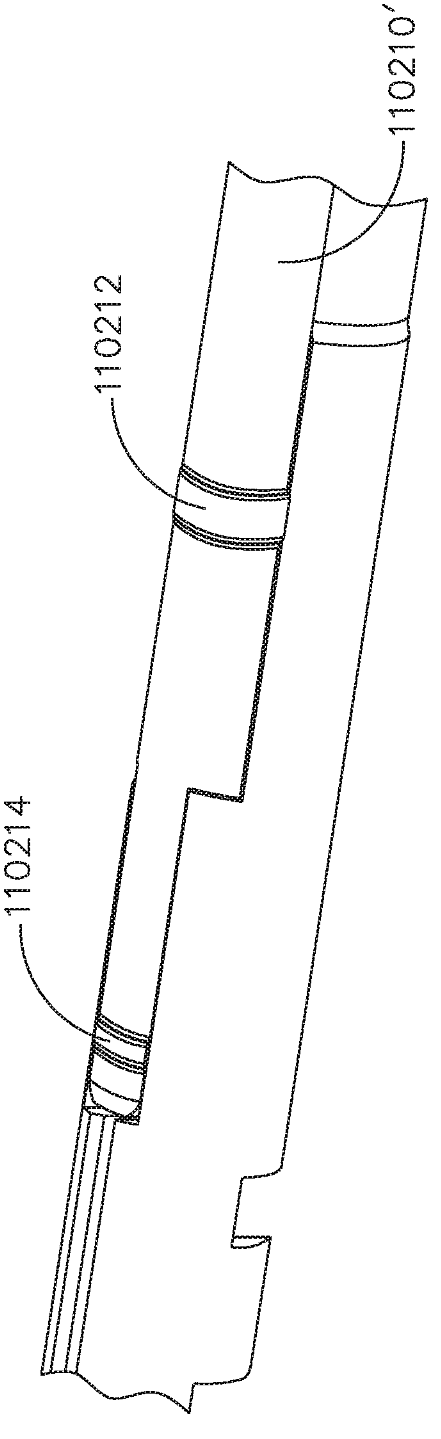
Figure 134:
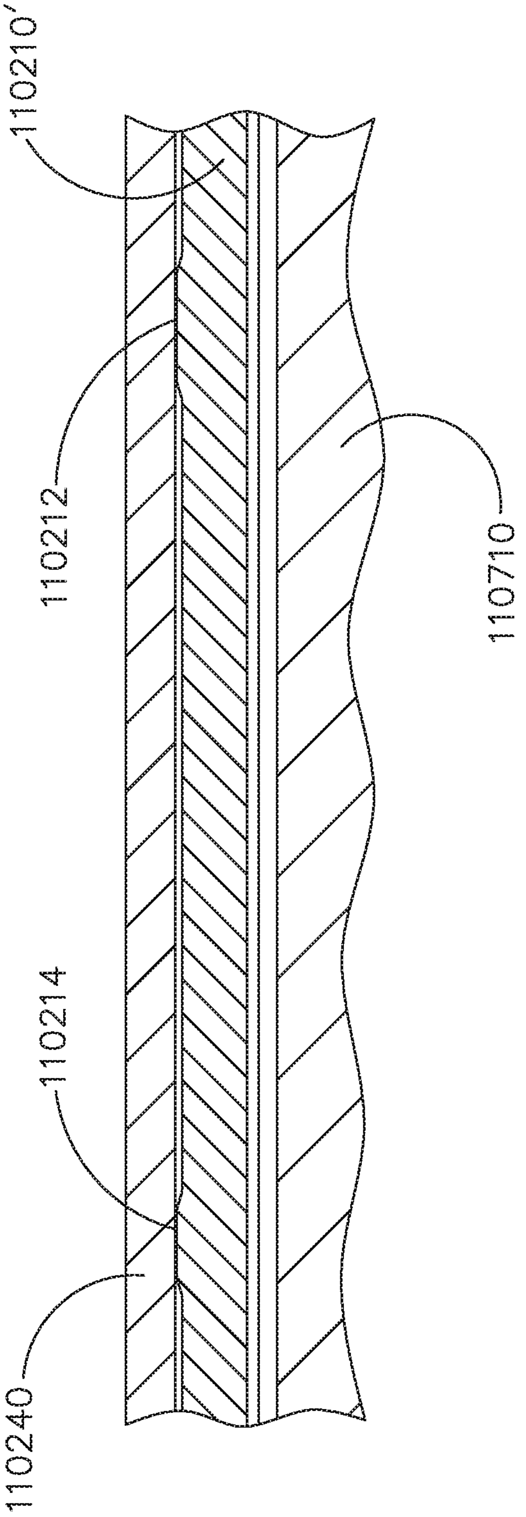
Figure 135:
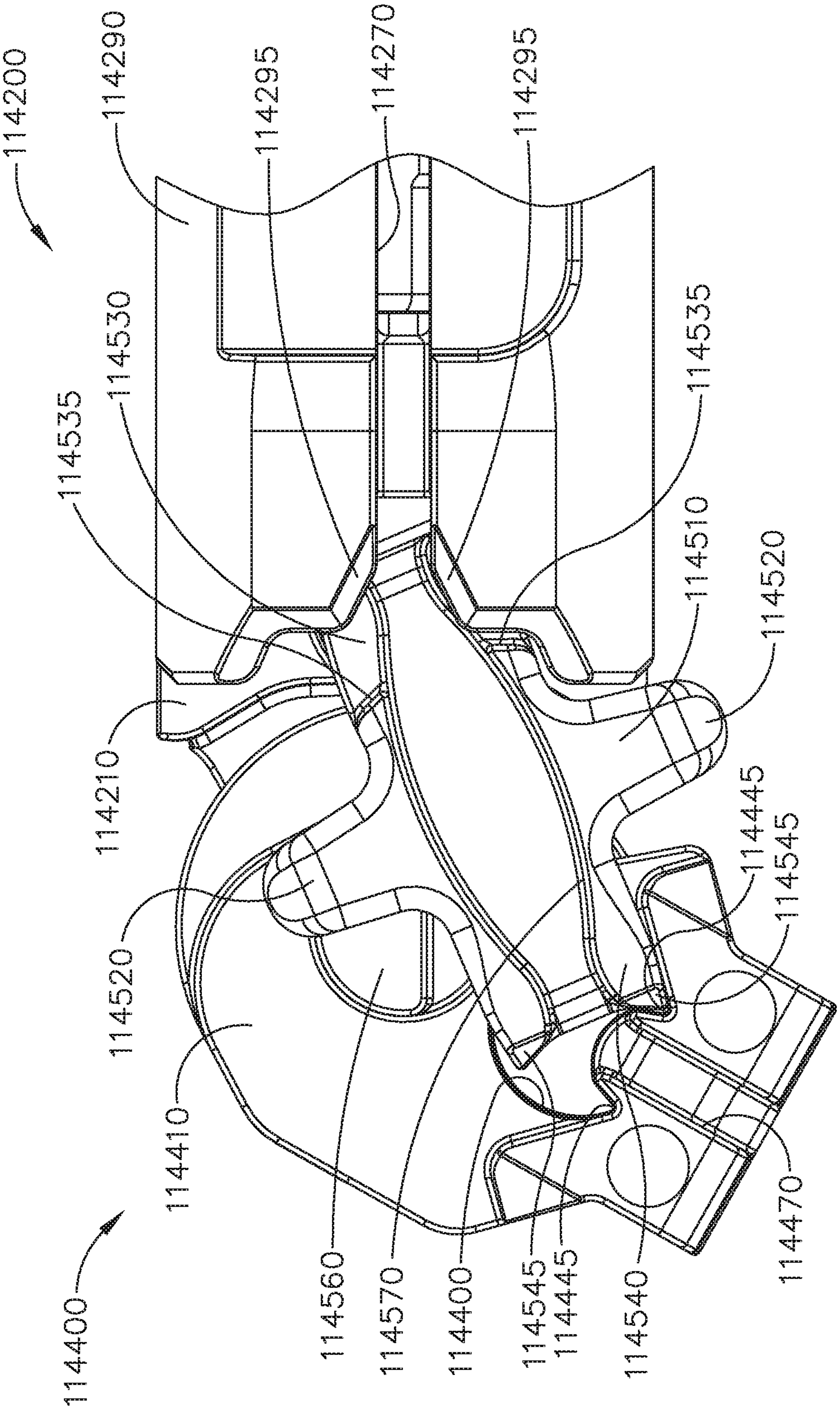
Figure 136:
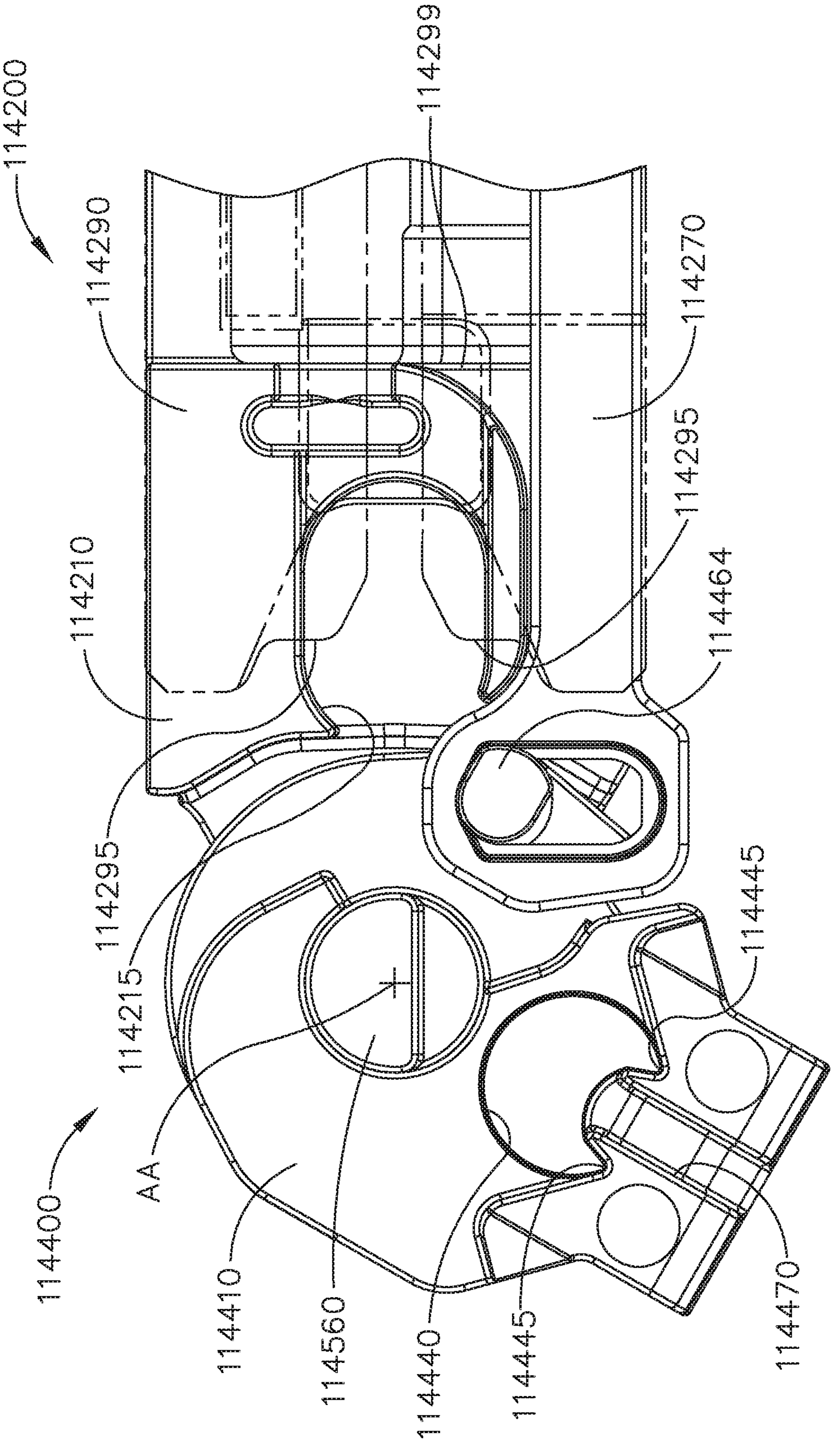
Figure 137:
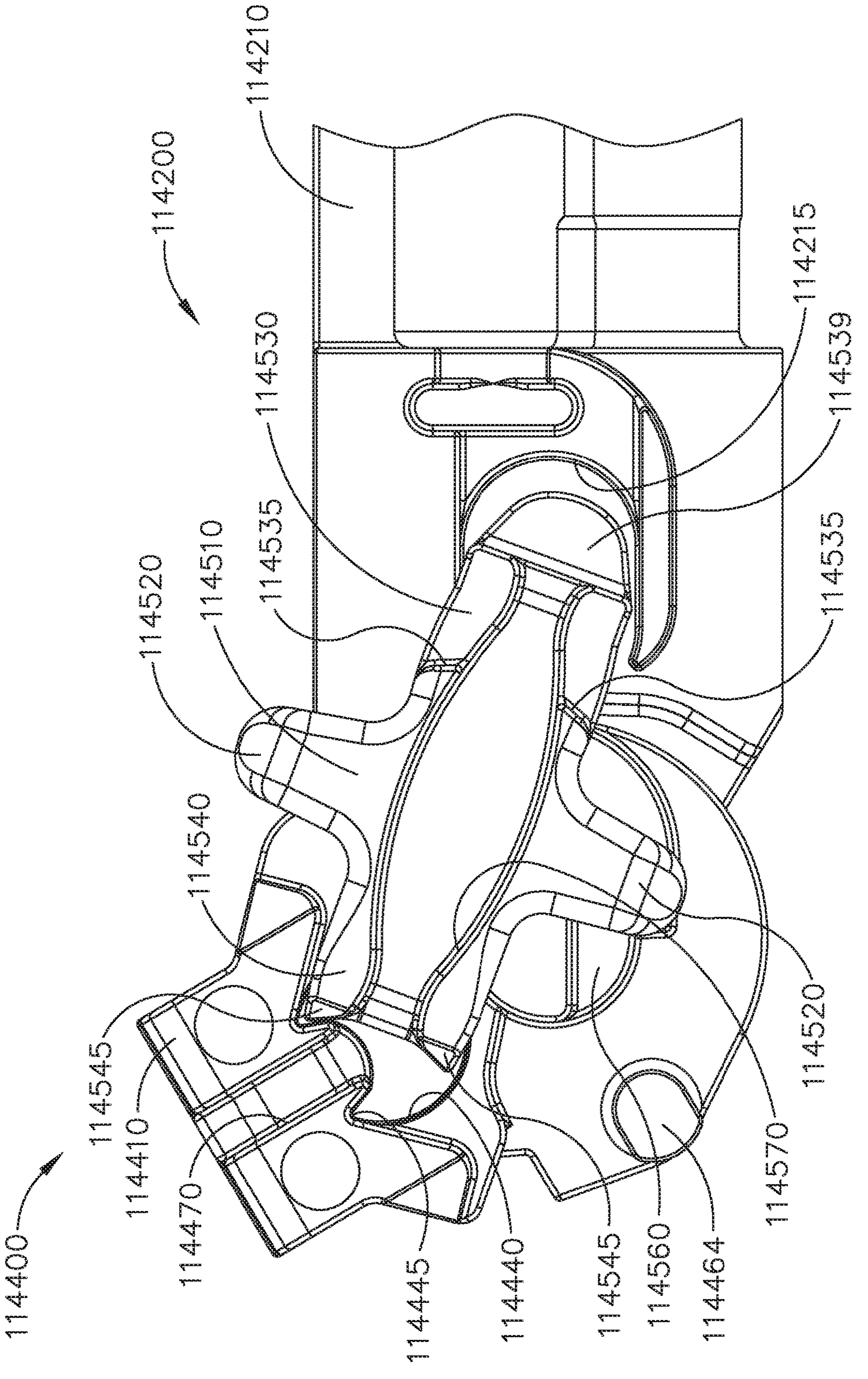
Figure 138:
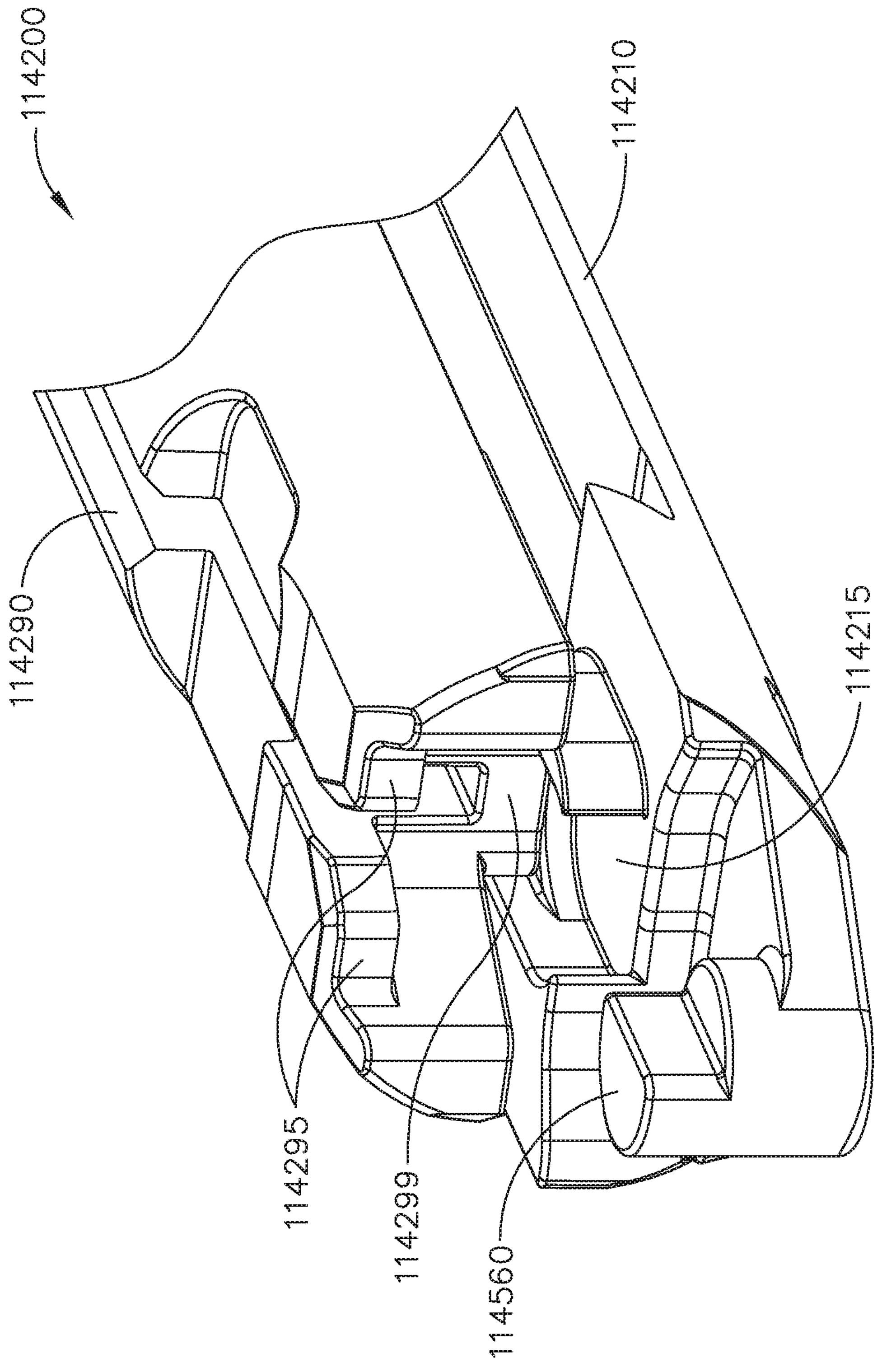
Figure 139:
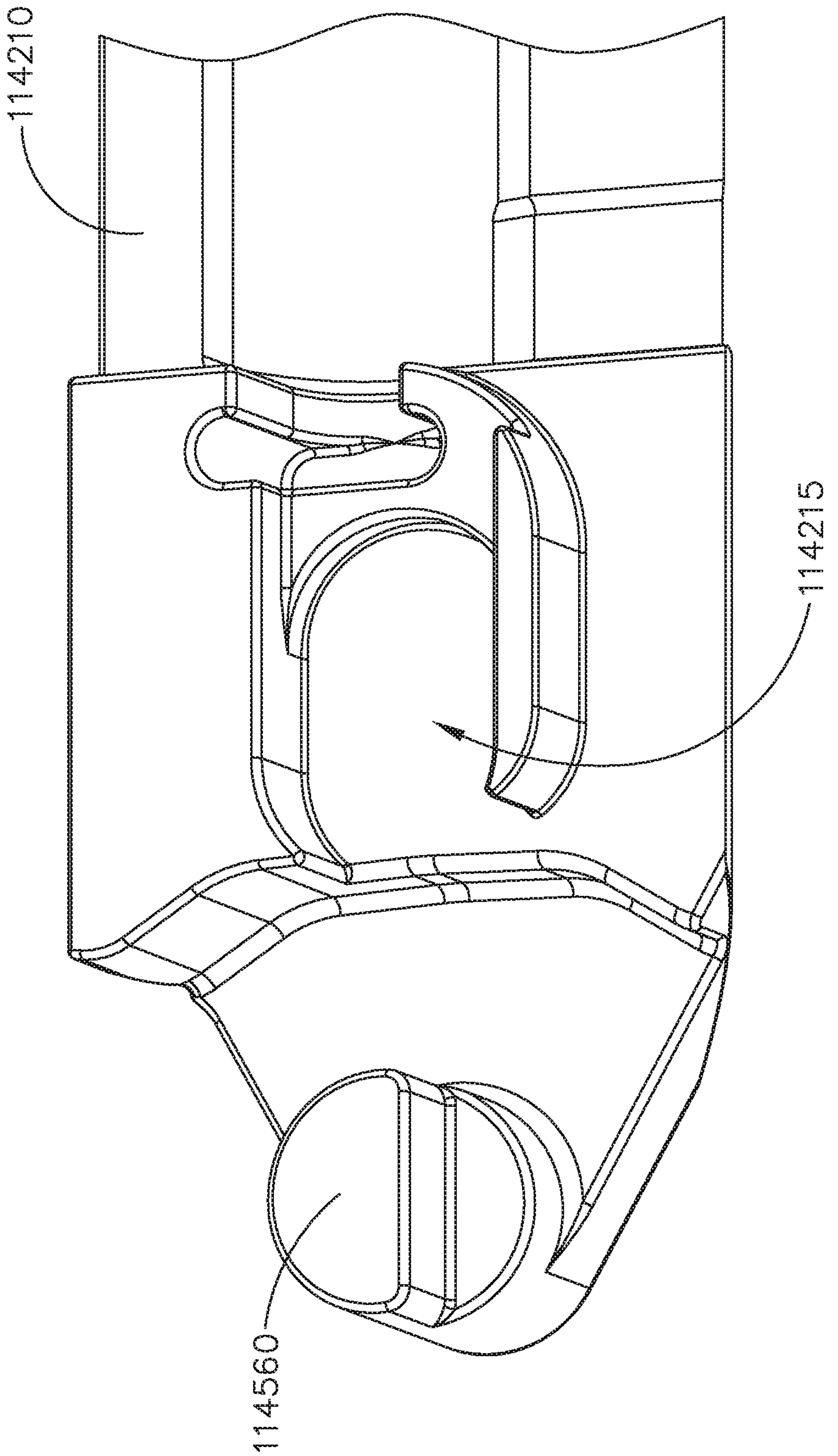
Figure 140:
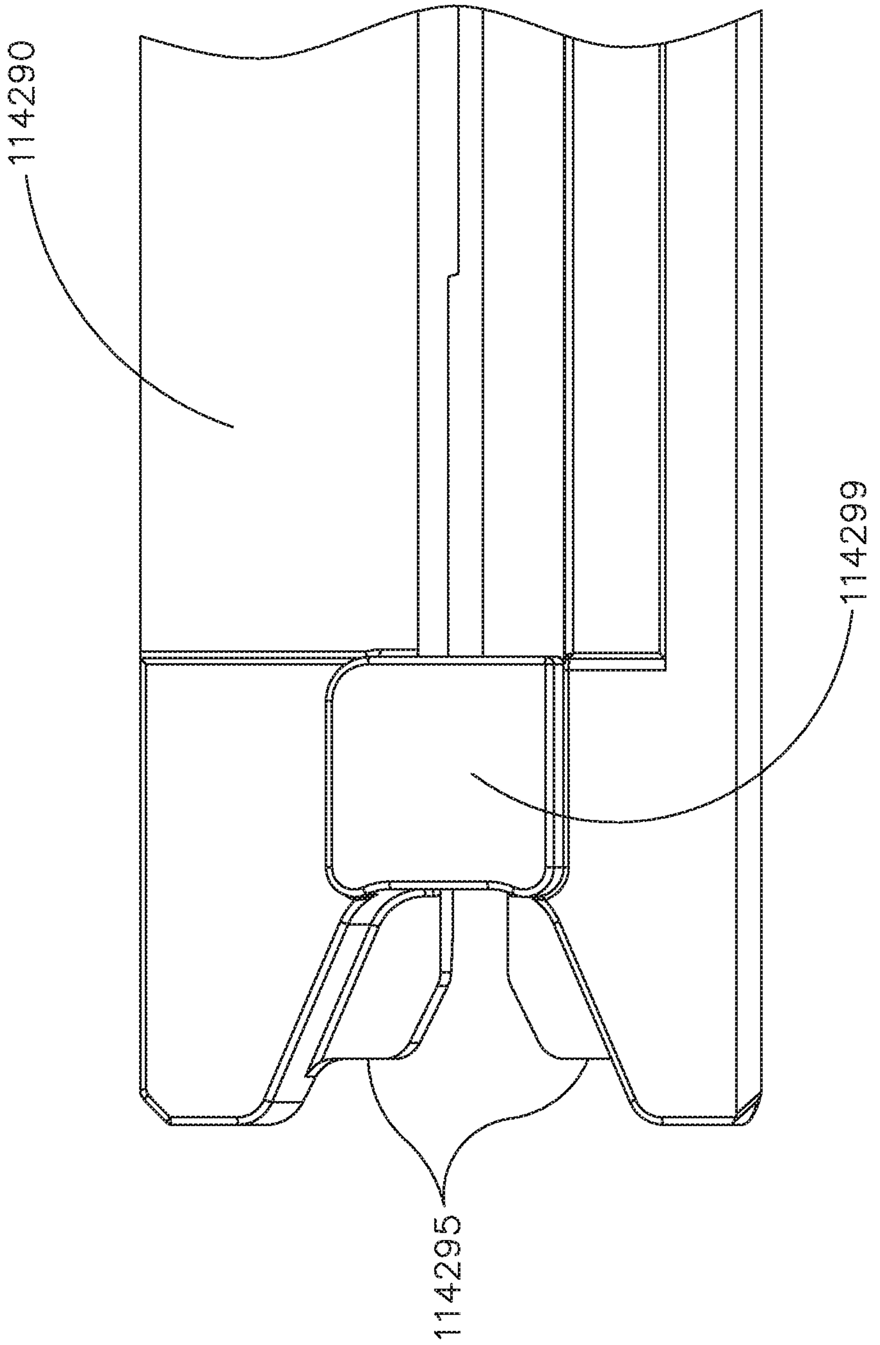
Figure 141:
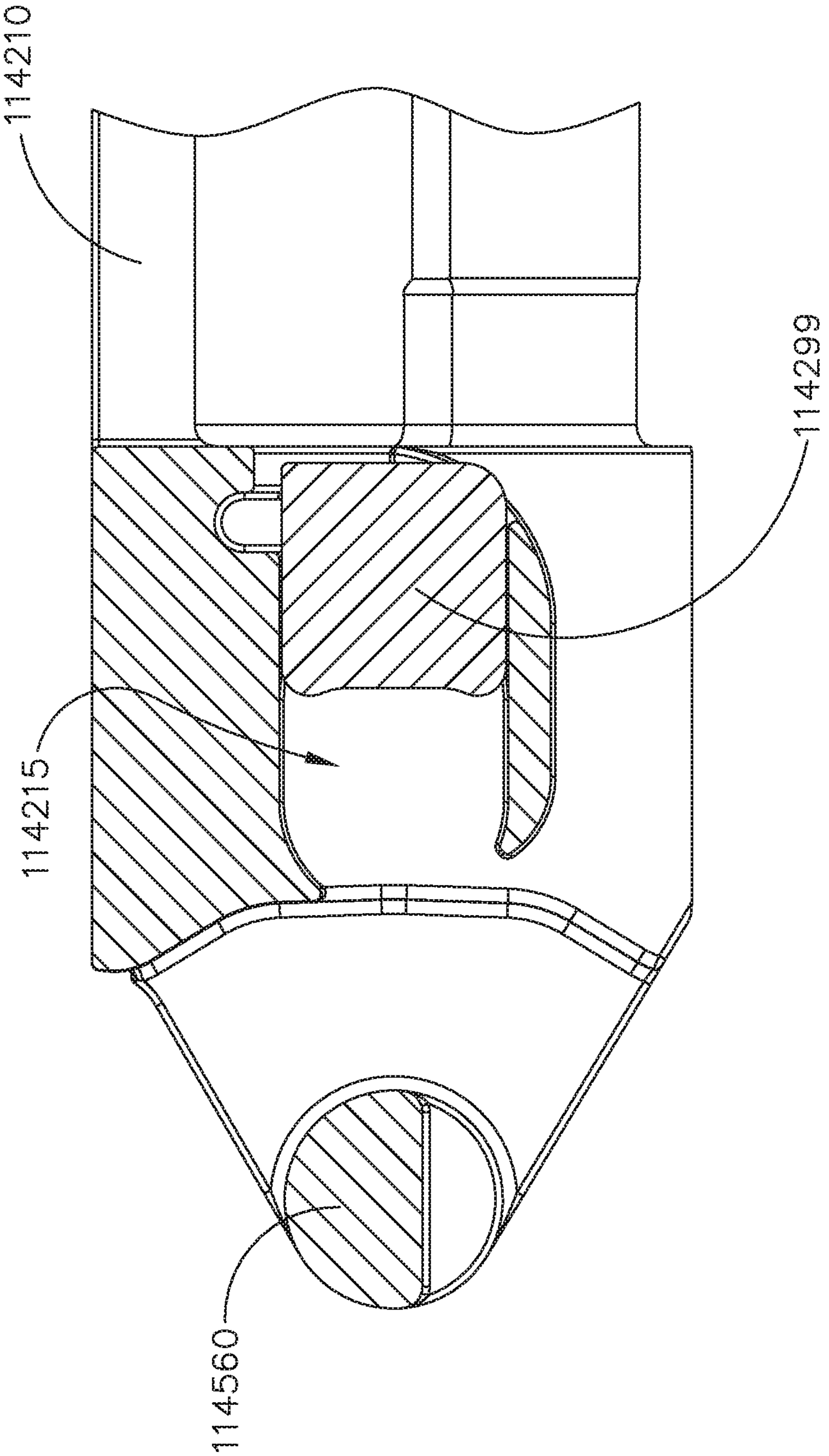
Figure 142:
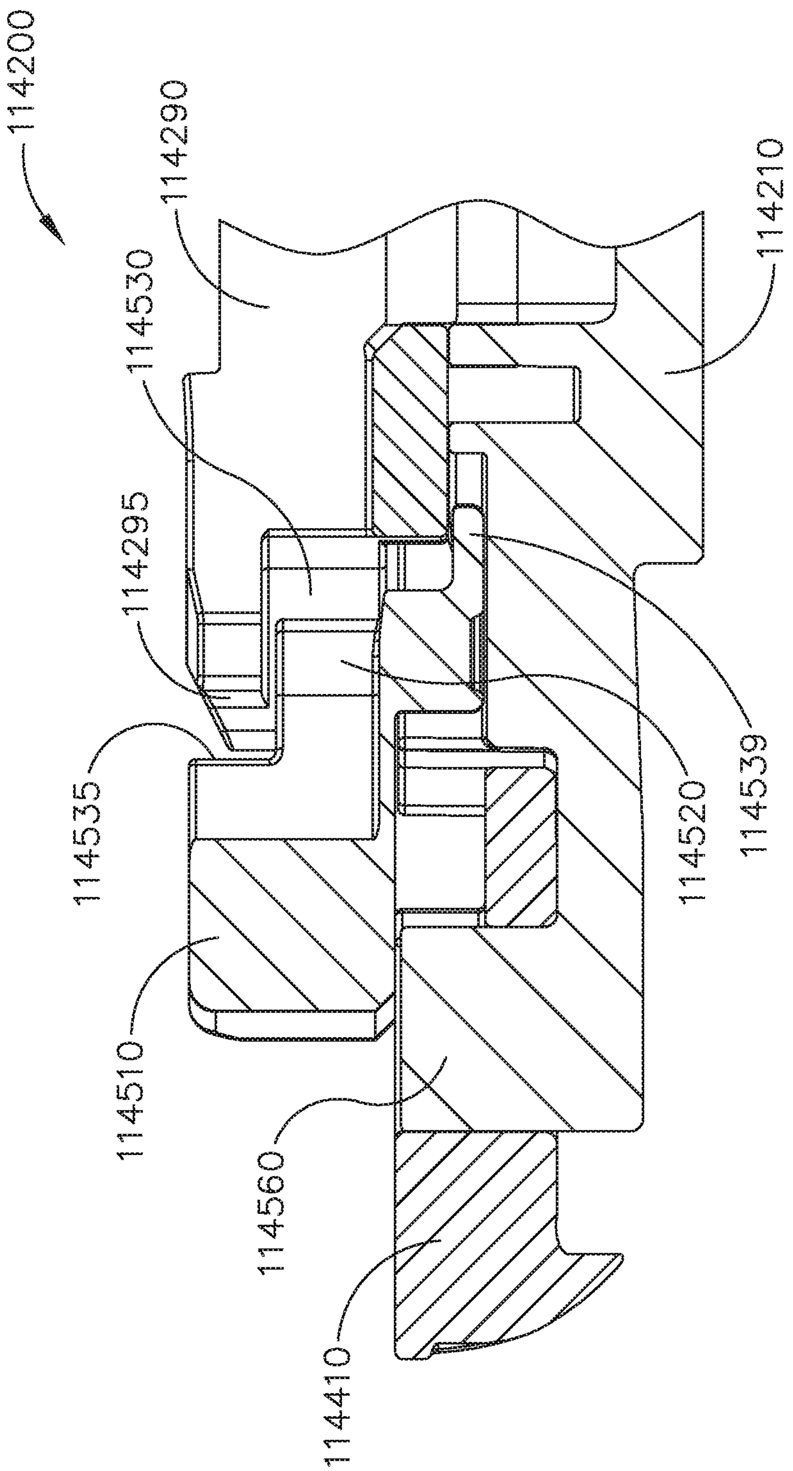
Figure 143:
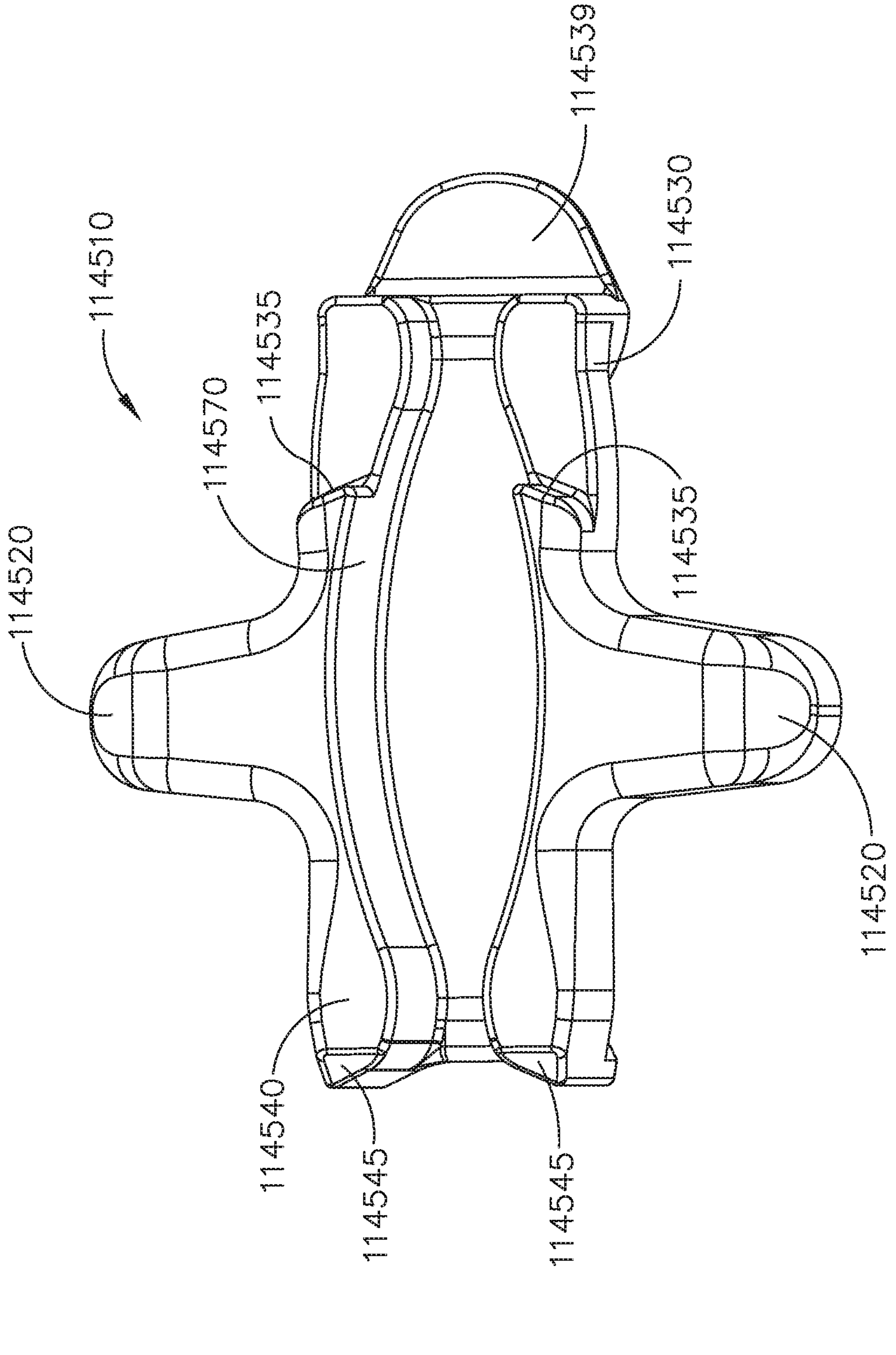
Figure 144:
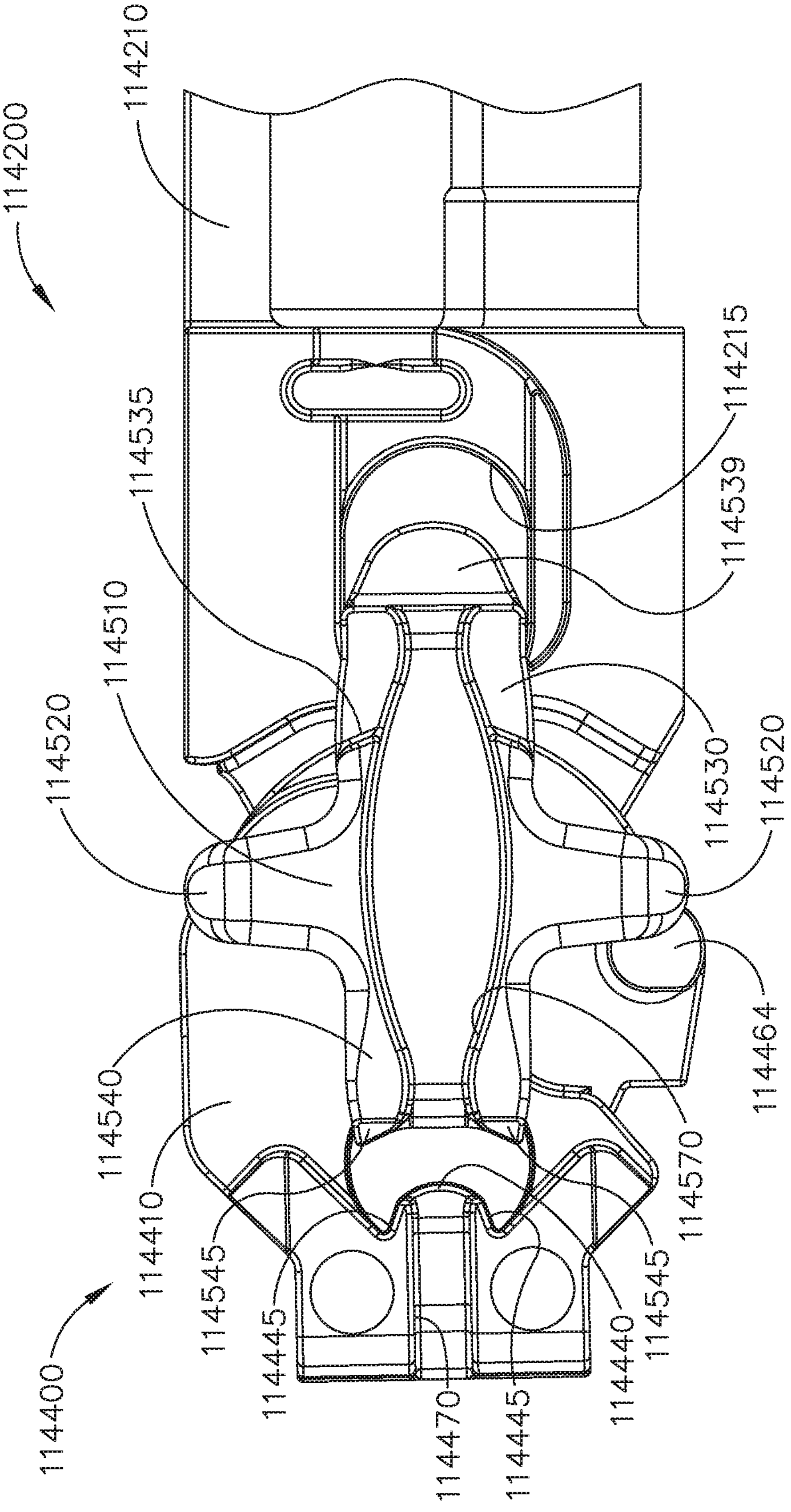
Figure 145:
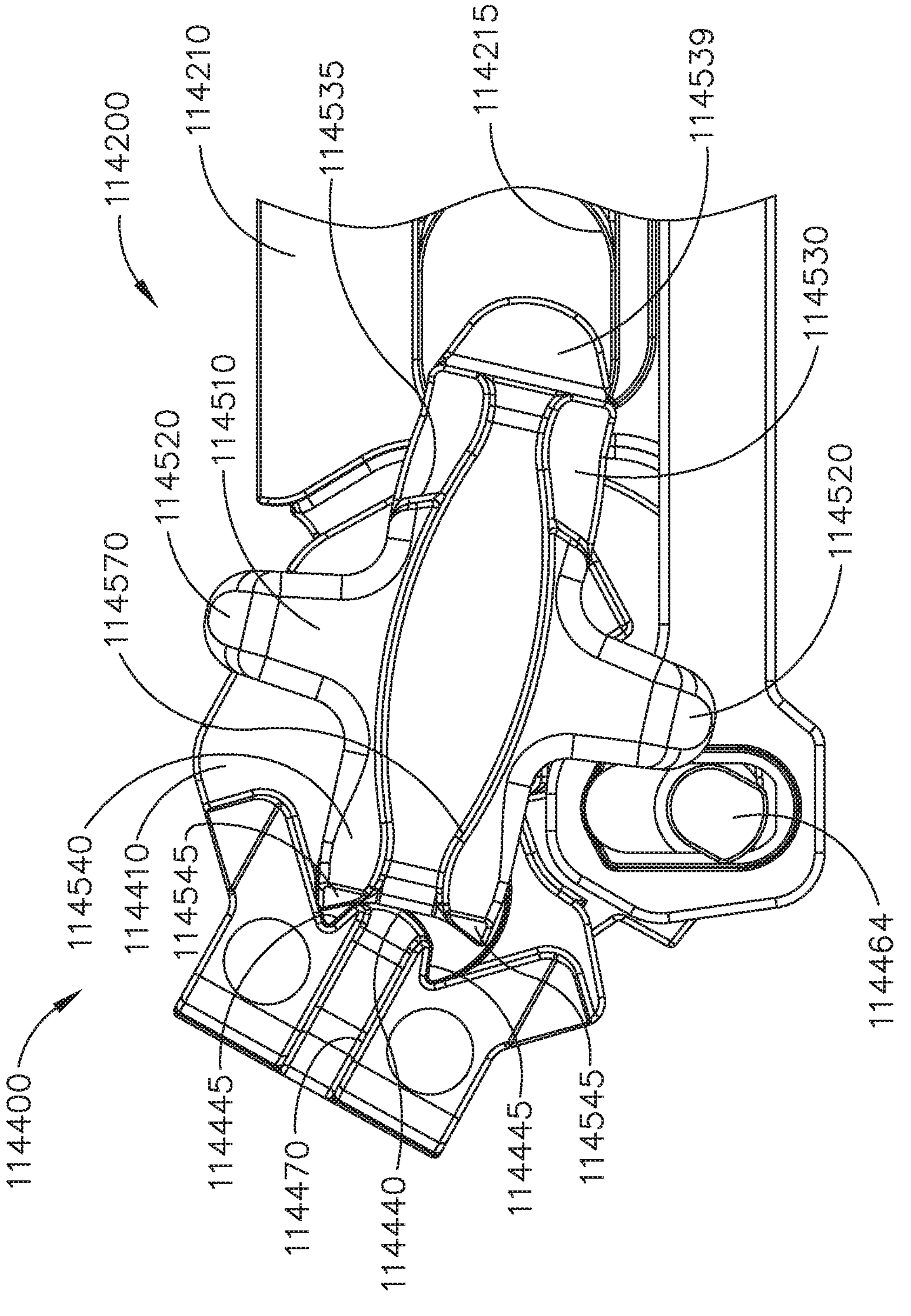
Figure 146:
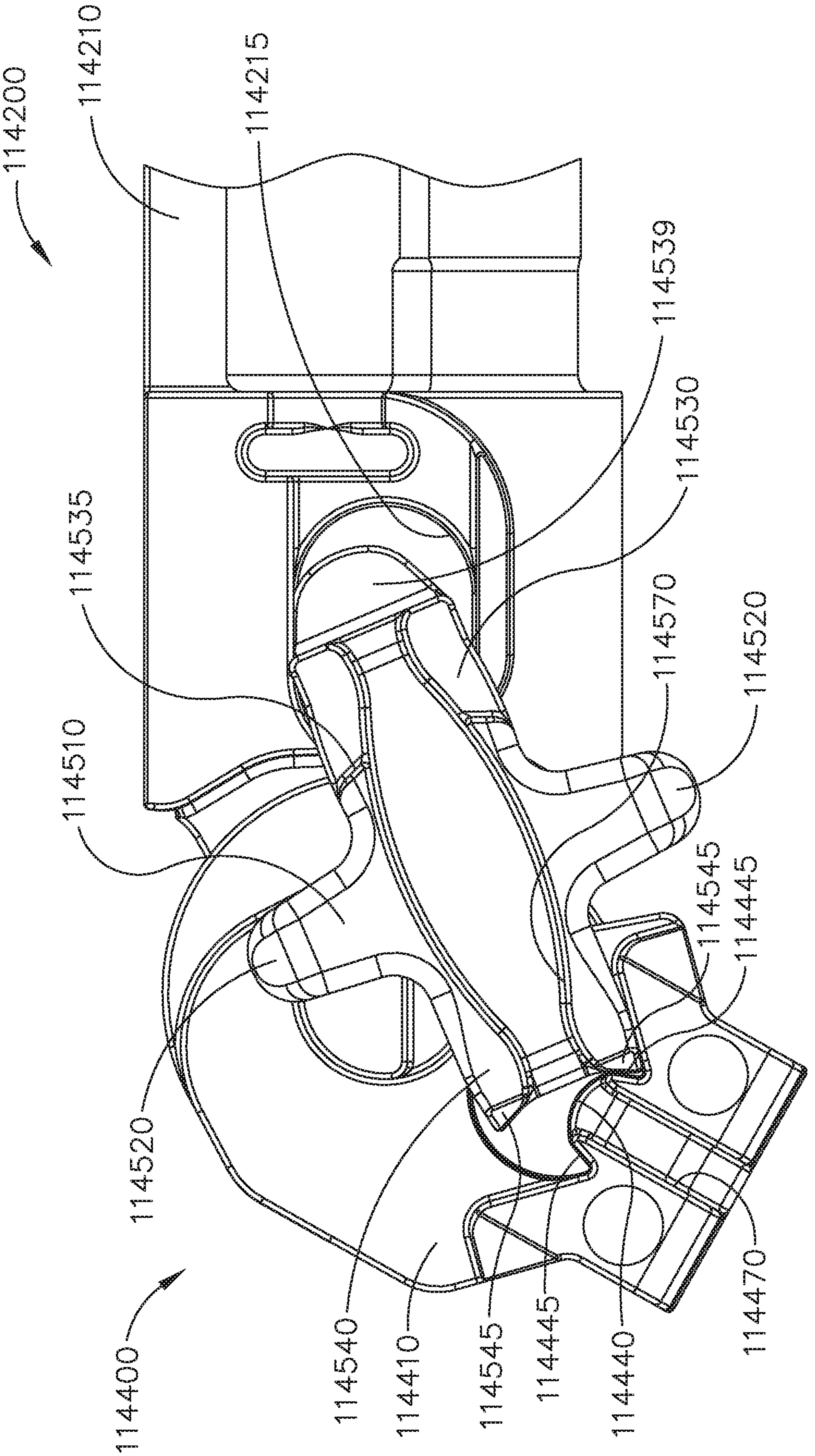
Figure 147:
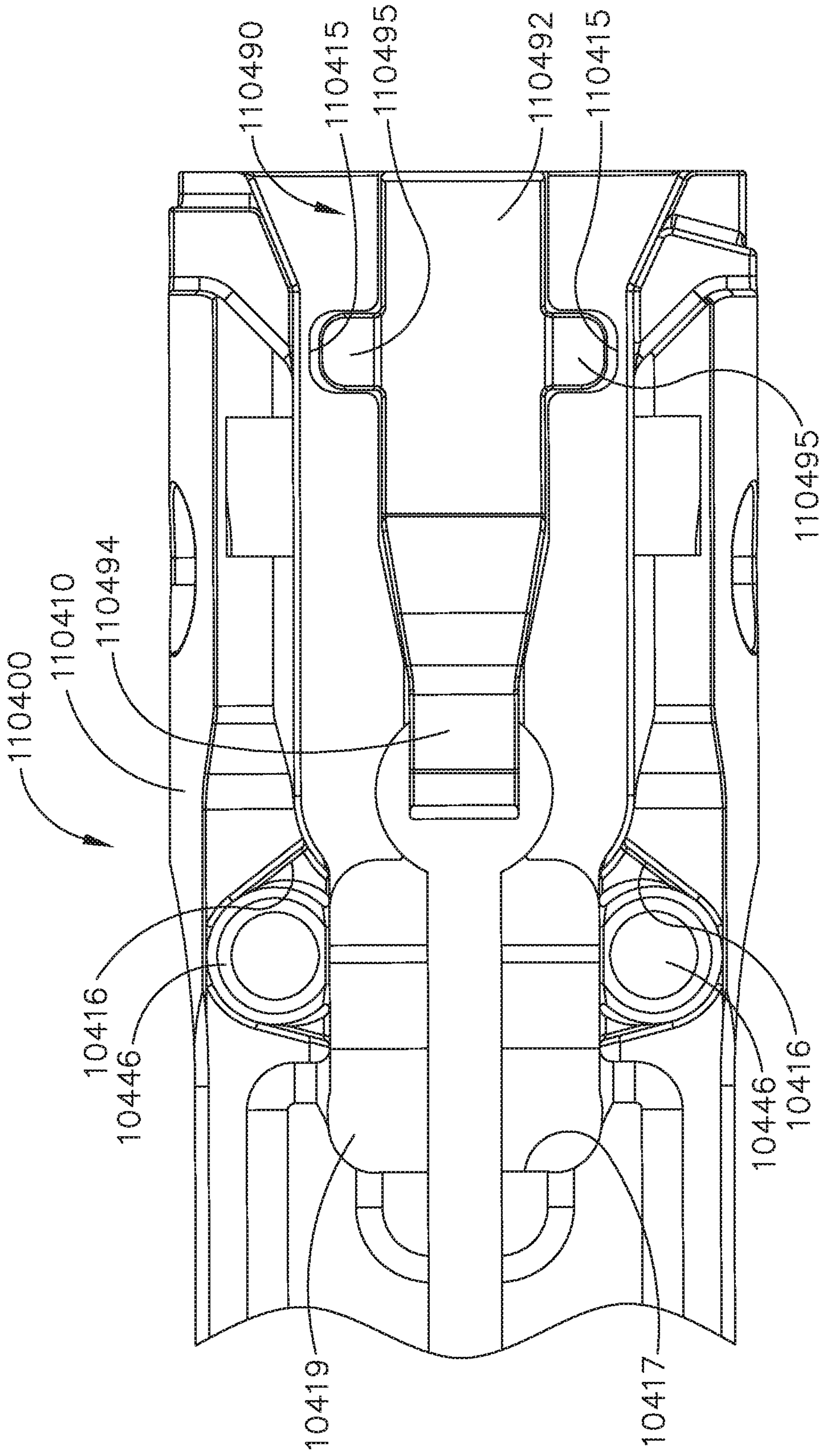
Figure 148:
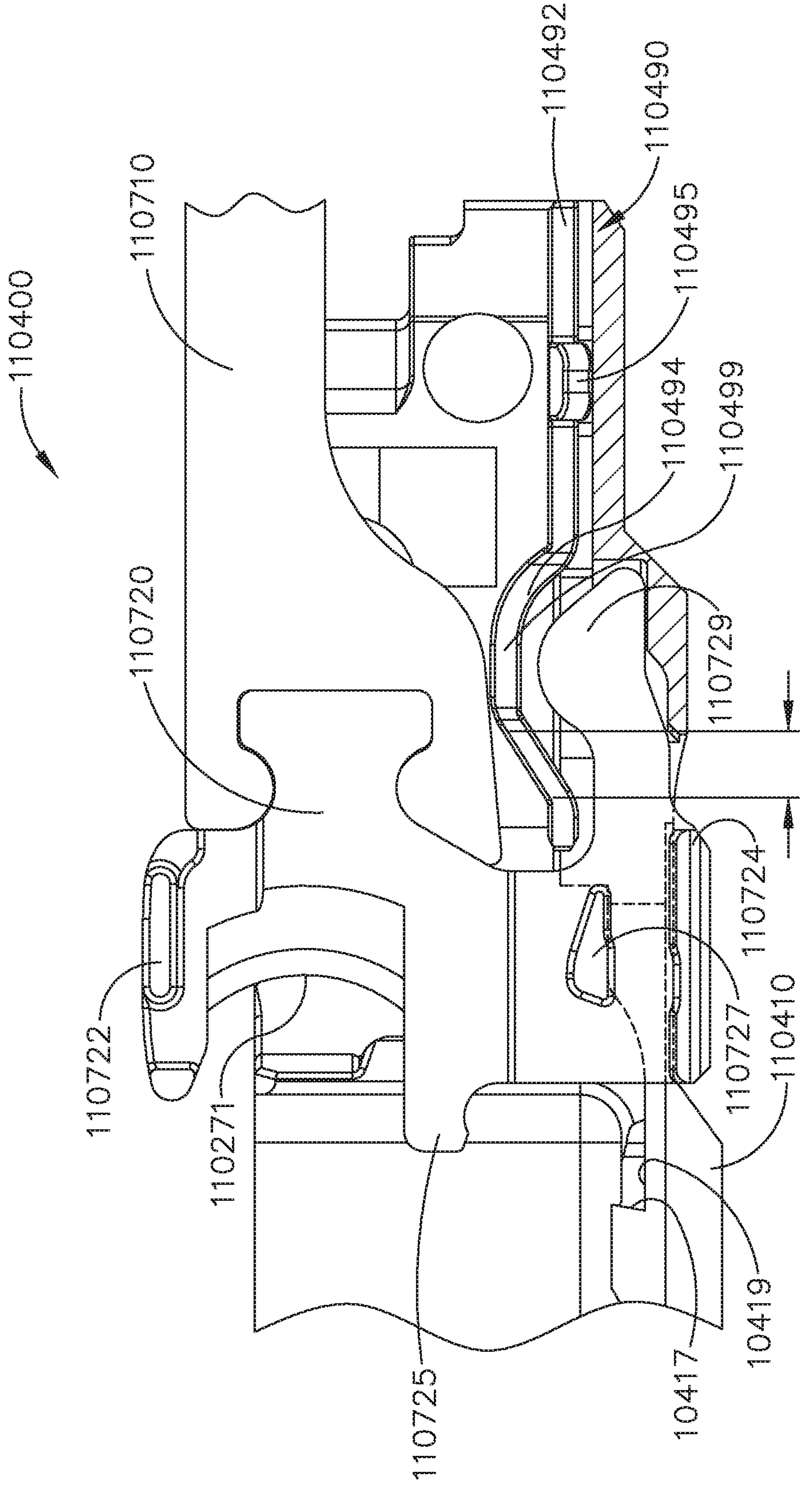
Figure 149:
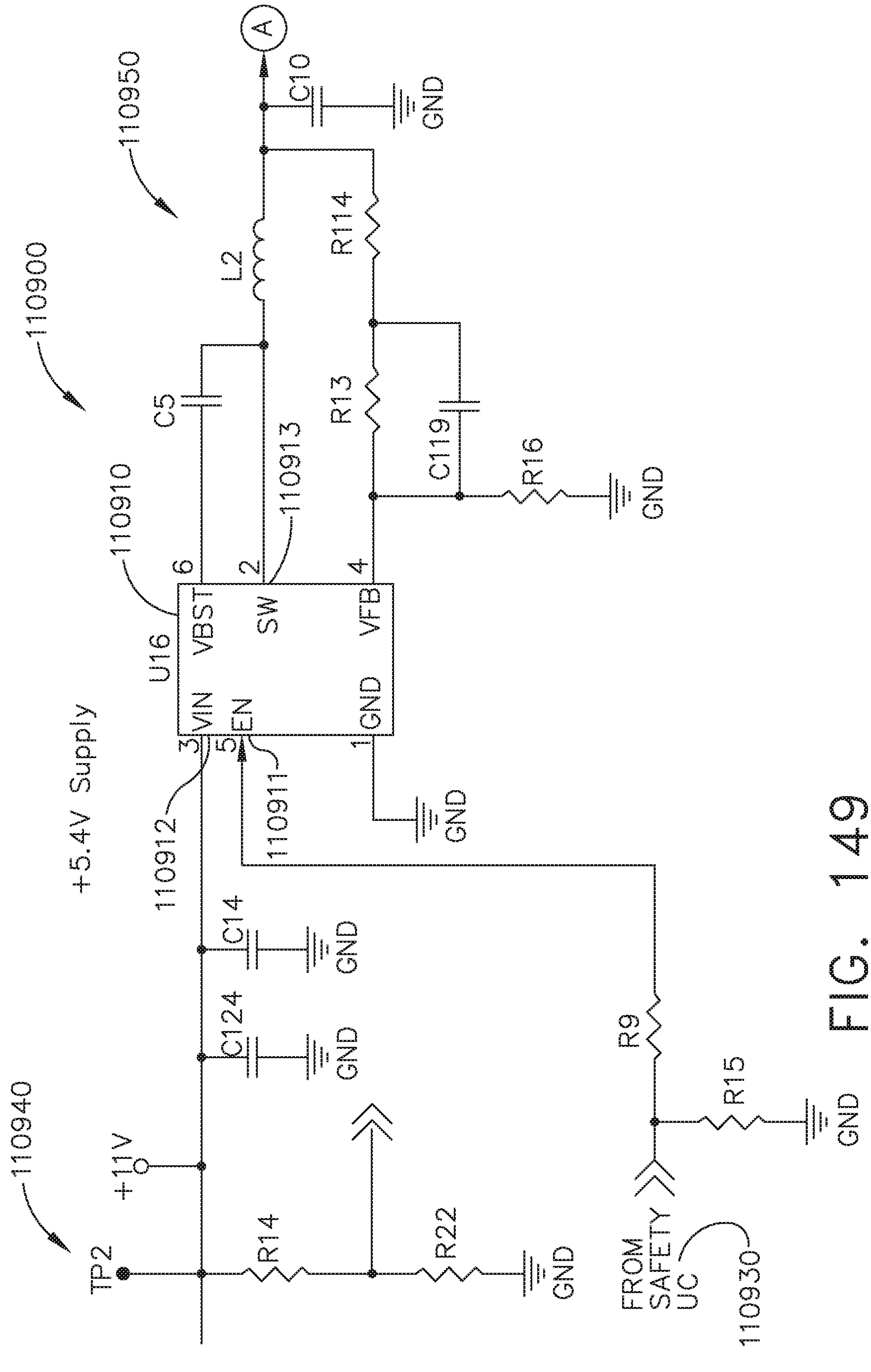
Figure 149A:
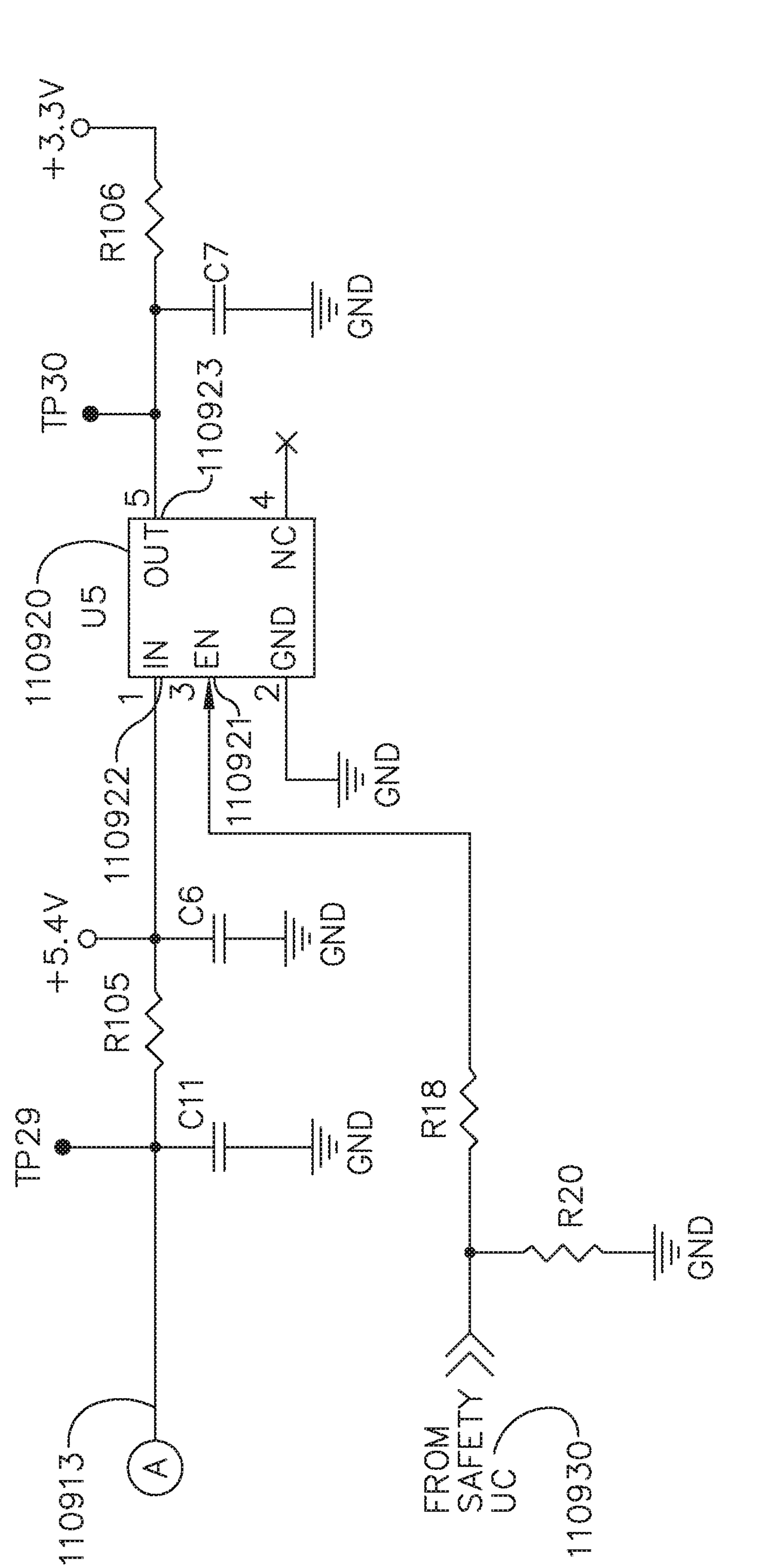
Figure 150:
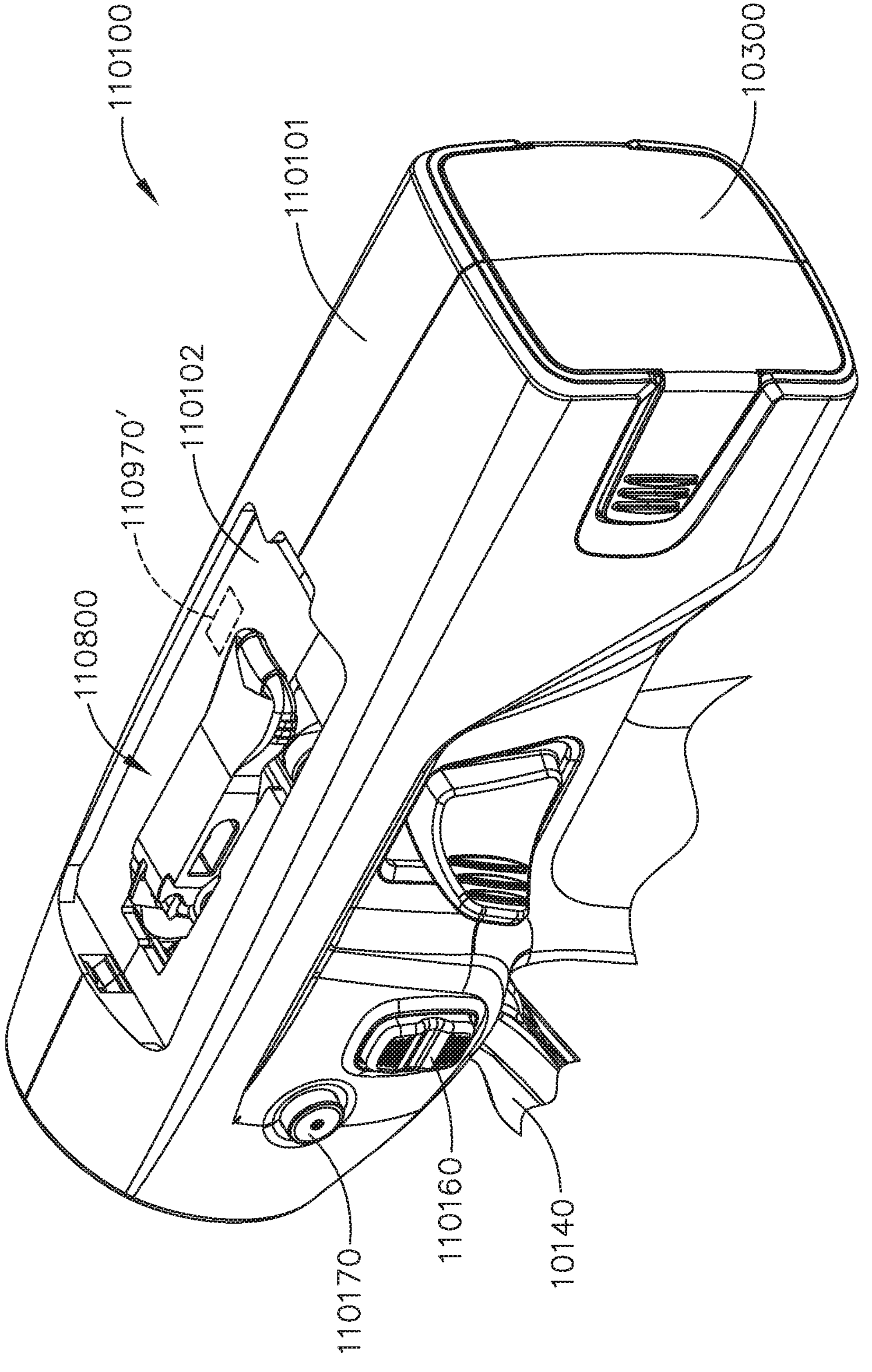
Figure 151:
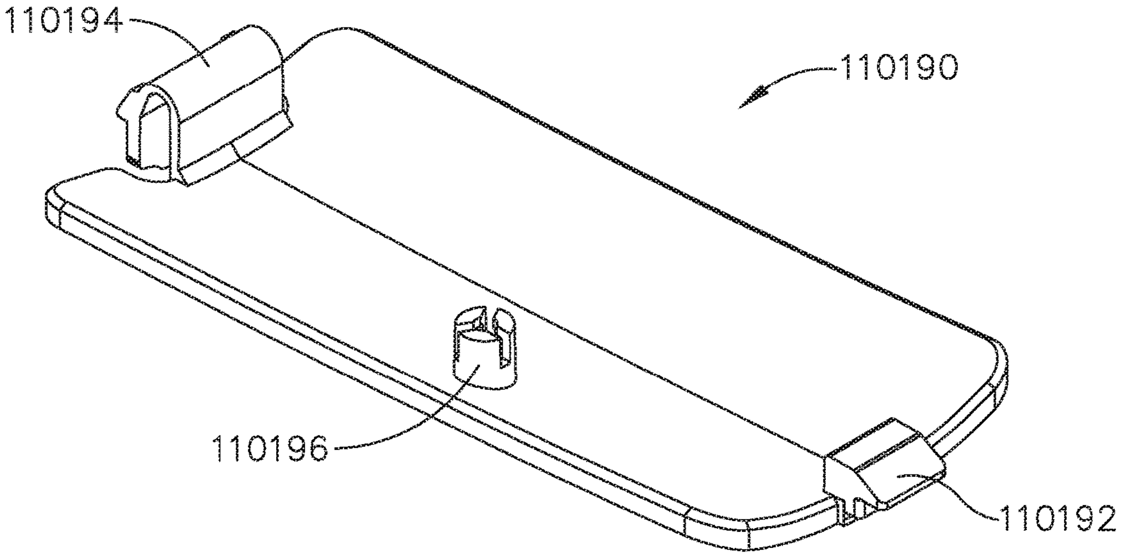
Figure 152:
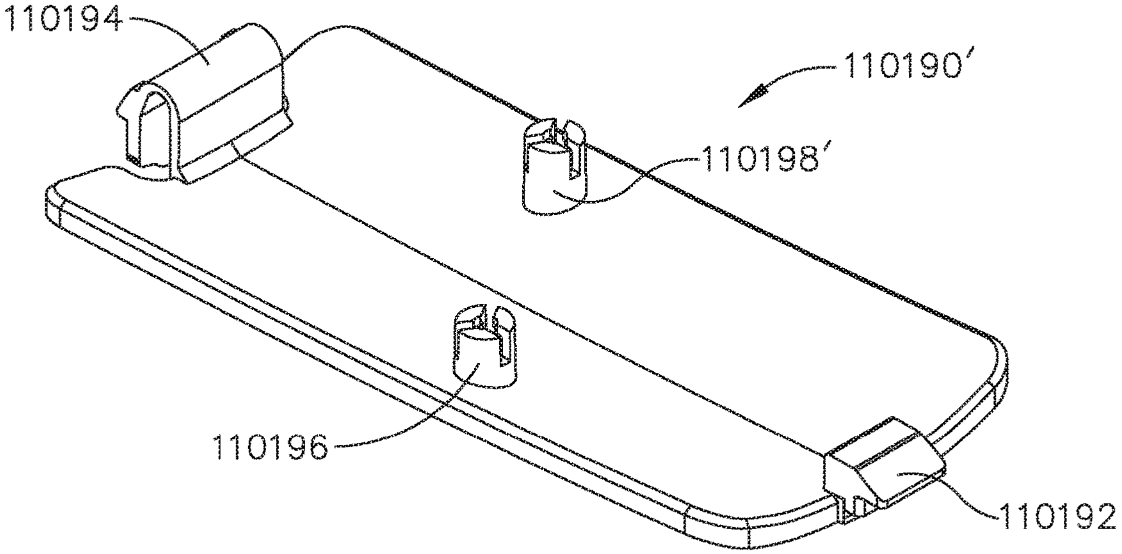
Figure 153:
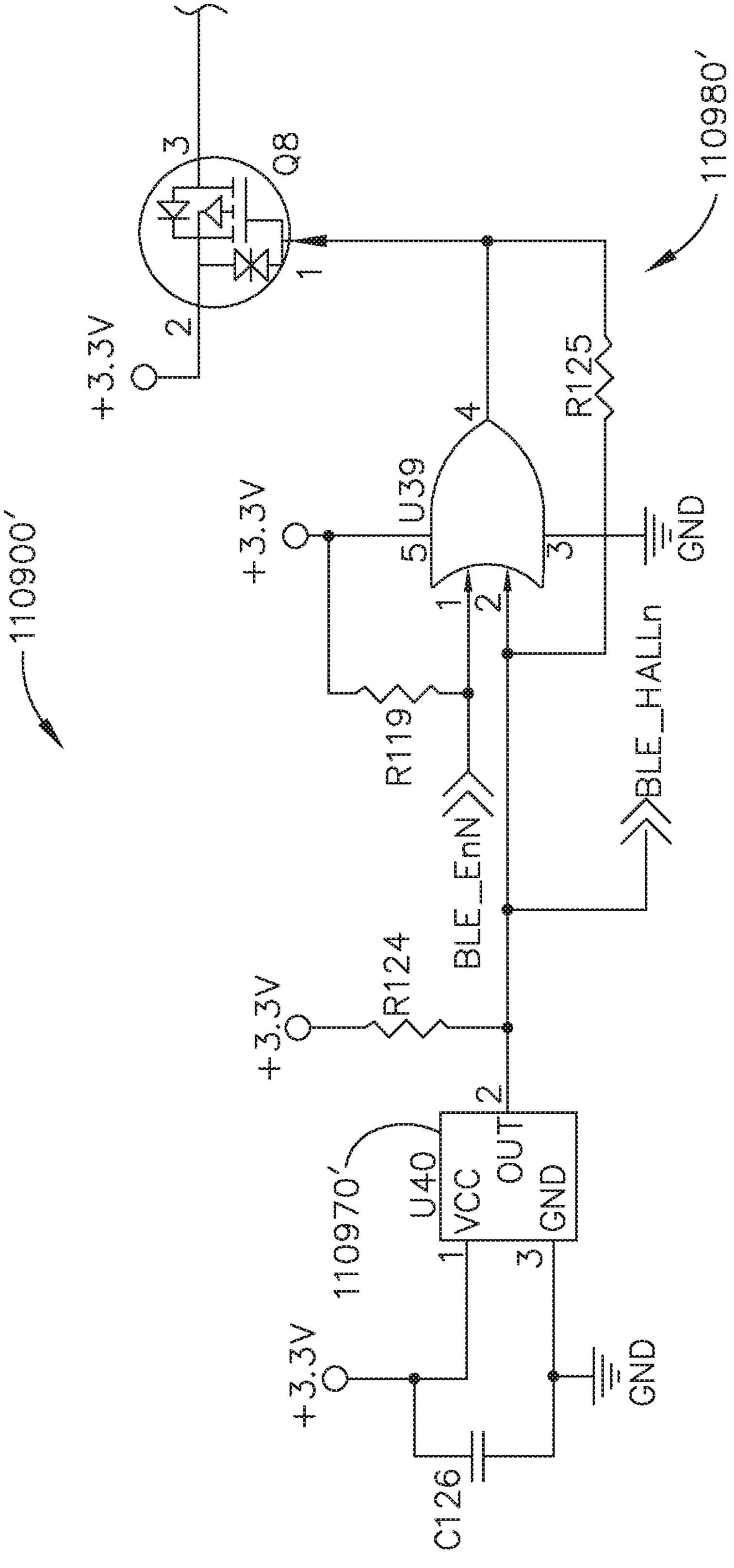

FIG. 113 is a graph depicting the force generated by the spring system of FIG. 112C;

FIG. 114 is a partial elevational view of the surgical instrument of FIG. 90 illustrated with an illuminated articulation control when the closure system is in a fully-closed configuration;

FIG. 115 is a partial elevational view of the surgical instrument of FIG. 90 illustrated with an illuminated articulation control when the closure system is in an open configuration;

FIG. 116 depicts a control system of the surgical instrument of FIG. 90;

FIG. 117 depicts a control system of the surgical instrument of FIG. 90;

FIG. 118 is a partial perspective view of the shaft and end effector of the surgical instrument of FIG. 90 illustrated with some components removed;

FIG. 119 is a perspective view of the components of an articulation lock of the surgical instrument of FIG. 90;

FIG. 120 is a partial perspective view of the articulation lock components of FIG. 119;

FIG. 121 is a plan view of an articulation lock in accordance with at least one embodiment;

FIG. 122 is a plan view of a lock tab of the articulation lock of FIG. 121;

FIG. 123 is a partial perspective view of a shaft and end effector of a surgical instrument in accordance with at least one embodiment illustrated with some components removed;

FIG. 124 illustrates an articulation lock of the surgical instrument of FIG. 123 in an unlocked configuration;

FIG. 125 illustrates the articulation lock of FIG. 124 in an unlocked configuration;

FIG. 126 is a perspective view of some components of the articulation lock of FIG. 124;

FIG. 127 is a partial elevational view of the end effector of the surgical instrument of FIG. 90 illustrated in a fully-clamped configuration;

FIG. 128 is a partial elevational view of the end effector of FIG. 90 illustrated in an open configuration;

FIG. 129 is a cross-sectional view of the end effector of FIG. 90 illustrated in a partially-closed configuration;

FIG. 130 is a partial cross-sectional view of a channel of the end effector of FIG. 127;

FIG. 131 is a partial cross-sectional view of the shaft of the surgical instrument of FIG. 90 illustrated with some components removed;

FIG. 132 is a partial cross-sectional view of the shaft of FIG. 90 illustrated with additional components removed;

FIG. 133 is a partial perspective view of an inner frame of the shaft of FIG. 90;

FIG. 134 is a partial cross-sectional view of the shaft of FIG. 90;

FIG. 135 is a partial plan view of a shaft and end effector of a surgical instrument in accordance with at least one embodiment illustrated with some components removed;

FIG. 136 is a partial plan view of the shaft and end effector of FIG. 135 illustrated with additional components removed;

FIG. 137 is a partial plan view of the shaft and end effector of FIG. 135 illustrated with additional components removed;

FIG. 138 is a partial perspective view of a frame of the shaft of FIG. 135;

FIG. 139 is a partial perspective view of a component of the frame of the shaft of FIG. 135;

FIG. 140 is a partial perspective view of a component of the frame of the shaft of FIG. 135;

FIG. 141 is a partial cross-sectional view of the frame of the shaft of FIG. 135;

FIG. 142 is a partial cross-sectional view of the shaft and end effector of FIG. 135 illustrated with components removed;

FIG. 143 is a plan view of a component of an articulation joint of the surgical instrument of FIG. 135;

FIG. 144 is a plan view of the end effector of the surgical instrument of FIG. 135 illustrated in an unarticulated position;

FIG. 145 illustrates the end effector of FIG. 144 articulated in a first direction;

FIG. 146 illustrates the end effector of FIG. 144 articulated in a second direction;

FIG. 147 is a partial plan view of a jaw of the end effector of the surgical instrument of FIG. 90 including a staple firing lockout;

FIG. 148 is a partial elevational view of a staple firing system and the staple firing lockout of FIG. 147;

FIG. 149 depicts a portion of a power regulation circuit of the surgical instrument of FIG. 90;

FIG. 149A depicts another portion of the power regulation circuit of FIG. 90;

FIG. 150 is a partial perspective view of the handle of FIG. 90;

FIG. 151 is a cover of the handle of FIG. 90;

FIG. 152 is a cover analog used during the manufacturing of the surgical instrument of FIG. 90; and FIG. 153 is a control circuit of the handle of FIG. 90.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application also owns the following U.S. Patent Applications that were filed on Oct. 29, 2020, and which are each herein incorporated by reference in their respective entireties:

U.S. patent application Ser. No. 17/084,179 entitled SURGICAL INSTRUMENT COMPRISING A RELEASABLE CLOSURE DRIVE LOCK;

U.S. patent application Ser. No. 17/084,190 entitled SURGICAL INSTRUMENT COMPRISING A STOWED CLOSURE ACTUATOR STOP;

U.S. patent application Ser. No. 17/084,193 entitled SURGICAL INSTRUMENT COMPRISING AN INDICATOR WHICH INDICATES THAT AN ARTICULATION DRIVE IS ACTUATABLE;

U.S. patent application Ser. No. 17/084,205, entitled SURGICAL INSTRUMENT COMPRISING AN ARTICULATION INDICATOR;

U.S. patent application Ser. No. 17/084,258 entitled METHOD FOR OPERATING A SURGICAL INSTRUMENT;

U.S. patent application Ser. No. 17/084,206 entitled SURGICAL INSTRUMENT COMPRISING AN ARTICULATION LOCK;

U.S. patent application Ser. No. 17/084,229 entitled SURGICAL INSTRUMENT COMPRISING SEALABLE INTERFACE;

U.S. patent application Ser. No. 17/084,180 entitled SURGICAL INSTRUMENT COMPRISING A LIMITED TRAVEL SWITCH;

U.S. design patent application Ser. No. 29/756,615 entitled SURGICAL STAPLING ASSEMBLY;

U.S. design patent application Ser. No. 29/756,620 entitled SURGICAL STAPLING ASSEMBLY;

U.S. patent application Ser. No. 17/084,188 entitled SURGICAL INSTRUMENT COMPRISING A STAGED VOLTAGE REGULATION START-UP SYSTEM; and U.S. patent application Ser. No. 17/084,193 entitled SURGICAL INSTRUMENT COMPRISING A SENSOR CONFIGURED TO SENSE WHETHER AN ARTICULATION DRIVE OF THE SURGICAL INSTRUMENT IS ACTUATABLE.

Applicant of the present application owns the following U.S. Patent Applications that were filed on Feb. 21, 2019 and which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,670, entitled STAPLE CARTRIDGE COMPRISING A LOCKOUT KEY CONFIGURED TO LIFT A FIRING MEMBER;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled STAPLING INSTRUMENT COMPRISING A DEACTIVATABLE LOCKOUT;

U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND CHANNEL ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Applicant of the present application owns the following U.S. Provisional Patent Applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. Patent Applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design patent application Ser. No. 29/660,252, entitled SURGICAL STAPLER ANVILS.

Applicant of the present application owns the following U.S. Patent Applications and U.S. Patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Patent Application Publication No. 2018/0168642;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Patent Application Publication No. 2018/0168646;

U.S. patent application Ser. No. 15/386,209, entitled SURGICAL END EFFECTORS AND FIRING MEMBERS THEREOF, now U.S. Patent Application Publication No. 2018/0168645;

U.S. patent application Ser. No. 15/386,198, entitled LOCKOUT ARRANGEMENTS FOR SURGICAL END EFFECTORS AND REPLACEABLE TOOL ASSEMBLIES, now U.S. Patent Application Publication No. 2018/0168644;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Patent Application Publication No. 2018/0168629;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630;

U.S. patent application Ser. No. 15/385,943, entitled SURGICAL STAPLING INSTRUMENTS AND STAPLE-FORMING ANVILS, now U.S. Patent Application Publication No. 2018/0168631;

U.S. patent application Ser. No. 15/385,950, entitled SURGICAL TOOL ASSEMBLIES WITH CLOSURE STROKE REDUCTION FEATURES, now U.S. Patent Application Publication No. 2018/0168635;

U.S. patent application Ser. No. 15/385,945, entitled STAPLE CARTRIDGES AND ARRANGEMENTS OF STAPLES AND STAPLE CAVITIES THEREIN, now U.S. Patent Application Publication No. 2018/0168632;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Patent Application Publication No. 2018/0168636;

U.S. patent application Ser. No. 15/385,953, entitled METHODS OF STAPLING TISSUE, now U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, now U.S. Patent Application Publication No. 2018/0168638;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Patent Application Publication No. 2018/0168640;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, now U.S. Patent Application Publication No. 2018/0168634;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Patent Application Publication No. 2018/0168599;

U.S. patent application Ser. No. 15/385,899, entitled SURGICAL INSTRUMENT COMPRISING IMPROVED JAW CONTROL, now U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602;

U.S. patent application Ser. No. 15/385,902, entitled SURGICAL INSTRUMENT COMPRISING A CUTTING MEMBER, now U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605;

U.S. patent application Ser. No. 15/385,905, entitled FIRING ASSEMBLY COMPRISING A LOCKOUT, now U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Patent Application Publication No. 2018/0168620;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626;

U.S. patent application Ser. No. 15/385,911, entitled SURGICAL STAPLERS WITH INDEPENDENTLY ACTUATABLE CLOSING AND FIRING SYSTEMS, now U.S. Patent Application Publication No. 2018/0168612;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Patent Application Publication No. 2018/0168616;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Patent Application Publication No. 2018/0168622;

U.S. patent application Ser. No. 15/385,924, entitled SURGICAL INSTRUMENT WITH PRIMARY AND SAFETY PROCESSORS, now U.S. Patent Application Publication No. 2018/0168624;

U.S. patent application Ser. No. 15/385,910, entitled ANVIL HAVING A KNIFE SLOT WIDTH, now U.S. Patent Application Publication No. 2018/0168611;

U.S. patent application Ser. No. 15/385,903, entitled CLOSURE MEMBER ARRANGEMENTS FOR SURGICAL INSTRUMENTS, now U.S. Patent Application Publication No. 2018/0168604;

U.S. patent application Ser. No. 15/385,906, entitled FIRING MEMBER PIN CONFIGURATIONS, now U.S. Patent Application Publication No. 2018/0168607;

U.S. patent application Ser. No. 15/386,188, entitled STEPPED STAPLE CARTRIDGE WITH ASYMMETRICAL STAPLES, now U.S. Patent Application Publication No. 2018/0168585;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593;

U.S. patent application Ser. No. 15/385,894, entitled SHAFT ASSEMBLY COMPRISING A LOCKOUT, now U.S. Patent Application Publication No. 2018/0168595;

U.S. patent application Ser. No. 15/385,895, entitled SHAFT ASSEMBLY COMPRISING FIRST AND SECOND ARTICULATION LOCKOUTS, now U.S. Patent Application Publication No. 2018/0168596;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Patent Application Publication No. 2018/0168621;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Patent Application Publication No. 2018/0168576;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Patent Application Publication No. 2018/0168580;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Patent Application Publication No. 2018/0168581;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Patent Application Publication No. 2018/0168582;

U.S. patent application Ser. No. 15/385,936, entitled ARTICULATABLE SURGICAL INSTRUMENTS WITH ARTICULATION STROKE AMPLIFICATION FEATURES, now U.S. Patent Application Publication No. 2018/0168583;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Patent Application Publication No. 2015/0297232;

U.S. patent application Ser. No. 14/318,997, entitled FASTENER CARTRIDGE COMPRISING DEPLOYABLE TISSUE ENGAGING MEMBERS, now U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Patent Application Publication No. 2015/0297235.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Patent Application Publication No. 2017/0367696;

U.S. patent application Ser. No. 15/191,834, entitled STAMPED STAPLES AND STAPLE CARTRIDGES USING THE SAME, now U.S. Patent Application Publication No. 2017/0367699;

U.S. patent application Ser. No. 15/191,788, entitled STAPLE CARTRIDGE COMPRISING OVERDRIVEN STAPLES, now U.S. Patent Application Publication No. 2017/0367698; and U.S. patent application Ser. No. 15/191,818, entitled STAPLE CARTRIDGE COMPRISING OFFSET LONGITUDINAL STAPLE ROWS, now U.S. Patent Application Publication No. 2017/0367697.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER, now U.S. Design Pat. No. D826,405;

U.S. Design patent application Ser. No. 29/569,227, entitled SURGICAL FASTENER, now U.S. Design Pat. No. D822,206;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Pat. No. 10,271,851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No. 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,262, entitled ROTARY POWERED SURGICAL INSTRUMENT WITH MANUALLY ACTUATABLE BAILOUT SYSTEM, now U.S. Patent Application Publication No. 2017/0281161;

U.S. patent application Ser. No. 15/089,277, entitled SURGICAL CUTTING AND STAPLING END EFFECTOR WITH ANVIL CONCENTRIC DRIVE MEMBER, now U.S. Patent Application Publication No. 2017/0281166;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent Application Publication No. 2017/0281186;
U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;
U.S. patent application Ser. No. 15/089,300, entitled SURGICAL STAPLING SYSTEM COMPRISING AN UNCLAMPING LOCKOUT, now U.S. Patent Application Publication No. 2017/0281179;
U.S. patent application Ser. No. 15/089,196, entitled SURGICAL STAPLING SYSTEM COMPRISING A JAW CLOSURE LOCKOUT, now U.S. Patent Application Publication No. 2017/0281183;
U.S. patent application Ser. No. 15/089,203, entitled SURGICAL STAPLING SYSTEM COMPRISING A JAW ATTACHMENT LOCKOUT, now U.S. Patent Application Publication No. 2017/0281184;
U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;
U.S. patent application Ser. No. 15/089,324, entitled SURGICAL INSTRUMENT COMPRISING A SHIFTING MECHANISM, now U.S. Patent Application Publication No. 2017/0281170;
U.S. patent application Ser. No. 15/089,335, entitled SURGICAL STAPLING INSTRUMENT COMPRISING MULTIPLE LOCKOUTS, now U.S. Patent Application Publication No. 2017/0281155;
U.S. patent application Ser. No. 15/089,339, entitled SURGICAL STAPLING INSTRUMENT, now U.S. Patent Application Publication No. 2017/0281173;
U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;
U.S. patent application Ser. No. 15/089,304, entitled SURGICAL STAPLING SYSTEM COMPRISING A GROOVED FORMING POCKET, now U.S. Patent Application Publication No. 2017/0281188;
U.S. patent application Ser. No. 15/089,331, entitled ANVIL MODIFICATION MEMBERS FOR SURGICAL STAPLERS, now U.S. Patent Application Publication No. 2017/0281180;
U.S. patent application Ser. No. 15/089,336, entitled STAPLE CARTRIDGES WITH ATRAUMATIC FEATURES, now U.S. Patent Application Publication No. 2017/0281164;
U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;
U.S. patent application Ser. No. 15/089,309, entitled CIRCULAR STAPLING SYSTEM COMPRISING ROTARY FIRING SYSTEM, now U.S. Patent Application Publication No. 2017/0281169; and
U.S. patent application Ser. No. 15/089,349, entitled CIRCULAR STAPLING SYSTEM COMPRISING LOAD CONTROL, now U.S. Patent Application Publication No. 2017/0281174.

Applicant of the present application also owns the U.S. Patent Applications identified below which were filed on Dec. 30, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Patent Application Publication No. 2017/0189018;
U.S. patent application Ser. No. 14/984,525, entitled MECHANISMS FOR COMPENSATING FOR DRIVETRAIN FAILURE IN POWERED SURGICAL INSTRUMENTS, now U.S. Patent Application Publication No. 2017/0189019; and
U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016, which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;
U.S. patent application Ser. No. 15/019,228, entitled SURGICAL INSTRUMENTS WITH MULTIPLE LINK ARTICULATION ARRANGEMENTS, now U.S. Patent Application Publication No. 2017/0224342;
U.S. patent application Ser. No. 15/019,196, entitled SURGICAL INSTRUMENT ARTICULATION MECHANISM WITH SLOTTED SECONDARY CONSTRAINT, now U.S. Patent Application Publication No. 2017/0224330;
U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Patent Application Publication No. 2017/0224331;
U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;
U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;
U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;
U.S. patent application Ser. No. 15/019,230, entitled ARTICULATABLE SURGICAL INSTRUMENTS WITH OFF-AXIS FIRING BEAM ARRANGEMENTS, now U.S. Patent Application Publication No. 2017/0224335; and
U.S. patent application Ser. No. 15/019,245, entitled SURGICAL INSTRUMENTS WITH CLOSURE STROKE REDUCTION ARRANGEMENTS, now U.S. Patent Application Publication No. 2017/0224343.

Applicant of the present application also owns the U.S. Patent Applications identified below which were filed on Feb. 12, 2016, which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Patent Application Publication No. 2017/0231626;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841;

U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 1:
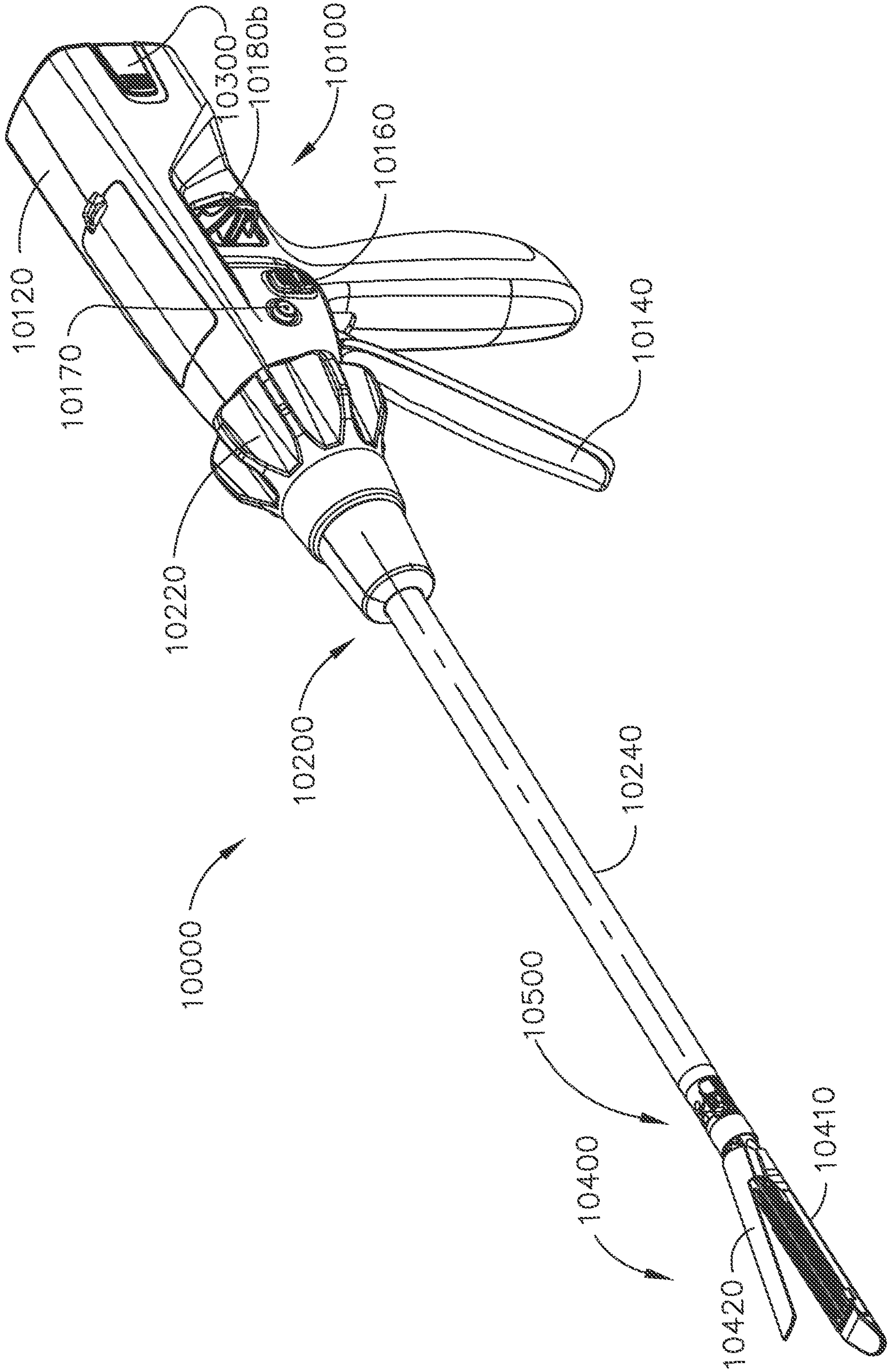
FIG. 1 is a perspective view of a surgical instrument in accordance with at least one embodiment.
Figure 1B:
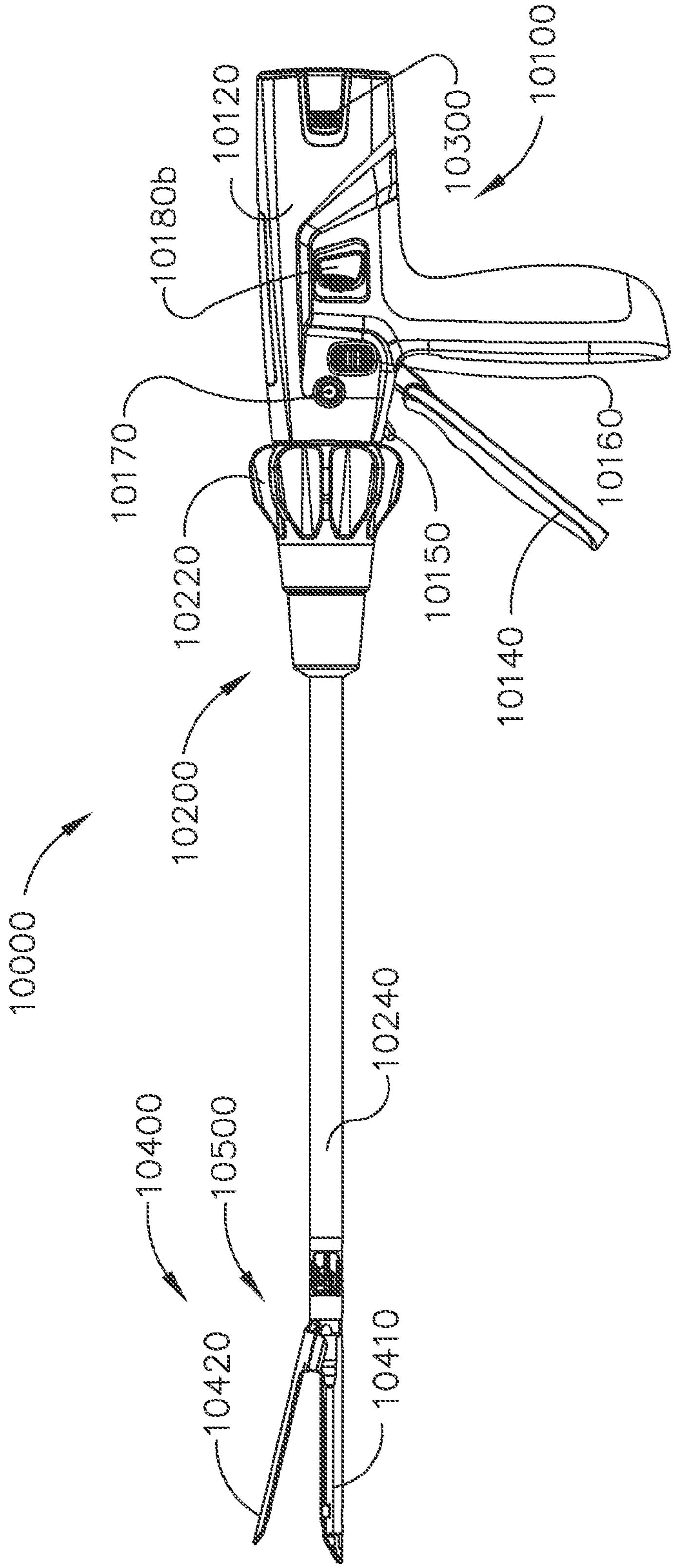
FIG. 1B is a left side elevation view of the surgical instrument of FIG. 1.
Figure 1C:
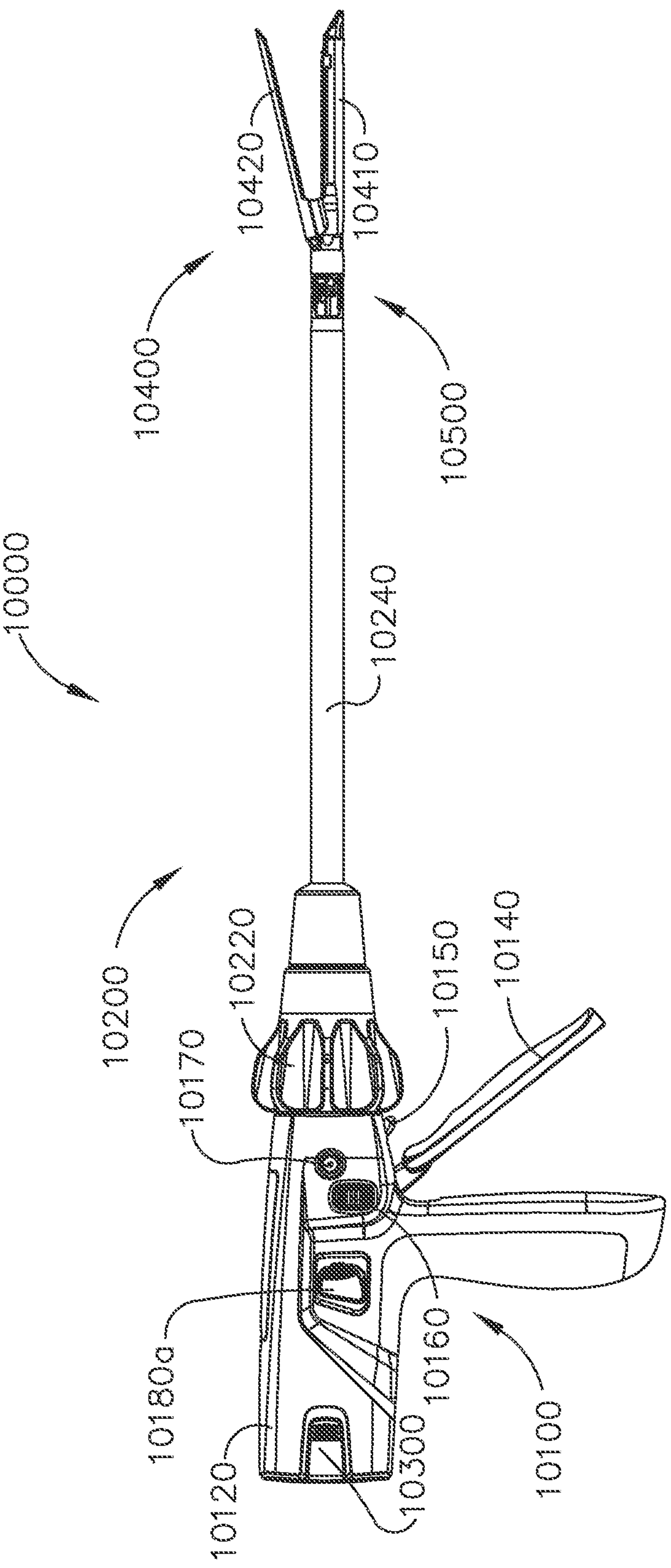
FIG. 1C is a right side elevation view of the surgical instrument of FIG. 1.
Figure 1D:
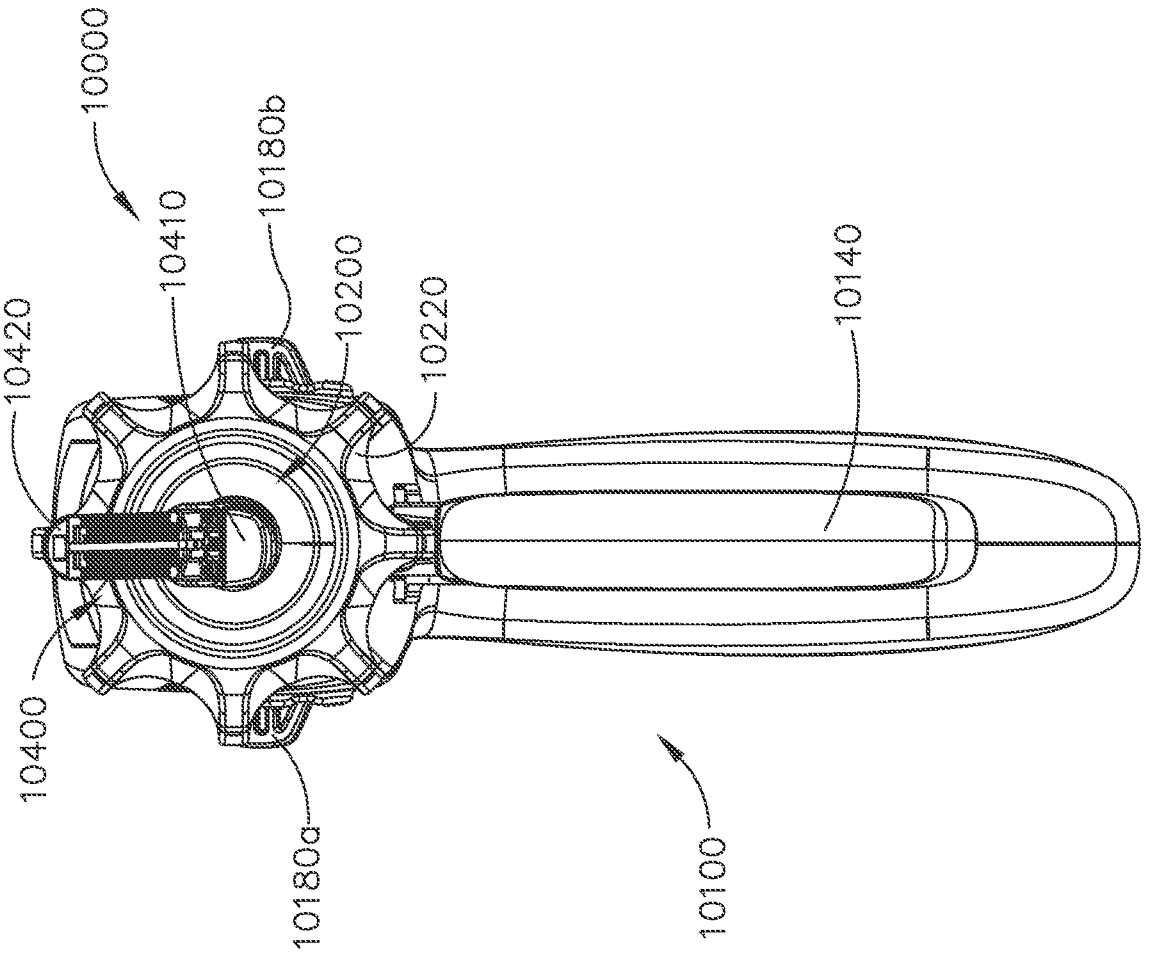
FIG. 1D is a front elevation view of the surgical instrument of FIG. 1.
Figure 1E:
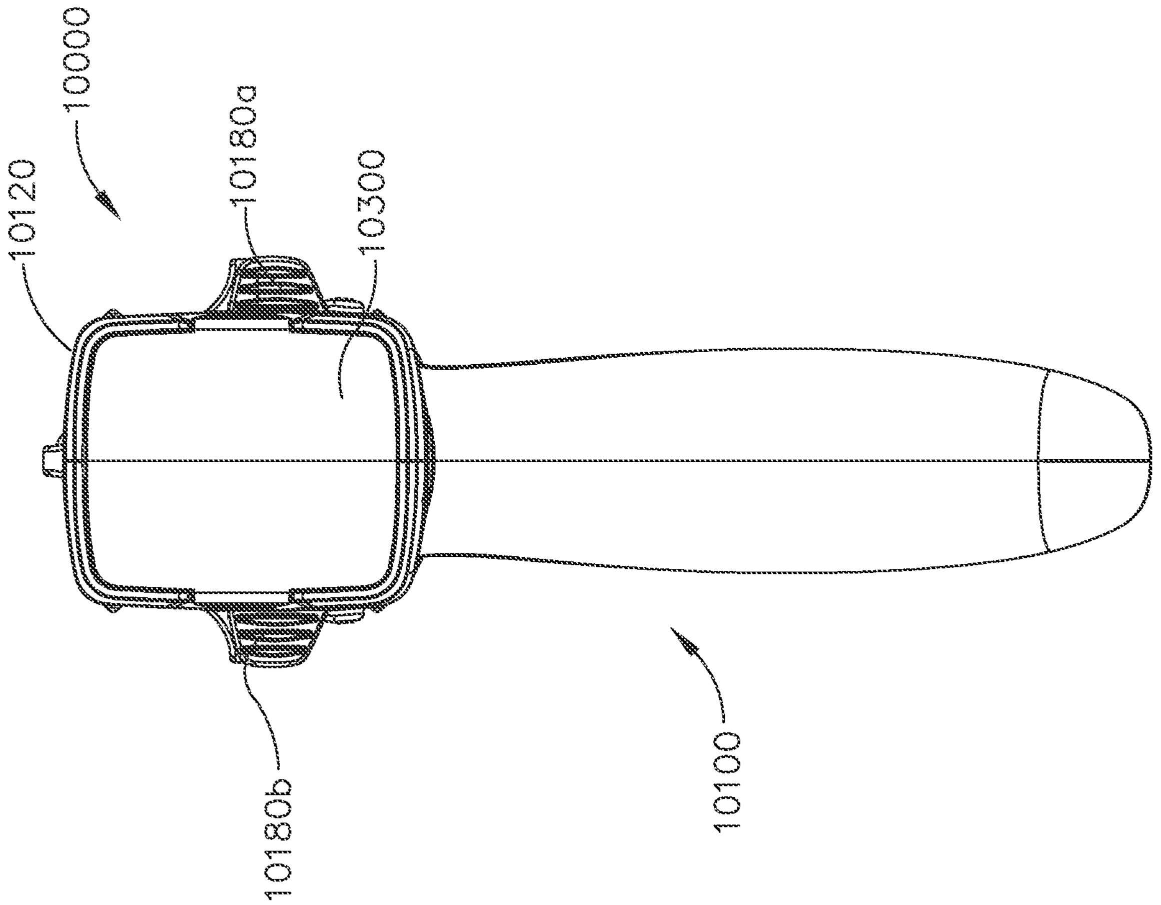
FIG. 1E is a back elevation view of the surgical instrument of FIG. 1.
Figure 1F:
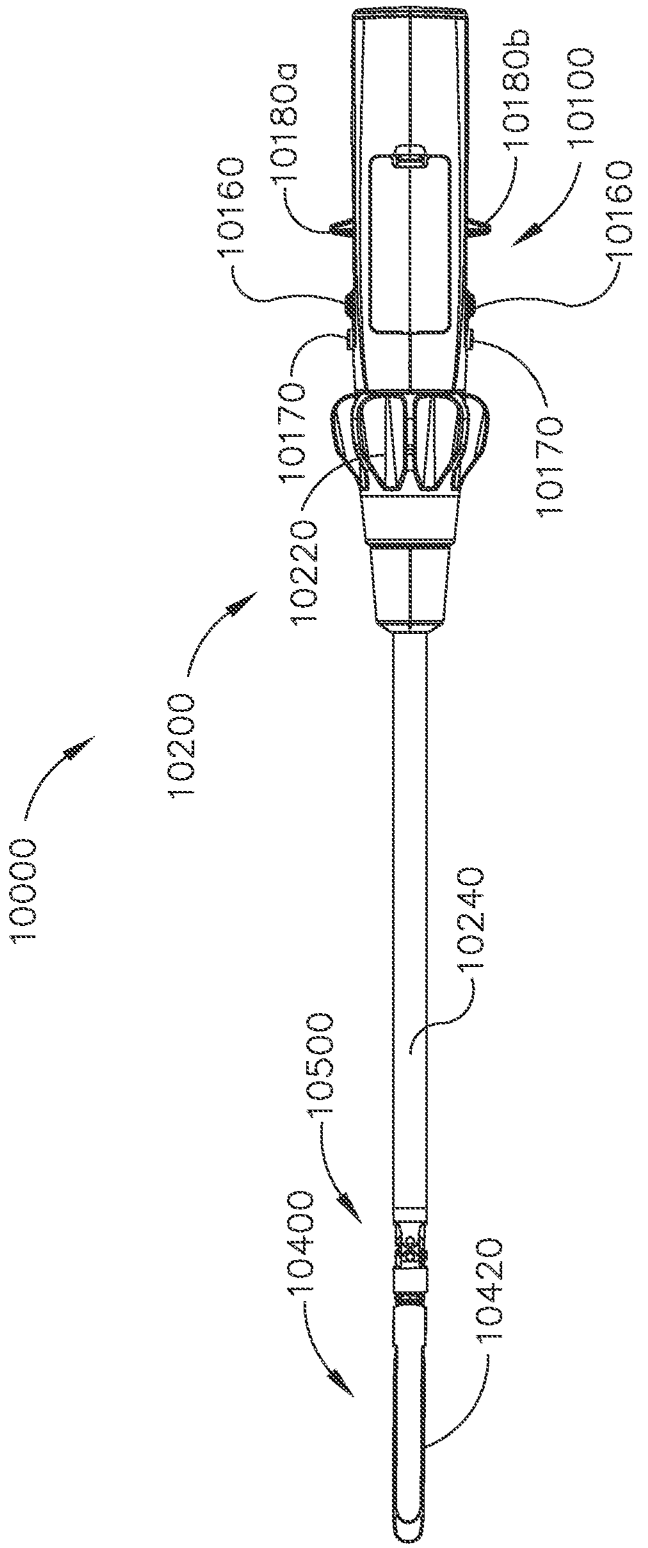
FIG. 1F is a plan view of the surgical instrument of FIG. 1.
Figure 1G:
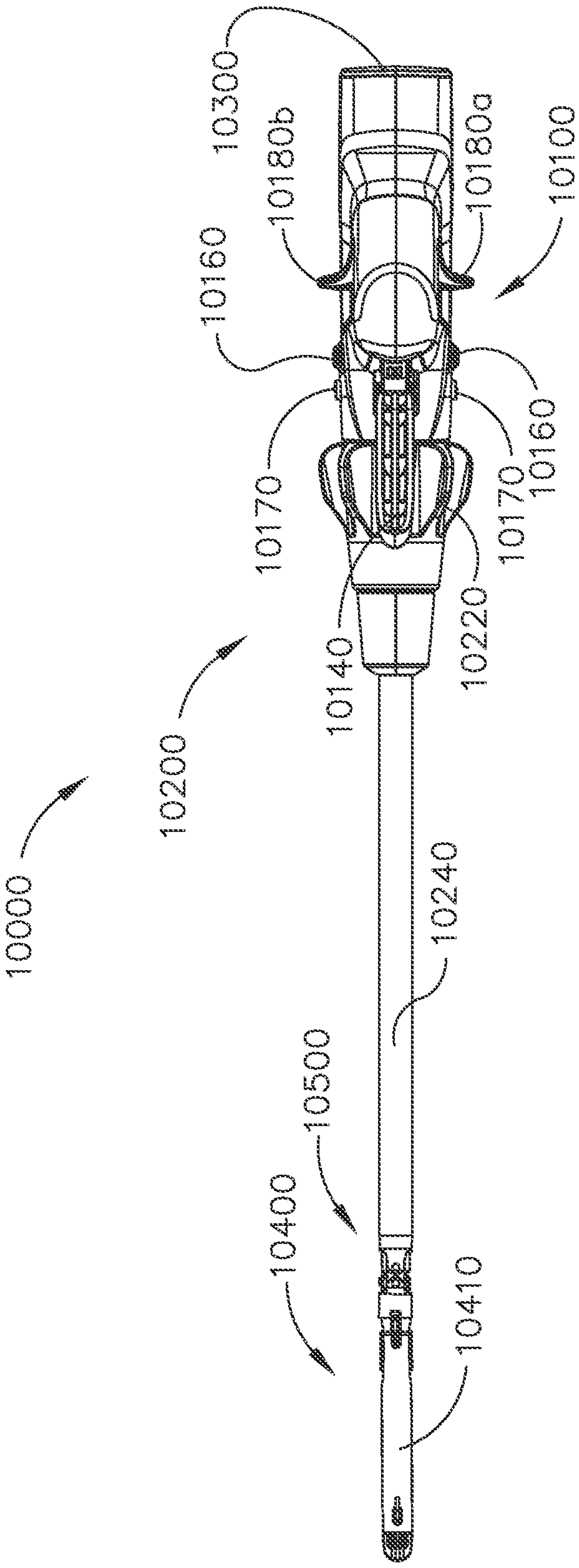
FIG. 1G is a bottom view of the surgical instrument of FIG. 1.
Figure 3:
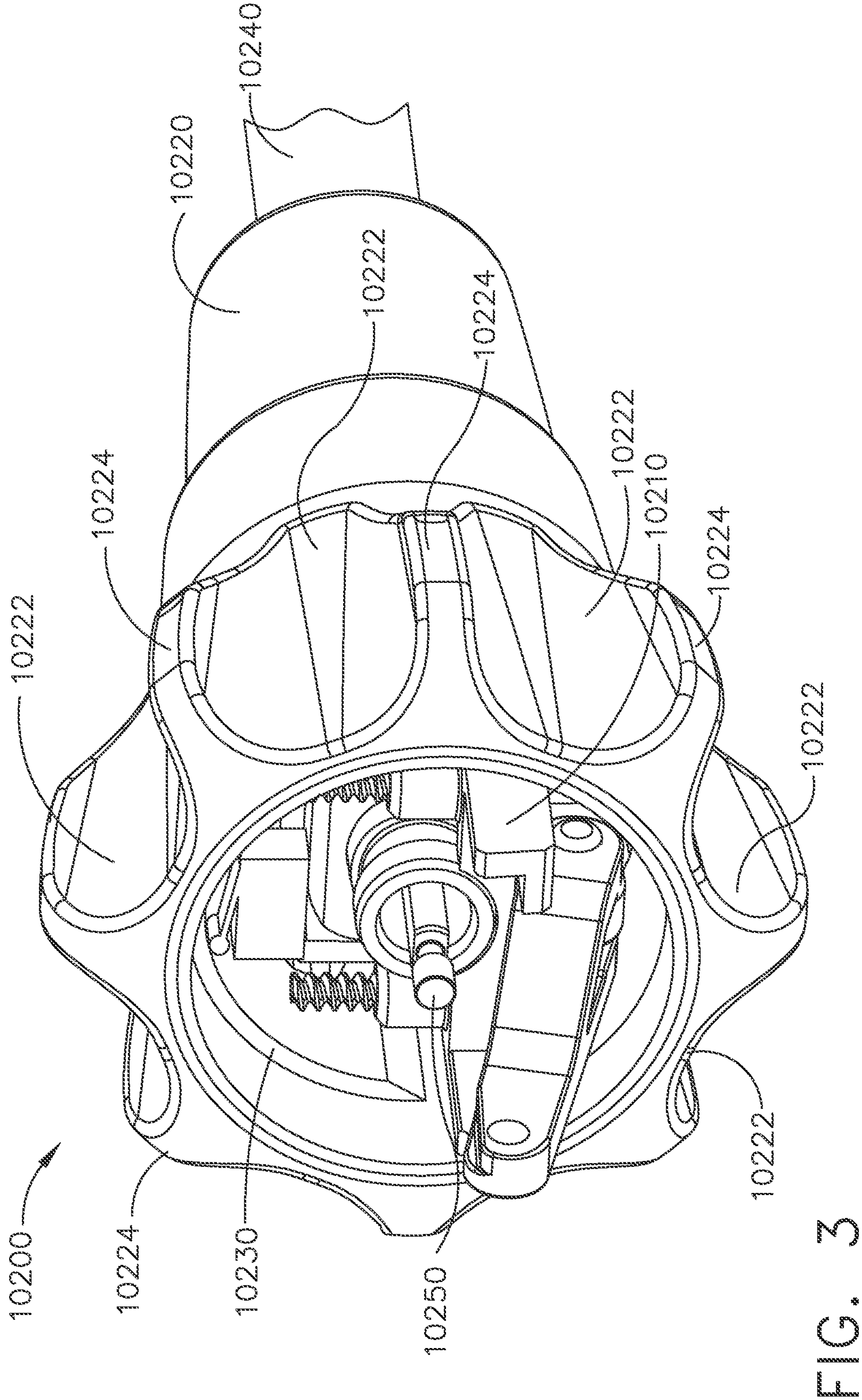
FIG. 3 is a partial perspective view of a shaft of the surgical instrument of FIG. 1.
Figure 4:
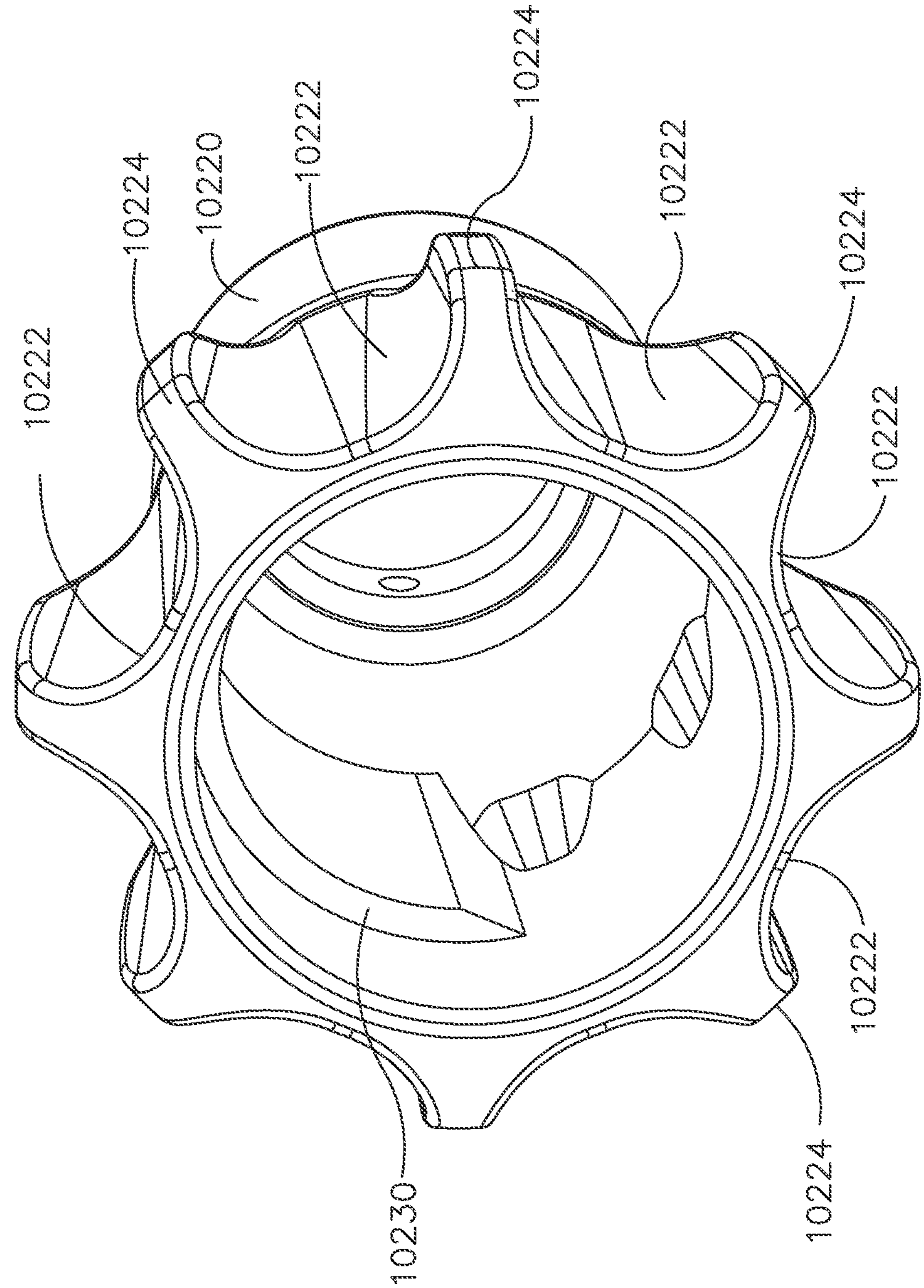
FIG. 4 is a perspective view of a nozzle of the shaft of FIG. 3.
Figure 5:
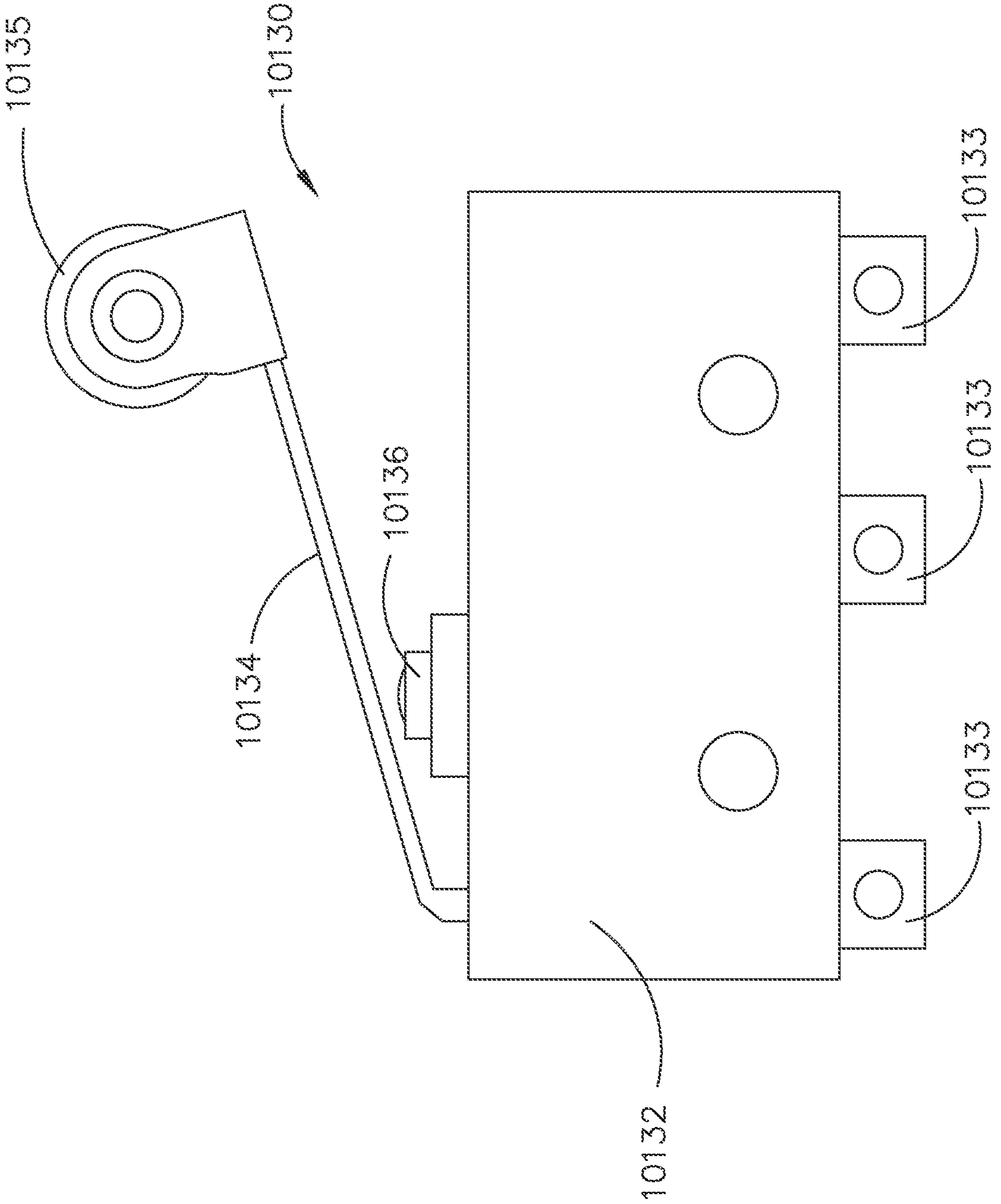
FIG. 5 is an elevational view of an orientation switch of the surgical instrument of FIG. 1.

A surgical instrument 10000 is illustrated in FIG. 1. The surgical instrument 10000 comprises a handle 10100, a shaft 10200 extending from the handle 10100, and an end effector 10400. The end effector 10400 comprises a first jaw 10410 configured to receive a staple cartridge and a second jaw 10420 movable relative to the first jaw 10410. The second jaw 10420 comprises an anvil including staple forming pockets defined therein. The surgical instrument 10000 further comprises a closure actuator 10140 configured to drive a closure system of the surgical instrument 10000 and move the second jaw 10420 between an unclamped position and a clamped position. Referring to FIG. 3, the closure actuator 10140 is operably coupled with a closure tube 10240 that is advanced distally when the closure actuator 10140 is closed. In such instances, the closure tube 10240 contacts the second jaw and cams and/or pushes the second jaw 10420 downwardly into its clamped position. The second jaw 10420 is pivotably coupled to the first jaw about a pivot axis. That said, in alternative embodiments, the second jaw can translate and rotate as it is being moved into its clamped position. Moreover, in various alternative embodiments, a surgical instrument comprises a staple cartridge jaw is movable between an unclamped position and a clamped position relative to an anvil jaw. In any event, the handle 10100 comprises a lock configured to releasably hold the closure actuator 10140 in its clamped position. The handle 10100 further comprises release actuators 10180*a*, 10180*b* which, when either one is actuated, unlock the closure actuator 10140 such that the end effector can be re-opened. In various alternative embodiments, the handle

10100 comprises an electric motor configured to move the closure tube 10240 proximally and/or distally when actuated by the clinician.

The end effector 10400 is attached to the shaft 10200 about an articulation joint 10500 and is rotatable within a plane about an articulation axis. The shaft 10200 defines a longitudinal axis and the end effector 10400 is articulatable between a position in which the end effector 10400 is aligned with the longitudinal axis and positions in which the end effector 10400 extends at a transverse angle relative to the longitudinal axis. The handle 10100 comprises an electric motor and a control system configured to control the operation of the electric motor. The electric motor comprises a brushless DC motor; however, the electric motor can comprise any suitable motor, such as a brushed DC motor, for example. The entire disclosure of U.S. Pat. No. 10,149,683, entitled POWERED SURGICAL CUTTING AND STAPLING APPARATUS WITH MANUALLY RETRACTABLE FIRING SYSTEM, which issued on Dec. 11, 2018, is incorporated by reference herein. The entire disclosure of U.S. Patent Application Publication No. 2018/0125481, entitled MOTOR-DRIVEN SURGICAL CUTTING INSTRUMENT, which published on May 10, 2018, is incorporated by reference herein. The handle 10100 further comprises a replaceable and/or rechargeable battery 10300 attachable to the handle housing which powers the surgical instrument 10000. The entire disclosure of U.S. Pat. No. 8,632,525, entitled POWER CONTROL ARRANGEMENTS FOR SURGICAL INSTRUMENTS AND BATTERIES, which issued on Jan. 21, 2014, is incorporated by reference herein. The electric motor is operably coupled with a firing drive 10250 of the surgical instrument 10000 and is configured to drive a firing member of the firing drive 10250 through a staple firing stroke. The electric motor comprises a rotatable output including a gear engaged with a translatable rack of the firing drive 10250. The electric motor is operated in a first direction to drive the firing member through the staple firing stroke and a second, or opposite, direction to retract the firing member and/or reset the firing drive 10250. The surgical instrument 10000 further comprises an actuator 10150 in communication with the motor control system which, when actuated or rotated, signals to the motor control system to operate the electric motor in the first direction and begin the staple firing stroke. If the actuator 10150 is released, the motor control system stops the electric motor. When the actuator 10150 is re-actuated, the motor control system operates the electric motor in the first direction once again to continue the staple firing stroke. When the firing member reaches the end of the staple firing stroke, the control system stops the electric motor awaiting input from the clinician. When the clinician releases the actuator 10150 at such point, the control system reverses the operation of the electric motor to retract the firing member back into its unfired position. The handle 10100 further comprises a retraction actuator in communication with the motor control system that reverses the direction of the electric motor to retract the firing drive when actuated by the clinician. When the retraction actuator is depressed, the staple firing stroke is terminated regardless of whether the firing member had reached the end of the staple firing stroke.

The electric motor of the surgical instrument 10000 is also used to selectively drive an articulation drive system to articulate the end effector 10400. More specifically, the articulation drive system comprises an articulation driver that is selectively engageable with the firing drive and, when the articulation driver is engaged with the firing drive, the articulation driver is movable proximally and distally by the operation of the electric motor to articulate the end effector 10400. When the electric motor is operated in its first direction, in such instances, the end effector 10400 is articulated in a first direction to push the articulation driver distally. Similarly, the end effector 10400 is articulated in a second direction when the electric motor is operated in its second direction to pull the articulation driver proximally. When the articulation driver is not engaged with the firing drive, the operation of the electric motor does not articulate the end effector 10400. Instead, in such instances, the electric motor only moves the firing drive. That said, it should be appreciated that the movement of the firing drive to articulate the end effector 10400 does not cause the staple firing stroke to be performed. The range of motion needed to articulate the end effector 10400 is small, as compared to the range of motion of the staple firing stroke, and occurs proximal to the beginning of the staple firing stroke such that the staples are not ejected and the tissue is not cut while the end effector 10400 is being articulated. The surgical instrument 10000 further comprises an articulation lock which unlocks when the articulation driver is moved longitudinally by the firing drive and then locks the end effector 10400 in position when the articulation driver is not being driven by the firing drive. The entire disclosure of U.S. Pat. No. 9,629,629, entitled CONTROL SYSTEMS FOR SURGICAL INSTRUMENTS, which issued on Apr. 25, 2017, is incorporated by reference herein. The above being said, a surgical instrument can comprise a separate articulation motor in addition to the firing motor for driving the articulation drive system.

Figure 2:
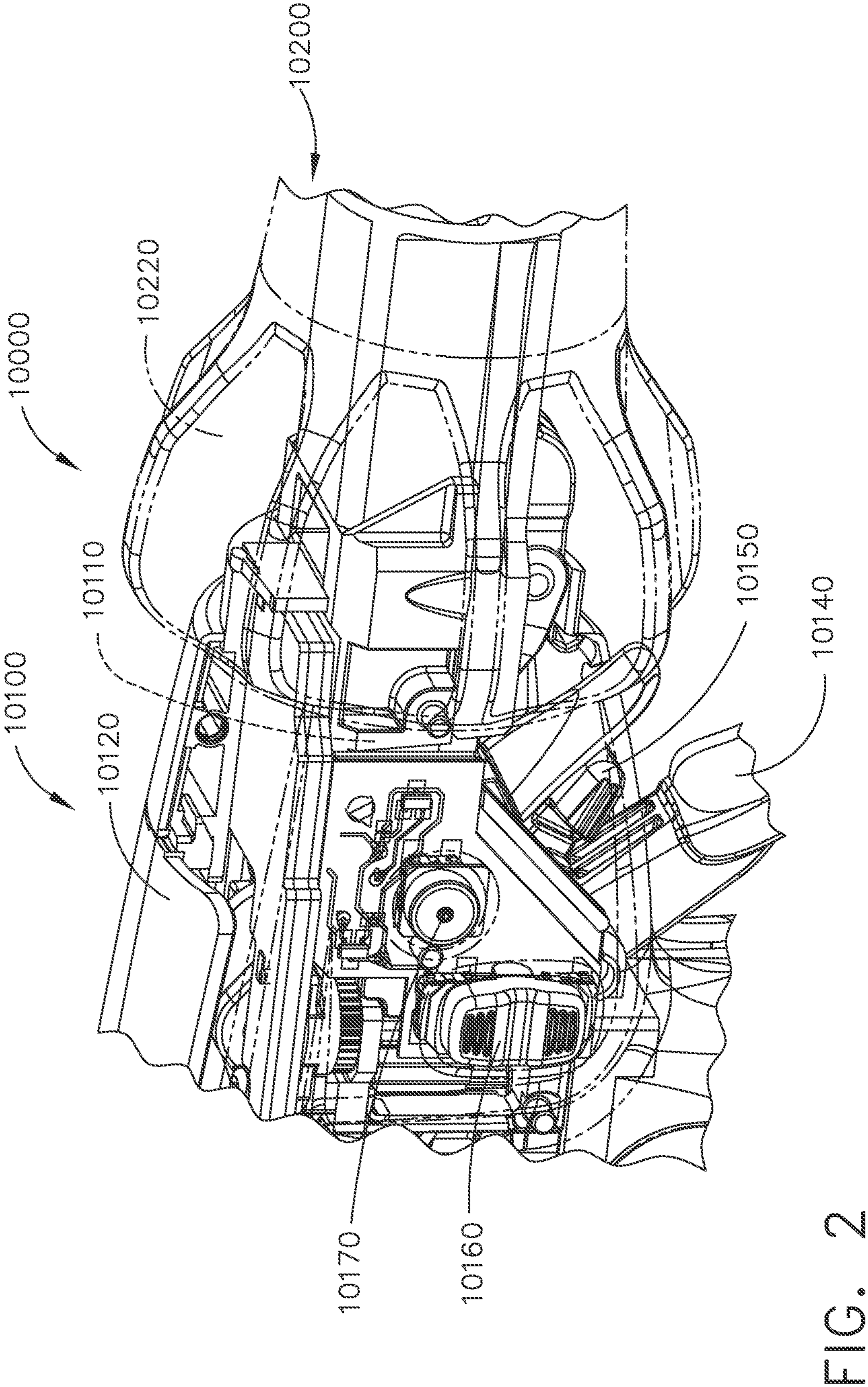
FIG. 2 is a partial perspective view of the surgical instrument of FIG. 1.

Further to the above, referring to FIG. 2, the handle 10100 comprises a frame 10110, a housing 10120, and an articulation actuator 10160. The articulation actuator 10160 comprises a rocker switch, for example, which is oriented vertically on the housing 10120 and is in communication with the motor control system. The rocker switch is rotatable upwardly and downwardly about an axis to articulate the end effector 10400. The upper portion of the articulation actuator 10160 is pushed by the clinician to articulate the end effector 10400 to the left and the lower portion of the articulation actuator 10160 is pushed to articulate the end effector 10400 to the right. Such an arrangement provides an intuitive interface for the clinician; however, any suitable arrangement could be used. The handle 10100 further comprises a home actuator 10170 in communication with the motor control system. When the home actuator 10170 is actuated by the clinician, the motor control system operates the electric motor to re-center the end effector 10400 along the longitudinal axis of the shaft 10200 of the surgical instrument 10000. To this end, the control system is configured to track the position of the end effector such that, when the home actuator 10170 is actuated, the control system operates the electric motor in the correct direction to articulate the end effector 10400 in the correct direction and the correct amount. In various instances, the surgical instrument 10000 comprises a linear encoder configured to track the position of the articulation driver, for example, such that, when the home actuator 10170 is actuated, the control system can properly center the end effector 10400.

Further to the above, the shaft 10200 is rotatable relative to the handle 10100. The shaft 10200 comprises a frame 10210 attached to the frame 10110 of the handle 10100. In embodiments where the shaft 10200 is readily removable from the handle 10100, the shaft frame 10210 can detach from the handle frame 10110. In embodiments where the shaft 10200 is not removable from the handle 10100, the shaft frame 10210 and the handle frame 10110 can be integrally formed. In any event, the shaft 10200 comprises a nozzle, or grip, 10220 fixedly mounted to the closure tube 10240 of the shaft 10200. The grip 10220 comprises finger grooves 10222 defined therein and ridges 10224 extending between the finger grooves 10222 that provide walls against which a clinician can push their finger and assist the clinician in rotating the shaft 10200 about its longitudinal axis.

Notably, further to the above, the end effector 10400 rotates with the shaft 10200 when the shaft 10200 is rotated about its longitudinal axis. Thus, the end effector 10400 rotates clockwise when the shaft 10200 is rotated clockwise by the clinician and counter-clockwise when the shaft 10200 is rotated counter-clockwise by the clinician. In various alternative embodiments, the surgical instrument 10000 comprises an electric motor configured to rotate the shaft 10200 about its longitudinal axis. In either event, the shaft 10200 is rotatable from a top-dead-center (TDC) position in which the anvil 10420 is positioned directly above the staple cartridge jaw 10410 to any other suitable position within a full 360 degree range of positions. For instance, the shaft 10200 is rotatable into a right 90 degree position in which the anvil 10420 is facing to the right of the handle 10100 or a left 90 degree position in which the anvil 10420 is facing to the left of the handle 10100. The shaft 10200 is also rotatable into a bottom-dead-center (BDC) position in which the staple cartridge jaw 10410 is positioned directly above the anvil 10420.

As described above, the end effector 10400 is both articulatable about the articulation joint 10500 and rotatable with the shaft 10200. When the end effector 10400 is rotated in a plane when the end effector 10400 is in its TDC position, as mentioned above, the articulation control 10160 is intuitive to the user—push up to articulate left and push down to articulate right. This arrangement is also intuitive even after the shaft 10200—and end effector 10400—have been rotated 90 degrees to the right or to the left. However, when the shaft 10200 and end effector 10400 have been rotated past 90 degrees in either direction, the articulation control 10160 can become counter-intuitive to the clinician. In fact, the articulation control 10160 can seem backwards. With this in mind, the control system of the surgical instrument 10000 is configured to flip the manner in which the surgical instrument responds to the articulation control 10160 when the shaft 10200 and end effector 10400 have been rotated past 90 degrees in either direction. In such instances, the controls become: push up to articulate right and push down to articulate left. To this end, as described in greater detail below, the surgical instrument 10000 is configured to detect the orientation of the shaft 10200 relative to the handle 10100, i.e., it is configured to detect whether the end effector 10400 is at least partially upside down with respect to the handle 10100 and then enter an alternative operational control mode in which the responsiveness of the surgical instrument 10000 to the articulation control 10160 has been reversed. Such an arrangement can make the surgical instrument 10000 easier to use in various instances.

Referring to FIGS. 2-5, the surgical instrument 10000 comprises a switch 10130 mounted to the handle 10100 in communication with the control system which is configured to detect the rotation of the shaft 10200 relative to the handle 10100. The switch 10130 comprises a switch body 10132 fixedly mounted to the handle frame 10110 and three electrical contacts 10133 which are part of a switch circuit in communication with the control system. The switch 10000 further comprises a switch arm 10134 rotatably connected to the switch body 10132 and an electrical contact 10136 positioned on the switch body 10132. The switch arm 10134 is comprised of an electrically-conductive material, such as brass, for example, and closes the switch circuit when the switch arm 10134 comes into contact with the electrical contact 10136. The switch arm 10134 is rotated between an open position (FIG. 5) and a closed position when the shaft 10200 is rotated past the left or right 90 degree positions. More specifically, the grip, or nozzle, 10220 comprises a cam 10230 defined thereon which pushes the switch arm 10134 into its closed position when the shaft 10200 and the end effector 10400 is at least partially upside down. When the shaft 10200 is rotated upwardly past the 90 degree positions, the cam 10230 permits the switch arm 10134 to resiliently move back into its open position and open the switch circuit. The switch arm 10134 comprises a roller 10135 mounted thereto to facilitate relative rotation between the switch arm 10134 and the grip 10220.

Figure 6:
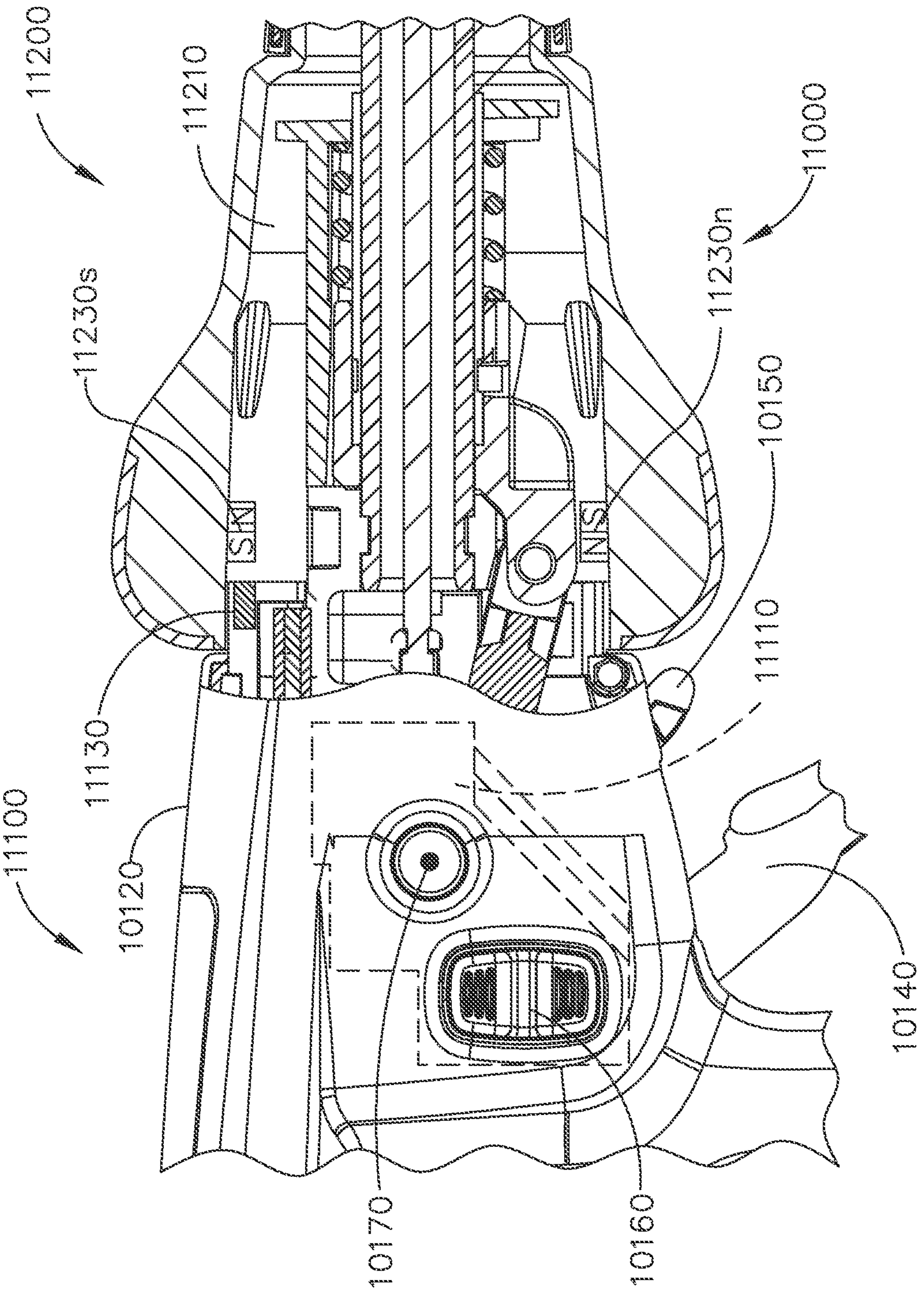
FIG. 6 is a partial perspective view of a surgical instrument in accordance with at least one embodiment comprising a handle including an orientation sensor and a shaft comprising magnetic elements detectable by the orientation sensor.

A surgical instrument 11000 is illustrated in FIG. 6. The surgical instrument 11000 is similar to the surgical instrument 10000 in many respects. The surgical instrument 11000 comprises a handle 11100 and a shaft 11200 extending from the handle 11100. The handle 11100 comprises a frame 11110 and the shaft 11200 comprises a frame 11210 attached to the handle frame 11110. The shaft 11200 comprises a grip, or nozzle, 11220, a first magnetic element **11230*s* positioned on one side of the grip 11220, and a second magnetic element 11230*n* positioned on the opposite side of the grip 11220. Stated another way, the first magnetic element 11230*s* and the second magnetic element 11230*n* are mounted 180 degrees apart. The handle 11100 further comprises a control system including at least one sensor 11130, such as a Hall Effect sensor, for example, mounted to the handle frame 11110 configured to sense the position of the magnetic elements 11230*s* and 11230*n* and, with this information, determine the orientation of the shaft 11200 relative to the handle 11100. Notably, the first magnetic element 11230*s* comprises a permanent magnet with a south pole facing toward the handle 11100 and a north pole facing away from the handle 11100 and the second magnetic element 11230*n* comprises a permanent magnet with a north pole facing toward the handle 11100 and a south pole facing away from the handle 11100. The magnetic elements 11230*s* and 11230*n* disturb the magnetic field emitted by the Hall Effect sensor and, when the shaft 11200 is at least partially upside down, the disturbance associated with such an orientation of the shaft 11200 is detected by the control system of the surgical instrument 11000 via a sensing circuit including the sensor 11130. In such instances, similar to the above, the control system enters into its second operating mode which flips the responsiveness of the surgical instrument 11000 to the articulation control 10160**, as described above.

Figure 8:
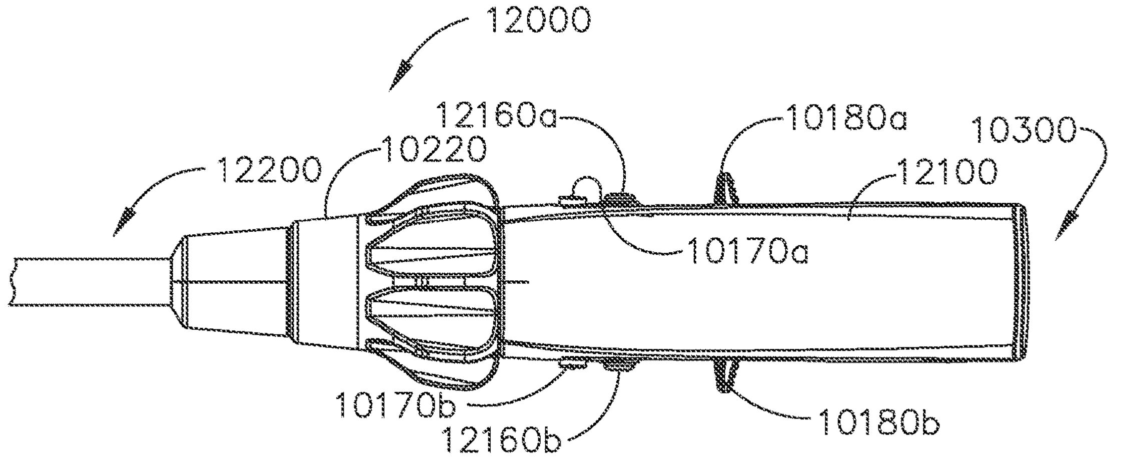
FIG. 8 is a partial plan view of the surgical instrument of FIG. 7.
Figure 7:
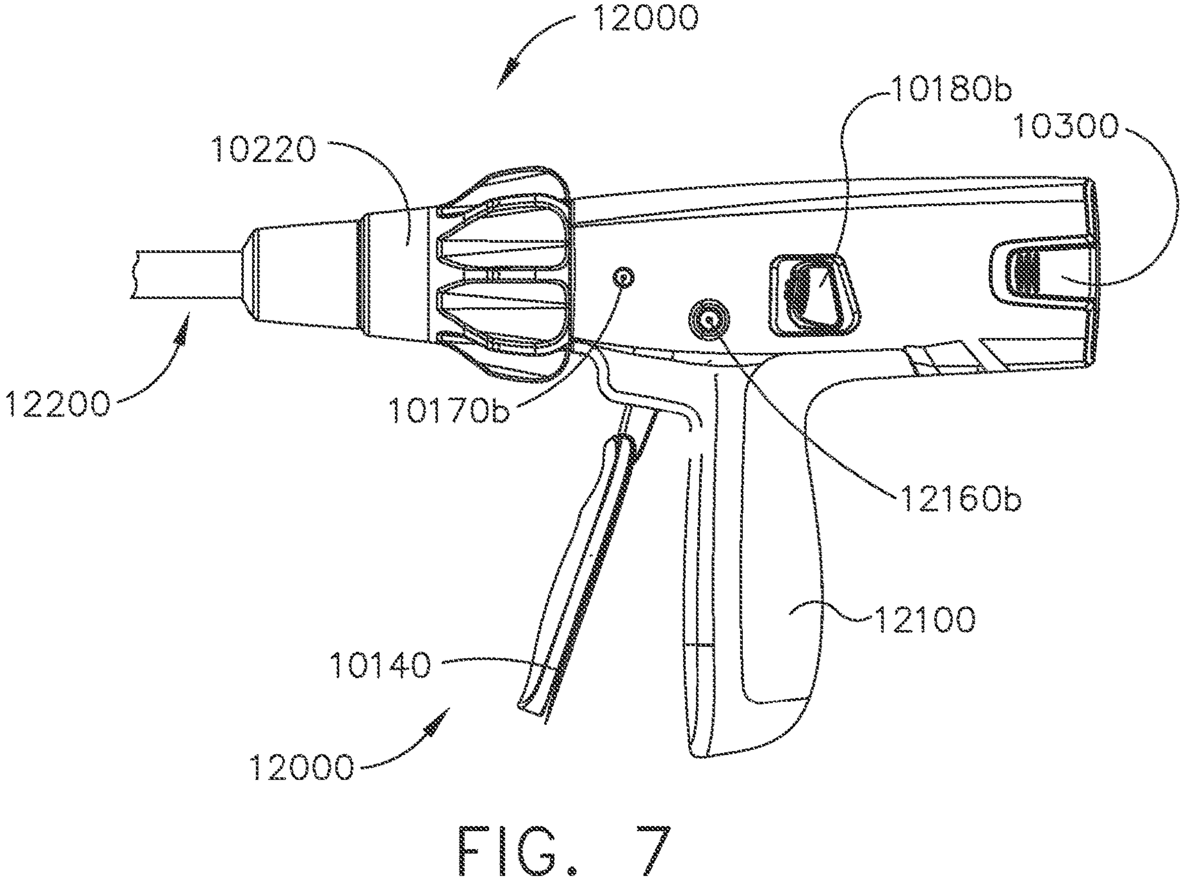
FIG. 7 is a partial elevational view of a surgical instrument in accordance with at least one embodiment comprising a handle and articulation actuators on opposing sides of the handle.

A surgical instrument 12000 is illustrated in FIGS. 7 and 8. The surgical instrument 12000 is similar to the surgical instrument 10000 in many respects. The surgical instrument 12000 comprises a handle 12100 and a shaft 12200 extending from the handle 12100. The handle 12100 comprises a housing, a first articulation control **12160*a* positioned on a first side of the handle housing, and a second articulation control 12160*b* positioned on a second, or opposite, side of the handle housing. The first articulation control 12160*a* is in communication with the control system of the surgical instrument 12000 via a first control circuit and the second articulation control 12160*b* is in communication with the control system via a second control circuit. The control system is configured to operate the electric motor of the staple firing drive in a first direction to articulate the end effector of the shaft 12200 in a first direction when the first articulation control 12160***a* is actuated and a second, or opposite, direction to articulate the end effector in a second, or opposite, direction with the second articulate control 12160*b* is actuated. The handle 12100 further comprises a centering, or home, actuator 10170*a* positioned on the first side of the handle 12100 and a second centering, or home, actuator 10170*b* on the second side of the handle 12100. Similar to the above, the actuators 10170*a* and 10170*b* are in communication with the control system which is configured such that the actuation of either centering actuator 10170*a* or 10170*b* causes the control system to operate the electric motor to re-center the end effector.

Figure 9:
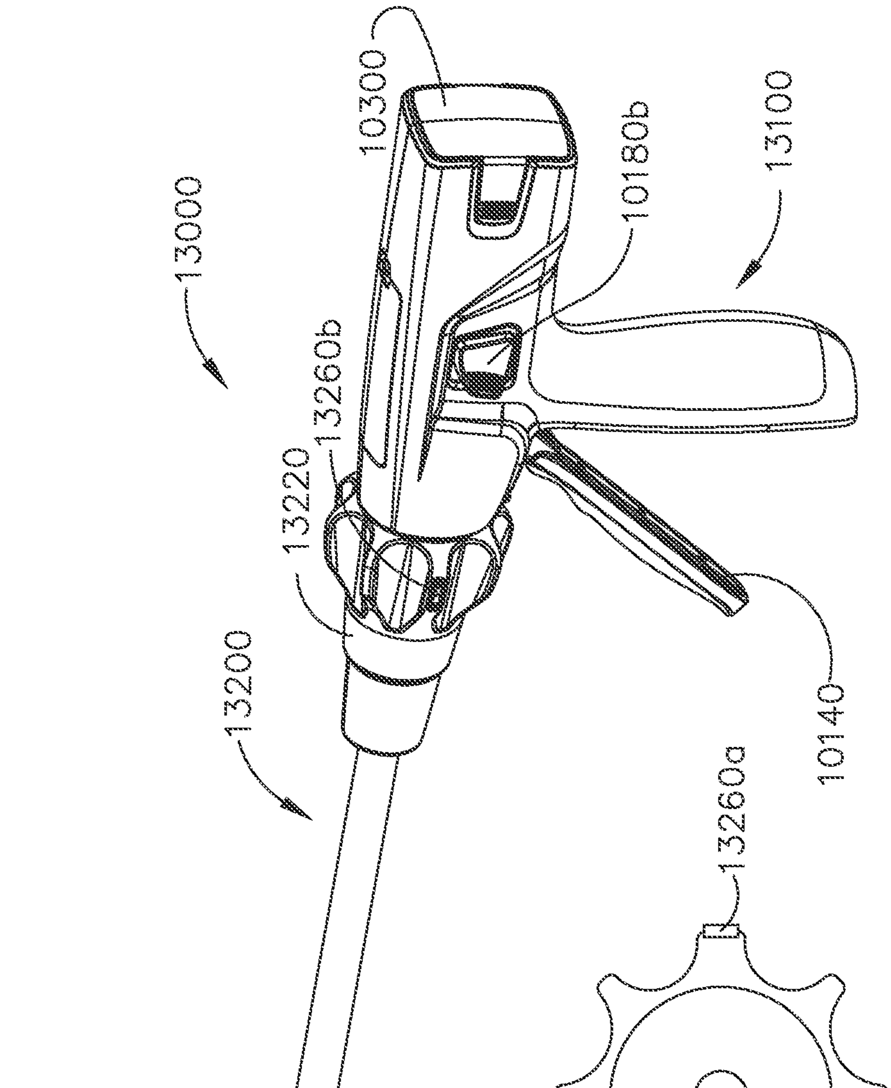
FIG. 9 is a perspective view of a surgical instrument in accordance with at least one embodiment comprising a handle and a rotatable shaft including articulation actuators on opposing sides of the shaft.
Figure 10:
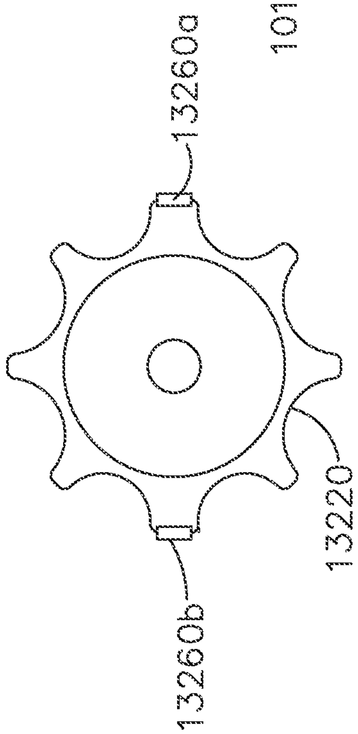
FIG. 10 is an end view of the shaft of FIG. 9.

A surgical instrument 13000 is illustrated in FIGS. 9 and 10. The surgical instrument 13000 is similar to the surgical instrument 10000 in many respects. The surgical instrument 13000 comprises a handle 13100 and a shaft 13200 extending from the handle 13100. The shaft 13200 comprises a housing, a first articulation control 13260*a* positioned on a first side of the shaft housing, and a second articulation control 13260*b* positioned on a second, or opposite, side of the shaft housing. The first articulation control 13260*a* is in communication with the control system of the surgical instrument 13000 via a first control circuit and the second articulation control 13260*b* is in communication with the control system via a second control circuit. The control system is configured to operate the electric motor of the staple firing drive in a first direction to articulate the end effector 10400 of the shaft 13200 in a first direction when the first articulation control 13260*a* is actuated and a second, or opposite, direction to articulate the end effector 10400 in a second, or opposite, direction when the second articulation control 13260*b* is actuated. Stated another way, the end effector 10400 articulates in the direction of the articulation control that is actuated. The first articulation control 13260*a* is positioned on a first finger ridge defined on a grip, or nozzle, 13220 of the shaft 13200 and the second articulation control 13260*b* is positioned on a second finger ridge defined on the grip 13220. Notably, the articulation controls 13260*a* and 13260*b* are positioned 180 degrees apart. Alternatively, the articulation controls 13260*a* and 13260*b* can be positioned in the finger grooves defined in the grip 13220, although any suitable arrangement could be used. This arrangement provides an advantage of having the articulation controls in a position which is readily accessible by the hand of the clinician during use and, as a result, they are usable in an intuitive manner as the relative arrangement of the articulation controls 13260*a* and 13260*b* and the articulation directions are fixed.

Figure 11:
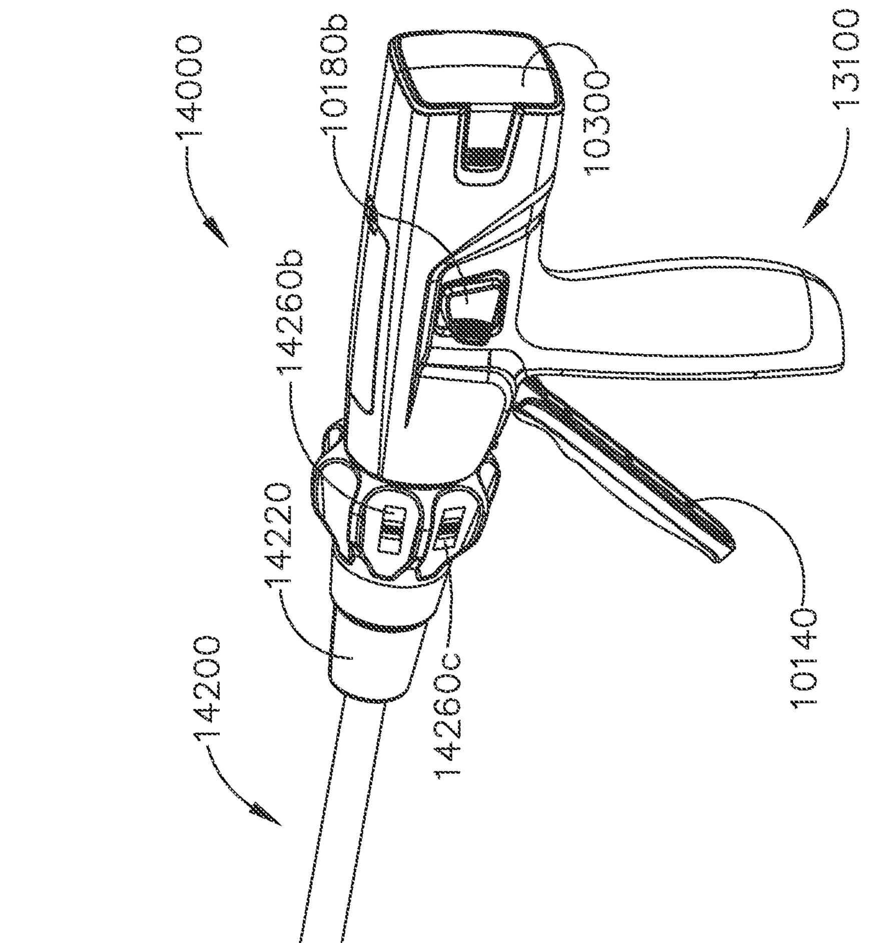
FIG. 11 is a perspective view of a surgical instrument in accordance with at least one embodiment comprising a handle and a rotatable shaft including two articulation actuators on opposing sides of the shaft.
Figure 12:
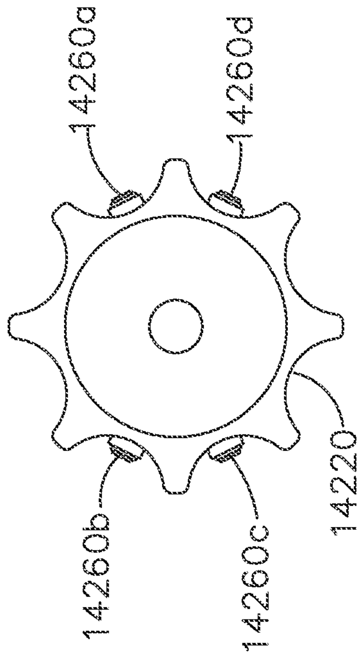
FIG. 12 is an end view of the shaft of FIG. 11.

A surgical instrument 14000 is illustrated in FIGS. 11 and 12. The surgical instrument 14000 is similar to the surgical instrument 13000 in many respects. The surgical instrument 14000 comprises a handle 13100 and a shaft 14200 extending from the handle 13100. The shaft 14200 comprises a housing, a first articulation control 14260*a* positioned on a first side of the shaft housing, and a second articulation control 14260*b* positioned on a second side of the shaft housing. The first articulation control 14260*a* is in communication with the control system of the surgical instrument 14000 via a first control circuit and the second articulation control 14260*b* is in communication with the control system via a second control circuit. The control system is configured to operate the electric motor of the staple firing drive in a first direction to articulate the end effector 10400 of the shaft 14200 in a first direction when the first articulation control 14260*a* is actuated and a second, or opposite, direction to articulate the end effector 10400 in a second, or opposite, direction when the second articulation control 14260*b* is actuated. The first articulation control 14260*a* is positioned in a first finger groove defined in a grip, or nozzle, 14220 of the shaft 14200 and the second articulation control 14260*b* is positioned in a second finger groove defined in the grip 14220, although any suitable arrangement could be used.

In addition to the above, the shaft 14200 further comprises a third articulation control 14260*c* positioned on the second side of the shaft housing and a fourth articulation control 14260*d* positioned on the first side of the shaft housing. The third articulation control 14260*c* is in communication with the control system of the surgical instrument 14000 via a third control circuit and the fourth articulation control 14260*b* is in communication with the control system via a fourth control circuit. The control system is configured to operate the electric motor of the staple firing drive in the second direction to articulate the end effector of the shaft 14200 in the second direction when the third articulation control 14260*c* is actuated and the first direction to articulate the end effector in the first direction when the fourth articulation control 14260*d* is actuated. The third articulation control 14260*c* is positioned in a third finger groove defined in the grip 14220 of the shaft 14200 and the fourth articulation control 14260*d* is positioned in a fourth finger groove defined in the grip 14220, although any suitable arrangement could be used.

Figure 13:
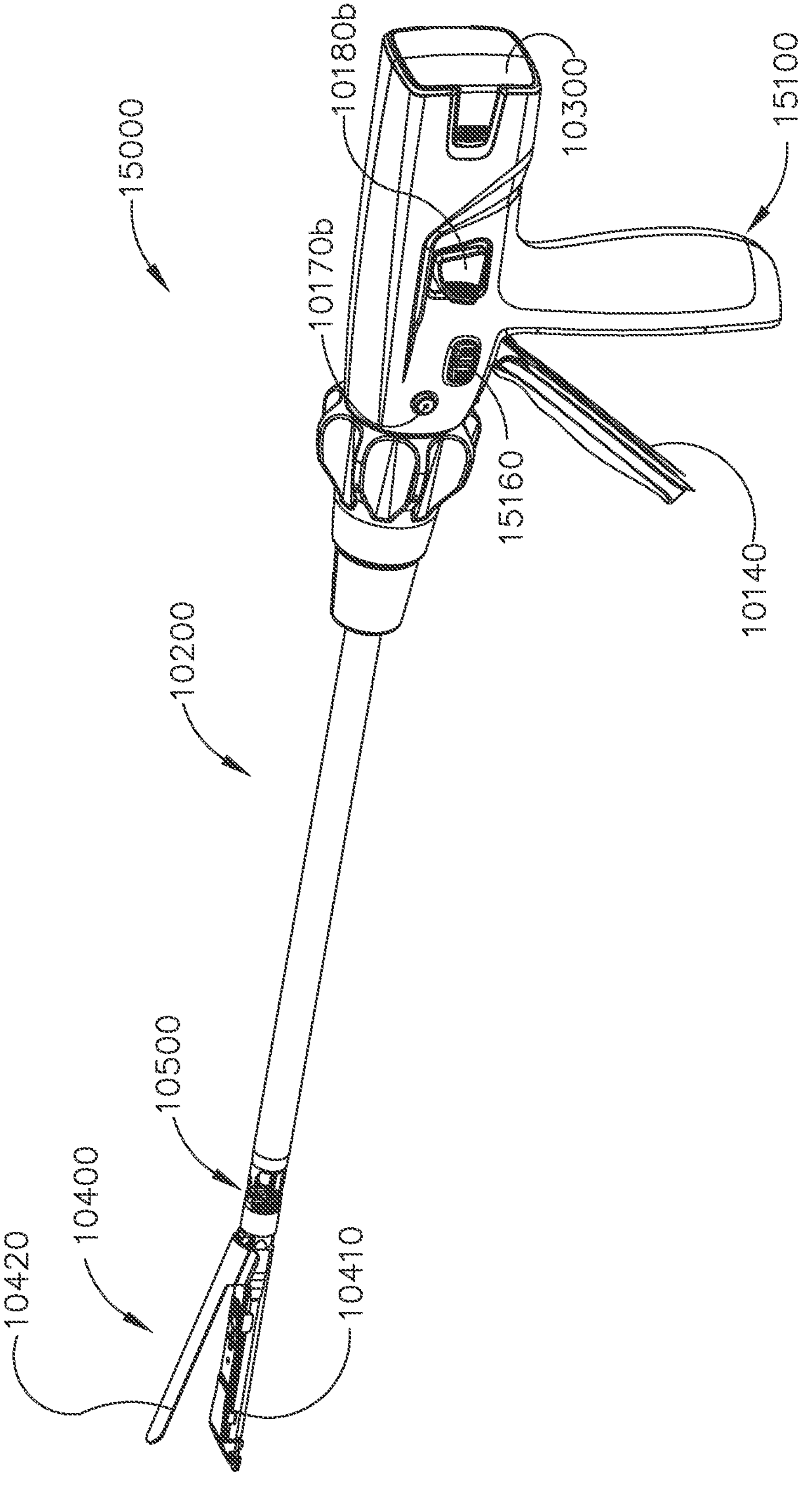
FIG. 13 is a perspective view of a surgical instrument in accordance with at least one embodiment comprising a slideable articulation actuator including two positions and a detent between the two positions.

A surgical instrument 15000 is illustrated in FIG. 13. The surgical instrument 15000 is similar to the surgical instrument 10000 in many respects. The surgical instrument 15000 comprises a handle 15100 and a shaft 10200 extending from the handle 15100. The handle 15100 comprises an articulation actuator 15160 in communication with the control system of the surgical instrument 15000. As opposed to the articulation actuator 10160 which is arranged vertically, the articulation actuator 15160 is arranged horizontally. The articulation actuator 15160 comprises a rotatable element which is rotatable within a plane which is parallel to, or at least substantially parallel to, the longitudinal axis of the shaft 10200. The rotatable element is rotatable distally to articulate the end effector 10400 to the right of the handle 15100 and proximally to articulate the end effector 10400 to the left of the handle 15100. This is true regardless of whether the end effector 10400 is rotated upwardly or downwardly owing to the control responsiveness flipping when the end effector 10400 is rotated past 90 degrees from its TDC position in either direction. That said, the controls of the articulation actuator 15160 can be reversed as outlined above. The articulation actuator 15160 comprises a distal contact which is part of a first articulation control circuit and a proximal contact which is part of a second articulation control circuit. The rotatable element engages the distal contact and closes the first articulation control circuit when the rotatable element is in its distal position. The rotatable element is not in contact with the proximal contact when the rotatable element is in its distal position and, as such, the second articulation control circuit is open. Similarly, the rotatable element engages the proximal contact and closes the second articulation control circuit when the rotatable element is in its proximal position. Correspondingly, the rotatable element is not in contact with the distal contact when the rotatable element is in its proximal position and, as such, the first articulation control circuit is open.

Further to the above, the articulation actuator 15160 comprises a detent in the middle of the range of motion of the rotatable element. The detent is configured to resist the motion of the rotatable element as the rotatable element moves from one side of the articulation actuator 15160 to the other. Such resistance to the motion of the rotatable element can signal to the clinician that they will articulate the end effector 10400 in the opposite direction once they move the rotatable element past that point. Moreover, such a detent provides a place to park the rotatable element such that the end effector 10400 is not being articulated in either direction. The rotatable element comprises a ridge alignable with its center, or parked, position which is pushable and pullable by the clinician to move the rotatable element. Such a ridge provides the clinician with a tactile sensation of the direction in which the rotatable element is rotated and, thus, a sense of the direction in which the end effector 10400 is being articulated.

The above being said, various embodiments are envisioned in which the flipping of the control responsiveness of a surgical instrument can be defeated. In at least one instance, the handle of the surgical instrument comprises an actuator in communication with the control system that, when actuated, causes the control system to not enter into its second, or flipped, operational mode. In at least one such instance, the handle further comprises an indicator, such as a light emitting diode (LED), for example, that is illuminated to indicate the status of the surgical instrument, i.e., whether or not the articulation controls will flip when the end effector is rotated past 90 degrees from its TDC position. In certain instances, the surgical instrument comprises an input screen in communication with a microprocessor of the control system which can receive an input to prevent the control system from entering into its second, or flipped, operational mode. In addition to or in lieu of the above, the flip point in which the surgical instrument enters into its second operation mode can be adjusted. In at least one such embodiment, the clinician can modify the flip point to 85 degrees, for example, in either direction from the TDC position of the end effector. Any suitable number, such as 80 degrees, 95 degrees, or 100 degrees, for example, could be used to suit the preference of the clinician. In at least one embodiment, the surgical instrument comprises an input screen in communication with the microprocessor of the control system which is configured to receive an input from the clinician to adjust the articulation control flip point.

During use, it is desirable for the articulation controls not to flip unexpectedly while the clinician is using the articulation controls. When the clinician starts articulating the end effector, the control system maintains the articulation control mode until the clinician releases the articulation control even if the end effector and shaft are rotated past a flip point during the articulation. Once the articulation has stopped, the control system can re-orient the articulation controls, or switch to the flipped articulation control mode if the end effector and shaft are still in an upside-down position. In certain embodiments, the control system does not immediately flip the articulation controls. Instead, the control system comprises a timer circuit and/or the microprocessor of the control system is programmed to wait a certain amount of time before flipping the controls. In at least one instance, the control system waits 5 seconds, for example, from the last time that the articulation controls were used before flipping the articulation controls. Alternatively, the control system can wait 2 seconds or 10 seconds, for example. Such an arrangement can help prevent confusion with the user of the surgical instrument. In various embodiments, the surgical instrument comprises a haptic feedback generator in communication with the control system which is activated by the control system when the articulation controls are flipped. Motor noise, light, sound, and/or a vibratory feedback, for example, can be used. In some embodiments, the shaft and/or handle comprises a mechanical switch which audibly clicks when the shaft is rotated past its flip point in either direction.

Figure 56:
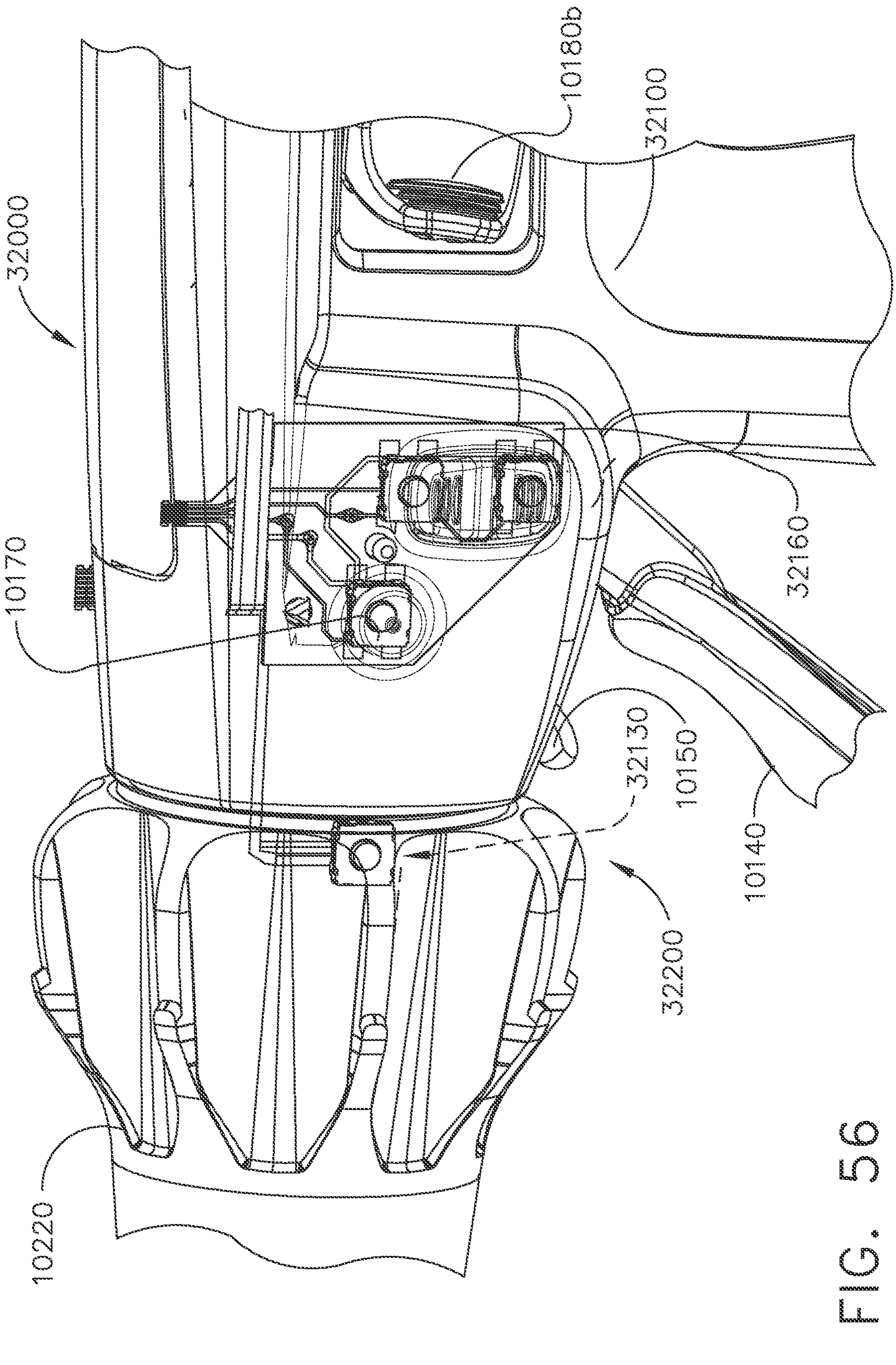
FIG. 56 is a partial perspective view of a surgical instrument in accordance with at least one embodiment.
Figure 57:
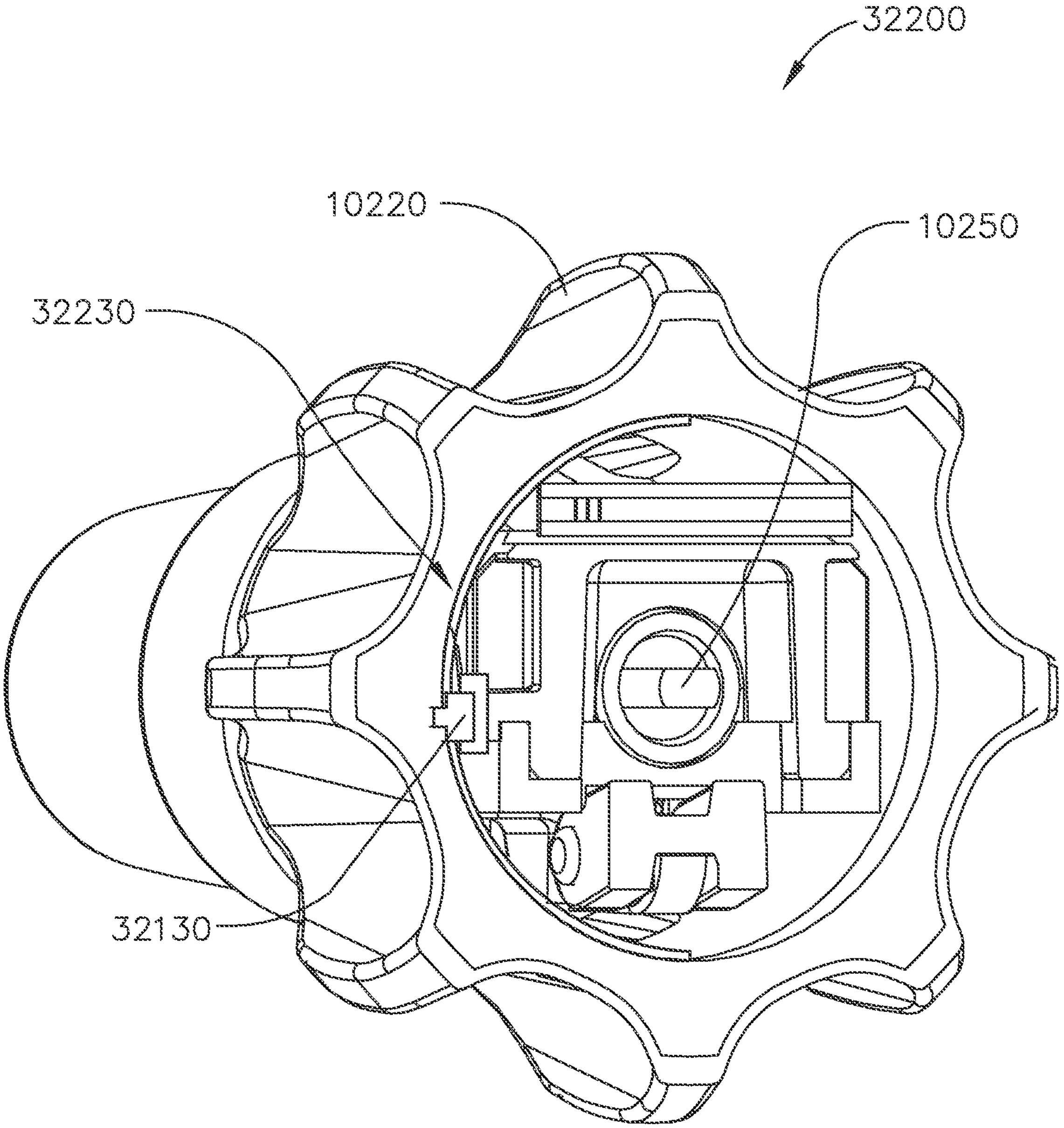
FIG. 57 is a partial perspective view of a shaft of the surgical instrument of FIG. 56.
Figure 58:
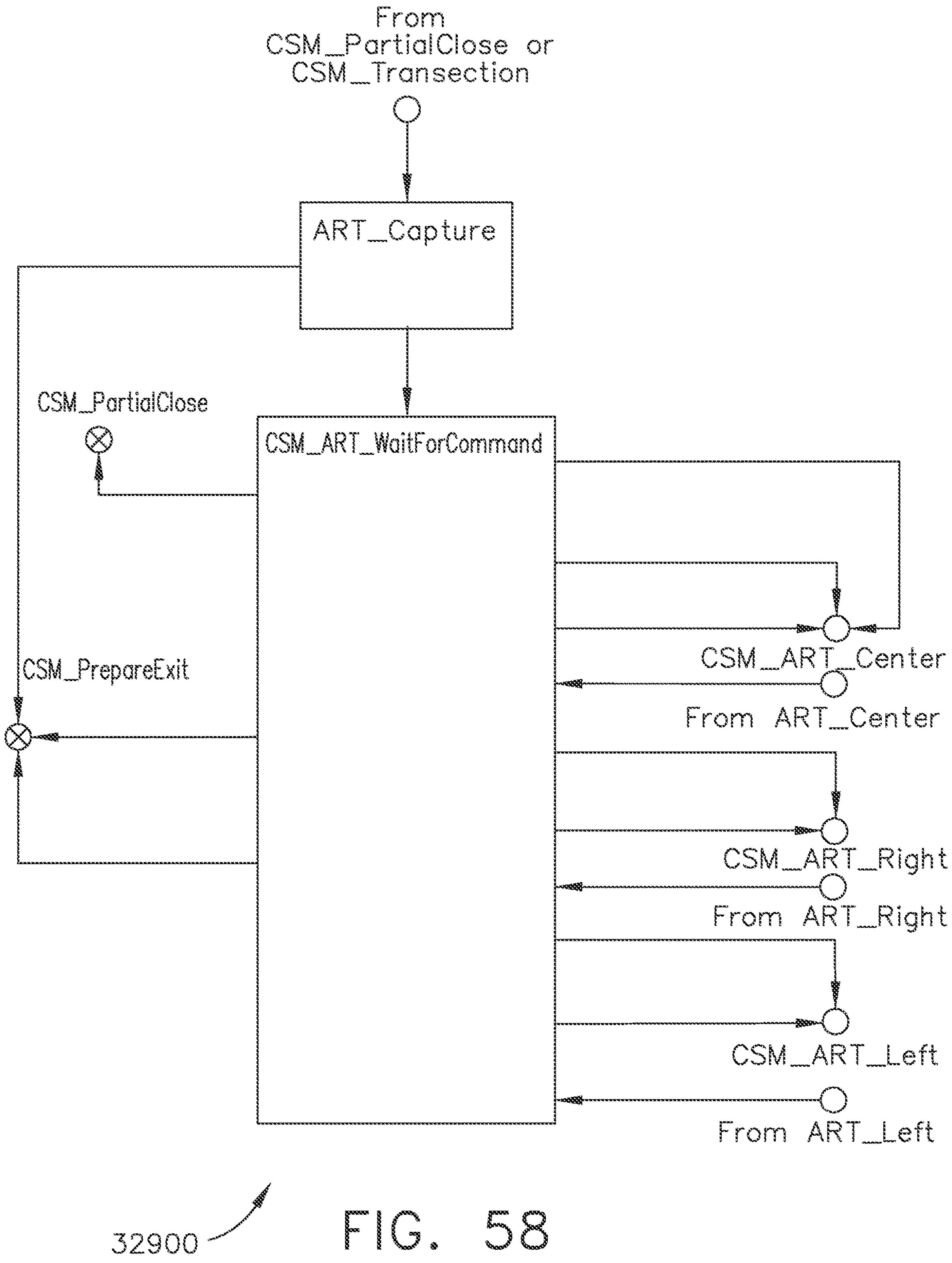
FIG. 58 is a control algorithm implemented by the surgical instrument of FIG. 56.

A surgical instrument 32000 is illustrated in FIGS. 56 and 57, the surgical instrument 32000 comprises a handle 32100 and a shaft 32200. The handle 32100 comprises an articulation control 32160 and an articulation flip switch 32130 in communication with the control system of the surgical instrument 32000. The articulation flip switch 32130 is mounted to a control board, such as a printed control board (PCB), for example, which comprises the hardware and software for the control system of the surgical instrument 32000. When the shaft 32200 is rotated past its 90 degree left or right position, the shaft 32200 contacts the articulation flip switch 32130 which is detected by the control system. At this point, the control system follows an algorithm for deciding when, or if, to the flip the articulation controls. An algorithm 32900 is illustrated in FIG. 58 which can control this, although any suitable algorithm could be used. Similar to the above, the shaft 32200 comprises a cam 32230 configured to contact the articulation flip switch 32130. As a result of the above, the articulation flip switch 32130 is open or “off” for 180 degrees of the rotation of the shaft 32200 and closed or “on” for the other 180 degrees of the rotation of the shaft 32200. The cam 32230 is molded into the shroud of the shaft 32200, but could comprise any suitable arrangement. The above being said, the throw of the cam 32230 is designed such that any lateral float or eccentricity in the rotation of the shaft 32200, or cam 32230, does not accidentally close or open the articulation flip switch 32130. To this end, the shaft 32200 comprises a fixed bearing for controlling the rotation of the shaft 32200 and the cam 32230. Notably, the articulation flip switch 32130 is sealed to prevent fluid ingress.

In various instances, a surgical instrument comprises an input configured to permit a clinician to select whether the articulation controls operate in their ordinary articulation control mode or their flipped articulation control mode. In at least one instance, the handle of the surgical instrument comprises an input switch in communication with the control system of the surgical instrument. When the input switch is open, for instance, the algorithm controls the orientation of the articulation controls according to a predetermined set of criteria. When the input switch is closed by the clinician, the algorithm does not use the predetermined set of criteria to control the orientation of the articulation controls. Instead, the algorithm uses the orientation of the articulation controls selected by the clinician. In at least one instance, the handle comprises three input switches in communication with the control system—a first switch which instructs the control system to use the “anvil up” articulation controls, a second switch which instructs the control system to use the “anvil down” articulation controls, and a third switch which instructs the control system to use the automatic controls. In some embodiments, the surgical instrument does not have the automatic flip controls described herein and can just comprise the first and second switch inputs. Such an arrangement can greatly reduce the cost and/or complexity of a surgical instrument.

Figure 55:
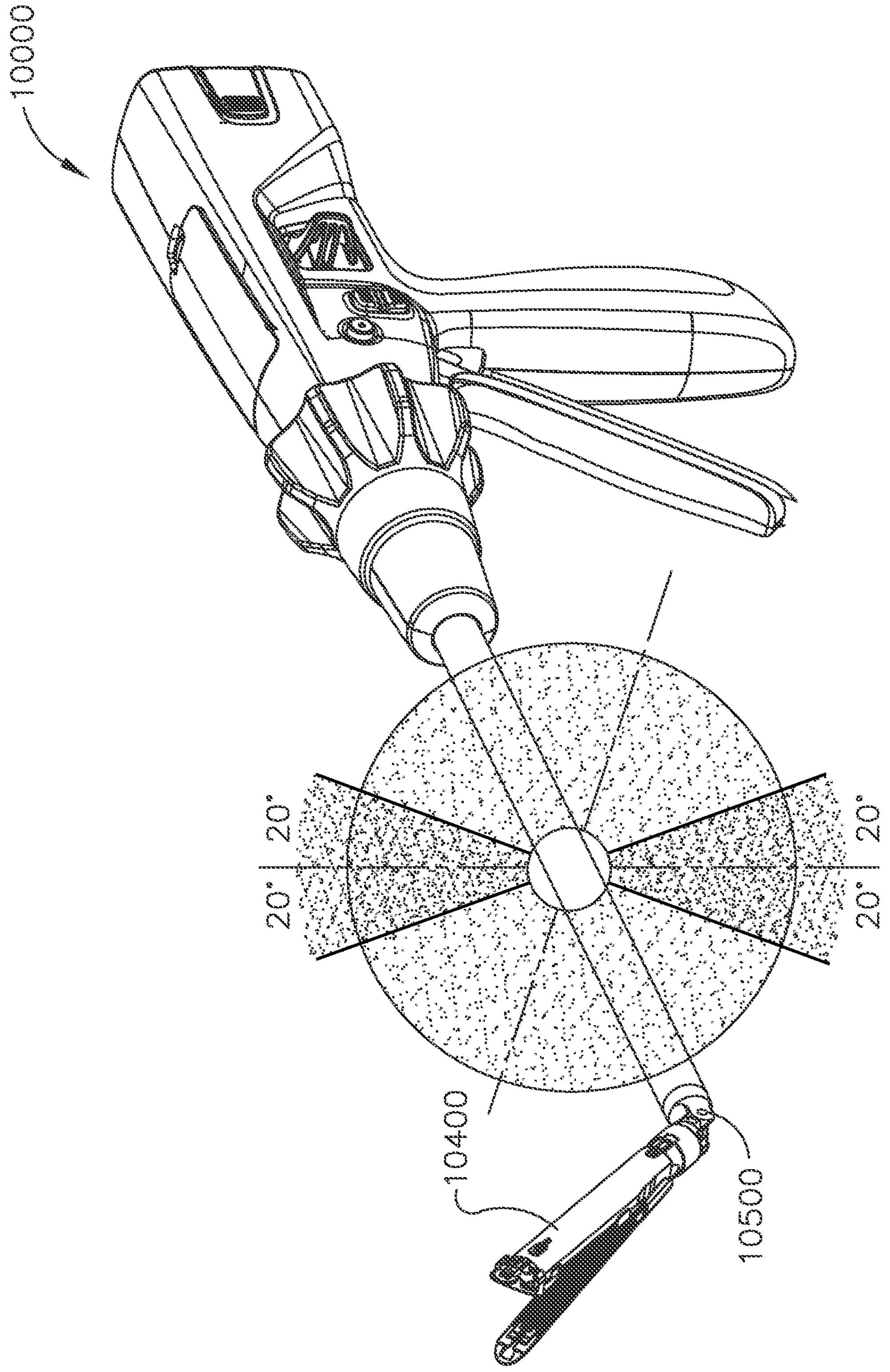
FIG. 55 is a perspective view of the surgical instrument of FIG. 1.

In various instances, further to the above, the flip point can be a specific point in the rotation of the shaft 10200. In certain instances, referring to FIG. 55, a grey zone can exist around the flip point. For instance, the grey zone can include 20 degrees to either side of the flip point, for example. While the shaft 10200 is in the grey zone, the algorithm of the control system is configured to not flip the articulation controls even though the shaft 10200 may have been rotated past the flip point. Such an arrangement allows the shaft 10200 to be rotated back and forth within the grey zone without repeatedly flipping the articulation controls. Once the shaft 10200 is rotated out of the grey zone, however, the control system algorithm flips the articulation controls—subject to any other criteria needed for flipping the articulation controls. In various instances, there is an interface between the range of "anvil up" orientations and the range of "anvil down" orientations. For a shaft that is rotatable 360 degrees, there are two such interfaces—180 degrees apart from another. Each of these interfaces is positioned within a transition range of orientations that extends into the range of "anvil up" orientations and the range of "anvil down" orientations. When the shaft 10200 is rotated from an "anvil up" orientation into a transition range, the control system does not flip the articulation controls—but further rotating the shaft 10200 out of the transition range into an "anvil down" orientation will cause the articulation controls to flip. Similarly, the control system does not flip the articulation controls when the shaft 10200 is rotated from an "anvil down" orientation into a transition range, but further rotating the shaft 10200 out of the transition range in an "anvil up" orientation will cause the articulation controls to flip. In at least one instance, each transition zone includes 5 degrees of orientations from the "anvil up" range and 5 degrees of orientations from the "anvil down" range, for example. In other embodiments, each transition zone includes 10 degrees of orientations from the "anvil up" range and 10 degrees of orientations from the "anvil down" range, for example.

In various embodiments, further to the above, the up and down orientations of the shaft 10200 are measured with respect to the handle and/or a housing rotatably supporting the shaft. In such instances, a handle comprises a top and a bottom—regardless of its gravitational orientation—and the up orientations of the shaft 10200 are associated with the top of the handle while the down orientations of the shaft 10200 are associated with the bottom of the handle. In at least one such embodiment, the shaft 10200 comprises a gravity sensor, such as an accelerometer and/or a gyroscope, for example, and the handle comprises a gravity sensor. In such embodiments, the shaft gravity sensor and the handle gravity sensor are in communication with the control system which is configured to assess the relative orientation between the shaft and the handle using the data from the gravity sensors. In other embodiments, the up and down orientations of the shaft 10200 are measured with respect to gravity regardless of the gravitational orientation of the handle. In at least one such embodiment, the shaft 10200 comprises a gravity sensor in communication with the control system and the up orientations of the shaft 10200 are associated with vertically up positions while the down orientations of the shaft 10200 are associated with vertically down positions.

Figure 14:
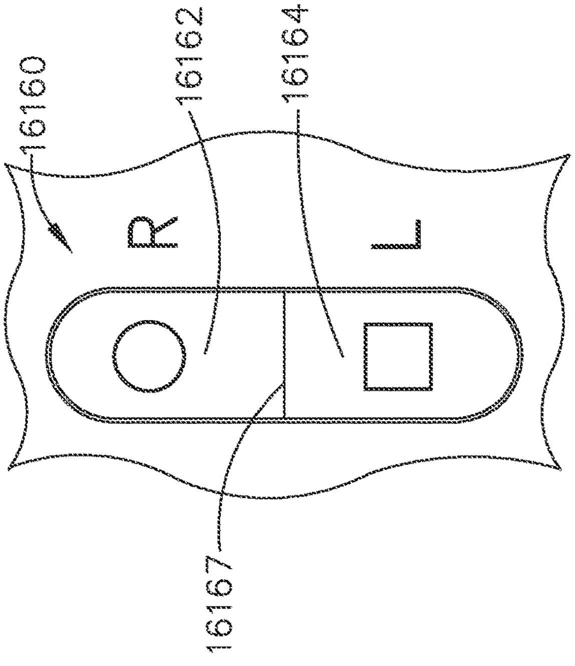
FIG. 14 illustrates a capacitive switch including first and second sides, a first light in the first side which illuminates when the first side is contacted, and a second light in the second side which illuminates when the second side is contacted.

An articulation control 16160 is illustrated in FIG. 14. The articulation control 16160 comprises a first capacitive switch 16162 and a second capacitive switch 16164. The first capacitive switch 16162 and the second capacitive switch 16164 are positioned on opposite sides of an axis 16167. The first capacitive switch 16162 is part of a first articulation control circuit in communication with a control system of a surgical instrument and the second capacitive switch 16164 is part of a second articulation control circuit in communication with the control system. The capacitance of the first capacitive switch 16162 changes when a clinician places their finger on the first capacitive switch 16162 which is detected by the control system and, in response to this change, the control system articulates the end effector of the surgical instrument to the right. The capacitance of the second capacitive switch 16164 changes when a clinician places their finger on the second capacitive switch 16164 which is detected by the control system and, in response to this change, the control system articulates the end effector of the surgical instrument to the left. In various instances, the axis 16167 comprises a dead zone which, if touched by the clinician, does not detectably, or sufficiently, change the capacitance of the first capacitive switch 16162 or the second capacitive switch 16164.

Figure 15:
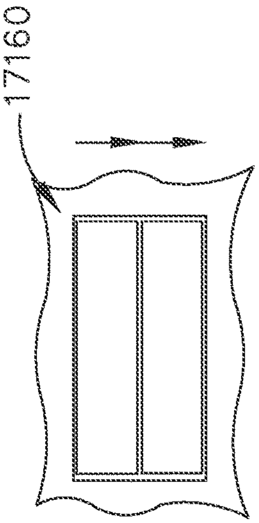
FIG. 15 illustrates a two-stage rocker switch for articulating an end effector of a surgical instrument in accordance with at least one embodiment.

A two-stage switch 17160 is illustrated in FIG. 15. When the switch 17160 is depressed into its first stage, a first articulation control circuit is closed. The first articulation control circuit is in communication with a control system of a surgical instrument. When the control system detects that the first articulation control circuit has been closed, the control system operates an articulation drive motor in a first direction to articulate the end effector of the surgical instrument in a first direction. When the switch 17160 is depressed into its second stage, a second articulation control circuit is closed. In various instances, the first stage comprises a first detent and the second stage comprises a second detent. In at least one such instance, the switch 17160 comprises a dual-detent switch that is depressable to two different depths, for example. In any event, the second articulation control circuit is in communication with the control system of the surgical instrument. When the control system detects that the second articulation control circuit has been closed, the control system operates an articulation drive motor in a second direction to articulate the end effector of the surgical instrument in a second direction. Further to the above, the second articulation control circuit is open when the first articulation control circuit is closed and, likewise, the first articulation control circuit is open when the second articulation control circuit is closed. The above being said, in alternative embodiments, the articulation control circuits can be opened when they are in their respective stages to operate the articulation motor.

Figure 17:
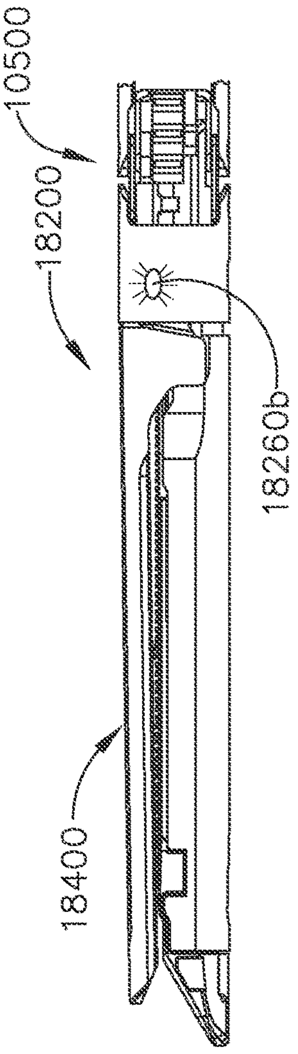
FIG. 17 is a partial elevational view of the surgical instrument of FIG. 16.
Figure 16:
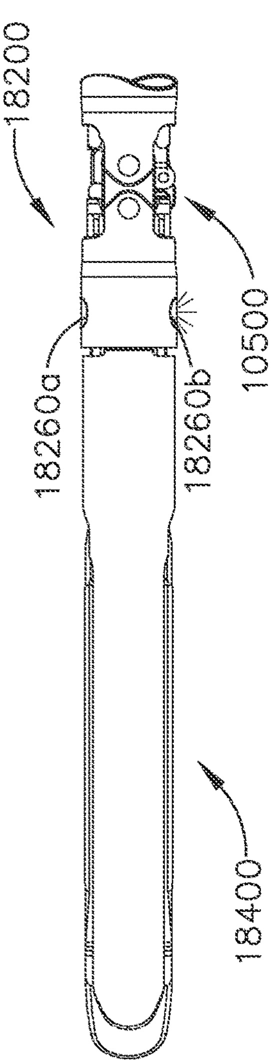
FIG. 16 is a partial top view of a surgical instrument in accordance with at least one embodiment comprising an end effector and lights positioned on opposite sides of the end effector which are illuminated to indicate the direction in which the end effector is being articulated.

Many clinicians, further to the above, prefer to look at the patient when performing an open surgery and/or at an endoscope monitor when performing a laparoscopic surgery. As such, the clinician does not usually look at the surgical instrument that they are holding and, instead, rely on the tactile feel and/or intuitive design of the surgical instrument to operate the surgical instrument. Stated another way, the clinician may not prefer to look down at the handle of the instrument they are holding to verify the direction that they are articulating the instrument. That being said, referring to FIGS. 16 and 17, a surgical instrument can comprise a shaft 18200 comprising indicator lights configured to indicate the direction in which an end effector, such as end effector 18400, for example, is being articulated. The articulation indicator lights are visible to the clinician while they are looking at the end effector 18400 of the surgical instrument—either directly or through an endoscope system monitor. In various instances, an endoscope system comprises an elongate flexible shaft including a camera, a light, and/or any other suitable optical device in communication with a control hub including a control system and/or a video monitor configured to display the output of the camera. In such instances, the end effector 18400 and the indicator lights are visible on the video monitor.

Further to the above, referring again to FIGS. 16 and 17, the shaft 18200 comprises a first indicator light 18260*a* positioned on the right side of the end effector 18400 in communication with the control system of the surgical instrument via a first electrical circuit. When the control system receives an input to articulate the end effector 18400 to the right, the control system operates the articulation drive motor in a direction which articulates the end effector 18400 to the right and, also, illuminates the first indicator light 18260*a*. When the control system no longer receives this input, the control system deactivates the articulation drive motor and the first indicator light 18260*a*. Similarly, the shaft 18200 comprises a second indicator light 18260*b* positioned on the left side of the end effector 18400 in communication with the control system of the surgical instrument via a second electrical circuit. When the control system receives an input to articulate the end effector 18400 to the left, the control system operates the articulation drive motor in a direction which articulates the end effector 18400 to the left and, also, illuminates the second indicator light 18260*b*. When the control system no longer receives this input, the control system deactivates the articulation drive motor and the second indicator light 18260*b*.

Figure 18:
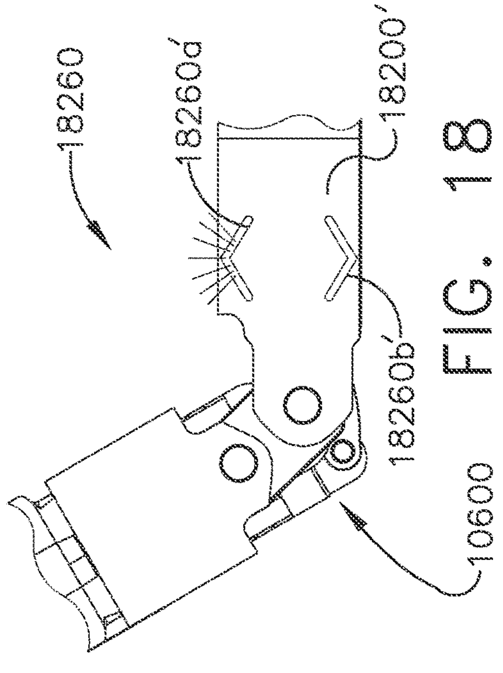
FIG. 18 is a partial elevational view of a surgical instrument in accordance with at least one embodiment comprising directional indicators which are illuminated to indicate which way the end effector is being articulated.

As discussed above, the first and second indicator lights 18260*a* and 18260*b* are positioned on the end effector 18400 in a position which is readily observable by the clinician when they are looking at the end effector 18400. The indicator lights 18260*a* and 18260*b* are positioned distally with respect to the articulation joint 10500; however, in alternative embodiments, the indicator lights 18260*a* and 18260*b* are positioned proximally to the articulation joint 10500. In various embodiments, a surgical instrument comprises more than one set of indicator lights. In at least one such embodiment, a first set of indicator lights 18260*a*, 18260*b* is positioned distally with respect to the articulation joint 10500 and a second set of indicator lights 18260*a*, 18260*b* is positioned proximally with respect to the articulation joint 10500. An alternative embodiment comprising indicator lights 18260*a*' and 18260*b*' on a shaft 18200' is illustrated in FIG. 18. The indicator light 18260*a*' comprises an LED in the shape of a right-facing arrow while the indicator light 18260*b*' comprises an LED in the shape of a left-facing arrow. The right-facing arrow 18260*a*' points to the right of the end effector—but not necessarily to the right of the surgical instrument handle and/or the clinician owing to the possible rotation of the shaft 18200'. Similarly, the left-facing arrow 18260*b*' points to the left of the end effector—but not necessarily to the left of the surgical instrument handle and/or the clinician owing to the possible rotation of the shaft 18200'. Stated another way, the arrows, when illuminated, point in the direction that the end effector is being articulated. Given that the arrows are observable with the end effector on an endoscope monitor, for example, the clinician will develop a sense for the direction that the end effector will move when an arrow is illuminated upon actuating the articulation actuator. If the clinician observes that the illuminated arrow is the opposite of what they expected when they actuate the articulation actuator, the clinician can quickly react and re-actuate the articulation actuator in the correct direction. In various alternative embodiments, the arrows 18260*a*' and 18260*b*' can change colors when they are actuated. For instance, the arrow 18260*a*' is illuminated red when the end effector is not articulated to the right, but is illuminated green when the end effector is articulated to the right. Likewise, the arrow 18260*b*' is illuminated red when the end effector is not articulated to the left, but is illuminated green when the end effector is articulated to the left.

In various embodiments, further to the above, the articulation indicator lights can be embedded in and/or positioned on the outer housing of the shaft. In certain embodiments, the indicator lights are positioned inside the shaft, but are viewable from outside the shaft through windows and/or openings defined in the shaft, for example.

Figures 26A, 26B:
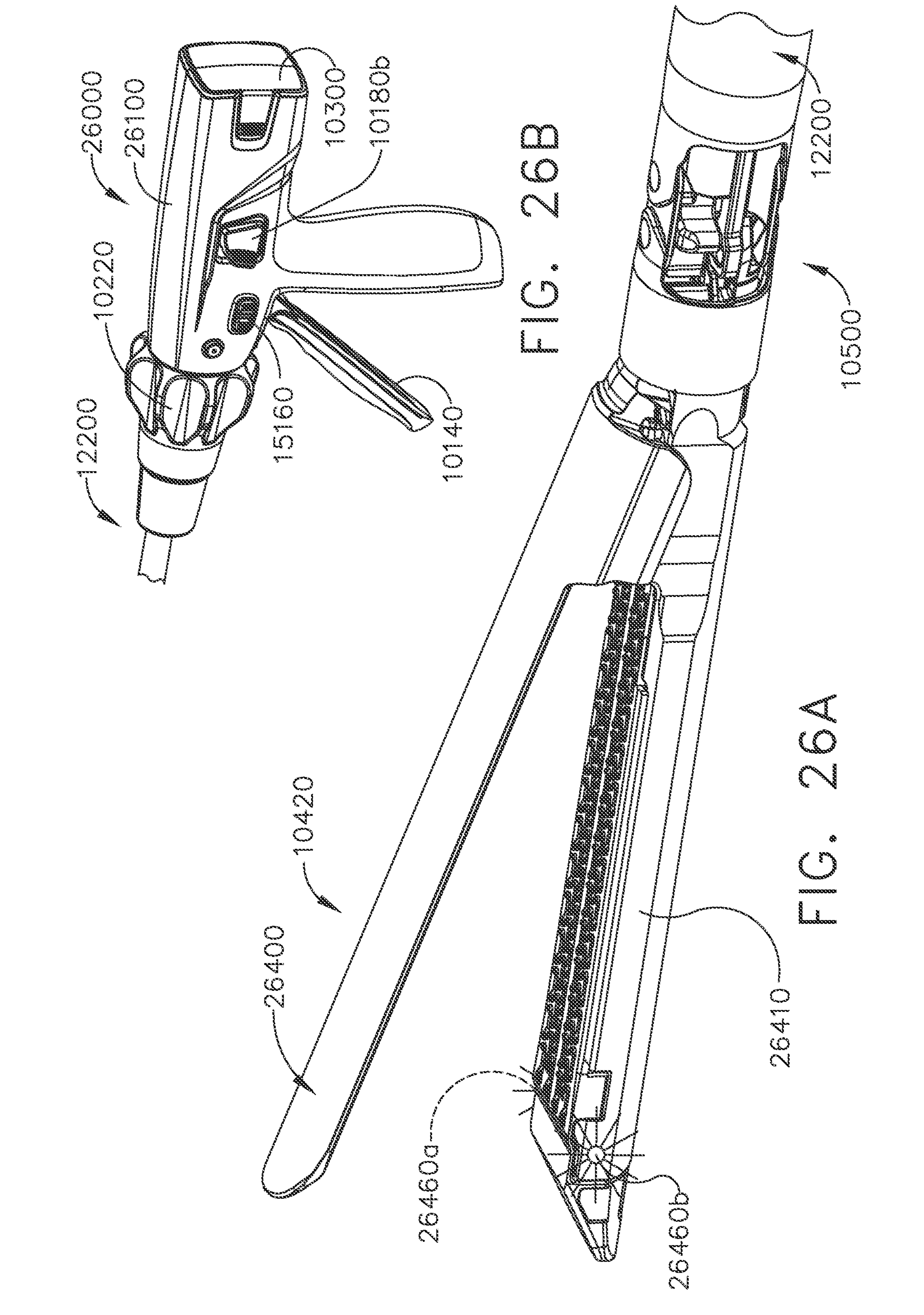
FIG. 26A illustrates a surgical instrument in accordance with at least one embodiment including an end effector and lights positioned on opposite sides of the end effector which are illuminated to indicate the direction in which the end effector is being articulated.
FIG. 26B is a perspective view of the surgical instrument of FIG. 26A.

A surgical instrument 26000 is illustrated in FIGS. 26A and 26B. The surgical instrument 26000 comprises a handle 26100 and a shaft 12200 extending from the handle 26100. The shaft 12200 comprises an end effector 26400 including a staple cartridge jaw 26410 and an anvil jaw 10420. The end effector 26400 further comprises a first articulation indicator light 26460*a* positioned on a first side of the end effector 26400 and a second articulation indicator light 26460*b* positioned on a second side of the end effector 26400. Similar to the above, the control system of the surgical instrument 26000 illuminates the first articulation indicator light 26460*a* when the end effector 26400 is articulated in the first direction. In such instances, the control system does not illuminate the second articulation indicator light 26460*b*. Correspondingly, the control system of the surgical instrument 26000 illuminates the second articulation indicator light 26460*b* when the end effector 26400 is articulated in the second direction. In such instances, the control system does not illuminate the first articulation indicator light 26460*a*. The indicator lights 26460*a* and 26460*b* are mounted to and/or embedded in the frame of the staple cartridge jaw 26410. That said, the indicator lights 26460*a* and 26460*b* can be mounted to and/or embedded in the staple cartridge positioned in the staple cartridge jaw 26410. In such instances, the staple cartridge jaw 26410 comprises an electrical circuit in communication with the control system of the surgical instrument that is placed in communication with an electrical circuit in the staple cartridge when the staple cartridge is seated in the staple cartridge jaw 26410.

Figure 27:
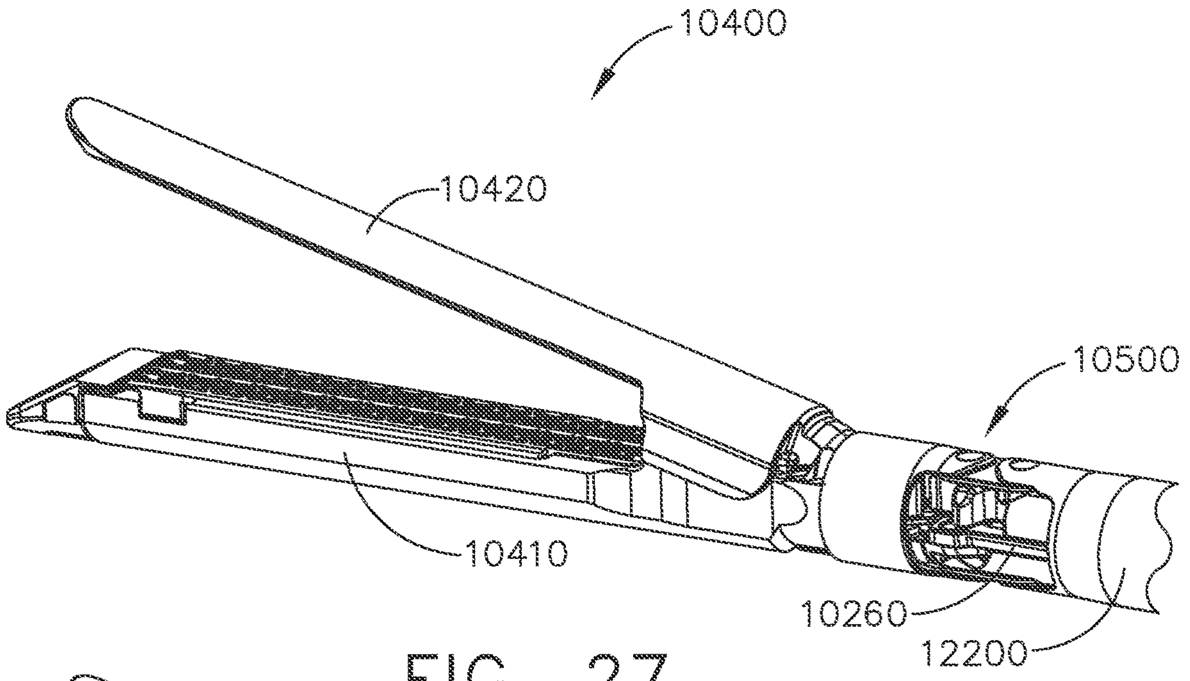
FIG. 27 illustrates a surgical instrument in accordance with at least one embodiment including an articulation joint, an end effector articulatable about the articulation joint, and a translatable articulation actuator configured to rotate the end effector about the articulation joint.
Figure 28:
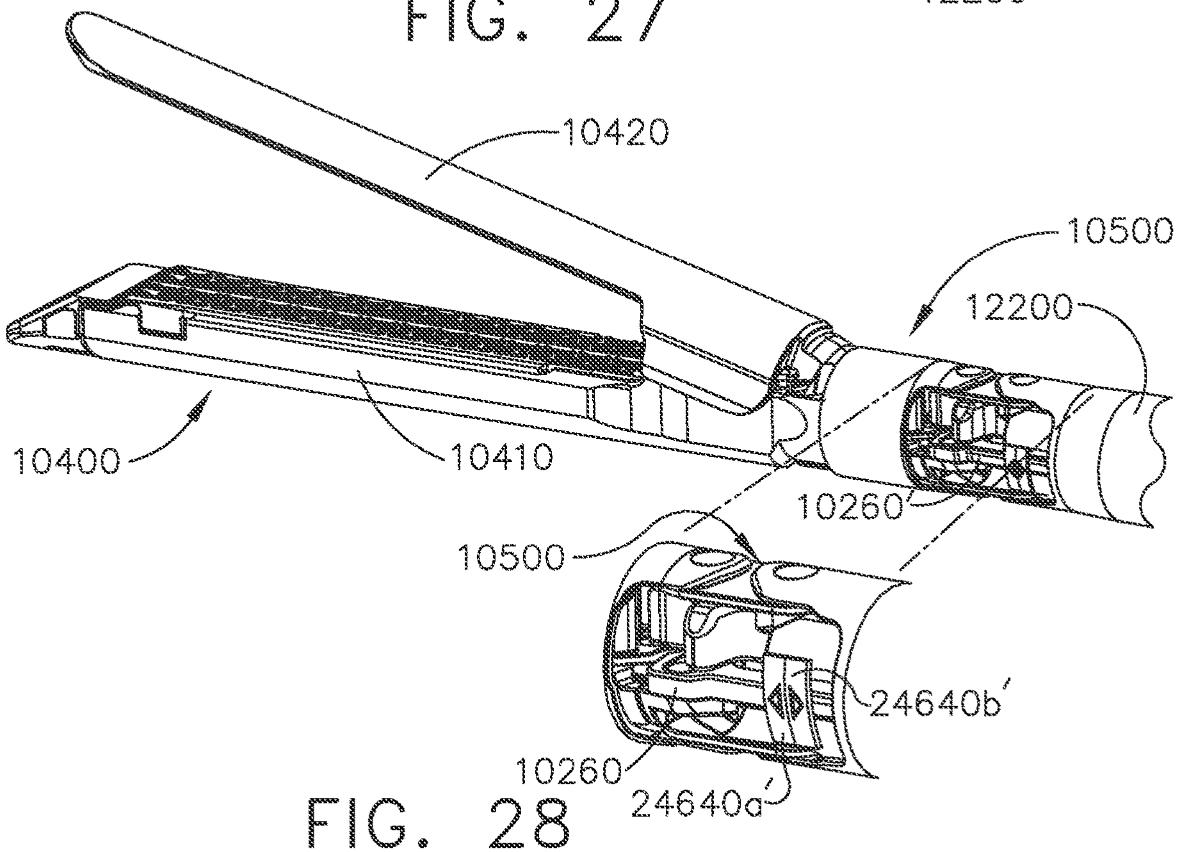
FIG. 28 is a partial perspective view of an articulatable end effector, an articulation actuator configured to rotate the end effector about an articulation joint, and demarcations on the articulation actuator which indicate the direction in which an end effector is articulated and/or is being articulated.

As discussed above, the articulation system of a surgical instrument can include an articulation driver which is movable proximally to articulate the end effector in a first direction and distally to articulate the end effector in a second direction. Referring to FIG. 27, a surgical instrument can comprise a handle 26100, a shaft 12200 extending from the handle 26100, and an end effector 10400 rotatably connected to the shaft 12200 about an articulation joint 10500. The shaft 12200 comprises an articulation driver 10260 comprising a proximal end operably coupled to an articulation drive system and a distal end coupled to the end effector 10400. To this end, the articulation driver 10260 extends distally past the articulation joint 10500 and, in this embodiment, is partially visible to a clinician holding the surgical instrument. The portion of the articulation driver 10260 visible to the clinician is also visible to the clinician through an endoscope monitor. In fact, a clinician may be able to observe the motion of the articulation driver 10260 through the endoscope monitor. The visible portion of the articulation driver 10260 comprises indicia, such as indicia 24640*a*' and 24640*b*', for example, thereon which correlates the movement of the articulation driver 10260 to the movement of the end effector 10400. In at least one instance, the indicia can comprise a first set of indicia which includes a distally-directed arrow 24640*a*' and a circular arrow indicating the direction that the end effector 10400 will be rotated if the articulation driver 10260 is moved distally. The indicia can also comprises a second set of indicia which includes a proximally-directed arrow 24640*b*' and a circular arrow in the opposite direction indicating the direction that the end effector 10400 will be rotated if the articulation driver 10260 is moved proximally. An alternative articulation driver 10260' is illustrated in FIG. 28 that comprises a laterally-extending portion which can be readily visible to the clinician. In such instances, the above-discussed indicia is positioned on the laterally-extending portion.

Figure 19:
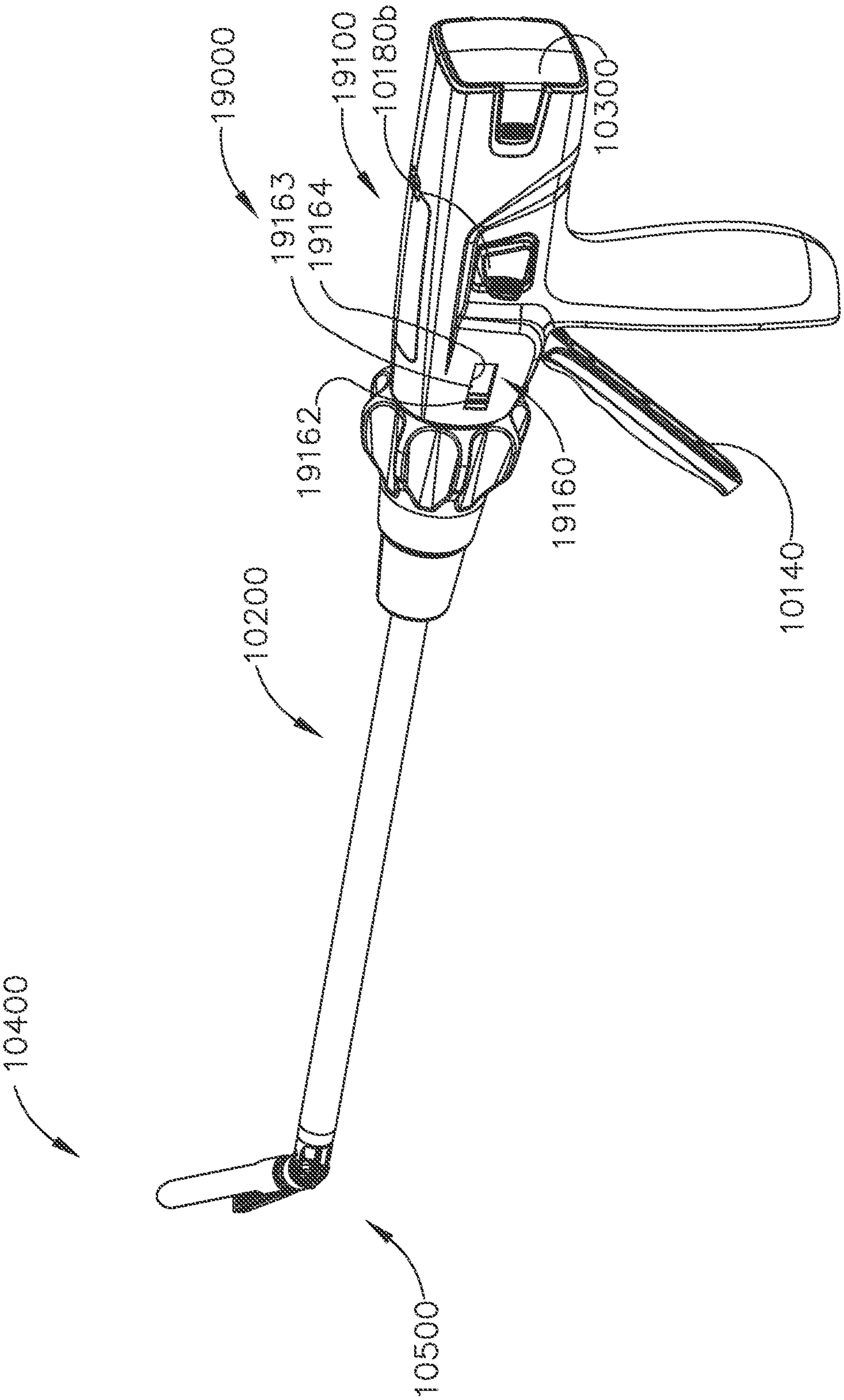
FIG. 19 is a perspective view of a surgical instrument in accordance with at least one embodiment including a slideable articulation switch including three positions—an articulate left position, an articulate right position, and a center, or home, position.

A surgical instrument 19000 is illustrated in FIG. 19. The surgical instrument 19000 is similar to the surgical instrument 15000 in many respects. The surgical instrument 19000 comprises a handle 19100 and a shaft 10200 extending from the handle 19100. The handle 19100 comprises an articulation actuator 19160 in communication with the control system of the surgical instrument 19000. As opposed to the articulation actuator 10160 which is arranged vertically, the articulation actuator 19160 is arranged horizontally. The articulation actuator 19160 comprises a slideable element 19162 which is slideable along an axis which is parallel to, or at least substantially parallel to, the longitudinal axis of the shaft 10200. In at least one instance, the axis of the articulation actuator 19160 is aligned with the longitudinal axis of the shaft 10200. The slideable element 19162 is positioned within a slot 19164 on the handle 19100 of the surgical instrument 19000. The slideable element 19162 is slideable distally to articulate the end effector 10400 to the right of the handle 19100 and proximally to articulate the end effector 10400 to the left of the handle 19100. This is true regardless of whether the end effector 10400 is rotated upwardly or downwardly owing to the control responsiveness flipping when the end effector 10400 is rotated past 90 degrees from its TDC position in either direction. That said, the controls of the articulation actuator 19160 can be reversed as outlined above.

The articulation actuator 19160 comprises a distal contact which is part of a first articulation control circuit and a proximal contact which is part of a second articulation control circuit. The slideable element 19162 engages the distal contact and closes the first articulation control circuit when the slideable element 19162 is in its distal position. The slideable element 19162 is not in contact with the proximal contact when the slideable element 19162 is in its distal position and, as such, the second articulation control circuit is open. Similarly, the slideable element 19162 engages the proximal contact and closes the second articulation control circuit when the slideable element 19162 is in its proximal position. Correspondingly, the slideable element 19162 is not in contact with the distal contact when the slideable element 19162 is in its proximal position and, as such, the first articulation control circuit is open. In any event, the articulation actuator 19160 comprises a detent 19163 in the middle of the range of motion of the slideable element 19162. The detent 19163 is configured to resist the motion of the slideable element 19162 as the slideable element 19162 moves from one side of the articulation actuator 19160 to the other. Such resistance to the motion of the slideable element 19162 can signal to the clinician that they will articulate the end effector 10400 in the opposite direction once they move the slideable element 19162 past that point. Moreover, such a detent 19163 provides a place to park the slideable element 19162 such that the end effector 10400 is not being articulated in either direction.

Figure 20:
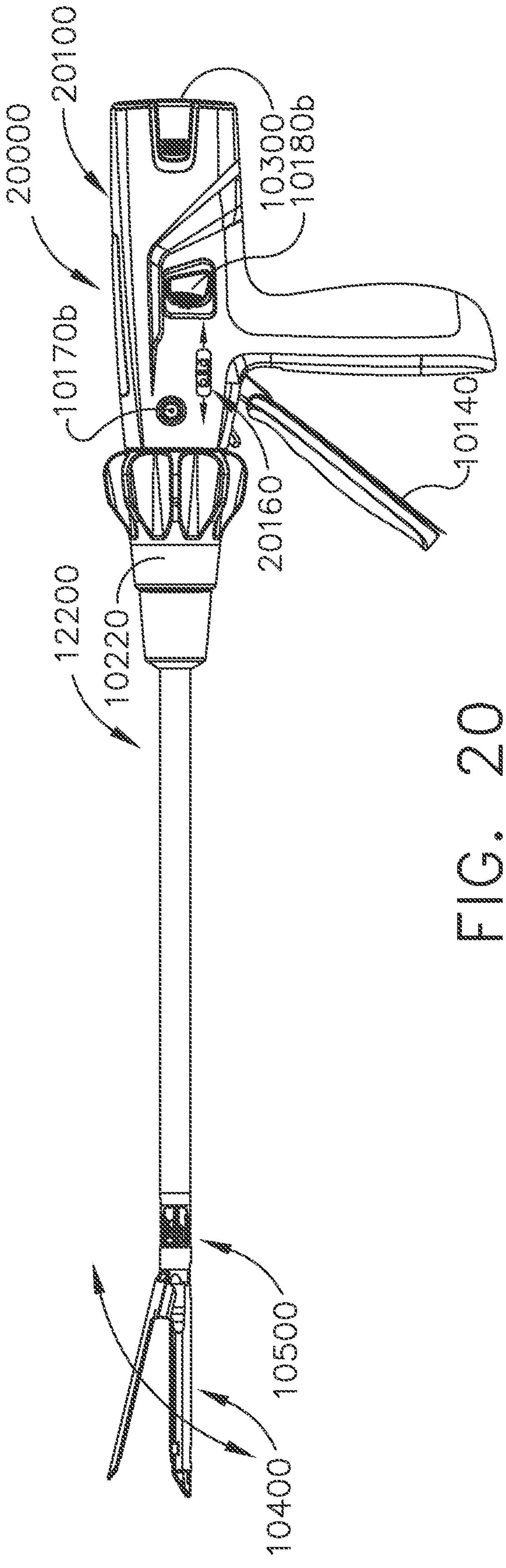
FIG. 20 is an elevational view of a surgical instrument in accordance with at least one embodiment including an articulation joystick actuatable along a longitudinal axis.

A surgical instrument 20000 is illustrated in FIG. 20. The surgical instrument 20000 is similar to the surgical instrument 10000 in many respects. The surgical instrument 20000 comprises a handle 20100 and a shaft 12200 extending from the handle 20100. The handle 20100 comprises an articulation actuator 20160 in communication with the control system of the surgical instrument 20000. The articulation actuator 20160 comprises a two-dimensional joystick movable within a plane which is aligned with, parallel to, or at least substantially parallel to, the longitudinal axis of the shaft 12200. The joystick is movable distally to articulate the end effector 10400 to the right of the handle 20100 and proximally to articulate the end effector 10400 to the left of the handle 20100. In at least one instance, the joystick comprises a handle having an inner end that is positioned in a sensor seat in communication with the control system of the surgical instrument 20000. The joystick is pivotable within the sensor seat by the clinician when the clinician manipulates the outer end of the joystick handle. Such movement of the joystick is detectable by the control system which operates the articulation system in response to the input from the sensor seat. The articulation actuator 20160 comprises one or more biasing mechanisms, such as springs, for example, configured to bias the joystick handle to a centered, or an at least substantially centered position, in the sensor seat in which the control system does not articulate the end effector 10400.

Figure 21:
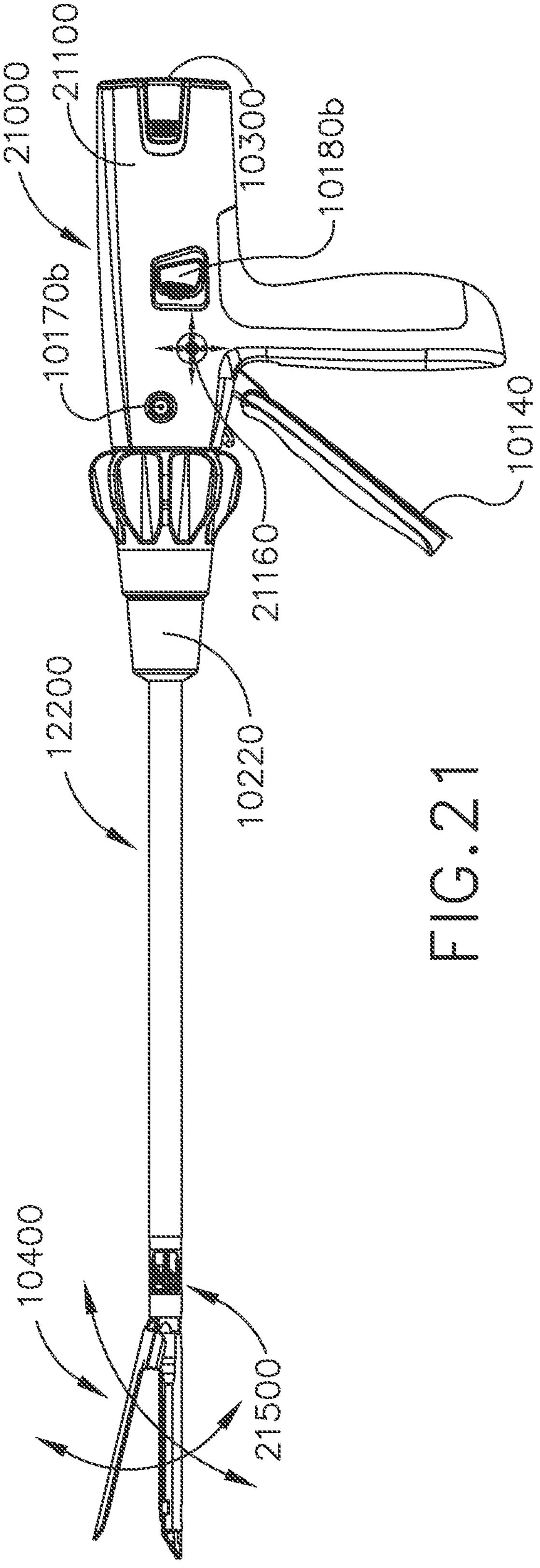
FIG. 21 is an elevational view of a surgical instrument in accordance with at least one embodiment including an end effector and an articulation joystick actuatable to articulate the end effector about more than one axis.

As discussed above, the end effector 10400 is articulatable within a plane. In alternative embodiments, a surgical instrument comprises a second articulation joint. In such embodiments, the end effector 10400 is rotatable within more than one plane. In various embodiments, a surgical instrument comprises an articulation joint which permits the end effector 10400 to be rotated within a three-dimensional spherical range of positions. Referring to FIG. 21, a surgical instrument 21000 comprises a shaft 21200 including an articulation joint 21500 which allows such articulation motion of the end effector 10400. The surgical instrument 21000 further comprises a handle 21100 including an articulation actuator 21160 in communication with a control system of the surgical instrument 21000. The articulation actuator 21160 comprises a three-dimensional joystick movable proximally, distally, upwardly, downwardly, and in compound directions. The joystick is movable distally to articulate the end effector to the right of the handle 20100 and proximally to articulate the end effector to the left of the handle 21100. The joystick is movable upwardly to articulate the end effector upwardly and downwardly to articulate the end effector downwardly, for example. The joystick is also movable in a direction which is both upward and distal to move the end effector in a direction which is both upward and to the right, for example. The joystick is also movable in a direction which is both downward and proximal to move the end effector in a direction which is both downward and to the left, for example. In at least one instance, the joystick comprises a handle having an inner end that is positioned in a sensor seat in communication with the control system of the surgical instrument 21000. The joystick is orbitable within the sensor seat by the clinician when the clinician manipulates the outer end of the handle. Such movement of the joystick is detectable by the control system which operates the articulation system in response to the input from the sensor seat. The articulation actuator 21160 comprises one or more biasing mechanisms, such as springs, for example configured to bias the joystick handle to a centered, or an at least substantially centered position, in the sensor seat in which the control system does not articulate the end effector 10400.

Figure 22B:
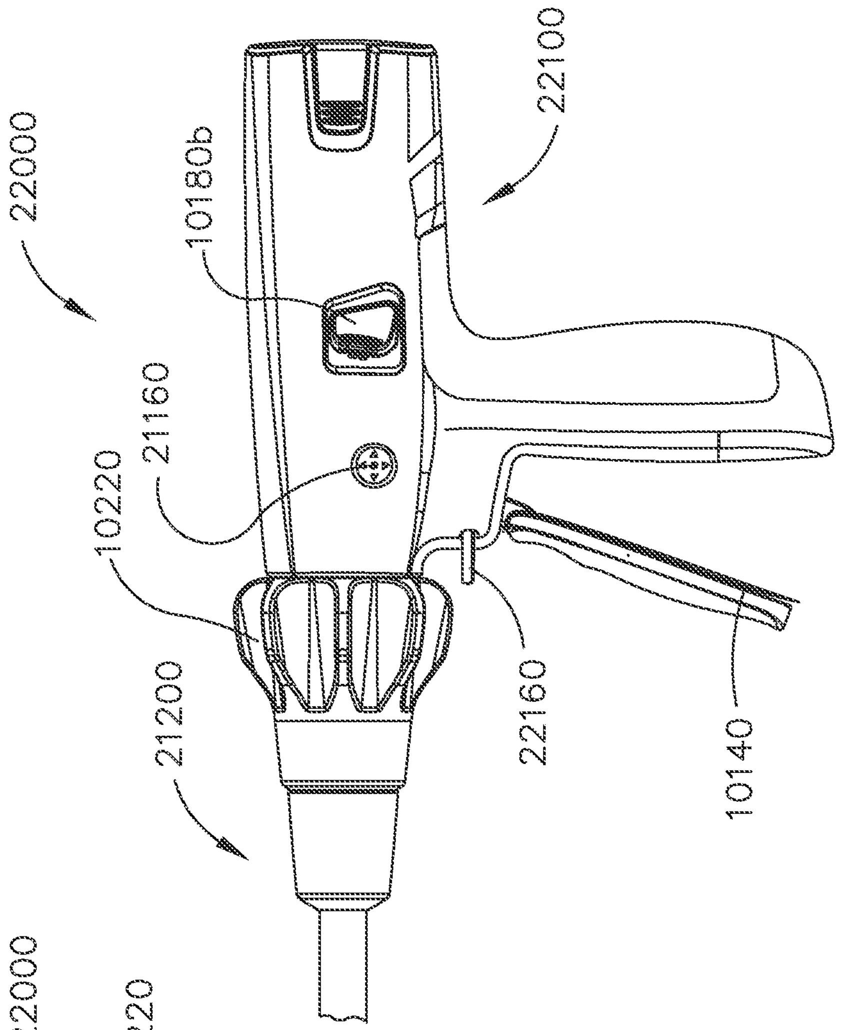
FIG. 22B is a partial side elevational view of the surgical instrument of FIG. 22A.
Figure 22A:
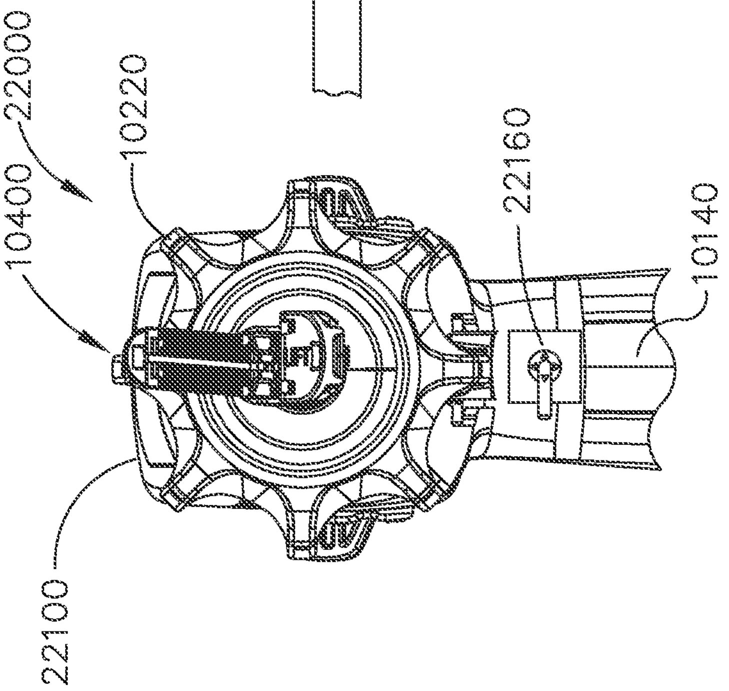
FIG. 22A is a front elevational view of a surgical instrument in accordance with at least one embodiment including a plurality of articulation controls.

A surgical instrument 22000 is illustrated in FIGS. 22A and 22B. The surgical instrument 22000 is similar to the surgical instrument 21000 in many respects. The surgical instrument 22000 comprises a handle 22100 and a shaft 21200 extending from the handle 22100. The handle 22100 comprises the articulation actuator 21160 positioned on the side of the handle 22100 and, in addition, an articulation actuator 22160 positioned on the front of the handle 22100. Similar to the articulation actuator 21160, the articulation actuator 22160 comprises a three-dimensional joystick in communication with the control system of the surgical instrument 21000 and is capable of articulating the end effector of the surgical instrument 21000 in a three-dimensional field. The front articulation actuator 22160 is readily accessible by the index finger of a clinician holding a pistol grip of the handle 22100. Alternative embodiments are envisioned which comprise the articulation actuator 22160, but not the articulation actuator 22160.

Figure 23:
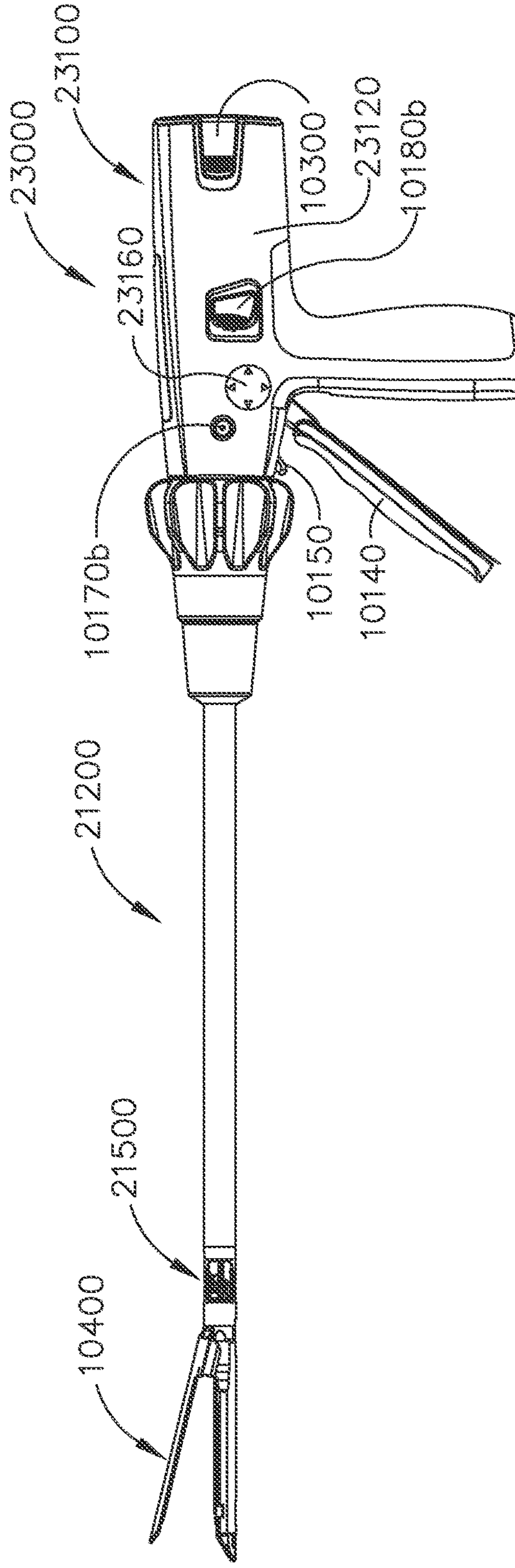
FIG. 23 is an elevational view of a surgical instrument in accordance with at least one embodiment including a 4-way tactile articulation control.

Referring to FIG. 23, a surgical instrument 23000 comprises a shaft 21200 including an articulation joint 21500 which allows for three-dimensional articulation motion of the end effector 10400. The surgical instrument 23000 further comprises a handle 23100 including a housing 23120 and, in addition, an articulation actuator 23160 in communication with a control system of the surgical instrument 23000. The articulation actuator 23160 comprises a four-way tactile control movable proximally, distally, upwardly, downwardly, and in compound directions. The four-way tactile control is movable distally to articulate the end effector to the right of the handle 23100 and proximally to articulate the end effector to the left of the handle 23100. The four-way tactile control is movable upwardly to articulate the end effector upwardly and downwardly to articulate the end effector downwardly. The four-way tactile control is also movable in a compound direction that is both upward and distal to move the end effector in a direction that is both upward and to the right, for example. The four-way tactile control is also movable in a compound direction that is both downward and proximal to move the end effector in a direction that is both downward and to the left, for example. In at least one instance, the four-way tactile control comprises four depressable actuators—one for each direction of right, left, up, and down—and each of which is part of a control circuit in communication with the control system of the surgical instrument 23000. The movement of the four-way tactile control is detectable by the control system which operates the articulation system in a three-dimensional range in response to the input from the articulation actuator 23160. The articulation actuator 23160 comprises one or more biasing mechanisms, such as springs, for example configured to bias the four-way tactile control to a centered, or an at least substantially centered position, in which the control system does not articulate the end effector 10400.

Figure 24:
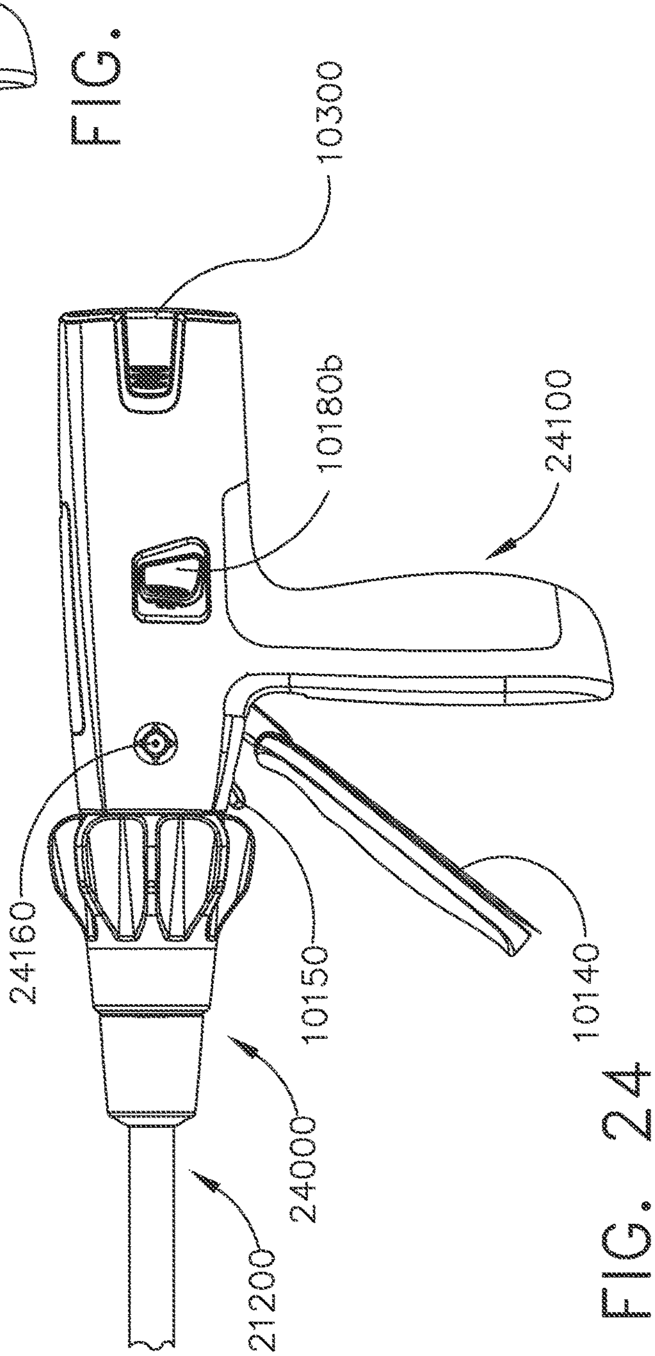
FIG. 24 is a partial elevational view of a surgical instrument in accordance with at least one embodiment including a 4-way tactile articulation control including a center, or home, actuator.

A surgical instrument 24000 is illustrated in FIG. 24. The surgical instrument 24000 is similar to the surgical instrument 23000 in many respects. The surgical instrument 24000 comprises a handle 24100 including an articulation actuator 24160. Similar to the articulation actuator 23160, the articulation actuator 24160 comprises a four-way tactile control. That said, the articulation actuator 24160 comprises an integral re-centering feature. More specifically, the articulation actuator 24160 comprises a depressable actuator positioned in the middle of the articulation actuator 24160 in communication with the control system of the surgical instrument 24000. When the center actuator is depressed, the control system operates to re-align the end effector 10400 with the longitudinal axis of the shaft 10200, much like the actuation of the actuator 10170 discussed above. As a result of the above, the re-centering actuator is positioned in the middle of the four directional actuators making for a compact and intuitive arrangement.

Figure 25:
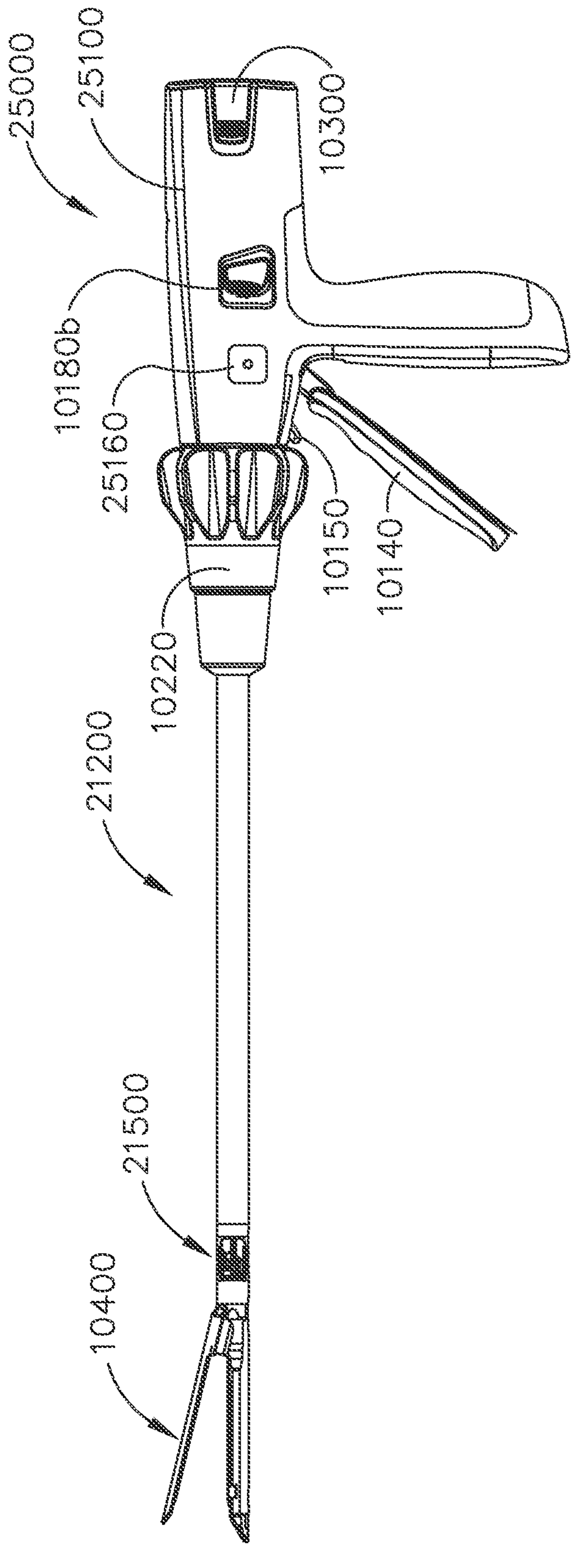
FIG. 25 is an elevational view of a surgical instrument in accordance with at least one embodiment including a 4-way capacitive surface.

A surgical instrument 25000 is illustrated in FIG. 25. The surgical instrument 25000 is similar to the surgical instrument 24000 in many respects. The surgical instrument 25000 comprises a handle 25100 including an articulation actuator 25160. Similar to the articulation actuator 23160, the articulation actuator 25160 comprises a four-way control in communication with a control system of the surgical instrument 25000. That said, the four-way control comprises a capacitive surface which allows a clinician to tap and/or drag their finger across the surface of the articulation actuator 25160 to control the articulation of the end effector in a three-dimensional range. In at least one instance, the articulation actuator comprises a touchscreen and an array of capacitive sensors positioned under the touchscreen configured to detect the presence and/or motion of the clinician's finger, for example. In use, tapping the top of the capacitive surface articulates the end effector 10400 upwardly, tapping the bottom of the capacitive surface articulates the end effector 10400 downwardly, tapping the distal end of the capacitive surface articulates the end effector 10400 to the right, and tapping the proximal end of the capacitive surface articulates the end effector 10400 to the left, for example. Tapping the center of the articulation screen re-centers the end effector 10400 along the longitudinal axis of the shaft 21200. When a rotating motion is made on the surface of the articulation actuator 25160, the control system rotates the end effector 10400 in the direction and/or speed indicated by the rotating motion. In various instances, the control system of the surgical instrument 25000 comprises a pulse width modulation (PWM) control circuit for controlling the speed of the electric motor used to drive the articulation system of the surgical instrument 25000. In at least one embodiment, the control system comprises a frequency modulation (FM) control circuit in addition to or in lieu of the PWM control circuit for controlling the speed of the articulation motor.

As discussed above, an end effector of a surgical instrument can be rotatable in more than one direction and/or plane. To achieve this, in various embodiments, a surgical instrument comprises a first motor-driven system for moving the end effector in a left-to-right manner and a second motor-driven system for moving the end effector in an up-to-down manner. Both motor-driven systems are in communication with the control system of the surgical instrument and are drivable sequentially and/or concurrently by the control system to position the end effector in the direction indicated by the input from the articulation actuator, or articulation actuators.

Figure 29:
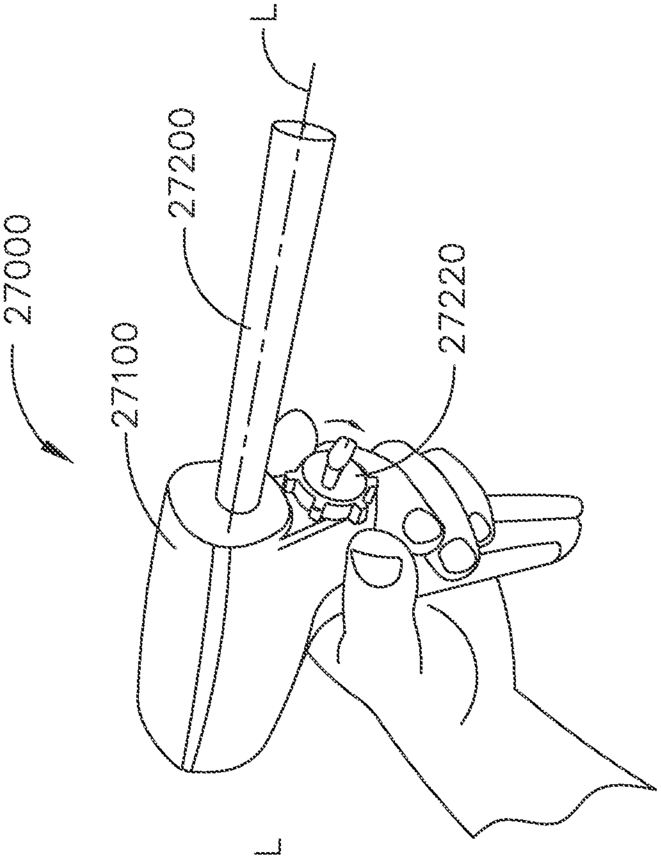
FIG. 29 is a perspective view of a surgical instrument in accordance with at least one embodiment comprising a handle, a rotatable shaft extending from the handle, and a rotatable actuator on the handle configured to rotate the shaft about a longitudinal axis.
Figure 30:
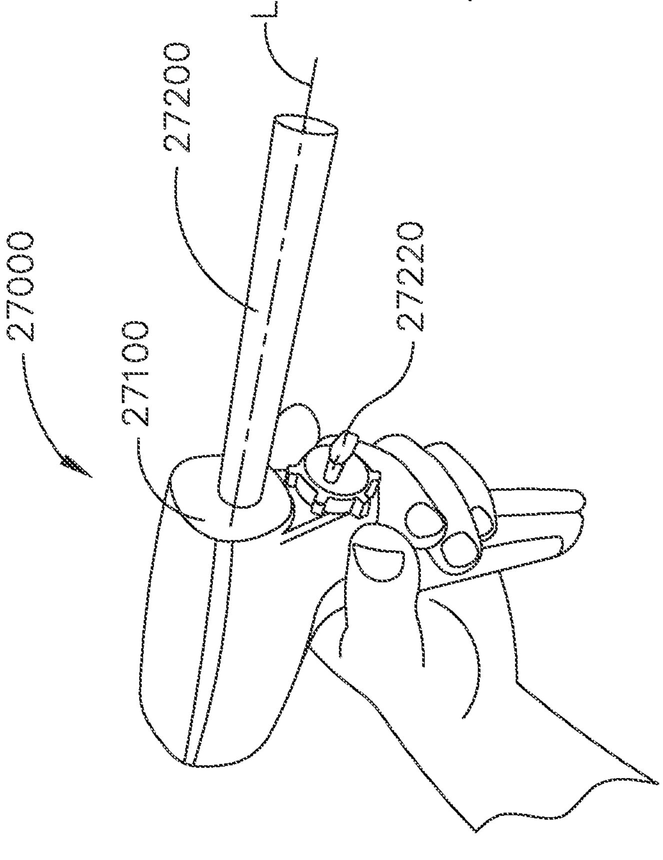
FIG. 30 is a perspective view of the surgical instrument of FIG. 29 illustrating the shaft in a rotated position.
Figure 31:
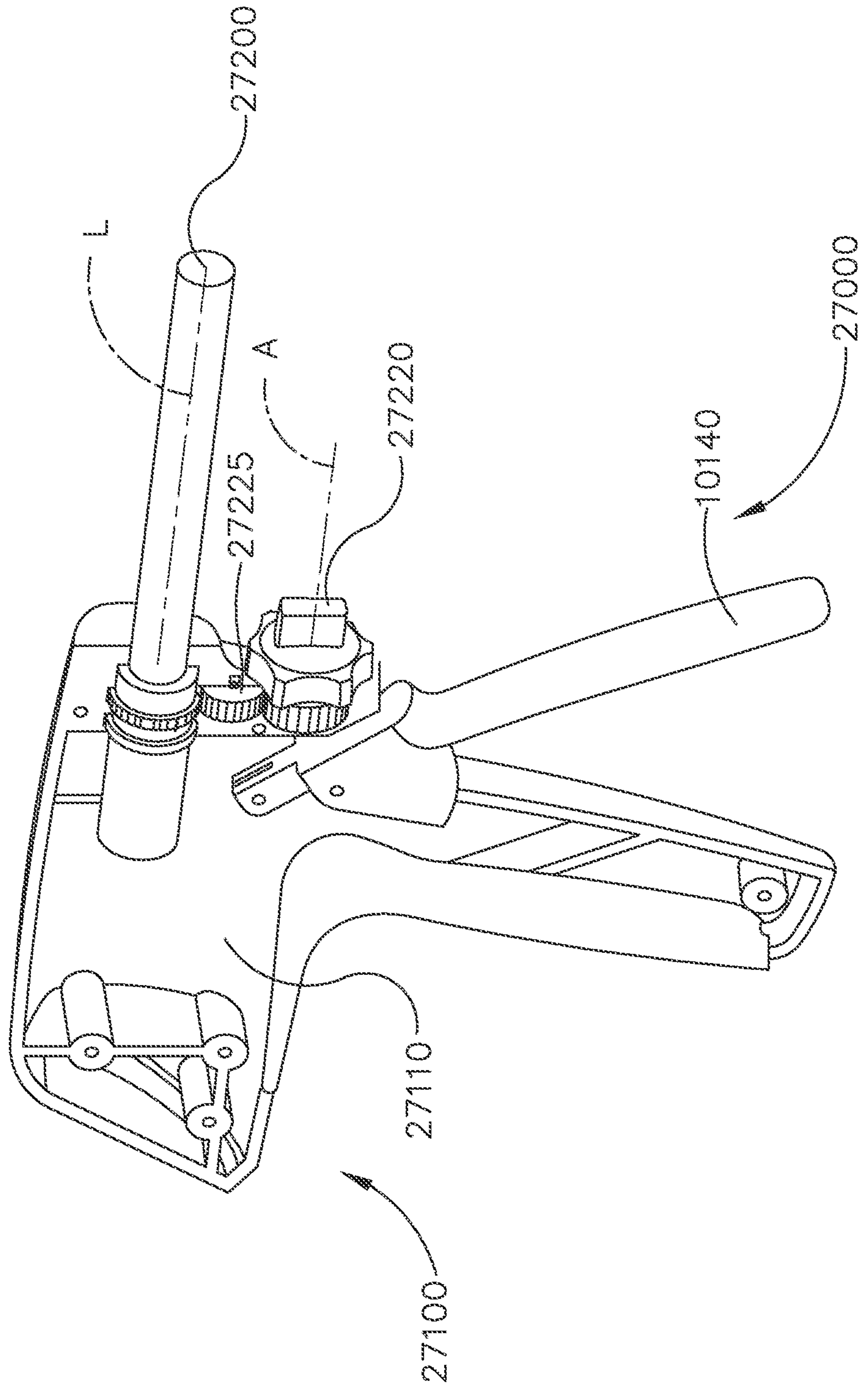
FIG. 31 is a perspective view of the surgical instrument of FIG. 29 illustrated with a portion of the handle housing removed.

Many of the surgical instruments described above comprise a grip configured to be grasped by a clinician to rotate the shaft about a longitudinal axis. In various instances, the clinician can hold the grip with one hand and can extend their index finger, for example, from that hand to grab the grip and rotate the shaft. Such an arrangement, however, requires the clinician to have a somewhat larger hand. While such a surgical instrument can be operated with one hand, a surgical instrument 27000 is illustrated in FIGS. 29 and 30 that may be easier to use. The surgical instrument 27000 comprises a handle 27100 and a shaft 27200 extending from the handle 27100 that is rotatable about a longitudinal axis. The handle 27100 comprises a handle frame 27110 and a housing that rotatably support the shaft 27200. The handle 27100 further comprises an actuator 27220 positioned on the front side of the handle housing 27110 which, when rotated by the clinician, rotates the shaft 27200 about its longitudinal axis L. The actuator 27220 is rotatably mounted to the handle housing 27110 and is rotatable about an axis A which is parallel to, or at least substantially parallel to, the longitudinal axis of the shaft 27200. The actuator 27220 comprises a ring of gear teeth extending around its perimeter which is operably engaged with a ring of gear teeth extending around the perimeter of the shaft 27200 via a transmission gear 27225 such that, when the actuator 27220 is rotated about its axis, the shaft 27200 is rotated about its longitudinal axis. That said, the gear teeth of the actuator 27220 are not directly engaged with the gear teeth of the shaft 27200; instead, the intermediate gear 27225—which is rotatably mounted in the handle 27100—is directly engaged with the gear teeth of the actuator 27220 and the shaft 27200. Such an arrangement synchronizes the motion of the actuator 27220 and the shaft 27200, i.e., rotating the actuator 27220 to the right rotates the shaft 27200 to the right and rotating the actuator 27220 to the left rotates the shaft 27200 to the left. Absent the introduction of the intermediate gear 27225, the shaft 27200 would rotate in an opposite direction, but such an arrangement may provide a torque balance that promotes the stability of the instrument.

Further to the above, embodiments are envisioned in which the rotation of the shaft 27200 is driven by an electric motor. In various embodiments, the actuator 27220, when rotated in the first direction, operates the electric motor to rotate the shaft 27200 in the first direction. Similarly, the electric motor rotates the shaft 27200 in the second direction when the actuator 27220 is rotated in the second direction. In at least one embodiment, the output shaft of the electric motor comprises a pinion gear operably intermeshed with the ring of gear teeth around the shaft 27200. Moreover, in at least one embodiment, the actuator 27220 comprises one or more sensors configured to detect the direction and degree of rotation of the actuator 27220 which are in communication with a control system of the surgical instrument. With this data, the control system is configured to control the direction and speed of the electric motor. In instances where the actuator 27220 is rotated a small amount in the first direction, for example, the shaft 27220 is rotated slowly in the first direction whereas the shaft 27220 is rotated quickly in the first direction when the actuator 27220 is rotated a larger amount in the first direction.

Further to the above, the actuator 27220 comprises a bar including a first end and a second end. The orientation of the bar is synchronized with the orientation of the shaft 27200. When the first end of the bar is directly above the second end, i.e., the first end is closest to the shaft 27200, the shaft 27200 is in its top-dead-center (TDC) position. Correspondingly, the shaft 27200 is in its bottom-dead-center (BDC) position when the second end of the bar is directly above the first end, i.e., the second end is closest to the shaft 27200. As a result of this arrangement, the user of the surgical instrument has an intuitive feel of the orientation of the shaft 27200 based on the orientation of the actuator 27220.

Figure 51:
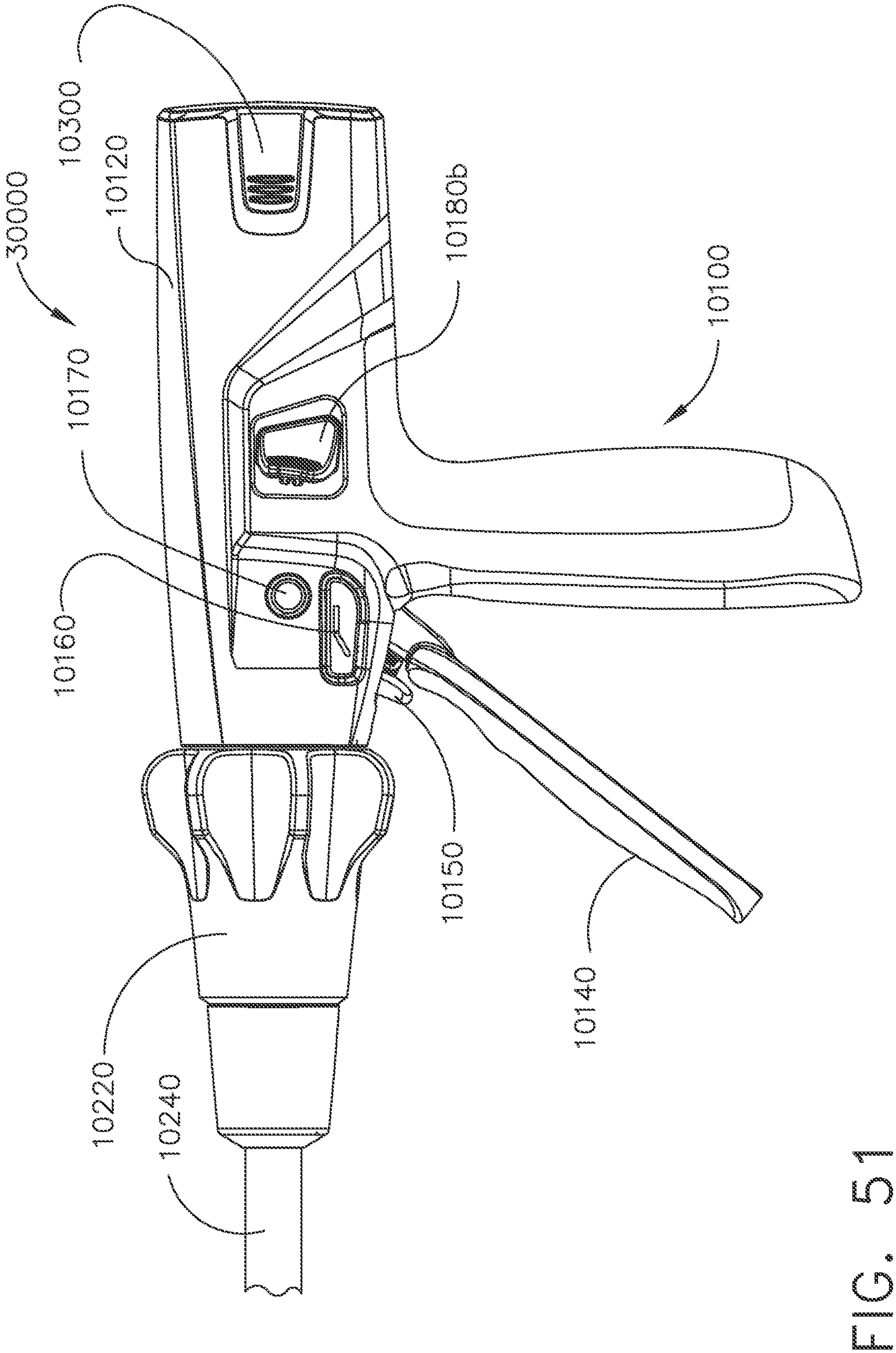
FIG. 51 is a partial elevational view of a surgical instrument in accordance with at least one embodiment.
Figure 52:
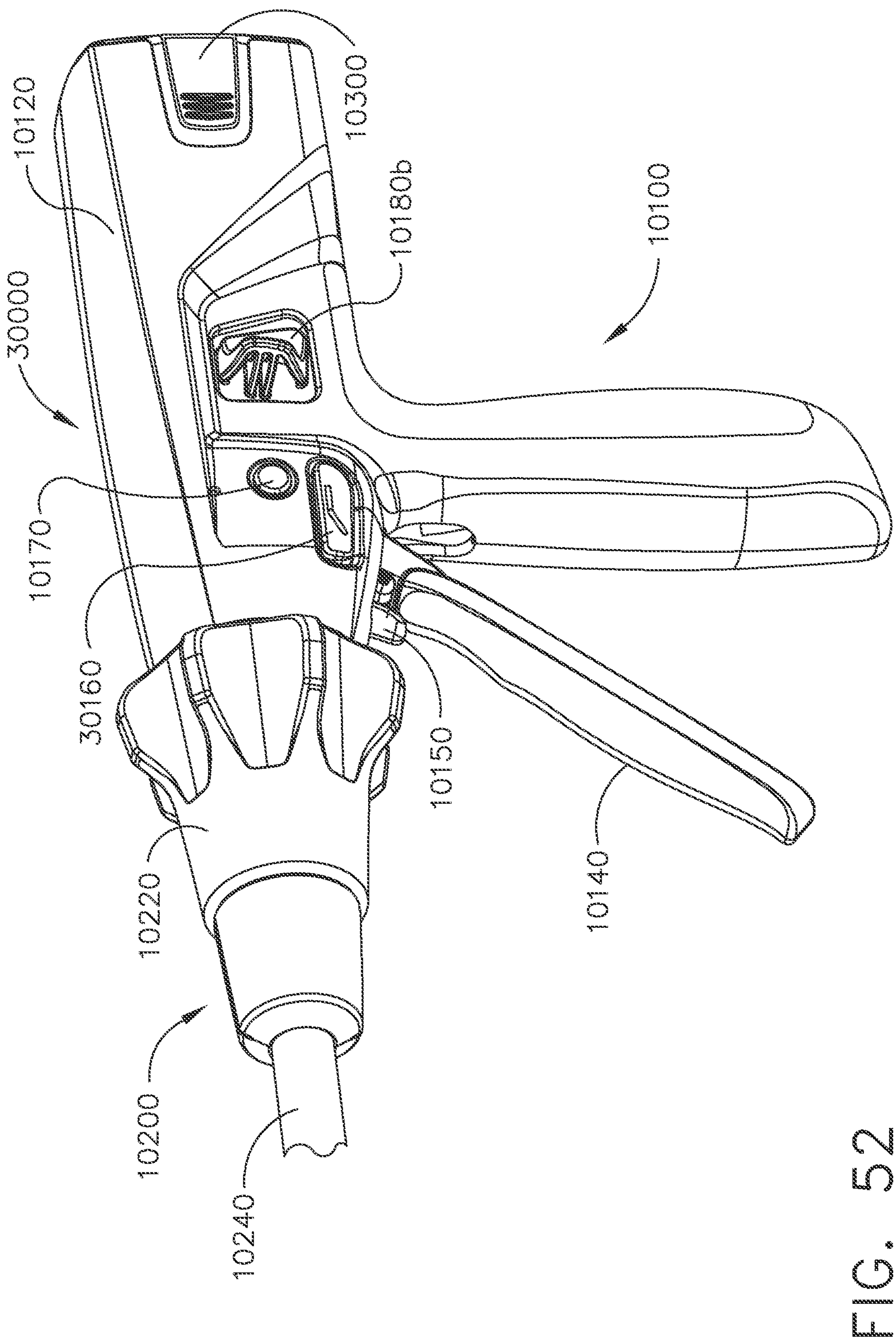
FIG. 52 is a partial perspective view of the surgical instrument of FIG. 51.
Figure 53:
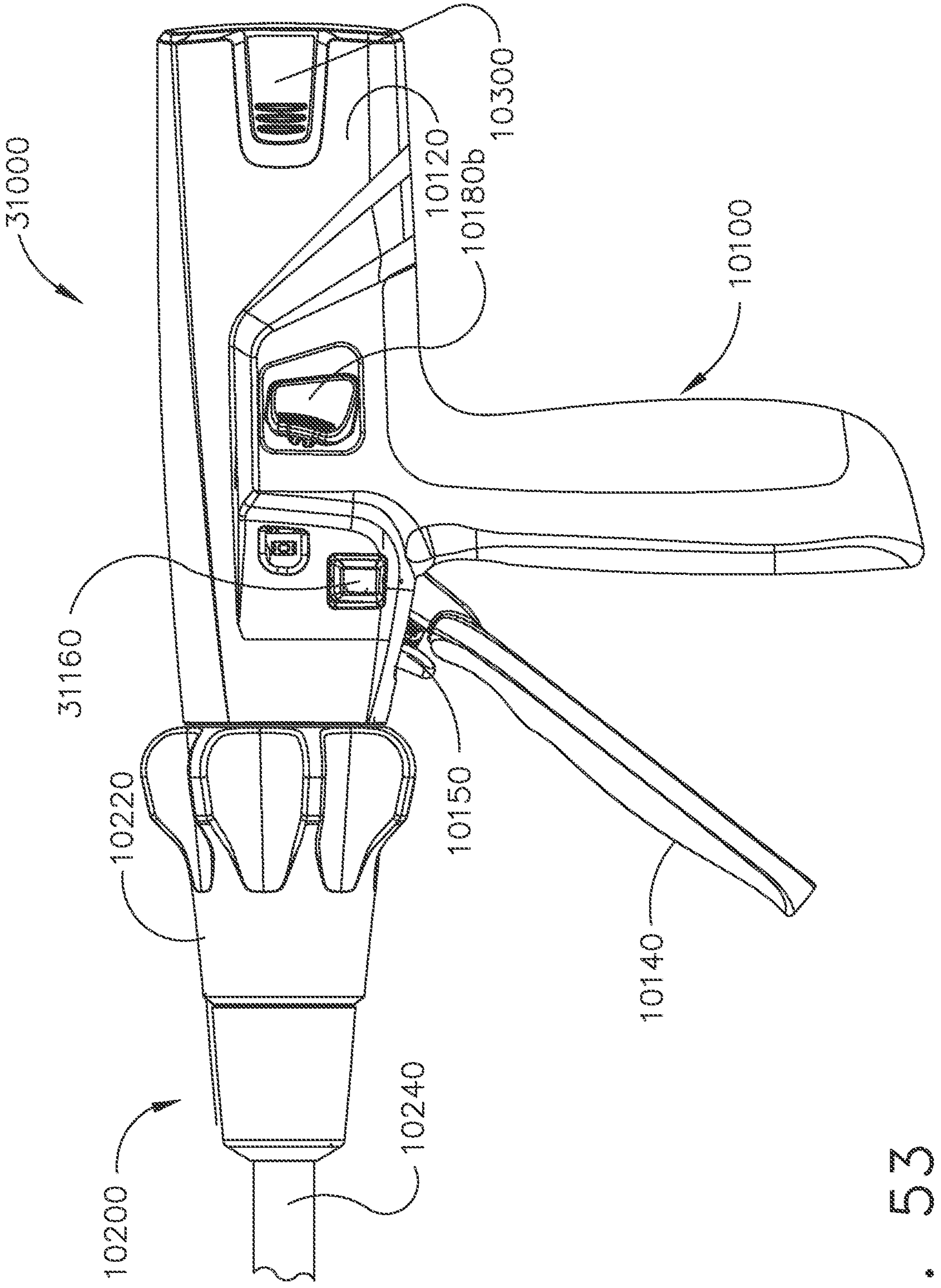
FIG. 53 is a partial elevational view of a surgical instrument in accordance with at least one embodiment.
Figure 54:
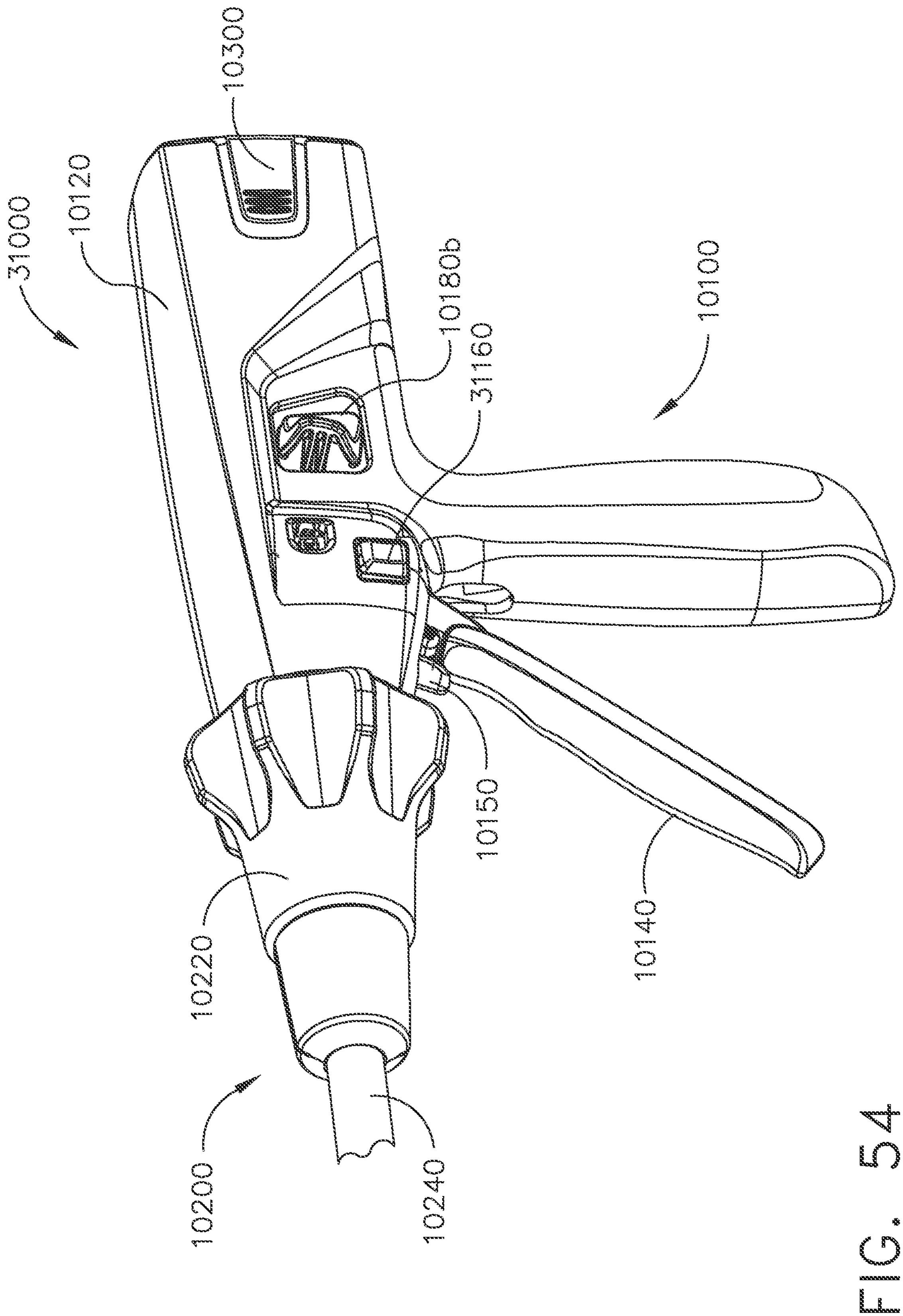
FIG. 54 is a partial perspective view of the surgical instrument of FIG. 53.

A surgical instrument 30000 is illustrated in FIGS. 51 and 52. The surgical instrument is similar to the surgical instrument 10000 in many respects. As opposed to the vertical articulation actuator 10160, the handle of the surgical instrument 30000 comprises a horizontal articulation actuator 30160. The horizontal articulation actuator 30160 comprises a rocker switch which can be rocked distally to rotate the end effector to the right and rocked proximally to rotate the end effector to the left. A surgical instrument 31000 is illustrated in FIGS. 53 and 54. The surgical instrument is similar to the surgical instrument 10000 in many respects. As opposed to the vertical articulation actuator 10160, the handle of the surgical instrument 31000 comprises an articulation actuator 31160. The articulation actuator 31160 comprises a multi-axis rocker switch that can be rocked proximal-to-distal to articulate the end effector in one plane and up-to-down to articulate the end effector in another plane. In various instances, the articulation planes are orthogonal to one another, but can be arranged in any suitable manner.

Figure 59:
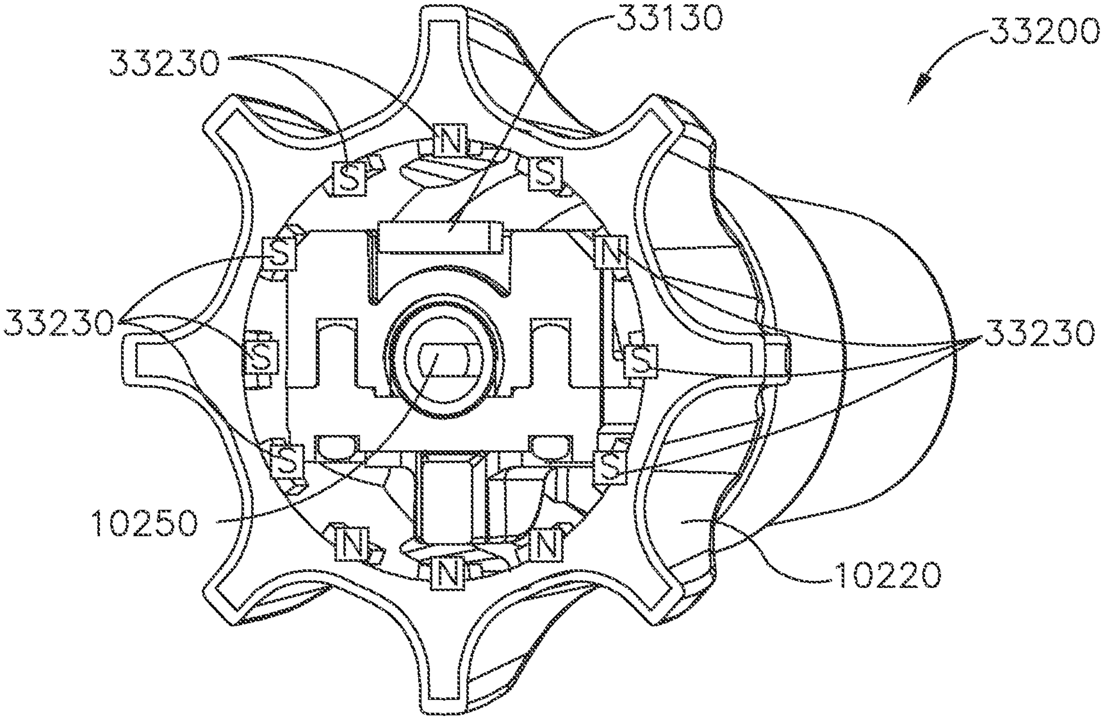
FIG. 59 is a partial perspective view of a shaft of a surgical instrument in accordance with at least one embodiment.

As discussed above, the control system of a surgical instrument can comprise an algorithm which, according to predetermined criteria, flips and/or otherwise re-orients the controls of the surgical instrument in certain instances. In various instances, as also discussed above, the algorithm can be configured to flip the articulation controls of the surgical instrument based on the rotation of the shaft relative to the handle. Referring to FIG. 59, a surgical instrument comprises a handle comprising a Hall Effect sensor 33130, and/or any other suitable sensor, in communication with the control system of the surgical instrument and, in addition, a shaft 33200 including an array of magnets 33230 arranged in a circular, or annular, pattern around the shroud, or grip, 10220 of the shaft 33200. Each magnet 33230 comprises a north pole (N) and a south pole (S) and the magnets 33230 are arranged in the manner indicated in FIG. 59—the N poles of some of the magnets 33230 are facing the handle while some S poles are facing toward the handle. When the shaft 33200 is rotated relative to the handle, this arrangement of the magnets 33230 allows the control system to track the position of the shaft 33200 and understand the orientation, or rotation, of the shaft 33200 relative to the handle. Within any three consecutive magnets 33230, for example, the pattern of magnets 33230 create a unique identifiable signature for a given rotation direction. That said, any suitable number and/or arrangement of discrete magnets could be used. Although twelve magnets 33230 are used, less than twelve magnets could be used—such as six magnets, for example. Moreover, more than twelve magnets could be used.

Figure 60:
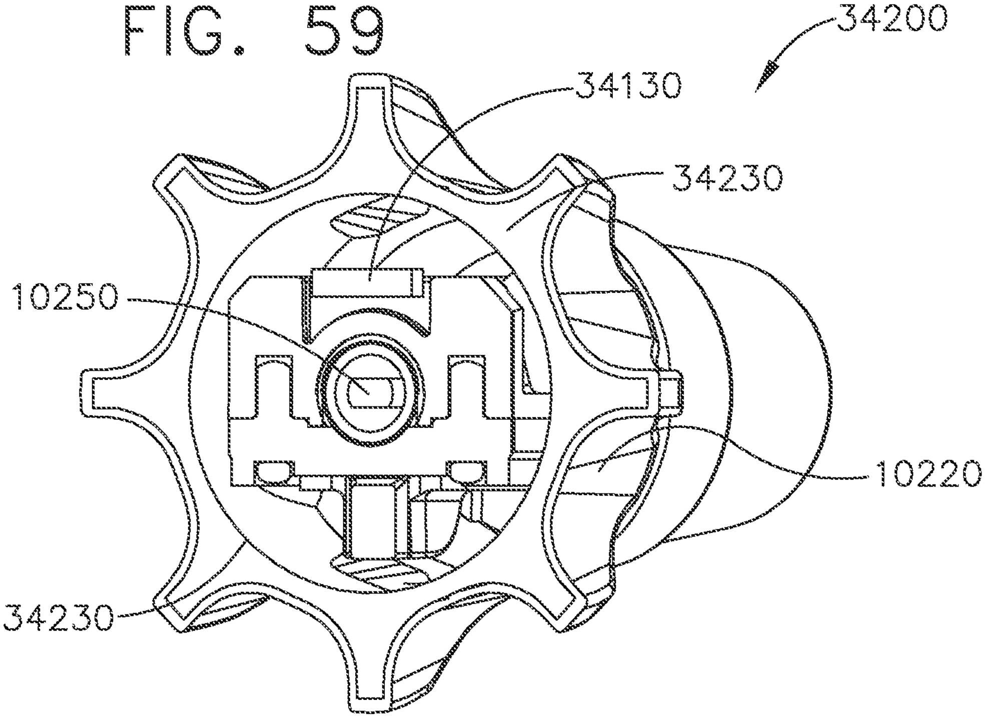
FIG. 60 is a partial perspective view of a shaft of a surgical instrument in accordance with at least one embodiment.

Referring to FIG. 60, a surgical instrument comprises a handle comprising a Hall Effect sensor 34130, and/or any other suitable sensor, in communication with the control system of the surgical instrument and, in addition, a shaft 34200 including a continuous annular magnet 34230 attached to the shroud, or grip, 10220 of the shaft 34200. In various instances, the annular magnet 34230 comprises a disc or ring embedded with magnetic microstructures which is detectable by the Hall Effect sensor. The annular magnet 34230 comprises a continuous, but varying, magnetic pattern around the perimeter thereof which provides a trackable pattern for the control system to assess the orientation, or rotation, of the shaft 34200. In other embodiments, the annular magnet 34230 comprises an intermittent magnetic pattern around the perimeter thereof that is trackable by the control system.

Figure 61:
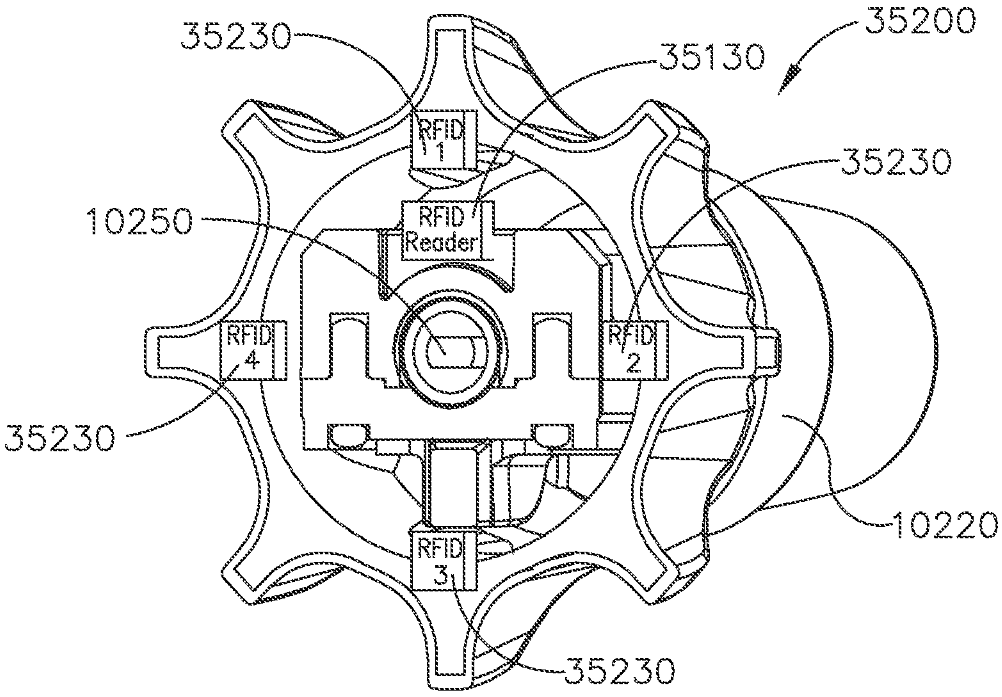
FIG. 61 is a partial perspective view of a shaft of a surgical instrument in accordance with at least one embodiment.

Referring to FIG. 61, a surgical instrument comprises a handle comprising a RFID reader 35130 in communication with the control system of the surgical instrument and, in addition, a shaft 35200 including a circular, or annular, array of RFID chips 35230 around the shroud, or grip, 10220 of the shaft 35200. Each RFID chip comprises a unique identification which is detectable by the RFID reader 35130 and, with this information, the control system is able to assess the orientation, or rotation, of the shaft 35200 relative to the handle. Notably, the RFID reader 35130 has a limited range to read the RFID chips 35230 and, thus, may be only able to read the most-adjacent RFID chip 35230. In some instances, the RFID reader 35130 can have sufficient range to read the two most-adjacent RFID chips 35230. The shaft 35200 comprises four RFID chips 35230, but can comprise any suitable number of RFID chips 35230. That said, the accuracy, or resolution, of the assessment made by the control system can be improved with more RFID chips in various instances.

Figure 62:
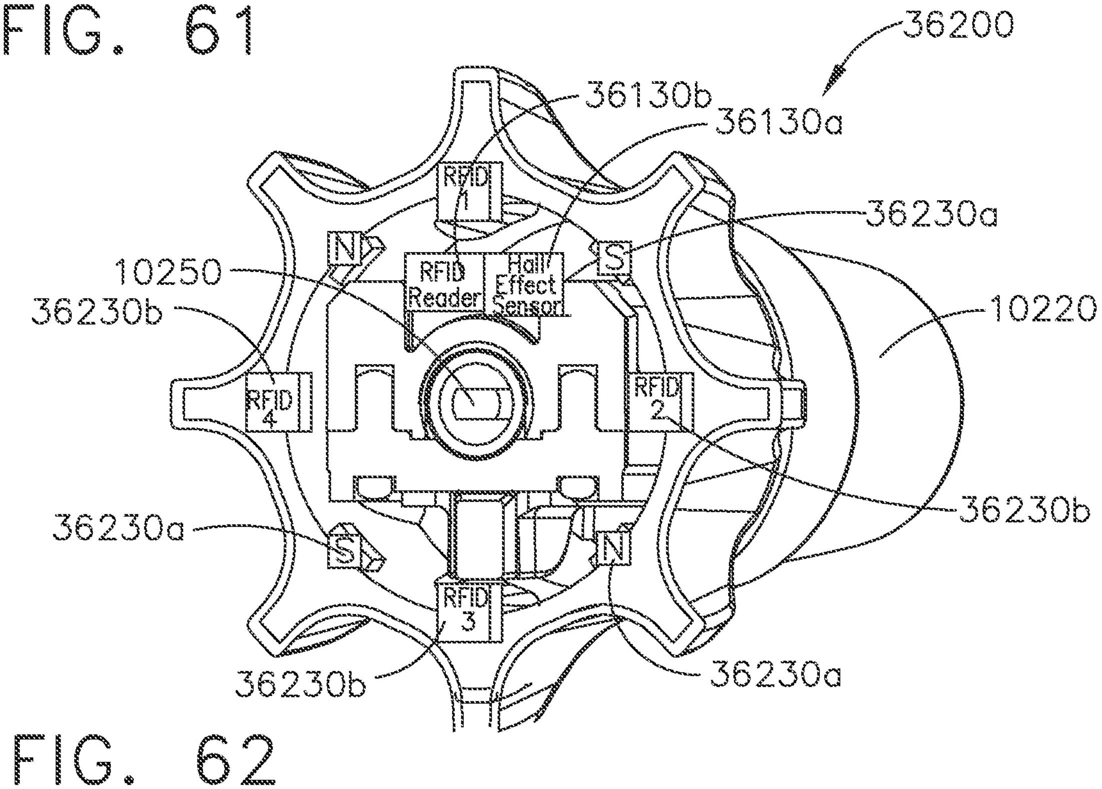
FIG. 62 is a partial perspective view of a shaft of a surgical instrument in accordance with at least one embodiment.

Referring to FIG. 62, a surgical instrument comprises a handle comprising a Hall Effect sensor 36130*a*, and/or any other suitable sensor, in communication with the control system of the surgical instrument and, in addition, a shaft 36200 including an array of magnets 36230*a* arranged in a circular, or annular, pattern around the shroud of the shaft 36200. The handle also comprises a RFID reader 36130*b* in communication with the control system of the surgical instrument and, in addition, a circular, or annular, array of RFID chips 36230*b* around the shroud of the shaft 36200. The control system is configured to use the data from the Hall Effect sensor 36130*a* and the RFID reader 36130*b* to assess the orientation of the shaft 36200 relative to the handle. Notably, the RFID chips 36230*b* are positioned intermediate the magnets 36230*a* which provides the control system with a detectable resolution between adjacent magnets 36230*a*. Similarly, the magnets 36230*a* are positioned intermediate the RFID chips 36230*b* which provides the control system with a detectable resolution between the RFID chips 36230*b*.

Figure 63:
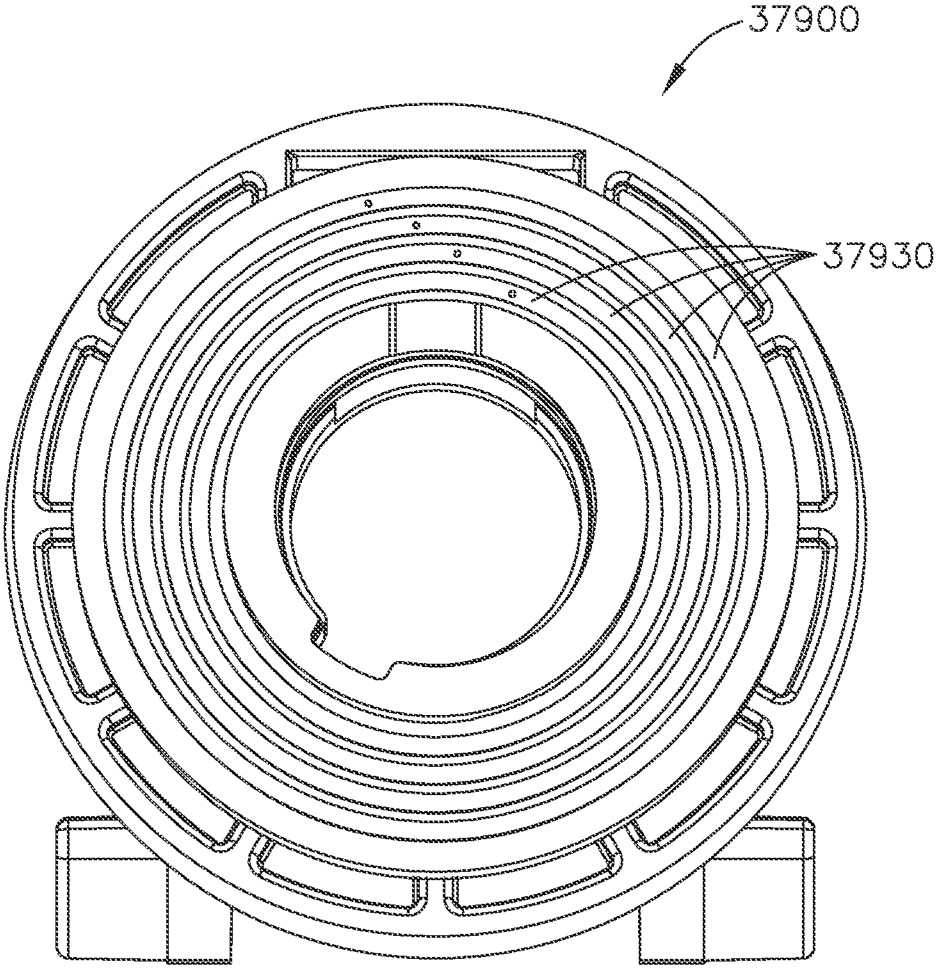
FIG. 63 is a perspective view of a slip ring assembly of a surgical instrument in accordance with at least one embodiment.
Figure 64:
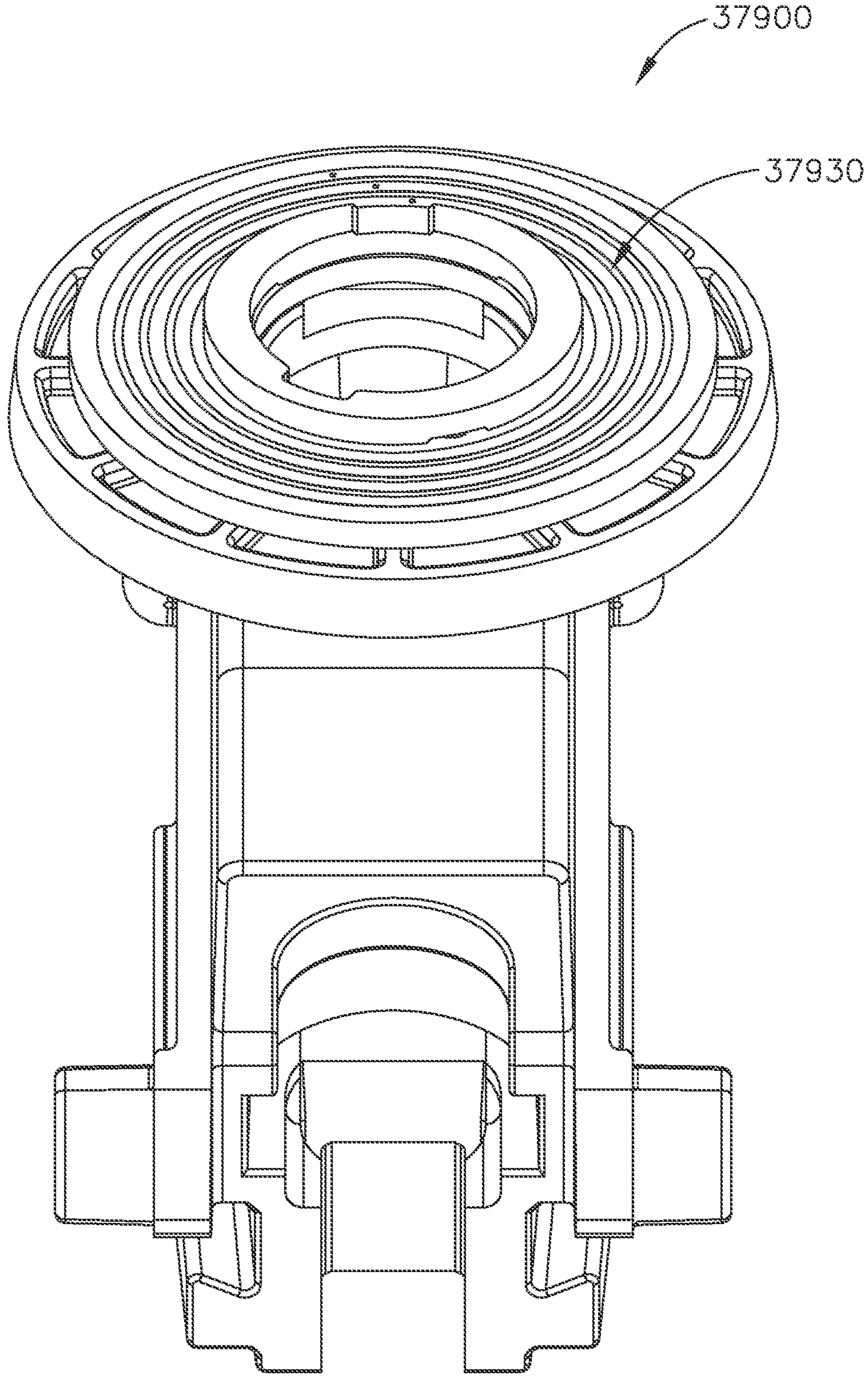
FIG. 64 is another perspective view of the slip ring assembly of FIG. 63.
Figure 65:
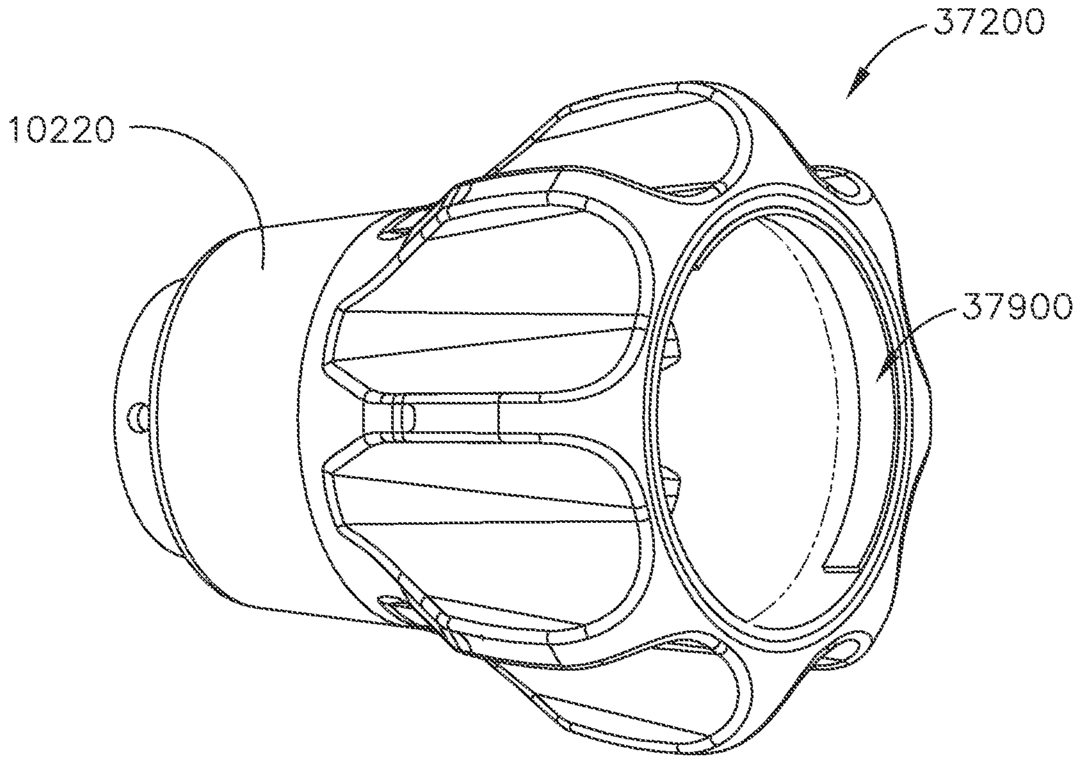
FIG. 65 is a perspective view of a shaft component of the surgical instrument of FIG. 63.
Figure 66:
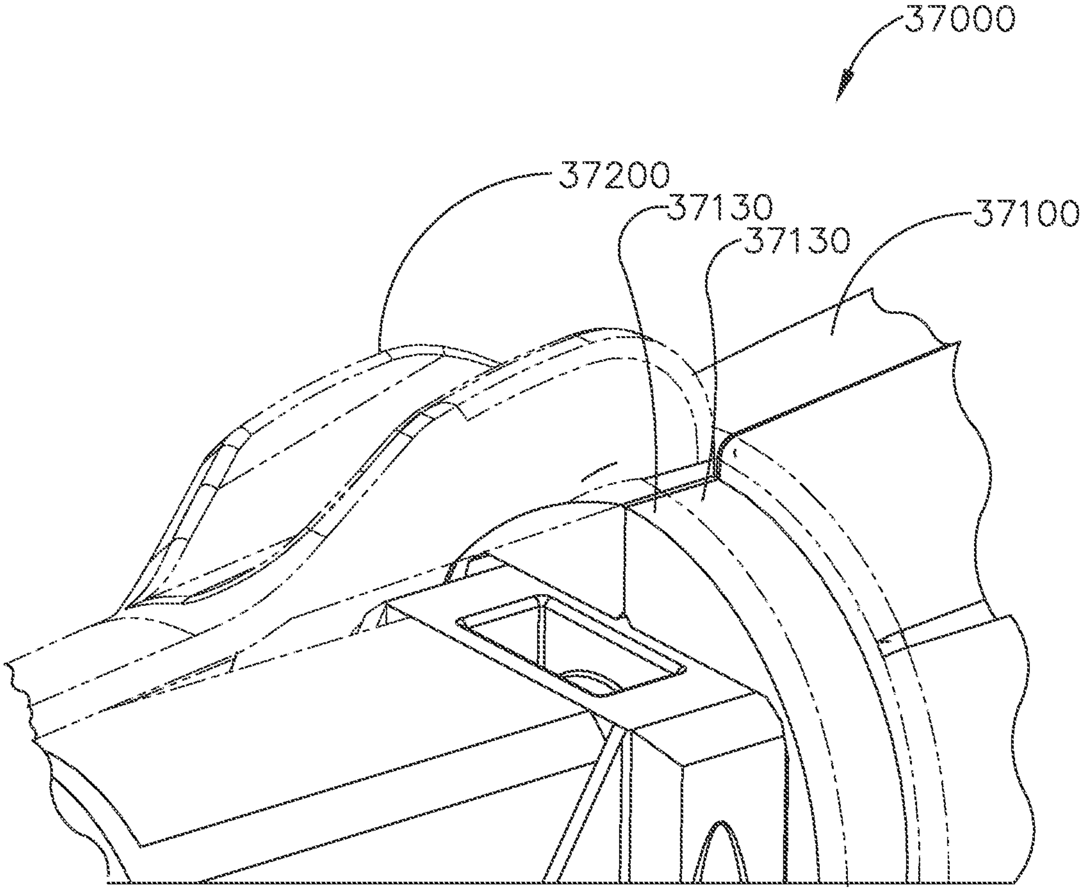
FIG. 66 is a partial perspective view of the surgical instrument of FIG. 63.

A surgical instrument 37000 is illustrated in FIGS. 63-66. The surgical instrument 37000 comprises a handle 37100 and a shaft 37200 extending from the handle 37100. The surgical instrument 37000 further comprises a slip joint 37900 between the handle 37100 and the shaft 37200. The slip joint 37900 comprises an electrical interface between the handle 37100 and the shaft 37200. The slip joint 37900 comprises annular rings 37930 mounted in the shaft 37200. Four annular rings 37930 are depicted in FIGS. 63 and 64, but a slip joint can comprise any suitable number of rings. The slip joint 37900 further comprises electrical contacts 37130 in the handle 37100. For instance, the slip joint 37900 comprises a first electrical contact 37130 engaged with a first annular ring 37930 and a second electrical contact 37130 engaged with a second annular ring 37930. That said, the slip joint 37900 can comprise any suitable number of electrical contacts to maintain power and/or signal communication between the handle and the shaft. Throughout the rotation of the shaft 37200, i.e., all 360 degrees, the electrical contacts 37130 remain in electrical contact with their respective annular rings 37930. In various instances, each electrical contact 37130 comprises a spring element configured to bias the electrical contact towards its respective annular ring 37930. The electrical contacts 37130 are in communication with the control system of the surgical instrument 37000—via separate circuits—such that the control system can assess the resistance of the circuits, and/or any other electrical properties of the circuits between the control system and the slip joint 37900. That said, the electrical contacts and rings of the slip joint 37900 can be part of any suitable circuit arrangement.

Further to the above, the slip joint 37900 can be used as an absolute position sensor for the shaft 37200 relative to the handle 37100. More specifically, an intermediate annular ring 37930, i.e., the annular ring 37930 between the first ring 37930 and the second ring 37930, can be used by the control system to assess the orientation of the shaft 37200. To this end, the slip joint 37900 comprises an intermediate electrical contact 37130 in electrical communication with the intermediate annular ring 37930 and the control system as part of an intermediate electrical circuit. The intermediate annular ring 37930 is comprised of a high-resistance material, as compared to the first and second annular rings 37930, and provides a 10,000 Ohm resistance, for example. The intermediate annular ring 37930 has a first portion which is electrically coupled to the first annular ring 37930, a second annular portion which is electrically coupled to the second annular ring 37930, and a small break therebetween. When the shaft 37200 is rotated relative to the handle 37100, the intermediate electrical contact 37130 slides along the intermediate annular ring 37930 and the resistance and voltage of the intermediate electrical circuit changes in a manner which is detectable by the control system owing to the closing and opening of the break by the intermediate contact 37130. The signal from the intermediate electrical circuit is digitized by an analog-digital converter of the control system, the data from which is usable by the control system to assess the orientation of the shaft 37200. In various instances, any suitable number of gaps in the intermediate annular ring 37930 and/or intermediate contacts 37130 can be used to provide a signal with sufficient resolution to determine the orientation, or rotation, of the shaft 37200 relative to the handle 37100.

In various embodiments, a resistive material is embedded in the shaft of a surgical instrument which is part of an electrical circuit that passes through a slip ring. As the shaft rotates, the resistance in the electrical circuit changes—which is detectable by the control system of the surgical instrument to assess the angular orientation of the shaft relative to the handle.

Figure 67:
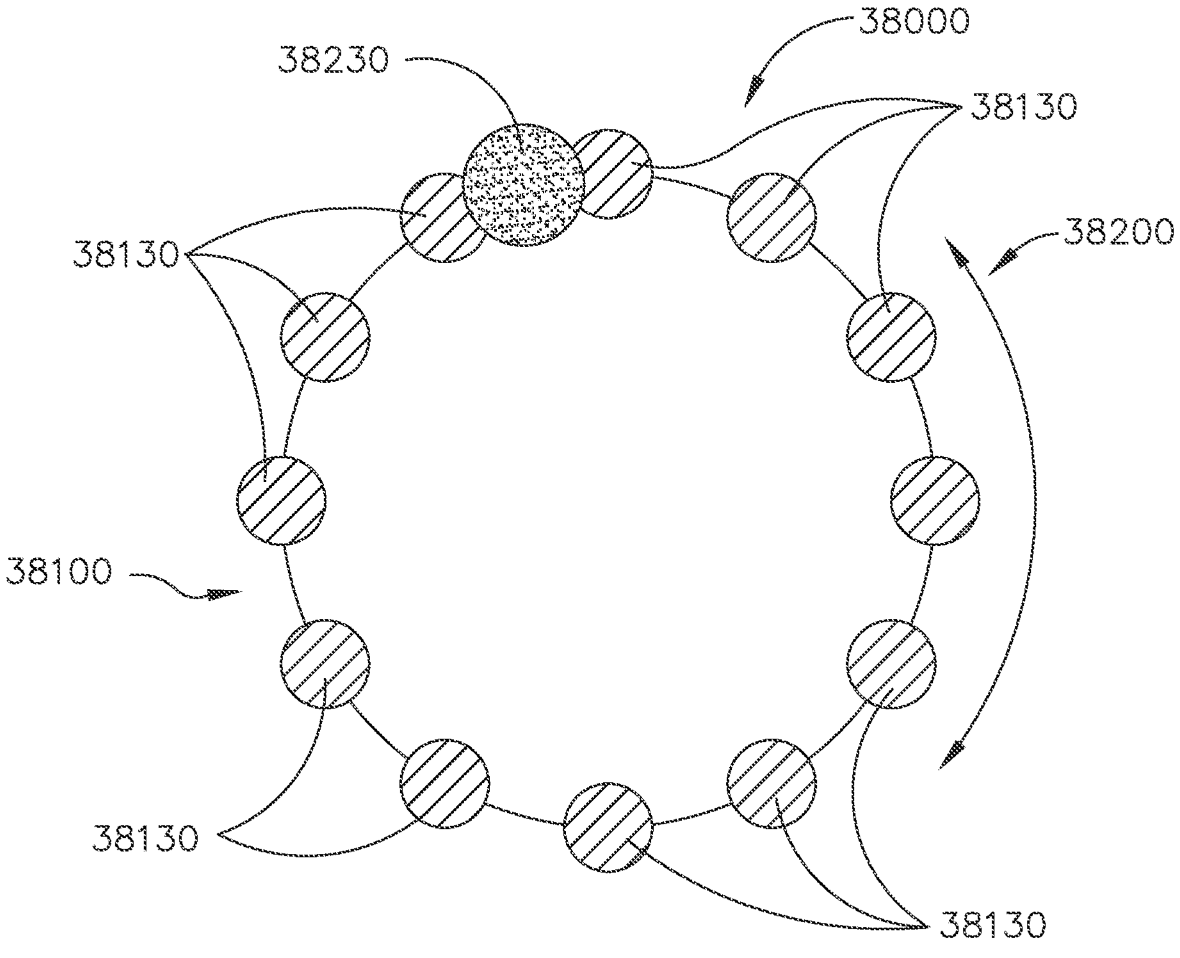
FIG. 67 is a diagram depicting a shaft orientation sensor array in accordance with at least one embodiment.

A representation of a surgical instrument 38000 is illustrated in FIG. 67. The surgical instrument 38000 comprises a handle 38100 and a shaft 38200 extending from the handle 38100. The handle 38100 comprises an annular array of Hall Effect sensors 38130 affixed to the frame and/or housing of the handle 38100. The Hall Effect sensors 38130 are positioned along a circumference in the handle 38100, as illustrated in FIG. 67. The Hall Effect sensors 38130 are in communication with the control system via electrical circuits. The shaft 38200 comprises a magnet 38230 mounted to the shroud of the shaft 38200 which is aligned, or at least substantially aligned, with the circumference of the Hall Effect sensors 38130. When the shaft 38200 is rotated about its longitudinal axis, the magnet 38230 moves along the sensor circumference. The sensors 38130 are positioned and arranged such that one or more of the sensors 38130 can detect the position of the magnet 38230 and, thus, the control system can determine the orientation of the shaft 38200 relative to the handle 38100 based on which Hall Effect sensors 38130 have detected the magnetic distortion, and the distortion intensity, created by the magnet 38230.

In various embodiments, a surgical instrument can include one or more optical sensors configured to detect the orientation of the shaft relative to the handle. In at least one embodiment, the handle of the surgical instrument comprises a light emitter and a light detector which are in communication with the control system of the surgical instrument. The shaft comprises a reflective surface that rotates with the shaft. The light emitter emits light onto the reflective surface and the light is reflected back into the light detector. The reflective surface comprises different portions with different reflectivities which creates patterns in the light reflected back to the light detector. With this information, the control system can assess the orientation of the shaft relative to the handle. In various instances, the reflective surface comprises openings and solid areas to create a binary off-on, or low-high, reflection response signal, for example.

In various embodiments, a surgical instrument comprises an electromechanical transducer, such as a linear variable differential transformer, for example, used in connection with a mechanical cam to measure the depth of the cam and relate it to the rotation angle of the shaft. In various embodiments, the handle of a surgical instrument comprises a magnetometer in communication with the control system and, in addition, and the shaft comprises a magnet which is detectable by the magnetometer.

In various embodiments, the shaft of a surgical instrument comprises a gyroscope sensor in the shaft which is used by the control system to assess the orientation of the shaft relative to the handle. In at least one such embodiment, the handle also comprises a gyroscope sensor in communication with the control system such that the relative orientation of the handle and the shaft can be assessed. In various embodiments, the shaft of a surgical instrument comprises a tilt sensor which is used by the control system to assess the orientation of the shaft relative to the handle. In at least one embodiment, a SQ-MIN-200 sensor can be used. A SQ-MIN-200 sensor acts like a normally-closed sensor which chatters open and closed as it is tilted or vibrated. That said, any suitable omnidirectional sensor, for example, could be used.

In various embodiments, a detectable element can be positioned on the clamp drive or closure tube of the shaft. When the shaft is rotated, the closure tube rotates with the shaft. Thus, the one or more sensors of the handle can detect the orientation of the shaft relative to the handle via the detectable element on the shaft. When the closure tube is translated to close the end effector, as described herein, the detectable element moves relative to the one or more sensors. Such translation of the detectable element can also be used to verify the closure of the end effector. In at least one instance, a Hall Effect sensor can be used to detect the rotation and translation of the detectable element. In various instances, the control system of a surgical instrument is configured to prevent the end effector from being articulated while the end effector is closed. This arrangement provides the feedback to the control system to determine not only the responsiveness of the articulation controls, but whether or not the control system should be responsive to the input from the articulation controls at all.

Figure 32:
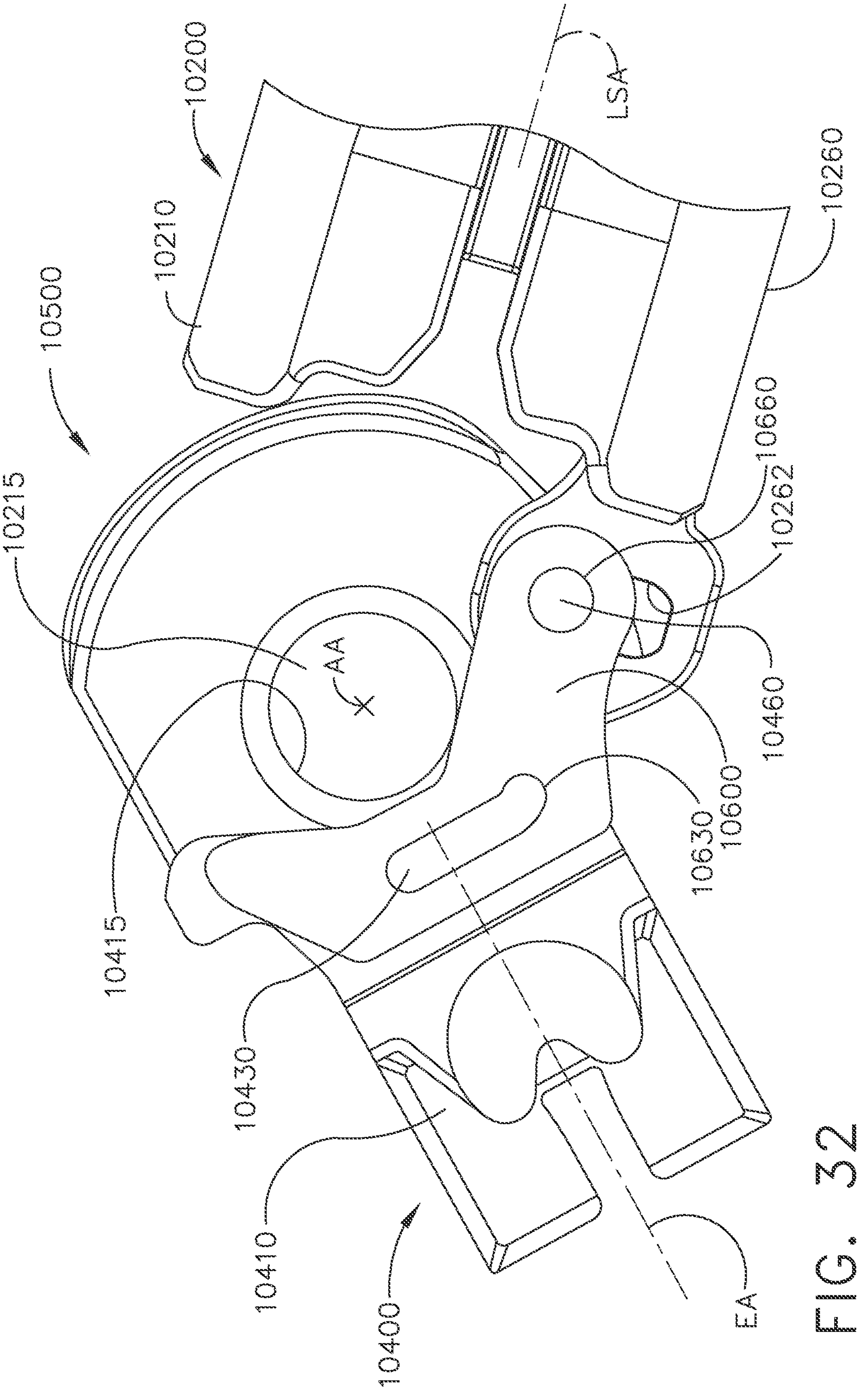
FIG. 32 is a partial detail view of the articulation joint of the surgical instrument of FIG. 1 illustrated with some components removed.

In various embodiments, referring again to FIGS. 27 and 28, the distal end of the articulation actuator 10260 of the surgical instrument 10000 is attached to the end effector 10400 such that the proximal and distal translation of the articulation actuator 10260 rotates the end effector 10400 about the articulation joint 10500. Referring to FIG. 32, the shaft 10200 of the surgical instrument 10000 comprises a shaft frame 10210 which slideably supports the articulation actuator 10260. Although not illustrated in FIG. 32, the shaft 10200 further comprises a pivot pin 10215 extending from the frame 10210. The pivot pin 10215 is closely received within a pivot aperture 10415 defined in the staple cartridge jaw 10410 of the end effector 10400 which defines an articulation axis AA of the articulation joint 10500. The articulation driver 10260 comprises a distal end including an aperture 10262 defined therein and the end effector 10400 further comprises an articulation pin 10460 extending from the proximal end of the staple cartridge jaw 10410 into the aperture 10262. When the articulation actuator 10260 is translated, as described above, the sidewalls of the aperture 10262 engage the articulation pin 10460 and either push or pull the articulation pin 10460—depending on the direction in which the articulation actuator 10260 is translated. The entire disclosure of U.S. Pat. No. 9,101,358, entitled ARTICULATABLE SURGICAL INSTRUMENT COMPRISING A FIRING DRIVE, which issued on Aug. 11, 2015, is incorporated by reference herein. The entire disclosure of U.S. Pat. No. 5,865,361, entitled SURGICAL STAPLING APPARATUS, which issued on Feb. 2, 2019, is incorporated by reference herein.

Further to the above, the end effector 10400 defines an end effector axis EA and the shaft 10200 defines a longitudinal shaft axis LSA. When the end effector 10400 is in an unarticulated position, the end effector axis EA is aligned, or at least substantially aligned, with the longitudinal shaft axis LSA. When the end effector 10400 is in an articulated position, as illustrated in FIG. 32, the end effector axis EA is transverse to the longitudinal shaft axis LSA. The aperture 10262 is elongate in order to accommodate relative movement between the articulation pin 10460 and the articulation driver 10260; however, for large articulation angles, the articulation driver 10260 may bind and/or flex which can, without more, result in the articulation driver 10260 decoupling from the articulation pin 10460. With that in mind, the end effector 10400 further comprises a retention plate 10600 configured to hold the articulation driver 10260 in engagement with the articulation pin 10460. The retention plate 10600 comprises a planar, or an at least substantially planar portion, which extends over the distal end of the articulation driver 10260 and comprises an aperture 10660 defined therein, the sidewalls of which are engaged with the articulation pin 10460. As a result, the articulation driver 10260 is trapped between the staple cartridge jaw 10410 and the retention plate 10600 such that the articulation driver 10260 does not unintentionally disengage from the staple cartridge jaw 10410. The retention plate 10600 is fixedly mounted to the staple cartridge jaw 10410 such that there is little, if any, relative movement between the retention plate 10600 and the staple cartridge jaw 10410. The staple cartridge jaw 10410 comprises a retention lug 10430 and the retention plate 10600 comprises an aperture 10630 defined therein, the sidewalls of which are engaged with the retention lug 10430 to hold the retention plate 10600 to the staple cartridge jaw 10410. In various instances, the retention plate 10600 can comprise a spring and/or biasing member.

Figure 33:
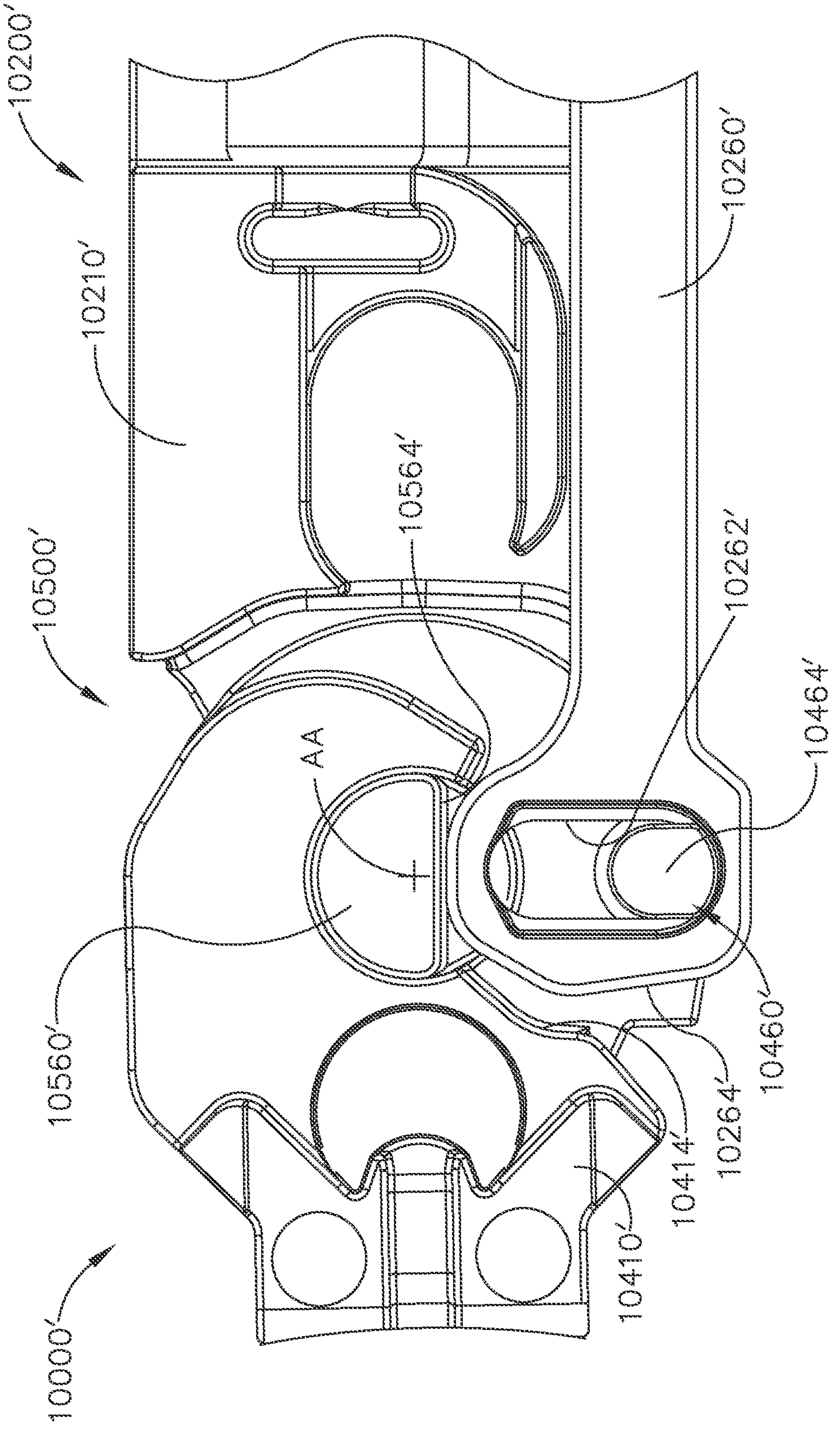
FIG. 33 is a partial detail view of an articulation joint in accordance with at least one alternative embodiment usable with the surgical instrument of FIG. 1.
Figure 34:
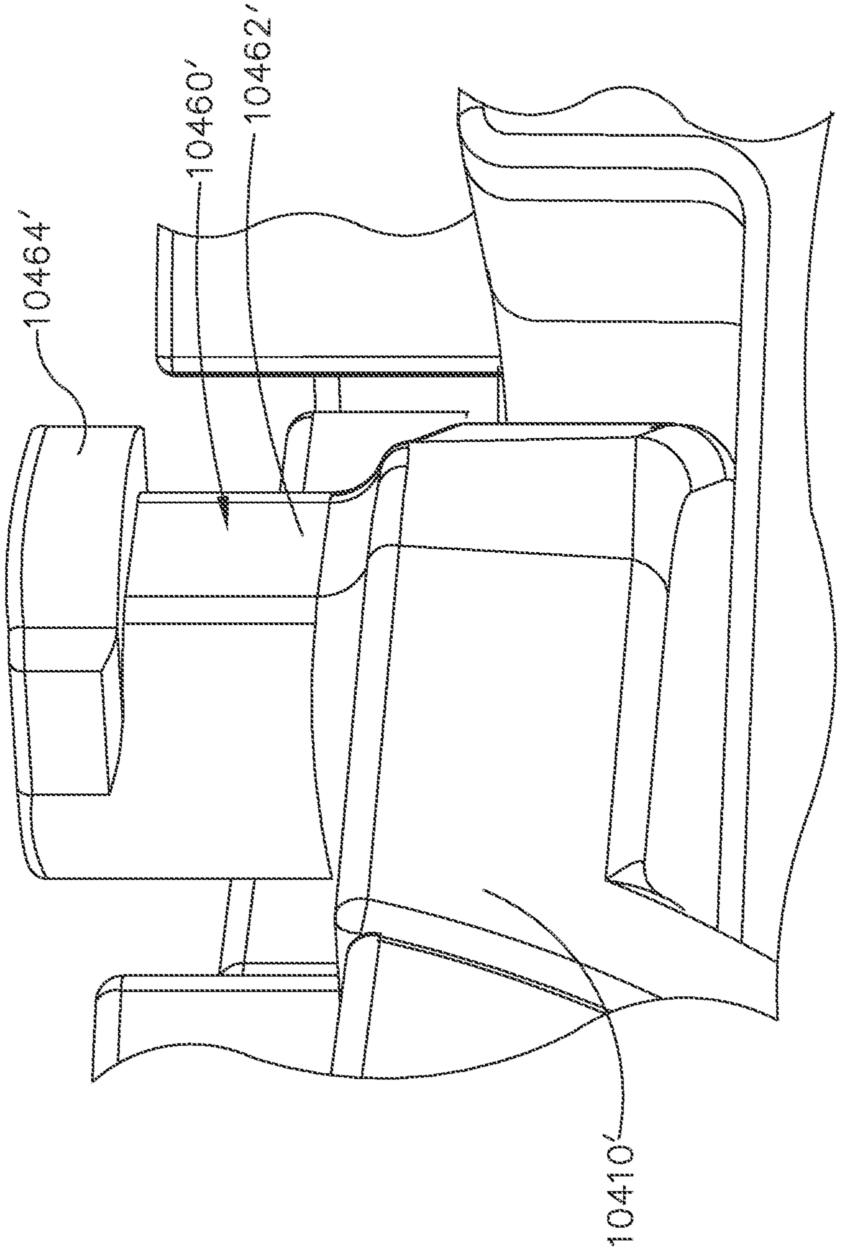
FIG. 34 is a partial perspective view of an articulation drive pin extending from a frame of the end effector of the embodiment of FIG. 33.
Figure 35:
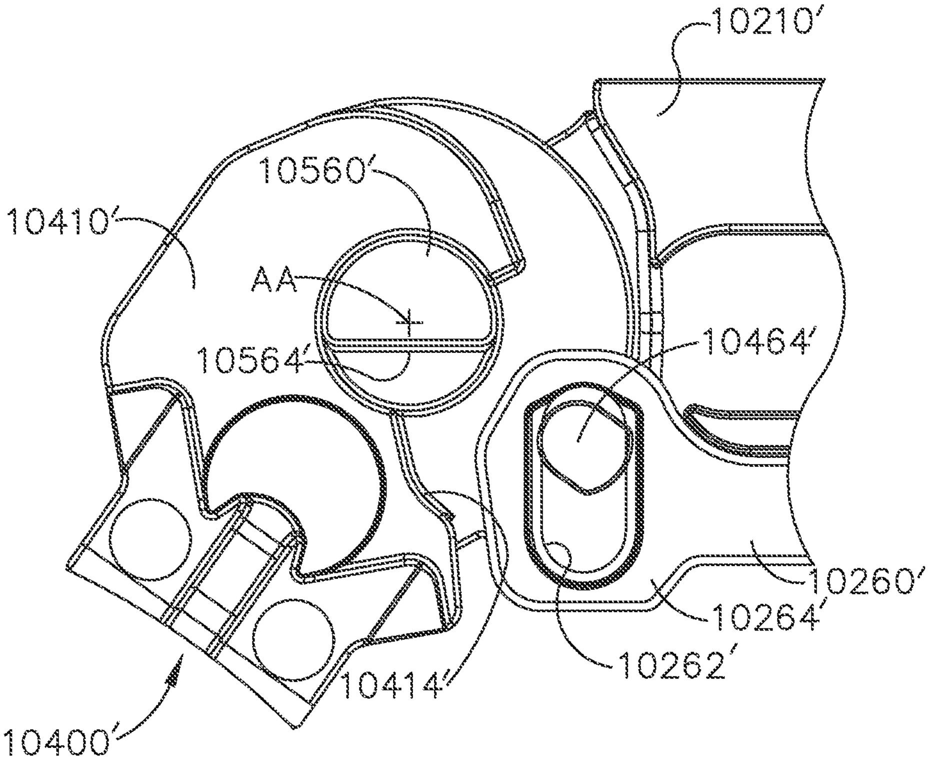
FIG. 35 is a partial detail view of the embodiment of FIG. 33 illustrating the end effector in an articulated position.
Figure 36:
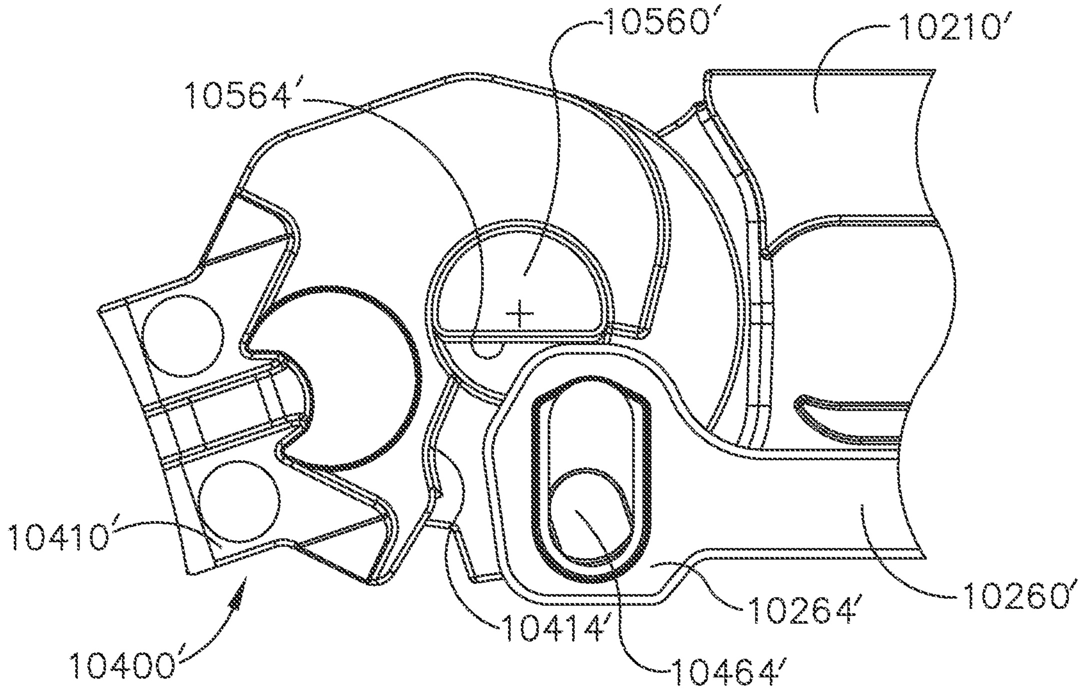
FIG. 36 is a partial detail view of the embodiment of FIG. 33 illustrating the end effector in another articulated position.
Figure 37:
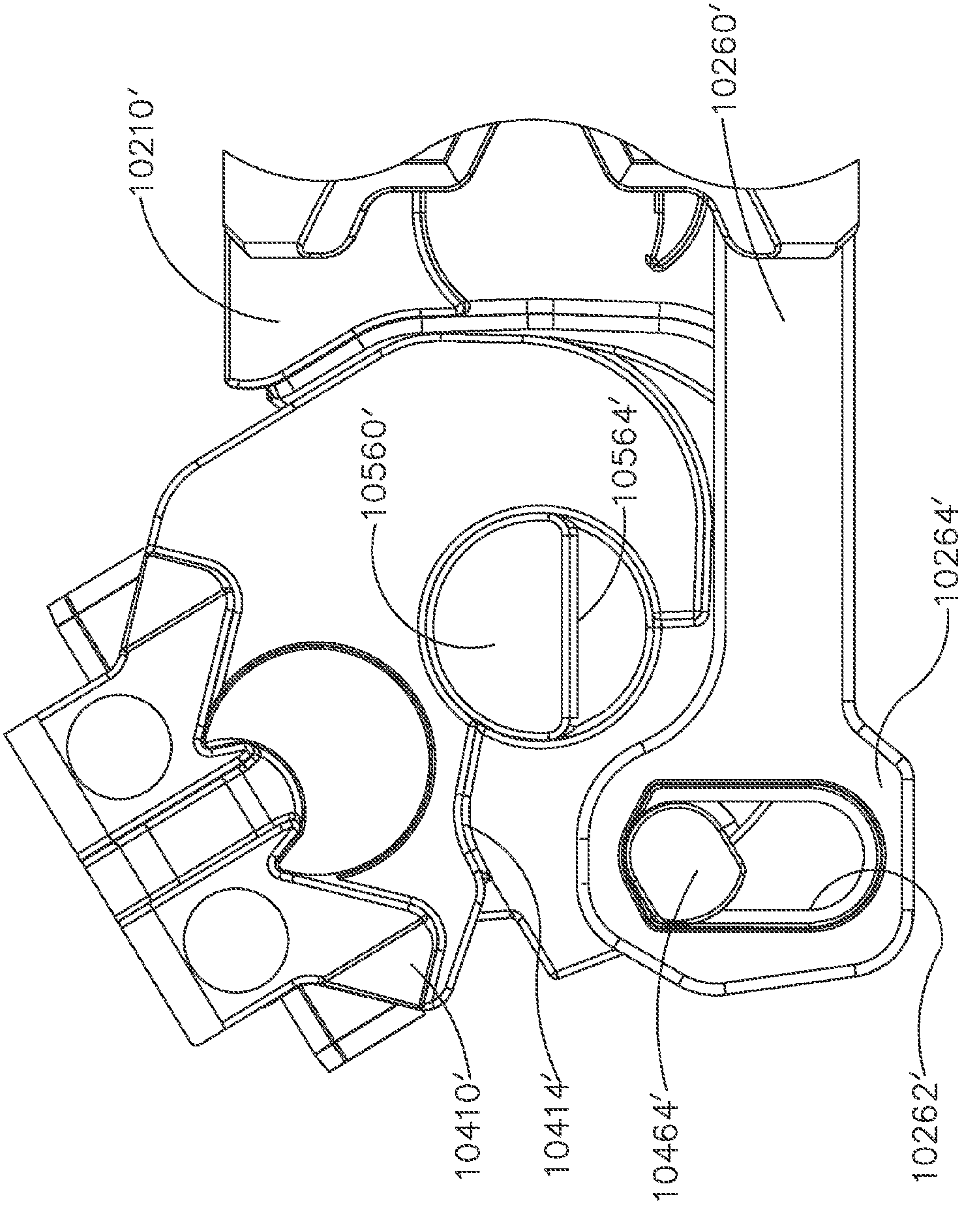
FIG. 37 is a partial detail view of the embodiment of FIG. 33 illustrating the end effector in another articulated position.
Figure 38:
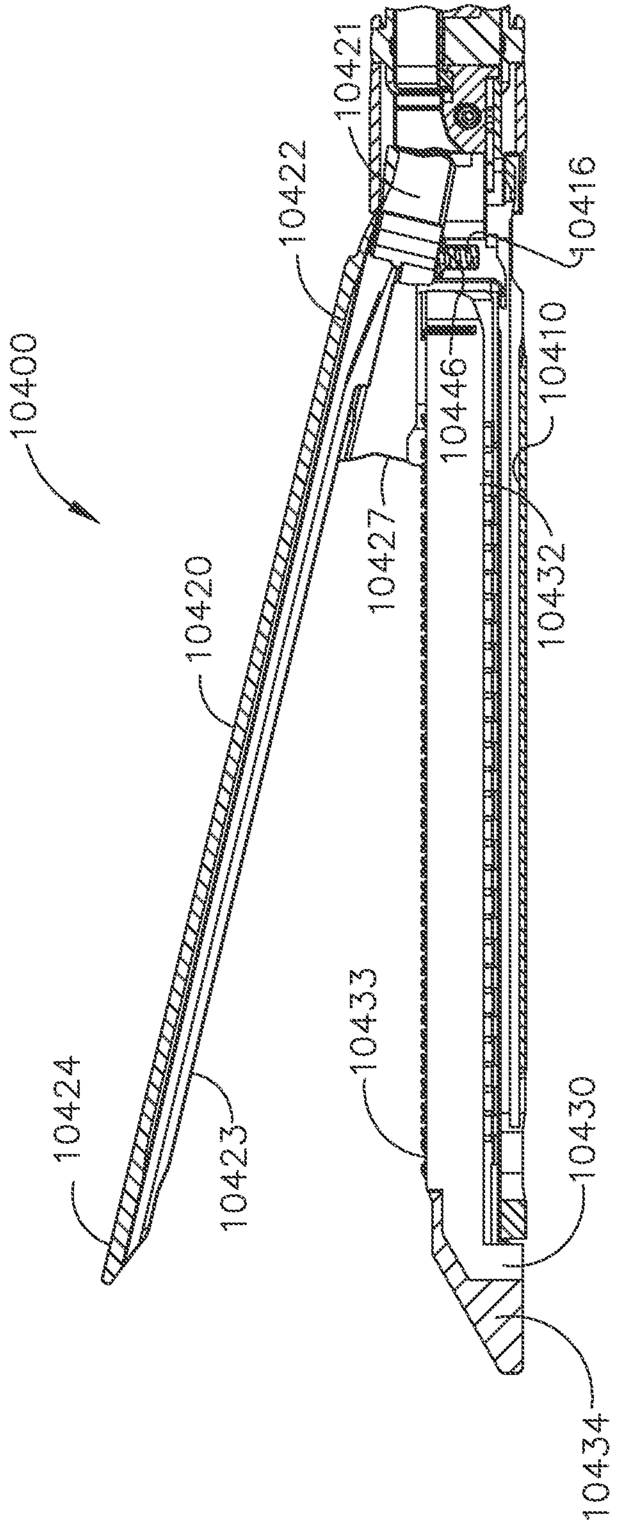
FIG. 38 is a cross-sectional view of the end effector of the surgical instrument of FIG. 1 illustrated in an open configuration.

In addition to or in lieu of the retention plate 10600, referring now to FIG. 33, a surgical instrument 10000' comprises an end effector 10400' and an articulation joint 10500' rotatably connecting the end effector to the shaft 10200'. Further to the above, the articulation joint 10500' comprises a pin 10560' extending from a shaft frame 10210' of the shaft 10200' that is closely received within an aperture defined in the staple cartridge jaw 10410' which defines the articulation axis AA for the articulation joint 10500'. The surgical instrument 10000' also comprises an articulation driver 10260' which comprises a distal end 10264' including a slot 10262' defined therein. Similar to the above, the staple cartridge jaw 10410' comprises an articulation pin 10460' extending from the staple cartridge jaw 10410' which extends into the slot 10262' of the distal end 10264' and the interaction between the sidewalls of the slot 10262' and the articulation pin 10460' drive the end effector 10400' about the articulation joint 10500'. Notably, the pin 10560' of the articulation joint 10500' comprises a clearance relief 10564' defined therein to provide clearance for the longitudinal movement of the articulation driver 10260'. The staple cartridge jaw 10410' also comprises a clearance relief 10414' defined therein to permit clearance for the rotation of the staple cartridge jaw 10410' about the articulation joint 10500'. In order to prevent the articulation driver 10260' from becoming decoupled from the staple cartridge jaw 10410', referring to FIGS. 34-37, the articulation pin 10460' comprises a retention shoulder 10464' extending from a cylindrical portion 10462'. The retention shoulder 10464' extends over a portion of the distal end 10264' of the articulation driver 10260' throughout the articulation of the end effector 10400'. Thus, regardless of whether the end effector 10400' is articulated all the way to the left (FIG. 35) or all the way to the right (FIG. 37), or anywhere in between, the retention shoulder 10464' prevents, or at least limits the possibility of, the articulation driver 10260' disengaging from the staple cartridge jaw 10410'.

In various embodiments, further to the above, the clearance relief 10414' comprises a retention shoulder or lip which prevents the articulation driver 10260' from decoupling from the articulation pin 10460'. The retention shoulder 10464' of the articulation pin 10460' is sized and configured such that the width of the retention shoulder 10464' is wider than the width of the slot 10262'. That said, the slot 10262' comprises a length which is larger than its width which permits the retention shoulder 10464' to be interested through the slot 10262' such that the articulation driver 10260' can be assembled to the articulation pin 10460'. The width of the slot 10262' is defined along an axis that is parallel to the longitudinal axis of the shaft while the length of the slot 10262' is defined along an axis that is orthogonal to the longitudinal axis of the shaft. Such an arrangement permits the end effector to articulate relative to the shaft while minimizing binding between the end effector and the articulation driver 10260'. That said, the articulation driver 10260' is comprised of a flexible material that permits the articulation driver 10260' to resiliently flex to accommodate the end articulation of the end effector.

Figure 44:
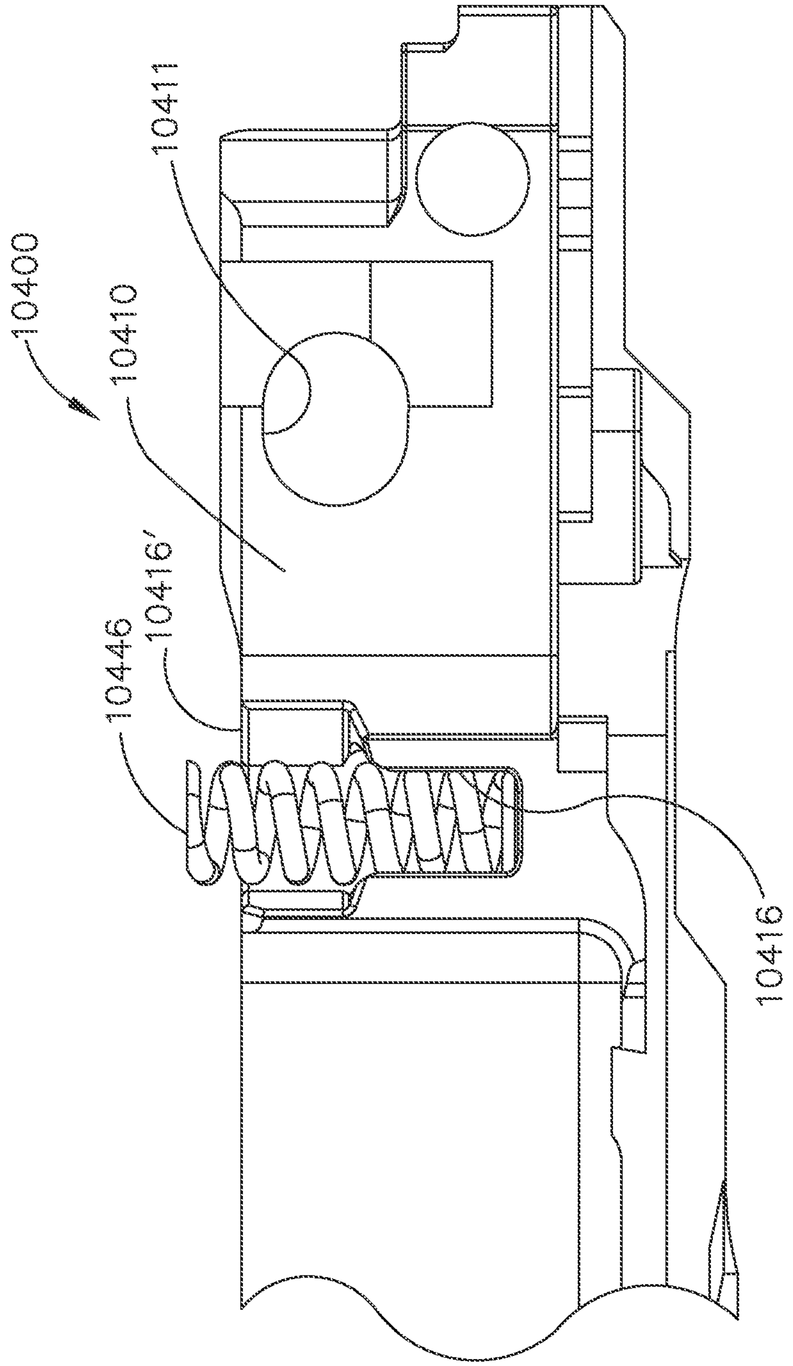
FIG. 44 is a partial cross-sectional view of a staple cartridge jaw of an end effector in accordance with at least one embodiment illustrated without a staple cartridge in the staple cartridge jaw.

As discussed above, the end effector 10400 comprises a staple cartridge jaw 10410 configured to receive a replaceable staple cartridge, such as staple cartridge 10430, for example, and an anvil jaw 10420 configured to deform the staples ejected from the staple cartridge 10430. The staple cartridge jaw 10410 comprises a channel including a bottom support and two lateral sidewalls extending upwardly configured to receive the staple cartridge 10430. The staple cartridge 10430 comprises a proximal end 10432, a distal end 10434, and a deck 10433 extending between the proximal end 10432 and the distal end 10434. When the staple cartridge 10430 is inserted into the staple cartridge jaw 10410, the proximal end 10432 is guided into position between the staple cartridge jaw 10410 and the anvil jaw 10420 and then seated into the staple cartridge jaw 10410. The anvil jaw 10420 comprises a proximal end 10422, a distal end 10424, a tissue compression surface 10423 extending between the proximal end 10422 and the distal end 10424, and a pivot 10421 rotatably connecting the anvil jaw 10420 to the staple cartridge jaw 10410. Referring to FIG. 44, the anvil jaw 10420 comprises lateral pins that extend into apertures 10411 defined in the staple cartridge jaw 10410. As discussed above, the anvil jaw 10420 is rotatable into a closed, or clamped, position by the closure drive of the stapling instrument 10000. When the closure drive is retracted, the anvil jaw 10420 is opened. Referring to FIGS. 38-43, the stapling instrument 10000 further comprises one or more biasing members, or springs, 10446 configured to open the anvil jaw 10420 when the closure drive is retracted. The surgical instrument 10000 comprises two opening springs 10446, but could comprise any suitable number of biasing members. In any event, each spring 10446 is positioned in a recess 10416 defined in the staple cartridge jaw 10410. The recesses 10416 closely receive the springs 10446 such that the springs 10446 do not buckle under a compressive load; however, the recesses 10416 are sized and configured to accommodate any lateral expansion of the springs 10446 as the anvil jaw 10420 is being closed.

Figure 42:
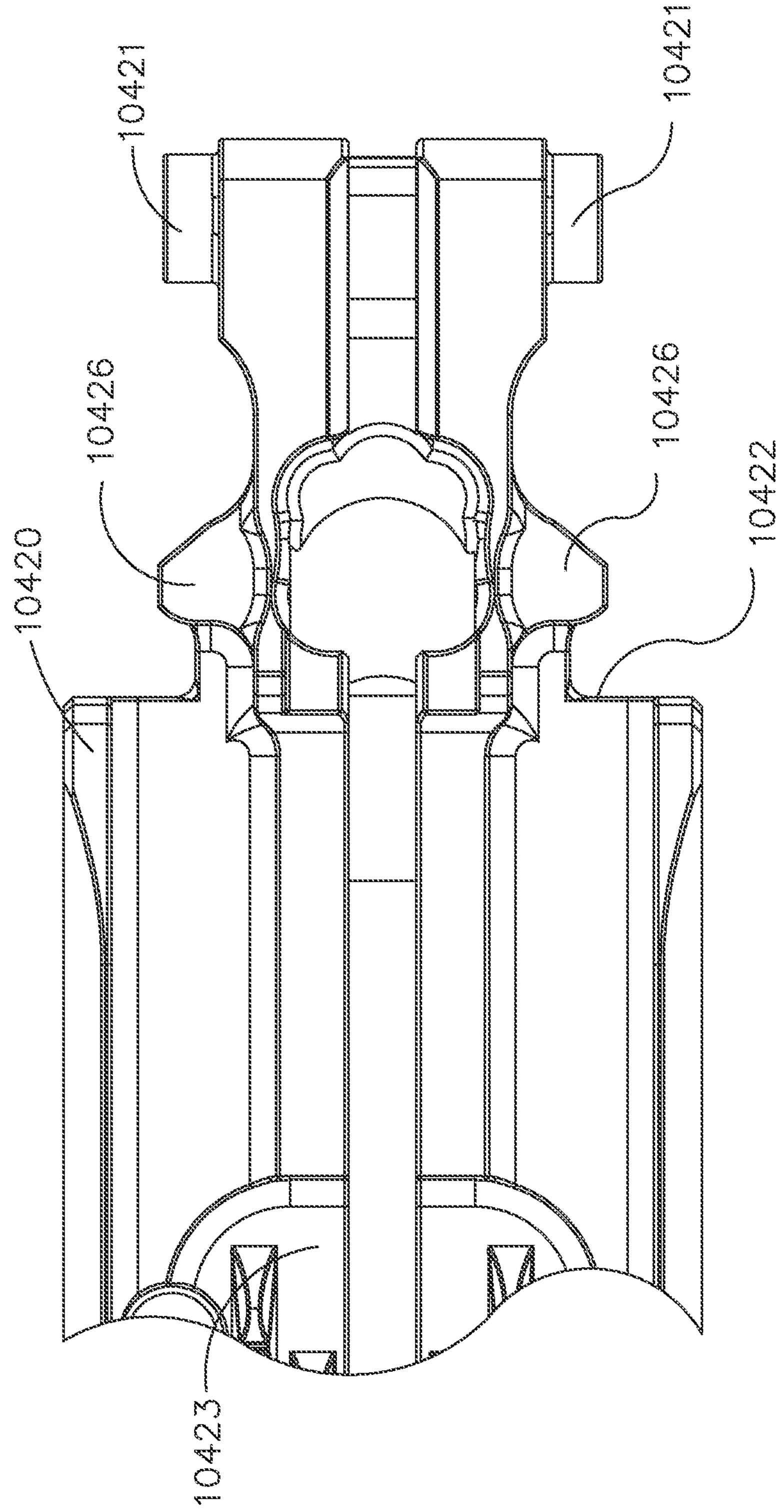
FIG. 42 is a partial perspective view of the anvil jaw of FIG. 40.
Figure 43:
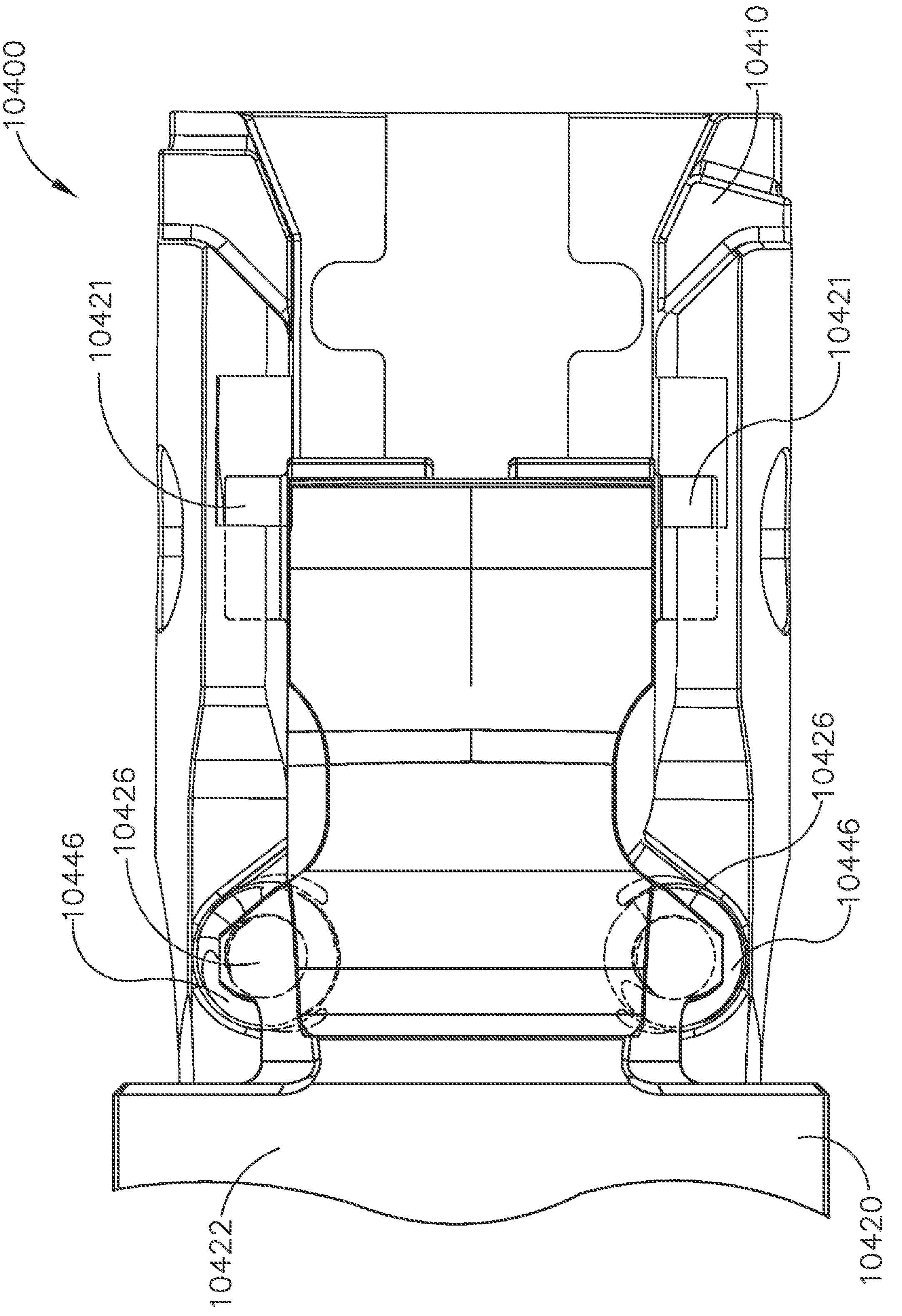
FIG. 43 is a partial top view of the pivot joint of FIG. 40.

Referring primarily to FIG. 42, the anvil jaw 10420 comprises lateral tabs 10426 adjacent the proximal end 10422 of the anvil 10420 which are in contact with the springs 10446. When the anvil jaw 10420 is closed, the springs 10446 are compressed between the lateral tabs 10426 and the bottom of the recesses 10416. When the closure system is retracted, the springs 10446 resiliently re-expand and push upwardly on the lateral tabs 10426 to rotate the anvil jaw 10420 into its open, or unclamped, position. Notably, referring primarily to FIG. 40, the staple cartridge jaw 10410 has a stop portion 10419 defined thereon which is contacted by the proximal end 10422 of the anvil 10420 when the anvil 10420 reaches its fully-open position. The anvil 10420 comprises a proximal stop surface 10429 which contacts the stop portion 10419 of the staple cartridge jaw 10410. In such instances, the anvil jaw 10420 cannot be opened any further. As a result of the above, the springs 10446 hold the anvil jaw 10420 against the stop portion 10419 of the staple cartridge jaw 10410 until the anvil jaw 10420 is closed once again.

Figure 39:
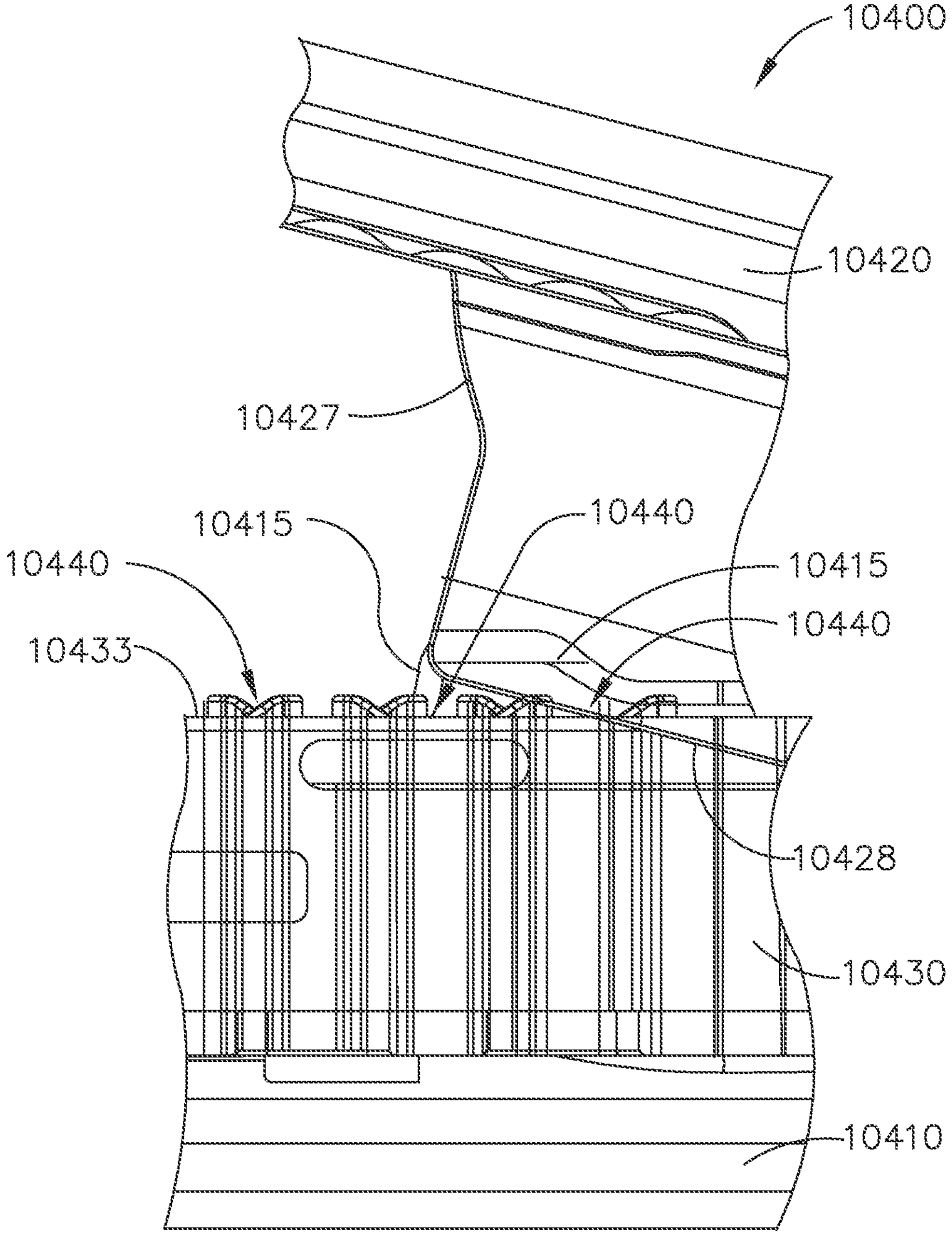
FIG. 39 is a partial cross-sectional view of the end effector of the surgical instrument of FIG. 1 illustrating tissue stops of the end effector.
Figure 40:
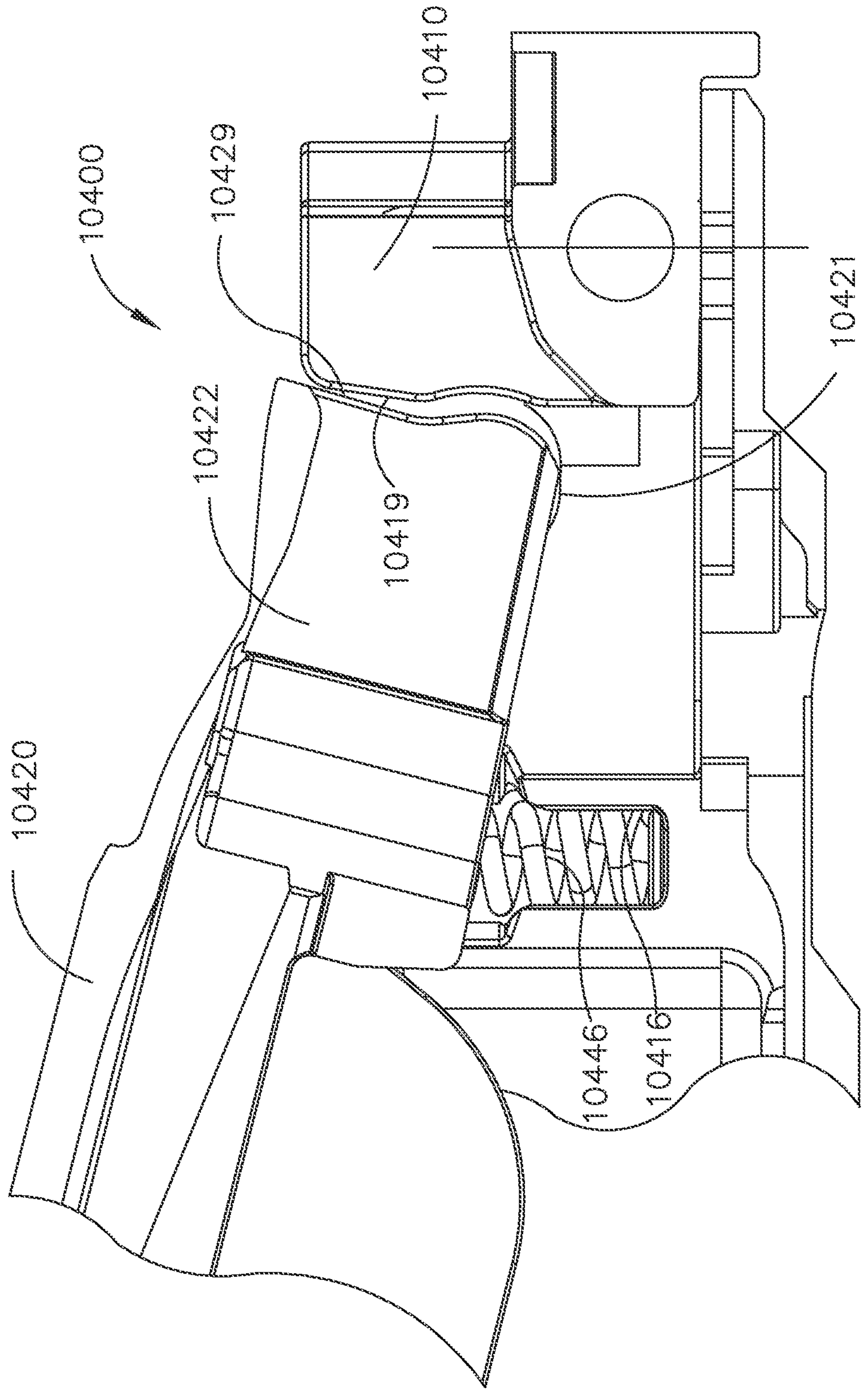
FIG. 40 is a partial cross-sectional view of the end effector of the surgical instrument of FIG. 1 illustrating a pivot joint between a staple cartridge jaw and an anvil jaw of the end effector.

When the anvil jaw 10420 is in its open position, the staple cartridge jaw 10410 is positioned on one side of the tissue that is to be stapled and the anvil jaw 10420 is positioned on the opposite side. In such instances, the end effector 10400 is moved relative to the tissue until the tissue is suitably positioned between the staple cartridge jaw 10410 and the anvil jaw 10420. The anvil jaw 10420 comprises lateral tissue stops 10427 which extend downwardly alongside the staple cartridge jaw 10410 which are configured to make sure that the tissue positioned within the end effector 10400 is positioned over the staple cavities in the staple cartridge 10430. Referring primarily to FIG. 39, the tissue stops 10427 extend distally with respect to the proximal-most staple cavities 10440. In at least one instance, the tissue stops 10427 extend distally with respect to at least one staple cavity 10440 in each longitudinal row of staple cavities 10440. As a result, the tissue stops 10427 make sure that the tissue captured in the end effector 10400 is not cut by the tissue cutting knife without being stapled. When the anvil jaw 10420 is closed, the tissue stops 10427 move relative to the staple cartridge jaw 10410. The tissue stops 10427 are sized and configured such that tissue does not become accidentally pinched between the tissue stops 10427 and the lateral sides of the staple cartridge jaw 10410. More specifically, the bottom edges 10428 of the tissue stops 10427 are configured such that they extend alongside the lateral sides of the staple cartridge jaw 10410 even when the anvil jaw 10420 is in its fully-open position, as illustrated in FIG. 39. Notably, the lateral sides 10415 of the staple cartridge jaw 10410 extend upwardly above the deck 10433 to make sure that there is overlap between the tissue stops 10427 and the lateral sides 10415 of the staple cartridge jaw 10410—when viewed from the side—throughout the entire range of motion of the anvil jaw 10420.

In various embodiments, further to the above, the distal edges of the tissue stops 10427 extend below the deck 10433 throughout the entire range of motion of the anvil jaw 10420. Thus, the distal edges of the tissue stops 10427 extend below the top surface of the deck 10433 when the anvil jaw 10420 is in its fully-open position and its fully-clamped position. Such an arrangement reduces the possibility of the tissue being pinched when the anvil jaw 10420 is moved. In certain embodiments, the staple cartridge comprises tissue stops that extend upwardly from the deck 10433 alongside the tissue stops 10427. Similar to the above, the distal edges of the tissue stops 10427 extend below the cartridge tissue stops through the entire range of motion of the anvil jaw 10420. Such an arrangement also reduces the possibility of the tissue being pinched when the anvil jaw 10420 is moved. Moreover, these arrangements would be useful in embodiments where the staple cartridge jaw 10410 moves relative to the anvil jaw 10420.

Figure 45A:
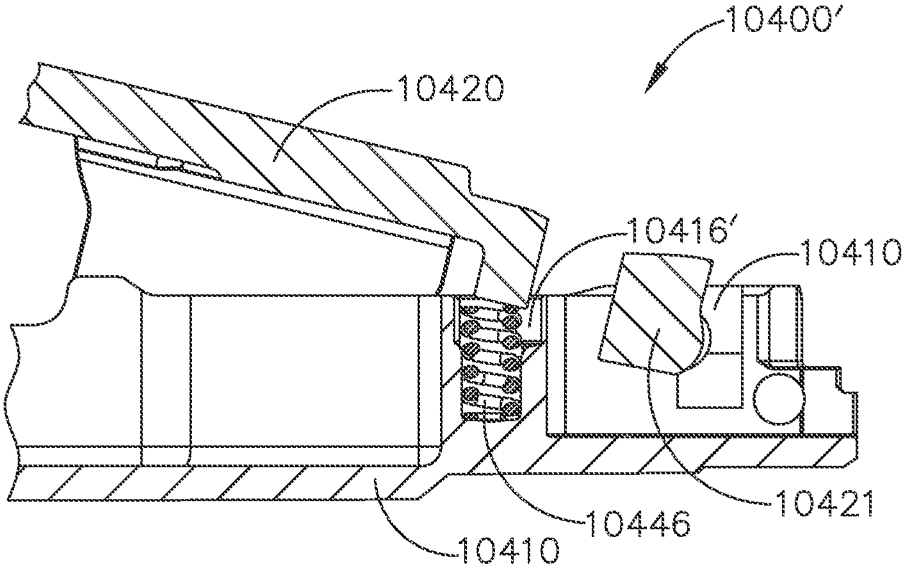
FIG. 45A is a partial cross-sectional view of the end effector of FIG. 44 in an open configuration.
Figure 45B:
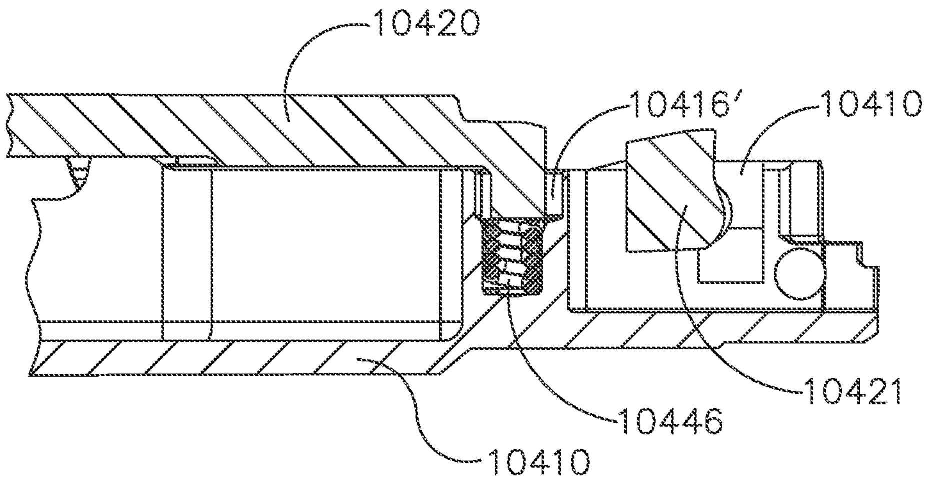
FIG. 45B is a partial cross-sectional view of the end effector of FIG. 44 in a closed configuration.

As discussed above and referring primarily to FIGS. 44, 45A, and 45B the end effector 10400 comprises a staple cartridge jaw 10410 that includes spring recesses 10416 defined therein which comprise wider top openings 10416'. The spring recesses 10416 still support the springs 10446 and keep them from buckling, but the wider top openings 10416' of the spring recesses 10416 provide clearance for the lateral tabs 10426 when the anvil jaw 10420 is in its closed position. In such an arrangement, the lateral tabs 10426 can move into the staple cartridge jaw 10410 to compress the springs 10446. In such instances, the springs 10446 can be highly compressed by the anvil jaw 10420, thereby assuring a strong opening force from the springs 10446 when the anvil jaw 10420 is released by the closure drive. The above being said, embodiments are envisioned without the wider top openings 10416'. In such embodiments, the springs are closely received by the spring recesses 10416 along the length of the springs 10446.

Figure 46:
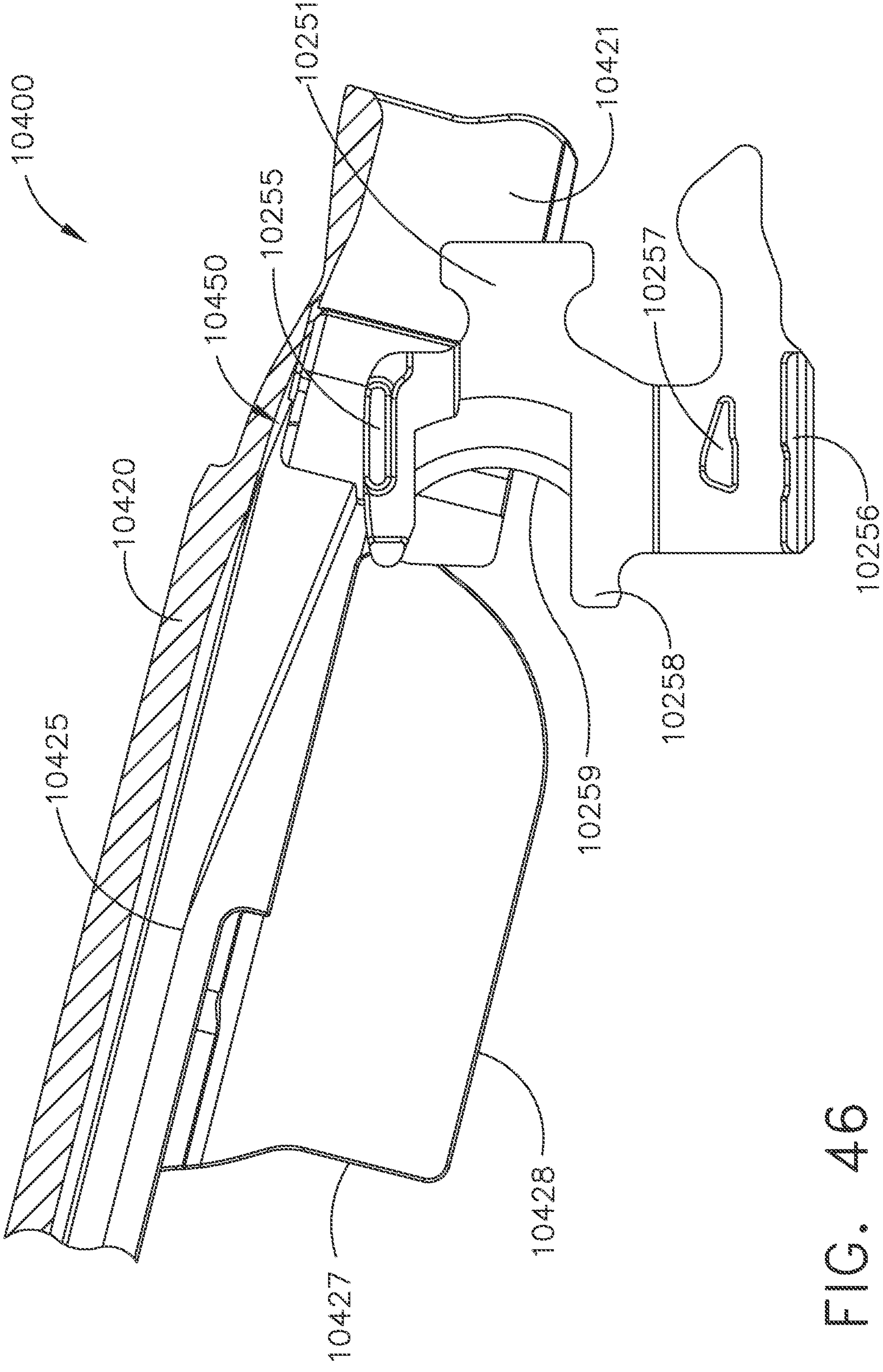
FIG. 46 is a partial cross-sectional view of the end effector of the surgical instrument of FIG. 1 illustrating a firing member in an unfired position.
Figure 47:
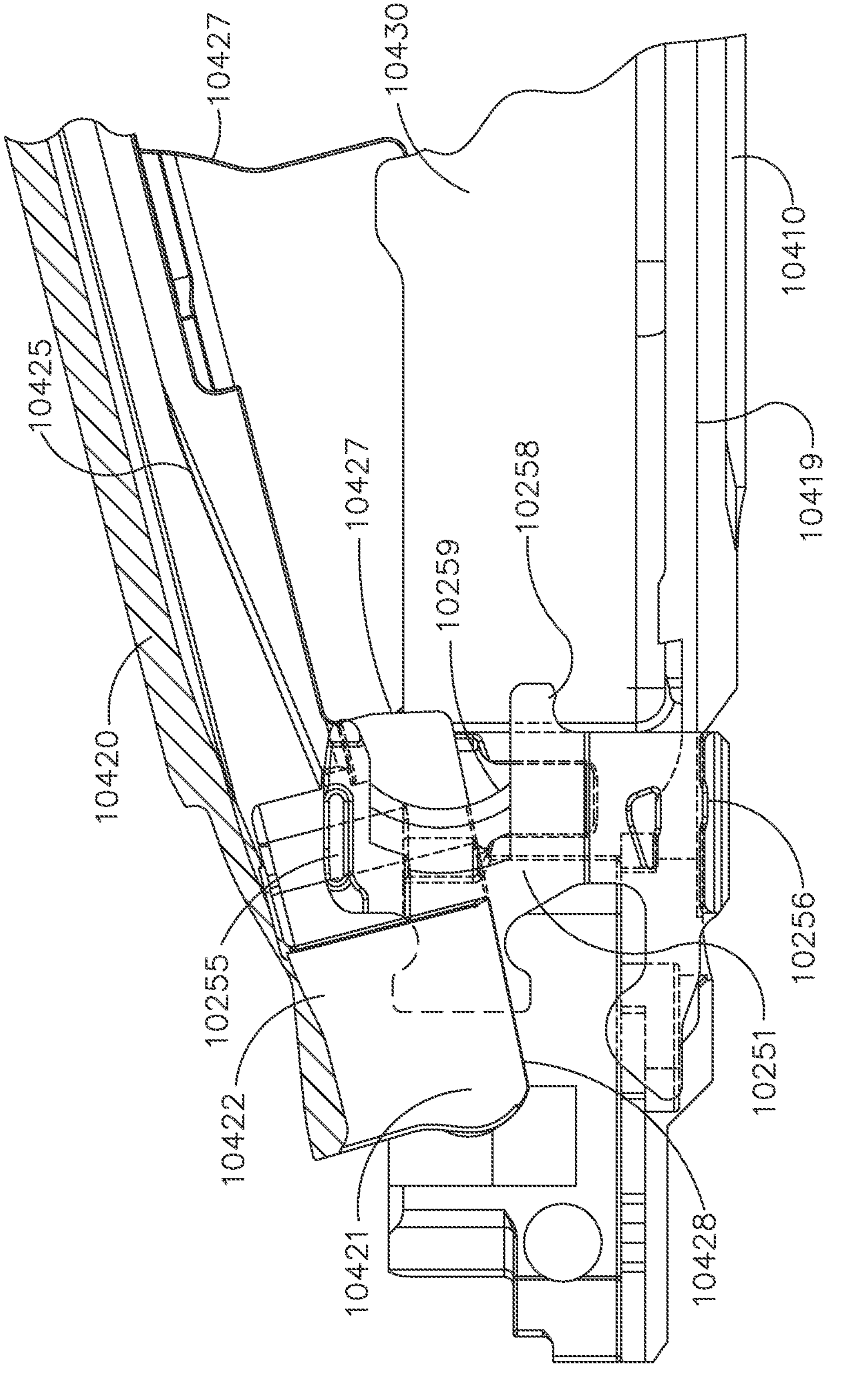
FIG. 47 is a partial cross-sectional view of the end effector of the surgical instrument of FIG. 1 illustrating a cartridge stop on the anvil jaw configured to stop the proximal insertion of a staple cartridge into the staple cartridge jaw.

The tissue cutting member 10251 of the firing drive of the stapling instrument 10000 is illustrated in FIGS. 46 and 47, the tissue cutting member comprises a body including a distal nose 10258 and a tissue cutting edge 10259 which pass through the end effector 10400 during a staple firing stroke. The tissue cutting member 10251 further comprises a top cam member 10255 configured to engage the anvil jaw 10420 and a bottom cam member 10256 configured to engage the staple cartridge jaw 10410 during the staple firing stroke. A longitudinal cam surface 10425 in a longitudinal slot of the anvil jaw 10420 can be seen in FIG. 46 which is engaged by the top cam member 10255 during the staple firing stroke. The staple cartridge jaw 10410 also has a longitudinal cam surface 10419 which is engaged by the bottom cam member 10256. The cam members 10255 and 10256 position the jaws 10410 and 10420 relative to one another during the staple firing stroke and hold the jaws 10410 and 10420 in their closed configuration throughout the staple firing stroke. The cam members 10255 and 10256 also set the staple forming gap between the staple drivers in the staple cartridge and the forming pockets defined in the anvil jaw 10420.

Notably, FIGS. 46 and 47 illustrate the anvil jaw 10420 in its open position and the tissue cutting member 10251 in its unfired position, i.e., its position before the staple firing stroke has begun. The anvil jaw 10420 comprises a clearance pocket 10450 defined therein which is aligned with the top cam member 10255 of the tissue cutting member 10251 when the tissue cutting member 10251 is in its unfired position. Such an arrangement allows the tissue cutting member 10251 to be parked just proximal to the longitudinal cam surface 10425 in the anvil jaw 10420, and the corresponding cam surface in the staple cartridge jaw 10410, when the tissue cutting member 10251 is in its unfired position. Such an arrangement provides for a shorter, and more maneuverable, end effector for a given staple line length. Moreover, the tissue cutting member 10251 comprises a tissue cutting edge 10259 that is positioned proximally with respect to the staple cavities defined in the staple cartridge and proximally with respect to the distal edges of the tissue stops when the tissue cutting member is in its unfired position. As a result, the tissue being inserted into the end effector is unlikely to be cut by the tissue cutting edge 10259 until the tissue cutting member 10251 is advanced distally from its unfired position during a firing stroke.

Figure 41:
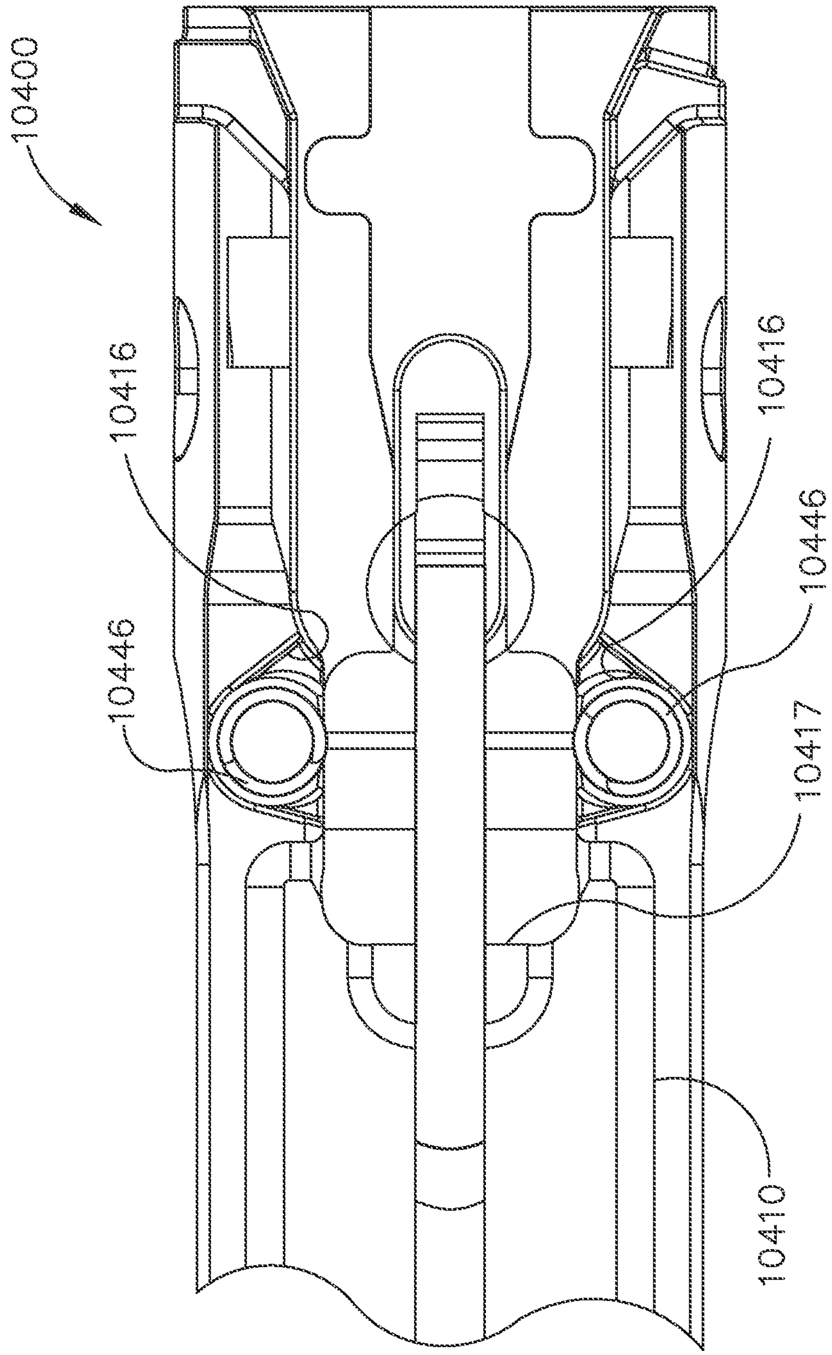
FIG. 41 is a partial plan view of the staple cartridge jaw of FIG. 40 without a staple cartridge positioned in the staple cartridge jaw.

Further to the above, it is desirable for the tissue cutting member 10251 to be in its unfired position at the beginning of the staple firing stroke. If the tissue cutting member 10251 is not in its unfired position at the outset of the staple firing stroke, a missing cartridge/spent cartridge lockout of the stapling instrument 10000 may be accidentally bypassed. Referring to FIG. 41, the lockout of the stapling instrument 10000 comprises a shoulder 10417 defined in the bottom of the staple cartridge jaw 10410. If a proper unspent staple cartridge is seated in the staple cartridge jaw 10410 at the outset of the staple firing stroke, and the tissue cutting member 10251 is in its unfired position at the outset of the staple firing stroke, the tissue cutting member 10251 will be lifted over the lockout shoulder 10417. More specifically, referring to FIG. 46, the nose 10258 of the tissue cutting member 10251 will be supported by a staple driving sled in the staple cartridge such that lockout tabs 10257 of the firing member 10251, and/or any other portion of the firing member 10251, do not contact the lockout shoulder 10417. If, however, a staple cartridge is not seated in the staple cartridge jaw 10410, a staple cartridge is seated the staple cartridge jaw 10410 but has been previously spent, or an incorrect staple cartridge is seated in the staple cartridge jaw 10410, the sled will not support the nose 10258 of the tissue cutting member 10251 and the lockout tabs 10257 will contact the lockout shoulder 10417 at the outset of the staple firing stroke—thereby preventing the staple firing stroke. If the tissue cutting member 10251 is somehow positioned distally with respect to the lockout shoulder 10417 at the outset of the staple firing stroke, however, the advantages provided by the lockout of the surgical instrument 10000 are lost.

The entire disclosures of U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein.

Figure 48:
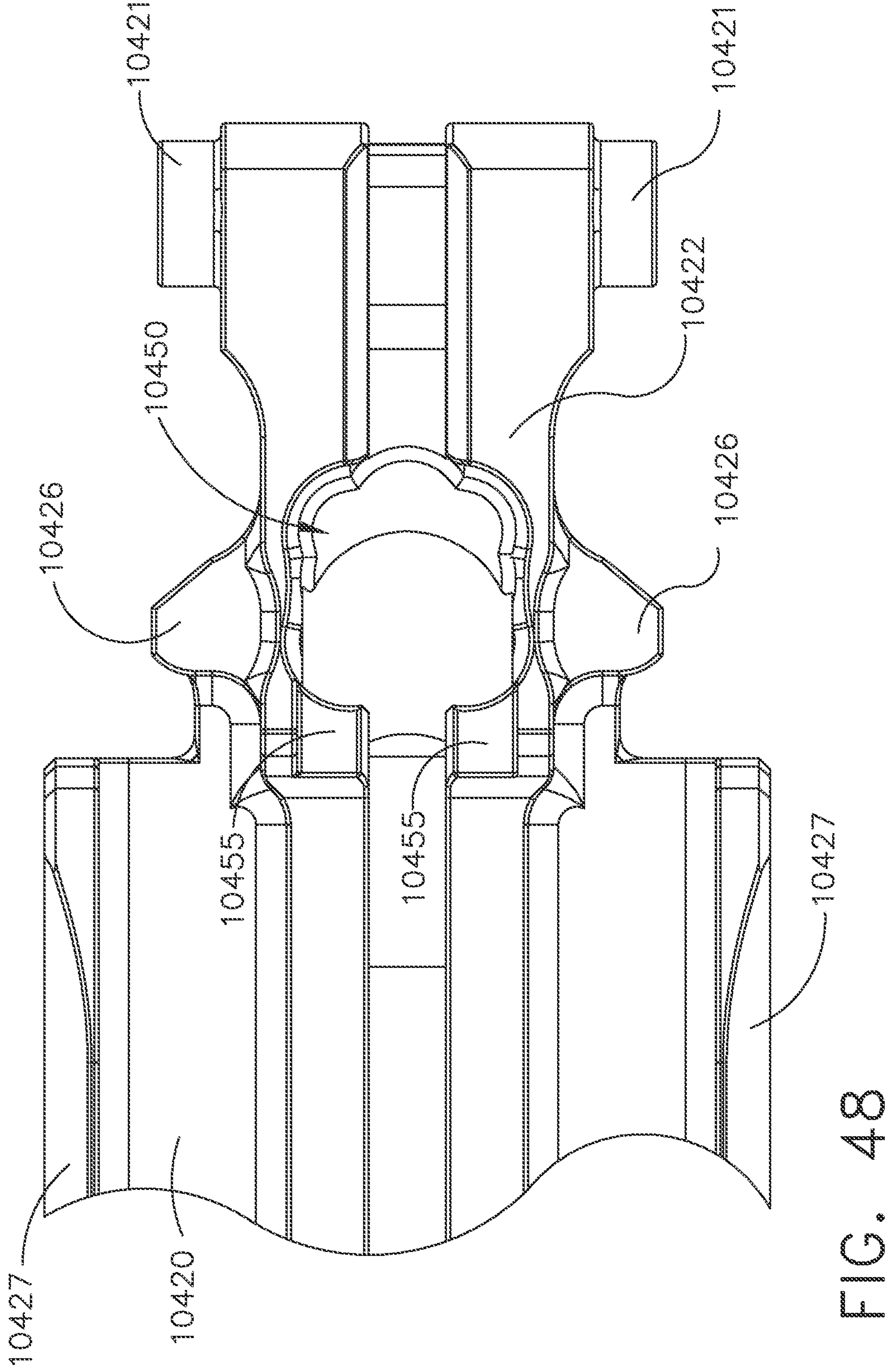
FIG. 48 is a partial perspective view of the anvil jaw of the surgical instrument of FIG. 1 illustrating surfaces configured to control the position of the firing member of FIG. 46 in its unfired position while the end effector is in an open configuration.
Figure 49:
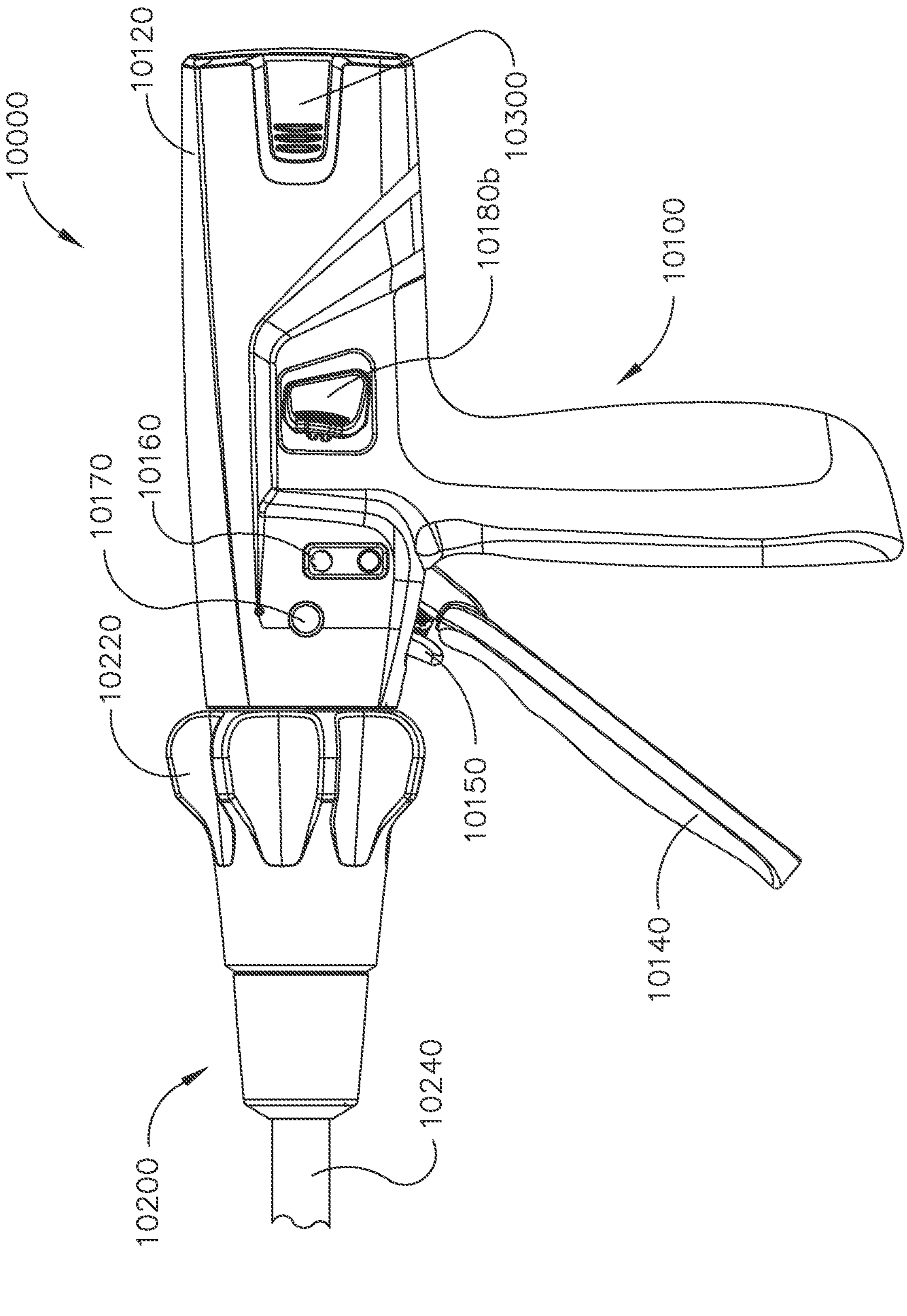
FIG. 49 is a partial elevational view of the surgical instrument of FIG. 1.
Figure 50:
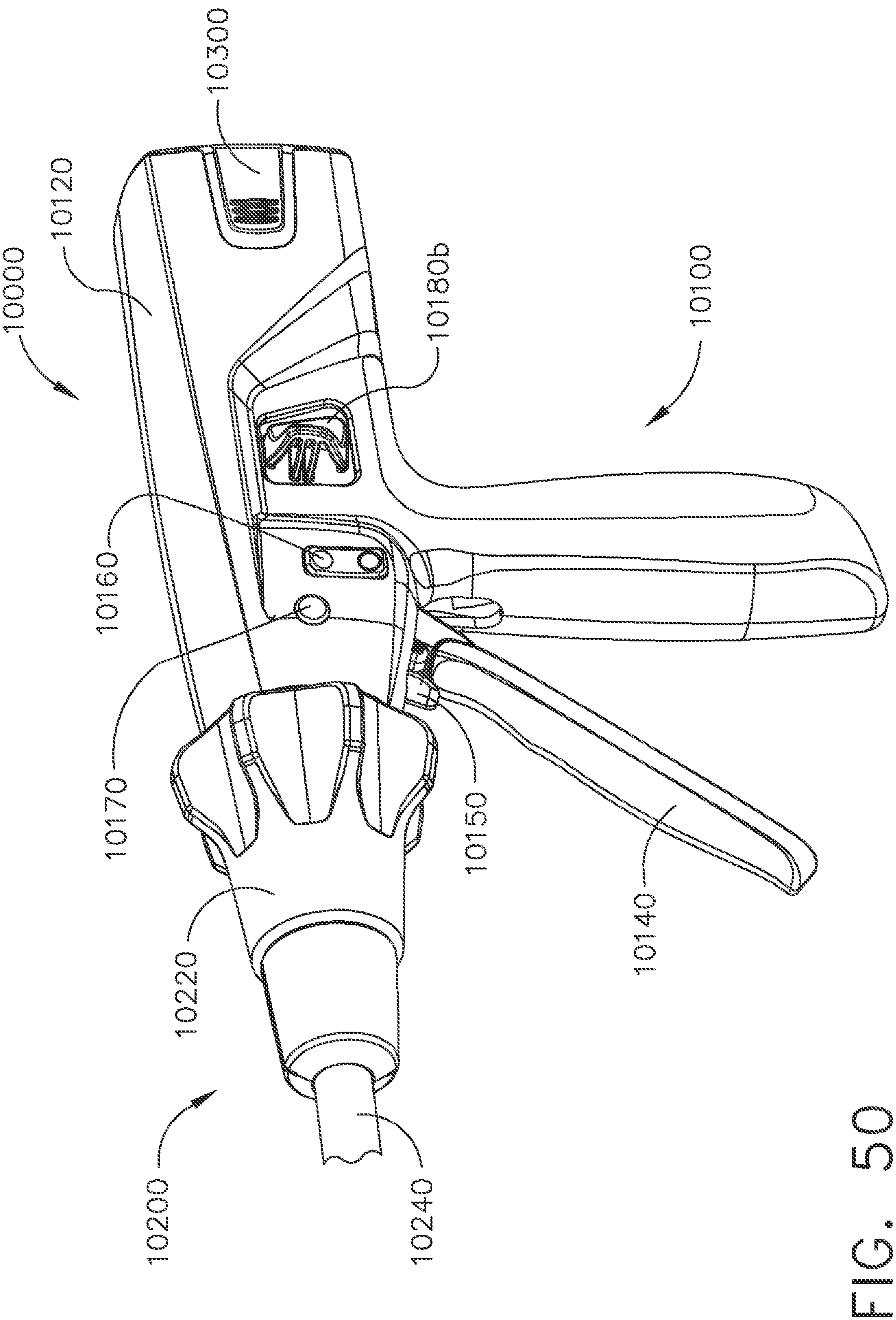
FIG. 50 is a partial perspective view of the surgical instrument of FIG. 1.

The above being said, referring to FIG. 48, the anvil jaw 10420 comprises shoulders, or stops, 10455 defined thereon which are configured to contact the top cam member 10255 of the tissue cutting member 10251 when the anvil jaw 10420 is moved into its open position. In such instances, the anvil jaw 10420 positions the tissue cutting member 10251 in its unfired position even if the tissue cutting member 10251 has been accidentally moved or positioned too far distally. Such an arrangement is particularly useful after the surgical instrument 10000 has already been used at least once and the staple firing system has been reset, or retracted as, in some instances, the tissue cutting member 10251 may not have been fully returned to its unfired position after the last staple firing stroke. As a result of the above, the possibility of the lockout of the surgical instrument 10000 being accidentally bypassed is reduced. Notably, the shoulders 10455 and the clearance pocket 10450 are positioned proximally with respect to the distal edges of the tissue stops 10427 which assures that the tissue cutting member 10251 is positioned proximally relative to the tissue captured within the end effector such that the tissue is not accidentally incised against the tissue cutting member 10251.

As discussed above, the articulation driver 10260 is translatable proximally and distally to articulate the end effector 10400 about the articulation joint 10500. That said, the articulation driver 10260 is actually a distal articulation driver of the articulation drive system. Referring to FIGS. 72 and 74-76, the articulation drive system further comprises a translatable proximal articulation driver 10270 which moves the distal articulation driver 10260. The articulation drive system also comprises an articulation lock 10280 positioned intermediate the proximal articulation driver 10270 and the distal articulation driver 10260, as described in greater detail below. The proximal articulation driver 10270 comprises an articulation rod 10272, a proximal push projection 10274 extending from the articulation rod 10272, and a distal pull projection 10276 extending from the articulation rod 10272. When the proximal articulation driver 10270 is pushed distally, the proximal push projection 10274 contacts the articulation lock 10280, unlocks the articulation lock 10280, and drives the distal articulation driver 10260 distally to articulate the end effector 10400. When the proximal articulation driver 10270 is stopped, the articulation lock 10280 automatically re-locks and holds the end effector 10400 in position. When the proximal articulation driver 10270 is pulled proximally, the distal pull projection 10276 contacts the articulation lock 10280, unlocks the articulation lock 10280, and pulls the distal articulation driver 10260 proximally to articulate the end effector 10400. Similar to the above, the articulation lock 10280 automatically re-locks when the proximal articulation driver 10270 stops. When the articulation lock 10280 is locked, the end effector 10400 is prevented from being back-driven or unintentionally moved out of its position. When the articulation lock 10280 is unlocked, the end effector 10400 can be articulated into a new position.

Figure 72:
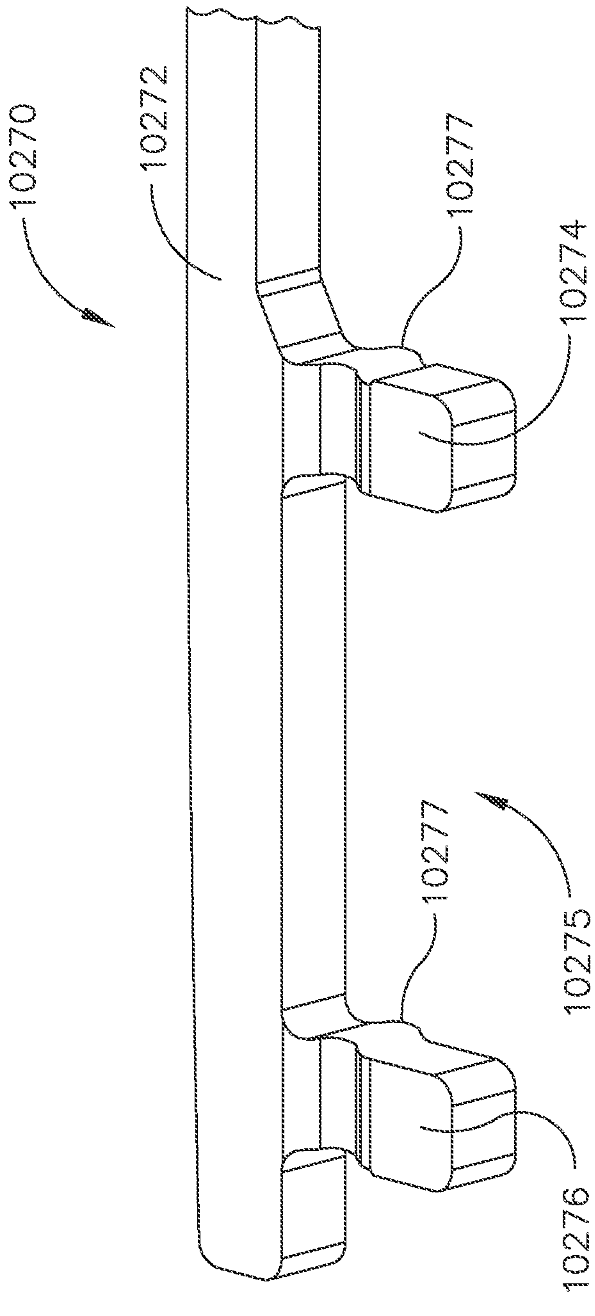
FIG. 72 is a perspective view of the distal end of a proximal articulation rod in accordance with at least one embodiment.

Further to the above, referring to FIG. 72, a space 10275 is defined between the projections 10274 and 10276 of the proximal articulation driver 10270. The distal articulation driver 10260 comprises a similar arrangement. More specifically, the distal articulation driver 10260 comprises a proximal projection 10269 and a distal projection 10267 with a space defined between them. The projections 10274 and 10276 of the proximal articulation driver 10270 are positioned within, and move within, this space defined between the projections 10267 and 10269 of the distal articulation driver 10260. The articulation lock 10280 comprises a stationary rod 10282 extending through the distal articulation driver 10260 and lock members 10284 rotatably and slideably mounted to the stationary rod 10282. The lock members 10284 are biased into a locked position by a spring 10286 positioned between two sets of lock members 10284 which causes the lock members 10284 to bite into the stationary rod 10282. When the proximal articulation rod 10270 is translated, however, the proximal articulation rod 10270 pushes on the lock members 10284 to rotate them out of their locked position so that the end effector 10400 can be articulated.

Figure 73:
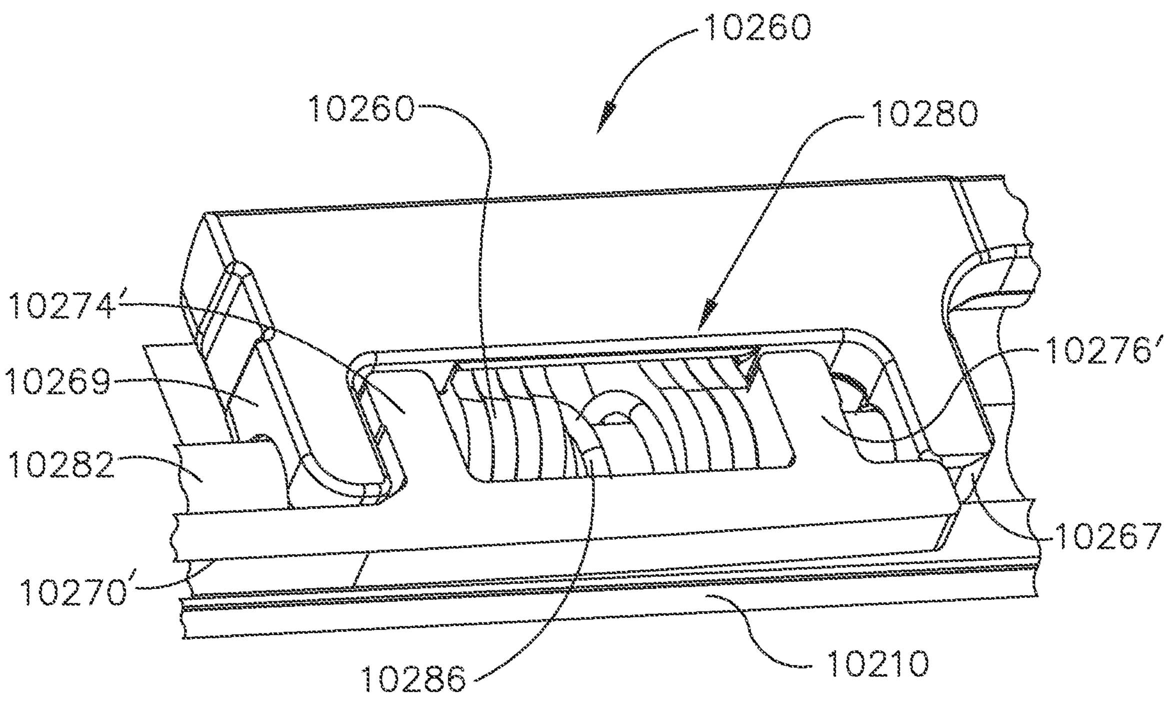
FIG. 73 is a perspective view of the interface between a proximal articulation rod and a distal articulation rod of an articulation drive in accordance with at least one embodiment.
Figure 73A:
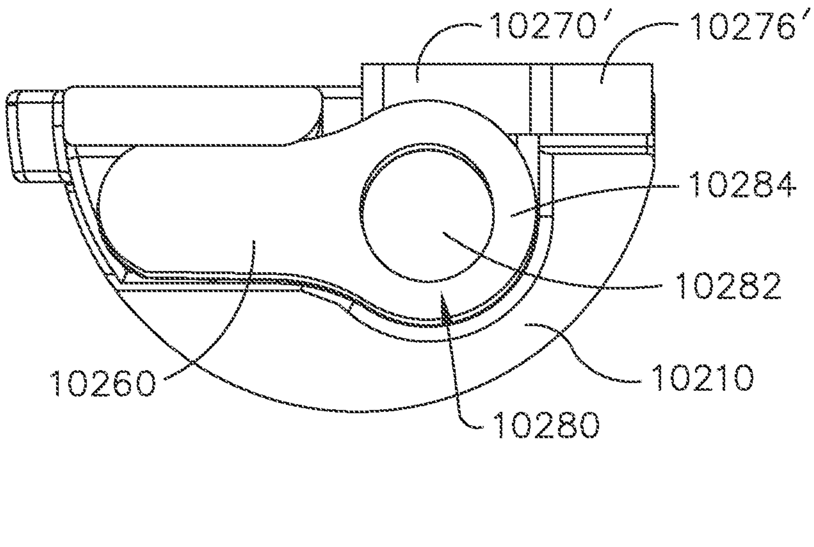
FIG. 73A is a detail view of the interface between the proximal articulation rod of FIG. 73 and an articulation lock.
Figure 74:
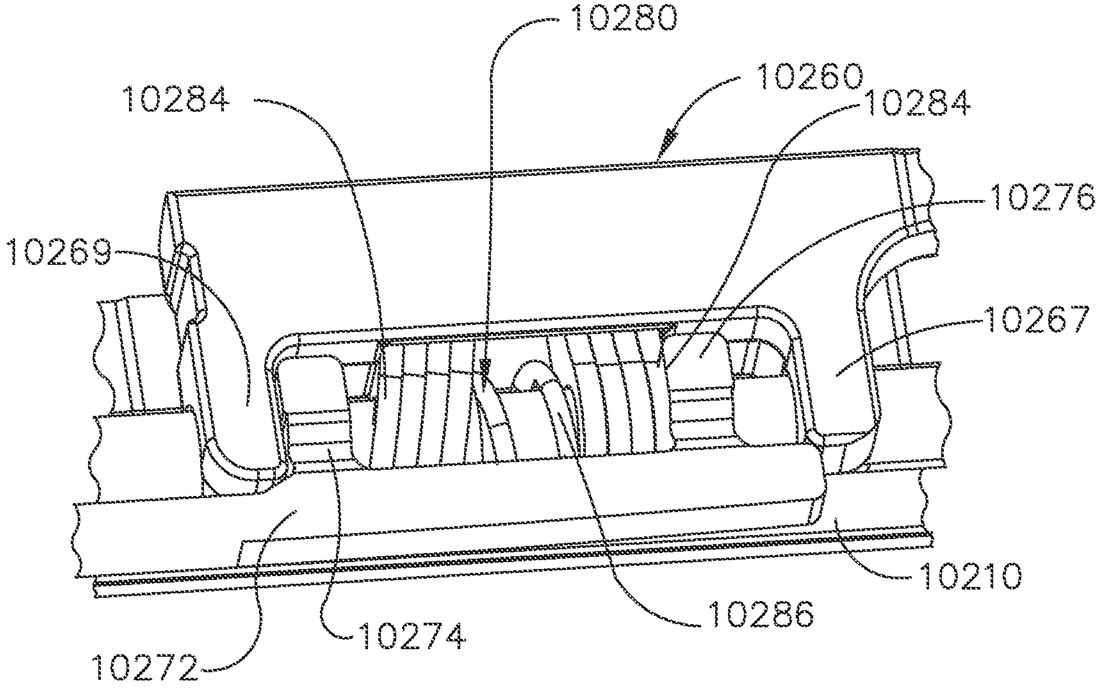
FIG. 74 is a perspective view of the interface between the proximal articulation rod of FIG. 72 with the distal articulation rod of FIG. 73.
Figure 74A:
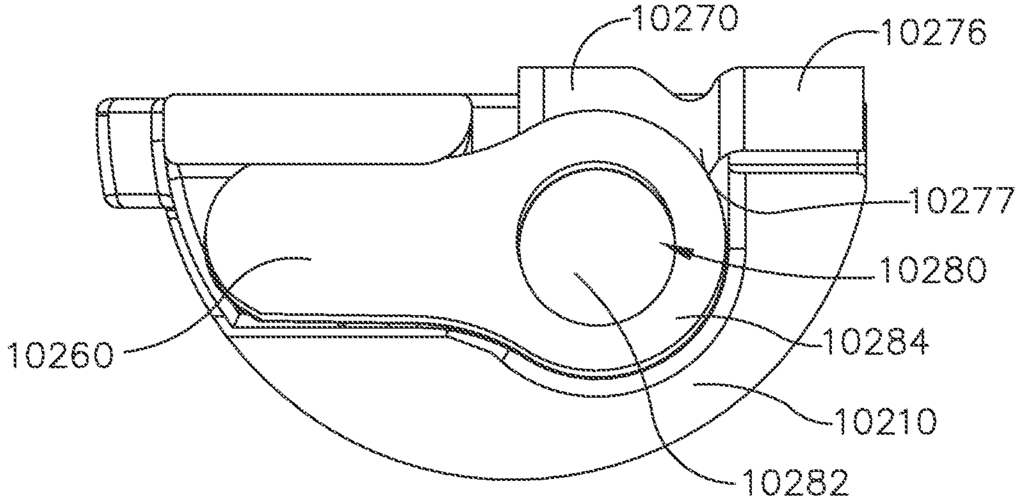
FIG. 74A is a detail view of the interface between the proximal articulation rod of FIG. 72 with the articulation lock of FIG. 73A.
Figure 75:
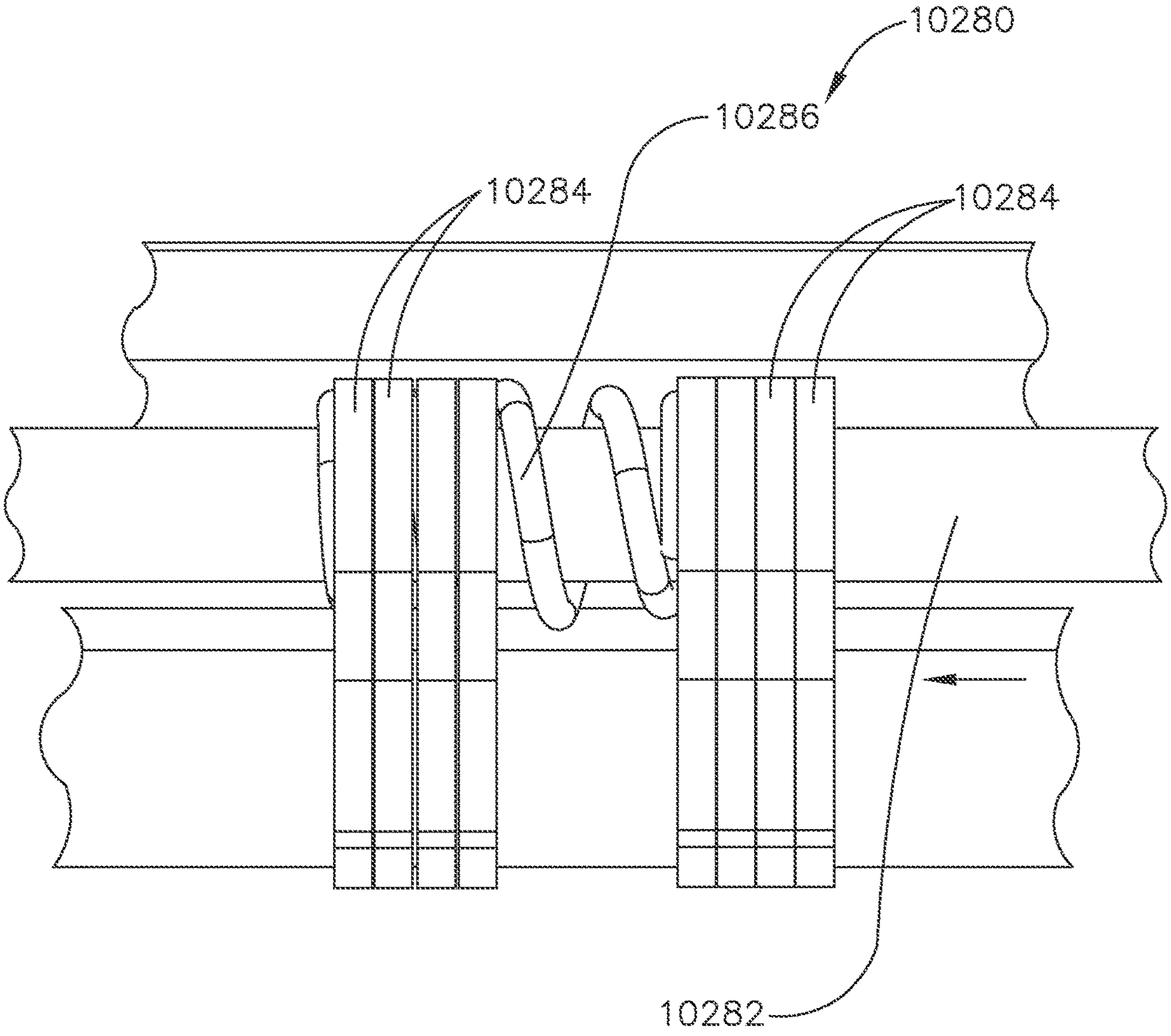
FIG. 75 is a perspective view of the articulation lock of FIG. 73A.
Figure 76:
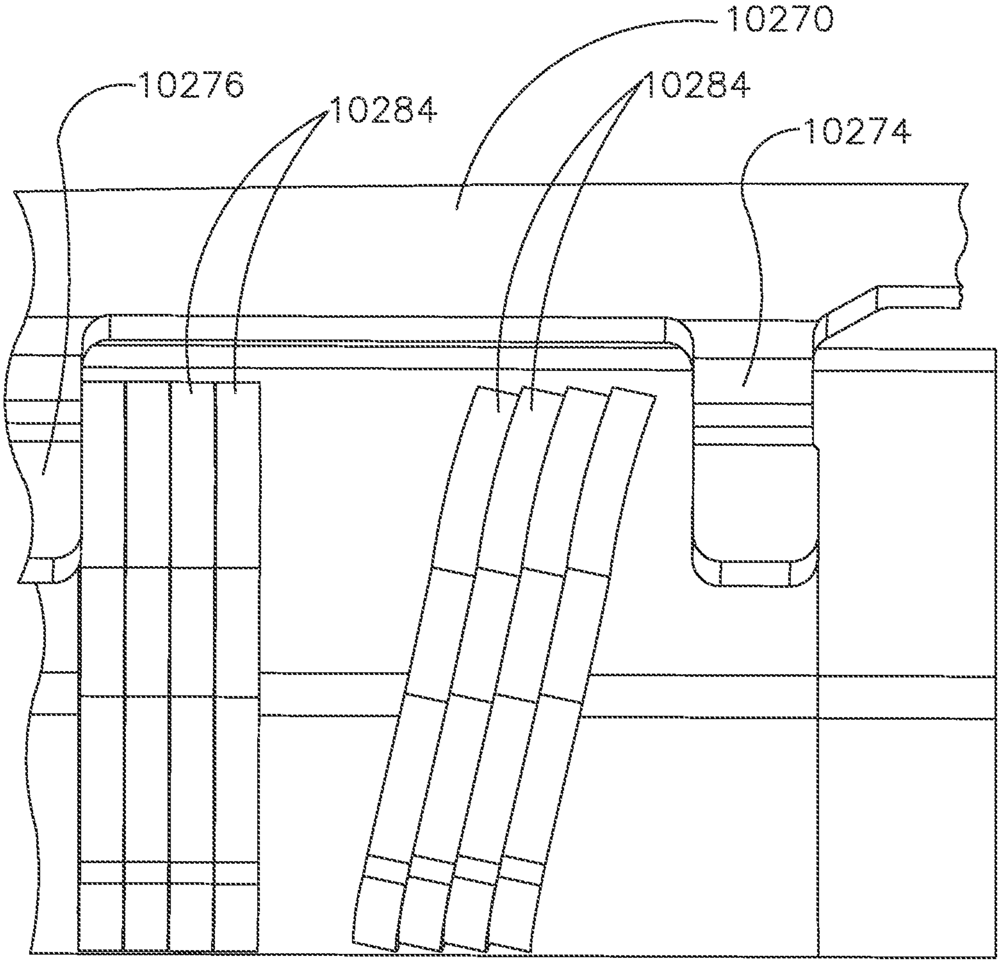
FIG. 76 is another perspective view of the articulation lock of FIG. 73A.

Further to the above, the projections 10274 and 10276 of the proximal articulation driver 10270 directly contact the lock members 10284. Referring to FIG. 74A, the projections 10274 and 10276 each comprises a projection, or bump, 10277 extending therefrom which engages the lock members 10284. The bumps 10277 provide a large pushing area for the proximal articulation driver 10270 to push against the lock members 10284. By way of comparison, a proximal articulation driver 10270' is illustrated in FIGS. 73 and 73A which does not have the bumps 10277 on its projections 10274' and 10276'. The arrangement of FIGS. 73 and 73A is still useful, but the contact area between the proximal articulation driver 10270' and lock members 10284 is smaller than the contact area between the proximal articulation driver 10270 and the lock members 10284. As a result of the larger contact area with the lock members 10284, the stress and strain in the proximal articulation driver 10270 is smaller than that of the proximal articulation driver 10270'. Moreover, the arrangement of the bumps 10277 can increase the torque arm between the proximal articulation driver 10270 and the lock members 10284 thereby lowering the force needed to unlock the articulation lock 10280.

Figure 77:
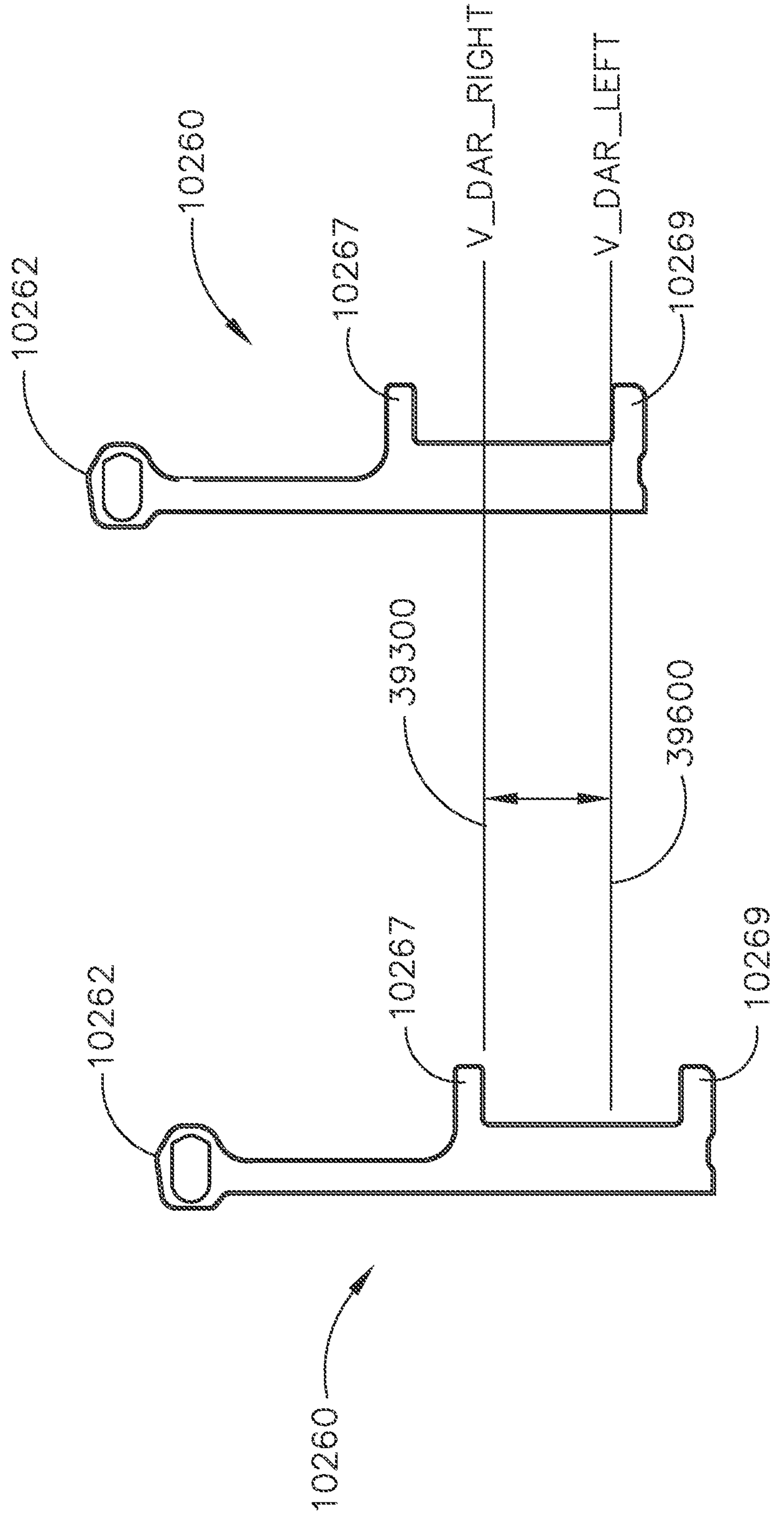
FIG. 77 illustrates the range of motion for the distal articulation rod of FIG. 73.
Figure 78:
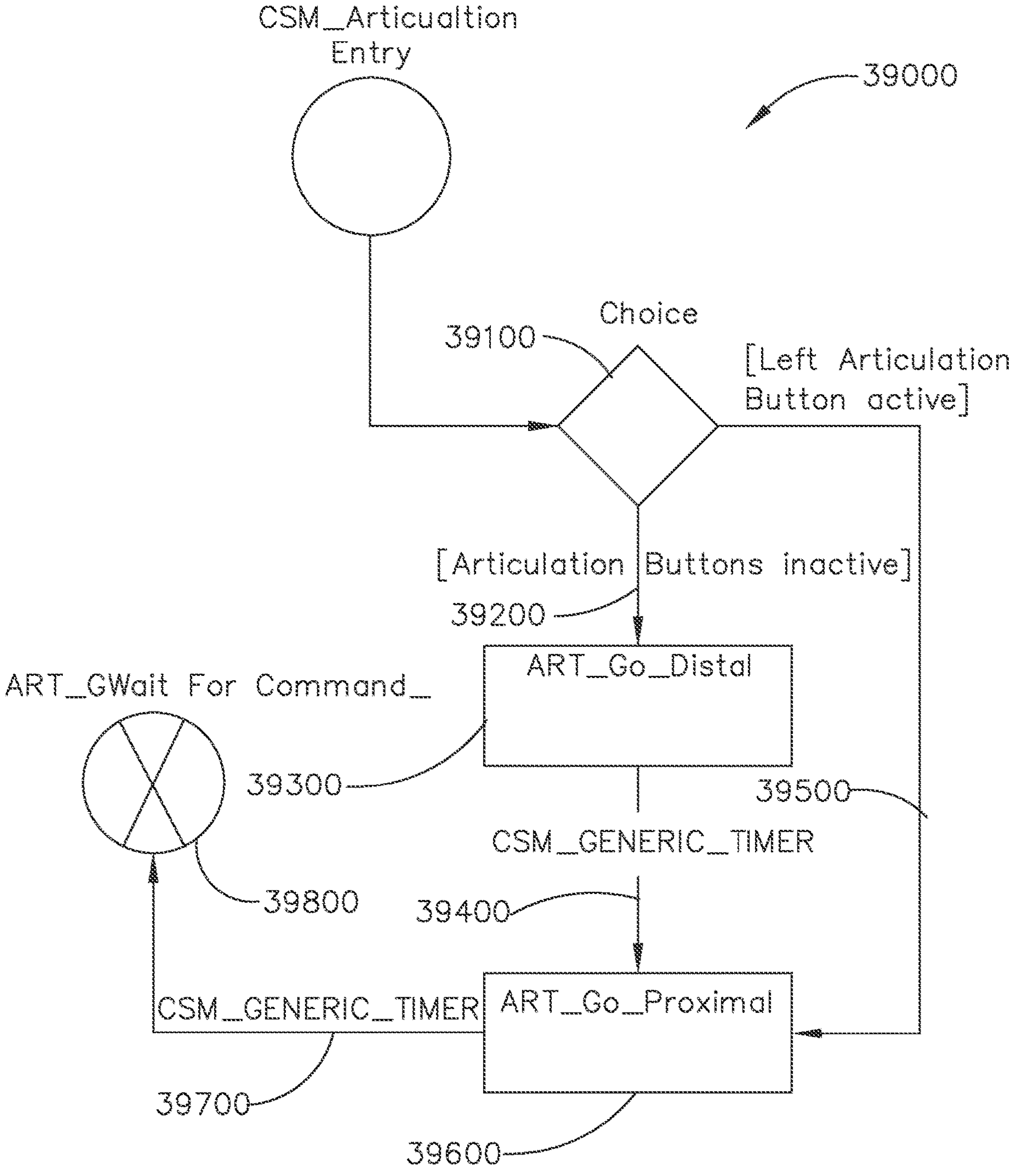
FIG. 78 is an algorithm for a control system to assess and acquire the position of an articulation system.

Described herein are various mechanisms and methods for determining the orientation of the shaft relative to the handle. Many of these mechanisms are able to evaluate the orientation of the shaft in real time and without regard to the previous orientation, or orientations, of the shaft. Such arrangements are particularly useful when the surgical instrument loses power, for example. When the surgical instrument re-powers, the control system can immediately assess the orientation of the shaft and the proper responsiveness of the articulation controls, for example. Moreover, the surgical instruments disclosed herein can be configured to immediately assess the articulation angle of the end effector when the surgical instrument is re-powered. Upon re-powering, the control system will evaluate whether the end effector is in a closed configuration or an open configuration. If the end effector is in a closed configuration upon re-powering, the control system will determine that the surgical instrument lost power during the staple firing mode and prompt the clinician to retract the staple firing system. If the end effector is in an open configuration upon re-powering, or once the end effector is in an open position upon re-powering, the control system will seek to make sure that the articulation drive system is coupled to the staple firing system such that the end effector can be straightened, or otherwise suitably oriented by the clinician, to remove the surgical instrument from the patient. FIG. 78 depicts an algorithm 39000 for the control system to assure that the articulation system is engaged with the staple firing drive. In this algorithm, the control system sweeps the staple firing drive between the positions associated with the furthest-right end effector position and its furthest-left end effector position such that, if the articulation drive was not already coupled to the firing drive, it would become so. These far-right and far-left orientations of the end effector correspond to the distal-most and proximal-most positions of the articulation driver 10260, as illustrated in FIG. 77. These positions are also the distal-most and the proximal-most positions, respectively, of the articulation driver 10270. The control system comprises one or more non-volatile device memories for storing information regarding the distal-most (far-right orientation) and proximal-most (far-left orientation) positions of the articulation drive system. As such, this information is available to the control system upon re-powering and the control system can limit its assessment to this range. In various embodiments, the surgical instrument can comprise a sensor configured to assess whether or not the articulation drive is mechanically coupled to the staple firing drive.

Further to the above, the algorithm 39000 comprises a step 39100 in which the control system assess whether or not an articulation button is depressed at the start-up, or initialization, of the surgical instrument. If it is determined at step 39100 that an articulation button is not depressed, the algorithm follows logic path 39200. In logic path 39200, the control system actuates the electric motor that drives the articulation system at step 39300 to push the articulation driver 10260 distally to articulate the end effector to the right. The control system then waits a predetermined amount of time at step 39400 before proceeding to step 39600 in which the control system actuates the motor in an opposite direction to pull the articulation driver 10260 proximally and articulate the end effector to the left. The control system then waits again for a predetermined amount of time at step 39700 and, after this time, waits for an input command at step 39800. In various embodiments, the control system comprises a timer circuit for counting the appropriate amount of time. If, on the other hand, the control system detects that the left articulation control is actuated at step 39100, the algorithm 39000 follows logic path 39500 and articulates the end effector to the left. If the control system detects that the right articulation control is actuated at step 39100, the algorithm 39000 follows a logic path that articulates the end effector to the right.

During a staple firing stroke, further to the above, the staples of a staple cartridge are progressively ejected by a firing member. The firing member ejects the proximal staples of the staple cartridge at the beginning of the staple firing stroke and the distal staples at the end of the staple firing stroke. In instances where all of the staples of a staple cartridge properly contact their staple forming pockets in the anvil positioned opposite to the staple cartridge, the staples will properly form and the staple firing force will be low. In instances where some of the staples miss their staple forming pockets, such staples may malform thereby increasing the force required to perform the staple firing stroke. Slowing the staple firing stroke may improve staple formation and lower the force required to perform the staple firing stroke. In various instances, detecting the force being applied by the staple firing system can be directly detected through one or more force sensors and/or strain gauges, for example. In other instances, detecting the force can be achieved by a current sensor or ammeter circuit, for example, which measures the current to the electric motor of the staple firing drive. The entire disclosure of U.S. patent application Ser. No. 16/361,793, entitled SURGICAL INSTRUMENT COMPRISING AN ADAPTIVE CONTROL SYSTEM, filed on Mar. 22, 2019 is incorporated by reference herein. These approaches may be suitable in various instances, but described below are embodiments and methods which assess the duty cycle of the staple firing system during the staple firing stroke.

Further to the above, the control system of the surgical instrument 10000 comprises a pulse width modulation (PWM) control circuit configured to control the speed of the firing drive electric motor. The PWM control circuit applies voltage pulses to the firing drive electric motor to perform the staple firing stroke. In various instances, the PWM control circuit increases the duration of the voltage pulses it applies to the firing drive electric motor in order to increase the speed of the firing drive electric motor and, correspondingly, the speed of the staple firing stroke. In other instances, the PWM control circuit decreases the duration of the voltage pulses it applies to the firing drive electric motor in order to decrease the speed of the firing drive electric motor and, correspondingly, the speed of the staple firing stroke. In either event, the PWM control circuit can make these pulse length adjustments without substantially increasing or decreasing the magnitude of the voltage pulses being applied to the motor. That said, embodiments are envisioned in which the magnitude of the voltage pulses, or certain voltage pulses, could be changed. In any event, as described in greater detail below, the control system is configured to drive the staple firing drive at a constant, or near constant, speed by adjusting the duration of the pulses via the PWM circuit. The entire disclosure of U.S. Pat. No. 8,499,992, entitled DEVICE AND METHOD FOR CONTROLLING COMPRESSION OF TISSUE, which issued on Aug. 6, 2013, is incorporated by reference herein.

The ratio of the time in which the voltage is applied to the electric motor (ON time) by the PWM circuit divided by the total time (ON time+OFF time) is the duty cycle of the staple firing drive motor. Thus, the duty cycle can range between 0% (completely OFF) and 100% (completely ON), i.e., a constant voltage without periodic interruptions. The terms ON and OFF suggest a non-zero voltage and a zero voltage; however, the terms ON and OFF are inclusive of HIGH and LOW voltages, respectively. The terms LOW or OFF include zero voltage and non-zero voltages that have a magnitude which is less than the HIGH or ON voltage. In view of the above, another way of expressing the duty cycle of the firing drive electric motor is the ratio of the time in which the voltage is applied to the electric motor (HIGH time) by the PWM circuit divided by the total time (HIGH time+LOW time).

The PWM control circuit applies the voltage pulses to the firing drive electric motor at regular intervals; however, the control system can comprise a frequency modulation (FM) control circuit to change the frequency of the voltage pulse intervals. In various instances, the FM control circuit decreases the interval between the voltage pulses to increase the speed of the firing drive electric motor and the staple firing stroke. Correspondingly, the FM control circuit increases the interval between the voltage pulses to decrease the speed of the firing drive electric motor and the staple firing stroke. In addition to or in lieu of the above, the control system can increase the magnitude of the voltage it applies to the firing drive electric motor to increase the speed of the firing drive electric motor and the staple firing stroke and/or decrease the magnitude of the voltage it applies to the firing drive electric motor to decrease the speed of the firing drive electric motor and the staple firing stroke.

Figure 79:
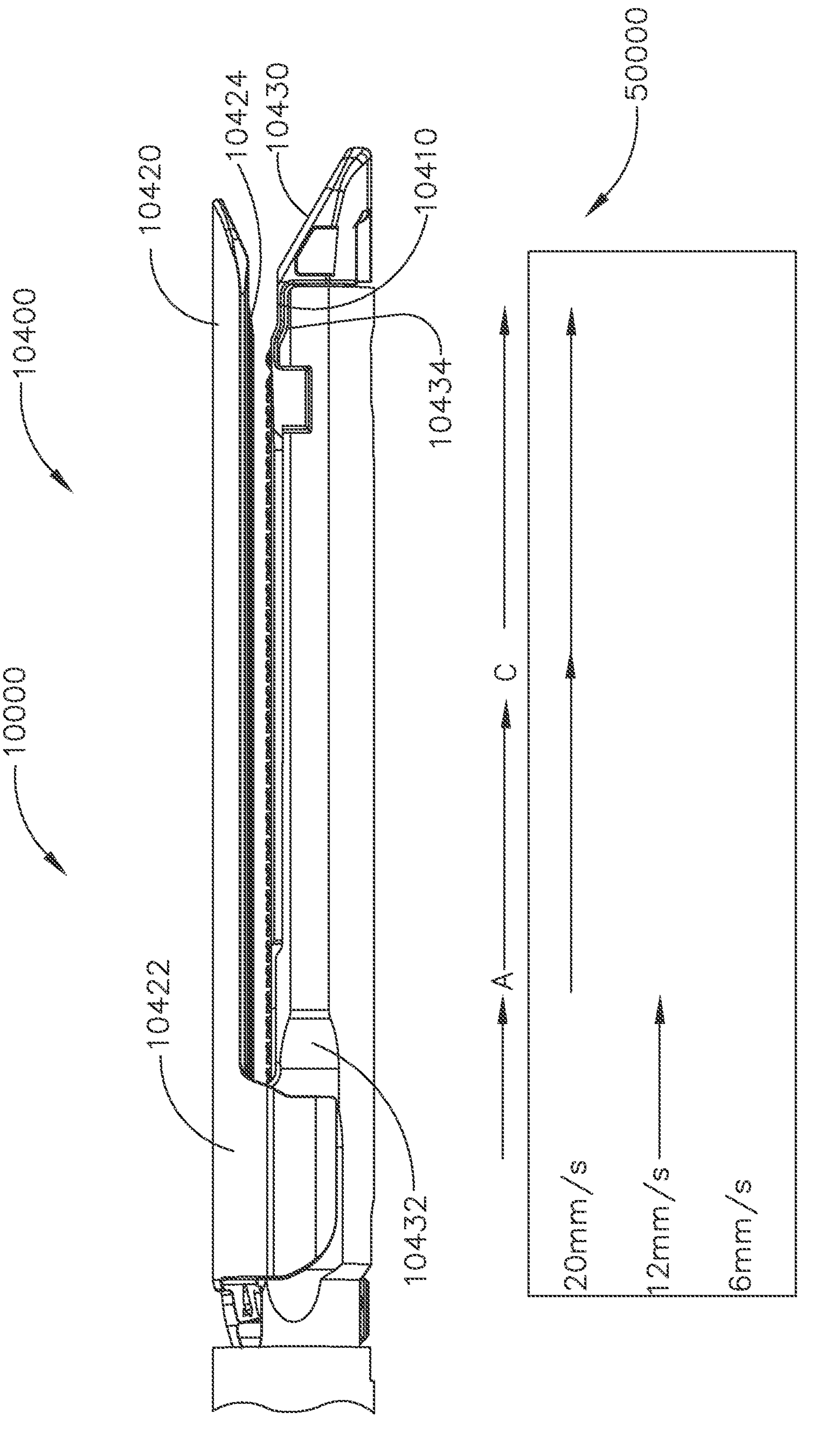
FIG. 79 depicts the end effector of the surgical instrument of FIG. 1 and a speed chart algorithm of the staple firing system during a staple firing stroke.

The control system of the surgical instrument 10000 comprises an algorithm for controlling the speed of the staple firing member. Referring to FIG. 79, the control system includes an algorithm 50000 configured to drive the staple firing member at a low speed, an intermediate speed, and a high speed. The low speed is 6 mm/s, or approximately 6 mm/s. The intermediate speed is 12 mm/s, or approximately 12 mm/s. The high speed is 20 mm/s, or approximately 20 mm/s. That said, a control system can be configured to operate the staple firing drive at any suitable number of speeds and/or at any suitable speed. The control system is configured to monitor the speed of the staple firing drive, via a motor speed sensor, and adjust the length of the voltage pulses applied to the electric motor of the staple firing drive to bring the speed of the staple firing drive to the target speed. For instance, if the target speed of the staple firing drive at a given point in the staple firing stroke is 12 mm/s and the actual speed is 11 mm/s, the control system increases the length of the voltage pulses it is applying to the electric motor to increase the speed of the staple firing drive. Stated another way, the control system increases the duty cycle of the firing drive electric motor to increase the speed of the staple firing drive. Correspondingly, the control system is configured to shorten the length of the voltage pulses it is applying to the firing drive electric motor if the speed of the staple firing drive exceeds the target speed until the speed of the staple firing drive reaches the target speed. Stated another way, the control system is configured to lower the duty cycle of the firing drive electric motor to decrease the speed of the staple firing drive. Notably, the target speed for the staple firing drive can change during the staple firing stroke, as described in greater detail below.

As discussed above, the firing member of the staple firing drive is moved distally during the staple firing stroke. Referring to FIGS. 47 and 79, the firing member is advanced distally from its proximal, unfired position to move the top cam member 10255 of the firing member up the ramp of the internal slot 10425 defined in the anvil 10420. The distance between the proximal, unfired position and the distal end of the internal slot ramp is 15 mm, or approximately 15 mm, for example. This initial 15 mm motion of the firing member can be used to close the end effector and/or pass over the firing lockout described above if a proper unspent staple cartridge is seated in the end effector. That being said, during this range of motion, the control system moves the firing member distally at the intermediate speed of 12 mm/s and evaluates the duty cycle needed to drive the staple firing member at this speed. If the duty cycle is between 40% and 60% in this initial range, the control system continues to drive the staple firing drive at the intermediate speed of 12 mm/s. If the duty cycle is above 60%, the control system lowers the target speed of the staple firing drive to the low speed of 6 mm/s. Such instances can arise when thick tissue is present between the anvil 10420 and the staple cartridge 10430. On the other hand, if the duty cycle is below 40% during this initial range, the control system increases the target speed to the high speed of 20 mm/s. Such instances can arise when thin tissue is present between the anvil 10420 and the staple cartridge 10430. In FIG. 79, the end of this initial range is demarcated by point A and, notably, staples are not deployed, or fired, during this initial range. After point A, the firing member fires the staples as the firing member is advanced distally until the firing member reaches the end of the staple firing stroke and/or the clinician stops the staple firing stroke by releasing the firing trigger.

Referring to the algorithm 50000 in FIG. 79, it can be seen that the staple firing member was driven at the intermediate speed, 12 mm/s, for the first 15 mm and then at the high speed, 20 mm/s, for the rest of the staple firing stroke. As described above, this shift in speed occurred because the control system measured that the duty cycle was below 40% during the first 15 mm of the staple firing stroke. Had the firing member been blocked by the lockout in the first 15 mm, however, the duty cycle would have spiked immediately to 100% and the control system is configured to immediately stop the staple firing stroke in response to such asymptotic duty cycle spikes. Once the firing member has passed this initial 15 mm distance, in various instances, the remainder of the staple firing stroke comprises approximately 30 mm, approximately 45 mm, or approximately 60 mm, for example. These lengths represent the different staple pattern lengths that are currently desirable in many staple cartridges, but any suitable staple pattern lengths could be used. In some embodiments, the control system does not re-evaluate the duty cycle of the staple firing drive to adjust the target speed of the firing member after an initial evaluation of the firing drive duty cycle. The control system of embodiment of FIG. 79, however, continues to evaluate the duty cycle of the staple firing drive throughout the staple firing stroke. At point C in the staple firing stroke, the control system makes another adjustment to the target speed or maintains the target speed according to the criteria set forth above. As depicted in FIG. 79, the duty cycle of the staple firing drive was determined to be between 40% and 60% at point C and, thus, the control system maintained the target speed of 20 mm/s. Point C is half way between point A and the end of the staple firing stroke, i.e., half way into the staple pattern. That said, point C can be at any suitable location. Moreover, the control system can be configured to adjust the target speed of the staple firing drive at any suitable number of points during the staple firing stroke. In at least one instance, the control system can make a target speed adjustment at every 15 mm during the staple firing stroke, for example. For a 30 mm staple cartridge, the control system could make a total of two target speed adjustments, as illustrated in FIG. 79. For a 45 mm staple cartridge, the control system could make a total of three target speed adjustments at 15 mm intervals and, for a 60 mm staple cartridge, the control system could make a total of four target speed adjustments at 15 mm intervals, for example.

Figure 80:
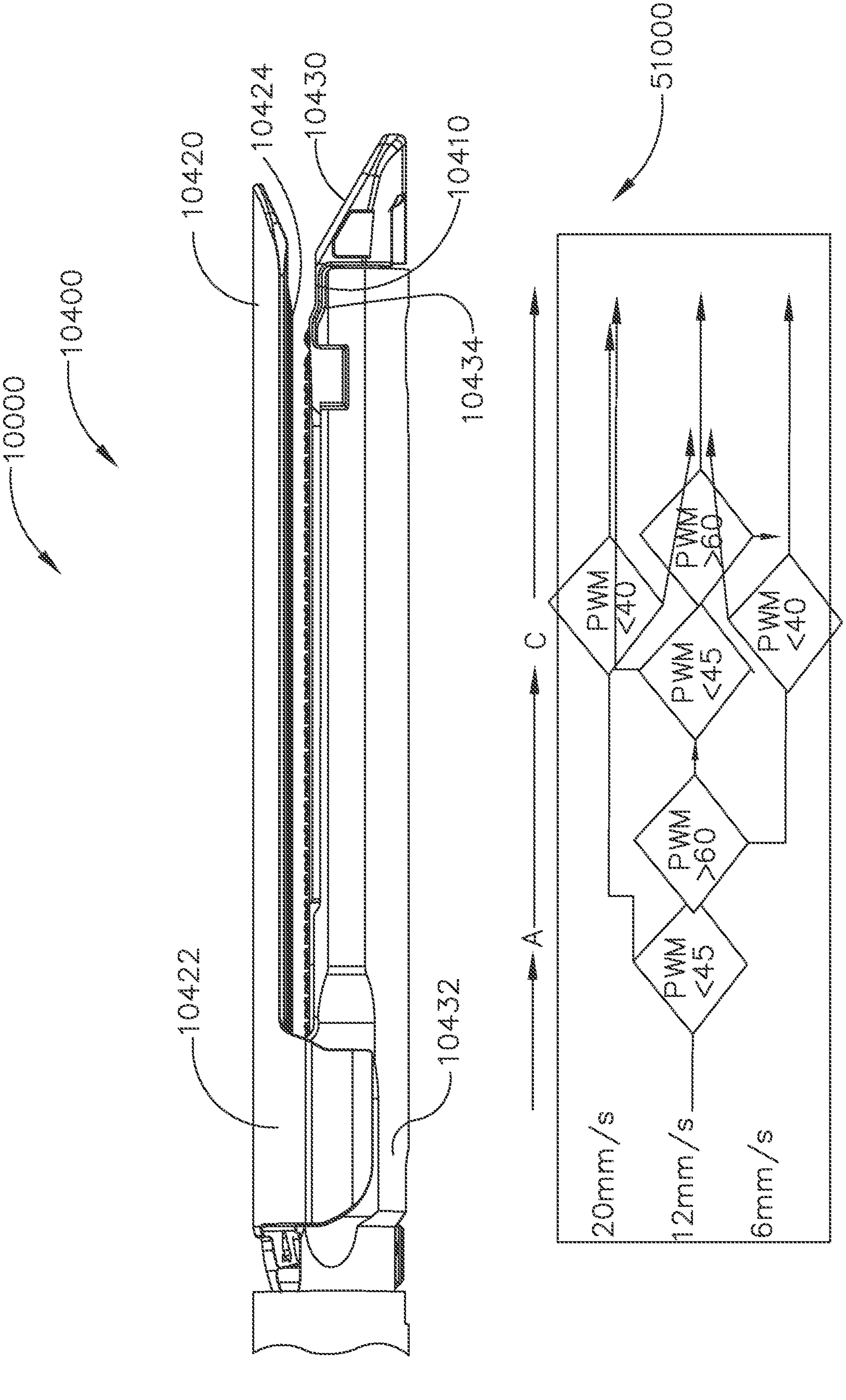
FIG. 80 depicts the end effector of the surgical instrument of FIG. 1 and a speed chart algorithm of the staple firing system in accordance with at least one embodiment.

For the examples given above, the control system used the same set of criteria for evaluating the duty cycle at every target speed adjustment point. That said, referring to FIG. 80, embodiments are envisioned in which the control system uses different sets of duty cycle criteria at different target speed adjustment points. For instance, the control system can use a first set of duty cycle criteria at the first target speed adjustment point and a second set of duty cycle criteria at the second target speed adjustment point. In at least one instance, referring to the algorithm 51000 in FIG. 80, the control system increases the target speed of the staple firing drive if the duty cycle is below 45% at the first target speed adjustment point. That said, the control system increases the target speed of the staple firing drive at the second target speed adjustment point if the duty cycle is below 40%. Any suitable threshold, or thresholds, could be used. In the embodiment illustrated in FIG. 80, the upper duty cycle threshold of 60% is the same at both the first and second target speed adjustment points in the algorithm 51000. If the duty cycle is in excess of 60%, the control system shortens the voltage pulses to slow the staple firing system. In other embodiments, the upper duty cycle threshold can be different at the first and second target speed adjustment points.

Figure 81:
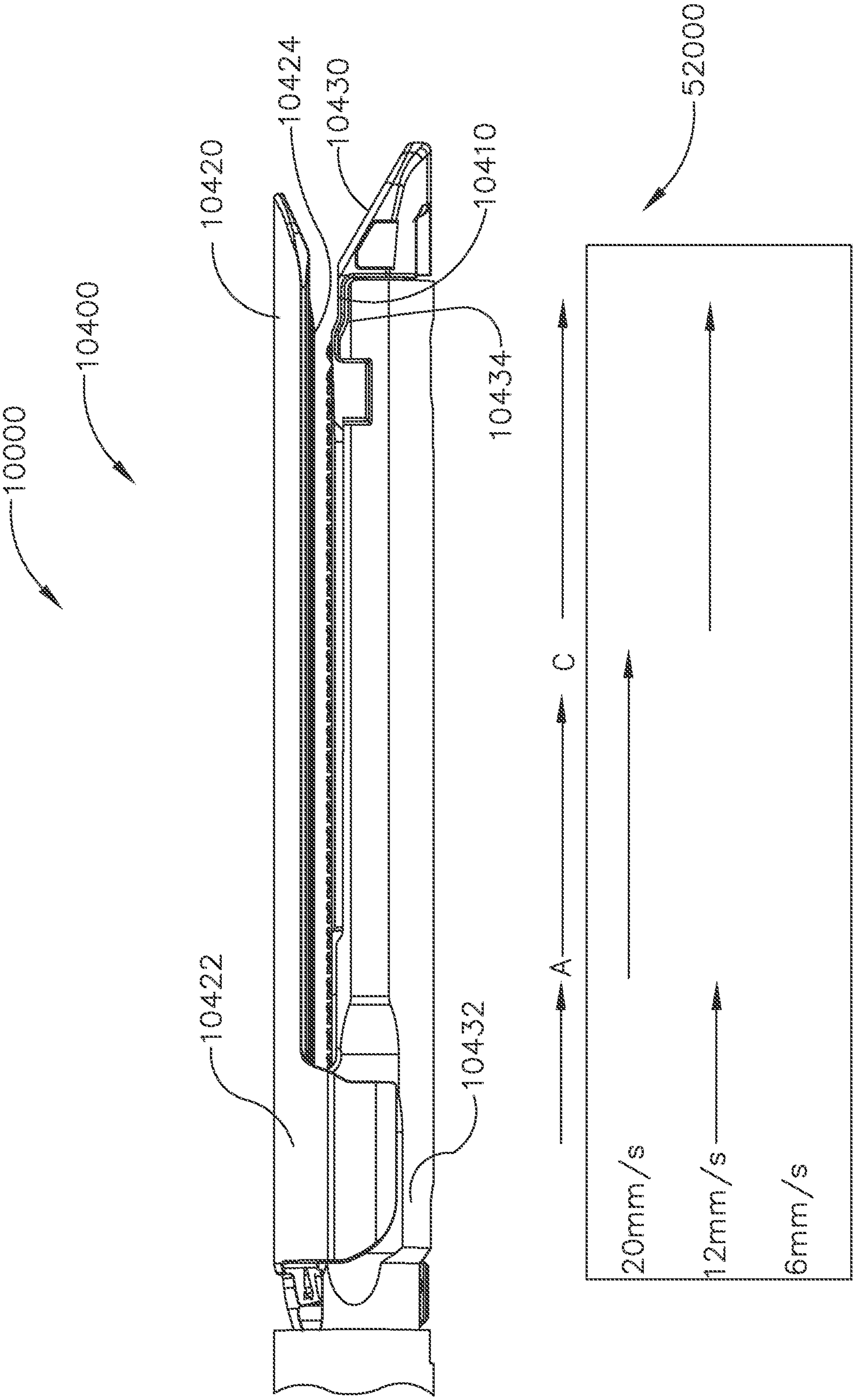
FIG. 81 depicts the end effector of the surgical instrument of FIG. 1 and a speed chart algorithm of the staple firing system during a staple firing stroke.

Further to the above, referring to FIG. 81, the algorithm of the control system increased the target speed at point A from the intermediate speed to the high speed but then lowered the target speed at point C from the high speed to the intermediate speed. At point C, the control system determined that the duty cycle of the firing drive electric motor was above 60% and lowered the target speed one level, i.e., from the high speed to the intermediate speed. Notably, the control system did not lower the target speed from the high speed to the low speed at point C as the control system is configured to only raise or lower the target speed one level at each check point. In order for the target speed of the staple firing drive to be lowered from the high speed to the low speed, the duty cycle would have to exceed the upper duty cycle threshold at two checkpoints. These checkpoints can be consecutive checkpoints, or non-consecutive checkpoints. That said, embodiments are envisioned in which the control system comprises a safety duty cycle threshold that, if exceeded, would cause the control system to drop the target speed of the staple firing drive to the low speed regardless of the speed of the staple firing drive prior to that checkpoint.

Figure 82A:
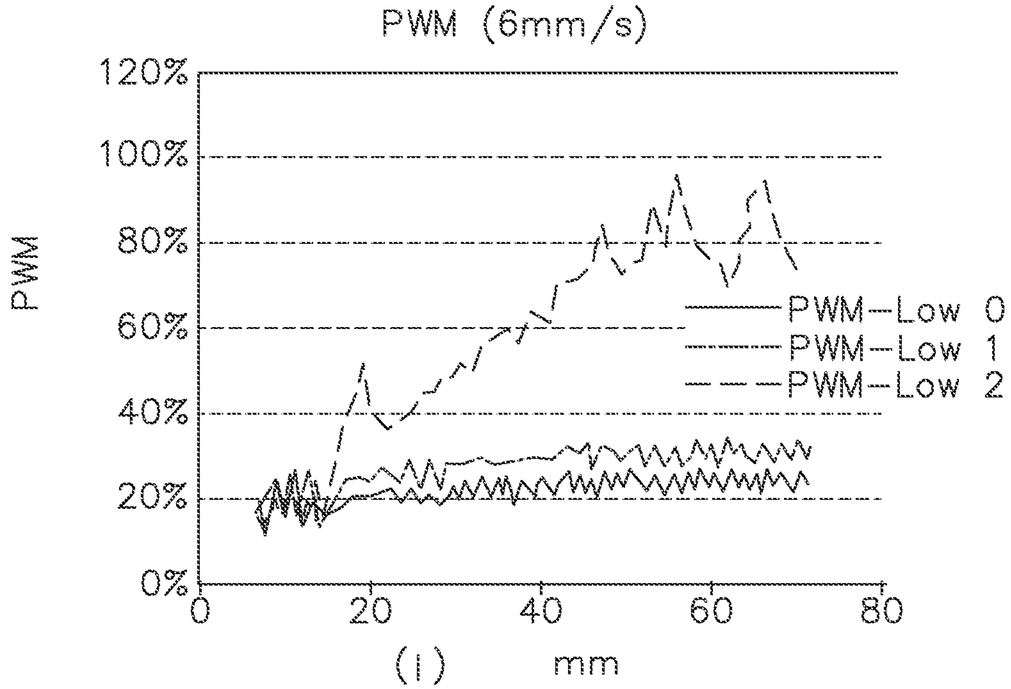
FIG. 82A depicts a graph of the duty cycle of and firing force experienced by the staple firing system of the surgical instrument of FIG. 1 during three staple firing strokes.
Figure 82A:
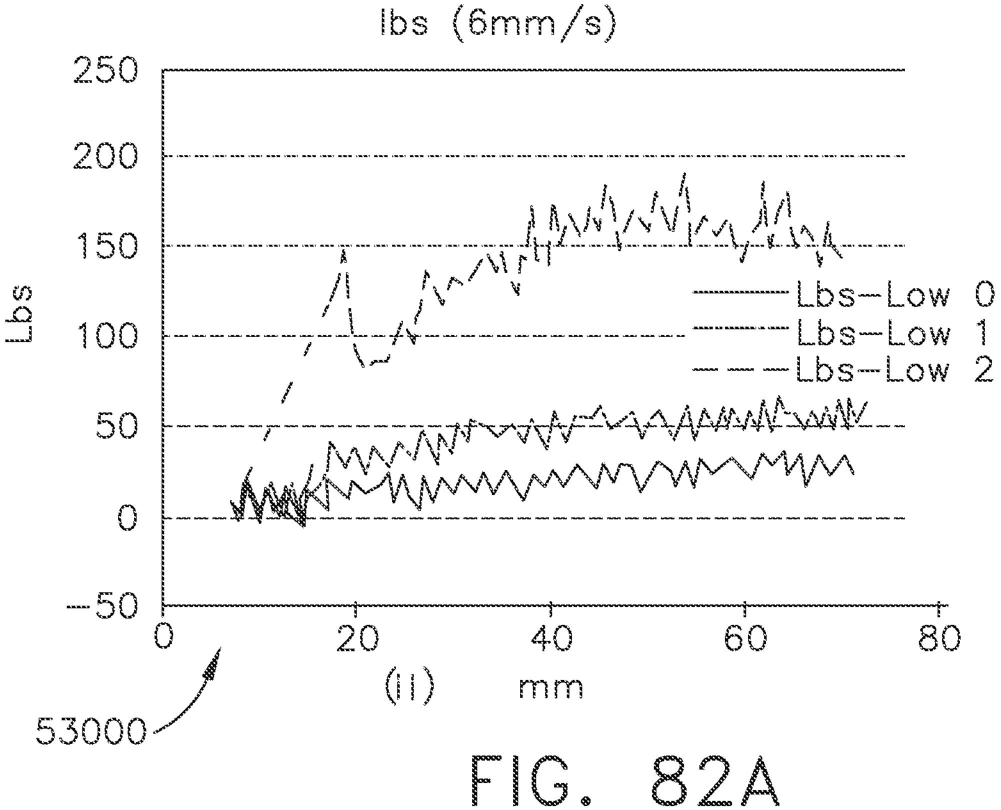

FIG. 82A depicts two graphs—a duty cycle graph (i) and a firing force graph (ii) of the staple firing drive. The duty cycle graph (i) and the firing force graph (ii) are correlated to demonstrate three different staple firing strokes. Two of the staple firing strokes in FIG. 82A stay below the 40% duty cycle threshold as the firing force is low. In such staple firing strokes, the control system increases the target speed of the staple firing system at each check point according to the current algorithm, although other algorithms are possible.

One of the staple firing strokes in FIG. 82A reaches a 100% duty cycle because the firing force is high. When the duty cycle is in excess of 60% at a target speed adjustment point, the control system decreases the target speed of the staple firing system according to the current algorithm, although other algorithms are possible. Notably, the duty cycle of this staple firing isn't above the 60% threshold at the beginning of the staple firing stroke and, as a result, the control system may not actually lower the target speed if the duty cycle didn't exceed the upper threshold of 60% until after the check point, or check points.

Figure 82B:
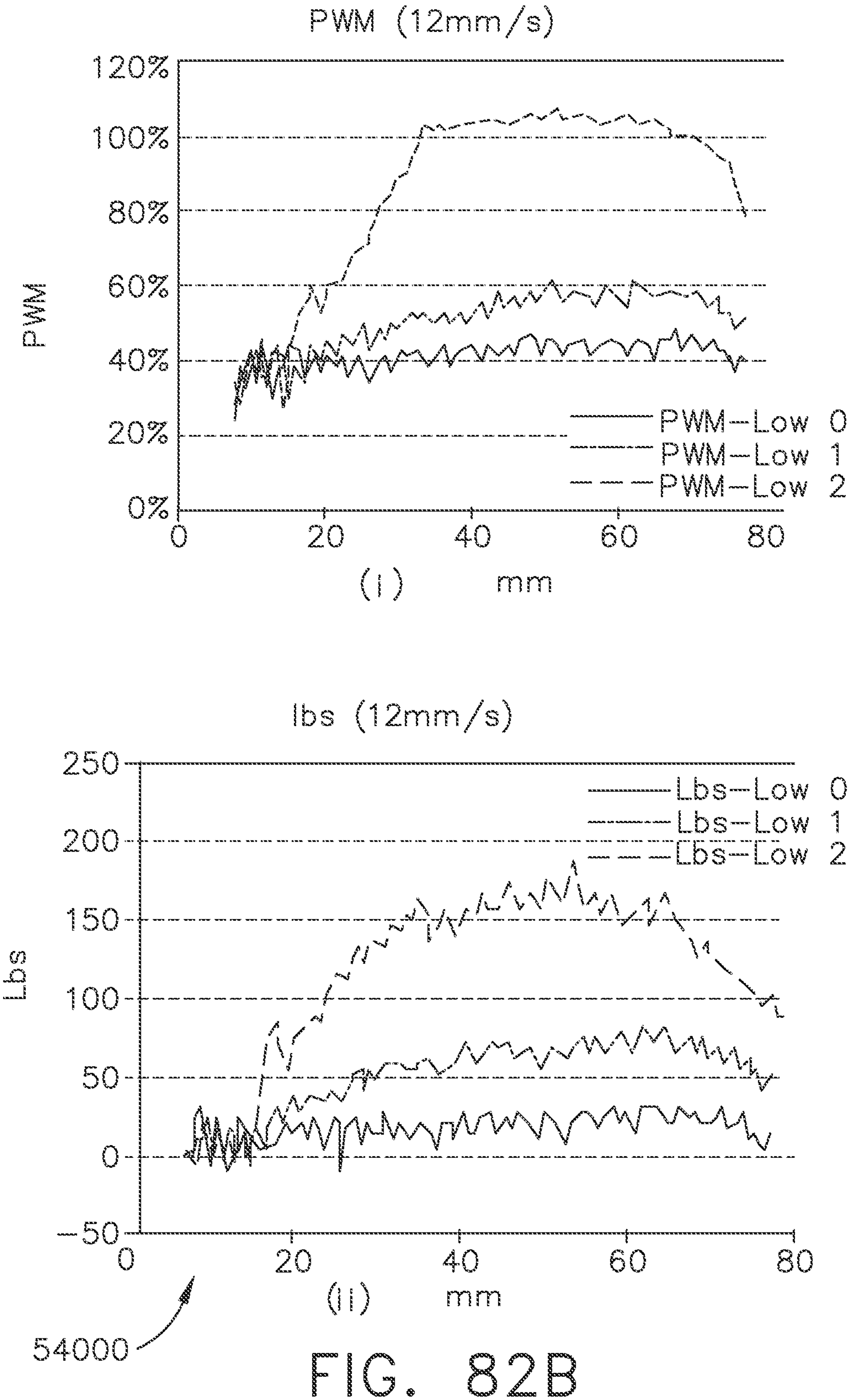
FIG. 82B depicts a graph of the duty cycle of and firing force experienced by the staple firing system of the surgical instrument of FIG. 1 during three staple firing strokes at a higher firing speed than that of FIG. 82A.

FIG. 82B depicts two graphs—a duty cycle graph (i) and a firing force graph (ii) of the staple firing drive. The duty cycle graph (i) and the firing force graph (ii) are correlated to demonstrate three different staple firing strokes. Two of the staple firing strokes in FIG. 82B stay between the 40% duty cycle threshold and the 60% duty cycle threshold as the firing force is relatively low. In such staple firing strokes, the control system does not change the target speed of the staple firing system according to the current algorithm, although other algorithms are possible. One of the staple firing strokes in FIG. 82B reaches a 100% duty cycle, however, because the firing force is high. When the duty cycle is in excess of 60% at a target speed adjustment point, the control system decreases the target speed of the staple firing system according to the current algorithm, although other algorithms are possible. In this instance, the duty cycle exceeded the upper duty cycle threshold at about 20 mm distal to the proximal, unfired starting position of the staple firing member. Stated another way, the duty cycle jumped above 60% as soon as the staple firing drive started to fire the staples, i.e., at 5 mm past the 15 mm initial range discussed above. As a result, the control system may not react to the elevated duty cycle until after a 30 mm checkpoint, for example.

Notably, further to the above, the graphs of FIGS. 82A and 82B, and several other graphs, depict a stream of dots along the staple firing stroke. These dots represent the data samples taken by the control system. The closeness of the dots represents a fairly high data sample rate, although lower or higher data sample rates could be used. As can be seen in these figures, the data is subject to a certain amount of jitter or chatter which can cause the control system to react to outlying data, especially when the duty cycle data is near the upper or lower duty cycle thresholds. In various instances, the control system can utilize a data smoothing algorithm which uses averages, and/or other statistical evaluations, of the data over a number of collected data points to determine the duty cycle at the target speed evaluation points. In at least one such instance, the control system uses the average of three consecutive duty cycle measurements, for example, to determine the duty cycle value used for assessing the algorithm criteria.

Figure 83A:
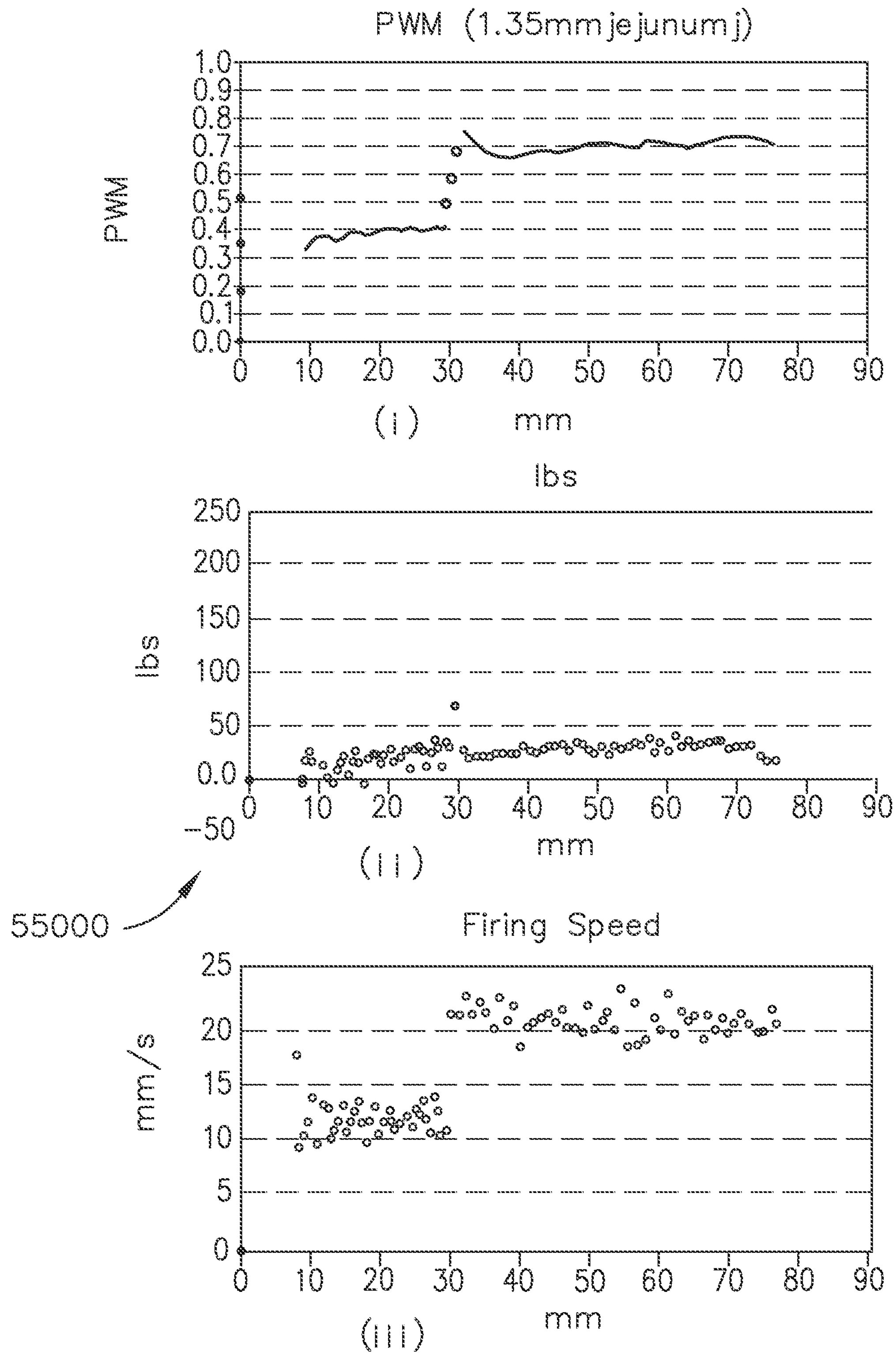
FIG. 83A depicts a graph of the duty cycle, firing force, and firing speed experienced by the staple firing system of the surgical instrument of FIG. 1 during a staple firing stroke through 1.35 mm thick jejunum tissue.
Figure 83B:
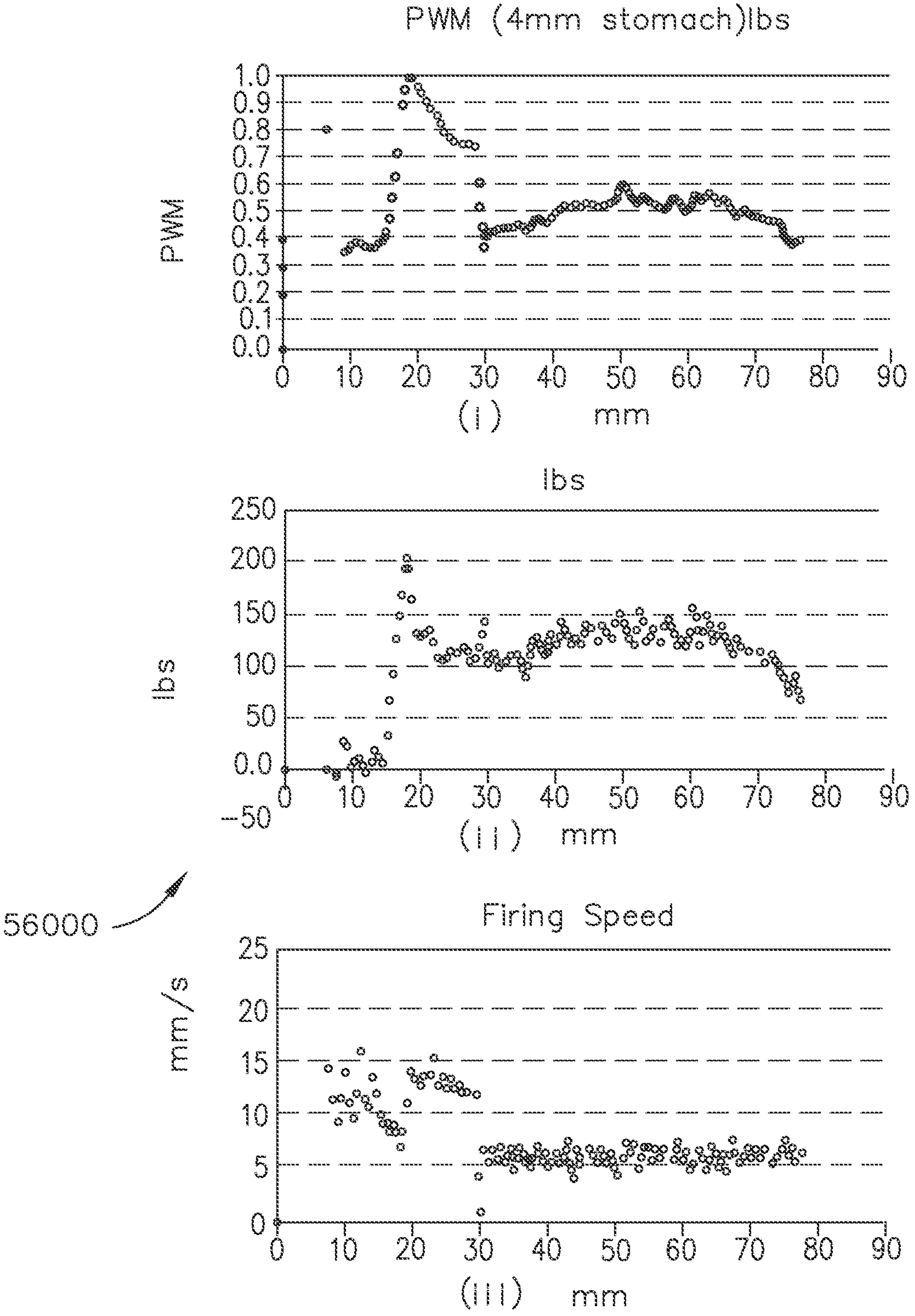
FIG. 83B depicts a graph of the duty cycle, firing force, and firing speed experienced by the staple firing system of the surgical instrument of FIG. 1 during a staple firing stroke through 4 mm thick stomach tissue.

FIG. 83A depicts three graphs—a duty cycle graph (i), a firing force graph (ii), and a firing speed graph (iii) of the staple firing drive. The duty cycle graph (i), the firing force graph (ii), and the firing speed graph (iii) are correlated to demonstrate a staple firing stroke. The duty cycle of the staple firing stroke jumps from below the lower duty cycle threshold of 40% to above the upper duty cycle threshold of 60% at about the 30 mm mark, which is about 15 mm into deforming the staples. This jump in duty cycle was not because the firing force increased; rather the jump in duty cycle occurred because the control system increased the duty cycle to increase the speed of the staple firing drive in accordance with its target speed selection criteria. FIG. 83B depicts a similar jump in the duty cycle at about 20 mm; however, this jump in duty cycle occurred because the staple firing member encountered an elevated resistance while deforming the staples and the control system responded by increasing the length of the voltage pulses it was applying to the electric motor in order to maintain the staple firing speed at its target speed. Stated another way, the control system spiked the duty cycle because the control system was struggling to maintain the intermediate speed, i.e., 12 mm/s, of the staple firing system. This situation did not last long as the control system re-lowered the duty cycle at the 30 mm target speed check point while lowering the speed of the staple firing stroke to its low, i.e., 6 mm/s, target speed.

Figure 84A:
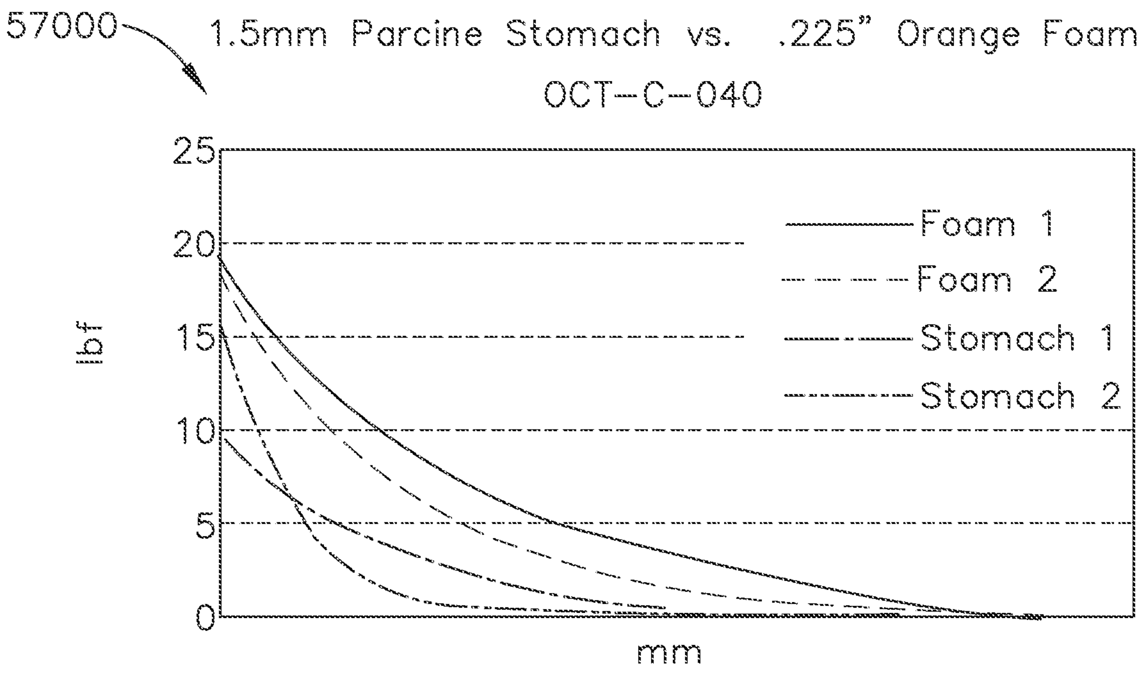
FIGS. 84A and 84B depict graphs comparing the firing force through tissue as compared to a tissue analogue.
Figure 84B:
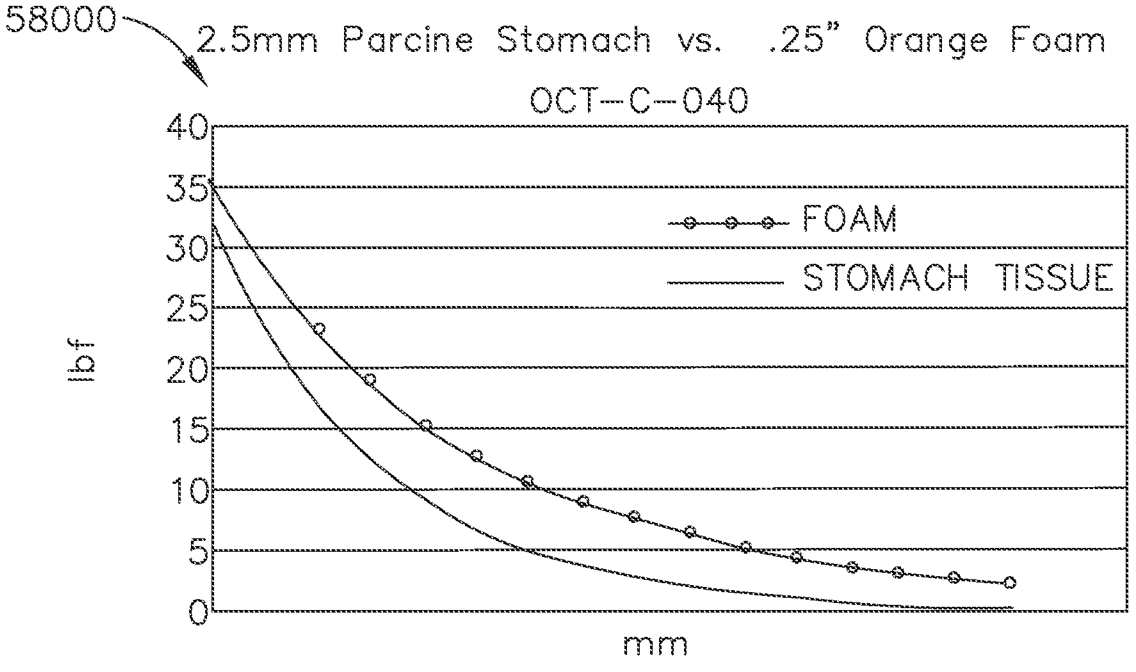

FIGS. 84A and 84B depict graphs which demonstrate that the firing force of the staple firing drive for stapling and cutting actual tissue tracks that of the firing force for stapling and cutting a tissue analogue, such as foam, for example.

Figure 85A:
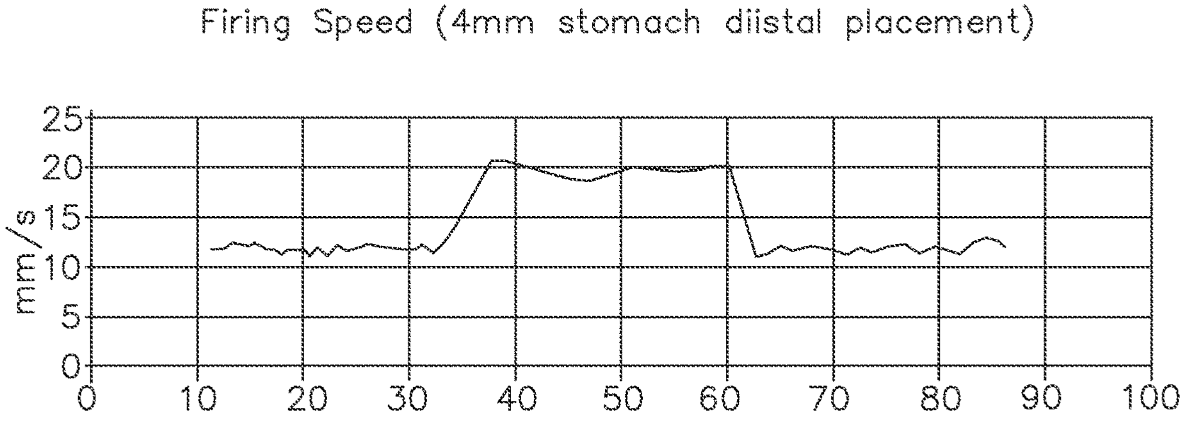
FIGS. 85A and 85B depict graphs demonstrating the duty cycle and the firing speed experienced by the staple firing system of the surgical instrument of FIG. 1 during several staple firing strokes.
Figure 85B:
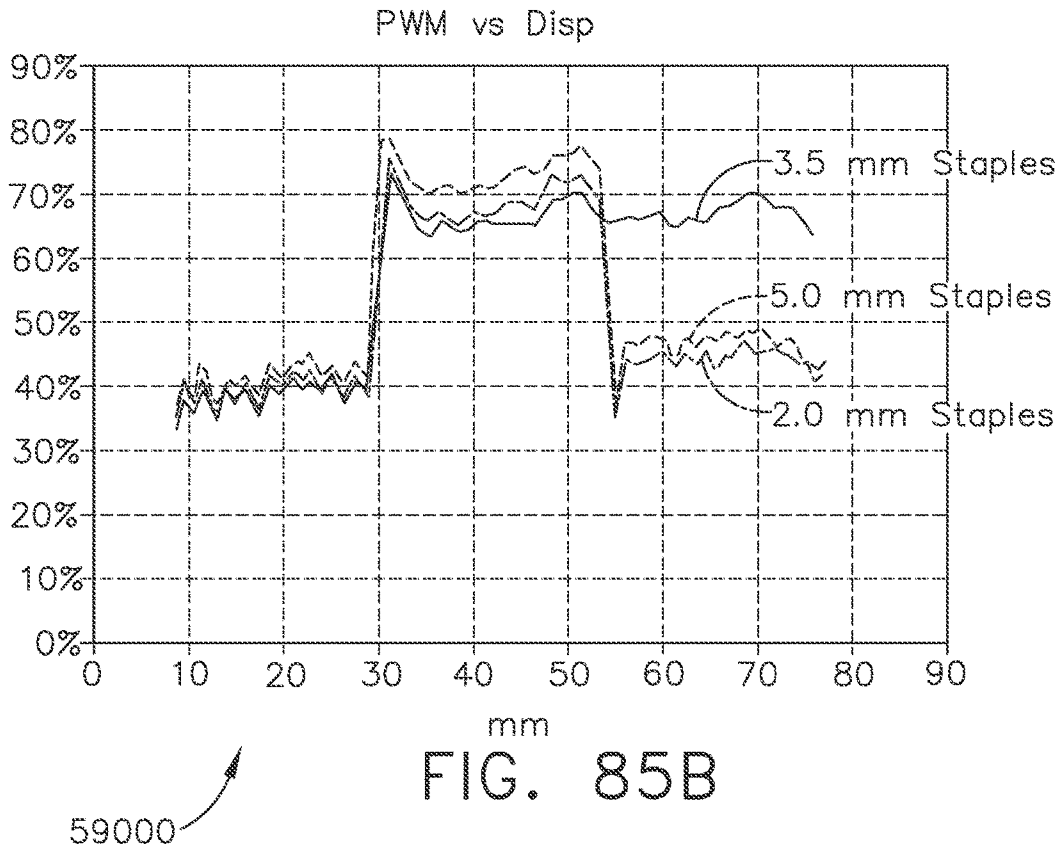

FIGS. 85A and 85B depict several staple firing stroke examples that occurred when stapling and cutting stomach tissue. The staple firing strokes followed a very similar duty cycle pattern. For instance, all of the staple firing strokes started below the lower duty cycle threshold and, in response, the control system increased the speed of the staple firing stroke from the intermediate speed to the high speed. To do so, the control system increased the duration of the voltage pulses being applied to the electric motor of the staple drive system at a first check point. In doing so, however, the duty cycle jumped above the upper duty cycle threshold and, at the next check point, the control system shortened the voltage pulses to lower the duty cycle and slow the staple firing stroke back to its intermediate speed. Notably, in one example, the speed of the staple firing drive was maintained at the high speed. In this example, the staples being deformed were smaller as compared to the staples used during the other staple firing strokes and they duty cycle stayed just under the threshold.

Figure 86C:
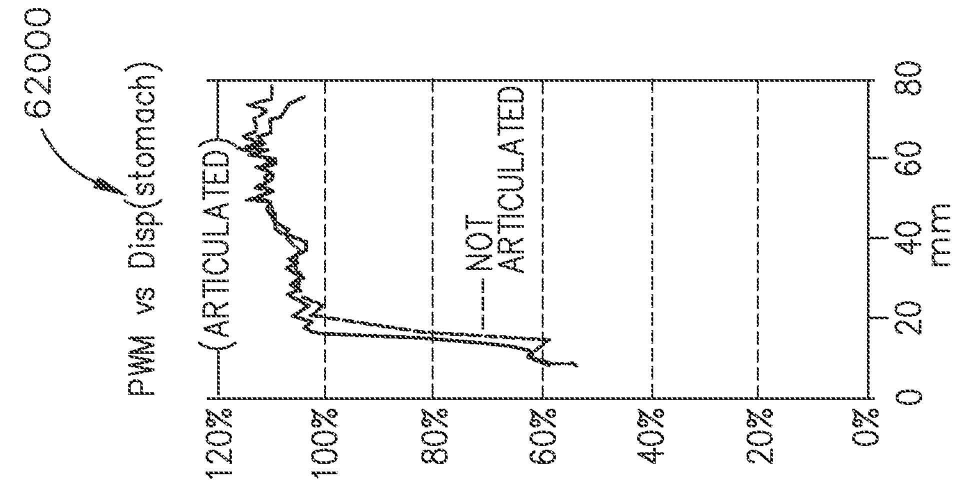
FIG. 86C depicts a graph of the duty cycle of the staple firing system of the surgical instrument of FIG. 1 during staple firing strokes through stomach tissue.
Figure 86B:
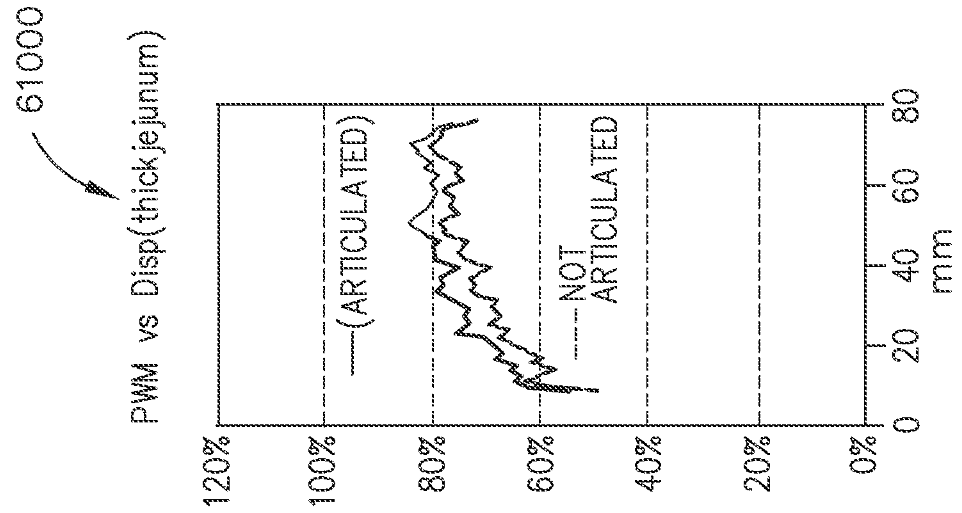
FIG. 86B depicts a graph of the duty cycle of the staple firing system of the surgical instrument of FIG. 1 during staple firing strokes through thick jejunum tissue.
Figure 86A:
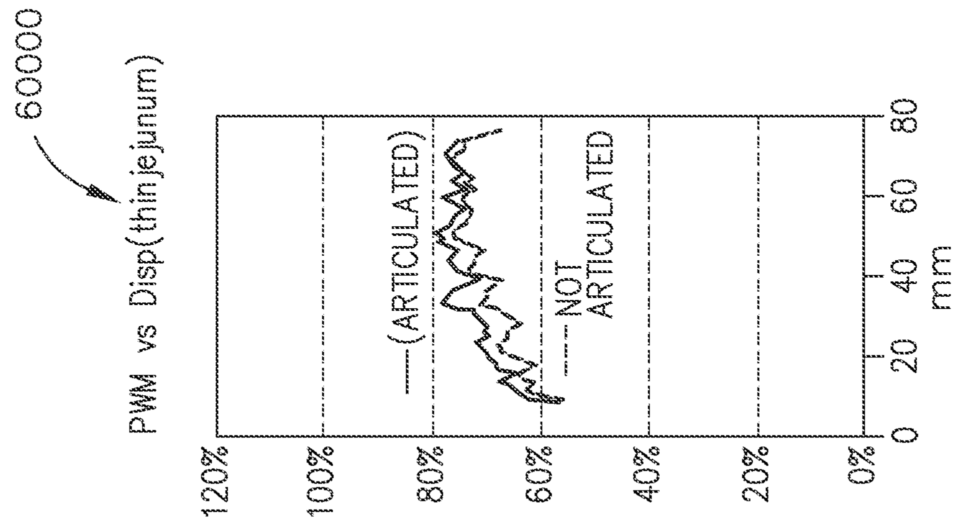
FIG. 86A depicts a graph of the duty cycle of the staple firing system of the surgical instrument of FIG. 1 during staple firing strokes through thin jejunum tissue.

FIG. 86A depicts the duty cycle of two staple firing strokes while stapling thin jejunum tissue—one that occurred when the end effector was articulated and one that occurred when the end effector was not articulated. As can be seen in FIG. 86A, the two duty cycle curves are very similar and are, notably, between about 60% and about 80% of the duty cycle. FIG. 86B depicts the duty cycle of two staple firing strokes while stapling thick jejunum tissue—one that occurred when the end effector was articulated and one that occurred when the end effector was not articulated. As can be seen in FIG. 86B, the two duty cycle curves are very similar and are, notably, between about 60% and about 80% of the duty cycle. Also, notably, the duty cycle is somewhat higher for the thick jejunum tissue (FIG. 86B) as compared to the thin jejunum tissue (FIG. 86A). FIG. 86C depicts the duty cycle of two staple firing strokes while stapling stomach tissue—one that occurred when the end effector was articulated and one that occurred when the end effector was not articulated. As can be seen in FIG. 86C, the two duty cycle curves are very similar and, notably, reach the maximum duty cycle once the staple firing drive starts deforming staples at about 15 mm from the proximal, unfired position of the firing member.

Figure 87:
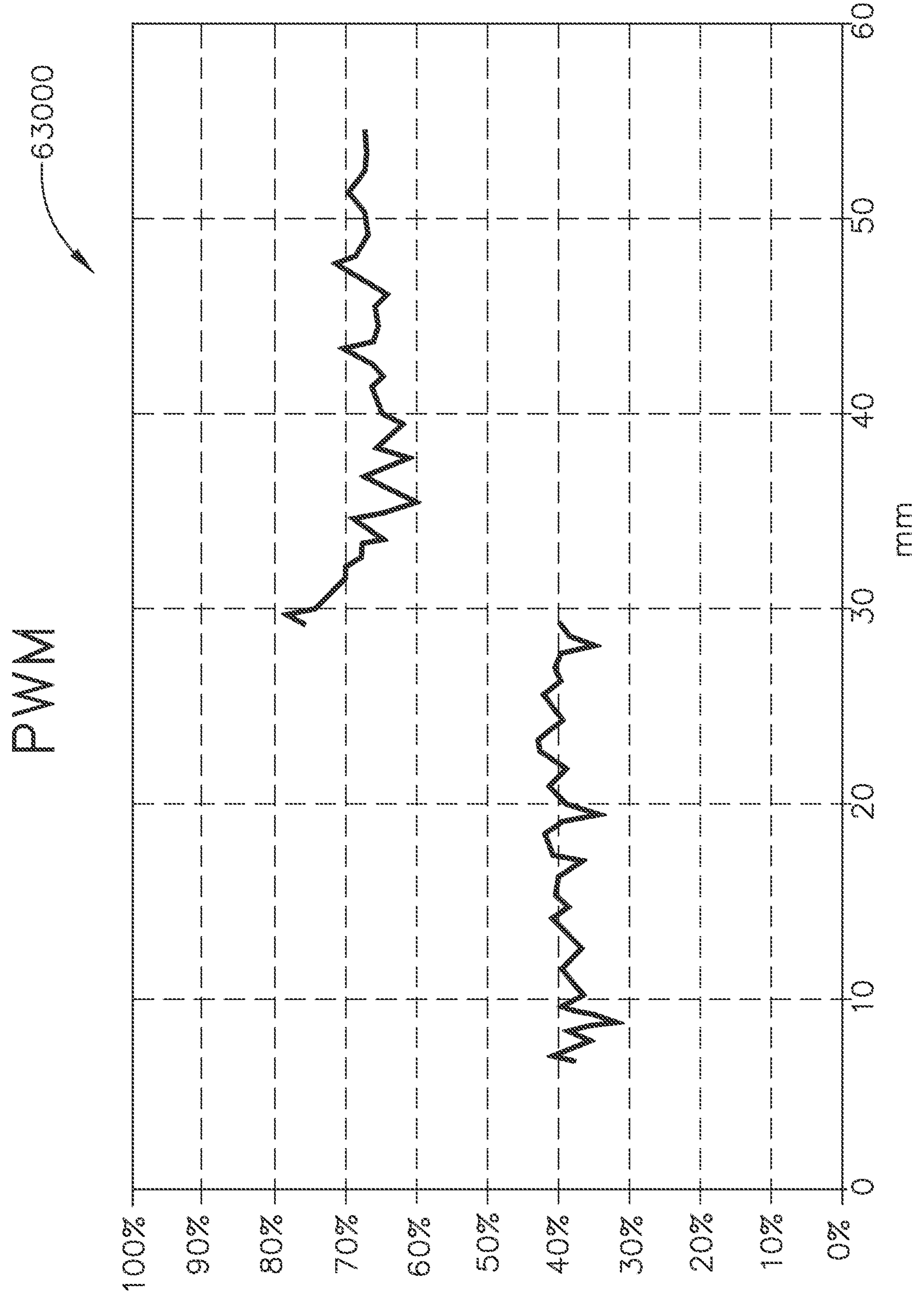
FIG. 87 depicts a graph of the duty cycle of the staple firing system of the surgical instrument of FIG. 1 during a staple firing stroke in which the control system increased the speed of the staple firing stroke.

FIG. 87 comprises a graph 63000 depicting the duty cycle of a staple firing stroke. As illustrated in the graph 63000, the duty cycle is just at or just below 40% for the first 30 mm of the staple firing stroke (15 mm of the initial travel and 15 mm of staple firing) and is then raised by the control system to increase the speed of the staple firing drive. Similar to the above, increasing the duty cycle in this instance overshot the duty cycle above the top duty cycle threshold of 60% where it remained for the rest of the staple firing stroke, i.e., the last 30 mm.

Figure 88:
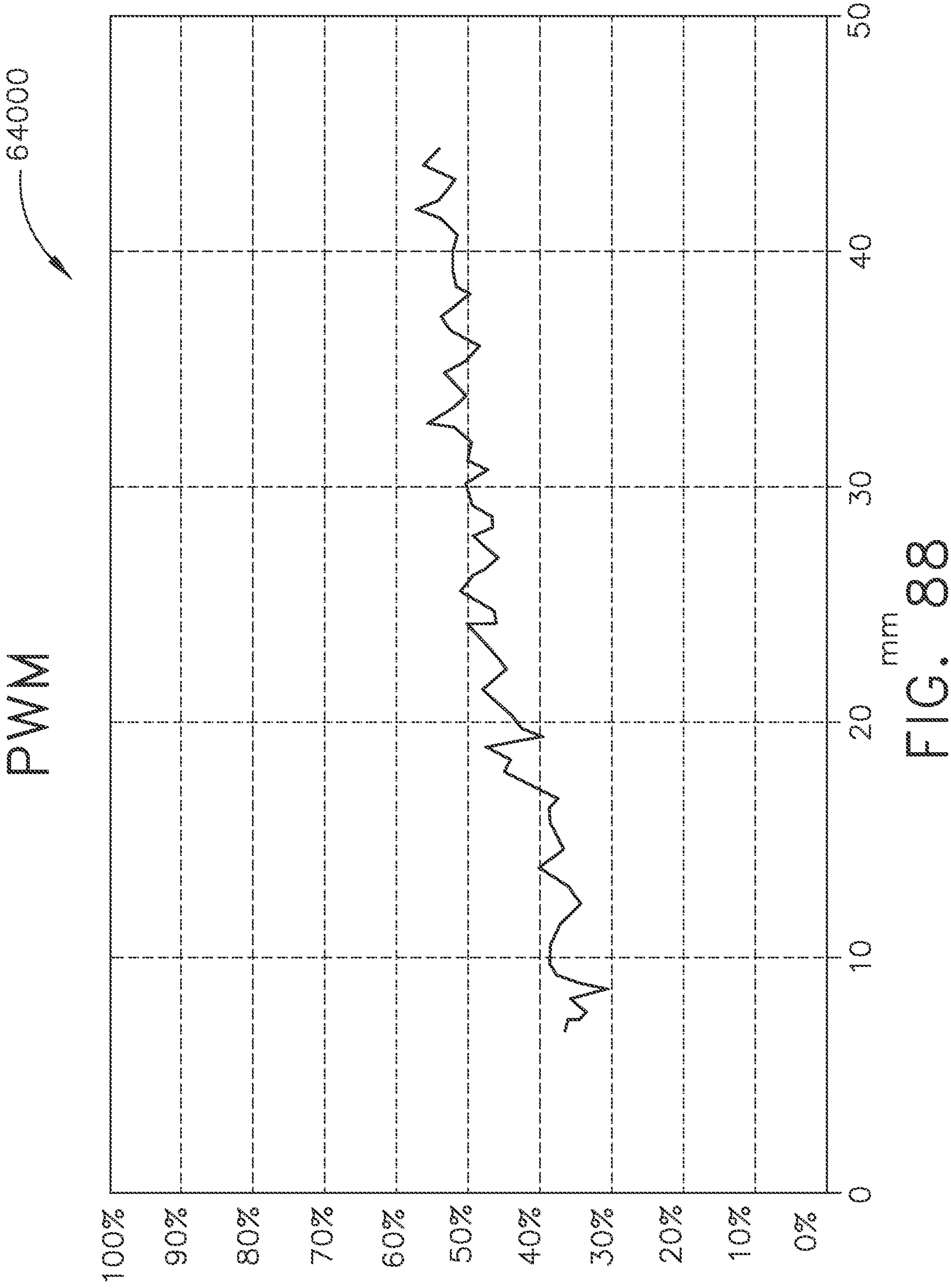
FIG. 88 depicts a graph of the duty cycle of the staple firing system of the surgical instrument of FIG. 1 during a staple firing stroke in which the control system substantially maintained the same speed throughout the staple firing stroke.

FIG. 88 comprises a graph 64000 depicting the duty cycle of a staple firing stroke. As illustrated in the graph 64000, the duty cycle begins below the 40% duty cycle threshold but then gradually increases into the zone between the upper and lower duty cycle thresholds. In such a zone, the control system does not increase or decrease the speed of the staple firing system and/or otherwise adjust the duty cycle of the firing drive electric motor other than to maintain the speed of the staple firing system at the intermediate target speed. As such, a smooth duty cycle curve is seen without abrupt changes.

Figure 89:
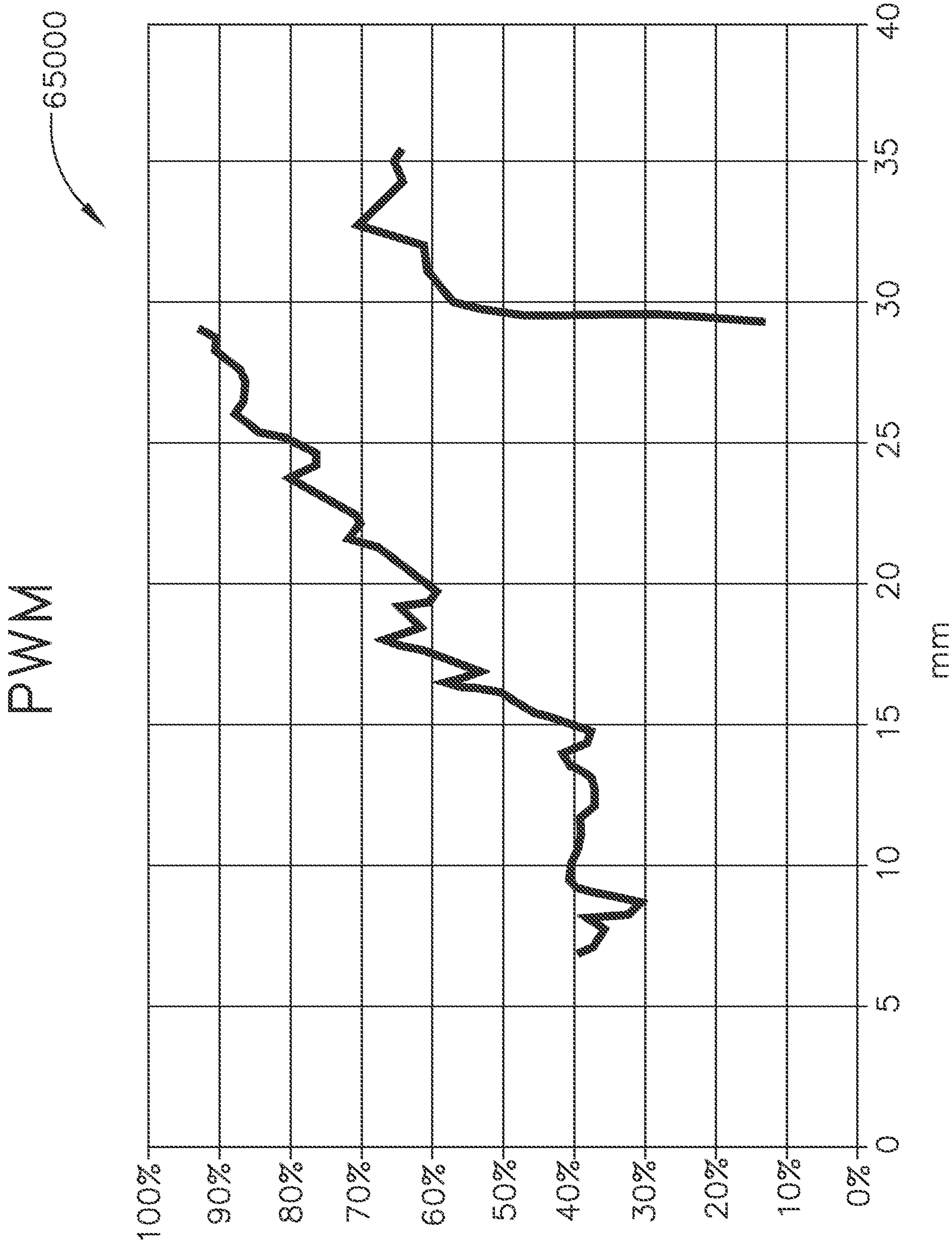
FIG. 89 depicts a graph of the duty cycle of the staple firing system of the surgical instrument of FIG. 1 during a staple firing stroke in which the control system decreased the speed of the staple firing stroke.

FIG. 89 comprises a graph 65000 depicting the duty cycle of a staple firing stroke. As illustrated in the graph 65000, the duty cycle begins at about the 40% lower duty cycle threshold and then proceeds upwardly quickly once the firing member starts deforming staples at the 15 mm point. In fact, the duty cycle increases to almost 100% until the next check point is reached at 30 mm where, as described above, the control system lowered the duty cycle to slow the staple firing drive. FIG. 89 depicts a drastic drop in the duty cycle at this point but returns to an elevated state just above the upper duty cycle threshold for the remainder of the staple firing stroke.

The lower duty cycle threshold is described as being 40% in many instances, and 45% in other instances. That said, the lower duty cycle threshold can be any suitable value, such as 30%, 33%, 35%, or 50%, for example. Similarly, the upper duty cycle threshold is described as being 60%. That said, the upper duty cycle threshold can be any suitable value, such as 50%, 55%, 65%, 67%, 70%, or 75%, for example.

As mentioned above, the staple firing stroke stops when the clinician releases the firing trigger. When the clinician actuates the firing trigger once again, the staple firing stroke resumes. In such instances, the control system returns the speed of the staple firing stroke to the speed just before the staple firing stroke was stopped. The control system comprises one or more memory devices for storing the speed of the staple firing stroke during the staple firing stroke such that the control system can access the stored speed to re-start the staple firing stroke. If the control system does not have access to this data, the control system can re-start the staple firing stroke in its intermediate speed, for example.

As described herein, the surgical instrument 10000 is configured to evaluate the speed of the staple firing stroke and compare the measured speed of the staple firing stroke to a target speed. The surgical instrument 10000 comprises an encoder in communication with the control system which is configured to measure the speed of the staple firing stroke. In at least one instance, a gear in the staple firing drive is observed by the encoder to evaluate the speed of the staple firing stroke. The gear comprises teeth which pass in front of the encoder as the gear is rotated during the staple firing stroke. The rate in which the teeth pass the encoder is used by the control system to assess the speed of the staple firing drive. In at least one instance, the gear makes one full rotation during the entire staple firing stroke. In addition to or in lieu of the above, the gear is comprised of metal and the control system comprises a Hall Effect sensor configured to sense the rate in which the metal gear teeth pass by the Hall Effect sensor. In various embodiments, the control system is configured to evaluate the speed of a translating component of the staple firing drive.

As described herein, an algorithm of a control system uses the duty cycle of the firing drive electric motor to assess whether the speed of the staple firing drive should be adapted, and in which direction, i.e., slower or faster. Various other algorithms use data in addition to the duty cycle of the firing drive electric motor to adapt the speed of the staple firing stroke. For instance, a speed adaptation algorithm can utilize the articulation angle of the end effector, the initial battery voltage, the operative battery voltage, the current through the motor, PID error, and/or any characterization of the PWM circuit made during the manufacturing process of the surgical instrument, for example. These parameters, among others, can be used in a mathematical operation, or evaluation equation, to determine whether or not to adapt the speed of the staple firing stroke, the direction in which the speed is to be adapted, and/or the amount of the adaptation. The parameters used can be instantaneous measurements and/or measurements averaged over several readings. The parameters used can include the rate of change, or change in slope, of the measurements. The values of the parameters can be added, subtracted, multiplied, and/or divided according to the evaluation equation.

FIGS. 68-71 depict an end effector 40000 comprising an anvil jaw 40420 and a cartridge jaw 10410. The anvil jaw 40420 comprises a proximal portion 40100 and a distal portion, or tip, 40200 attached to the proximal portion 40100. The distal portion 40200 is rotatable between a first operational orientation (FIG. 68) and a second operational orientation (FIG. 70 and FIG. 71) to provide a clinician with the ability to choose between a straight anvil tip and an angled anvil tip before using the end effector 40000.

The proximal portion 40100 comprises an angled distal end that can be characterized by a first angle 40120 and a second angle 40130. The first angle 40120 is measured with reference to a top plane defined by the top of the proximal portion 40100 while the second angle 40130 is measured with reference to a bottom plane defined by the bottom of the proximal portion 40100. In various instances, the first angle 40120 and the second angle 40130 are supplementary angles. In at least one instance, the first angle 40120 and the second angle 40130 are substantially supplementary. The distal portion 40200 comprises an angled proximal end which is attached to the distal end of the proximal portion 40100. The angled proximal end of the distal portion 40200 can be characterized by a first angle 40220 and a second angle 40230. In various instances, the first angle 40220 and the second angle 40230 are supplementary angles. In at least one instance, the first angle 40220 and the second angle 40230 are substantially supplementary. In various instances, the first angle 40120 and the first angle 40220 are supplementary angles and the second angle 40130 and the second angle 40230 are supplementary angles. This configuration permits the proximal portion 40100 and the distal portion 40200 of the anvil jaw 40420 to have a complimentary, angled attachment plane where a distal face 40110 of the proximal portion 40100 and a proximal face 40210 of the distal portion 40200 abut each other in both the first orientation and the second orientation.

Figure 68:
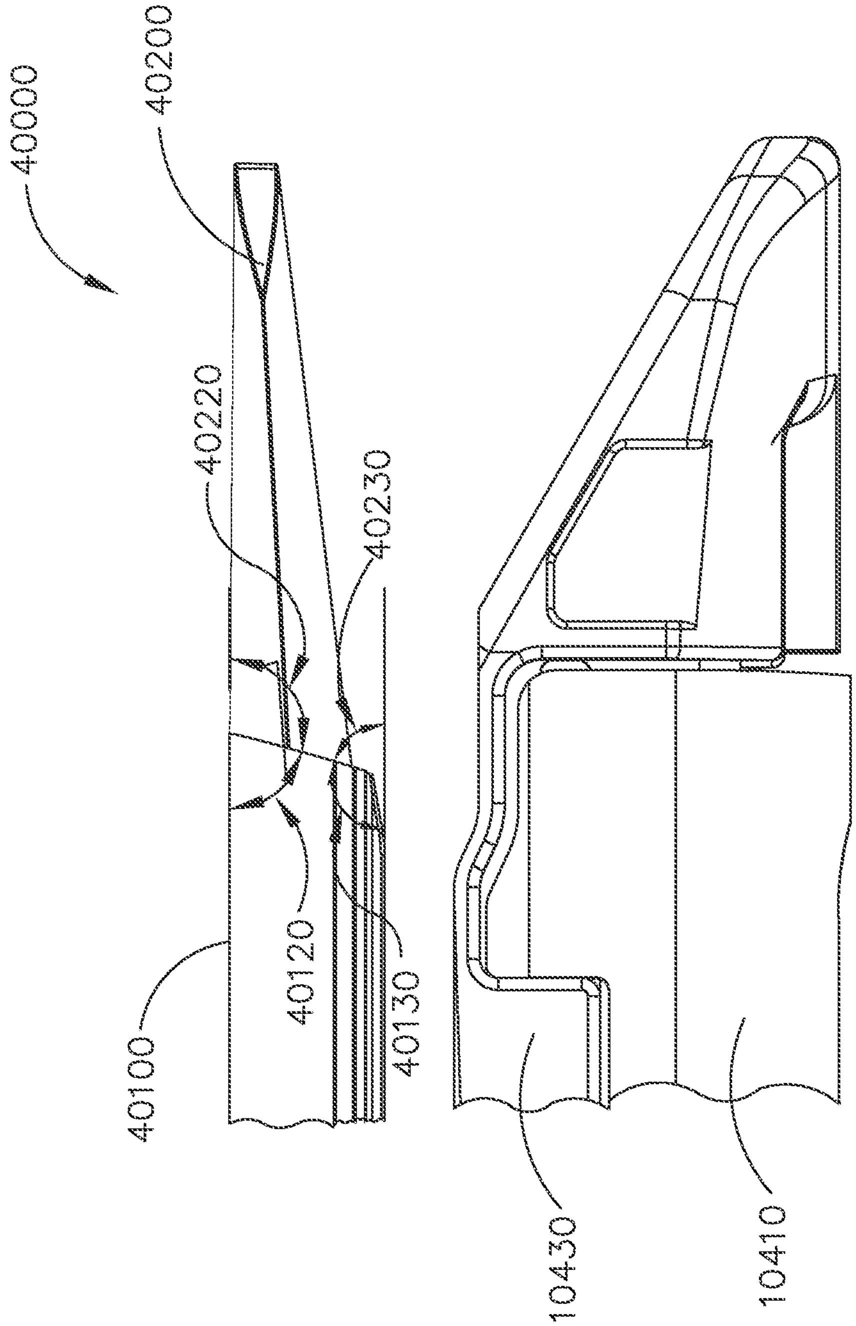
FIG. 68 is a partial elevational view of an end effector comprising an anvil jaw and a cartridge jaw, wherein the anvil jaw comprises a distal portion that rotatable between a first operational orientation and a second operational orientation which is different than the first operational orientation, and wherein the distal portion of the anvil jaw is illustrated in the first operational orientation.
Figure 69:
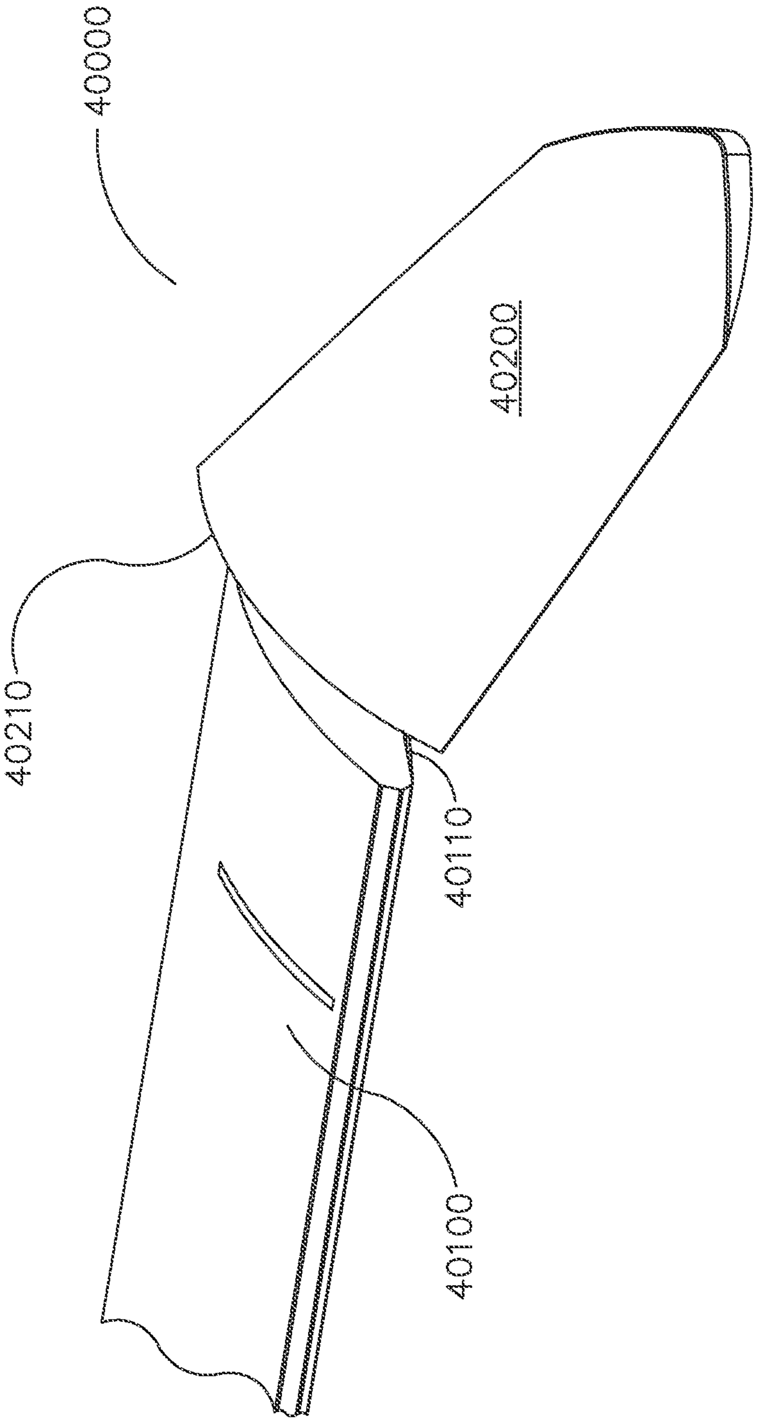
FIG. 69 is a partial perspective view of the anvil jaw of FIG. 68, wherein the distal portion of the anvil jaw is illustrated in a partially rotated orientation.
Figure 69A:
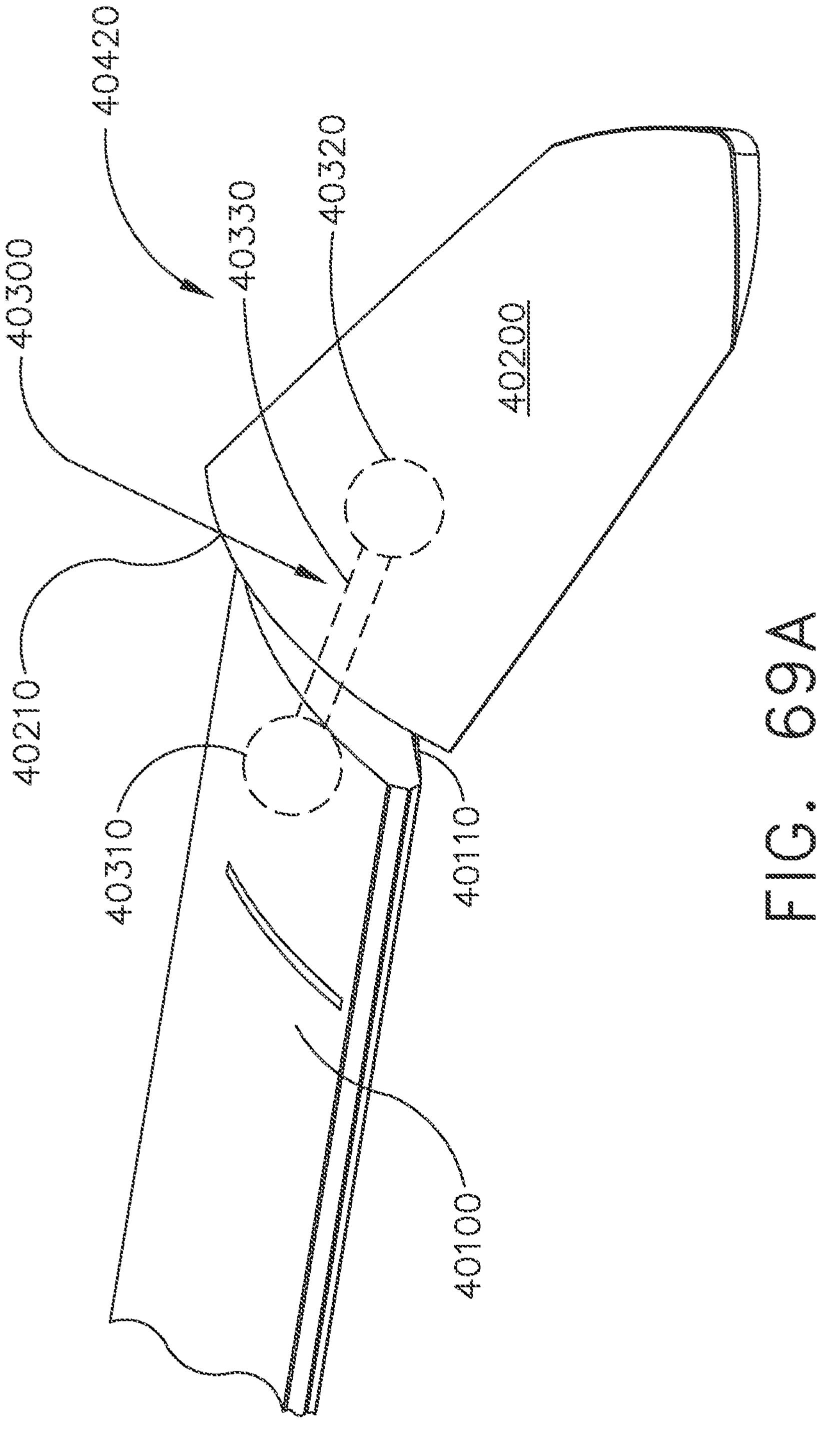
FIG. 69A depicts a connector holding the distal portion to the anvil jaw of FIG. 68.
Figure 70:
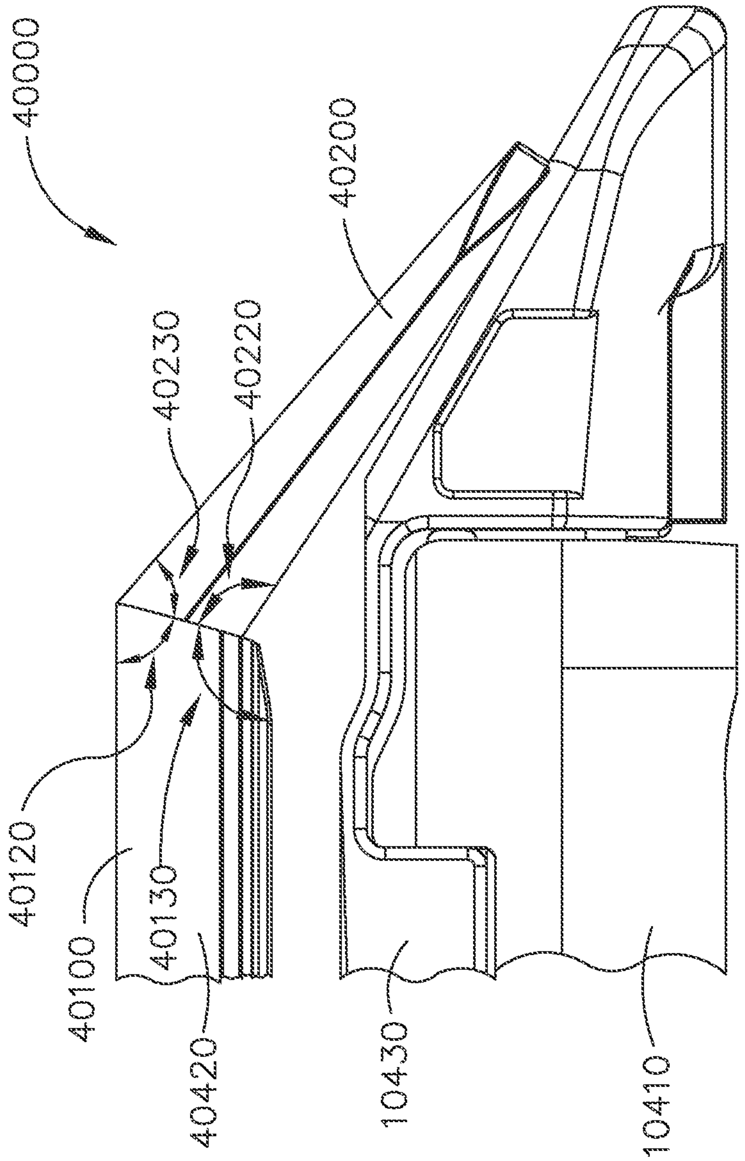
FIG. 70 is a partial elevational view of the end effector of FIG. 68, wherein the distal portion of the anvil jaw is illustrated in the second operational orientation.
Figure 71:
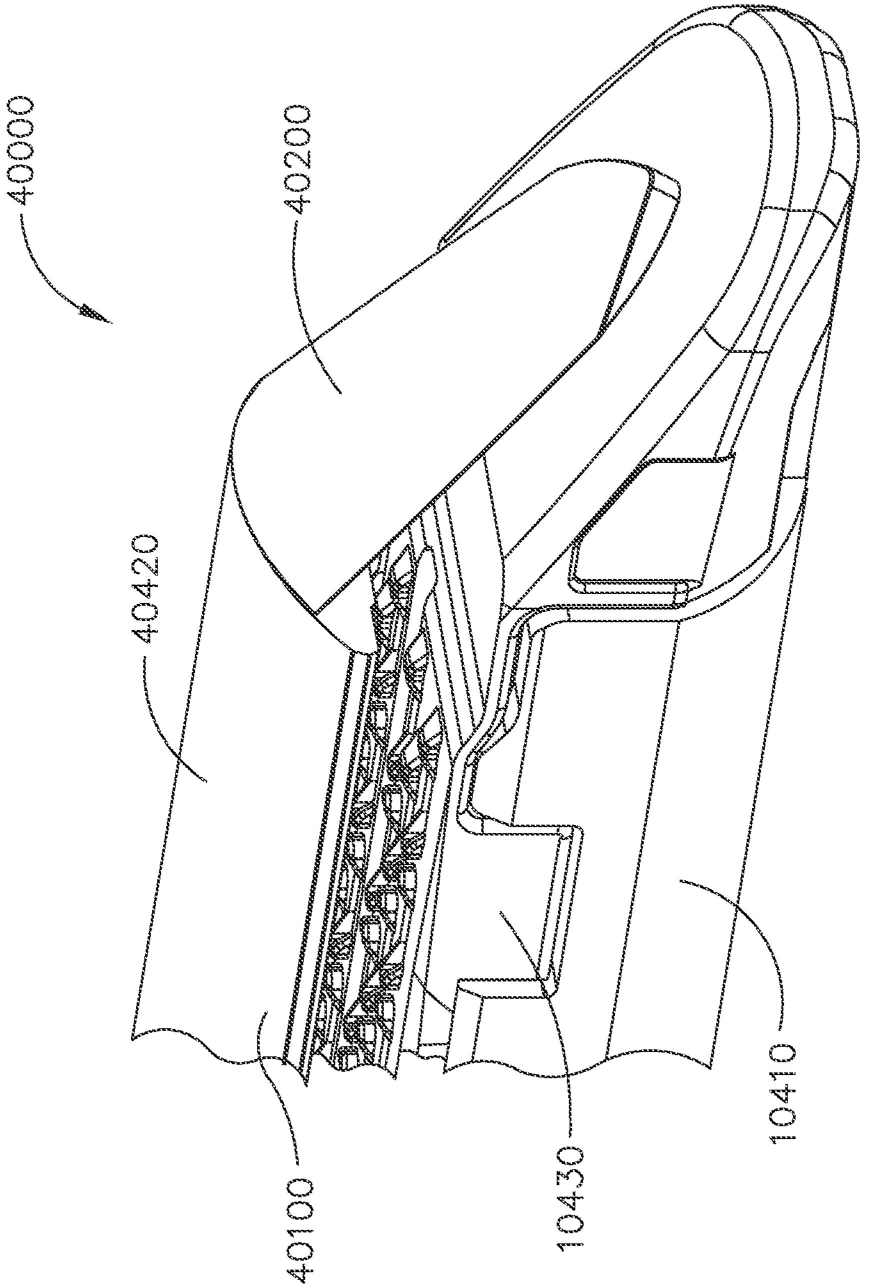
FIG. 71 is a partial perspective view of the end effector of FIG. 68, wherein the distal portion of the anvil jaw is illustrated in the second operational orientation.

Utilizing an attachment mechanism, referring to FIGS. 69 and 69A, the distal portion 40200 is rotatable relative to the proximal portion 40100 such that the distal portion 40200 can be rotated into different orientations. To move the distal portion 40200 into the second orientation shown in FIG. 70, the distal portion 40200 is rotated 180 degrees from the first orientation show in FIG. 68. This configuration allows a user to change the anvil jaw 40420 between a straight-tipped anvil jaw and an angle-tipped anvil jaw. In the second orientation shown in FIGS. 70 and 71, the first angle 40120 and the second angle 40230 abut each other and, correspondingly, the first angle 40220 and the second angle 40130 abut each other. The angles at the attachment interface in the second orientation (FIG. 70) are not supplementary as they were in the first orientation (FIG. 68).

The attachment mechanism used can be any suitable attachment mechanism. In at least one instance, referring to FIG. 69A, the attachment mechanism comprises a flexible rotatable pin 40300 anchored to the proximal portion 40100 and the distal portion 40200. Such a mechanism allows rotation of the rotatable portion between different orientations while keeping the proximal portion 40100 and the distal portion 40200 attached to each other. One or more spring members and/or detents may be used in conjunction with the pin to hold the portions in either the first operational orientation or the second operational orientation. The attachment mechanism may be embedded in either the proximal portion 40100 and/or the distal portion 40200. The attachment mechanism may comprise a bi-stable compliance mechanism configured to bias the portion 40200 into either orientation to prevent the inadvertent partial rotation of the rotatable distal portion 40200. The attachment mechanism may comprise spring-loaded detents, a living hinge, sliding members, and/or various other locking members. The attachment mechanisms may also comprise interference and/or friction-fit interfaces between the proximal portion 40100 and the distal portion 40200.

Further to the above, and referring again to FIG. 69A, the flexible pin 40300 comprises a spherical first end 40310 mounted in a chamber defined in the proximal anvil portion 40100, a spherical second end 40320 mounted in a chamber defined in the distal anvil portion 40200, and a flexible connector 40330 connecting the first end 40310 and the second end 40320. The spherical first end 40310 and the spherical second end 40320 can rotate within their respective chambers such that the flexible pin 40300 can rotate relative to the proximal portion 40100 and/or such that the distal portion 40200 can rotate relative to the flexible pin 40300. In either event, such relative rotation permits the rotation of the distal portion 40200 as described above. The length of the flexible connector 40330 is selected such that the flexible connector 40300 is in a resiliently stretched state for every orientation of the distal portion 40200. As a result, the flexible connector 40330 acts to pull the distal portion 40200 against the first anvil portion 40100. Given that the proximal portion 40100 includes the staple forming pockets and the distal portion 40200 does not comprise staple forming pockets, the retention force provided by the pin 40300 does not need to withstand staple forming forces and is sufficient to hold the distal portion 40200 in place while the end effector 40000 is being positioned in the patient. The pin can be spring loaded in the socket such that the spring pulls the head proximally in the chamber thus holding the proximal portion 40100 and the distal portion 40200 together. To rotate the distal portion 40200 between orientations, the distal portion 40200 can be pulled distally to overcome the biasing force, twisted into another orientation, and released so that the spring may pull the distal portion 40200 against the proximal portion 40100. The interface between the distal portion 40200 and the proximal portion may further comprise interlocking features extending therefrom to prevent inadvertent movement relative to each other. For example, teeth may extend from one portion and into corresponding slots defined in the other portion when the distal portion 40200 is in its first and second orientations, but not when the distal portion 40200 is pulled away from the proximal portion 40100.

In at least one instance, the distal portion 40200 comprises two halves, for example, which are assembled around the attachment mechanism. The two halves may utilize an elastomer to hold the halves together around the pin, for example. In at least one instance, a snap-fit mechanism can be used to assemble the two halves together around the attachment mechanism.

In various instances, the proximal portion 40100 and the distal portion 40200 are comprised of one or more materials. For example, the proximal portion 40100 may be comprised of one or more materials and the distal portion 40200 may be comprised of one or more materials. In at least one instance, the distal portion 40200 is comprised of metal toward the attachment interface and is comprised of an over-molded soft tip extending distally from the metal portion. The soft tip may be comprised of rubber and/or plastic, for example. The anvil jaw 40410 may further comprise an intermediate component positioned between the proximal portion 40100 and the distal portion 40200. The intermediate component can house one or more parts of the attachment mechanism. The intermediate component may also provide an atheistically pleasing and/or functional transition piece between the proximal portion 40100 and the distal portion 40200 which may be useful in a scenario where the proximal portion 40100 and the distal portion 40200 comprise more than one material.

In at least one instance, the first portion 40100 and the second portion 40200 comprise edges designed to eliminate any sharp edges presented by rotation of the second portion 40200 relative to the first portion 40100.

As discussed above, the surgical instruments disclosed herein may comprise control systems. Each of the control systems can comprise a circuit board having one or more processors and/or memory devices. Among other things, the control systems are configured to store sensor data, for example. They are also configured to store data which identifies the type of staple cartridge attached to a stapling instrument, for example. More specifically, the type of staple cartridge can be identified when attached to the stapling instrument by the sensors and the sensor data can be stored in the control system. This information can be obtained by the control system to assess whether or not the staple cartridge is suitable for use.

Figure 91:
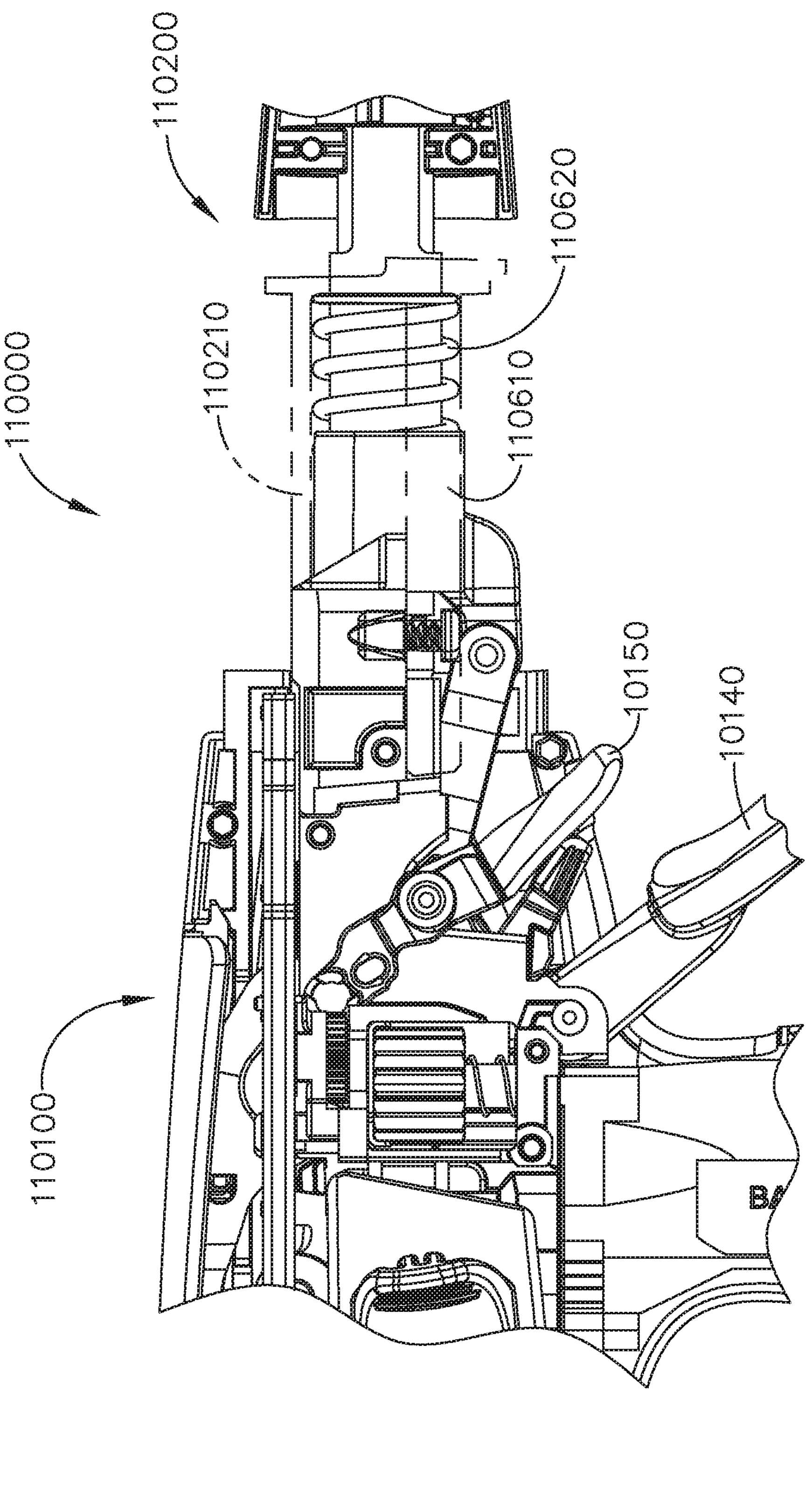
FIG. 91 is a partial elevational view of the surgical instrument of FIG. 90 illustrated with some components removed.
Figure 92:
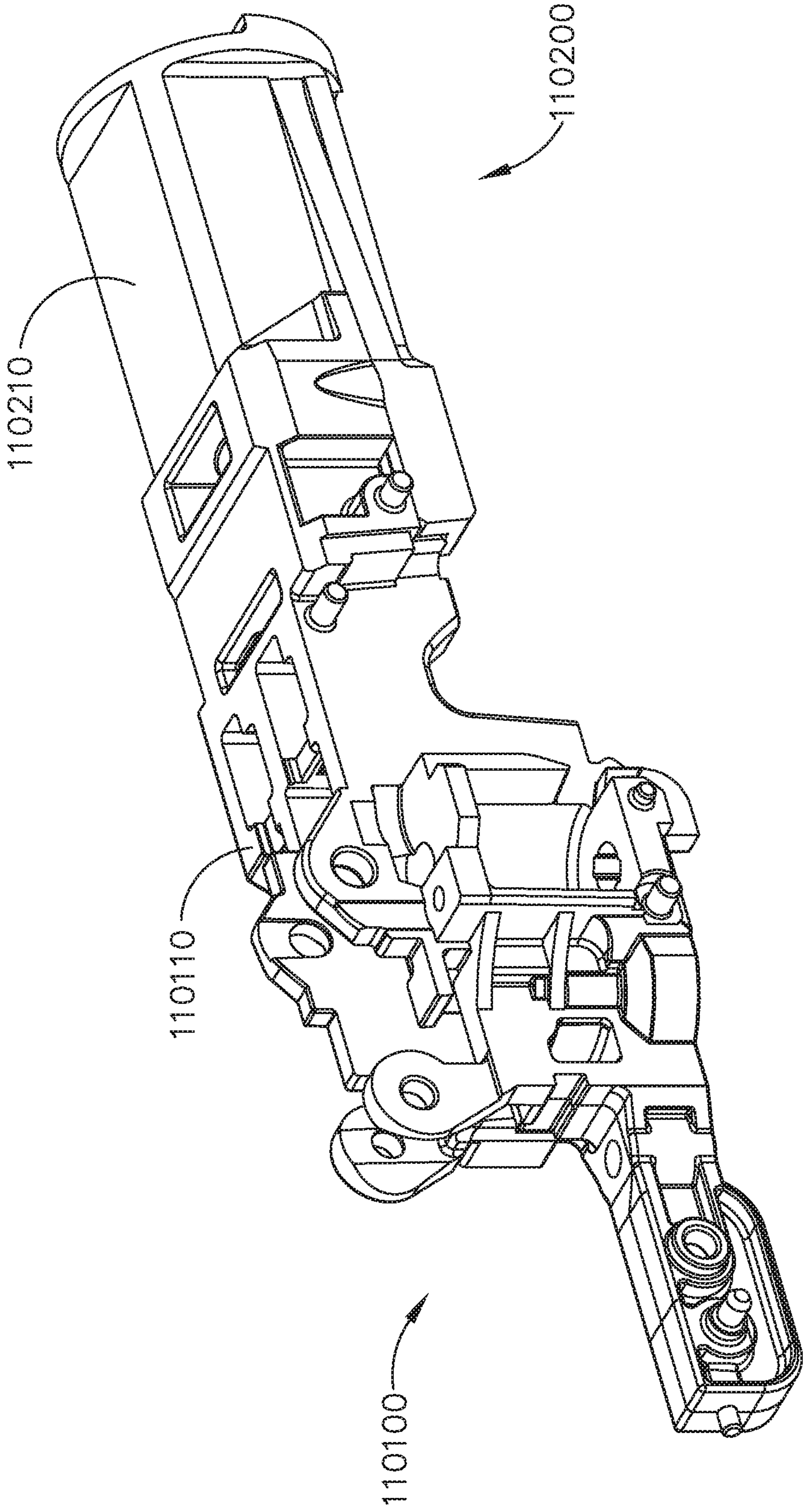
FIG. 92 is a perspective view of a frame of the handle of FIG. 90 connected to a frame of the shaft of FIG. 90.
Figure 93:
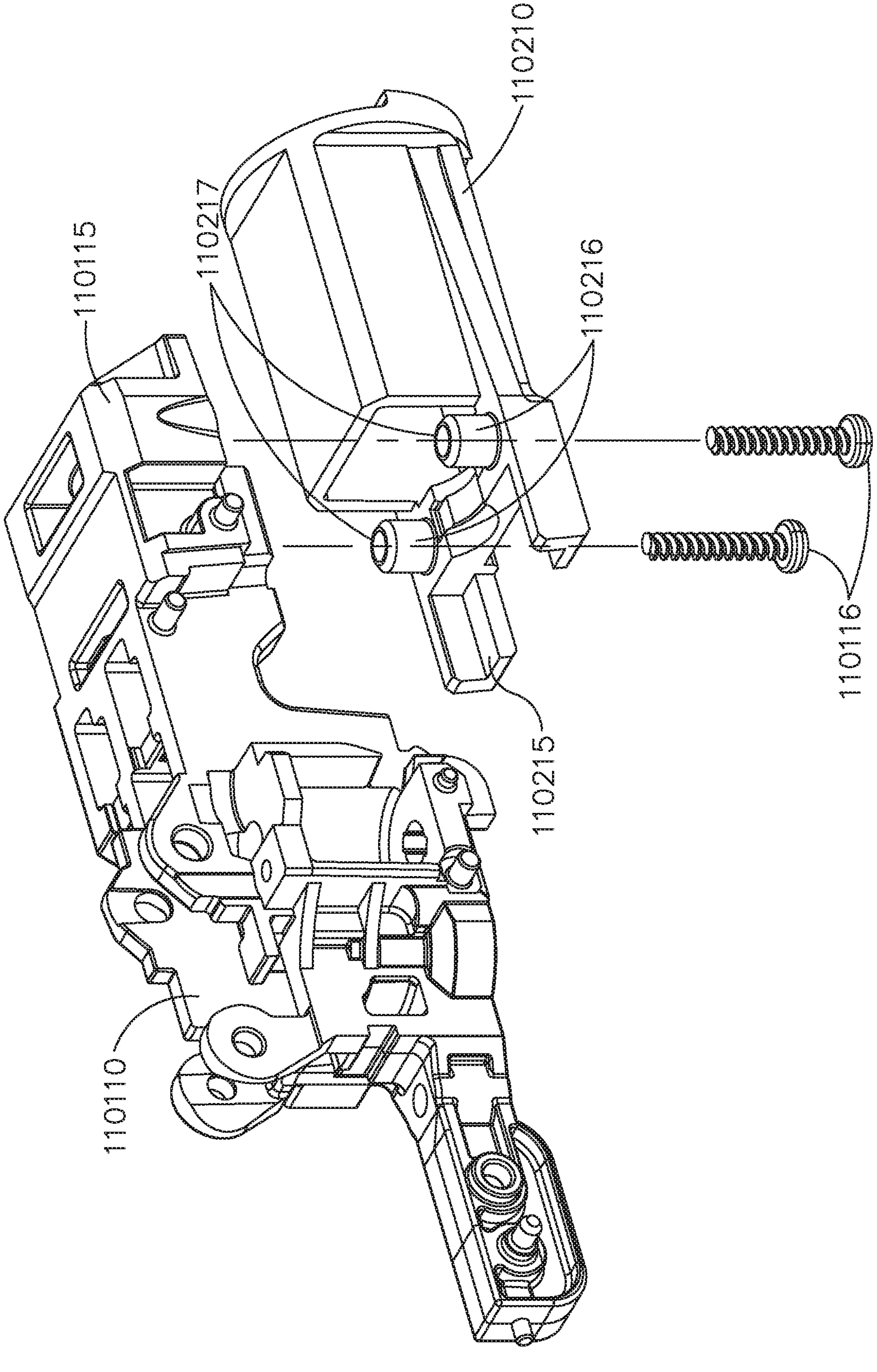
FIG. 93 is an exploded view of the handle frame and the shaft frame of FIG. 92.

A surgical instrument 110000 is illustrated in FIG. 90. The surgical instrument 110000 comprises a handle 110100, a shaft 110200 extending from the handle 110100, and an end effector 110400 rotatably connected to the shaft 110200 about an articulation joint 110500. The surgical instrument 110000 is similar to the other surgical instruments disclosed herein and such similarities are not discussed herein for the sake of brevity. The shaft 110200 is fixedly attached to the handle 110100. Referring to FIGS. 91-93, the handle 110100 comprises a handle frame 110110 and the shaft 110200 comprises a shaft frame 110210. The handle frame 110110 comprises a distal portion 110115 which extends over and nests with a proximal portion 110215 of the shaft frame 110210. The shaft frame 110210 comprises alignment projections 110216 extending therefrom which are closely received within apertures defined in the handle frame 110110. Each of the projections 110216 comprises an aperture 110217 defined therethrough which is configured to receive a self-tapping screw 110116, for example. The self-tapping screws are configured to gain purchase into the handle frame 110115 and fixedly secure the shaft 110200 to the handle 110100. In various instances, referring again to FIG. 90, a force can be applied to the end effector 110400 to dislodge a staple cartridge positioned therein without creating relative movement between the shaft 110200 and the handle 110100.

Further to the above, the surgical instrument 110100 comprises an articulation drive which is actuatable to articulate the end effector 110400 about an articulation axis AA, a closure drive including a closure actuator 10140, described above, which is actuatable to move a jaw 110420 of the end effector 110400 toward a jaw 110410, and a staple firing drive which is actuatable to fire the staples from the staple cartridge seated in the end effector 110400 during a staple firing stroke. The staple firing drive comprises an electric motor configured to advance a firing member distally through the staple firing stroke and retract the firing member proximally back into its unfired position. Similar to other embodiments described herein, the articulation drive is selectively engageable with the staple firing drive. An articulation member of the articulation drive is driveable by the staple firing drive when the articulation drive is engaged with the staple firing drive and, correspondingly, the articulation drive is not driveable by the staple firing drive when the articulation drive is not engaged with the staple firing drive. As described further below, the closure drive decouples the articulation drive from the staple firing drive when the closure drive is sufficiently actuated.

Figure 94:
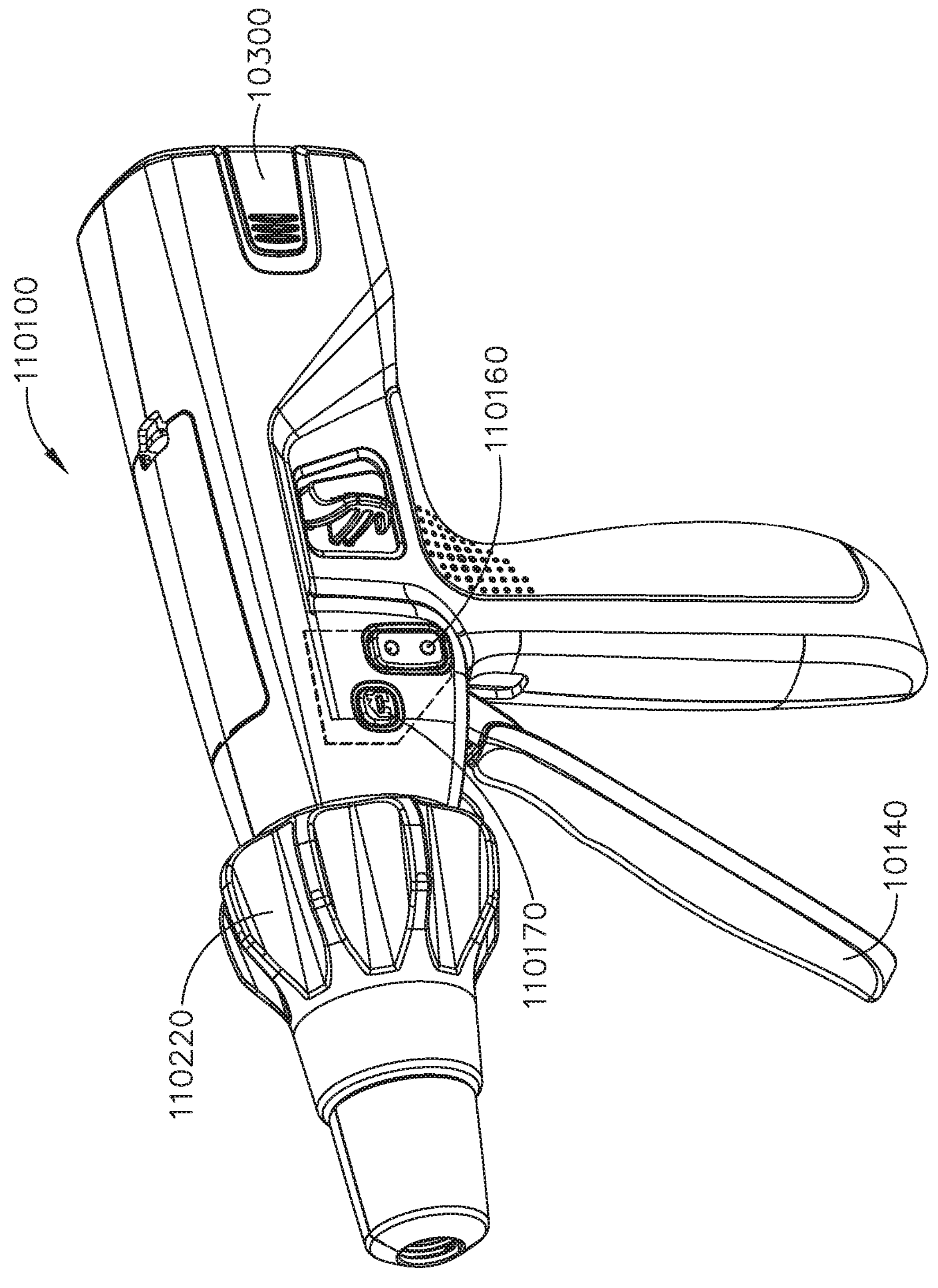
FIG. 94 is a perspective view of the handle of FIG. 90.
Figure 95:
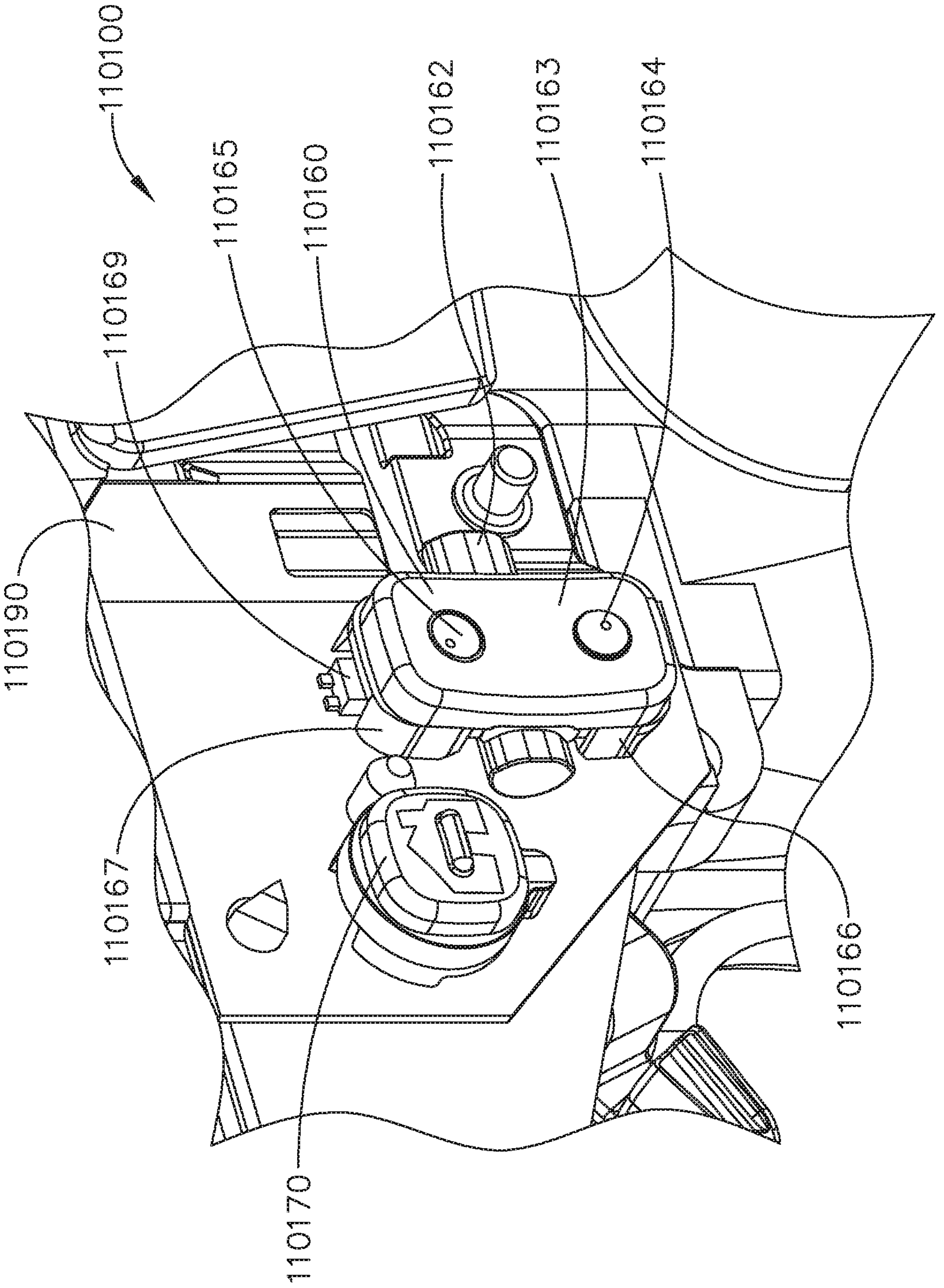
FIG. 95 is a partial perspective view of the handle of FIG. 90 illustrated with some components removed.
Figure 96:
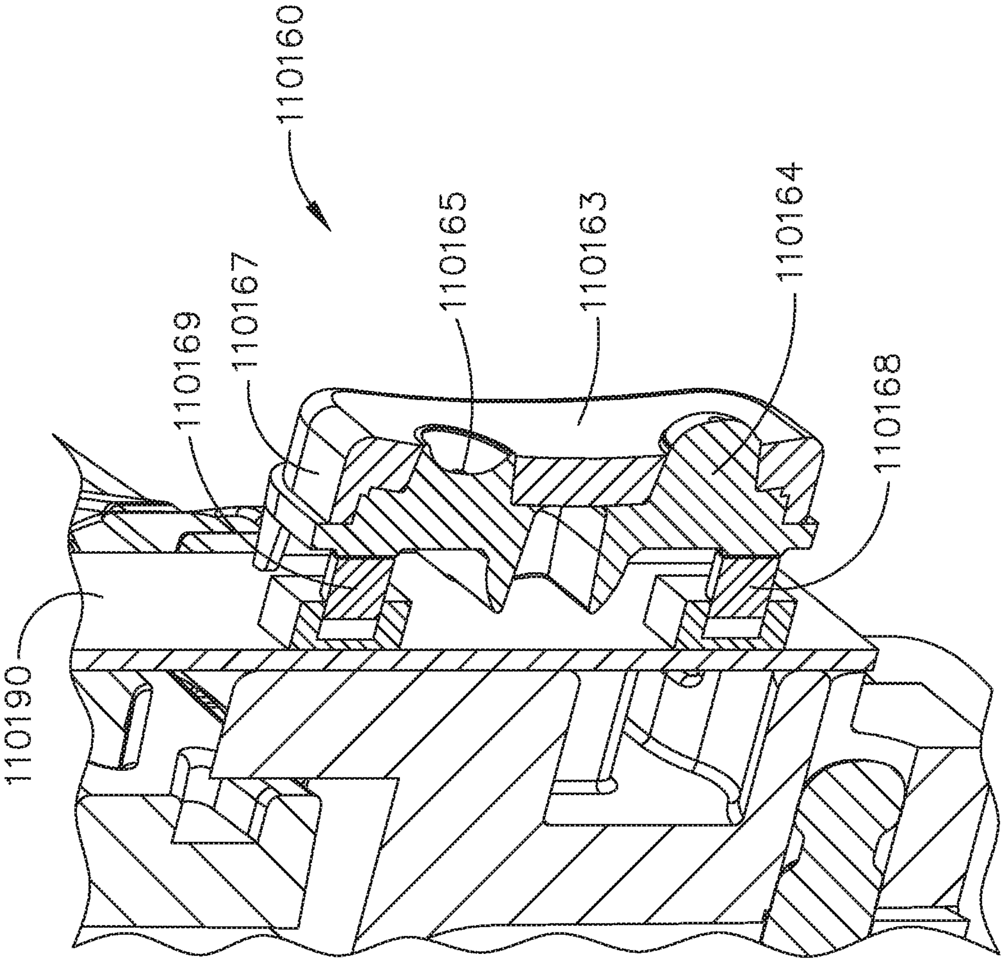
FIG. 96 is a partial cross-sectional view of a switch of the handle of FIG. 90.
Figure 97:
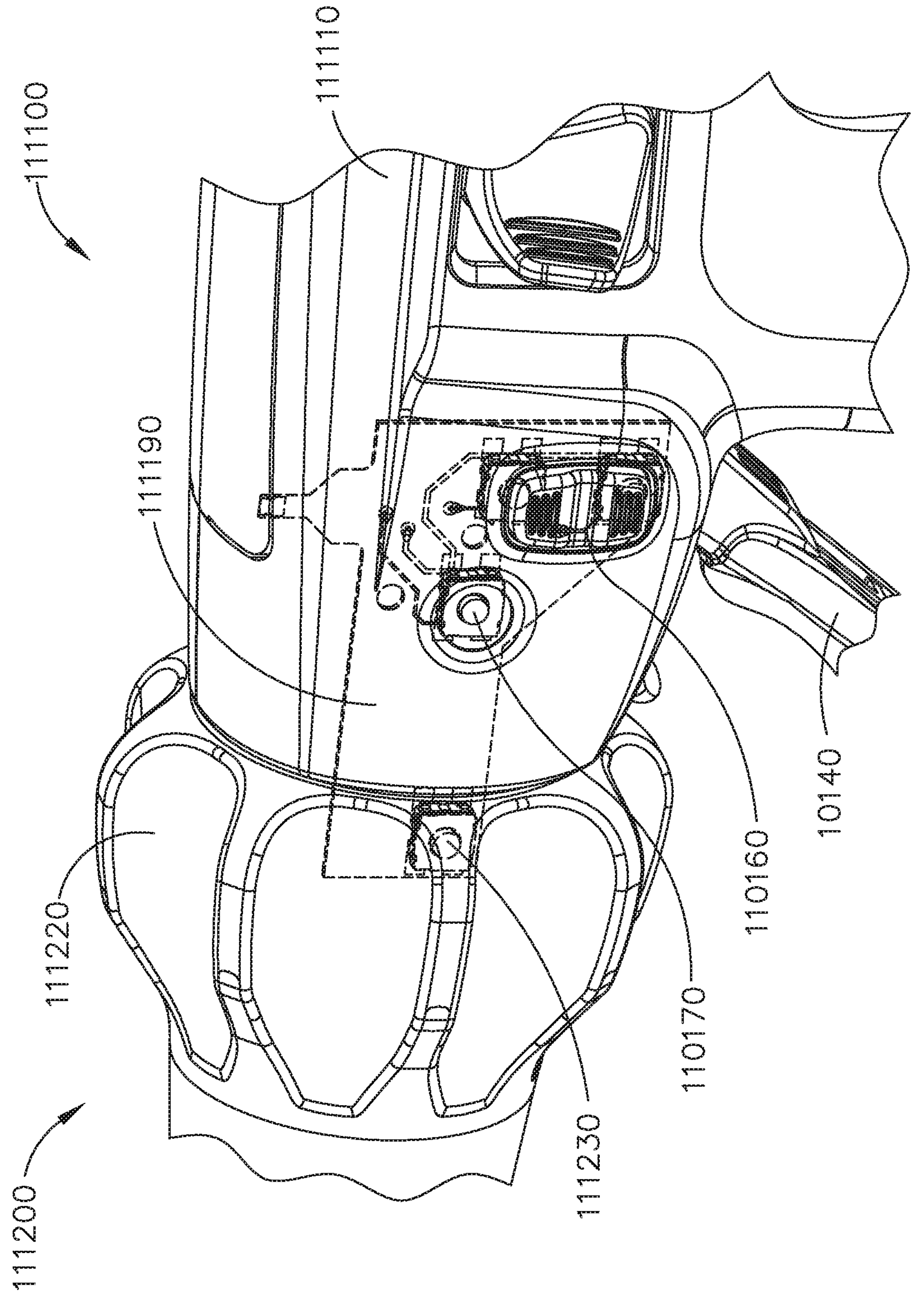
FIG. 97 is a partial perspective view of a handle and a shaft of a surgical instrument in accordance with at least one embodiment.
Figure 98:
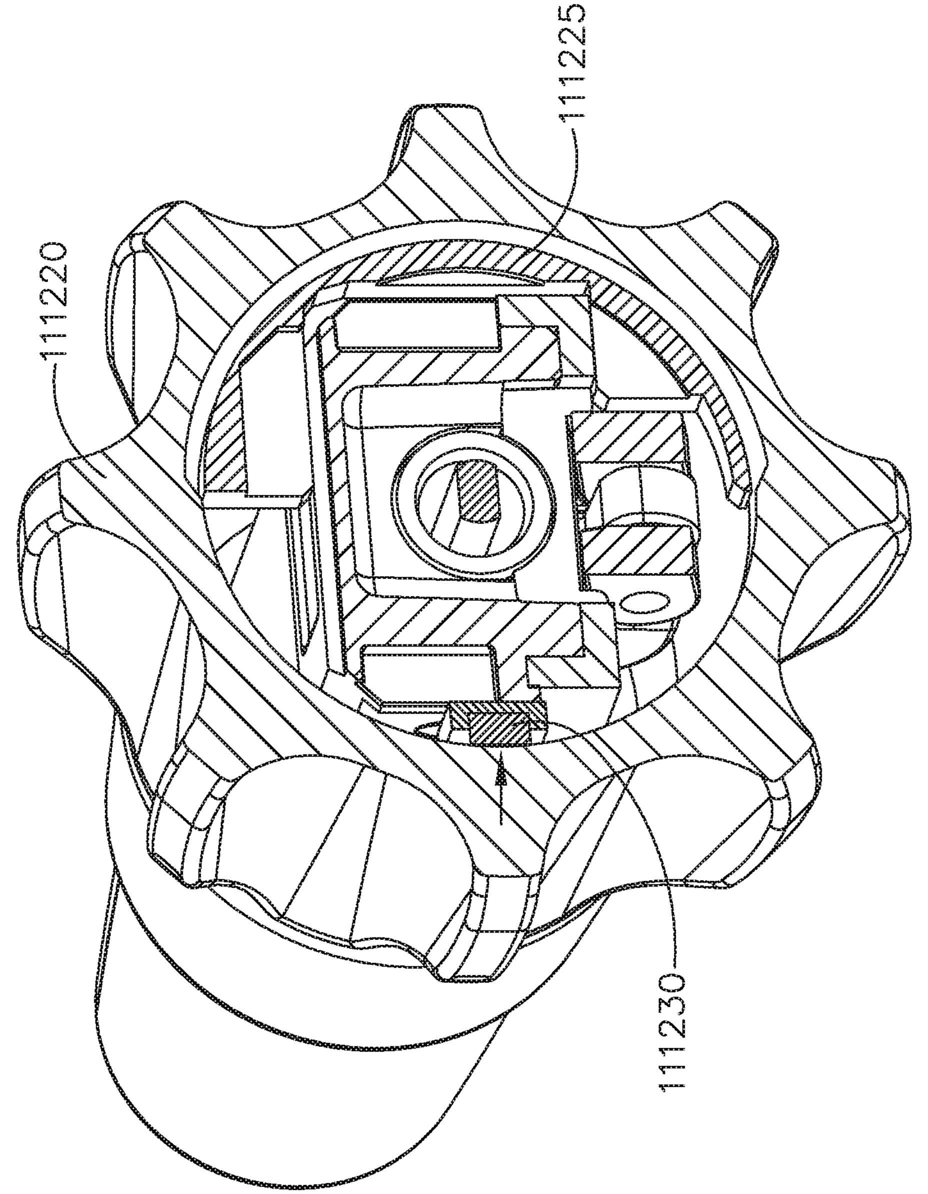
FIG. 98 is a partial cross-sectional view of the shaft of FIG. 97 illustrated in a first rotational position.
Figure 99:
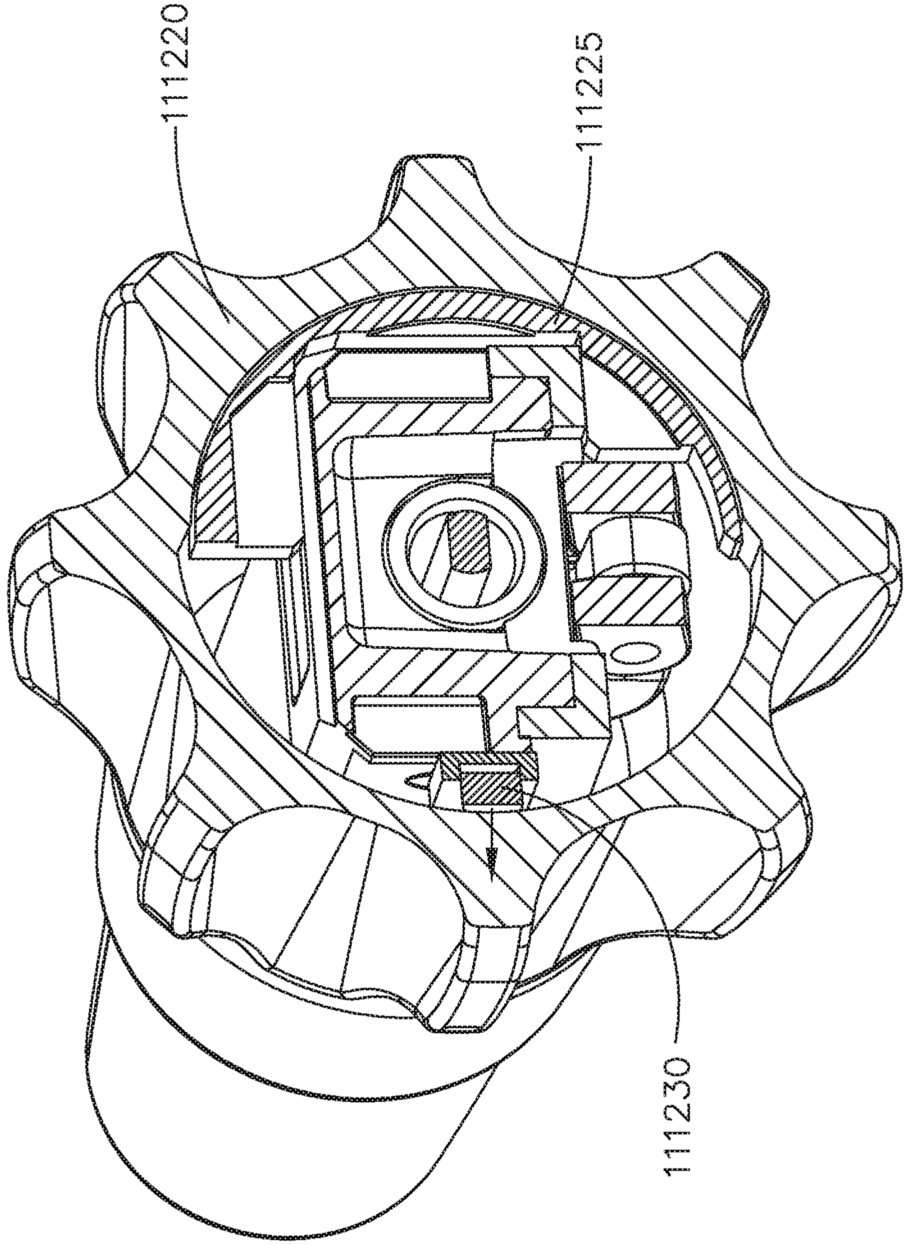
FIG. 99 is a partial cross-sectional view of the shaft of FIG. 97 illustrated in a second rotational position.

Referring to FIGS. 94-96, the handle 110100 comprises an articulation actuator 110160 which is actuatable to articulate the end effector 110400. The articulation actuator 110160 comprises a rocker switch, for example, including a rocker body 110163 which is rotatably mounted to a circuit board 110190 about a pivot 110162. The articulation actuator 110160 further comprises a first contact 110168 mounted to the circuit board 110190 which is moved from an open state to a closed state when a first end 110164 of the rocker body 110163 is depressed. When the first end 110164 is released, a biasing member in the first contact 110168 returns the first contact back into its open state. The articulation actuator 110160 also comprises a second contact 110169 mounted to the circuit board 110190 which is moved from an open state to a closed state when a second end 110165 of the rocker body 110163 is depressed. When the second end 110165 is released, a biasing member in the second contact 110169 returns the second contact back into its open state. The first contact 110168 and the second contact 110169 are in communication with a control system of the surgical instrument 110000. When the control system detects that the first contact 110168 has been closed, the control system operates the electric motor of the staple firing system to articulate the end effector 110400 in a first direction. Correspondingly, the control system operates the electric motor of the staple firing system to articulate the end effector 110400 in a second direction when the control system detects that the second contact 110169 has been closed.

Further to the above, the rocker body 110163 comprises a first stand-off 110166 that contacts the circuit board 110190 when the rocker body 110163 is depressed in the first direction and limits the travel of the rocker body 110163. Similarly, the rocker body 110163 comprises a second stand-off 110167 that contacts the circuit board 110190 when the rocker body 110163 is depressed in the second direction and limits the travel of the rocker body 110163. Such an arrangement prevents or reduces the possibility of the articulation actuator 110160 from being damaged. Such an arrangement can also be adapted to other actuators on the handle 110100, such as an actuator 110170, for example. The actuator 110170 comprises a switch in communication with the control system of the surgical instrument 110100 which, when closed, causes the control system to automatically re-center the end effector 110400 along a longitudinal axis LA (FIG. 90) of the shaft 110200.

Figure 100:
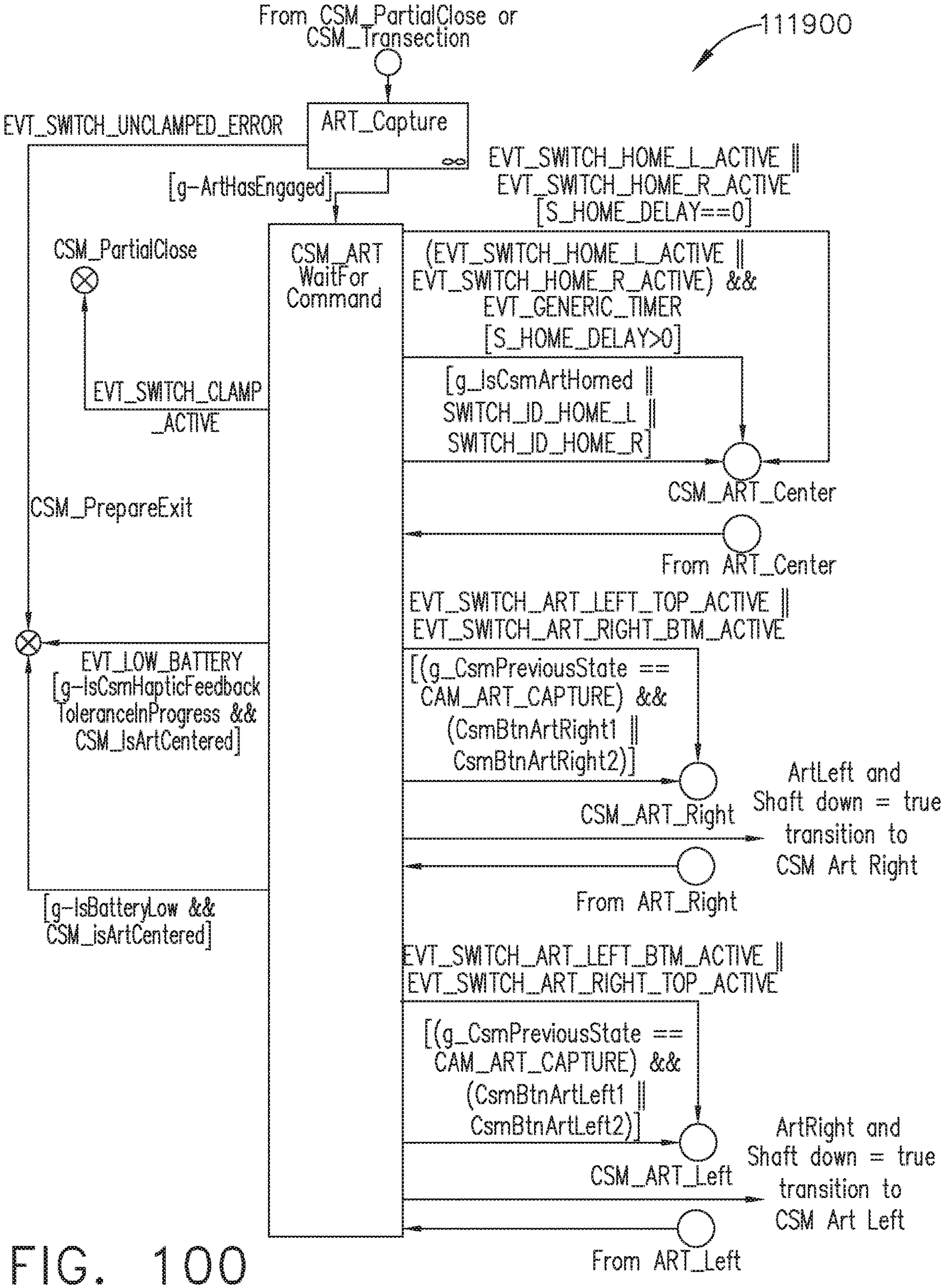
FIG. 100 depicts a control system of the surgical instrument of FIG. 97.

Further to the above, the shaft 110200 and the end effector 110400 are rotatable relative to the handle 110100 about the longitudinal axis LA. In use, a clinician can grasp a nozzle-shaped portion, or nozzle, 110220 of the shaft 110200 to rotate the shaft 110200 about the longitudinal axis. Similar to the above, referring to FIGS. 97-100, a surgical instrument can comprise a handle 111100 and a shaft 111200 rotatable relative to the handle 111100 about a longitudinal axis LA where the rotation of the shaft 111200 relative to the handle 111100 can be sensed by a sensor, or switch, 111230. The switch 111230 is mounted to a circuit board 111190 and, similar to the above, the switch 111230 is switched between a first, or open, state and a second, or closed, state when a cam 111225 of the nozzle 111220 comes into contact with the switch 111230. As a result, the rotation of the shaft 111200 is divided into two ranges—a first range of orientations in which the switch 111230 is in the first state and a second range of orientations in which the switch 111230 is in the second state. The switch 111230 is in communication with the control system of the surgical instrument 111000 and, depending on the input provided by the switch 111230, the control system controls the articulation of the end effector in a first response state and a second response state. In the second response state, the response of the articulation drive to the actuation of the articulation actuator 110160 is reversed, or flipped, as compared to the first response state. As described above, such an arrangement provides a more intuitive operation of the surgical instrument 111000 when the shaft 111200 is in a flipped, or upside-down, orientation. See the control system 111900 of FIG. 100, for example. This control system can be used in connection with any of the embodiments disclosed herein, such as the surgical instrument 110000, for example.

In various embodiments, further to the above, the control system of the surgical instrument 110000 becomes unresponsive to the articulation actuators 110160 and 110170 when the closure trigger 10140 is initially actuated to close the end effector 110400. Moreover, in such embodiments, the initial actuation of the closure trigger 10140 causes the articulation drive to decouple from the staple firing drive. Such embodiments entirely avoid the possibility of the end effector 110400 articulating while the end effector 110400 is clamped onto the tissue. That said, such embodiments require the clinician to estimate where the second jaw 110420 will contact the tissue when the second jaw 110420 is eventually closed after the end effector 110400 has been articulated. If the clinician has already partially-closed the end effector 110400, in such embodiments, the clinician must re-open the end effector 110400 to re-articulate the end effector 110400. In such embodiments, re-opening the end effector 110400 re-engages the articulation drive with the staple firing drive and the control system becomes responsive once again to the articulation actuators 110160 and 110170. In alternative embodiments, the end effector 110400 of the surgical instrument 110000 can be articulated while the end effector 110400 is in a partially-closed, or partially-clamped, configuration. Once the end effector 110400 is closed more than the partially-closed configuration, in these embodiments, the articulation drive is decoupled from the staple firing drive and the control system is no longer responsive to the articulation controls 110160 and 110170 until the end effector 110400 is re-opened or at least returned back to its partially-closed configuration.

Figure 101:
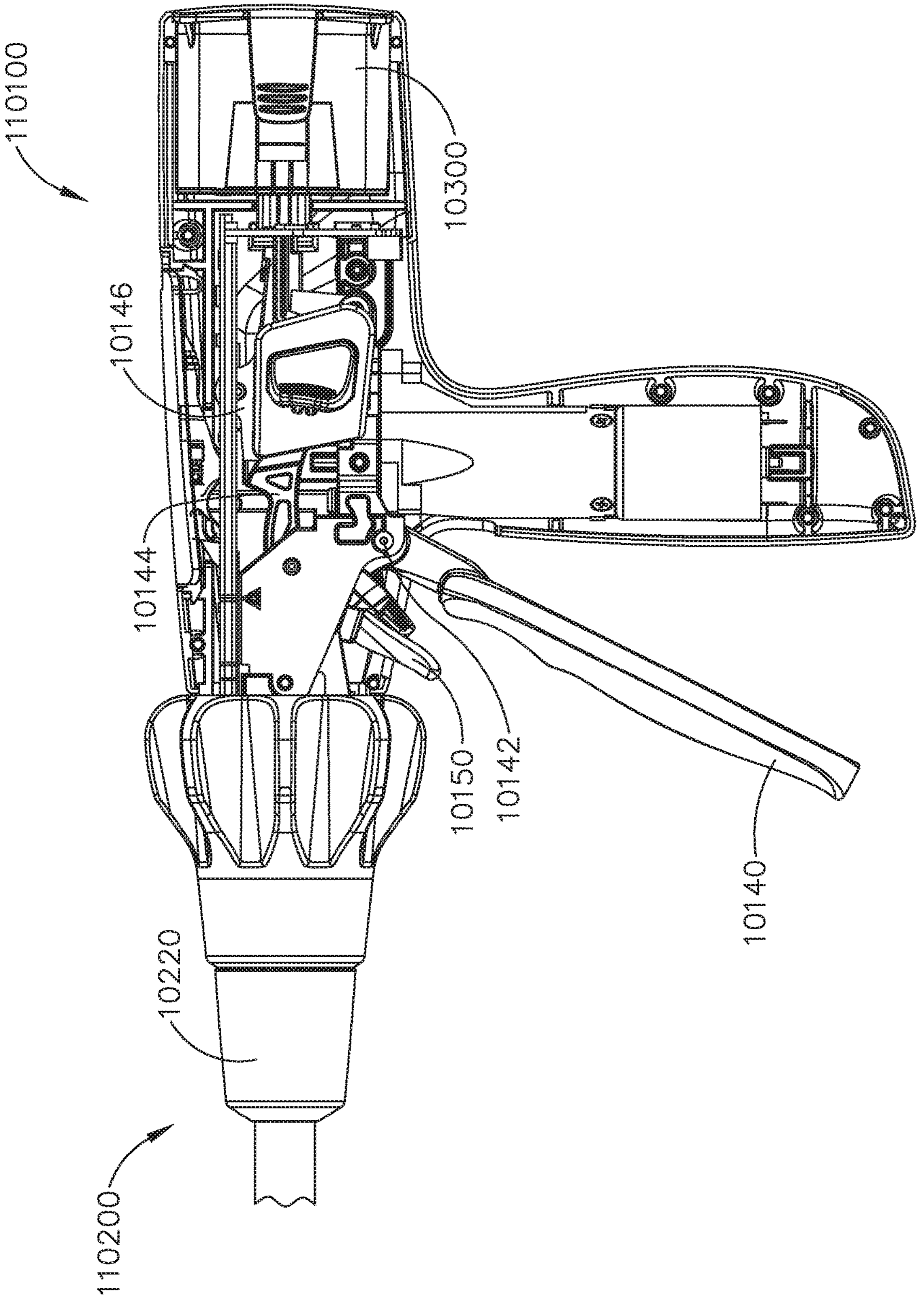
FIG. 101 is an elevational view of the handle of FIG. 90 illustrated with some components removed illustrating a closure actuator of the handle in a partially-closed position.
Figure 102:
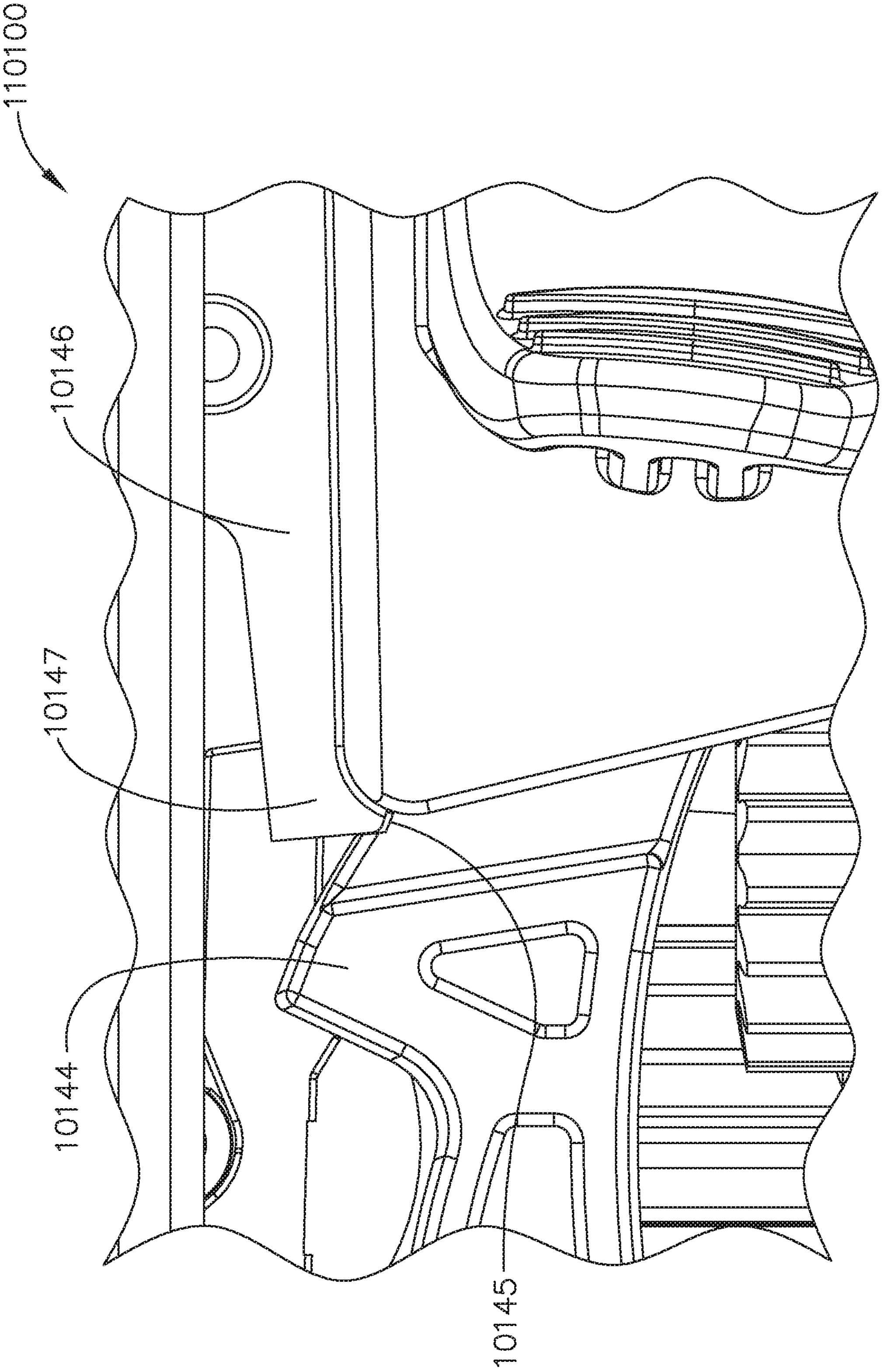
FIG. 102 is a partial detail view of the closure system of the handle of FIG. 90 illustrated in a partially-closed configuration.
Figure 103:
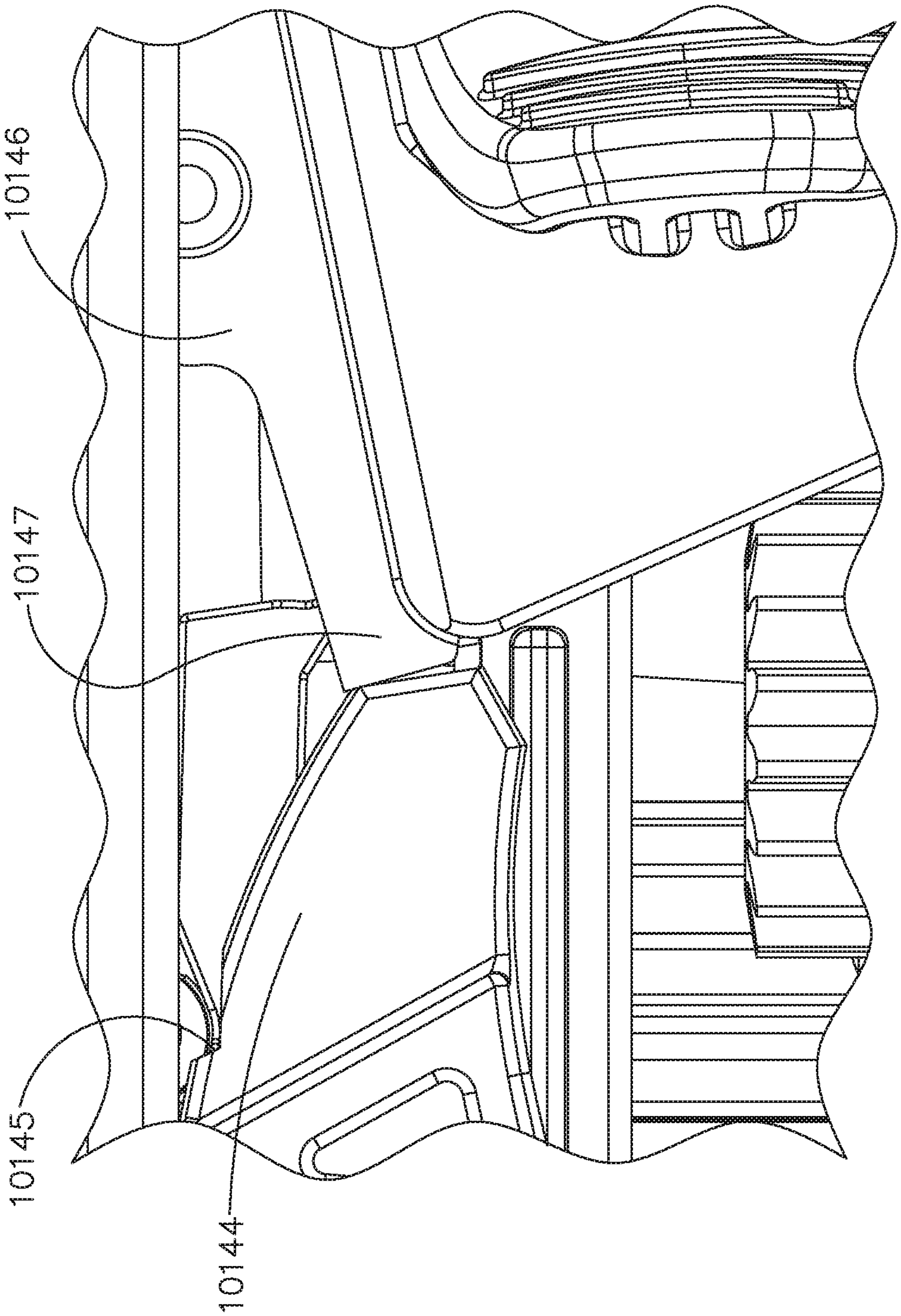

Further to the above, the partially-closed configuration of the end effector 110400 is a predefined, or predetermined, position of the second jaw 110420. In at least one such embodiment, referring to FIGS. 101-103, the surgical instrument 110100 comprises a closure lock 10146 configured to releasably hold the closure actuator 10140 in the predefined, partially-closed position. When the closure actuator 10140 is in this partially-closed position, the articulation drive is still engaged with the staple firing drive and the control system is responsive to the articulation controls 110160 and 110170. Stated another way, the articulation drive is engaged with the staple firing drive and the control system is responsive to the articulation controls 110160 and 110170 when the closure actuator 10140 is in a position between, and including, the open position and the predefined, partially-closed position. FIG. 102 illustrates a lock arm 10147 of the closure lock 10146 seated in a notch, or recess, 10145 defined in a top portion 10144 of the closure actuator 10140. The lock arm 10147 engages the notch 10145 as the closure actuator 10140 is being closed, i.e., when the closure actuator 10140 reaches the partially-closed position discussed above. In various instances, the lock arm 10147 entering the notch 10145 can make an audible click which can indicate to the clinician closing the closure actuator 10140 that any additional closure of the closure actuator 10140 will disable the articulation drive and controls. The lock arm 10147 entering into the notch 10145 can also provide a tactile feedback to the clinician. At such point, the clinician is afforded an opportunity to observe the articulated position of the end effector 110400 and the partially-closed configuration of the end effector 110400 while the closure actuator 10140 is held in position. If the clinician is unsatisfied with the position of the end effector 110400 in this instance, the clinician is afforded an opportunity to articulate the end effector 110400 once again using the articulation controls 110160 and 110170 without having to re-open the end effector 110400. Closing the closure actuator 10140 beyond this position, however, decouples the articulation drive from the staple firing drive and makes the control system unresponsive to the articulation controls 110160 and 110170. In such instances, the lock arm 10147 flexes out of engagement with the notch 10145 such that the top portion 10144 rotates past the lock arm 10147 until the closure actuator 10140 reaches the end of its stroke. At such point, referring to FIG. 103, the lock arm 10147 unflexes and falls in behind the top portion 10144 to releasably hold the closure actuator 10140 in its fully-closed position. Applying a force to the closure actuator 10140 can flex the lock arm 10147 out of the way once again so as to return the closure actuator 10140 to its above-discussed partially-closed position and/or fully-open position. When the closure actuator 10140 is returned to the partially-closed position, and/or anywhere in-between the partially-closed position and the open position, the articulation drive is re-engaged with the staple firing drive and the control system is once again responsive to the articulation controls 110160 and 110170.

Figure 104:
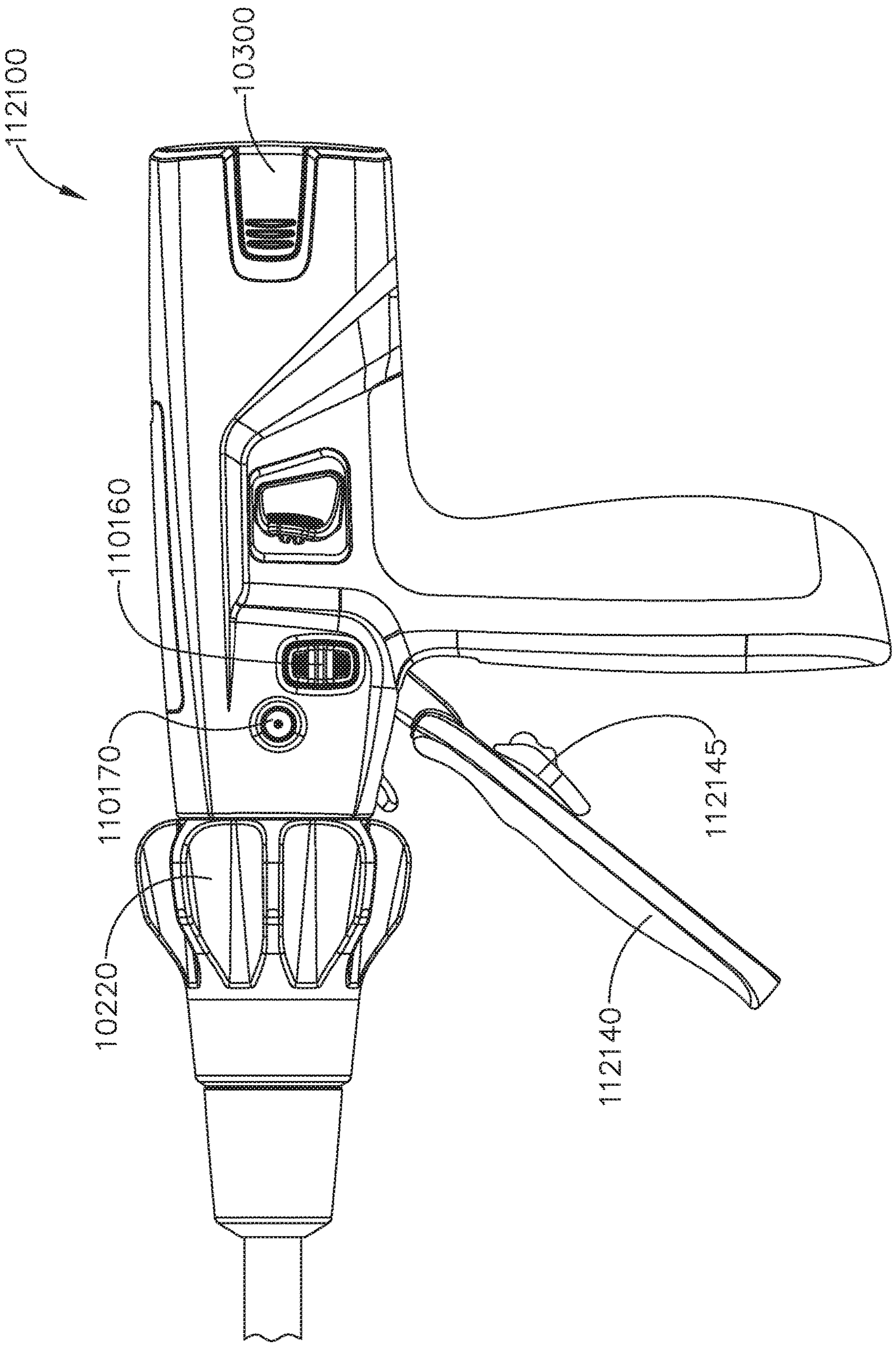
Figure 105:
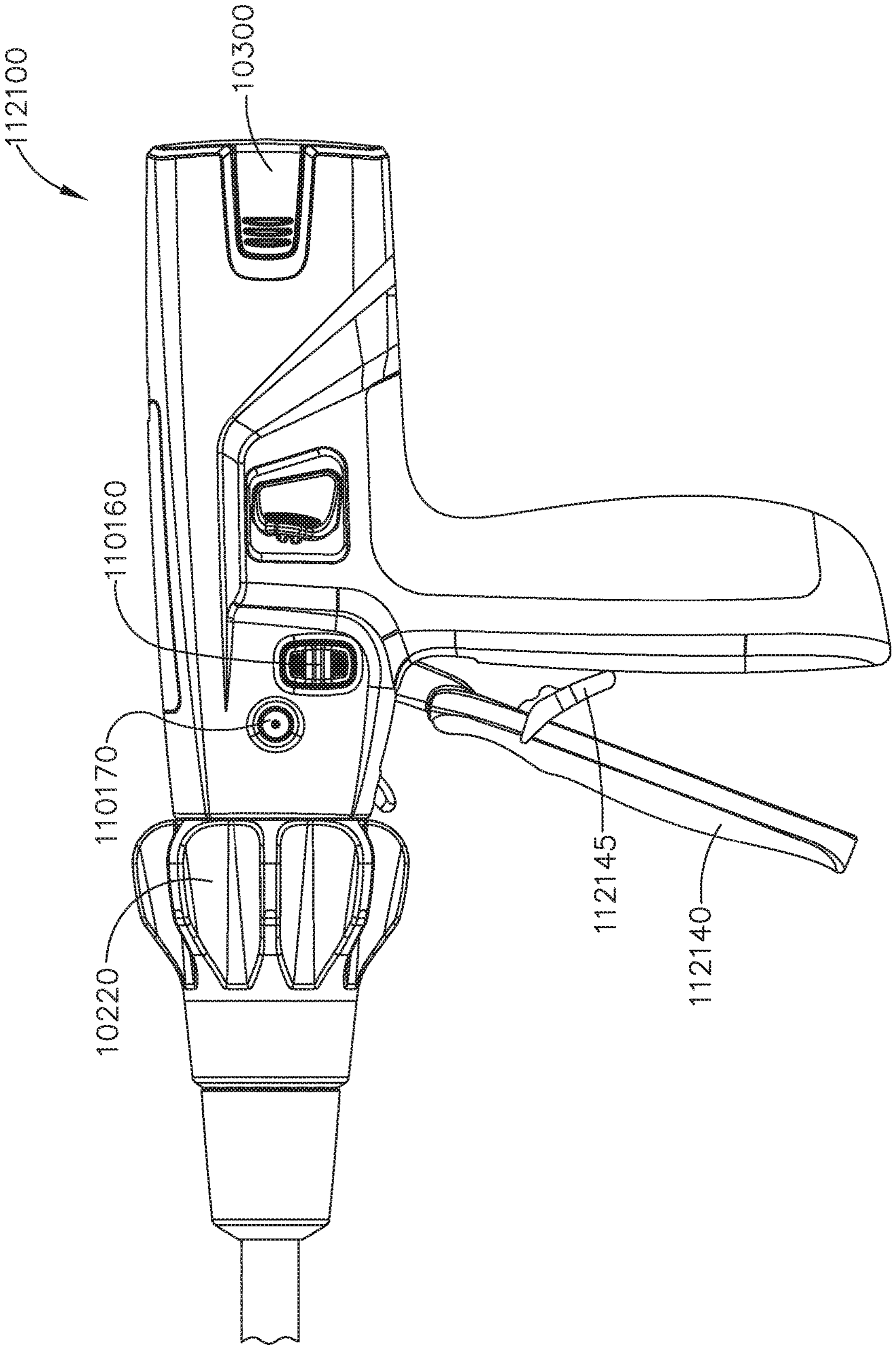
Figure 106:
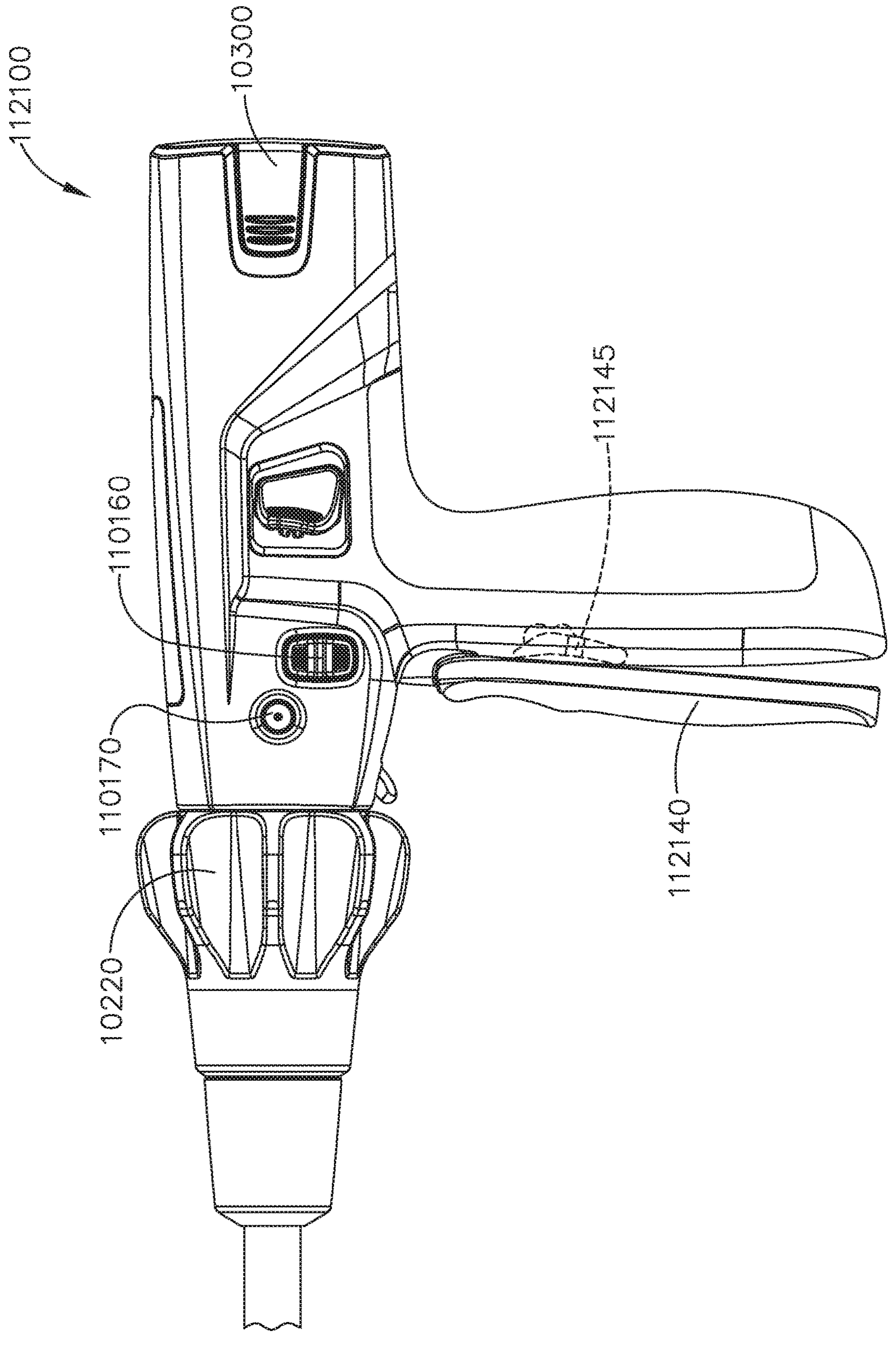

A surgical instrument including a handle 112100 is illustrated in FIGS. 104-106 which comprises a selectively actuatable closure actuator block. The handle 112100 comprises a closure actuator 112140 which, similar to the closure actuator 10140, is rotated from a fully-open position (FIG. 104) to a fully-clamped position (FIG. 106) to close the end effector 110400. The closure actuator 112140 comprises a deployable block 112145 rotatably mounted thereto which is rotatable between a stowed position (FIG. 104) to a deployed position (FIG. 105) which can support the closure actuator 112140 in a partially-closed position. In this partially-closed position of the closure actuator 112140, similar to the above, the articulation drive is still operably engaged with the staple firing drive and the control system is still responsive to the articulation controls 110160 and 110170. At such point, the clinician can choose to deactivate the closure block 112145 and fully close the end effector 110400. Doing so, similar to the above, will decouple the articulation drive from the staple firing drive and make the control system non-responsive to the articulation controls 110160 and 110170. The clinician can decide whether or not to deploy the closure block 112145. If the closure block 112145 is not deployed, the closure actuator 112140 will not be stopped in its predefined, partially-closed position and the articulation drive will be deactivated as the end effector 110400 is closed. When the closure actuator 10140 is returned to the its partially-closed position, and/or anywhere in-between the partially-closed position and the open position, the articulation drive is re-engaged with the staple firing drive and the control system is once again responsive to the articulation controls 110160 and 110170. The control system comprises a sensor system configured to assess whether the closure actuator 112140 is in its open position, partially-closed position, and/or fully-closed position.

Figure 107:
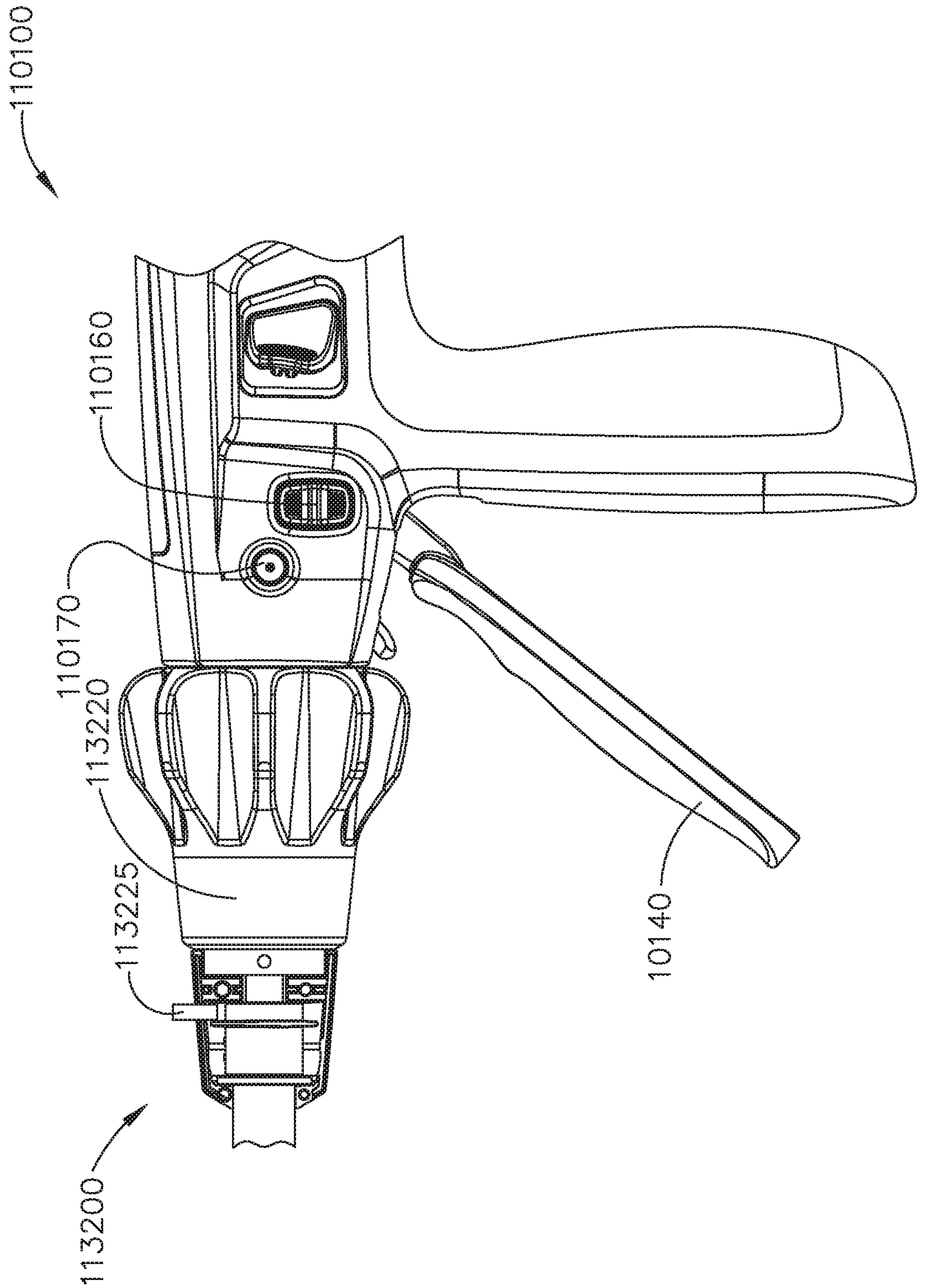
Figure 108:
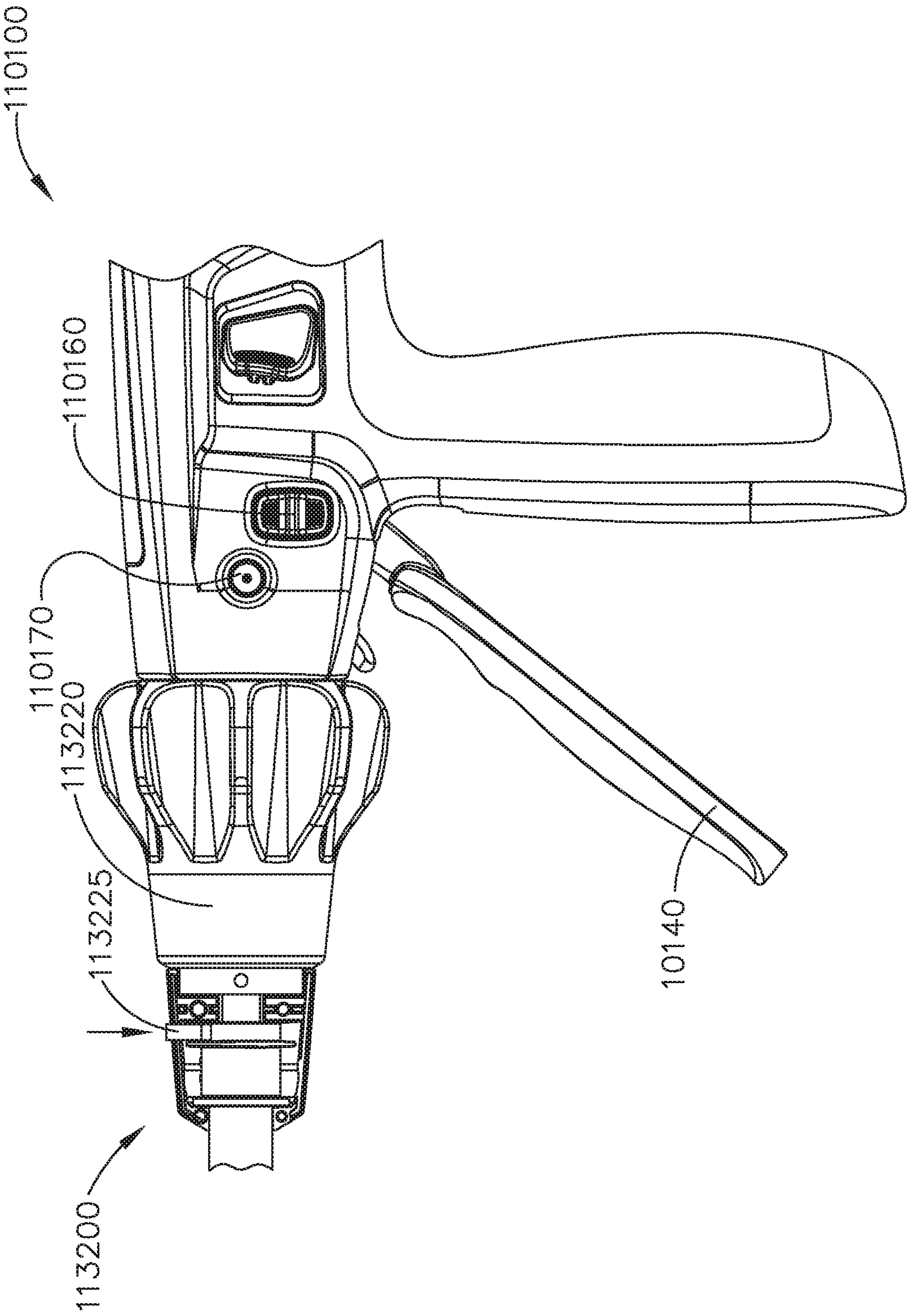

Further to the above, automatic locks and/or deployable blocks can be used separately and/or together in various embodiments. Another example is illustrated in FIGS. 107 and 108 which includes a shaft 113200 extending from a handle 110100. The shaft 113200 comprises a nozzle 113220 which is used to rotate the shaft 113200 about a longitudinal axis. The nozzle 113220 includes an actuator 113225 which is manually depressed by the clinician to block the closure drive in a state which corresponds to the above-discussed predefined, partially-closed position.

Figure 109:
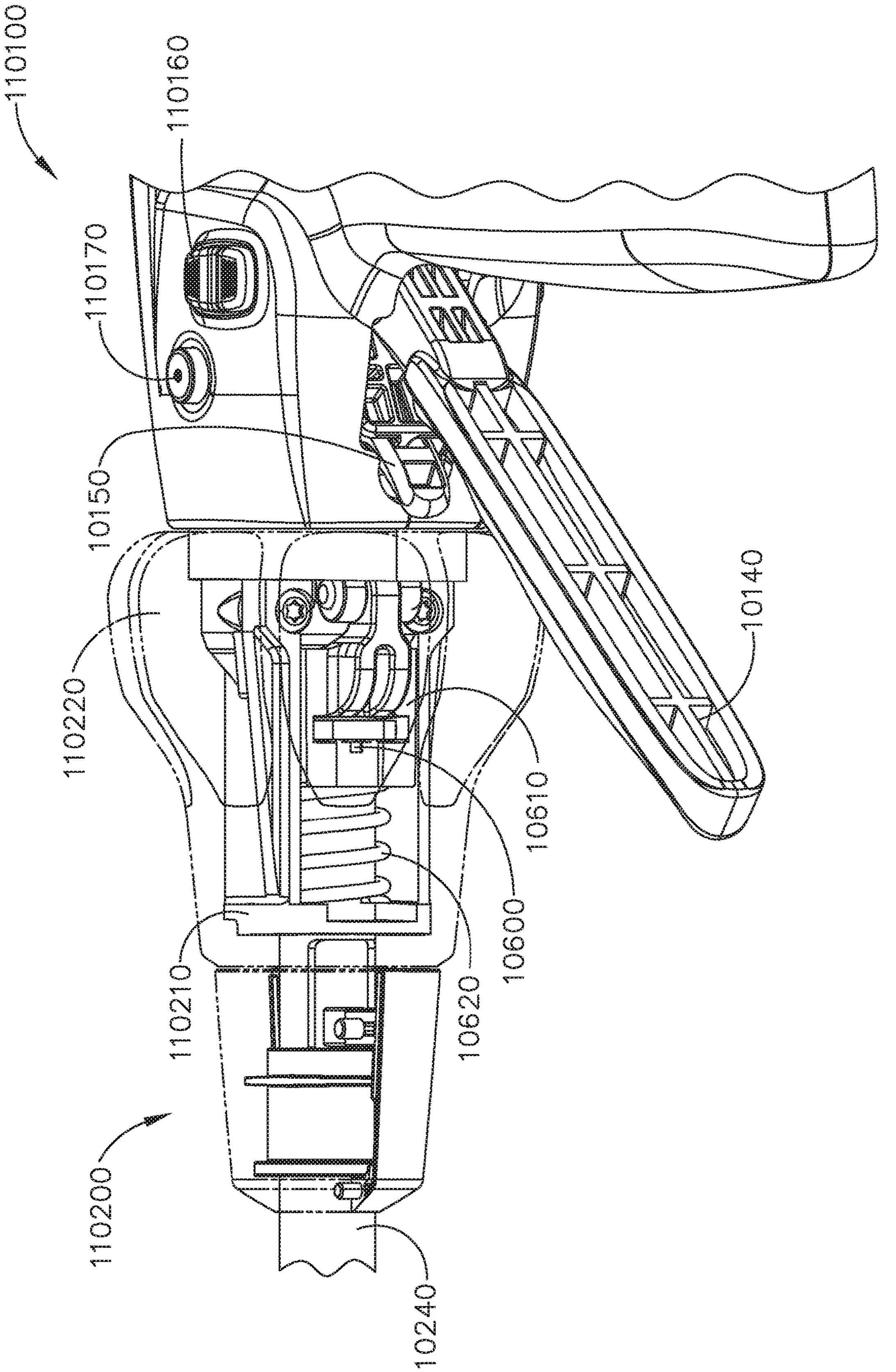
Figure 110:
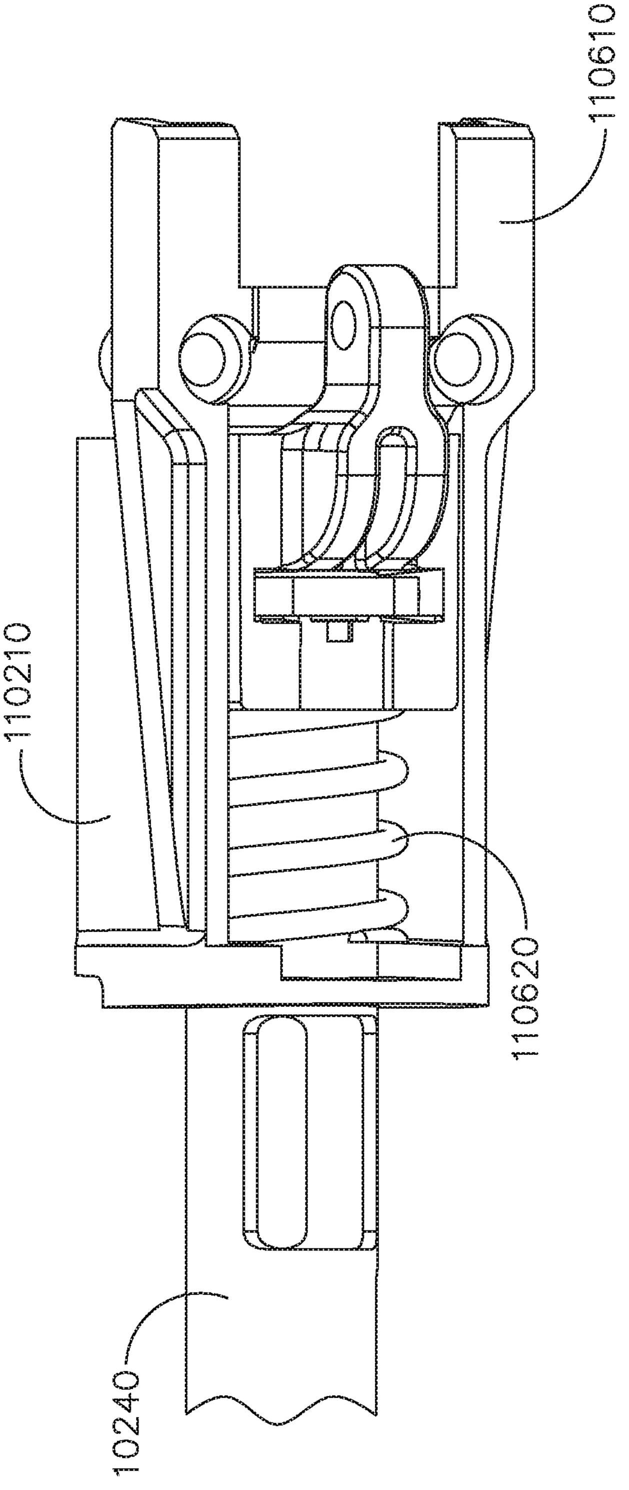

When the closure actuator 10140 is closed, referring now to FIGS. 109 and 110, the closure actuator 10140 drives a closure drive 10600 to close the second jaw 110420 of the end effector 110400. The closure drive 10600 includes a carriage 110610 which is pushed distally by the top portion 10144 of the closure actuator 10140 as the closure actuator 10140 is moved into its closed position by the clinician. The closure drive 10600 further includes a closure tube assembly 10240 mounted to the carriage 110610 which moves distally with the carriage 110610. The closure tube assembly 10240 comprises a distal end which interfaces with the second jaw 110420 and moves the second jaw 110420 downwardly toward the first jaw 110410 as the closure tube assembly 10240 is advanced distally. The closure drive 10600 also includes a spring 110620 positioned intermediate the carriage 110610 and the shaft frame 110210 which is resiliently compressed between the carriage 110610 and the shaft frame 110210 as the carriage 110610 is advanced distally during the closure stroke. After the closure stroke is completed, the spring 110620 is held in its compressed state by the closure lock 10146 (FIG. 102), discussed above, until the closure lock 10146 is overcome by an opening force provided by opening actuators 10180*a* and 10180*b* (FIG. 90) on the handle 110100. At such point, the compressed spring 110620 pushes the carriage 110610 and the closure tube assembly 10240 proximally to re-position the closure actuator 10140 in its unactuated position and to permit jaw opening springs 10446 (FIG. 147) in the end effector 110400 to open the second jaw 110420.

Figure 111:
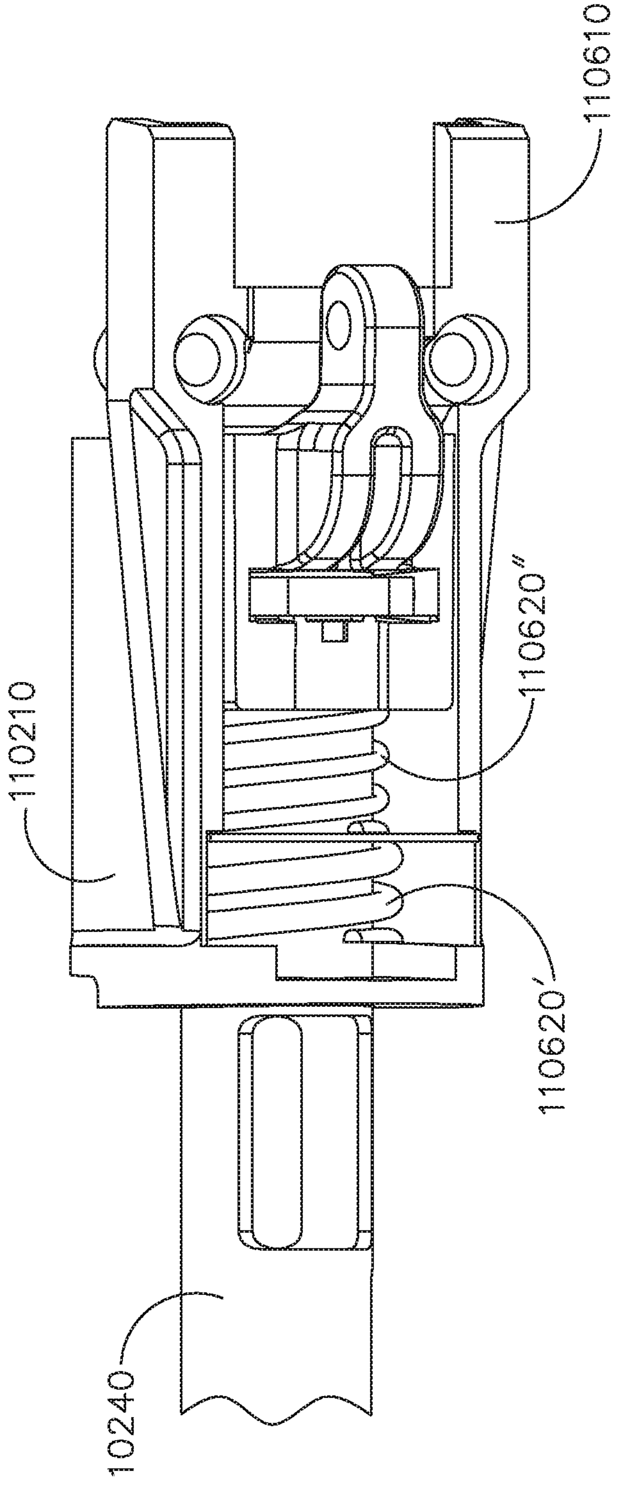

In various alternative embodiments, further to the above, a closure drive can include more than one spring that is compressed between the closure carriage 110610 and the shaft frame 110210. Referring to FIG. 111, a closure drive can comprise a distal spring 110620' and a proximal spring 110620" in series with one another. The distal spring 110620' is stiffer than the proximal spring 110620" such that the proximal spring 110620" is compressed significantly before the distal spring 110620' compresses significantly. As a result, the initial movement of the closure actuator 10140 from its fully-open position will encounter a light force owing to the compression of the proximal spring 110620" that suddenly increases once the distal spring 110620' begins to compress significantly. In at least one such instance, the proximal spring 110620" reaches its fully-compressed, or solid, state before the distal spring 110620' begins to compress significantly. This sudden increase in the force being applied to the closure actuator 10140 can correspond to the point in the closure stroke in which the articulation system has been deactivated. In such instances, the clinician is provided with tactile feedback that the articulation system can no longer be used to articulate the end effector 110400 unless the closure actuator 110400 is at least partially released, or re-opened, back beyond the force transition point. A graphical representation of the force applied to the closure actuator 10140 by the springs 110620' and 110620" is depicted in FIG. 113. The force applied to the closure actuator 10140 is depicted by line 110650 which includes an initial portion 110650*a* and a final portion 110650*b*. In the initial portion 110650*a*, as outlined above, the proximal spring 110620" compresses easily during the initial portion of the closing stroke resulting in a low force, around 100 N, being applied to the closure actuator 10140. At the half-way point in the closure stroke, for example, the force applied to the closure actuator 10140 in the final portion 110650*b* increases significantly owing to the solid state of the proximal spring 110620" and the higher spring rate of the distal spring 110620'. This force transition is demarcated as datum 110651 in FIG. 113 which also demarcates the deactivation of the articulation system.

Further to the above, FIG. 112A depicts the spring 110620, discussed above, which has a constant spring rate along the length thereof. FIG. 112C is a graphical representation of a spring system including the distal spring 110620' and the proximal spring 110620" which have different spring rates. In various instances, the effect provided by the distal spring 110620' and the proximal spring 110620" can be combined into a single spring, such as spring 110620'" in FIG. 112B, for example. In at least one embodiment, the spring 110620'" comprises a spring rate which changes along the length thereof. In various embodiments, springs positioned intermediate the closure carriage 110610 and the shaft frame 110210 can comprise a parallel and/or series arrangement. Regardless of the spring arrangement used, the spring arrangement can provide a tactile feedback to the clinician that an operational transition or threshold has been crossed.

Referring to FIG. 114, the surgical instrument 110000 comprises a visual indicator which indicates that the articulation drive has been decoupled from the staple firing drive and that the control system is no longer responsive to the articulation controls 110160 and 110170. The rocker body 110163 of the articulation actuator 110160 is comprised of a translucent material, such as a translucent plastic, for example. In at least one embodiment, the rocker body 110163 is comprised of clear polycarbonate, for example. The articulation actuator 110160 further comprises a light, such as a light emitting diode (LED), for example, positioned within and/or underneath the rocker body 110163. The light is in communication with the control system of the surgical instrument 110000 and is illuminated by the control system when the articulation drive is not engaged with the staple firing drive. In such instances, the clinician is provided with visual feedback that the articulation control 110160 is no longer responsive to inputs. Similarly, the articulation control 110170 comprises a button housing comprised of a translucent material and a light in communication with the control system. Similar to the articulation control 110160, the light of the articulation control 110170 is illuminated by the control system when the articulation drive is not engaged with the staple firing drive. In various embodiments, the articulation actuator 110160 is not illuminated when the closure actuator 10140 is in within a range of positions between, and including, its fully-open position and a predetermined partially-closed position, discussed above. When the closure actuator 10140 is closed beyond the predetermined partially-closed position, the articulation actuator 110160 is illuminated—at least until the closure actuator 10140 is returned back into the predetermined partially-closed position.

In various alternative embodiments, the light of the actuator 110160, and/or the actuator 110170, is illuminated with a first color, such as green, for example, when the articulation drive is engaged with the staple firing drive and a second color, such as red, for example, when the articulation drive is not engaged with the staple firing drive. In at least one such embodiment, the light in the articulation actuator 110160 comprises a two-color LED, for example.

Referring to FIG. 115, the surgical instrument 110000 can comprise a visual indicator which indicates that the articulation drive is engaged with the staple firing drive and that the control system is responsive to the articulation controls 110160 and 110170. The light in the articulation control 110160 is in communication with the control system of the surgical instrument 110000 and is illuminated by the control system when the articulation drive is engaged with the staple firing drive. In such instances, the clinician is provided with visual feedback that the articulation control 110160 is responsive to inputs. Similar to the articulation control 110160, the light of the articulation control 110170 is illuminated by the control system when the articulation drive is engaged with the staple firing drive. In various embodiments, the articulation actuator 110160 is illuminated when the closure actuator 10140 is in within a range of positions between, and including, its fully-open position and a predetermined partially-closed position, discussed above. When the closure actuator 10140 is closed beyond the predetermined partially-closed position, the articulation actuator 110160 is deilluminated—at least until the closure actuator 10140 is returned back into the predetermined partially-closed position. Further details are provided in the control system schematics 110900" and 110900'" illustrated in FIGS. 116 and 117, respectively.

As described above, the articulation drive of the surgical instrument 110000 is selectively engageable with the staple firing drive. When the articulation drive is engaged with the staple firing drive, the articulation actuator 110160 is actuatable to operate the electric motor of the staple firing drive and translate an articulation member of the articulation drive longitudinally. Referring to FIGS. 118-120, the surgical instrument 110000 further comprises an articulation lock system 110260 including two sets of articulation locks 110280 which releasably hold the articulation drive system (and end effector 110400) in position when the articulation drive is not being driven by the electric motor, as described in greater detail below. As also described in greater detail below, the two sets of articulation locks 110280 self-unlock when the articulation drive is driven by the electric motor of the staple firing drive.

Referring to FIG. 118, the articulation drive of the surgical instrument 110000 comprises a proximal drive member 110250 which is translated proximally and distally by the electric motor, depending on the direction in which the articulation actuator 110160 is actuated. When the proximal drive member 110250 is driven distally, the proximal drive member 110250 contacts a first set of articulation locks 110280 which are shifted from a locked position to an unlocked position by the distal movement of the proximal drive member 110250. The shifting of the first set of articulation locks 110280 shifts a second set of articulation locks 110280 into an unlocked position via a spring 10286 (FIG. 73) positioned intermediate the first and second sets of articulation locks 110280. Thus, the distal motion of the proximal drive member 110250 unlocks both sets of articulation locks 110280 and drives both sets of articulation locks 110280 distally. The articulation locks 110280 are engaged with a distal articulation member 110270 which is driven distally by the articulation locks 110280 when the articulation locks 110280 are driven distally by the proximal articulation member 110250. When the proximal drive member 110250 stops moving, the spring 10286 biases the articulation locks 110280 back into their locked positions to re-lock the end effector 110400 in position. When the proximal member 110250 is driven proximally, the proximal drive member 110250 contacts the second set of articulation locks 110280, shifts the first and second sets of articulation locks 110280 into their unlocked positions, and drives the first and second sets of articulation locks 110280 and the distal articulation member 112070 proximally. When the proximal drive member 110250 stops moving, similar to the above, the spring 10286 biases the articulation locks 110280 back into their locked positions to re-lock the end effector 110400 in position.

When the articulation locks 110280 are moved proximally and distally by the proximal drive member 110250 of the articulation drive, as described above, the articulation locks 110280 slide along a lock rail 110282. Referring primarily to FIG. 120, the lock rail 110282 extends through apertures 110285 defined in the lock ends 110284 of the articulation locks 110280. Notably, the lock rail 110282 comprises two flat lock surfaces 110282*a* which are positioned on opposite sides and two arcuate lock surfaces 110282*b* which are positioned on opposite sides. Each aperture 110285 comprises opposing flat lock sides 110285*a* which engage the flat lock surfaces 110282*a* of the lock rail 110282 when the articulation locks 110280 are in their locked positions. In various instances, the flat lock sides 110285*a* comprise edges which bite into the lock rail 110282 when the articulation locks 110280 are in their locked positions. Such an arrangement strongly resists back-driving forces transmitted into the articulation drive when a torque and/or force is applied to the end effector 110400 which tends to articulate or de-articulate the end effector 110400. When the articulation locks 110280 are shifted into the unlocked positions by the articulation drive, as described above, the flat lock sides 110285*a* of the apertures 110285 can slide along the flat lock surfaces 110282*a* of the lock rail 110282 which permits the end effector 110400 to be articulated. Each aperture 110285 further comprises opposing arcuate sides 110285*b* which slide along the arcuate lock surfaces 110282*b* of the lock rail 110282.

In various instances, the surgical instrument 110000 can comprise one or more position sensors which can be used to verify that the articulation drive system is engaged with or disengaged from the staple firing system. In at least one such embodiment, the surgical instrument 110000 comprises a Hall Effect sensor, for example, configured to assess whether or not the articulation drive member is aligned with and/or engaged with the staple firing drive member. In addition to or in lieu of a position sensor, the surgical instrument 110000 can comprise a force and/or force-related sensor configured to assess whether or not the articulation drive system is engaged with the staple firing drive system. In at least one such embodiment, the control system of the surgical instrument 110000 includes at least one strain gauge mounted on the proximal articulation drive member 110250, for example, which is configured to detect the strain in the proximal articulation drive member 110250. The strain loading in the articulation drive member 110250 follows a predictable pattern when the articulation drive member 110250 is advanced proximally or distally to unlock the articulation lock assembly 110260. For instance, a large force is needed to unlock the articulation lock assembly 110260 which then decreases once the end effector 110400 starts to articulate. In various instances, a processor of the surgical instrument control system is configured to compare the sensed strain loading data from the strain gauge to the expected strain data stored in a memory device of the control system. If the sensed data matches, or sufficiently matches, the stored data within an acceptable margin of error, the control system will determine that the articulation drive is engaged with the staple firing drive and permit the surgical instrument 110000 to continue to respond the articulation controls 110160 and 110170. The handle 110100 can also include an indicator light in communication with the control system that is illuminated by the control system when the control system determines that the articulation drive is coupled to the staple firing drive. Such an indicator light can be the articulation actuator 110160, the articulation actuator 110170, and/or an indicator light adjacent the articulation actuators 110160 and 110170, for example.

If, however, the sensed data does not sufficiently match the stored data, the control system will determine that the articulation drive is not engaged with the staple firing drive and will not permit the surgical instrument 110000 to continue to be responsive to the articulation controls 110160 and 110170. When the articulation drive is not engaged with the staple firing drive, the articulation drive member is not driven by the electric motor and, thus, little, if any, strain will be present in the articulation drive member 110250 which provides a pattern that is clearly discernable from the above-described pattern. Similar to the above, the handle 110100 can also include an indicator light in communication with the control system that is illuminated by the control system when the control system determines that the articulation drive is not coupled to the staple firing drive. Such an indicator light can be part of the articulation actuator 110160, the articulation actuator 110170, and/or an indicator light adjacent the articulation actuators 110160 and 110170, for example.

Further to the above, the proximal articulation drive member 110250 comprises an electrical circuit in communication with the at least one strain sensor mounted to the proximal articulation drive member 110250. The electrical circuit comprises an electrical contact that travels within and is in contact with an elongate longitudinal electrical contact in the handle 110100 which is, in turn, in communication with the processor of the surgical instrument 110000. As a result of this slideable electrical interface, the at least one strain sensor remains in communication with the control system throughout the travel of the proximal articulation drive member 110250. Other contact arrangements can be used. Moreover, other types of force sensors could be used, such as force transducers, for example. Also, any suitable portion of the articulation drive system could be used to assess whether the articulation drive system is engaged with the staple firing system.

An articulation lock in accordance with at least one alternative embodiment is illustrated in FIGS. 121 and 122. The articulation lock comprises a lock rail 110282', a first set of articulation locks 110280*a*', and a second set of articulation locks 110280*b*'. Similar to the articulation locks 110280, the articulation locks 110280*a*' and 110280*b*' are shiftable between locked and unlocked positions when the proximal articulation drive member 110250 is driven longitudinally. The lock rail 110282' comprises a first portion 110282*a*' which is gripped by the first articulation locks 110280*a*', a second portion 110282*b*' which is gripped by the second articulation locks 110280*b*', and a spring 110282*c*' connecting the first portion 110282*a*' and the second portion 110282*b*' of the lock rail 110282'. The flexibility of the spring 110282*c*' creates a force reaction in the articulation drive system which is observable and detectable by the control system to assess whether the articulation driver is engaged with the staple firing drive. Moreover, each articulation lock 110280*a*' comprises a kick-out 110284*a*' and, similarly, each articulation lock 110280*b*' comprises a kick-out 110284*b*'. The kick-outs 110284*a*' are nested with one another and in contact one another. Similarly, the kick-outs 110284*b*' are nested with one another and in contact one another. The length L and radius R of the kick-outs 110284*a*' and 110284*b*' are designed to create an improved locking/unlocking force and/or displacement profile of the articulation lock which is observable and detectable by the control system to assess whether the articulation driver is engaged with the staple firing drive.

A surgical instrument in accordance with at least one alternative embodiment is illustrated in FIGS. 123-126. The surgical instrument comprises a shaft 114200, an end effector 114400, an articulation drive configured to articulate the end effector 114400 about an articulation joint, and an articulation lock 114280. The articulation drive comprises a proximal articulation driver 114250, a distal articulation driver 114270, and an articulation lock spring 114260 positioned intermediate a distal arm 114272 and a proximal arm 114274 of the distal articulation driver 114270. When the articulation drive system is at rest, i.e., not being driven to articulate the end effector 114400, referring to FIG. 123, the articulation lock spring 114260 comprises a distal end 114262 positioned against the distal arm 114272 of the distal articulation driver 114270 and a proximal end 114264 engaged with the proximal articulation driver 114250. In such instances, as illustrated in FIG. 123, the proximal end 114264 of the articulation lock spring 114260 is seated in a notch, or recess, 114255 defined in the proximal articulation driver 114250. Moreover, in such instances, the lock spring 114260 is in a locked condition in which it is engaged with a lock rail 10282 of the shaft 114200. Referring primarily to FIG. 126, the lock rail 10282 extends through an aperture in the lock spring 114260 and, when the lock spring 114260 is in its locked condition, the coils of the lock spring 114260 are tightly engaged, or gripped, with a circular outer surface of the lock rail 10282. As a result, a significant drag force can be created which resists or prevents the articulation of the end effector 114400 when the end effector 114400 experiences a back-driving torque and/or force which tends to articulate or de-articulate the end effector 114400. In order to release the grip of the lock spring 114260 and unlock the articulation lock 114280, the diameter of the lock spring 114260 must be increased, as described in greater detail below.

When the proximal articulation driver 114250 is advanced distally to articulate the end effector 114400, referring to FIG. 124, a proximal cam arm 114254 of the proximal articulation driver 114250 engages the proximal arm 114274 of the distal articulation driver 114270 to push the distal articulation driver 114270 distally. The distal end of the distal articulation driver 114270 is engaged with a frame 114410 of the end effector 114400 such that the longitudinal translation of the distal articulation driver 114270 rotates the end effector 114400. When the proximal articulation driver 114250 contacts the distal articulation driver 114270, further to the above, the proximal end 114264 of the articulation lock spring 114260 is unseated from the notch 114255 and driven inwardly by the proximal articulation driver 114250. In such instances, the diameter of the articulation lock spring 114260 increases to release its grip on the lock rail 10282 and permit the end effector 114400 to be articulated by the articulation drive. When the distal motion of the proximal articulation driver 114250 is stopped, the articulation lock spring 114260 resiliently returns to its locked condition and re-grasps the lock rail 10282.

When the proximal articulation driver 114250 is moved proximally to articulate the end effector 114400 in an opposite direction, referring to FIG. 125, a distal cam arm 114252 of the proximal articulation driver 114250 engages the distal arm 114272 of the distal articulation driver 114270 to pull the distal articulation driver 114270 proximally. In such instances, further to the above, the proximal end 114264 of the articulation lock spring 114260 is unseated from the notch 114255 and driven inwardly by the proximal articulation driver 114250. In such instances, the diameter of the articulation lock spring 114260 increases to release its grip on the lock rail 10282 and permit the end effector 114400 to be articulated by the articulation drive. When the proximal motion of the proximal articulation driver 114250 is stopped, the articulation lock spring 114260 resiliently returns to its locked condition and re-grasps the lock rail 10282.

As discussed above, the actuation of the closure drive of the surgical instrument 110000 deactivates the articulation drive system at some point during the closure stroke. As the closure drive reaches the end of its closure stroke, the second jaw 110420 contacts the first jaw 110410 in a manner which indicates to the clinician using the surgical instrument 110000 that the second jaw 110420 is reaching its fully-clamped position. Referring to FIGS. 127-130, the second jaw 110420 is pivotably coupled to the first jaw 110410 and is rotatable between a fully-open position (FIG. 128) and a fully-clamped position (FIG. 127) during the closure stroke. When the second jaw 110420 is in its fully-open position (FIG. 128), the flanges, or tissue stops, 110428 of the second jaw 110420 are not engaged with the first jaw 110410. As the second jaw 110420 is closed, referring to FIG. 129, the tissue stops 110428 come into contact with the outside walls 110418 of the first jaw 110410. The inside surfaces 110429 of the tissue stops are un-angled, or parallel to the closing motion of the second jaw 110420. Referring primarily to FIG. 130, the outside surfaces 110419 of the outside walls 110418 are angled inwardly, or non-parallel to the closing motion of the second jaw 110420. Owing to this arrangement, an interference between the tissue stops 110428 of the second jaw 110420 and the outside walls 110418 of the first jaw 110410 is created during the closing motion of the second jaw 110420 and increases gradually as the second jaw 110420 is moved into its fully-closed position. This increasing interference between the jaws 110410 and 110420 creates an increasing resistance force within the closure drive which is transmitted back through the closure tube 110240 into the closure trigger 10140. The clinician pulling the closure trigger 10140 can feel the increasing resistance force being transmitted through the closure trigger 10140 and understand that the second jaw 10420 is reaching its fully-closed position.

Referring primarily to FIG. 130, each outside surface 110419 comprises a top angled surface 110419*a*, a second angled surface 110419*b*, and a final angled surface 110419*c*, for example. The first jaw 110410 comprises a channel 110412, which is configured to receive a staple cartridge therein, which comprises a top width defined between the top angled surfaces 110419*a*. The top width of the channel 110412 is narrower than an intermediate width defined between the intermediate angled surfaces 110419*b* which is narrower than a final width defined between the final angled surfaces 110419*c*. In addition to providing a tactile feedback to the clinician, the above-described arrangement maintains a proper lateral alignment between the first jaw 110410 and the second jaw 110420.

As discussed above, the actuation of the closure drive 10600 of the surgical instrument 110000 decouples the articulation drive from the staple firing drive at some point during the closure stroke. Referring to FIGS. 131 and 132, the surgical instrument 110000 comprises a transmission 110230 which is switched from a first state, or configuration, to a second state, or configuration when the closure drive 10600 is closed. When the transmission 110230 is in its first state, the proximal articulation driver 110250 is coupled to a firing member of the staple firing drive. When the transmission 110230 is in its second state, the proximal articulation driver 110250 is disengaged from the firing member. During the closure stroke, a cam portion of the closure drive 10600 contacts the transmission 110230 to rotate the transmission 110230 from its first state into its second state. The transmission 110230 comprises a cam member 110232 mounted within a rotatable collar 110234 which is contacted by the cam portion of the closure drive during the closure stroke. The cam member 110232 is comprised of a harder material than the cam portion of the closure drive 10600. In various instances, the scratch hardness and/or indentation hardness of the cam member 110232 is higher than the cam portion of the closure drive 10600. In at least one embodiment, the rotatable collar 110234 is comprised of plastic and the cam member 110232 is comprised of metal, such as cast zinc, for example. In various alternative embodiments, the cam portion of the closure drive 10600 is comprised of metal and the cam member 110232 of the transmission 110230 is comprised of the same metal. In any event, the transmission 110230 further comprises a spring which is compressed when the collar 110234 is rotated into its second state. The compressed spring is configured to re-expand and bias the collar 110234 back into its first state when the closure drive is retracted.

When the closure drive is advanced distally during the closure stroke, further to the above, the closure tube 110240 is advanced distally to engage and close the second jaw 110420 of the end effector 110400. Referring to FIGS. 133 and 134, the frame 110210' of the shaft 110220 can comprise one or more sealing interfaces which are engaged by the closure tube 110240 as it is advanced distally. The shaft frame 110210' is cylindrical, or at least substantially cylindrical, and comprises a first sealing interface 110212 and a second sealing interface 110214. The first sealing interface 110212 comprises a ring, or ridge, extending partially around the shaft frame 110210'; however, the first sealing interface 110212 could extend around the entire circumference of the shaft frame 110210' in other embodiments. Similarly, the second sealing interface 110214 comprises a ring, or ridge, extending partially around the shaft frame 110210'; however, the second sealing interface 110214 could extend around the entire circumference of the shaft frame 110210' in other embodiments. The first sealing interface 110212 and the second sealing interface 110214 are comprised of plastic and are configured to resiliently deform when they are engaged by the closure tube 110240. The resilient deformation of the interfaces 110212 provides a liquid-tight and/or gas-tight interface between the closure tube 110240 and the frame 110210' which can limit the ingress of fluids into the shaft 110200 and/or handle 110100 of the surgical instrument 110000. In various embodiments, the sealing interfaces 110212 and 110214 can be comprised of any suitable material, such as rubber and/or silicone, for example.

Once the end effector 110400 has been sufficiently closed, further to the above, the staple firing drive of the surgical instrument 110000 can be actuated to fire the staples contained in the staple cartridge seated in the end effector 110400 during a staple firing stroke. Referring to FIG. 148, the staple firing drive comprises a firing member, or bar, 110710 which is advanced distally by the electric motor of the staple firing drive in response to an actuation of the firing trigger 10150 (FIG. 91). The staple firing drive further comprises a coupling element 110720 attached to the distal end of the firing bar 110710. In at least one embodiment, the interface between the firing bar 110710 and the coupling element 110720 comprises a dovetail arrangement, for example. The coupling element 110720 is moveable between a proximal unfired position, illustrated in FIG. 148, and a distal fired position during a staple firing stroke. The coupling element 110720 comprises a cam 110724 configured to engage the first jaw 110410 and a cam 110722 configured to engage the second jaw 110420 during the staple firing stroke and hold the second jaw 110420. The cams 110722 and 110724 co-operate to hold the second jaw 110420 in position relative to the first jaw 110410 during the staple firing stroke, although embodiments are envisioned without the cams 110722 and 110724. The coupling element 110720 further comprises a tissue cutting edge 110271 configured to transect the tissue captured between the first jaw 110410 and the second jaw 110420 during the staple firing stroke.

Further to the above, the surgical instrument 110000 comprises a staple firing lockout to prevent the staple firing stroke when a staple cartridge is missing from the first jaw 110410 and/or when the staple cartridge seated in the first jaw 110410 has already been at least partially fired. To this end, the coupling element 110720 further comprises a proximally-extending tail 110729 which is biased downwardly, i.e., toward the bottom of the first jaw 110410, at the beginning of the staple firing stroke by a firing lockout spring 110490 mounted in the shaft 110200. If an unfired staple cartridge is not seated in the first jaw 110410 at the beginning of the staple firing stroke, the firing lockout spring 110490 will push the coupling element 110720 downwardly such that a laterally-extending lock shoulder 110727 extending from the coupling element 110720 enters into a lock recess 10419 defined in the first jaw 10410 and contacts a lock shoulder 10417 at the distal end of the lock recess 10419 which blocks the distal advancement of the staple firing drive to prevent the staple firing stroke. If an unfired staple cartridge is seated in the first jaw 110410 at the beginning of the staple firing stroke, a distal end 110725 of the coupling element 110720 is supported by a sled in the staple cartridge which prevents the coupling element 110720 from being pushed into the lock recess 110419 by the firing lockout spring 110490 and, as a result, the coupling element 110720 can be advanced distally to perform the staple firing stroke.

Further to the above, the firing lockout spring 110490 comprises a proximal portion 110492 mounted to the shaft 110200 and a distal end 110494 which is free to move relative to the proximal portion 110492. The distal end 110494 comprises an arcuate portion 110499 which extends over the proximal tail 110729 which is contacted by the proximal tail 110729 when the staple firing drive is actuated. The firing lockout spring 110490 further comprises lateral supports 110495 extending therefrom which supports the distal end 110494 over the proximal tail 110729. The lateral supports 110495 are positioned within recesses 110415 defined in the first jaw 110410 which hold the lateral supports 110495 in position. As a result of this arrangement, the firing lockout spring 110490 is prevented from bottoming out on the first jaw 110410 and shortening the effective length of the firing lockout spring 110490. Moreover, as a result of this arrangement, the firing lockout spring 110490 is able to flex and/or move upwardly to permit the coupling member 110720 to pass thereby without yielding or permanently deforming the firing lockout spring 110490. When the coupling member 110720 is returned to its proximal unfired position after the staple firing stroke, the firing lockout spring 110490 is moved upwardly by the coupling member 110720 to permit the coupling member tail 110729 to move thereunder.

Further to the above, referring to FIGS. 135-146, an articulation joint of a surgical instrument described herein can be configured to support the firing bar 110710 of the staple firing drive during the staple firing stroke. As discussed above, a surgical instrument can comprise a shaft 114200 and an end effector 114400 rotatably connected to the shaft 114200 about an articulation joint. Referring primarily to FIG. 135, the shaft 114200 comprises a frame 114210 which includes a pivot pin 114560 extending therefrom which is closely received in a pivot aperture defined in a frame 114410 of the end effector 114400. The pivot pin 114560 and the pivot aperture co-operate to define the articulation axis AA of the articulation joint. Similar to the above, referring primarily to FIG. 136, the end effector frame 114410 comprises an articulation drive pin 14464 extending therefrom which is engaged with the distal articulation driver 114270 and driven by the articulation drive system to articulate the end effector 114400 relative to the shaft 114200.

Referring again to FIGS. 135 and 136, the articulation joint further comprises a firing bar guide 114510 configured to slide relative to the pivot pin 114560 of the articulation joint. The firing bar guide 114510 comprises a proximal end 114530 which includes a proximal control pin that extends downwardly into a guide aperture 114215 defined in the shaft frame 114210. The proximal control pin is configured to move within the shaft guide aperture 114215 but its lateral and longitudinal motion is constrained by the sidewalls of the shaft guide aperture 114215. Similarly, the firing bar guide 114510 comprises a distal end 114540 which includes a distal control pin that extends downwardly into a guide aperture 114440 defined in the end effector frame 114410. The distal control pin is configured to move within the end effector guide aperture 114440 but its lateral and longitudinal motion is constrained by the sidewalls of the end effector guide aperture 114440. The firing bar guide 114510 further comprises arcuate guide walls 114570 which support the sides of the firing bar 110710 as the firing bar 110710 slides relative thereto. The guide walls 114570 prevent the firing bar 110710 from buckling, among other things.

Further to the above, the shaft 114200 further comprises a retainer 114290 attached to the shaft frame 114210. The retainer 114290 further comprises a distal end including control surfaces 114295 defined thereon which are configured to constrain the rotation of the firing bar guide 114510 within the articulation joint. When the end effector 114400 is articulated to the left, as illustrated in FIG. 135, a left shoulder 114535 defined on the firing bar guide 114510 contacts the control surfaces 114295 on the retainer 114290. When the end effector is articulated to the right, as illustrated in FIG. 137, a right shoulder 114535 defined on the firing bar guide 114510 contacts the control surfaces 114295 on the retainer 114290. Regardless of whether the firing bar guide 114510 is in its left-most orientation, its right-most orientation, or anywhere in-between, the knife bar guide walls 114570 are aligned with a knife bar guide slot 114270 defined in the shaft 114200 and a knife bar guide slot 114470 defined in the end effector 114400 to provide a continuous, or at least nearly continuous, supported path for the firing bar 110710 through the articulation joint.

Further to the above, the end effector frame 114410 comprises control notches 114445 defined therein which are configured to receive corresponding distal projections 114545 extending from the distal end of the firing bar guide 114510. When the end effector 114400 is fully-articulated to the left, as illustrated in FIG. 135, a left distal projection 114545 of the firing bar guide 114510 is captured in a left control notch 114445. Simultaneously, the left shoulder 114535 of the firing bar guide 114510 is in contact with the left control surface 114295 of the retainer 114290. In such instances, the firing bar guide 114510 is held in place within the articulation joint. Moreover, in such instances, the firing bar guide 114510 can control the left-most articulation of the end effector 114400. When the end effector 114400 is fully-articulated to the right, as illustrated in FIG. 137, a right distal projection 114545 of the firing bar guide 114510 is captured in a right control notch 114445. Simultaneously, the right shoulder 114535 of the firing bar guide 114510 is in contact with the right control surface 114295 of the retainer 114290. In such instances, the firing bar guide 114510 is held in place within the articulation joint. Moreover, in such instances, the firing bar guide 114510 can control the right-most articulation of the end effector 114400.

Referring to FIG. 140, the shaft retainer 114290 comprises two lateral sides which are connected at the distal end thereof by a connector 114299. Such an arrangement reduces, if not prevents, relative movement between the two lateral sides of the shaft retainer 114290. When the shaft retainer 114290 is assembled to the shaft frame 114210, referring to FIG. 141, the connector 114299 of the shaft retainer 114290 extends into the shaft aperture 114215. Referring to FIGS. 142 and 143, the proximal end 114530 of the firing bar guide 114510 comprises a recessed portion which is configured to slide under the shaft retainer 114290. As a result, the shaft retainer 114290 retains the firing bar guide 114510 from lifting upwardly. The firing bar guide 114510 further comprises a lip 114539 extending proximally from the proximal end 114530 thereof. As illustrated in FIG. 142, the lip 14539 is configured to slide under the connector 114299. As a result, similar to the above, the connector 114299 of the shaft retainer 114290 retains the firing bar guide 114510 from lifting upwardly.

Referring again to FIG. 135, the firing bar guide 114510 comprises lateral wings 114520 extending therefrom. The lateral wings 114520 are configured to inhibit or prevent patient tissue from entering into the articulation joint and becoming pinched between the shaft 114200 and the end effector 114400 when the end effector 114400 is articulated.

Referring to FIGS. 149 and 149A, the surgical instrument 110000 comprises a power management system 110900 configured to control the manner in which the surgical instrument 110000 is powered up. The power management system 110900 comprises a first voltage regulator 110910, a second voltage regulator 110920, and a processor 110930 configured to control the first voltage regulator 110910 and the second voltage regulator 110920. The power management system 110900 further comprises a first component architecture 110940 of the surgical instrument 110000 which is powered at a first voltage, a second component architecture 110950 which is powered at a second voltage, and a third component architecture 110960 which is powered at a third voltage. The first component architecture 110940 is supplied with the first voltage when the battery 10300 is assembled to the handle 110100 and/or when the surgical instrument 110000 is powered on. In at least one embodiment, the first voltage is approximately 11 VDC, for example, and is immediately supplied to the first component architecture 110940.

The first voltage regulator 110910 comprises a control input 110911 which is in communication with the processor 110930, a supply input 110912 in communication with the first component architecture 110940, and a supply output 110913 in communication with the second component architecture 110950. The first voltage regulator 110910 comprises a Texas Instruments TPS561208 step-down voltage regulator, for example, which is switchable from an off condition to an on condition when a voltage exceeding a threshold voltage, such as 1.6 VDC, for example, is applied to the control input 110911 by the processor 110930. When the first voltage regulator 110910 is in its off condition, the second component architecture 110950 is unpowered. When the first voltage regulator 110910 is in its on condition, the second component architecture 110950 is supplied with a second voltage of 5.4 VDC, for example, from the supply output 110913 of the first voltage regulator 110910. In such instances, certain components and/or systems of the surgical instrument 110100 are, as a result, supplied with power at the second voltage.

The second voltage regulator 110920 comprises a control input 110921 which is in communication with the processor 110930, a supply input 110922 in communication with the second component architecture 110950, and a supply output 110923 in communication with the third component architecture 110960. The second voltage regulator 110920 comprises a Texas Instruments TLV741P low-dropout linear voltage regulator, for example, which is switchable from an off condition to an on condition when a voltage exceeding a threshold voltage is applied to the control input 110921 by the processor 110930. When the second voltage regulator 110920 is in its off condition, the third component architecture 110960 is unpowered. When the second voltage regulator 110920 is in its on condition, the third component architecture 110960 is supplied with a voltage of 3.3 VDC, for example, from the supply output 110923 of the second voltage regulator 110920. In such instances, certain components and/or systems of the surgical instrument 110100 are, as a result, supplied with power at the third voltage.

Further to the above, the processor 110930 is configured to sequentially stage, or stagger, the power-up of the first component architecture 110940, the second component architecture 110950, and the third component architecture 110960. As discussed above, the first component architecture 110940 is immediately powered when the surgical instrument 110000 is powered on. At such point, however, the processor does not supply the first voltage regulator 110910 and the second voltage regulator 110920 with an enabling voltage to their control inputs 110911 and 110921, respectively, and, as a result, the second component architecture 110950 and the third component architecture 110960 are unpowered. Instead, the processor 110930 is configured to wait a first period of time before supplying the enabling voltage to the control input 110911 of the first voltage regulator 110910 and then wait a second period of time before supplying the enabling voltage to the control input 110921 of the second voltage regulator 110920. As a result, the second component architecture 110950 is powered up before the third component architecture 110960. Such an arrangement can prevent a fuse in the power management system 110900 from being overpowered, or blown. The first period of time and the second period of time can comprise fixed times determined by a timer circuit, for example. In at least one alternative embodiment, a first timer circuit can be used to delay the power-up of the first voltage regulator 110910 and a second timer circuit can be used to delay the power-up of the second voltage regulator 110920 in lieu of a processor. In certain embodiments, the processor and/or a separate circuit can be configured to monitor spikes in the current supplied to the surgical instrument 110000 from the battery 10300 and wait until the spike has sufficiently abated before powering up the next component architecture in the power-up sequence.

Referring to FIG. 150, the handle 110100 of the surgical instrument 110000, comprises a retraction system 110800 that can be used by the clinician to manually retract the staple firing system in the event that the electric motor is unable to retract the firing bar 110710 after the staple firing stroke. As can be seen in FIG. 150, the retraction system 10800 comprises an actuator which is stowed in a cavity 110102 defined in the handle 110100. The handle 110100 comprises two housing halves that are assembled, or snap-fit, together to form an outer housing 110101 of the handle 110100 and, in addition, referring to FIG. 151, a cover 110190 that is releasably secured to the outer housing 110101. The cover 110190 comprises a lip 110192 which extends under the outer housing 110101 and a latch 110194 which releasably secures the cover 110190 to the outer housing 110101. When the staple firing system is functioning properly, the cover 110190 is typically attached to the outer housing 110101 and the actuator of the retraction system 10800 is hidden under the cover 110190. When the clinician wants to use the manual retraction system, the clinician removes the cover 110190, raises the retraction system actuator, and then ratchets the retraction system actuator back and forth to retract the firing bar 110710.

Further to the above, the cover 110190 further comprises a detectable element 110196, such as a magnetic element comprised of iron and/or nickel, for example. The surgical instrument 110000 comprises a position sensor, such as a Hall Effect sensor, for example, in communication with the control system 110900 which is configured to detect the presence of the detectable element 110196. If the control system 110900 determines that the cover 110190 is attached to the outer housing 110101 based on data from the Hall Effect sensor, the control system 110900 is configured to supply battery power to the first component architecture 110940, and the component architectures 101950 and 101960, as described above. If, however, the control system determines that the cover 110190 is not attached to the housing 110101 based on data from the Hall Effect sensor, the control system 110900 is configured to deny power to the electric motor of the staple firing drive while the retraction system 110800 is being operated. In various instances, the control system 110900 can comprise a sensor configured to detect when the firing bar 110170 has been sufficiently retracted and, at that point, make power available to the electric motor once again so that the end effector 110400 can be articulated, as described above, using the electric motor if it is possible to do so. Reattaching the cover 110190 to the housing 110101 will also cause the control system 110900 to make power available to the electric motor once again.

A cover analog 110190' is illustrated in FIG. 152. The cover analog 110190' is similar to the cover 110190 in every respect except one, i.e., the cover analog 110190' comprises an additional detectable element 110198' that can be used during the manufacturing process to activate certain functions of the surgical instrument 110000 that are not available during the ordinary use of the surgical instrument 110000 in a surgical suite and/or during a surgery. Referring to FIG. 153, a control system circuit 110900' includes a Hall Effect sensor 110970' which is configured to detect the presence of the detectable element 110198'. Like the detectable element 110196, the detectable element 110198' can be a magnetic element comprised of iron and/or nickel, for example. If the control system circuit 110900' determines that the cover analog 110190' is attached to the outer housing 110101 based on data from the Hall Effect sensor 110970', the control system circuit 110900' is configured to power up a radio antenna circuit 110980' of the control system circuit 110900' which is used to receive data, or programming, during the manufacturing process. After the surgical instrument 110000 has been sufficiently programmed during the manufacturing process, the cover analog 110190' is removed from the handle 110100 and the cover 110190 is attached to the handle 110100 in its place. At such point, the control system circuit 110900' will determine that the cover analog 110190' is no longer attached to the handle 110100 and depower the radio antenna circuit 110980'. The surgical instrument 110000, at this point, is ready to be used during surgery. If the surgical instrument 110000 needs to be re-programmed, the cover 110190 is removed and replaced with the cover analog 110190' to reactivate the radio antenna circuit 110980'. The frequency of the wireless signals can comprise any suitable frequency. Moreover, an optical receiver can be used to receive optical signals in addition to or in lieu of a radio antenna. The optical receiver could be powered in the same way as described above.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein. The disclosures of International Patent Publication No. WO 2017/083125, entitled STAPLER WITH COMPOSITE CARDAN AND SCREW DRIVE, published May 18, 2017, International Patent Publication No. WO 2017/083126, entitled STAPLE PUSHER WITH LOST MOTION BETWEEN RAMPS, published May 18, 2017, International Patent Publication No. WO 2015/153642, entitled SURGICAL INSTRUMENT WITH SHIFTABLE TRANSMISSION, published Oct. 8, 2015, U.S. Patent Application Publication No. 2017/0265954, filed Mar. 17, 2017, entitled STAPLER WITH CABLE-DRIVEN ADVANCEABLE CLAMPING ELEMENT AND DUAL DISTAL PULLEYS, U.S. Patent Application Publication No. 2017/0265865, filed Feb. 15, 2017, entitled STAPLER WITH CABLE-DRIVEN ADVANCEABLE CLAMPING ELEMENT AND DISTAL PULLEY, and U.S. Patent Publication No. 2017/0290586, entitled STAPLING CARTRIDGE, filed on Mar. 29, 2017, are incorporated herein by reference in their entireties.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical instrument, comprising:
- a shaft;
- a first jaw, comprising:
  - a first proximal end;
  - a first distal end;
  - a first lateral wall; and
  - a second lateral wall positioned opposite said first lateral wall; and
- a second jaw rotatably connected to said first jaw about a rotation joint, wherein said second jaw is rotatable relative to said first jaw between an open position, a partially-clamped position, and a fully-clamped position, and wherein said second jaw comprises:
  - a second proximal end;
  - a second distal end;
  - a first lateral flange, wherein said first lateral flange is not in contact with said first lateral wall when said second jaw is in said open position, and wherein said first lateral flange is in contact with said first lateral wall when said second jaw is in said partially-clamped position and when said second jaw is in said fully-clamped position; and
  - a second lateral flange positioned opposite said first lateral flange, wherein said second lateral flange is not in contact with said second lateral wall when said second jaw is in said open position, and wherein said second lateral flange is in contact with said second lateral wall when said second jaw is in said partially-clamped position and when said second jaw is in said fully-clamped position to align said second jaw relative to said first jaw.

2. The surgical instrument of claim 1, further comprising a replaceable staple cartridge.

3. The surgical instrument of claim 1, wherein said first jaw defines a first center plane, wherein said first lateral wall comprises a first outer surface angled inwardly toward said first center plane, and wherein said second lateral wall comprises a second outer wall angled inwardly toward said first center plane.

4. The surgical instrument of claim 1, further comprising:
a first lateral spring positioned intermediate said first jaw and said second jaw; and
a second lateral spring positioned intermediate said first jaw and said second jaw.

5. A surgical instrument, comprising:
a shaft;
a first jaw, comprising:
a first proximal end;
a first distal end;
a first lateral wall; and
a second lateral wall positioned opposite said first lateral wall; and
a second jaw rotatably connected to said first jaw about a rotation joint, wherein said second jaw is rotatable relative to said first jaw between an open position, a partially-clamped position, and a fully-clamped position during a closing motion, and wherein said second jaw comprises:
a second proximal end;
a second distal end;
a first lateral flange, wherein said first lateral flange is not in contact with said first lateral wall when said second jaw is in said open position, and wherein said first lateral flange is configured to contact said first lateral wall once said second jaw is in said partially-clamped position during said closing motion; and
a second lateral flange positioned opposite said first lateral flange, wherein said second lateral flange is not in contact with said second lateral wall when said second jaw is in said open position, wherein said second lateral flange is configured to contact said second lateral wall once said second jaw is in said partially-clamped position during said closing motion, and wherein said contact between said first lateral flange and said second lateral flange and said first jaw creates an interference force that increases as said second jaw is moved from said partially-clamped position to said fully-clamped position.

6. The surgical instrument of claim 5, further comprising a replaceable staple cartridge.

7. The surgical instrument of claim 5, wherein said first jaw defines a first center plane, wherein said first lateral wall comprises a first outer surface angled inwardly toward said first center plane, and wherein said second lateral wall comprises a second outer wall angled inwardly toward said first center plane.

8. The surgical instrument of claim 5, further comprising:
a first lateral spring positioned intermediate said first jaw and said second jaw; and
a second lateral spring positioned intermediate said first jaw and said second jaw.

9. A surgical instrument, comprising:
a shaft;
a replaceable staple cartridge;
a first jaw, comprising:
a first proximal end;
a gradually sloping surface; and
a first distal end; and
a second jaw rotatably connected to said first jaw about a rotation joint, wherein said second jaw is rotatable relative to said first jaw between an open position, a partially-clamped position, and a fully-clamped position during a closing motion, and wherein said second jaw comprises:
a second jaw shape that differs from a shape of said first jaw;

a second proximal end;
a second distal end; and
a lateral flange, wherein said lateral flange is not in contact with said first jaw when said second jaw is in said open position, and wherein said lateral flange is configured to contact said gradually sloping surface of said first jaw once said second jaw is in said partially-clamped position during said closing motion, and wherein said contact between said lateral flange and said gradually sloping surface of said first jaw creates an interference force that increases as said second jaw is moved from said partially-clamped position to said fully-clamped position.

10. The surgical instrument of claim 9, further comprising:
a first lateral spring positioned intermediate said first jaw and said second jaw; and
a second lateral spring positioned intermediate said first jaw and said second jaw.

11. An end effector for a surgical stapler, wherein said end effector comprises:
a channel comprising a pair of channel sidewalls configured to operably support a surgical staple cartridge therebetween; and
an anvil supported relative to said channel for selective rotation relative to said channel between a fully-open position and a fully-clamped position, wherein said anvil comprises a pair of anvil tissue stops, wherein each said anvil tissue stop comprises a tissue stop distal edge located distal to a proximal-most staple cavity in the surgical staple cartridge operably supported between said channel sidewalls, and wherein each said anvil tissue stop is configured to slidably engage a gradually sloping surface on a corresponding one of said channel sidewalls to create an increasing resistive force during movement of said anvil from said fully-open position to said fully-clamped position.

12. The end effector of claim 11, wherein each said gradually sloping surface is formed on an outer surface of a corresponding one of said channel sidewalls.

13. The end effector of claim 12, wherein said outer surface of each said channel sidewall comprises:
a top angled surface;
a second angled surface; and
a final angled surface.

14. The end effector of claim 13, wherein a first distance between said top angled surfaces on said channel sidewalls defines a top width, wherein a second distance between said second angled surfaces on said channel sidewalls defines an intermediate width that is greater than the top width, and wherein a third distance between said final angled surfaces on said channel sidewalls defines a third width that is greater than the intermediate width.

15. The end effector of claim 13, wherein the resistive force increases as said anvil tissue stops move from slidably contacting said top angled surfaces to slidably contacting said second angled surfaces.

16. The end effector of claim 15, wherein the resistive force increases as said anvil tissue stops move from slidably contacting said second angled surfaces to slidably contacting said final angled surfaces.

* * * * *